United States Patent
Gradl et al.

(10) Patent No.: US 10,815,215 B2
(45) Date of Patent: Oct. 27, 2020

(54) 2,4,5-TRISUBSTITUTED 1,2,4-TRIAZOLONES USEFUL AS INHIBITORS OF DHODH

(71) Applicants: BAYER AKTIENGESELLSCHAFT, Leverkusen (DE); BAYER PHARMA AKTIENGELLSCHAFT, Berlin (DE); THE BROAD INSTITUTE, INC., Cambridge, MA (US); PRESIDENT AND FELLOWS OF HARVARD COLLEGE, Cambridge, MA (US); THE GENERAL HOSPITAL CORPORATION, Boston, MA (US)

(72) Inventors: Stefan Nikolaus Gradl, Berlin (DE); Duy Nguyen, Berlin (DE); Knut Eis, Berlin (DE); Judith Günther, Berlin (DE); Timo Stellfeld, Berlin (DE); Andreas Janzer, Berlin (DE); Sven Christian, Berlin (DE); Thomas Müller, Langenfeld (DE); Sherif El Sheikh, Mülheim/Ruhr (DE); Han Jie Zhou, Foster City, CA (US); Changjia Zhao, Beijing (CN); David B. Sykes, Cambridge, MA (US); Steven James Ferrara, Cambridge, MA (US); Kery Liu, Beijing (CN); Michael Kröber, Berlin (DE); Claudia Merz, Berlin (DE); Michael Niehues, Berlin (DE); Martina Schäfer, Berlin (DE); Katja Zimmermann, Düsseldorf (DE); Carl Friedrich Nising, Leverkusen (DE)

(73) Assignees: BAYER AKTIENGESELLSCHAFT, Leverkusen (DE); BAYER PHARMA AKTIENGELLSCHAFT, Berlin (DE); THE BROAD INSTITUTE, INC., Cambridge, MA (US); PRESIDENT AND FELLOWS OF HARVARD COLLEGE, Cambridge, MA (US); THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 16/345,168

(22) PCT Filed: Oct. 25, 2017

(86) PCT No.: PCT/EP2017/077252
§ 371 (c)(1),
(2) Date: Apr. 25, 2019

(87) PCT Pub. No.: WO2018/077923
PCT Pub. Date: May 3, 2018

(65) Prior Publication Data
US 2020/0123129 A1    Apr. 23, 2020

Related U.S. Application Data

(63) Continuation-in-part of application No. PCT/CN2016/103643, filed on Oct. 27, 2016.
(Continued)

(51) Int. Cl.
*C07D 401/12* (2006.01)
*A61P 35/00* (2006.01)
(Continued)

(52) U.S. Cl.
CPC ............ *C07D 401/12* (2013.01); *A61P 35/00* (2018.01); *C07D 249/12* (2013.01);
(Continued)

(58) Field of Classification Search
CPC .................................................... C07D 249/12
See application file for complete search history.

(56) References Cited

FOREIGN PATENT DOCUMENTS

| CN | 103006645 A | 4/2013 |
|---|---|---|
| WO | 2012028579 A1 | 3/2012 |
| WO | 2013186692 A1 | 12/2013 |

OTHER PUBLICATIONS

Munier-Lehmann, H. et al., "On Dihydroorotate Dehydrogenases and Their Inhibitors and Uses," Journal of Medicinal Chemistry, vol. 56, No. 8, Apr. 25, 2013, pp. 3148-3167.
(Continued)

*Primary Examiner* — Joseph R Kosack
(74) *Attorney, Agent, or Firm* — Melissa Hunter-Ensor; Scott Goncher; Greenberg Traurig, LLP

(57) ABSTRACT

The present invention provides triazolone compounds of general formula (I): in which $R^1$, $R^2$, $R^3$, $R^4$ and $R^5$ are as defined herein, methods of preparing said compounds, intermediate compounds useful for preparing said compounds, pharmaceutical compositions and combinations comprising said compounds and the use of said compounds for manufacturing pharmaceutical compositions for the treatment or prophylaxis of diseases, in particular of hyperproliferative disorders, as a sole agent or in combination with other active ingredients.

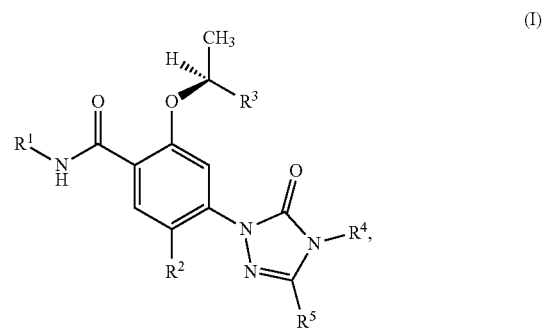

20 Claims, No Drawings

Related U.S. Application Data

(60) Provisional application No. 62/569,296, filed on Oct. 6, 2017.

(51) Int. Cl.
| | | |
|---|---|---|
| *C07D 249/12* | (2006.01) | |
| *C07D 403/12* | (2006.01) | |
| *C07D 405/12* | (2006.01) | |
| *C07D 413/12* | (2006.01) | |
| *A61K 45/06* | (2006.01) | |

(52) U.S. Cl.
CPC ......... *C07D 403/12* (2013.01); *C07D 405/12* (2013.01); *C07D 413/12* (2013.01); *A61K 45/06* (2013.01)

(56) References Cited

OTHER PUBLICATIONS

Park, J., "Facile Access to a Variety of 2, 5-Biaryl-1, 2, 4-triazol-3-ones via Regioselective N-Arylation of Triazolones Bull.," Korean Chem. Soc., Dec. 31, 2013, vol. 31, No. 8, pp. 2143-2146.

International Search Report and Written Opinion for corresponding PCT Patent Application No. PCT/EP2017/077252, dated Nov. 22, 2017 (9 pages).

International Search Report and Written Opinion for corresponding PCT Patent Application No. PCT/CN2016/103643, dated Jun. 2, 2017 (15 pages).

2,4,5-TRISUBSTITUTED 1,2,4-TRIAZOLONES USEFUL AS INHIBITORS OF DHODH

This application is the U.S. national phase application, pursuant to 35 U.S.C. § 371, of PCT International Application Ser. No.: PCT/EP2017/077252, filed Oct. 25, 2017, designating the United States and published in English, which claims priority to and the benefit of PCT International Application Ser. No.: PCT/CN2016/103643, filed Oct. 27, 2016, and U.S. Provisional Application No. 62/569,296, filed Oct. 6, 2017, the entire contents of each of which are incorporated herein by reference.

The present invention provides 2,4,5-trisubstituted 1,2,4-triazolone compounds of general formula (I) as described and defined herein, methods of preparing said compounds, intermediate compounds useful for preparing said compounds, pharmaceutical compositions and combinations comprising said compounds, and the use of said compounds for manufacturing pharmaceutical compositions for the treatment or prophylaxis of diseases, in particular of hyperproliferative and/or inflammatory disorders, as a sole agent or in combination with other active ingredients.

BACKGROUND

The present invention provides 2,4,5-trisubstituted 1,2,4-triazolone compounds of general formula (I) which inhibit Dihydroorotate Dehydrogenase (DHODH).

Acute myeloid leukemia (AML) is the most common acute leukemia in humans with a 5 year survival of only about 30%. AML is a malignancy of the myeloid line of blood cells. The incidence rates and chances of cure are highly age dependent. The chemotherapy standard of care for AML has not changed significantly over the last decades highlighting the need for novel therapies. A major hallmark of AML is differentiation arrest of the leukemic cells at early stages of cellular differentiation. The potential of leukemic differentiation therapy can be seen with the success of ATRA or arsenic trioxide inducing differentiation in acute promyelocytic leukemia (APL). Around 10% of AML belong to the APL subtype where leukemic cells are harbouring a chromosomal translocation resulting in fusions of oncoproteins involving the retinoic acid receptor. While treatment with ATRA or arsenic trioxide leads to a dramatic increase of patient survival, with overall survival rates of over 70%, unfortunately a comparable differentiation therapy for the non-APL AMLs is lacking (Management of acute promyelocytic leukemia: recommendations from an expert panel on behalf of the European LeukemiaNet, Sanz M. A. et al, Blood 2009, 113(9), 1875-1891). Therefore new therapies inducing differentiation of AML cells are of high interest and medical need.

Dihydroorotate Dehydrogenase (DHODH)

DHODH is located in the mitochondria and the enzyme responsible for the 4$^{th}$ and rate limiting step in de novo pyrimidine synthesis converting dihydroorotate to orotate (Dihydroorotat-ubiquinone oxidoreductase links mitochondria in the biosynthesis of pyrimidine nucleotides, Löffler M. et al, Molecular and Cellular Biochemistry 1997, 174, 125-129).

As pyrimdine production is essential for DNA and RNA synthesis DHODH is highly important for cellular proliferation. The enzyme is considered an attractive drug target for cancer, immunological, parasitic and viral diseases and DHODH small molecule inhibitors like Leflunomide/Teriflunomide and Brequinar have been approved for clinical use in Rheumatoid Arthritis and Multiple Sclerosis. Additionally, preclinical studies indicate that DHODH inhibitors may be useful for the treatment of haematological cancer indications, for the treatment of solid tumors (e.g., neuroblastoma, melanoma, colon, breast and lung tumors), for the treatment of parasitic diseases (e.g., malaria), and for viral disease therapy.

U.S. Pat. No. 6,444,613 B1 relates to the field of defoliants, in particular thidiazuron-comprising mixtures, and their use in crops of cotton. These mixtures comprise among others 2,4,5-trisubstituted 1,2,4-triazolone compounds as herbicides, which inhibit the enzyme protoporphyrinogen-(IX) oxidase (PPO inhibitors).

WO199802422 describes substituted aromatic carbonyl compounds, among others 2,4,5-trisubstituted 1,2,4-triazolone compounds, as herbicides.

From CN106543139 some triazolone compounds are known as agrochemicals.

US 2016/0251341 A1 describes triazole compounds as serine protease inhibitors useful for the inhibition of thrombin and/or kallikrein.

WO2010/077686 A1 describes sirtuin-modulating compounds, e.g. isoindolinone and related compounds, and methods of use thereof. The sirtuin-modulating compounds may be used for increasing the lifespan of a cell, and treating and/or preventing a wide variety of diseases and disorders including, for example, diseases or disorders related to aging or stress, diabetes, obesity, neurodegenerative diseases, cardiovascular disease, blood clotting disorders, inflammation, cancer, and/or flushing as well as diseases or disorders that would benefit from increased mitochondrial activity.

WO 2013/186692 A1 describes triazolone compounds as mPGES-1 inhibitors, useful in the treatment of pain and/or inflammation from a variety of diseases or conditions, such as asthma, osteoarthritis, rheumatoid arthritis, acute or chronic pain and neurodegenerative diseases.

However, the state of the art does not describe the specific 2,4,5-trisubstituted 1,2,4-triazolone compounds of general formula (I) of the present invention as described and defined herein.

DESCRIPTION

It has now been found, and this partially constitutes the basis of the present invention, that the compounds of the present invention (e.g. the compounds of general formula (I)) have surprising and advantageous properties.

In particular, the compounds of the present invention have surprisingly been found to effectively inhibit DHODH and may therefore be used for the treatment or prophylaxis of hyperproliferative and/or inflammatory disorders, such as cancer, for example.

In accordance with one aspect, the present invention provides compounds of general formula (I)

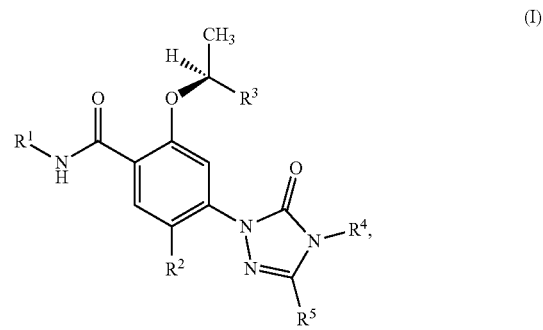

in which $R^1$ represents a group selected from
- a $C_5$-$C_8$-alkyl group,
- a $C_2$-$C_8$-haloalkyl group,
- a $C_4$-$C_8$-cycloalkyl group,
    - which is optionally substituted, one or two times, each substituent independently selected from a halogen atom or a group selected from hydroxy, phenyl and —N($R^7$)($R^8$),
        - and wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
- a $C_1$-$C_6$-alkyl group which is substituted with a $C_3$-$C_8$-cycloalkyl group,
- a $C_2$-$C_6$-alkyl group which is substituted with a cyano group, a hydroxy group, a $C_3$-$C_8$-heterocycloalkyl group, or a phenyl group
- a $C_3$-$C_6$-alkyl group which is substituted with a monocyclic- or bicyclic heteroaryl group,
- a ($C_2$-$C_6$-hydroxyalkyl)-O—($C_2$-$C_6$-alky)- group,
- a —($C_3$-$C_6$-alkyl)-N($R^7$)($R^8$) group,
- a —($C_3$-$C_8$-cycloalkyl)-N($R^7$)($R^8$) group,
- a —($C_3$-$C_6$-alkyl)-C(=O)N($R^7$)($R^8$) group,
- a 4-7-membered heterocycloalkyl group, a 5- to 7-membered heterocycloalkenyl group, wherein said 4-7-membered heterocycloalkyl group and said 5- to 7-membered heterocycloalkenyl group are connected to the rest of the molecule via a carbon atom, and which is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
    - wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
- a phenyl group,
    - which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), hydroxy, cyano, $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$), —O—C(=O)—($C_1$-$C_6$-alkyl)-, —SH, —S—($C_1$-$C_6$-alkyl), —S—($C_2$-$C_6$-alkenyl), —S(=O)$_2$N($R^7$)($R^8$), —S(=O)$_2$($C_1$-$C_6$-alkyl), —S(=O)$_2$—($C_2$-$C_6$-alkenyl), —S(=O)(=N$R^{11}$)($C_1$-$C_3$-alkyl), —N(O)$_2$, —P(=O)($C_1$-$C_3$-alkyl)$_2$ and SF$_5$,
    - or
    - wherein two vicinal substituents may form together a 5- or 6-membered, optionally heterocyclic, aromatic or non-aromatic ring, having optionally 1-3 heteroatoms independently selected from —N=, —NH—, —N($R^7$)—, —O—, —S—, and optionally containing a C(=O) group, and wherein the so formed ring is optionally substituted one or two times, each substituent independently selected from a halogen atom or a group selected from
        - $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$)
- a bicyclic aryl group,
- a partially saturated mono- or bicyclic aryl- or heteroaryl group, and
- a monocyclic- or bicyclic heteroaryl group,
    - which is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, —O($C_2$-$C_6$-alkenyl), $C_3$-$C_8$-cycloalkoxy, aryl, —O-aryl, cyano, C(=O)O$R^6$, hydroxy, —SH, —S—($C_1$-$C_6$-alkyl), —S—($C_2$-$C_6$-alkenyl), —S(=O)$_2$($C_1$-$C_6$-alkyl), —S(=O)$_2$—($C_2$-$C_6$-alkenyl), —N(O)$_2$, and —N($R^7$)($R^8$), $R^2$ represents a hydrogen atom or a halogen atom, $R^3$ represents a group selected from,
- a $C_1$-$C_6$-alkyl group,
    - which is optionally substituted with a $C_3$-$C_8$-cycloalkyl group or a NR$^7$R$^8$ group,
- a $C_3$-$C_8$-cycloalkyl group,
- a $C_1$-$C_6$-haloalkyl group,
- a $C_1$-$C_6$-hydroxyalkyl group,
- a $C_2$-$C_6$-alkenyl group,
- a $C_2$-$C_6$-alkynyl group,
- a $C_4$-$C_8$-cycloalkenyl group,
- a ($C_1$-$C_6$-alkyl)-N($R^7$)R$^8$ group,
- a —($C_1$-$C_6$-alkyl)-(4- to 7-membered nitrogen containing heterocycloalkyl) group, wherein said 4- to 7-membered nitrogen containing heterocycloalkyl group is connected to the alkyl group via a carbon atom of the heterocycloalkyl group and which is optionally substituted with a $C_1$-$C_3$-alkyl group, and
- a phenyl group,
    - which is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —S(=O)$_2$—($C_2$-$C_6$-alkenyl), —N(O)$_2$, and —N($R^7$)($R^8$)

$R^4$ represents a group selected from,
- a $C_1$-$C_6$-alkyl group,
    - which is optionally substituted with a group selected from $C_3$-$C_8$-cycloalkyl and phenyl,
        - wherein said phenyl group is optionally substituted, one, two or three times, each substituent independently selected from a halogen atom or a group selected from
            - $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)

$OR^6$, hydroxy, —SH, —S—$(C_1$-$C_6$-alkyl), —S—$(C_2$-$C_6$-alkenyl), $S(=O)_2(C_1$-$C_6$-alkyl), —$S(=O)_2$—$(C_2$-$C_6$-alkenyl), —$N(O)_2$, and —$N(R^7)(R^8)$ a $C_2$-$C_6$-alkenyl group,
a $C_3$-$C_8$-cycloalkyl group,
a $C_2$-$C_6$-haloalkyl group,
a $C_2$-$C_6$-hydroxyalkyl group,
a —$(C_2$-$C_6$-alkyl)-$N(R^7)(R^8)$ group,
a —$C(=O)OR^6$ group,
a —$C(=O)NR^7R^8$ group, and
a —$S(=O)(=NR^{11})(C_1$-$C_3$-alkyl) group, $R^5$ represents a halogen atom or a group selected from
a $C_1$-$C_6$-alkyl group,
a $C_3$-$C_8$-cycloalkyl group,
a $C_1$-$C_6$-haloalkyl group,
a $C_1$-$C_6$-hydroxyalkyl group,
a —$(C_1$-$C_6$-alkyl)-$N(R^7)(R^8)$ group,
a —$(C_1$-$C_6$-alkyl)-O—$(C_1$-$C_6$-alkyl) group,
a $C_2$-$C_6$-alkenyl group,
a $C_2$-$C_6$-alkynyl group,
a $C_1$-$C_6$-alkoxy group,
a $C_1$-$C_6$-alkylsulfanyl group, and
a —$N(R^7)(R^8)$ group,
a —$C(=O)OR^6$ group,
a —$C(=O)N(R^7)(R^8)$ group,
a —$S(=O)(=NR^{11})(C_1$-$C_3$-alkyl) group, and
a phenyl group
which is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —$(C_1$-$C_6$-alkyl)-aryl, -aryl-$(C_1$-$C_6$-alkyl), $C_3$-$C_8$-cycloalkyl, $C_1$-$C_6$-alkoxy, —$O(C_2$-$C_6$-alkenyl), $C_1$-$C_6$-haloalkoxy, $C_3$-$C_8$-cycloalkoxy, aryl, —O-aryl, cyano, —$C(=O)OR^6$, hydroxy, —SH, —S—$(C_1$-$C_6$-alkyl), —S—$(C_2$-$C_6$-alkenyl), $S(=O)_2(C_1$-$C_6$-alkyl), —$S(=O)_2$—$(C_2$-$C_6$-alkenyl), —$N(O)_2$, and —$N(R^7)(R^8)$ $R^6$ represents a hydrogen atom or a group selected from
a $C_1$-$C_6$-alkyl group and a benzyl group, $R^7$ and $R^8$ represent, independently for each occurrence, a hydrogen atom or a group selected from
a $C_1$-$C_6$-alkyl group, a $C_2$-$C_6$-hydroxyalkyl group, a $C_3$-$C_6$-cycloalkyl group, and a —$(C_2$-$C_6$-alkyl)-$N(R^9)(R^{10})$ group,
or
$R^7$ and $R^8$ together with the nitrogen to which they are attached represent a nitrogen containing 4- to 7-membered heterocycloalkyl group,
which is optionally substituted with a group selected from $C_1$-$C_3$-alkyl, —$S(=O)_2(C_1$-$C_3$-alkyl) and —$C(=O)O(C_1$-$C_4$-alkyl), $R^9$ and $R^{10}$ represent, independently for each occurrence, a hydrogen atom or a $C_1$-$C_3$-alkyl group,
or
$R^9$ and $R^{10}$ together with the nitrogen to which they are attached represent a nitrogen containing 4- to 7-membered heterocycloalkyl group, $R^{11}$ represents a hydrogen atom or a group selected from
a cyano group and a —$C(=O)(C_1$-$C_3$-haloalkyl) group,
or a tautomer, an N-oxide, a salt, a salt of a tautomer or a salt of an N-oxid thereof.

DETAILED DESCRIPTION

Definitions

The term "substituted" means that one or more hydrogen atoms on the designated atom or group are replaced with a selection from the indicated group, provided that the designated atom's normal valency under the existing circumstances is not exceeded. Combinations of substituents and/or variables are permissible.

The term "optionally substituted" means that the number of substituents can be equal to or different from zero. Unless otherwise indicated, it is possible that optionally substituted groups are substituted with as many optional substituents as can be accommodated by replacing a hydrogen atom with a non-hydrogen substituent on any available carbon or nitrogen atom. Commonly, it is possible for the number of optional substituents, when present, to be 1, 2, 3, 4 or 5, in particular 1, 2 or 3.

As used herein, the term "one or more", e.g. in the definition of the substituents of the compounds of general formula (I) of the present invention, means "1, 2, 3, 4 or 5, particularly 1, 2, 3 or 4, more particularly 1, 2 or 3, even more particularly 1 or 2".

As used herein, an oxo substituent represents an oxygen atom, which is bound to a carbon atom or to a sulfur atom via a double bond.

The term "ring substituent" means a substituent attached to an aromatic or nonaromatic ring which replaces an available hydrogen atom on the ring.

Should a composite substituent be composed of more than one parts, e.g. ($C_1$-$C_3$-alkoxy)-($C_1$-$C_6$-alkyl)-, it is possible for the position of a given part to be at any suitable position of said composite substituent, i.e. the $C_1$-$C_3$-alkoxy part can be attached to any carbon atom of the $C_1$-$C_6$-alkyl part of said ($C_1$-$C_3$-alkoxy)-($C_1$-$C_6$alkyl)- group. A hyphen at the beginning or at the end of such a composite substituent indicates the point of attachment of said composite substituent to the rest of the molecule. Should a ring, comprising carbon atoms and optionally one or more heteroatoms, such as nitrogen, oxygen or sulfur atoms for example, be substituted with a substituent, it is possible for said substituent to be bound at any suitable position of said ring, be it bound to a suitable carbon atom and/or to a suitable heteroatom.

The term "comprising" when used in the specification includes "consisting of".

If within the present text any item is referred to as "as mentioned herein", it means that it may be mentioned anywhere in the present text.

The terms as mentioned in the present text have the following meanings:

The term "halogen atom" means a fluorine, chlorine, bromine or iodine atom, particularly a fluorine, chlorine or bromine atom.

The term "$C_1$-$C_8$-alkyl" means a linear or branched, saturated, monovalent hydrocarbon group having 1, 2, 3, 4, 5 or 6 carbon atoms, e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl, 1,3-dimethylbutyl, heptyl or octyl group, or an isomer thereof. Particularly, said group has 1, 2, 3, 4, 5 or 6 carbon atoms ("$C_1$-$C_6$-alkyl"), e.g. a methyl, ethyl, propyl, isopropyl, butyl, sec-butyl, isobutyl, tert-butyl, pentyl, isopentyl, 2-methylbutyl, 1-methylbutyl, 1-ethylpropyl, 1,2-dimethylpropyl, neo-pentyl, 1,1-dimethylpropyl, hexyl, 1-methylpentyl, 2-methylpentyl, 3-methylpentyl, 4-methylpentyl, 1-ethylbutyl, 2-ethylbutyl, 1,1-dimethylbutyl, 2,2-dimethylbutyl, 3,3-dimethylbutyl, 2,3-dimethylbutyl, 1,2-dimethylbutyl or 1,3-dimethylbutyl group. Particularly, said group has 1, 2, 3 or 4 carbon atoms ("$C_1$-$C_4$-alkyl"), e.g. a methyl, ethyl, propyl, isopropyl, butyl, sec-butyl isobutyl, or tert-butyl group, more particularly 1, 2 or 3 carbon atoms ("$C_1$-$C_3$-alkyl"), e.g. a methyl, ethyl, n-propyl or isopropyl group.

The term "$C_1$-$C_6$-hydroxyalkyl" means a linear or branched, saturated, monovalent hydrocarbon group in which the term "$C_1$-$C_6$-alkyl" is defined supra, and in which 1 or 2 hydrogen atoms are replaced with a hydroxy group, e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl, 1,3-dihydroxypropan-2-yl, 3-hydroxy-2-methylpropyl, 2-hydroxy-2-methyl-propyl, 1-hydroxy-2-methyl-propyl group. Particularly, said group has 1, 2 or 3 carbon atoms ("$C_1$-$C_3$-hydroxyalkyl"), e.g. a hydroxymethyl, 1-hydroxyethyl, 2-hydroxyethyl, 1,2-dihydroxyethyl, 3-hydroxypropyl, 2-hydroxypropyl, 1-hydroxypropyl, 1-hydroxypropan-2-yl, 2-hydroxypropan-2-yl, 2,3-dihydroxypropyl or 1,3-dihydroxypropan-2-yl group.

The term "$C_1$-$C_6$-cyanoalkyl" means a linear or branched, saturated, monovalent hydrocarbon group in which the term "$C_1$-$C_6$-alkyl" is defined supra, and in which 1 or 2 hydrogen atoms are replaced with a cyano group, e.g. a cyanomethyl, 1-cyanoethyl, 2-cyanoethyl, 1,2-dicyanoethyl, 3-cyanopropyl, 2-cyanopropyl, 1-cyanopropyl, 1-hydroxypropan-2-yl, 2-cyanopropan-2-yl, 2,3-dicyanopropyl, 1,3-dicyanopropan-2-yl, 3-cyano-2-methylpropyl, 2-cyano-2-methyl-propyl, 1-cyano-2-methyl-propyl group. Particularly, said group has 1, 2 or 3 carbon atoms ("$C_1$-$C_3$-cyanoalkyl"), e.g. a cyanomethyl, 1-cyanoethyl, 2-cyanoethyl, 1,2-dicyanoethyl, 3-cyanopropyl, 2-cyanopropyl, 1-cyanopropyl, 1-cyanopropan-2-yl, 2-cyanopropan-2-yl, 2,3-dicyanopropyl or 1,3-dicyanopropan-2-yl group, more particularly said group has 1, 2 or 3 carbon atoms ("$C_1$-$C_3$-cyanoalkyl"), e.g. a cyanomethyl, 1-cyanoethyl, 2-cyanoethyl, 3-cyanopropyl, 2-cyanopropyl, 1-cyanopropyl, 1-cyanopropan-2-yl or 2-cyanopropan-2-yl group.

The term "$C_1$-$C_6$-alkylsulfanyl" means a linear or branched, saturated, monovalent group of formula ($C_1$-$C_6$-alkyl)-S—, in which the term "$C_1$-$C_6$-alkyl" is as defined supra, e.g. a methylsulfanyl, ethylsulfanyl, propylsulfanyl, isopropylsulfanyl, butylsulfanyl, sec-butylsulfanyl, isobutylsulfanyl, tert-butylsulfanyl, pentylsulfanyl, isopentylsulfanyl, hexylsulfanyl group.

The term "$C_2$-$C_8$-haloalkyl" means a linear or branched, saturated, monovalent hydrocarbon group in which the term "$C_2$-$C_8$-alkyl" is as defined supra, and in which one or more of the hydrogen atoms are replaced, identically or differently, with a halogen atom. Particularly, said halogen atom is a fluorine atom. Said $C_2$-$C_8$-haloalkyl group is, for example, 2-fluoroethyl, 2,2-difluoroethyl, 2,2,2-trifluoroethyl, pentafluoroethyl, 3,3,3-trifluoropropyl or 1,3-difluoropropan-2-yl. Particularly, said group has 2, 3, 4 5 or 6 carbon atoms ("$C_2$-$C_6$-haloalkyl").

The term "$C_1$-$C_6$-haloalkyl" means a linear or branched, saturated, monovalent hydrocarbon group in which the term "$C_1$-$C_6$-alkyl" is as defined supra, and in which one or more of the hydrogen atoms are replaced, identically or differently, with a halogen atom. Particularly, said halogen atom is a fluorine atom. Said $C_1$-$C_6$-haloalkyl group is, for example, fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl. Particularly, said group has 1, 2, 3 or 4 carbon atoms ("$C_1$-$C_4$-haloalkyl"), more particularly 1, 2 or 3 carbon atoms ("$C_1$-$C_3$-haloalkyl"), e.g. fluoromethyl, difluoromethyl, trifluoromethyl, 2-fluoroethyl, 2,2-difluoroethyl, 2,2,2-trifluoroethyl, pentafluoroethyl, 3,3,3-trifluoropropyl or 1,3-difluoropropan-2-yl.

For any alkyl group being substituted the position of the substitutent may be at any position of the alkyl group independently whether the alkyl group is defined as "an alkyl group which is substituted by [substituent X]" or "a [substituent X]—$C_1$-$C_6$-alkyl" group.

The term "$C_1$-$C_6$-alkoxy" means a linear or branched, saturated, monovalent group of formula ($C_1$-$C_6$-alkyl)-O—, in which the term "$C_1$-$C_6$-alkyl" is as defined supra, e.g. a methoxy, ethoxy, n-propoxy, isopropoxy, n-butoxy, sec-butoxy, isobutoxy, tert-butoxy, pentyloxy, isopentyloxy or n-hexyloxy group, or an isomer thereof. Particularly, said group has 1, 2 or 3 carbon atoms ("$C_1$-$C_3$-alkoxy"), e.g. a methoxy, ethoxy, n-propoxy or isopropoxy group.

The term "$C_1$-$C_6$-haloalkoxy" means a linear or branched, saturated, monovalent $C_1$-$C_6$-alkoxy group, as defined supra, in which one or more of the hydrogen atoms is replaced, identically or differently, with a halogen atom. Particularly, said halogen atom is a fluorine atom. Said $C_1$-$C_6$-haloalkoxy group is, for example, fluoromethoxy, difluoromethoxy, trifluoromethoxy, 2,2,2-trifluoroethoxy or pentafluoroethoxy. Particularly, said group has 1, 2 or 3 carbon atoms ("$C_1$-$C_3$-haloalkoxy"), e.g. a fluoromethoxy, difluoromethoxy, trifluoromethoxy, 2,2,2-trifluoroethoxy or pentafluoroethoxy group.

The term "$C_2$-$C_6$-alkenyl" means a linear or branched, monovalent hydrocarbon group, which contains one double bond, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then it is possible for said double bonds to be isolated from, or conjugated with, each other. Said alkenyl group is, for example, an ethenyl (or "vinyl"), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, or 1-(1,1-dimethylethyl)ethenyl group. Particularly, said group is allyl.

The term "$C_2$-$C_6$-alkynyl" means a linear or branched, monovalent hydrocarbon group which contains one triple bond, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl (or "propargyl"), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methyl-pent-4-ynyl, 2-methylpent-3-ynyl, 1-methylpent-3-ynyl, 4-methylpent-2-ynyl, 1-methyl-pent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl group.

The term "bicyclic aryl group means an aromatic ring system selected from naphthyl, indenyl.

The term "partially saturated mono- or bicyclic aryl- or heteroaryl" includes dihydrophenyl, tetrahydrophenyl, 5- to 7-membered heterocycloalkenyl (as further defined below), indanyl, tetralinyl, tetralonyl, dihydroquinolinyl, tetrahydroquinolinyl, dihydroquinazolinyl, tetrahydroquinazolinyl, dihydroisoquinolinyl, tetrahydroisoquinolinyl, dihydrocinnolinyl, tetrahydrocinnolinyl, dihydrophthalazinyl, tetrahydrophthalazinyl, dihydroquinoxalinyl, tetrahydroquinoxalinyl, dihydropteridinyl or tetrahydropteridinyl, dihydroindolyl, dihydrobenzofuranyl, dihydrobenzothienyl, dihydrobenzimidazolyl dihydrobenzoxazolyl, dihydrobenzisoxazolyl, dihydrobenzimidazolyl, dihydrobenzothiazolyl, dihydrobenzotriazolyl, dihydroindazolyl, dihydroisoindolyl, dihydroindolizinyl or dihydropurinyl.

The term "$C_3$-$C_8$-cycloalkyl" means a saturated, monovalent, mono- or bicyclic hydrocarbon ring which contains 3, 4, 5, 6, 7 or 8 carbon atoms ("$C_3$-$C_8$-cycloalkyl"). Said $C_3$-$C_8$-cycloalkyl group is for example, a monocyclic hydrocarbon ring, e.g. a cyclopropyl, cyclobutyl, cyclopentyl, cyclohexyl, cycloheptyl or cyclooctyl group, or a bicyclic hydrocarbon ring, e.g. a bicyclo[4.2.0]octyl or octahydropentalenyl. Particularly, said group contains 3, 4, 5 or 6 carbon atoms ("$C_3$-$C_6$-cycloalkyl"), e.g. a cyclopropyl, cyclobutyl, cyclopentyl or cyclohexyl group. Particularly, said group contains 4, 5, 6, 7 or 8 carbon atoms ("$C_4$-$C_8$-cycloalkyl"), e.g. a cyclobutyl, cyclopentyl, cyclohexyl, cycloheptyl or cyclooctyl group.

The term "$C_4$-$C_8$-cycloalkenyl" means a monovalent, mono- or bicyclic hydrocarbon ring which contains 4, 5, 6, 7 or 8 carbon atoms and one double bond. Particularly, said ring contains 4, 5 or 6 carbon atoms ("$C_4$-$C_6$-cycloalkenyl"). Said $C_4$-$C_8$-cycloalkenyl group is for example, a monocyclic hydrocarbon ring, e.g. a cyclobutenyl, cyclopentenyl, cyclohexenyl, cycloheptenyl or cyclooctenyl group, or a bicyclic hydrocarbon ring, e.g. a bicyclo[2.2.1]hept-2-enyl or bicyclo[2.2.2]oct-2-enyl.

The term "$C_3$-$C_8$-cycloalkoxy" means a saturated, monovalent, mono- or bicyclic group of formula ($C_3$-$C_8$-cycloalkyl)-O—, which contains 3, 4, 5, 6, 7 or 8 carbon atoms, in which the term "$C_3$-$C_8$-cycloalkyl" is defined supra, e.g. a cyclopropyloxy, cyclobutyloxy, cyclopentyloxy, cyclohexyloxy, cycloheptyloxy or cyclooctyloxy group. Particularly, said group has 3, 4, 5 or 6 carbon atoms ("$C_3$-$C_6$-cycloalkoxy"), e.g. a cyclopropyloxy, cyclobutyloxy, cyclopentyloxy or cyclohexyloxy group.

The terms "4- to 7-membered heterocycloalkyl" and "4- to 6-membered heterocycloalkyl" mean a monocyclic, saturated heterocycle with 4, 5, 6 or 7 or, respectively, 4, 5 or 6 ring atoms in total, which contains one or two identical or different ring heteroatoms from the series N, O and S being possible for said heterocycloalkyl group to be attached to the rest of the molecule via any one of the carbon atoms or, if present and not excluded otherwise, a nitrogen atom.

Said heterocycloalkyl group, without being limited thereto, can be a 4-membered ring, such as azetidinyl, oxetanyl or thietanyl, for example; or a 5-membered ring, such as tetrahydrofuranyl, 1,3-dioxolanyl, thiolanyl, pyrrolidinyl, imidazolidinyl, pyrazolidinyl, 1,1-dioxidothiolanyl, 1,2-oxazolidinyl, 1,3-oxazolidinyl or 1,3-thiazolidinyl, for example; or a 6-membered ring, such as tetrahydropyranyl, tetrahydrothiopyranyl, piperidinyl, morpholinyl, dithianyl, thiomorpholinyl, piperazinyl, 1,3-dioxanyl, 1,4-dioxanyl or 1,2-oxazinanyl, for example, or a 7-membered ring, such as azepanyl, 1,4-diazepanyl or 1,4-oxazepanyl, for example.

The terms "4- to 7-membered nitrogen containing heterocycloalkyl" and "4- to 6-membered nitrogen containing heterocycloalkyl" mean a monocyclic, saturated heterocycle with 4, 5, 6 or 7 or, respectively, 4, 5 or 6 ring atoms in total, containing one ring nitrogen atom and optionally one further ring heteroatom from the series: N, O, S atom.

Said nitrogen containing heterocycloalkyl group, without being limited thereto, can be a 4-membered ring, such as azetidinyl for example; or a 5-membered ring, such as pyrrolidinyl, imidazolidinyl, pyrazolidinyl, 1,2-oxazolidinyl, 1,3-oxazolidinyl or 1,3-thiazolidinyl, for example; or a 6-membered ring, such as piperidinyl, morpholinyl, thiomorpholinyl, piperazinyl or 1,2-oxazinanyl, for example, or a 7-membered ring, such as azepanyl, 1,4-diazepanyl or 1,4-oxazepanyl, for example.

The term "5- to 7-membered heterocycloalkenyl" means a monocyclic, unsaturated, non-aromatic heterocycle with 5, 6 or 7 ring atoms in total, which contains one or two double bonds and one or two ring heteroatoms independently selected from the series: N, O, S.

Said heterocycloalkenyl group is, for example, 4H pyranyl, 2H pyranyl, 2,5 dihydro 1H pyrrolyl, [1,3]dioxolyl, 4H [1,3,4]thiadiazinyl, 2,5 dihydrofuranyl, 2,3 dihydrofuranyl, 2,5 dihydrothio-phenyl, 2,3 dihydrothiophenyl, 4,5 dihydrooxazolyl or 4H [1,4]thiazinyl.

The term "4-7-membered, optionally unsaturated, heterocyclic group" includes the terms "4- to 7-membered heterocycloalkyl" and "5- to 7-membered heterocycloalkenyl".

The term "aryl" means phenyl and naphthyl.

The term "phenyl groups of which two vicinal substituents may form together a 5- or 6-membered, optionally aromatic or non-aromatic ring, and optionally containing a C(=O) group" includes naphthalinyl, indanyl and tetralinyl.

The term "heteroaryl" means a monovalent, monocyclic or bicyclic aromatic ring having 5, 6, 8, 9 or 10 ring atoms (a "5- to 10-membered heteroaryl" group), particularly 5, 6, 9 or 10 ring atoms, which contains at least one ring heteroatom and optionally one, two or three further ring heteroatoms from the series: N, O and/or S, and which is bound via a ring carbon atom or optionally via a ring nitrogen atom (if allowed by valency).

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl; or a 9-membered heteroaryl group, such as, for example, benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, such as, for example, quinolinyl, quinazolinyl, isoquinolinyl, cinnolinyl, phthalazinyl, quinoxalinyl or pteridinyl.

In general, and unless otherwise mentioned, the heteroaryl or heteroarylene groups include all possible isomeric forms thereof, e.g.: tautomers and positional isomers with respect to the point of linkage to the rest of the molecule. Thus, for some illustrative non-restricting examples, the term pyridinyl includes pyridin-2-yl, pyridin-3-yl and pyridin-4-yl; or the term thienyl includes thien-2-yl and thien-3-yl.

The term "$C_1$-$C_6$", as used in the present text, e.g. in the context of the definition of "$C_1$-$C_6$-alkyl", "$C_1$-$C_6$-haloalkyl", "$C_1$-$C_6$-hydroxyalkyl", "$C_1$-$C_6$-alkoxy" or "$C_1$-$C_6$-haloalkoxy" means an alkyl group having a finite number of carbon atoms of 1 to 6, i.e. 1, 2, 3, 4, 5 or 6 carbon atoms.

Further, as used herein, the term "$C_3$-$C_8$", as used in the present text, e.g. in the context of the definition of "$C_3$-$C_8$-cycloalkyl", means a cycloalkyl group having a finite number of carbon atoms of 3 to 8, i.e. 3, 4, 5, 6, 7 or 8 carbon atoms.

When a range of values is given, said range encompasses each value and sub-range within said range.

For example:

"$C_1$-$C_8$" encompasses $C_1$, $C_2$, $C_3$, $C_4$, $C_5$, $C_6$, $C_7$, $C_8$, $C_1$-$C_8$, $C_1$-$C_7$, $C_1$-$C_6$, $C_1$-$C_5$, $C_1$-$C_4$, $C_1$-$C_3$, $C_1$-$C_2$, $C_2$-$C_8$, $C_2$-$C_7$, $C_2$-$C_6$, $C_2$-$C_5$, $C_2$-$C_4$, $C_2$-$C_3$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_1$-$C_6$" encompasses $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_1$-$C_4$" encompasses $C_1$, $C_2$, $C_3$, $C_4$, $C_1$-$C_4$, $C_1$-$C_3$, $C_1$-$C_2$, $C_2$-$C_4$, $C_2$-$C_3$ and $C_3$-$C_4$;

"$C_1$-$C_3$" encompasses $C_1$, $C_2$, $C_3$, $C_1$-$C_3$, $C_1$-$C_2$ and $C_2$-$C_3$;

"$C_2$-$C_6$" encompasses $C_2$, $C_3$, $C_4$, $C_5$, $C_6$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$;

"$C_3$-$C_8$" encompasses $C_3$, $C_4$, $C_5$, $C_6$, $C_7$, $C_8$, $C_3$-$C_8$, $C_3$-$C_7$, $C_3$-$C_6$, $C_3$-$C_5$, $C_3$-$C_4$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_3$-$C_6$" encompasses $C_3$, $C_4$, $C_5$, $C_6$, $C_3$-$C_6$, $C_3$-$C_5$, $C_3$-$C_4$, $C_4$-$C_6$, $C_4$-$C_5$, and $C_5$-$C_6$;

"$C_4$-$C_8$" encompasses $C_4$, $C_5$, $C_6$, $C_7$, $C_8$, $C_4$-$C_8$, $C_4$-$C_7$, $C_4$-$C_6$, $C_4$-$C_5$, $C_5$-$C_8$, $C_5$-$C_7$, $C_5$-$C_6$, $C_6$-$C_8$, $C_6$-$C_7$ and $C_7$-$C_8$;

"$C_4$-$C_7$" encompasses $C_4$, $C_5$, $C_6$, $C_7$, $C_4$-$C_7$, $C_4$-$C_6$, $C_4$-$C_5$, $C_5$-$C_7$, $C_5$-$C_6$ and $C_6$-$C_7$;

"$C_4$-$C_6$" encompasses $C_4$, $C_5$, $C_6$, $C_4$-$C_6$, $C_4$-$C_5$ and $C_5$-$C_6$;

"$C_5$-$C_{10}$" encompasses $C_5$, $C_6$, $C_7$, $C_8$, $C_9$, $C_{10}$, $C_5$-$C_{10}$, $C_5$-$C_9$, $C_5$-$C_8$, $C_5$-$C_7$, $C_5$-$C_6$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$;

"$C_6$-$C_{10}$" encompasses $C_6$, $C_7$, $C_8$, $C_9$, $C_{10}$, $C_6$-$C_{10}$, $C_6$-$C_9$, $C_6$-$C_8$, $C_6$-$C_7$, $C_7$-$C_{10}$, $C_7$-$C_9$, $C_7$-$C_8$, $C_8$-$C_{10}$, $C_8$-$C_9$ and $C_9$-$C_{10}$.

As used herein, the term "as defined supra" means as defined anywhere in the specification and claims.

As used herein, the term "leaving group" means an atom or a group of atoms that is displaced in a chemical reaction as stable species taking with it the bonding electrons. In particular, such a leaving group is selected from the group comprising: halide, in particular fluoride, chloride, bromide or iodide, (methylsulfonyl)oxy, [(trifluoromethyl)sulfonyl]oxy, [(nonafluorobutyl)-sulfonyl]oxy, (phenylsulfonyl)oxy, [(4-methylphenyl)sulfonyl]oxy, [(4-bromophenyl)sulfonyl]oxy, [(4-nitrophenyl)sulfonyl]oxy, [(2-nitrophenyl)sulfonyl]oxy, [(4-isopropylphenyl)sulfonyl]oxy, [(2,4,6-triisopropylphenyl)sulfonyl]oxy, [(2,4,6-trimethylphenyl)sulfonyl]oxy, [(4-tert-butyl-phenyl)sulfonyl]oxy and [(4-methoxyphenyl)sulfonyl]oxy.

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

By "subject" is meant a mammal, including, but not limited to, a human or non-human mammal, such as a bovine, equine, canine, ovine, rodent, or feline.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" in relation to an isotope means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I, respectively.

With respect to the treatment and/or prophylaxis of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3$H or $^{14}$C, are incorporated are useful e.g. in drug and/or substrate tissue distribution studies. These isotopes are particularly preferred for the ease of their incorporation and detectability. Positron emitting isotopes such as $^{18}$F or $^{11}$C may be incorporated into a compound of general formula (I). These isotopic variants of the compounds of general formula (I) are useful for in vivo imaging applications. Deuterium-containing and $^{13}$C-containing compounds of general formula (I) can be used in mass spectrometry analyses in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds. Deuterium gas is also a useful reagent for incorporating deuterium into molecules. Catalytic deuteration of olefinic bonds and acetylenic bonds is a rapid route for incorporation of deuterium. Metal catalysts (i.e. Pd, Pt, and Rh) in the presence of deuterium gas can be used to directly exchange deuterium for hydrogen in functional groups containing hydrocarbons. A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

In another embodiment the present invention concerns a deuterium-containing compound of general formula (I) having 1, 2, 3 or 4 deuterium atoms, particularly with 1, 2 or 3 deuterium atoms.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention optionally contain one or more asymmetric centres, depending upon the location and nature of the various substituents desired. It is possible that one or more asymmetric carbon atoms are present in the (R) or (S) configuration, which can result in racemic mixtures in the case of a single asymmetric centre, and in diastereomeric mixtures in the case of multiple asymmetric centres. In certain instances, it is possible that asymmetry also be present due to restricted rotation about a given bond, for example, the central bond adjoining two substituted aromatic rings of the specified compounds.

Preferred isomers are those which produce the more desirable biological activity. These separated, pure or partially purified isomers or racemic mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials.

In order to distinguish different types of isomers from each other reference is made to IUPAC Rules Section E (Pure Appl Chem 45, 11-30, 1976).

Isolation of a single stereoisomer, e.g. a single enantiomer or a single diastereomer, of a compound of the present invention is achieved by any suitable state of the art method, such as chromatography, especially chiral chromatography, for example.

Further, it is possible for the compounds of the present invention to exist as tautomers. For example, any compound of the present invention which contains an imidazopyridine moiety as a heteroaryl group for example can exist as a 1H tautomer, or a 3H tautomer, or even a mixture in any amount of the two tautomers, namely:

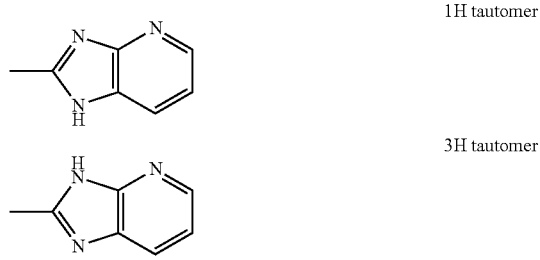

1H tautomer 3H tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also provides useful forms of the compounds of the present invention, such as metabolites, hydrates, solvates, prodrugs, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, or "mineral acid", such as hydrochloric, hydrobromic, hydroiodic, sulfuric, sulfamic, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, pivalic, 2-hydroxyethanesulfonic, itaconic, trifluoromethanesulfonic, dodecylsulfuric, ethanesulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium, magnesium or strontium salt, or an aluminium or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium.

Those skilled in the art will further recognise that it is possible for acid addition salts of the claimed compounds to be prepared by reaction of the compounds with the appropriate inorganic or organic acid via any of a number of known methods. Alternatively, alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

One aspect of the invention are tautomers, an N-oxides, or a salt thereof, and a salt of a tautomer or an N-oxide.

The present invention includes diastereomers, racemates, tautomers, N-oxides, hydrates, solvates, and salts of the compounds of the present invention, and mixtures of same.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "hydrochloride", "trifluoroacetate", "sodium salt", or "x HCl", "x CF$_3$COOH", "x Na$^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Moreover, the present invention also includes prodrugs of the compounds according to the invention. The term "prodrugs" here designates compounds which themselves can be biologically active or inactive, but are converted (for example metabolically or hydrolytically) into compounds according to the invention during their residence time in the body.

In accordance with certain embodiments, the present invention provides compounds of general formula (I), supra, in which R$^1$ represents a group selected from
  a C$_4$-C$_8$-cycloalkyl group,
    which is optionally substituted, one or two times, each substituent independently selected from a halogen atom or a group selected from hydroxy, phenyl and —N(R$^7$)(R$^8$),
    and wherein said phenyl substituent is optionally substituted, one, two or three times, each substituent independently selected from a halogen atom or a group selected from C$_1$-C$_3$-alkyl, C$_1$-C$_4$-haloalkyl, C$_1$-C$_3$-alkoxy and hydroxy,
  a —(C$_3$-C$_8$-cycloalkyl)-N(R$^7$)(R$^8$) group,
  a 4-7-membered heterocycloalkyl group, a 5- to 7-membered heterocycloalkenyl group, wherein said 4-7-membered heterocycloalkyl group and said 5- to 7-membered heterocycloalkenyl group are connected to the rest of the molecule via a carbon atom, and which is optionally substituted one or two times, each substituent independently selected from a group selected from
    C$_1$-C$_3$-alkyl, 5- to 6-membered heteroaryl, —C(=O)O(C$_1$-C$_4$-alkyl), —C(=O)(C$_1$-C$_6$-alkyl), —C(=O)(C$_3$-C$_6$-cycloalkyl), —S(=O)$_2$(C$_1$-C$_6$-alkyl) and oxo (=O),
    wherein said 5- to 6-membered heteroaryl substituent is optionally substituted, one, two or three times, each substituent independently selected from a halogen atom or a group selected from C$_1$-C$_3$-alkyl, C$_1$-C$_4$-haloalkyl, C$_1$-C$_3$-alkoxy and hydroxy,
  a phenyl group,
    which is optionally substituted, one, two, three, four or five times, each substituent independently selected from a halogen atom or a group selected from
      C$_1$-C$_6$-alkyl, C$_3$-C$_8$-cycloalkyl, C$_1$-C$_6$-haloalkyl, C$_2$-C$_6$-alkenyl, C$_2$-C$_6$-alkynyl, aryl, —(C$_1$-C$_6$-alkyl)-aryl, -aryl-(C$_1$-C$_6$-alkyl), hydroxy, cyano, C$_1$-C$_6$-hydroxyalkyl, C$_1$-C$_6$-alkoxy, —O(C$_2$-C$_6$-alkenyl), C$_1$-C$_6$-haloalkoxy, C$_3$-C$_8$-cycloalkoxy, aryl, —O-aryl, cyano, —C(=O)OR$^6$, —C(=O)N(R$^7$)(R$^8$), —N(R$^7$)(R$^8$), —(C$_1$-C$_6$-alkyl)-N(R$^7$)(R$^8$), —(C$_1$-C$_6$-alkyl)-C(=O)OR$^6$, —(C$_1$-C$_6$-alkyl)-C(=O)N(R$^7$)(R$^8$), —O—C(=O)—(C$_1$-C$_6$-alkyl)-, —SH, —S—(C$_1$-C$_6$-alkyl), —S—(C$_2$-C$_6$-alkenyl), —S(=O)$_2$N(R$^7$)(R$^8$), —S(=O)$_2$(C$_1$-C$_6$-alkyl), —S(=O)$_2$—(C$_2$-C$_6$-alkenyl), —S(=O)(=NR$^{11}$)(C$_1$-C$_3$-alkyl), —N(O)$_2$, —P(=O)(C$_1$-C$_3$-alkyl)$_2$ and SF$_5$,
    or
    wherein two vicinal substituents may form together a 5- or 6-membered, optionally heterocyclic, aromatic or non-aromatic ring, having optionally 1-3 heteroatoms independently selected from —N=, —NH—, —N(R$^7$)—, —O—, —S—, and optionally containing a C(=O) group, and wherein the so formed ring is optionally substituted one or two times, each substituent independently selected from a halogen atom or a group selected from
      C$_1$-C$_6$-alkyl, C$_1$-C$_6$-haloalkyl, C$_2$-C$_6$-alkenyl, C$_2$-C$_6$-alkynyl, aryl, —(C$_1$-C$_6$-alkyl)-aryl, -aryl-(C$_1$-C$_6$-alkyl), C$_3$-C$_8$-cycloalkyl, C$_1$-C$_6$-alkoxy, —O(C$_2$-C$_6$-alkenyl), C$_1$-C$_6$-haloalkoxy, C$_3$-C$_8$-cycloalkoxy, aryl, —O-aryl, cyano, —C(O)OH, hydroxy, —SH, —S—(C$_1$-C$_6$-alkyl), —S—(C$_2$-C$_6$-alkenyl), —S(=O)$_2$(C$_1$-C$_6$-alkyl), —N(O)$_2$, and —N(R$^7$)(R$^8$)
  and
  a bicyclic aryl group,
  a partially saturated mono- or bicyclic aryl- or heteroaryl group,
  a monocyclic- or bicyclic heteroaryl group,
    which is optionally substituted one, two or three times, each substituent independently selected from a halogen atom or a group selected from C$_1$-C$_6$-alkyl, C$_1$-C$_6$-haloalkyl, C$_2$-C$_6$-alkenyl, C$_2$-C$_6$-alkynyl, —(C$_1$-C$_6$-alkyl)-aryl, -aryl-(C$_1$-C$_6$-alkyl), C$_3$-C$_8$-cycloalkyl, C$_1$-C$_6$-alkoxy, C$_1$-C$_6$-haloalkoxy, —O(C$_2$-C$_6$-alkenyl), C$_3$-C$_8$-cycloalkoxy, aryl, —O-aryl, cyano, C(=O)OR$^6$, hydroxy, —SH, —S—(C$_1$-C$_6$-alkyl), —S—(C$_2$-C$_6$-alkenyl), —S(=O)$_2$(C$_1$-C$_6$-alkyl), —S(=O)$_2$—(C$_2$-C$_6$-alkenyl), —N(O)$_2$, and —N(R$^7$)(R$^8$), R$^2$ represents a hydrogen atom or a halogen atom,
R$^3$ represents a group selected from,
  a C$_1$-C$_6$-alkyl group,
    which is optionally substituted with a C$_3$-C$_8$-cycloalkyl group or a NR$^7$R$^8$ group,
  a C$_3$-C$_8$-cycloalkyl group,
  a C$_1$-C$_6$-haloalkyl group,
  a C$_1$-C$_6$-hydroxyalkyl group,
  a C$_2$-C$_6$-alkenyl group,
  a C$_2$-C$_6$-alkynyl group,
  a C$_4$-C$_8$-cycloalkenyl group,
  a (C$_1$-C$_6$-alkyl)-N(R$^7$)R$^8$ group,
  a —(C$_1$-C$_6$-alkyl)-(4- to 7-membered nitrogen containing heterocycloalkyl) group, wherein said 4- to 7-membered nitrogen containing heterocycloalkyl group is connected to the alkyl group via a carbon atom of the heterocycloalkyl group and which is optionally substituted with a C$_1$-C$_3$-alkyl group, and
  a phenyl group,
    which is optionally substituted, one, two or three times, each substituent independently selected from a halogen atom or a group selected from C$_1$-C$_6$-alkyl, C$_1$-C$_6$-haloalkyl, C$_2$-C$_6$-alkenyl, C$_2$-C$_6$-alkynyl, aryl, —(C$_1$-C$_6$-alkyl)-aryl, -aryl-(C$_1$-C$_6$-alkyl), C$_3$-C$_8$-cycloalkyl, C$_1$-C$_6$-alkoxy, —O(C$_2$-C$_6$-alkenyl), C$_1$-C$_6$-haloalkoxy, C$_3$-C$_8$-cycloalkoxy, aryl, —O-aryl, cyano, —C(O)OH, hydroxy, —SH, —S—(C$_1$-C$_6$-alkyl), —S—(C$_2$-C$_6$-alkenyl), —S(=O)$_2$(C$_1$-C$_6$-alkyl), —S(=O)$_2$—(C$_2$-C$_6$-alkenyl), —N(O)$_2$, and —N(R$^7$)(R$^8$)

R⁴ represents a group selected from,
a $C_1$-$C_6$-alkyl group,
which is optionally substituted with a group selected from $C_3$-$C_8$-cycloalkyl and phenyl,
wherein said phenyl group is optionally substituted, one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR⁶, hydroxy, —SH, —S—($C_1$-$C_6$-alkyl), —S—($C_2$-$C_6$-alkenyl), S(=O)$_2$($C_1$-$C_6$-alkyl), —S(=O)$_2$—($C_2$-$C_6$-alkenyl), —N(O)$_2$, and —N(R⁷)(R⁸) a $C_2$-$C_6$-alkenyl group,
a $C_3$-$C_8$-cycloalkyl group,
a $C_2$-$C_6$-haloalkyl group,
a $C_2$-$C_6$-hydroxyalkyl group,
a —($C_2$-$C_6$-alkyl)-N(R⁷)(R⁸) group,
R⁵ represents a halogen atom or a group selected from
a $C_1$-$C_6$-alkyl group,
a $C_3$-$C_8$-cycloalkyl group,
a $C_1$-$C_6$-haloalkyl group which is optionally substituted with a hydroxy group,
a $C_1$-$C_6$-hydroxyalkyl group,
a —($C_1$-$C_6$-alkyl)-N(R⁷)(R⁸) group,
a —($C_1$-$C_6$-alkyl)-O—($C_1$-$C_6$-alkyl) group,
a $C_2$-$C_6$-alkenyl group,
a $C_2$-$C_6$-alkynyl group,
a $C_1$-$C_6$-alkoxy group,
a $C_1$-$C_6$-alkylsulfanyl group, and
a —N(R⁷)(R⁸) group,
a —C(=O)OR⁶ group,
a —C(=O)N(R⁷)(R⁸) group,
a —S(=O)(=NR¹¹)($C_1$-$C_3$-alkyl) group, and
a phenyl group
which is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR⁶, hydroxy, —SH, —S—($C_1$-$C_6$-alkyl), —S—($C_2$-$C_6$-alkenyl), S(=O)$_2$($C_1$-$C_6$-alkyl), —S(=O)$_2$—($C_2$-$C_6$-alkenyl), —N(O)$_2$, and —N(R⁷)(R⁸)
R⁶ represents a hydrogen atom or a group selected from
a $C_1$-$C_6$-alkyl group and a benzyl group,
R⁷ and R⁸ represent, independently for each occurrence, a hydrogen atom or a group selected from
a $C_1$-$C_6$-alkyl group, a $C_2$-$C_6$-hydroxyalkyl group, a $C_3$-$C_6$-cycloalkyl group, and a —($C_2$-$C_6$-alkyl)-N(R⁹)(R¹⁰) group,
or
R⁷ and R⁸ together with the nitrogen to which they are attached represent a nitrogen containing 4- to 7-membered heterocycloalkyl group,
which is optionally substituted with a group selected from $C_1$-$C_3$-alkyl, —S(=O)$_2$($C_1$-$C_3$-alkyl) and —C(=O)O($C_1$-$C_4$-alkyl),
R⁹ and R¹⁰ represent, independently for each occurrence, a hydrogen atom or a $C_1$-$C_3$-alkyl group,
or R⁹ and R¹⁰ together with the nitrogen to which they are attached represent a nitrogen containing 4- to 7-membered heterocycloalkyl group,
R¹¹ represents a hydrogen atom or a group selected from
a cyano group and a —C(=O)($C_1$-$C_3$-haloalkyl) group,
or a tautomer, an N-oxide, a salt, a salt of a tautomer or a salt of an N-oxide thereof.

In accordance with certain embodiments, the present invention provides compounds of general formula (I), supra,

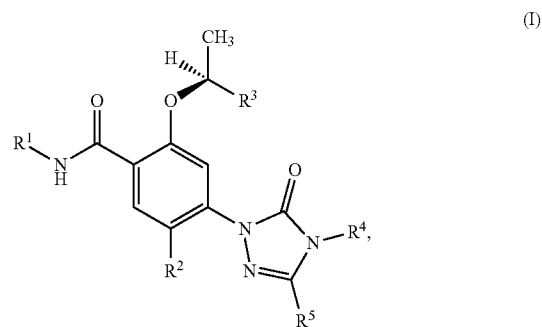

(I)

in which:
R¹ represents a group selected from
a $C_5$-$C_8$-alkyl group,
a $C_2$-$C_8$-haloalkyl group,
a $C_4$-$C_8$-cycloalkyl group,
a $C_1$-$C_6$-alkyl group which is substituted with a $C_3$-$C_8$-cycloalkyl group,
a $C_2$-$C_6$-alkyl group which is substituted with a cyano group or a phenyl group,
a $C_3$-$C_6$-alkyl group which is substituted with a monocyclic- or bicyclic heteroaryl group,
a $C_2$-$C_6$-hydroxyalkyl group,
a ($C_2$-$C_6$-hydroxyalkyl)-O—($C_2$-$C_6$-alky)- group,
a —($C_3$-$C_6$-alkyl)-N(R⁷)(R⁸) group,
a —($C_3$-$C_8$-cycloalkyl)-N(R⁷)(R⁸) group,
a —($C_3$-$C_6$-alkyl)-C(=O)N(R⁷)(R⁸) group,
a 4-7-membered, optionally unsaturated, heterocyclic group,
a phenyl group, and
a monocyclic- or bicyclic heteroaryl group,
wherein said cycloalkyl groups are optionally substituted, one or two times, each substituent independently selected from a halogen atom or a group selected from
hydroxy, phenyl and —N(R⁷)(R⁸),
wherein said phenyl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and
wherein said 4- to 7-membered heterocycloalkyl group and 5- to 7-membered heterocycloalkenyl group are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
and
wherein said 4-7-membered, optionally unsaturated, heterocyclic group is connected to the rest of the molecule via a carbon atom,
and
wherein said phenyl groups are optionally substituted, one, two, three, four or five times, each substituent independently selected from a halogen atom or a group selected from
$C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(O)OH, —C(=O)OR$^6$, —C(=O)N(R$^7$)(R$^8$), —N(R$^7$)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$), —SH, —S—($C_1$-$C_6$-alkyl), —S—($C_2$-$C_6$-alkenyl), —S(=O)$_2$($C_1$-$C_6$-alkyl), —S(=O)$_2$N(R$^7$)(R$^8$), —S(=O)$_2$($C_1$-$C_3$-alkyl), —S(=O)(=NR$^{11}$)($C_1$-$C_3$-alkyl), —N(O)$_2$, —P(=O)($C_1$-$C_3$-alkyl)$_2$ and SF$_5$,
or wherein two vicinal substituents of said phenyl groups may form together a 5- or 6-membered, optionally heterocyclic, aromatic or non-aromatic ring, having optionally 1-3 heteroatoms independently selected from —N=, —NH—, —N(R$^7$)—, —O—, —S—, and optionally containing a C(=O) group, and wherein the so formed ring is optionally substituted one or two times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N(R$^7$)(R$^8$)
and
wherein said monocyclic or bicyclic heteroaryl group is optionally substituted one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, —O($C_2$-$C_6$-alkenyl), $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N(R$^7$)(R$^8$), R$^2$ represents a hydrogen atom or a halogen atom,
R$^3$ represents a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a $C_2$-$C_6$-alkenyl group, a $C_2$-$C_6$-alkynyl group,
a $C_4$-$C_8$-cycloalkenyl group, a ($C_1$-$C_6$-alkyl)-N(R$^7$)R$^8$ group,
a —($C_1$-$C_6$-alkyl)-(4- to 7-membered nitrogen containing heterocycloalkyl) group and
a phenyl group,
wherein said $C_1$-$C_6$-alkyl group is optionally substituted with a $C_3$-$C_8$-cycloalkyl group,
and
wherein said 4- to 7-membered nitrogen containing heterocycloalkyl group is optionally substituted with a $C_1$-$C_3$-alkyl group,
and
wherein said 4- to 7-membered nitrogen containing heterocycloalkyl group is connected to the alkyl group via a carbon atom of the heterocycloalkyl group, and
wherein said phenyl group is optionally substituted, one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N(R$^7$)(R$^8$)

R$^4$ represents a group selected from
a $C_1$-$C_6$-alkyl group, a $C_3$-$C_8$-cycloalkyl group, a $C_2$-$C_6$-haloalkyl group,
a $C_2$-$C_6$-hydroxyalkyl group and a —($C_2$-$C_6$-alkyl)-N(R$^7$)(R$^8$) group,
wherein said $C_1$-$C_6$-alkyl group is optionally substituted with a group selected from
$C_3$-$C_8$-cycloalkyl and phenyl,
wherein said phenyl group is optionally substituted, one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N(R$^7$)(R$^8$)

R$^5$ represents a halogen atom or a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a ($C_1$-$C_3$-alkoxy)-($C_1$-$C_6$-alkyl)- group,
a $C_2$-$C_6$-alkenyl group, a $C_2$-$C_6$-alkynyl group, a $C_1$-$C_6$-alkoxy group,
a $C_1$-$C_6$-alkylsulfanyl group, a —($C_1$-$C_6$-alkyl)-N(R$^7$)(R$^8$) group and a —N(R$^7$)(R$^8$) group, R$^6$ represents a hydrogen atom or a group selected from a $C_1$-$C_6$-alkyl group and a benzyl group, R$^7$ and R$^8$ represent, independently for each occurrence, a hydrogen atom or a group selected from
a $C_1$-$C_6$-alkyl group, a $C_2$-$C_6$-hydroxyalkyl group and a —($C_2$-$C_6$-alkyl)-N(R$^9$)(R$^{10}$) group,
or
R$^7$ and R$^8$ together with the nitrogen to which they are attached represent a nitrogen containing 4- to 7-membered heterocycloalkyl group,
wherein said 4- to 7-membered nitrogen containing heterocycloalkyl group is optionally substituted with a group selected from
$C_1$-$C_3$-alkyl, —S(=O)$_2$($C_1$-$C_3$-alkyl) and —C(=O)O($C_1$-$C_4$-alkyl), $R^9$ and $R^{10}$ represent, independently for each occurrence, a hydrogen atom or a $C_1$-$C_3$-alkyl group,
or
$R^9$ and $R^{10}$ together with the nitrogen to which they are attached represent a nitrogen containing 4- to 7-membered heterocycloalkyl group,
$R^{11}$ represents a hydrogen atom or a group selected from
a cyano group and a —C(=O)($C_1$-$C_3$-haloalkyl) group,
or a tautomer, an N-oxide, a salt, a salt of a tautomer or a salt of an N-oxide thereof.

In accordance with certain embodiments, the present invention provides compounds of general formula (I), supra, in which:

$R^1$ represents a group selected from
a $C_5$-$C_8$-alkyl group,
a $C_2$-$C_8$-haloalkyl group,
a $C_4$-$C_8$-cycloalkyl group,
a $C_1$-$C_6$-alkyl group which is substituted with a $C_3$-$C_8$-cycloalkyl group,
a $C_2$-$C_6$-alkyl group which is substituted with a cyano group or a phenyl group,
a $C_3$-$C_6$-alkyl group which is substituted with a monocyclic- or bicyclic heteroaryl group,
a $C_2$-$C_6$-hydroxyalkyl group,
a ($C_2$-$C_6$-hydroxyalkyl)-O—($C_2$-$C_6$-alky)- group,
a —($C_3$-$C_6$-alkyl)-N($R^7$)($R^8$) group,
a —($C_3$-$C_8$-cycloalkyl)-N($R^7$)($R^8$) group,
a —($C_3$-$C_6$-alkyl)-C(=O)N($R^7$)($R^8$) group,
a 4-7-membered heterocycloalkyl group, a 5- to 7-membered heterocycloalkenyl group,
a phenyl group, and
a monocyclic- or bicyclic heteroaryl group,
wherein said cycloalkyl groups are optionally substituted, one or two times, each substituent independently selected from a halogen atom or a group selected from
hydroxy, phenyl and —N($R^7$)($R^8$),
wherein said phenyl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and
wherein said 4- to 7-membered heterocycloalkyl group and 5- to 7-membered heterocycloalkenyl group are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
and
wherein said 4-7-membered, optionally unsaturated, heterocyclic group is connected to the rest of the molecule via a carbon atom,
and
wherein said phenyl groups are optionally substituted, one, two, three, four or five times, each substituent independently selected from a halogen atom or a group selected from
$C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(O)OH, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$), —SH, —S—($C_1$-$C_6$-alkyl), —S—($C_2$-$C_6$-alkenyl), —S(=O)$_2$, —S(=O)$_2$N($R^7$)($R^8$), —S(=O)$_2$($C_1$-$C_3$-alkyl), —S(=O)(=N$R^{11}$)($C_1$-$C_3$-alkyl), —N(O)$_2$, —P(=O)($C_1$-$C_3$-alkyl)$_2$ and SF$_5$,
or wherein two vicinal substituents of said phenyl groups may form together a 5- or 6-membered, optionally heterocyclic, aromatic or non-aromatic ring, having optionally 1-3 heteroatoms independently selected from —N=, —NH—, —N($R^7$)—, —O—, —S—, and optionally containing a C(=O) group, and wherein the so formed ring is optionally substituted one or two times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$)
wherein said monocyclic or bicyclic heteroaryl group is optionally substituted one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, —O($C_2$-$C_6$-alkenyl), $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$), $R^2$ represents a hydrogen atom or a halogen atom,
$R^3$ represents a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a $C_2$-$C_6$-alkenyl group, a $C_2$-$C_6$-alkynyl group,
a $C_4$-$C_8$-cycloalkenyl group, a ($C_1$-$C_6$-alkyl)-N($R^7$)$R^8$ group,
a —($C_1$-$C_6$-alkyl)-(4- to 7-membered nitrogen containing heterocycloalkyl) group and
a phenyl group,
wherein said $C_1$-$C_6$-alkyl group is optionally substituted with a $C_3$-$C_8$-cycloalkyl group,
and
wherein said 4- to 7-membered nitrogen containing heterocycloalkyl group is optionally substituted with a $C_1$-$C_3$-alkyl group,
and
wherein said 4- to 7-membered nitrogen containing heterocycloalkyl group is connected to the alkyl group via a carbon atom of the heterocycloalkyl group, and
wherein said phenyl group is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$)

$R^4$ represents a group selected from
- a $C_1$-$C_6$-alkyl group, a $C_3$-$C_8$-cycloalkyl group, a $C_2$-$C_6$-haloalkyl group,
- a $C_2$-$C_6$-hydroxyalkyl group and a —($C_2$-$C_6$-alkyl)-N($R^7$)($R^8$) group,
  - wherein said $C_1$-$C_6$-alkyl group is optionally substituted with a group selected from
  - $C_3$-$C_8$-cycloalkyl and phenyl,
    - wherein said phenyl group is optionally substituted, one, two or three times, each substituent independently selected from a halogen atom or a group selected from
      - $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$)

$R^5$ represents a halogen atom or a group selected from
- a $C_1$-$C_6$-alkyl group, a $C_3$-$C_8$-cycloalkyl group, a $C_1$-$C_6$-haloalkyl group,
- a $C_1$-$C_6$-hydroxyalkyl group, a ($C_1$-$C_3$-alkoxy)-($C_1$-$C_6$-alkyl)- group,
- a $C_2$-$C_6$-alkenyl group, a $C_2$-$C_6$-alkynyl group, a $C_1$-$C_6$-alkoxy group,
- a $C_1$-$C_6$-alkylsulfanyl group, a —($C_1$-$C_6$-alkyl)-N($R^7$)($R^8$) group and a —N($R^7$)($R^8$) group, $R^6$ represents a hydrogen atom or a group selected from
- a $C_1$-$C_6$-alkyl group and a benzyl group, $R^7$ and $R^8$ represent, independently for each occurrence, a hydrogen atom or a group selected from
- a $C_1$-$C_6$-alkyl group, a $C_2$-$C_6$-hydroxyalkyl group and a —($C_2$-$C_6$-alkyl)-N($R^9$)($R^{10}$) group,
or
$R^7$ and $R^8$ together with the nitrogen to which they are attached represent a nitrogen containing 4- to 7-membered heterocycloalkyl group,
  - wherein said 4- to 7-membered nitrogen containing heterocycloalkyl group is optionally substituted with a group selected from
  - $C_1$-$C_3$-alkyl, —S(=O)$_2$($C_1$-$C_3$-alkyl) and —C(=O)O($C_1$-$C_4$-alkyl), $R^9$ and $R^{10}$ represent, independently for each occurrence, a hydrogen atom or a $C_1$-$C_3$-alkyl group,
or
$R^9$ and $R^{10}$ together with the nitrogen to which they are attached represent a nitrogen containing 4- to 7-membered heterocycloalkyl group, $R^{11}$ represents a hydrogen atom or a group selected from
- a cyano group and a —C(=O)($C_1$-$C_3$-haloalkyl) group,
or a tautomer, an N-oxide, a salt, a salt of a tautomer or a salt of an N-oxide thereof.

In accordance with certain embodiments, the present invention provides compounds of general formula (I), supra, in which:

$R^1$ represents a group selected from
- a $C_5$-$C_8$-alkyl group,
- a $C_2$-$C_8$-haloalkyl group,
- a $C_4$-$C_8$-cycloalkyl group,
  - wherein said cycloalkyl groups are optionally substituted, one or two times, each substituent independently selected from a halogen atom or a group selected from
  - hydroxy, phenyl and —N($R^7$)($R^8$),
    - wherein said phenyl substituent is optionally substituted, one, two or three times, each substituent independently selected from a halogen atom or a group selected from
    - $C_1$-$C_3$-alkyl, $C_1$-$C_4$-haloalkyl, $C_1$-$C_3$-alkoxy and hydroxy,
- a $C_1$-$C_6$-alkyl group which is substituted with a $C_3$-$C_8$-cycloalkyl group,
- a $C_2$-$C_6$-alkyl group which is substituted with a cyano group, a hydroxy group or a phenyl group,
- a $C_3$-$C_6$-alkyl group which is substituted with a monocyclic- or bicyclic heteroaryl group,
- a ($C_2$-$C_6$-hydroxyalkyl)-O—($C_2$-$C_6$-alky)- group,
- a —($C_3$-$C_6$-alkyl)-N($R^7$)($R^8$) group,
- a —($C_3$-$C_8$-cycloalkyl)-N($R^7$)($R^8$) group,
- a —($C_3$-$C_6$-alkyl)-C(=O)N($R^7$)($R^8$) group,
- a 4- to 7-membered heterocycloalkyl group,
  - which is optionally substituted one or two times, each substituent independently selected from a group selected from
  - $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
    - wherein said 5- to 6-membered heteroaryl substituent is optionally substituted, one, two or three times, each substituent independently selected from a halogen atom or a group selected from
    - $C_1$-$C_3$-alkyl, $C_1$-$C_4$-haloalkyl, $C_1$-$C_3$-alkoxy and hydroxy,
  - and wherein said- to 7-membered heterocycloalkyl group is connected to the rest of the molecule via a carbon atom of the said heterocycloalkyl- or heterocycloalkenyl group,
- a 5- to 7-membered heterocycloalkenyl group,
  - which is optionally substituted one or two times, each substituent independently selected from a group selected from
  - $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
    - wherein said 5- to 6-membered heteroaryl substituent is optionally substituted, one, two or three times, each substituent independently selected from a halogen atom or a group selected from
    - $C_1$-$C_3$-alkyl, $C_1$-$C_4$-haloalkyl, $C_1$-$C_3$-alkoxy and hydroxy,
  - and wherein said 5- to 7-membered heterocycloalkenyl group is connected to the rest of the molecule via a carbon atom of the said heterocycloalkyl- or heterocycloalkenyl group,
- a phenyl group,
  - wherein said phenyl group is optionally substituted, one, two, three, four or five times, each substituent independently selected from a halogen atom or a group selected from
  - $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$), —S(=O)$_2$N($R^7$)($R^8$), —S(=O)$_2$($C_1$-$C_3$-alkyl), —S(=O)(=N$R^{11}$)($C_1$-$C_3$-alkyl), —P(=O)($C_1$-$C_3$-alkyl)$_2$ and SF$_5$, or in which two substituents of said phenyl groups, when they are attached to adjacent ring atoms, are optionally linked to one another in such a way that they jointly form a group selected from —CH$_2$—N($R^7$)—CH$_2$—, —CH$_2$—O—CH$_2$—, —O—CH$_2$—C(=O)—NH— and —NH—C(=O)—NH—, an indanyl group, a tetralinyl group
  wherein said indanyl or tetralinyl group is optionally substituted one or two times, each substituent independently selected from a halogen atom or a group selected from
    $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$), and
a monocyclic- or bicyclic heteroaryl group,
  which is optionally substituted one, two or three times, each substituent independently selected from a halogen atom or a group selected from $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$), $R^2$ represents a hydrogen atom or a halogen atom,
$R^3$ represents a group selected from
  a $C_1$-$C_6$-alkyl group,
    which is optionally substituted with a $C_3$-$C_8$-cycloalkyl group or a N$R^7R^8$ group,
  a $C_3$-$C_8$-cycloalkyl group, a $C_1$-$C_6$-haloalkyl group,
  a $C_1$-$C_6$-hydroxyalkyl group, a $C_2$-$C_6$-alkenyl group, a $C_2$-$C_6$-alkynyl group,
  a $C_4$-$C_8$-cycloalkenyl group, a ($C_1$-$C_6$-alkyl)-N($R^7$)$R^8$ group,
  a —($C_1$-$C_6$-alkyl)-(4- to 7-membered nitrogen containing heterocycloalkyl) group and wherein said 4- to 7-membered nitrogen containing heterocycloalkyl group is optionally substituted with a $C_1$-$C_3$-alkyl group,
    and
  wherein said 4- to 7-membered nitrogen containing heterocycloalkyl group is connected to the alkyl group via a carbon atom of the heterocycloalkyl group,
  a phenyl group,
    wherein said phenyl group is optionally substituted, one, two or three times, each substituent independently selected from a halogen atom or a group selected from
    $C_1$-$C_3$-alkyl, $C_1$-$C_4$-haloalkyl, $C_1$-$C_3$-alkoxy and hydroxy,
$R^4$ represents a group selected from
  a $C_2$-$C_6$-alkylenyl group, a $C_3$-$C_8$-cycloalkyl group, a $C_2$-$C_6$-haloalkyl group,
  a $C_2$-$C_6$-hydroxyalkyl group and a —($C_2$-$C_6$-alkyl)-N($R^7$)($R^8$) group,
  a $C_1$-$C_6$-alkyl group,
    which is optionally substituted with a group selected from $C_3$-$C_8$-cycloalkyl and phenyl,
      wherein said phenyl group is optionally substituted, one, two or three times, each substituent independently selected from a halogen atom or a group selected from
      $C_1$-$C_3$-alkyl, $C_1$-$C_4$-haloalkyl, $C_1$-$C_3$-alkoxy and hydroxy,
$R^5$ represents a halogen atom or a group selected from
  a $C_1$-$C_6$-alkyl group,
  a $C_3$-$C_8$-cycloalkyl group,
  a $C_1$-$C_6$-haloalkyl group,
  a $C_1$-$C_6$-hydroxyalkyl group, which is optionally substituted with a hydroxy group,
  a ($C_1$-$C_3$-alkoxy)-($C_1$-$C_6$-alkyl)- group,
  a $C_2$-$C_6$-alkenyl group, a $C_2$-$C_6$-alkynyl group,
  a $C_1$-$C_6$-alkoxy group,
  a $C_1$-$C_6$-alkylsulfanyl group,
  a —($C_1$-$C_6$-alkyl)-N($R^7$)($R^8$) group,
  a —N($R^7$)($R^8$) group,
  a —C(=O)O$R^6$ group,
  a —C(=O)N($R^7$)($R^8$) group, and a —S(=O)(=N$R^{11}$)($C_1$-$C_3$-alkyl) group,
$R^6$ represents a hydrogen atom or a group selected from a $C_1$-$C_6$-alkyl group and a benzyl group,
$R^7$ and $R^8$ represent, independently for each occurrence, a hydrogen atom or a group selected from
  a $C_1$-$C_6$-alkyl group, a $C_2$-$C_6$-hydroxyalkyl group, a —($C_2$-$C_6$-alkyl)-N($R^9$)($R^{10}$) group, and $C_3$-$C_6$-cycloalkyl group
or
$R^7$ and $R^8$ together with the nitrogen to which they are attached represent a nitrogen containing 4- to 7-membered heterocycloalkyl group,
  wherein said 4- to 7-membered nitrogen containing heterocycloalkyl group is optionally substituted with a group selected from $C_1$-$C_3$-alkyl, —S(=O)$_2$($C_1$-$C_3$-alkyl) and —C(=O)O($C_1$-$C_4$-alkyl),
$R^9$ and $R^{10}$ represent, independently for each occurrence, a hydrogen atom or a $C_1$-$C_3$-alkyl group,
or
$R^9$ and $R^{10}$ together with the nitrogen to which they are attached represent a nitrogen containing 4- to 7-membered heterocycloalkyl group,
$R^{11}$ represents a hydrogen atom or a group selected from
  a cyano group and a —C(=O)($C_1$-$C_3$-haloalkyl) group,
or a tautomer, an N-oxide, a salt, a salt of a tautomer or a salt of an N-oxide thereof.

In accordance with certain embodiments, the present invention provides compounds of general formula (I), supra, in which $R^1$ represents a group selected from
  a $C_4$-$C_8$-cycloalkyl group,
    wherein said cycloalkyl groups are optionally substituted, one or two times, each substituent independently selected from a halogen atom or a group selected from
    hydroxy, phenyl and —N($R^7$)($R^8$),
      wherein said phenyl substituent is optionally substituted, one, two or three times, each substituent independently selected from a halogen atom or a group selected from
      $C_1$-$C_3$-alkyl, $C_1$-$C_4$-haloalkyl, $C_1$-$C_3$-alkoxy and hydroxy,
  a —($C_3$-$C_8$-cycloalkyl)-N($R^7$)($R^8$) group,
  a 4- to 7-membered heterocycloalkyl group,
    which is optionally substituted one or two times, each substituent independently selected from a group selected from
    $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said- to 7-membered heterocycloalkyl group is connected to the rest of the molecule via a carbon atom of the said heterocycloalkyl- or heterocycloalkenyl group, a 5- to 7-membered heterocycloalkenyl group,
  which is optionally substituted one or two times, each substituent independently selected from a group selected from
  $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
    wherein said 5- to 6-membered heteroaryl substituent is optionally substituted, one, two or three times, each substituent independently selected from a halogen atom or a group selected from
    $C_1$-$C_3$-alkyl, $C_1$-$C_4$-haloalkyl, $C_1$-$C_3$-alkoxy and hydroxy,
  and wherein said 5- to 7-membered heterocycloalkenyl group is connected to the rest of the molecule via a carbon atom of the said heterocycloalkyl- or heterocycloalkenyl group, a phenyl group,
  wherein said phenyl group is optionally substituted, one, two, three, four or five times, each substituent independently selected from a halogen atom or a group selected from
  $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)OR$^6$, —C(=O)N(R$^7$)(R$^8$), —N(R$^7$)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{11}$)($C_1$-$C_3$-alkyl), —P(=O)($C_1$-$C_3$-alkyl)$_2$ and SF$_5$,
  or in which two substituents of said phenyl groups, when they are attached to adjacent ring atoms, are optionally linked to one another in such a way that they jointly form a group selected from
  —CH$_2$—N(R$^7$)—CH$_2$—, —CH$_2$—O—CH$_2$—, —O—CH$_2$—C(=O)—NH— and —NH—C(=O)—NH—, an indanyl group, a tetralinyl group
  wherein said indanyl or tetralinyl group is optionally substituted one or two times, each substituent independently selected from a halogen atom or a group selected from
  $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N(R$^7$)(R$^8$), and a monocyclic- or bicyclic heteroaryl group,
  which is optionally substituted one, two or three times, each substituent independently selected from a halogen atom or a group selected from
  $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N(R$^7$)(R$^8$), R$^2$ represents a hydrogen atom or a halogen atom, R$^3$ represents a group selected from
  a $C_1$-$C_6$-alkyl group,
    which is optionally substituted with a $C_3$-$C_8$-cycloalkyl group or a NR$^7$R$^8$ group,
  a $C_3$-$C_8$-cycloalkyl group, a $C_1$-$C_6$-haloalkyl group,
  a $C_1$-$C_6$-hydroxyalkyl group, a $C_2$-$C_6$-alkenyl group, a $C_2$-$C_6$-alkynyl group,
  a $C_4$-$C_8$-cycloalkenyl group, a ($C_1$-$C_6$-alkyl)-N(R$^7$)R$^8$ group,
  a —($C_1$-$C_6$-alkyl)-(4- to 7-membered nitrogen containing heterocycloalkyl) group and wherein said 4- to 7-membered nitrogen containing heterocycloalkyl group is optionally substituted with a $C_1$-$C_3$-alkyl group,
  and
    wherein said 4- to 7-membered nitrogen containing heterocycloalkyl group is connected to the alkyl group via a carbon atom of the heterocycloalkyl group,
  a phenyl group,
    wherein said phenyl group is optionally substituted, one, two or three times, each substituent independently selected from a halogen atom or a group selected from
    $C_1$-$C_3$-alkyl, $C_1$-$C_4$-haloalkyl, $C_1$-$C_3$-alkoxy and hydroxy, R$^4$ represents a group selected from
  a $C_2$-$C_6$-alkylenyl group, a $C_3$-$C_8$-cycloalkyl group, a $C_2$-$C_6$-haloalkyl group,
  a $C_2$-$C_6$-hydroxyalkyl group and a —($C_2$-$C_6$-alkyl)-N(R$^7$)(R$^8$) group,
  a $C_1$-$C_6$-alkyl group,
    which is optionally substituted with a group selected from $C_3$-$C_8$-cycloalkyl and phenyl,
      wherein said phenyl group is optionally substituted, one, two or three times, each substituent independently selected from a halogen atom or a group selected from
      $C_1$-$C_3$-alkyl, $C_1$-$C_4$-haloalkyl, $C_1$-$C_3$-alkoxy and hydroxy, R$^5$ represents a halogen atom or a group selected from
  a $C_1$-$C_6$-alkyl group,
  a $C_3$-$C_8$-cycloalkyl group,
  a $C_1$-$C_6$-haloalkyl group,
  a $C_1$-$C_6$-hydroxyalkyl group, which is optionally substituted with a hydroxy group,
  a ($C_1$-$C_3$-alkoxy)-($C_1$-$C_6$-alkyl)- group,
  a $C_2$-$C_6$-alkenyl group, a $C_2$-$C_6$-alkynyl group,
  a $C_1$-$C_6$-alkoxy group,
  a $C_1$-$C_6$-alkylsulfanyl group,
  a —($C_1$-$C_6$-alkyl)-N(R$^7$)(R$^8$) group,
  a —N(R$^7$)(R$^8$) group,
  a —C(=O)OR$^6$ group,
  a —C(=O)N(R$^7$)(R$^8$) group, and a —S(=O)(=NR$^{11}$)($C_1$-$C_3$-alkyl) group, R$^6$ represents a hydrogen atom or a group selected from
  a $C_1$-$C_6$-alkyl group and a benzyl group, R$^7$ and R$^8$ represent, independently for each occurrence, a hydrogen atom or a group selected from
  a $C_1$-$C_6$-alkyl group, a $C_2$-$C_6$-hydroxyalkyl group, a —($C_2$-$C_6$-alkyl)-N(R$^9$)(R$^{10}$) group, and $C_3$-$C_6$-cycloalkyl group
or
R$^7$ and R$^8$ together with the nitrogen to which they are attached represent a nitrogen containing 4- to 7-membered heterocycloalkyl group,
  wherein said 4- to 7-membered nitrogen containing heterocycloalkyl group is optionally substituted with a group selected from $C_1$-$C_3$-alkyl, —S(=O)$_2$($C_1$-$C_3$-alkyl) and —C(=O)O ($C_1$-$C_4$-alkyl), $R^9$ and $R^{10}$ represent, independently for each occurrence, a hydrogen atom or a $C_1$-$C_3$-alkyl group, or $R^9$ and $R^{10}$ together with the nitrogen to which they are attached represent a nitrogen containing 4- to 7-membered heterocycloalkyl group, $R^{11}$ represents a hydrogen atom or a group selected from a cyano group and a —C(=O)($C_1$-$C_3$-haloalkyl) group, or a tautomer, an N-oxide, a salt, a salt of a tautomer or a salt of an N-oxide thereof.

In accordance with certain embodiments, the present invention provides compounds of general formula (I), supra, in which:

$R^1$ represents a group selected from a $C_5$-$C_8$-alkyl group, a $C_2$-$C_8$-haloalkyl group, a $C_4$-$C_8$-cycloalkyl group, a $C_1$-$C_6$-alkyl group which is substituted with a $C_3$-$C_8$-cycloalkyl group, a $C_2$-$C_6$-alkyl group which is substituted with a cyano group or a phenyl group, a $C_3$-$C_6$-alkyl group which is substituted with a monocyclic- or bicyclic heteroaryl group, a $C_2$-$C_6$-hydroxyalkyl group, a ($C_2$-$C_6$-hydroxyalkyl)-O—($C_2$-$C_6$-alky)- group, a —($C_3$-$C_6$-alkyl)-N($R^7$)($R^8$) group, a —($C_3$-$C_8$-cycloalkyl)-N($R^7$)($R^8$) group, a —($C_3$-$C_6$-alkyl)-C(=O)N($R^7$)($R^8$) group, a 4- to 7-membered heterocycloalkyl group, a 5- to 7-membered heterocycloalkenyl group, a phenyl group, an indanyl group, a tetralinyl group and a monocyclic- or bicyclic heteroaryl group, wherein said cycloalkyl groups are optionally substituted, one or two times, each substituent independently selected from a halogen atom or a group selected from hydroxy, phenyl and —N($R^7$)($R^8$), wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said 4- to 7-membered heterocycloalkyl group and 5- to 7-membered heterocycloalkenyl group are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said 4- to 7-membered heterocycloalkyl group and 5- to 7-membered heterocycloalkenyl group are connected to the rest of the molecule via a carbon atom of the said heterocycloalkyl- or heterocycloalkenyl group, and wherein said phenyl groups are optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$), —S(=O)$_2$N($R^7$)($R^8$), —S(=O)$_2$($C_1$-$C_3$-alkyl), —S(=O)(=N$R^{11}$)($C_1$-$C_3$-alkyl), —P(=O)($C_1$-$C_3$-alkyl)$_2$ and $SF_5$, or in which two substituents of said phenyl groups, when they are attached to adjacent ring atoms, are optionally linked to one another in such a way that they jointly form a group selected from —CH$_2$—N($R^7$)—CH$_2$—, —CH$_2$—O—CH$_2$—, —O—CH$_2$—C(=O)—NH— and —NH—C(=O)—NH—, and wherein said indanyl or tetralinyl group is optionally substituted one or two times, each substituent independently selected from a halogen atom or a group selected from $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$), and wherein said monocyclic or bicyclic heteroaryl group is optionally substituted one, two or three times, each substituent independently selected from a halogen atom or a group selected from $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$), $R^2$ represents a hydrogen atom or a fluorine atom, $R^3$ represents a group selected from a $C_1$-$C_6$-alkyl group, a $C_3$-$C_8$-cycloalkyl group, a $C_1$-$C_6$-haloalkyl group, a $C_1$-$C_6$-hydroxyalkyl group, a $C_2$-$C_6$-alkenyl group, a $C_2$-$C_6$-alkynyl group, a $C_4$-$C_8$-cycloalkenyl group, a ($C_1$-$C_6$-alkyl)-N($R^7$)$R^8$ group, a —($C_1$-$C_6$-alkyl)-(4- to 7-membered nitrogen containing heterocycloalkyl) group and a phenyl group, wherein said $C_1$-$C_6$-alkyl group is optionally substituted with a $C_3$-$C_8$-cycloalkyl group, and wherein said 4- to 7-membered nitrogen containing heterocycloalkyl group is optionally substituted with a $C_1$-$C_3$-alkyl group, and wherein said 4- to 7-membered nitrogen containing heterocycloalkyl group is connected to the alkyl group via a carbon atom of the heterocycloalkyl group, and wherein said phenyl group is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, $R^4$ represents a group selected from
a $C_1$-$C_6$-alkyl group, a $C_3$-$C_8$-cycloalkyl group, a $C_2$-$C_6$-haloalkyl group,
a $C_2$-$C_6$-hydroxyalkyl group and a —($C_2$-$C_6$-alkyl)-N($R^7$)($R^8$) group,
wherein said $C_1$-$C_6$-alkyl group is optionally substituted with a group selected from
$C_3$-$C_8$-cycloalkyl and phenyl,
wherein said phenyl group is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy, $R^5$ represents a halogen atom or a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a ($C_1$-$C_3$-alkoxy)-($C_1$-$C_6$-alkyl)- group,
a $C_2$-$C_6$-alkenyl group, a $C_2$-$C_6$-alkynyl group, a $C_1$-$C_6$-alkoxy group,
a $C_1$-$C_6$-alkylsulfanyl group, a —($C_1$-$C_6$-alkyl)-N($R^7$)($R^8$) group and a —N($R^7$)($R^8$) group, $R^6$ represents a hydrogen atom or a group selected from
a $C_1$-$C_6$-alkyl group and a benzyl group, $R^7$ and $R^8$ represent, independently for each occurrence, a hydrogen atom or a group selected from
a $C_1$-$C_6$-alkyl group, a $C_2$-$C_6$-hydroxyalkyl group and a —($C_2$-$C_6$-alkyl)-N($R^9$)($R^{10}$) group,
or
$R^7$ and $R^8$ together with the nitrogen to which they are attached represent a nitrogen containing 4- to 7-membered heterocycloalkyl group,
wherein said 4- to 7-membered nitrogen containing heterocycloalkyl group is optionally substituted with a group selected from
$C_1$-$C_3$-alkyl, —S(=O)$_2$($C_1$-$C_3$-alkyl) and —C(=O)O($C_1$-$C_4$-alkyl), $R^9$ and $R^{10}$ represent, independently for each occurrence, a hydrogen atom or a $C_1$-$C_3$-alkyl group,
or
$R^9$ and $R^{10}$ together with the nitrogen to which they are attached represent a nitrogen containing 4- to 7-membered heterocycloalkyl group, $R^{11}$ represents a hydrogen atom or a group selected from
a cyano group and a —C(=O)($C_1$-$C_3$-haloalkyl) group,
or a tautomer, an N-oxide, or a salt thereof, and a salt of a tautomer or an N-oxide.

In accordance with certain embodiments, the present invention provides compounds of general formula (I), supra, in which:

$R^1$ represents a group selected from
a $C_4$-$C_8$-cycloalkyl group,
a —($C_3$-$C_8$-cycloalkyl)-N($R^7$)($R^8$) group,
a 4- to 7-membered heterocycloalkyl group,
a 5- to 7-membered heterocycloalkenyl group, a phenyl group, an indanyl group, a tetralinyl group and a monocyclic- or bicyclic heteroaryl group,
wherein said cycloalkyl groups are optionally substituted, one or two times, each substituent independently selected from a halogen atom or a group selected from
hydroxy, phenyl and —N($R^7$)($R^8$),
wherein said phenyl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and
wherein said 4- to 7-membered heterocycloalkyl group and 5- to 7-membered heterocycloalkenyl group are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
wherein said 5- to 6-membered heteroaryl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and
wherein said 4- to 7-membered heterocycloalkyl group and 5- to 7-membered heterocycloalkenyl group are connected to the rest of the molecule via a carbon atom of the said heterocycloalkyl- or heterocycloalkenyl group,
wherein said phenyl groups are optionally substituted, one, two, three, four or five times, each substituent independently selected from a halogen atom or a group selected from
$C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$), —S(=O)$_2$N($R^7$)($R^8$), —S(=O)$_2$($C_1$-$C_3$-alkyl), —S(=O)(=N$R^{11}$)($C_1$-$C_3$-alkyl), —P(=O)($C_1$-$C_3$-alkyl)$_2$ and SF$_5$,
or in which two substituents of said phenyl groups, when they are attached to adjacent ring atoms, are optionally linked to one another in such a way that they jointly form a group selected from
—CH$_2$—N($R^7$)—CH$_2$—, —CH$_2$—O—CH$_2$—, —O—CH$_2$—C(=O)—NH— and —NH—C(=O)—NH—,
and
wherein said indanyl or tetralinyl group is optionally substituted one or two times, each substituent independently selected from a halogen atom or a group selected from
$C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$),
and
wherein said monocyclic or bicyclic heteroaryl group is optionally substituted one, two or three times, each substituent independently selected from a halogen atom or a group selected from
$C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$), $R^2$ represents a hydrogen atom or a fluorine atom,
$R^3$ represents a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a $C_2$-$C_6$-alkenyl group, a $C_2$-$C_6$-alkynyl group,
a $C_4$-$C_8$-cycloalkenyl group, a ($C_1$-$C_6$-alkyl)-N($R^7$)$R^8$ group, a —($C_1$-$C_6$-alkyl)-(4- to 7-membered nitrogen containing heterocycloalkyl) group and
a phenyl group,
  wherein said $C_1$-$C_6$-alkyl group is optionally substituted with a $C_3$-$C_8$-cycloalkyl group,
  and
  wherein said 4- to 7-membered nitrogen containing heterocycloalkyl group is optionally substituted with a $C_1$-$C_3$-alkyl group,
  and
  wherein said 4- to 7-membered nitrogen containing heterocycloalkyl group is connected to the alkyl group via a carbon atom of the heterocycloalkyl group,
  and
  wherein said phenyl group is optionally substituted, one, two or three times, each substituent independently selected from a halogen atom or a group selected from
    $C_1$-$C_3$-alkyl, $C_1$-$C_4$-haloalkyl, $C_1$-$C_3$-alkoxy and hydroxy, $R^4$ represents a group selected from
  a $C_1$-$C_6$-alkyl group, a $C_3$-$C_8$-cycloalkyl group, a $C_2$-$C_6$-haloalkyl group,
  a $C_2$-$C_6$-hydroxyalkyl group and a —($C_2$-$C_6$-alkyl)-N($R^7$)($R^8$) group,
    wherein said $C_1$-$C_6$-alkyl group is optionally substituted with a group selected from
    $C_3$-$C_8$-cycloalkyl and phenyl,
      wherein said phenyl group is optionally substituted, one, two or three times, each substituent independently selected from a halogen atom or a group selected from
        $C_1$-$C_3$-alkyl, $C_1$-$C_4$-haloalkyl, $C_1$-$C_3$-alkoxy and hydroxy, $R^5$ represents a halogen atom or a group selected from
  a $C_1$-$C_6$-alkyl group, a $C_3$-$C_8$-cycloalkyl group, a $C_1$-$C_6$-haloalkyl group,
  a $C_1$-$C_6$-hydroxyalkyl group, a ($C_1$-$C_3$-alkoxy)-($C_1$-$C_6$-alkyl)- group,
  a $C_2$-$C_6$-alkenyl group, a $C_2$-$C_6$-alkynyl group, a $C_1$-$C_6$-alkoxy group,
  a $C_1$-$C_6$-alkylsulfanyl group, a —($C_1$-$C_6$-alkyl)-N($R^7$)($R^8$) group and a —N($R^7$)($R^8$) group, $R^6$ represents a hydrogen atom or a group selected from
  a $C_1$-$C_6$-alkyl group and a benzyl group, $R^7$ and $R^8$ represent, independently for each occurrence, a hydrogen atom or a group selected from
  a $C_1$-$C_6$-alkyl group, a $C_2$-$C_6$-hydroxyalkyl group and a —($C_2$-$C_6$-alkyl)-N($R^9$)($R^{10}$) group,
  or
$R^7$ and $R^8$ together with the nitrogen to which they are attached represent a nitrogen containing 4- to 7-membered heterocycloalkyl group,
  wherein said 4- to 7-membered nitrogen containing heterocycloalkyl group is optionally substituted with a group selected from
    $C_1$-$C_3$-alkyl, —S(=O)$_2$($C_1$-$C_3$-alkyl) and —C(=O)O($C_1$-$C_4$-alkyl), $R^9$ and $R^{10}$ represent, independently for each occurrence, a hydrogen atom or a $C_1$-$C_3$-alkyl group,
  or
$R^9$ and $R^{10}$ together with the nitrogen to which they are attached represent a nitrogen containing 4- to 7-membered heterocycloalkyl group, $R^{11}$ represents a hydrogen atom or a group selected from
  a cyano group and a —C(=O)($C_1$-$C_3$-haloalkyl) group, or a tautomer, an N-oxide, or a salt thereof, and a salt of a tautomer or an N-oxide.

In accordance with certain embodiments, the present invention provides compounds of general formula (I), supra, in which:

$R^1$ represents a group selected from
  a $C_5$-$C_8$-alkyl group,
  a $C_2$-$C_8$-haloalkyl group,
  a $C_4$-$C_8$-cycloalkyl group,
    which is optionally substituted, one or two times, each substituent independently selected from a halogen atom or a group selected from hydroxy, phenyl and —N($R^7$)($R^8$),
      wherein said phenyl substituent is optionally substituted, one, two or three times, each substituent independently selected from a halogen atom or a group selected from
        $C_1$-$C_3$-alkyl, $C_1$-$C_3$-haloalkyl, $C_1$-$C_3$-alkoxy and hydroxy,
  a $C_1$-$C_3$-alkyl group which is substituted with a $C_3$-$C_6$-cycloalkyl group,
  a $C_2$-$C_6$-alkyl group which is substituted with a cyano group, a hydroxy group or a phenyl group,
  a $C_3$-$C_6$-alkyl group which is substituted with a monocyclic or bicyclic heteroaryl group,
  a ($C_2$-$C_3$-hydroxyalkyl)-O—($C_2$-$C_6$-alky)- group,
  a —($C_3$-$C_6$-alkyl)-N($R^7$)($R^8$) group,
  a —($C_3$-$C_6$-cycloalkyl)-N($R^7$)($R^8$) group,
  a —($C_3$-$C_6$-alkyl)-C(=O)N($R^7$)($R^8$) group,
  a 4- to 6-membered heterocycloalkyl group,
    which is optionally substituted one or two times, each substituent independently selected from a group selected from
      $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
        wherein said 5- to 6-membered heteroaryl group is optionally substituted, one, two or three times, each substituent independently selected from a halogen atom or a group selected from
          $C_1$-$C_3$-alkyl, $C_1$-$C_3$-haloalkyl, $C_1$-$C_3$-alkoxy and hydroxy,
    wherein said 4- to 6-membered heterocycloalkyl group is connected to the rest of the molecule via a carbon atom or nitrogen atom of the said heterocycloalkyl- or heterocycloalkenyl group,
  a 5- to 6-membered heterocycloalkenyl group,
    which is optionally substituted one or two times, each substituent independently selected from a group selected from
      $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
        wherein said 5- to 6-membered heteroaryl group is optionally substituted, one, two or three times, each substituent independently selected from a halogen atom or a group selected from
          $C_1$-$C_3$-alkyl, $C_1$-$C_3$-haloalkyl, $C_1$-$C_3$-alkoxy and hydroxy,
    wherein said 5- to 6-membered heterocycloalkenyl group is connected to the rest of the molecule via a carbon atom or nitrogen atom of the said heterocycloalkyl- or heterocycloalkenyl group, a phenyl group,
  which is optionally substituted, one, two, three, four or five times, each substituent independently selected from a halogen atom or a group selected from
    $C_1$-$C_4$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(=O)OR$^6$, —C(=O)N(R$^7$)(R$^8$), —N(R$^7$)(R$^8$), —($C_1$-$C_3$-alkyl)-N(R$^7$)(R$^8$), —($C_1$-$C_3$-alkyl)-C(=O)OR$^6$, —($C_1$-$C_3$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{11}$)($C_1$-$C_3$-alkyl), —P(=O)($C_1$-$C_3$-alkyl)$_2$ and SF$_5$,
  or in which two substituents of said phenyl groups, when they are attached to adjacent ring atoms, are optionally linked to one another in such a way that they jointly form a group selected from
    —CH$_2$—N(R$^7$)—CH$_2$—, —CH$_2$—O—CH$_2$—, —O—CH$_2$—C(=O)—NH— and —NH—C(=O)—NH—,
an indanyl group,
  which is optionally substituted one or two times, each substituent independently selected from a halogen atom or a group selected from
    $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N(R$^7$)(R$^8$),
a tetralinyl group and
  which is optionally substituted one or two times, each substituent independently selected from a halogen atom or a group selected from
    $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N(R$^7$)(R$^8$),
a monocyclic- or bicyclic heteroaryl group,
  which is optionally substituted one, two or three times, each substituent independently selected from a halogen atom or a group selected from
    $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N(R$^7$)(R$^8$),
R$^2$ represents a hydrogen atom or a halogen atom,
R$^3$ represents a group selected from
  a $C_1$-$C_6$-alkyl group, a $C_3$-$C_8$-cycloalkyl group, a $C_1$-$C_6$-haloalkyl group,
  a $C_1$-$C_6$-hydroxyalkyl group, a $C_2$-$C_6$-alkenyl group, a $C_2$-$C_6$-alkynyl group,
  a $C_4$-$C_6$-cycloalkenyl group, a ($C_1$-$C_6$-alkyl)-N(R$^7$)R$^8$ group,
  a —($C_1$-$C_6$-alkyl)-(4- to 6-membered nitrogen containing heterocycloalkyl) group and
  a phenyl group,
    wherein said $C_1$-$C_6$-alkyl group is optionally substituted with a $C_3$-$C_6$-cycloalkyl group or a NR$^7$R$^8$ group,
    and
    wherein said 4- to 6-membered nitrogen containing heterocycloalkyl group is optionally substituted with a $C_1$-$C_3$-alkyl group,
    and
    wherein said 4- to 6-membered nitrogen containing heterocycloalkyl group is connected to the alkyl group via a carbon atom of the heterocycloalkyl group,
    and
    wherein said phenyl group is optionally substituted, one, two or three times, each substituent independently selected from a halogen atom or a group selected from
      $C_1$-$C_3$-alkyl, $C_1$-$C_3$-haloalkyl, $C_1$-$C_3$-alkoxy and hydroxy,
R$^4$ represents a group selected from
  a $C_2$-$C_6$-alkylenyl group, a $C_3$-$C_6$-cycloalkyl group, a $C_2$-$C_6$-haloalkyl group, a $C_2$-$C_6$-hydroxyalkyl group and a —($C_2$-$C_6$-alkyl)-N(R$^7$)(R$^8$) group,
  a $C_1$-$C_6$-alkyl group,
    which is optionally substituted with a group selected from
      $C_3$-$C_6$-cycloalkyl and phenyl,
      wherein said phenyl substituent is optionally substituted, one, two or three times, each substituent independently selected from a halogen atom or a group selected from
        $C_1$-$C_3$-alkyl, $C_1$-$C_3$-haloalkyl, $C_1$-$C_3$-alkoxy and hydroxy,
R$^5$ represents a halogen atom or a group selected from
  a $C_1$-$C_6$-alkyl group,
  a $C_3$-$C_6$-cycloalkyl group,
  a $C_1$-$C_6$-haloalkyl group, which is optionally substituted with a hydroxy group,
  a $C_1$-$C_6$-hydroxyalkyl group,
  a ($C_1$-$C_3$-alkoxy)-($C_1$-$C_6$-alkyl)- group,
  a $C_2$-$C_6$-alkenyl group, a $C_2$-$C_6$-alkynyl group,
  a $C_1$-$C_6$-alkoxy group,
  a $C_1$-$C_6$-alkylsulfanyl group,
  a —($C_1$-$C_6$-alkyl)-N(R$^7$)(R$^8$) group,
  a —N(R$^7$)(R$^8$) group,
  a —C(=O)OR$^6$ group,
  a —C(=O)N(R$^7$)(R$^8$) group, and a —S(=O)(=NR$^{11}$)($C_1$-$C_3$-alkyl) group
R$^6$ represents a hydrogen atom or a group selected from
  a $C_1$-$C_4$-alkyl group and a benzyl group,
R$^7$ and R$^8$ represent, independently for each occurrence, a hydrogen atom or a group selected from
  a $C_1$-$C_3$-alkyl group, a $C_2$-$C_3$-hydroxyalkyl group, a —($C_2$-$C_3$-alkyl)-N(R$^9$)(R$^{10}$) group and $C_3$-$C_6$-cycloalkyl group,
or
R$^7$ and R$^8$ together with the nitrogen to which they are attached represent a nitrogen containing 4- to 6-membered heterocycloalkyl group,
  wherein said 4- to 6-membered nitrogen containing heterocycloalkyl group is optionally substituted with a group selected from
    $C_1$-$C_3$-alkyl, —S(=O)$_2$($C_1$-$C_3$-alkyl) and —C(=O)O($C_1$-$C_4$-alkyl),
R$^9$ and R$^{10}$ represent, identically or differently, a hydrogen atom or a $C_1$-$C_3$-alkyl group,
or
R$^9$ and R$^{10}$ together with the nitrogen to which they are attached represent a nitrogen containing 4- to 6-membered heterocycloalkyl group,
R$^{11}$ represents a hydrogen atom or a group selected from
  a cyano group and a —C(=O)($C_1$-$C_3$-haloalkyl) group,
or a tautomer, an N-oxide, a salt, a salt of a tautomer or a salt of an N-oxide thereof.

In accordance with certain embodiments, the present invention provides compounds of general formula (I), supra, in which:

$R^1$ represents a group selected from
- a $C_4$-$C_8$-cycloalkyl group,
  - which is optionally substituted, one or two times, each substituent independently selected from a halogen atom or a group selected from
    - hydroxy, phenyl and —N($R^7$)($R^8$),
      - wherein said phenyl substituent is optionally substituted, one, two or three times, each substituent independently selected from a halogen atom or a group selected from
        - $C_1$-$C_3$-alkyl, $C_1$-$C_3$-haloalkyl, $C_1$-$C_3$-alkoxy and hydroxy,
- a —($C_3$-$C_6$-cycloalkyl)-N($R^7$)($R^8$) group,
- a —($C_3$-$C_6$-alkyl)-C(=O)N($R^7$)($R^8$) group,
- a 4- to 6-membered heterocycloalkyl group,
  - which is optionally substituted one or two times, each substituent independently selected from a group selected from
    - $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
      - wherein said 5- to 6-membered heteroaryl group is optionally substituted, one, two or three times, each substituent independently selected from a halogen atom or a group selected from
        - $C_1$-$C_3$-alkyl, $C_1$-$C_3$-haloalkyl, $C_1$-$C_3$-alkoxy and hydroxy,
  - wherein said 4- to 6-membered heterocycloalkyl group is connected to the rest of the molecule via a carbon atom or nitrogen atom of the said heterocycloalkyl- or heterocycloalkenyl group,
- a 5- to 6-membered heterocycloalkenyl group,
  - which is optionally substituted one or two times, each substituent independently selected from a group selected from
    - $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
      - wherein said 5- to 6-membered heteroaryl group is optionally substituted, one, two or three times, each substituent independently selected from a halogen atom or a group selected from
        - $C_1$-$C_3$-alkyl, $C_1$-$C_3$-haloalkyl, $C_1$-$C_3$-alkoxy and hydroxy,
  - wherein said 5- to 6-membered heterocycloalkenyl group is connected to the rest of the molecule via a carbon atom or nitrogen atom of the said heterocycloalkyl- or heterocycloalkenyl group,
- a phenyl group,
  - which is optionally substituted, one, two, three, four or five times, each substituent independently selected from a halogen atom or a group selected from
    - $C_1$-$C_4$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(=O)O$R^6$, —C(=O)N($R^7$)($R^8$), —N($R^7$)($R^8$), —($C_1$-$C_3$-alkyl)-N($R^7$)($R^8$), —($C_1$-$C_3$-alkyl)-C(=O)O$R^6$, —($C_1$-$C_3$-alkyl)-C(=O)N($R^7$)($R^8$), —S(=O)$_2$N($R^7$)($R^8$), —S(=O)$_2$($C_1$-$C_3$-alkyl), —S(=O)(=N$R^{11}$)($C_1$-$C_3$-alkyl), —P(=O)($C_1$-$C_3$-alkyl)$_2$ and SF$_5$,
  - or in which two substituents of said phenyl groups, when they are attached to adjacent ring atoms, are optionally linked to one another in such a way that they jointly form a group selected from
    - —CH$_2$—N($R^7$)—CH$_2$—, —CH$_2$—O—CH$_2$—, —O—CH$_2$—C(=O)—NH— and —NH—C(=O)—NH—,
- an indanyl group,
  - which is optionally substituted one or two times, each substituent independently selected from a halogen atom or a group selected from
    - $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$),
- a tetralinyl group and
  - which is optionally substituted one or two times, each substituent independently selected from a halogen atom or a group selected from
    - $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$),
- a monocyclic- or bicyclic heteroaryl group,
  - which is optionally substituted one, two or three times, each substituent independently selected from a halogen atom or a group selected from
    - $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), $R^2$ represents a hydrogen atom or a halogen atom, $R^3$ represents a group selected from
- a $C_1$-$C_6$-alkyl group, a $C_3$-$C_8$-cycloalkyl group, a $C_1$-$C_6$-haloalkyl group,
- a $C_1$-$C_6$-hydroxyalkyl group, a $C_2$-$C_6$-alkenyl group, a $C_2$-$C_6$-alkynyl group,
- a $C_4$-$C_6$-cycloalkenyl group, a ($C_1$-$C_6$-alkyl)-N($R^7$)$R^8$ group,
- a —($C_1$-$C_6$-alkyl)-(4- to 6-membered nitrogen containing heterocycloalkyl) group and a phenyl group,
  - wherein said $C_1$-$C_6$-alkyl group is optionally substituted with a $C_3$-$C_6$-cycloalkyl group or a NR$^7$R$^8$ group,
  - and
  - wherein said 4- to 6-membered nitrogen containing heterocycloalkyl group is optionally substituted with a $C_1$-$C_3$-alkyl group,
  - and
  - wherein said 4- to 6-membered nitrogen containing heterocycloalkyl group is connected to the alkyl group via a carbon atom of the heterocycloalkyl group,
  - and
  - wherein said phenyl group is optionally substituted, one, two or three times, each substituent independently selected from a halogen atom or a group selected from
    - $C_1$-$C_3$-alkyl, $C_1$-$C_3$-haloalkyl, $C_1$-$C_3$-alkoxy and hydroxy, $R^4$ represents a group selected from
- a $C_2$-$C_6$-alkylenyl group, a $C_3$-$C_6$-cycloalkyl group, a $C_2$-$C_6$-haloalkyl group, a $C_2$-$C_6$-hydroxyalkyl group and a —($C_2$-$C_6$-alkyl)-N($R^7$)($R^8$) group,
- a $C_1$-$C_6$-alkyl group,
  - which is optionally substituted with a group selected from
    - $C_3$-$C_6$-cycloalkyl and phenyl,
      - wherein said phenyl substituent is optionally substituted, one, two or three times, each substituent independently selected from a halogen atom or a group selected from
        - $C_1$-$C_3$-alkyl, $C_1$-$C_3$-haloalkyl, $C_1$-$C_3$-alkoxy and hydroxy, $R^5$ represents a halogen atom or a group selected from
a $C_1$-$C_6$-alkyl group,
a $C_3$-$C_6$-cycloalkyl group,
a $C_1$-$C_6$-haloalkyl group, which is optionally substituted with a hydroxy group,
a $C_1$-$C_6$-hydroxyalkyl group,
a ($C_1$-$C_3$-alkoxy)-($C_1$-$C_6$-alkyl)- group,
a $C_2$-$C_6$-alkenyl group, a $C_2$-$C_6$-alkynyl group,
a $C_1$-$C_6$-alkoxy group,
a $C_1$-$C_6$-alkylsulfanyl group,
a —($C_1$-$C_6$-alkyl)-N($R^7$)($R^8$) group,
a —N($R^7$)($R^8$) group,
a —C(═O)O$R^6$ group,
a —C(═O)N($R^7$)($R^8$) group, and a —S(═O)(═N$R^{11}$)($C_1$-$C_3$-alkyl) group $R^6$ represents a hydrogen atom or a group selected from
a $C_1$-$C_4$-alkyl group and a benzyl group, $R^7$ and $R^8$ represent, independently for each occurrence, a hydrogen atom or a group selected from
a $C_1$-$C_3$-alkyl group, a $C_2$-$C_3$-hydroxyalkyl group, a —($C_2$-$C_3$-alkyl)-N($R^9$)($R^{10}$) group and $C_3$-$C_6$-cycloalkyl group,
or $R^7$ and $R^8$ together with the nitrogen to which they are attached represent a nitrogen containing 4- to 6-membered heterocycloalkyl group,
wherein said 4- to 6-membered nitrogen containing heterocycloalkyl group is optionally substituted with a group selected from
$C_1$-$C_3$-alkyl, —S(═O)$_2$($C_1$-$C_3$-alkyl) and —C(═O)O($C_1$-$C_4$-alkyl), $R^9$ and $R^{10}$ represent, identically or differently, a hydrogen atom or a $C_1$-$C_3$-alkyl group,
or $R^9$ and $R^{10}$ together with the nitrogen to which they are attached represent a nitrogen containing 4- to 6-membered heterocycloalkyl group, $R^{11}$ represents a hydrogen atom or a group selected from
a cyano group and a —C(═O)($C_1$-$C_3$-haloalkyl) group,
or a tautomer, an N-oxide, a salt, a salt of a tautomer or a salt of an N-oxide thereof.

In accordance with certain embodiments, the present invention provides compounds of general formula (I), supra, in which:

$R^1$ represents a group selected from
a $C_5$-$C_8$-alkyl group, a $C_2$-$C_8$-haloalkyl group, a $C_4$-$C_8$-cycloalkyl group,
a $C_1$-$C_3$-alkyl group which is substituted with a $C_3$-$C_6$-cycloalkyl group,
a $C_2$-$C_6$-alkyl group which is substituted with a cyano group or a phenyl group,
a $C_3$-$C_6$-alkyl group which is substituted with a monocyclic or bicyclic heteroaryl group,
a $C_2$-$C_6$-hydroxyalkyl group, a ($C_2$-$C_3$-hydroxyalkyl)-O—($C_2$-$C_6$-alky)- group,
a —($C_3$-$C_6$-alkyl)-N($R^7$)($R^8$) group, a —($C_3$-$C_6$-cycloalkyl)-N($R^7$)($R^8$) group,
a —($C_3$-$C_6$-alkyl)-C(═O)N($R^7$)($R^8$) group, a 4- to 6-membered heterocycloalkyl group, a 5- to 6-membered heterocycloalkenyl group, a phenyl group, an indanyl group, a tetralinyl group and a monocyclic- or bicyclic heteroaryl group,
wherein said cycloalkyl groups are optionally substituted, one or two times, each substituent independently selected from a halogen atom or a group selected from
hydroxy, phenyl and —N($R^7$)($R^8$),
wherein said phenyl substituent is optionally substituted, one, two or three times, each substituent independently selected from a halogen atom or a group selected from
$C_1$-$C_3$-alkyl, $C_1$-$C_3$-haloalkyl, $C_1$-$C_3$-alkoxy and hydroxy,
and
wherein said 4- to 6-membered heterocycloalkyl group and said 5- to 6-membered heterocycloalkenyl group are optionally substituted one or two times, each substituent independently selected from a group selected from
$C_1$-$C_3$-alkyl, 5- to 6-membered heteroaryl, —C(═O)O($C_1$-$C_4$-alkyl), —C(═O)($C_1$-$C_3$-alkyl), —C(═O)($C_3$-$C_6$-cycloalkyl), —S(═O)$_2$($C_1$-$C_3$-alkyl) and oxo (═O),
wherein said 5- to 6-membered heteroaryl group is optionally substituted, one, two or three times, each substituent independently selected from a halogen atom or a group selected from
$C_1$-$C_3$-alkyl, $C_1$-$C_3$-haloalkyl, $C_1$-$C_3$-alkoxy and hydroxy,
and
wherein said 4- to 6-membered heterocycloalkyl group and said 5- to 6-membered heterocycloalkenyl group are connected to the rest of the molecule via a carbon atom of the said heterocycloalkyl- or heterocycloalkenyl group,
and
wherein said phenyl groups are optionally substituted, one, two, three, four or five times, each substituent independently selected from a halogen atom or a group selected from
$C_1$-$C_4$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(═O)O$R^6$, —C(═O)N($R^7$)($R^8$), —N($R^7$)($R^8$), —($C_1$-$C_3$-alkyl)-N($R^7$)($R^8$), —($C_1$-$C_3$-alkyl)-C(═O)O$R^6$, —($C_1$-$C_3$-alkyl)-C(═O)N($R^7$)($R^8$), —S(═O)$_2$N($R^7$)($R^8$), —S(═O)$_2$($C_1$-$C_3$-alkyl), —S(═O)(═N$R^{11}$)($C_1$-$C_3$-alkyl), —P(═O)($C_1$-$C_3$-alkyl)$_2$ and SF$_5$,
or in which two substituents of said phenyl groups, when they are attached to adjacent ring atoms, are optionally linked to one another in such a way that they jointly form a group selected from —CH$_2$—N($R^7$)—CH$_2$—, —CH$_2$—O—CH$_2$—, —O—CH$_2$—C(═O)—NH— and —NH—C(═O)—NH—,
and
wherein said indanyl- or tetralinyl group is optionally substituted one or two times, each substituent independently selected from a halogen atom or a group selected from
$C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$),
and
wherein said monocyclic or bicyclic heteroaryl group is optionally substituted one, two or three times, each substituent independently selected from a halogen atom or a group selected from
$C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), $R^2$ represents a hydrogen atom or a fluorine atom, $R^3$ represents a group selected from
- a $C_1$-$C_6$-alkyl group, a $C_3$-$C_8$-cycloalkyl group, a $C_1$-$C_6$-haloalkyl group,
- a $C_1$-$C_6$-hydroxyalkyl group, a $C_2$-$C_6$-alkenyl group, a $C_2$-$C_6$-alkynyl group,
- a $C_4$-$C_6$-cycloalkenyl group, a ($C_1$-$C_6$-alkyl)-N($R^7$)$R^8$ group,
- a —($C_1$-$C_6$-alkyl)-(4- to 6-membered nitrogen containing heterocycloalkyl) group and
- a phenyl group,
  - wherein said $C_1$-$C_6$-alkyl group is optionally substituted with a $C_3$-$C_6$-cycloalkyl group,
  - and
  - wherein said 4- to 6-membered nitrogen containing heterocycloalkyl group is optionally substituted with a $C_1$-$C_3$-alkyl group,
  - and
  - wherein said 4- to 6-membered nitrogen containing heterocycloalkyl group is connected to the alkyl group via a carbon atom of the heterocycloalkyl group,
  - wherein said phenyl group is optionally substituted, one, two or three times, each substituent independently selected from a halogen atom or a group selected from
    - $C_1$-$C_3$-alkyl, $C_1$-$C_3$-haloalkyl, $C_1$-$C_3$-alkoxy and hydroxy, $R^4$ represents a group selected from
- a $C_1$-$C_6$-alkyl group, a $C_3$-$C_6$-cycloalkyl group, a $C_2$-$C_6$-haloalkyl group,
- a $C_2$-$C_6$-hydroxyalkyl group and a —($C_2$-$C_6$-alkyl)-N($R^7$)($R^8$) group,
  - wherein said $C_1$-$C_6$-alkyl group is optionally substituted with a group selected from
    - $C_3$-$C_6$-cycloalkyl and phenyl,
      - wherein said phenyl group is optionally substituted, one, two or three times, each substituent independently selected from a halogen atom or a group selected from
        - $C_1$-$C_3$-alkyl, $C_1$-$C_3$-haloalkyl, $C_1$-$C_3$-alkoxy and hydroxy, $R^5$ represents a halogen atom or a group selected from
- a $C_1$-$C_6$-alkyl group, a $C_3$-$C_6$-cycloalkyl group, a $C_1$-$C_6$-haloalkyl group,
- a $C_1$-$C_6$-hydroxyalkyl group, a ($C_1$-$C_3$-alkoxy)-($C_1$-$C_6$-alkyl)- group,
- a $C_2$-$C_6$-alkenyl group, a $C_2$-$C_6$-alkynyl group, a $C_1$-$C_6$-alkoxy group,
- a $C_1$-$C_6$-alkylsulfanyl group, a —($C_1$-$C_6$-alkyl)-N($R^7$)($R^8$) group and a —N($R^7$)($R^8$) group, $R^6$ represents a hydrogen atom or a group selected from
- a $C_1$-$C_4$-alkyl group and a benzyl group, $R^7$ and $R^8$ represent, independently for each occurrence, a hydrogen atom or a group selected from
- a $C_1$-$C_3$-alkyl group, a $C_2$-$C_3$-hydroxyalkyl group and a —($C_2$-$C_3$-alkyl)-N($R^9$)($R^{10}$) group, or $R^7$ and $R^8$ together with the nitrogen to which they are attached represent a nitrogen containing 4- to 6-membered heterocycloalkyl group,
  - wherein said 4- to 6-membered nitrogen containing heterocycloalkyl group is optionally substituted with a group selected from
    - $C_1$-$C_3$-alkyl, —S(=O)$_2$($C_1$-$C_3$-alkyl) and —C(=O)O($C_1$-$C_4$-alkyl), $R^9$ and $R^{10}$ represent, identically or differently, a hydrogen atom or a $C_1$-$C_3$-alkyl group, or $R^9$ and $R^{10}$ together with the nitrogen to which they are attached represent a nitrogen containing 4- to 6-membered heterocycloalkyl group, $R^{11}$ represents a hydrogen atom or a group selected from
- a cyano group and a —C(=O)($C_1$-$C_3$-haloalkyl) group, and tautomers, N-oxides, and salts thereof, and salts of tautomers or N-oxides.

In accordance with certain embodiments, the present invention provides compounds of general formula (I), supra, in which:

$R^1$ represents a group selected from
- a $C_4$-$C_8$-cycloalkyl group,
- a —($C_3$-$C_6$-cycloalkyl)-N($R^7$)($R^8$) group,
- a 4- to 6-membered heterocycloalkyl group, a 5- to 6-membered heterocycloalkenyl group, a phenyl group, an indanyl group, a tetralinyl group and a monocyclic- or bicyclic heteroaryl group,
  - wherein said cycloalkyl groups are optionally substituted, one or two times, each substituent independently selected from a halogen atom or a group selected from
    - hydroxy, phenyl and —N($R^7$)($R^8$),
      - wherein said phenyl substituent is optionally substituted, one, two or three times, each substituent independently selected from a halogen atom or a group selected from
        - $C_1$-$C_3$-alkyl, $C_1$-$C_3$-haloalkyl, $C_1$-$C_3$-alkoxy and hydroxy,
  - and
  - wherein said 4- to 6-membered heterocycloalkyl group and said 5- to 6-membered heterocycloalkenyl group are optionally substituted one or two times, each substituent independently selected from a group selected from
    - $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
      - wherein said 5- to 6-membered heteroaryl group is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy,
  - and
  - wherein said 4- to 6-membered heterocycloalkyl group and said 5- to 6-membered heterocycloalkenyl group are connected to the rest of the molecule via a carbon atom of the said heterocycloalkyl- or heterocycloalkenyl group,
  - and
  - wherein said phenyl groups are optionally substituted, one, two, three, four or five times, each substituent independently selected from a halogen atom or a group selected from
    - $C_1$-$C_4$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(=O)O$R^6$, —C(=O)N($R^7$)($R^8$), —N($R^7$)($R^8$), —($C_1$-$C_3$-alkyl)-N($R^7$)($R^8$), —($C_1$-$C_3$-alkyl)-C(=O)O$R^6$, —($C_1$-$C_3$-alkyl)-C(=O)N($R^7$)($R^8$), —S(=O)$_2$N($R^7$)($R^8$), —S(=O)$_2$($C_1$-$C_3$-alkyl), —S(=O)(=N$R^{11}$)($C_1$-$C_3$-alkyl), —P(=O)($C_1$-$C_3$-alkyl)$_2$ and SF$_5$, or in which two substituents of said phenyl groups, when they are attached to adjacent ring atoms, are optionally linked to one another in such a way that they jointly form a group selected from
—CH$_2$—N(R$^7$)—CH$_2$—, —CH$_2$—O—CH$_2$—, —O—CH$_2$—C(=O)—NH— and —NH—C(=O)—NH—,
and
wherein said indanyl- or tetralinyl group is optionally substituted one or two times, each substituent independently selected from a halogen atom or a group selected from
C$_1$-C$_3$-alkyl, C$_1$-C$_3$-haloalkyl, C$_3$-C$_6$-cycloalkyl, C$_1$-C$_3$-alkoxy, C$_1$-C$_3$-haloalkoxy, C$_3$-C$_6$-cycloalkoxy, cyano, hydroxy and —N(R$^7$)(R$^8$),
and
wherein said monocyclic or bicyclic heteroaryl group is optionally substituted one, two or three times, each substituent independently selected from a halogen atom or a group selected from
C$_1$-C$_3$-alkyl, C$_1$-C$_3$-haloalkyl, C$_3$-C$_6$-cycloalkyl, C$_1$-C$_3$-alkoxy, C$_1$-C$_3$-haloalkoxy, C$_3$-C$_6$-cycloalkoxy, cyano, hydroxy and —N(R$^7$)(R$^8$),
R$^2$ represents a hydrogen atom or a fluorine atom,
R$^3$ represents a group selected from
a C$_1$-C$_6$-alkyl group, a C$_3$-C$_8$-cycloalkyl group, a C$_1$-C$_6$-haloalkyl group,
a C$_1$-C$_6$-hydroxyalkyl group, a C$_2$-C$_6$-alkenyl group, a C$_2$-C$_6$-alkynyl group,
a C$_4$-C$_6$-cycloalkenyl group, a (C$_1$-C$_6$-alkyl)-N(R$^7$)R$^8$ group,
a —(C$_1$-C$_6$-alkyl)-(4- to 6-membered nitrogen containing heterocycloalkyl) group and a phenyl group,
wherein said C$_1$-C$_6$-alkyl group is optionally substituted with a C$_3$-C$_6$-cycloalkyl group,
and
wherein said 4- to 6-membered nitrogen containing heterocycloalkyl group is optionally substituted with a C$_1$-C$_3$-alkyl group,
and
wherein said 4- to 6-membered nitrogen containing heterocycloalkyl group is connected to the alkyl group via a carbon atom of the heterocycloalkyl group,
and
wherein said phenyl group is optionally substituted, one, two or three times, each substituent independently selected from a halogen atom or a group selected from
C$_1$-C$_3$-alkyl, C$_1$-C$_3$-haloalkyl, C$_1$-C$_3$-alkoxy and hydroxy,
R$^4$ represents a group selected from
a C$_1$-C$_6$-alkyl group, a C$_3$-C$_6$-cycloalkyl group, a C$_2$-C$_6$-haloalkyl group,
a C$_2$-C$_6$-hydroxyalkyl group and a —(C$_2$-C$_6$-alkyl)-N(R$^7$)(R$^8$) group,
wherein said C$_1$-C$_6$-alkyl group is optionally substituted with a group selected from
C$_3$-C$_6$-cycloalkyl and phenyl,
wherein said phenyl group is optionally substituted, one, two or three times, each substituent independently selected from a halogen atom or a group selected from
C$_1$-C$_3$-alkyl, C$_1$-C$_3$-haloalkyl, C$_1$-C$_3$-alkoxy and hydroxy,
R$^5$ represents a halogen atom or a group selected from
a C$_1$-C$_6$-alkyl group, a C$_3$-C$_6$-cycloalkyl group, a C$_1$-C$_6$-haloalkyl group,
a C$_1$-C$_6$-hydroxyalkyl group, a (C$_1$-C$_3$-alkoxy)-(C$_1$-C$_6$-alkyl)- group,
a C$_2$-C$_6$-alkenyl group, a C$_2$-C$_6$-alkynyl group, a C$_1$-C$_6$-alkoxy group,
a C$_1$-C$_6$-alkylsulfanyl group, a —(C$_1$-C$_6$-alkyl)-N(R$^7$)(R$^8$) group and a —N(R$^7$)(R$^8$) group,
R$^6$ represents a hydrogen atom or a group selected from
a C$_1$-C$_4$-alkyl group and a benzyl group,
R$^7$ and R$^8$ represent, independently for each occurrence, a hydrogen atom or a group selected from
a C$_1$-C$_3$-alkyl group, a C$_2$-C$_3$-hydroxyalkyl group and a —(C$_2$-C$_3$-alkyl)-N(R$^9$)(R$^{10}$) group,
or
R$^7$ and R$^8$ together with the nitrogen to which they are attached represent a nitrogen containing 4- to 6-membered heterocycloalkyl group,
wherein said 4- to 6-membered nitrogen containing heterocycloalkyl group is optionally substituted with a group selected from
C$_1$-C$_3$-alkyl, —S(=O)$_2$(C$_1$-C$_3$-alkyl) and —C(=O)O(C$_1$-C$_4$-alkyl),
R$^9$ and R$^{10}$ represent, identically or differently, a hydrogen atom or a C$_1$-C$_3$-alkyl group,
or
R$^9$ and R$^{10}$ together with the nitrogen to which they are attached represent a nitrogen containing 4- to 6-membered heterocycloalkyl group,
R$^{11}$ represents a hydrogen atom or a group selected from
a cyano group and a —C(=O)(C$_1$-C$_3$-haloalkyl) group,
and tautomers, N-oxides, and salts thereof, and salts of tautomers or N-oxides.

In accordance with further embodiments, the present invention provides compounds of general formula (I), supra, in which:
R$^1$ represents a group selected from
a C$_5$-C$_8$-alkyl group,
a C$_4$-C$_8$-cycloalkyl group,
which is optionally substituted, one or two times, with a phenyl group,
wherein said phenyl substituent is optionally substituted, one, two or three times, each substituent independently selected from a halogen atom,
a C$_1$-C$_3$-alkyl group which is substituted with a C$_3$-C$_6$-cycloalkyl group,
a C$_2$-C$_6$-alkyl group which is substituted with a hydroxy group or a phenyl group,
a C$_3$-C$_6$-alkyl group which is substituted with a monocyclic or bicyclic heteroaryl group,
a —(C$_3$-C$_6$-alkyl)-N(R$^7$)(R$^8$) group,
a —(C$_3$-C$_6$-alkyl)-C(=O)N(R$^7$)(R$^8$) group,
a 4- to 6-membered heterocycloalkyl group,
which is optionally substituted one or two times, each substituent independently selected from a C$_1$-C$_3$-alkyl group,
and
which is connected to the rest of the molecule via a carbon atom of the said heterocycloalkyl group,
a phenyl group,
which is optionally substituted, one, two, three or four times, each substituent independently selected from a halogen atom or a group selected from C$_1$-C$_4$-alkyl, C$_1$-C$_3$-haloalkyl, C$_1$-C$_3$-hydroxyalkyl, C$_1$-C$_3$-alkoxy, hydroxy, —C(=O)OR$^6$, —C(=O)N(R$^7$)(R$^8$), N(R$^7$)(R$^8$), —(C$_1$-C$_3$-alkyl)-N(R$^7$)(R$^8$), —O—C(=O)—(C$_1$-C$_4$-alkyl), —S—C$_1$-C$_3$-alkyl, —S(=O)$_2$(C$_1$-C$_3$-alkyl), —S(=O)(=NR$^{11}$)(C$_1$-C$_3$-alkyl) and —P(=O)(C$_1$-C$_3$-alkyl)$_2$, an indanyl group and a monocyclic- or bicyclic heteroaryl group,
  which are optionally substituted one, two or three times, each substituent independently selected from a halogen atom or a group selected from $C_1$-$C_3$-alkyl and $C_1$-$C_3$-alkoxy, $R^2$ represents a hydrogen atom or a halogen atom, $R^3$ represents a group selected from
  a $C_1$-$C_6$-alkyl group, a $C_3$-$C_8$-cycloalkyl group, a $C_1$-$C_6$-haloalkyl group,
  a $C_2$-$C_6$-alkenyl group and a phenyl group,
    wherein said $C_1$-$C_6$-alkyl group is optionally substituted with a $C_3$-$C_6$-cycloalkyl group or a $NR^7R^8$ group $R^4$ represents a group selected from
  a $C_2$-$C_6$-alkenyl group, a $C_3$-$C_6$-cycloalkyl group and a $C_2$-$C_6$-hydroxyalkyl group,
  a $C_1$-$C_6$-alkyl group,
    which is optionally substituted with a group selected from $C_3$-$C_6$-cycloalkyl and phenyl, $R^5$ represents a halogen atom or a group selected from
  a $C_1$-$C_6$-alkyl group,
  a $C_3$-$C_6$-cycloalkyl group,
  a $C_1$-$C_6$-haloalkyl group, which is optionally substituted with a hydroxy group,
  a $C_1$-$C_6$-hydroxyalkyl group,
  a ($C_1$-$C_3$-alkoxy)-($C_1$-$C_6$-alkyl)- group,
  a $C_1$-$C_6$-alkoxy group,
  $C_1$-$C_6$-alkylsulfanyl group,
  —($C_1$-$C_6$-alkyl)-N($R^7$)($R^8$) group,
  a —N($R^7$)($R^8$) group,
  a —C(=O)O$R^6$ group,
  a —C(=O)N($R^7$)($R^8$) group, and a —S(=O)(=N$R^{11}$)($C_1$-$C_3$-alkyl) group $R^6$ represents a hydrogen atom or a $C_1$-$C_4$-alkyl group, $R^7$ and $R^8$ represent, independently for each occurrence, a hydrogen atom or a $C_1$-$C_3$-alkyl group or a cyclopropyl group, $R^{11}$ represents a hydrogen atom, or a tautomer, an N-oxide, a salt, a salt of a tautomer or a salt of an N-oxide thereof.

In accordance with further embodiments, the present invention provides compounds of general formula (I), supra, in which:

$R^1$ represents a group selected from
  a $C_4$-$C_8$-cycloalkyl group,
    which is optionally substituted, one or two times, with a phenyl group, wherein said phenyl substituent is optionally substituted, one, two or three times, each substituent independently selected from a halogen atom, a 4- to 6-membered heterocycloalkyl group,
    which is optionally substituted one or two times, each substituent independently selected from a $C_1$-$C_3$-alkyl group,
    and
    which is connected to the rest of the molecule via a carbon atom of the said heterocycloalkyl group,
  a phenyl group,
    which is optionally substituted, one, two, three or four times, each substituent independently selected from a halogen atom or a group selected from $C_1$-$C_4$-alkyl, $C_1$-$C_3$-haloalkyl, $C_1$-$C_3$-hydroxyalkyl, $C_1$-$C_3$-alkoxy, hydroxy, —C(=O)O$R^6$, —C(=O)N($R^7$)($R^8$), N($R^7$)($R^8$), —($C_1$-$C_3$-alkyl)-N($R^7$)($R^8$), —O—C(=O)—($C_1$-$C_4$-alkyl), —S—$C_1$-$C_3$-alkyl, —S(=O)$_2$($C_1$-$C_3$-alkyl), —S(=O)(=N$R^{11}$)($C_1$-$C_3$-alkyl) and —P(=O)($C_1$-$C_3$-alkyl)$_2$, an indanyl group and a monocyclic- or bicyclic heteroaryl group,
  which are optionally substituted one, two or three times, each substituent independently selected from a halogen atom or a group selected from $C_1$-$C_3$-alkyl and $C_1$-$C_3$-alkoxy, $R^2$ represents a hydrogen atom or a halogen atom, $R^3$ represents a group selected from
  a $C_1$-$C_6$-alkyl group, a $C_3$-$C_8$-cycloalkyl group, a $C_1$-$C_6$-haloalkyl group,
  a $C_2$-$C_6$-alkenyl group and a phenyl group,
    wherein said $C_1$-$C_6$-alkyl group is optionally substituted with a $C_3$-$C_6$-cycloalkyl group or a $NR^7R^8$ group $R^4$ represents a group selected from
  a $C_2$-$C_6$-alkenyl group, a $C_3$-$C_6$-cycloalkyl group and a $C_2$-$C_6$-hydroxyalkyl group,
  a $C_1$-$C_6$-alkyl group,
    which is optionally substituted with a group selected from $C_3$-$C_6$-cycloalkyl and phenyl, $R^5$ represents a halogen atom or a group selected from
  a $C_1$-$C_6$-alkyl group,
  a $C_3$-$C_6$-cycloalkyl group,
  a $C_1$-$C_6$-haloalkyl group, which is optionally substituted with a hydroxy group,
  a $C_1$-$C_6$-hydroxyalkyl group,
  a ($C_1$-$C_3$-alkoxy)-($C_1$-$C_6$-alkyl)- group,
  a $C_1$-$C_6$-alkoxy group,
  $C_1$-$C_6$-alkylsulfanyl group,
  —($C_1$-$C_6$-alkyl)-N($R^7$)($R^8$) group,
  a —N($R^7$)($R^8$) group,
  a —C(=O)O$R^6$ group,
  a —C(=O)N($R^7$)($R^8$) group, and a —S(=O)(=N$R^{11}$)($C_1$-$C_3$-alkyl) group $R^6$ represents a hydrogen atom or a $C_1$-$C_4$-alkyl group, $R^7$ and $R^8$ represent, independently for each occurrence, a hydrogen atom or a $C_1$-$C_3$-alkyl group or a cyclopropyl group, $R^{11}$ represents a hydrogen atom, or a tautomer, an N-oxide, a salt, a salt of a tautomer or a salt of an N-oxide thereof.

In accordance with further embodiments, the present invention provides compounds of general formula (I), supra, in which:

$R^1$ represents a group selected from
  a $C_5$-$C_8$-alkyl group, a $C_4$-$C_8$-cycloalkyl group,
  a $C_1$-$C_3$-alkyl group which is substituted with a $C_3$-$C_6$-cycloalkyl group,
  a $C_2$-$C_6$-alkyl group which is substituted with a phenyl group,
  a $C_3$-$C_6$-alkyl group which is substituted with a monocyclic or bicyclic heteroaryl group,
  a $C_2$-$C_6$-hydroxyalkyl group, a —($C_3$-$C_6$-alkyl)-N($R^7$)($R^8$) group,
  a —($C_3$-$C_6$-alkyl)-C(=O)N($R^7$)($R^8$) group, a 4- to 6-membered heterocycloalkyl group,
  a phenyl group, an indanyl group and a monocyclic- or bicyclic heteroaryl group,
    wherein said cycloalkyl groups are optionally substituted, one or two times, with a phenyl group,
      wherein said phenyl substituent is optionally substituted, one, two or three times, each substituent independently selected from a halogen atom,
      and wherein said 4- to 6-membered heterocycloalkyl group is optionally substituted one or two times, each substituent independently selected from a $C_1$-$C_3$-alkyl group,
and
wherein said 4- to 6-membered heterocycloalkyl group is connected to the rest of the molecule via a carbon atom of the said heterocycloalkyl group,
and
wherein said phenyl groups are optionally substituted, one, two, three or four times, each substituent independently selected from a halogen atom or a group selected from
$C_1$-$C_4$-alkyl, $C_1$-$C_3$-haloalkyl, $C_1$-$C_3$-hydroxyalkyl, $C_1$-$C_3$-alkoxy, hydroxy, —C(=O)OR$^6$, —N(R$^7$)(R$^8$), —($C_1$-$C_3$-alkyl)-N(R$^7$)(R$^8$), —S(=O)$_2$($C_1$-$C_3$-alkyl), —S(=O)(=NR$^{11}$)($C_1$-$C_3$-alkyl) and —P(=O)($C_1$-$C_3$-alkyl)$_2$,
and
wherein said monocyclic or bicyclic heteroaryl group is optionally substituted one, two or three times, each substituent independently selected from a halogen atom or a group selected from
$C_1$-$C_3$-alkyl and $C_1$-$C_3$-alkoxy,
R$^2$ represents a hydrogen atom or a fluorine atom,
R$^3$ represents a group selected from
a $C_1$-$C_6$-alkyl group, a $C_3$-$C_8$-cycloalkyl group, a $C_1$-$C_6$-haloalkyl group,
a $C_2$-$C_6$-alkenyl group and a phenyl group,
wherein said $C_1$-$C_6$-alkyl group is optionally substituted with a $C_3$-$C_6$-cycloalkyl group,
R$^4$ represents a group selected from
a $C_1$-$C_6$-alkyl group, a $C_3$-$C_6$-cycloalkyl group and a $C_2$-$C_6$-hydroxyalkyl group,
wherein said $C_1$-$C_6$-alkyl group is optionally substituted with a group selected from
$C_3$-$C_6$-cycloalkyl and phenyl,
R$^5$ represents a halogen atom or a group selected from
a $C_1$-$C_6$-alkyl group, a $C_3$-$C_6$-cycloalkyl group, a $C_1$-$C_6$-haloalkyl group,
a $C_1$-$C_6$-hydroxyalkyl group, a ($C_1$-$C_3$-alkoxy)-($C_1$-$C_6$-alkyl)- group, a $C_1$-$C_6$-alkoxy group, a $C_1$-$C_6$-alkylsulfanyl group, a —($C_1$-$C_6$-alkyl)-N(R$^7$)(R$^8$) group and a —N(R$^7$)(R$^8$) group,
R$^6$ represents a hydrogen atom or a $C_1$-$C_4$-alkyl group,
R$^7$ and R$^8$ represent, independently for each occurrence, a hydrogen atom or a $C_1$-$C_3$-alkyl group,
R$^{11}$ represents a hydrogen atom,
and tautomers, N-oxides, and salts thereof, and salts of tautomers or N-oxides.

In accordance with further embodiments, the present invention provides compounds of general formula (I), supra, in which:
R$^1$ represents a group selected from
a $C_4$-$C_8$-cycloalkyl group,
a 4- to 6-membered heterocycloalkyl group,
a phenyl group, an indanyl group and a monocyclic- or bicyclic heteroaryl group,
wherein said cycloalkyl groups are optionally substituted, one or two times, with a phenyl group,
wherein said phenyl substituent is optionally substituted, one, two or three times, each substituent independently selected from a halogen atom,
and
wherein said 4- to 6-membered heterocycloalkyl group is optionally substituted one or two times, each substituent independently selected from a $C_1$-$C_3$-alkyl group,
and
wherein said 4- to 6-membered heterocycloalkyl group is connected to the rest of the molecule via a carbon atom of the said heterocycloalkyl group,
and
wherein said phenyl groups are optionally substituted, one, two, three or four times, each substituent independently selected from a halogen atom or a group selected from
$C_1$-$C_4$-alkyl, $C_1$-$C_3$-haloalkyl, $C_1$-$C_3$-hydroxyalkyl, $C_1$-$C_3$-alkoxy, hydroxy, —C(=O)OR$^6$, —N(R$^7$)(R$^8$), —($C_1$-$C_3$-alkyl)-N(R$^7$)(R$^8$), —S(=O)$_2$($C_1$-$C_3$-alkyl), —S(=O)(=NR$^{11}$)($C_1$-$C_3$-alkyl) and —P(=O)($C_1$-$C_3$-alkyl)$_2$,
and
wherein said monocyclic or bicyclic heteroaryl group is optionally substituted one, two or three times, each substituent independently selected from a halogen atom or a group selected from
$C_1$-$C_3$-alkyl and $C_1$-$C_3$-alkoxy,
R$^2$ represents a hydrogen atom or a fluorine atom,
R$^3$ represents a group selected from
a $C_1$-$C_6$-alkyl group, a $C_3$-$C_8$-cycloalkyl group, a $C_1$-$C_6$-haloalkyl group,
a $C_2$-$C_6$-alkenyl group and a phenyl group,
wherein said $C_1$-$C_6$-alkyl group is optionally substituted with a $C_3$-$C_6$-cycloalkyl group,
R$^4$ represents a group selected from
a $C_1$-$C_6$-alkyl group, a $C_3$-$C_6$-cycloalkyl group and a $C_2$-$C_6$-hydroxyalkyl group,
wherein said $C_1$-$C_6$-alkyl group is optionally substituted with a group selected from
$C_3$-$C_6$-cycloalkyl and phenyl,
R$^5$ represents a halogen atom or a group selected from
a $C_1$-$C_6$-alkyl group, a $C_3$-$C_6$-cycloalkyl group, a $C_1$-$C_6$-haloalkyl group,
a $C_1$-$C_6$-hydroxyalkyl group, a ($C_1$-$C_3$-alkoxy)-($C_1$-$C_6$-alkyl)- group, a $C_1$-$C_6$-alkoxy group, a $C_1$-$C_6$-alkylsulfanyl group, a —($C_1$-$C_6$-alkyl)-N(R$^7$)(R$^8$) group and a —N(R$^7$)(R$^8$) group,
R$^6$ represents a hydrogen atom or a $C_1$-$C_4$-alkyl group,
R$^7$ and R$^8$ represent, independently for each occurrence, a hydrogen atom or a $C_1$-$C_3$-alkyl group,
R$^{11}$ represents a hydrogen atom,
and tautomers, N-oxides, and salts thereof, and salts of tautomers or N-oxides.

In accordance with other embodiments, the present invention provides compounds of general formula (I), supra, in which:
R$^1$ represents a group selected from
a $C_5$-$C_7$-alkyl group,
a $C_5$-$C_7$-cycloalkyl group,
a $C_1$-$C_2$-alkyl group which is substituted with a $C_5$-$C_7$-cycloalkyl group,
a $C_2$-$C_6$-alkyl group which is substituted with a phenyl group,
a $C_2$-$C_5$-hydroxyalkyl group,
a —($C_3$-$C_8$-alkyl)-N(R$^7$)(R$^8$) group,
a —($C_3$-$C_8$-alkyl)-C(=O)N(R$^7$)(R$^8$) group,
a 5- to 6-membered heterocycloalkyl group,
which is optionally substituted one or two times, with a $C_1$-$C_3$-alkyl group,
and which is connected to the rest of the molecule via a
carbon atom,
a phenyl group,
which is optionally substituted, one, two or three times,
each substituent independently selected from a halogen atom or a group selected from $C_1$-$C_3$-alkyl, $C_1$-$C_3$-haloalkyl, $C_1$-$C_3$-alkoxy, hydroxy, —C(=O)OR$^6$, —C(=O)N(R$^7$)(R$^8$), —N(R$^7$)(R$^8$), —($C_1$-$C_3$-alkyl)-N(R$^7$)(R$^8$), —O—C(=O)—($C_1$-$C_4$-alkyl), —S—$C_1$-$C_3$-alkyl, —S(=O)$_2$—$C_1$-$C_3$-alkyl, —S(=O)(=NH)($C_1$-$C_3$-alkyl) and
an indanyl group, and
a monocyclic heteroaryl group,
which is optionally substituted one or two times, each substituent independently selected from a group selected from
$C_1$-$C_3$-alkyl and $C_1$-$C_3$-alkoxy,
R$^2$ represents a hydrogen atom or a halogen atom,
R$^3$ represents a group selected from
a $C_1$-$C_6$-alkyl group, a $C_3$-$C_6$-cycloalkyl group, a $C_1$-$C_6$-haloalkyl group, a $C_2$-$C_6$-alkenyl group and a phenyl group,
wherein said $C_1$-$C_6$-alkyl group is optionally substituted with a cyclopropyl group or a NR$^7$R$^8$ group,
R$^4$ represents a group selected from
a $C_2$-$C_4$-alkenyl group, a $C_3$-$C_6$-cycloalkyl group and a $C_1$-$C_3$-hydroxyalkyl group,
a $C_1$-$C_5$-alkyl group,
which is optionally substituted with a group selected from cyclopropyl and phenyl,
R$^5$ represents a halogen atom or a group selected from
a $C_1$-$C_4$-alkyl group,
a $C_3$-$C_8$-cycloalkyl group,
a $C_1$-$C_3$-haloalkyl group, which is optionally substituted with a hydroxy group,
a $C_1$-$C_3$-hydroxyalkyl group,
($C_1$-$C_3$-alkyl)-O—($C_1$-$C_3$-alkyl)- group,
a $C_1$-$C_4$-alkoxy group,
a $C_1$-$C_3$-alkylsulfanyl group,
a —($C_1$-$C_3$-alkyl)-N(R$^7$)(R$^8$) group,
R$^6$ represents a hydrogen atom or a $C_1$-$C_3$-alkyl group,
R$^7$ and R$^8$ represent, independently for each occurrence, a hydrogen atom or a $C_1$-$C_3$-alkyl group or a cyclopropyl group,
or a tautomer, an N-oxide, a salt, a salt of a tautomer or a salt of an N-oxide thereof.

In accordance with other embodiments, the present invention provides compounds of general formula (I), supra, in which:
R$^1$ represents a group selected from
a $C_5$-$C_7$-alkyl group, a $C_5$-$C_7$-cycloalkyl group,
a $C_1$-$C_2$-alkyl group which is substituted with a $C_5$-$C_7$-cycloalkyl group,
a $C_2$-$C_5$-hydroxyalkyl group, a —($C_3$-$C_8$-alkyl)-N(R$^7$)(R$^8$) group,
a —($C_3$-$C_8$-alkyl)-C(=O)N(R$^7$)(R$^8$) group, a 5- to 6-membered heterocycloalkyl group,
a phenyl group, an indanyl group, and a monocyclic heteroaryl group,
which 5- to 6-membered heterocycloalkyl group is optionally substituted one or two times, with a $C_1$-$C_3$-alkyl group,
and
wherein said 5- to 6-membered heterocycloalkyl group is connected to the rest of the molecule via a carbon atom of the said heterocycloalkyl group,
and
wherein said phenyl groups are optionally substituted, one, two or three times, each substituent independently selected from a halogen atom or a group selected from
$C_1$-$C_4$-alkyl, $C_1$-$C_3$-haloalkyl, $C_1$-$C_3$-alkoxy, hydroxy, —C(=O)OR$^6$, —N(R$^7$)(R$^8$) and —($C_1$-$C_3$-alkyl)-N(R$^7$)(R$^8$),
and which monocyclic heteroaryl group is optionally substituted one or two times, each substituent independently selected from a group selected from
$C_1$-$C_3$-alkyl and $C_1$-$C_3$-alkoxy,
$R^2$ represents a hydrogen atom or a fluorine atom,
$R^3$ represents a group selected from
a $C_1$-$C_6$-alkyl group, a $C_3$-$C_6$-cycloalkyl group, a $C_1$-$C_6$-haloalkyl group, a $C_2$-$C_6$-alkenyl group and a phenyl group,
wherein said $C_1$-$C_6$-alkyl group is optionally substituted with a cyclopropyl group,
$R^4$ represents a group selected from
a $C_1$-$C_5$-alkyl group, a $C_3$-$C_6$-cycloalkyl group and a $C_2$-$C_3$-hydroxyalkyl group,
wherein said $C_1$-$C_4$-alkyl group is optionally substituted with a group selected from
cyclopropyl and phenyl,
$R^5$ represents a halogen atom or a group selected from
a $C_1$-$C_4$-alkyl group, a $C_3$-$C_6$-cycloalkyl group, a $C_1$-$C_3$-haloalkyl group,
a $C_1$-$C_3$-hydroxyalkyl group, ($C_1$-$C_3$-alkyl)-O—($C_1$-$C_3$-alkyl)- group, a $C_1$-$C_4$-alkoxy group,
a $C_1$-$C_3$-alkylsulfanyl group, a —($C_1$-$C_3$-alkyl)-N($R^7$)($R^8$) group and a —N($R^7$)($R^8$) group,
$R^6$ represents a hydrogen atom or a $C_1$-$C_3$-alkyl group,
$R^7$ and $R^8$ represent, independently for each occurrence, a hydrogen atom or a $C_1$-$C_3$-alkyl group,
and tautomers, N-oxides, and salts thereof, and salts of tautomers or N-oxides.

In accordance with other embodiments, the present invention provides compounds of general formula (I), supra, in which:
$R^1$ represents a group selected from
a $C_5$-$C_7$-cycloalkyl group,
a 5- to 6-membered heterocycloalkyl group,
a phenyl group, an indanyl group, and a monocyclic heteroaryl group,
which 5- to 6-membered heterocycloalkyl group is optionally substituted one or two times, with a $C_1$-$C_3$-alkyl group,
and
wherein said 5- to 6-membered heterocycloalkyl group is connected to the rest of the molecule via a carbon atom of the said heterocycloalkyl group,
and
wherein said phenyl groups are optionally substituted, one, two or three times, each substituent independently selected from a halogen atom or a group selected from
$C_1$-$C_4$-alkyl, $C_1$-$C_3$-haloalkyl, $C_1$-$C_3$-alkoxy, hydroxy, —C(=O)O$R^6$, —N($R^7$)($R^8$) and —($C_1$-$C_3$-alkyl)-N($R^7$)($R^8$), and
which monocyclic heteroaryl group is optionally substituted one or two times, each substituent independently selected from a group selected from $C_1$-$C_3$-alkyl and $C_1$-$C_3$-alkoxy,
$R^2$ represents a hydrogen atom or a fluorine atom,
$R^3$ represents a group selected from
a $C_1$-$C_6$-alkyl group, a $C_3$-$C_6$-cycloalkyl group, a $C_1$-$C_6$-haloalkyl group, a $C_2$-$C_6$-alkenyl group and a phenyl group,
wherein said $C_1$-$C_6$-alkyl group is optionally substituted with a cyclopropyl group,
$R^4$ represents a group selected from
a $C_1$-$C_5$-alkyl group, a $C_3$-$C_6$-cycloalkyl group and a $C_2$-$C_3$-hydroxyalkyl group,
wherein said $C_1$-$C_4$-alkyl group is optionally substituted with a group selected from
cyclopropyl and phenyl,
$R^5$ represents a halogen atom or a group selected from
a $C_1$-$C_4$-alkyl group, a $C_3$-$C_6$-cycloalkyl group, a $C_1$-$C_3$-haloalkyl group,
a $C_1$-$C_3$-hydroxyalkyl group, ($C_1$-$C_3$-alkyl)-O—($C_1$-$C_3$-alkyl)- group, a $C_1$-$C_4$-alkoxy group,
a $C_1$-$C_3$-alkylsulfanyl group, a —($C_1$-$C_3$-alkyl)-N($R^7$)($R^8$) group and a —N($R^7$)($R^8$) group,
$R^6$ represents a hydrogen atom or a $C_1$-$C_3$-alkyl group,
$R^7$ and $R^8$ represent, independently for each occurrence, a hydrogen atom or a $C_1$-$C_3$-alkyl group,
and tautomers, N-oxides, and salts thereof, and salts of tautomers or N-oxides.

In accordance with further embodiments, the present invention provides compounds of general formula (I), supra, in which:
$R^1$ represents a group selected from
a $C_5$-$C_7$-alkyl group,
a $C_5$-$C_7$-cycloalkyl group,
a $C_1$-$C_2$-alkyl group which is substituted with a $C_5$-$C_6$-cycloalkyl group,
a $C_2$-$C_6$-alkyl group which is substituted with a phenyl group,
a $C_2$-$C_4$-hydroxyalkyl group,
a —($C_3$-$C_4$-alkyl)-N($R^7$)($R^8$) group,
a $CH_3CH_2CH$=C(=O)$NH_2$ group,
a 5- to 6-membered heterocycloalkyl group,
which is optionally substituted one or two times, with a $C_1$-$C_3$-alkyl group,
and
which is connected to the rest of the molecule via a carbon atom,
a phenyl group,
which is optionally substituted, one, two or three times, each substituent independently selected from a halogen atom or a group selected from $C_1$-$C_3$-alkyl, $C_1$-$C_3$-haloalkyl, $C_1$-$C_3$-alkoxy, hydroxy, —C(=O)O$R^6$, —C(=O)N($R^7$)($R^8$), —N($R^7$)($R^8$), —O—C(=O)—($C_1$-$C_4$-alkyl), —S—$C_1$-$C_3$-alkyl, —S(=O)$_2$—$C_1$-$C_3$-alkyl, —S(=O)(=NH)($C_1$-$C_3$-alkyl) and —($C_1$-$C_3$-alkyl)-N($R^7$)($R^8$),
an indanyl group, and
a monocyclic heteroaryl group,
which is optionally substituted one or two times, each substituent independently selected from a group selected from
$C_1$-$C_3$-alkyl and $C_1$-$C_3$-alkoxy,
$R^2$ represents a hydrogen atom or a halogen atom,
$R^3$ represents a group selected from
a $C_1$-$C_6$-alkyl group, a $C_3$-$C_6$-cycloalkyl group, a $C_1$-$C_3$-haloalkyl group, a $C_2$-$C_6$-alkenyl group and a phenyl group,
wherein said $C_1$-$C_6$-alkyl group is optionally substituted with a cyclopropyl group or a N($R^7$)($R^8$) group,
$R^4$ represents a group selected from
a $C_2$-$C_4$-alkenyl group,
a $C_3$-$C_8$-cycloalkyl group,
a $C_1$-$C_3$-hydroxyalkyl group,
a $C_1$-$C_4$-alkyl group,
which is optionally substituted with a group selected from cyclopropyl and phenyl,
$R^5$ represents a halogen atom or a group selected from
a $C_1$-$C_4$-alkyl group,
a $C_3$-$C_8$-cycloalkyl group, a $C_1$-$C_3$-haloalkyl group, which is optionally substituted with a hydroxy group,
a $C_1$-$C_3$-hydroxyalkyl group,
a $CH_3O$—($C_1$-$C_2$-alkyl)- group,
a $C_1$-$C_3$-alkoxy group,
a methylsulfanyl group,
a —($C_1$-$C_2$-alkyl)-$N(R^7)(R^8)$ group,
a —$N(R^7)(R^8)$ group,
a —$C(=O)OR^6$ group,
a —$C(=O)N(R^7)(R^8)$ group, and
a —$S(=O)(=NR^{11})(C_1$-$C_3$-alkyl) group
$R^6$ represents a hydrogen atom or a methyl group,
$R^7$ and $R^8$ represent, independently for each occurrence, a hydrogen atom or a $C_1$-$C_3$-alkyl group or a cyclopropyl group,
or a tautomer, an N-oxide, a salt, a salt of a tautomer or a salt of an N-oxide thereof.

In accordance with further embodiments, the present invention provides compounds of general formula (I), supra, in which:
$R^1$ represents a group selected from
a $C_5$-$C_7$-cycloalkyl group,
a 5- to 6-membered heterocycloalkyl group,
which is optionally substituted one or two times, with a $C_1$-$C_3$-alkyl group,
and
which is connected to the rest of the molecule via a carbon atom,
a phenyl group,
which is optionally substituted, one, two or three times, each substituent independently selected from a halogen atom or a group selected from $C_1$-$C_3$-alkyl, $C_1$-$C_3$-haloalkyl, $C_1$-$C_3$-alkoxy, hydroxy, —$C(=O)OR^6$, —$C(=O)N(R^7)(R^8)$, —$N(R^7)(R^8)$, —O—C(=O)—($C_1$-$C_4$-alkyl), —S—$C_1$-$C_3$-alkyl, —$S(=O)_2$—$C_1$-$C_3$-alkyl, —$S(=O)(=NH)(C_1$-$C_3$-alkyl) and —($C_1$-$C_3$-alkyl)-$N(R^7)(R^8)$,
an indanyl group, and
a monocyclic heteroaryl group,
which is optionally substituted one or two times, each substituent independently selected from a group selected from
$C_1$-$C_3$-alkyl and $C_1$-$C_3$-alkoxy,
$R^2$ represents a hydrogen atom or a halogen atom,
$R^3$ represents a group selected from
a $C_1$-$C_6$-alkyl group, a $C_3$-$C_6$-cycloalkyl group, a $C_1$-$C_3$-haloalkyl group, a $C_2$-$C_6$-alkenyl group and a phenyl group,
wherein said $C_1$-$C_6$-alkyl group is optionally substituted with a cyclopropyl group or a $N(R^7)(R^8)$ group,
$R^4$ represents a group selected from
a $C_2$-$C_4$-alkenyl group,
a $C_3$-$C_8$-cycloalkyl group,
a $C_1$-$C_3$-hydroxyalkyl group,
a $C_1$-$C_4$-alkyl group,
which is optionally substituted with a group selected from cyclopropyl and phenyl,
$R^5$ represents a halogen atom or a group selected from
a $C_1$-$C_4$-alkyl group,
a $C_3$-$C_8$-cycloalkyl group,
a $C_1$-$C_3$-haloalkyl group, which is optionally substituted with a hydroxy group,
a $C_1$-$C_3$-hydroxyalkyl group,
a $CH_3O$—($C_1$-$C_2$-alkyl)- group,
a $C_1$-$C_3$-alkoxy group,
a methylsulfanyl group,
a —($C_1$-$C_2$-alkyl)-$N(R^7)(R^8)$ group,
a —$N(R^7)(R^8)$ group,
a —$C(=O)OR^6$ group,
a —$C(=O)N(R^7)(R^8)$ group, and
a —$S(=O)(=NR^{11})(C_1$-$C_3$-alkyl) group
$R^6$ represents a hydrogen atom or a methyl group,
$R^7$ and $R^8$ represent, independently for each occurrence, a hydrogen atom or a $C_1$-$C_3$-alkyl group or a cyclopropyl group,
or a tautomer, an N-oxide, a salt, a salt of a tautomer or a salt of an N-oxide thereof.

In accordance with further embodiments, the present invention provides compounds of general formula (I), supra, in which:
$R^1$ represents a group selected from
a $C_5$-$C_7$-alkyl group, a $C_5$-$C_7$-cycloalkyl group,
a $C_1$-$C_2$-alkyl group which is substituted with a $C_5$-$C_6$-cycloalkyl group,
a $C_3$-$C_4$-hydroxyalkyl group, a —($C_3$-$C_4$-alkyl)-$N(R^7)(R^8)$ group, a $CH_3CH_2CH=C(=O)NH_2$ group, a 5- to 6-membered heterocycloalkyl group, a phenyl group, an indanyl group, and a monocyclic heteroaryl group,
wherein said 5- to 6-membered heterocycloalkyl group is optionally substituted one or two times, with a $C_1$-$C_3$-alkyl group,
and
wherein said 5- to 6-membered heterocycloalkyl group is connected to the rest of the molecule via a carbon atom of the said heterocycloalkyl group,
and
wherein said phenyl groups are optionally substituted, one, two or three times, each substituent independently selected from a halogen atom or a group selected from
$C_1$-$C_4$-alkyl, $C_1$-$C_3$-haloalkyl, $C_1$-$C_3$-alkoxy, hydroxy, —$C(=O)OR^6$, —$N(R^7)(R^8)$ and —($C_1$-$C_3$-alkyl)-$N(R^7)(R^8)$,
and
wherein said monocyclic heteroaryl group is optionally substituted one or two times, each substituent independently selected from a group selected from
$C_1$-$C_3$-alkyl and $C_1$-$C_3$-alkoxy,
$R^2$ represents a hydrogen atom or a fluorine atom,
$R^3$ represents a group selected from
a $C_1$-$C_6$-alkyl group, a $C_3$-$C_6$-cycloalkyl group, a $C_1$-$C_6$-haloalkyl group, a $C_2$-$C_6$-alkenyl group and a phenyl group,
wherein said $C_1$-$C_6$-alkyl group is optionally substituted with a cyclopropyl group,
$R^4$ represents a group selected from
a $C_1$-$C_4$-alkyl group, a $C_3$-$C_8$-cycloalkyl group and a $C_2$-$C_3$-hydroxyalkyl group,
wherein said $C_1$-$C_4$-alkyl group is optionally substituted with a group selected from
cyclopropyl and phenyl,
$R^5$ represents a halogen atom or a group selected from
a $C_1$-$C_4$-alkyl group, a $C_3$-$C_6$-cycloalkyl group, a $C_1$-haloalkyl group,
a $C_1$-$C_3$-hydroxyalkyl group, a methoxy-($C_1$-$C_2$-alkyl)- group, a $C_1$-$C_3$-alkoxy group,
a methylsulfanyl group, a —($C_1$-$C_2$-alkyl)-$N(R^7)(R^8)$ group and a —$N(R^7)(R^8)$ group,
$R^6$ represents a hydrogen atom or a methyl group,
$R^7$ and $R^8$ represent, independently for each occurrence, a hydrogen atom or a $C_1$-$C_3$-alkyl group,
or a tautomer, an N-oxide, or a salt thereof, and a salt of a tautomer or an N-oxide.

In accordance with further embodiments, the present invention provides compounds of general formula (I), supra, in which:

$R^1$ represents a group selected from
- a $C_5$-$C_7$-cycloalkyl group,
- a 5- to 6-membered heterocycloalkyl group, a phenyl group, an indanyl group, and a monocyclic heteroaryl group,
  - wherein said 5- to 6-membered heterocycloalkyl group is optionally substituted one or two times, with a $C_1$-$C_3$-alkyl group,
  - and
  - wherein said 5- to 6-membered heterocycloalkyl group is connected to the rest of the molecule via a carbon atom of the said heterocycloalkyl group,
  - and
  - wherein said phenyl groups are optionally substituted, one, two or three times, each substituent independently selected from a halogen atom or a group selected from
    $C_1$-$C_4$-alkyl, $C_1$-$C_3$-haloalkyl, $C_1$-$C_3$-alkoxy, hydroxy, —C(=O)OR$^6$, —N(R$^7$)(R$^8$) and —($C_1$-$C_3$-alkyl)-N(R$^7$)(R$^8$),
  - and
  - wherein said monocyclic heteroaryl group is optionally substituted one or two times, each substituent independently selected from a group selected from $C_1$-$C_3$-alkyl and $C_1$-$C_3$-alkoxy, $R^2$ represents a hydrogen atom or a fluorine atom,
$R^3$ represents a group selected from
- a $C_1$-$C_6$-alkyl group, a $C_3$-$C_6$-cycloalkyl group, a $C_1$-$C_6$-haloalkyl group, a $C_2$-$C_6$-alkenyl group and a phenyl group,
  - wherein said $C_1$-$C_6$-alkyl group is optionally substituted with a cyclopropyl group, $R^4$ represents a group selected from
- a $C_1$-$C_4$-alkyl group, a $C_3$-$C_8$-cycloalkyl group and a $C_2$-$C_3$-hydroxyalkyl group,
  - wherein said $C_1$-$C_4$-alkyl group is optionally substituted with a group selected from cyclopropyl and phenyl, $R^5$ represents a halogen atom or a group selected from
- a $C_1$-$C_4$-alkyl group, a $C_3$-$C_6$-cycloalkyl group, a $C_1$-haloalkyl group,
- a $C_1$-$C_3$-hydroxyalkyl group, a methoxy-($C_1$-$C_2$-alkyl)-group, a $C_1$-$C_3$-alkoxy group,
- a methylsulfanyl group, a —($C_1$-$C_2$-alkyl)-N(R$^7$)(R$^8$) group and a —N(R$^7$)(R$^8$) group, $R^6$ represents a hydrogen atom or a methyl group,
$R^7$ and $R^8$ represent, independently for each occurrence, a hydrogen atom or a $C_1$-$C_3$-alkyl group,
and a tautomer, an N-oxide, or a salt thereof, and a salt of a tautomer or an N-oxide.

In accordance with further embodiments, the present invention provides compounds of general formula (I), supra, in which:

$R^1$ represents a group selected from
- a $C_5$-$C_7$-alkyl group, a $C_5$-$C_7$-cycloalkyl group,
- a $C_1$-$C_2$-alkyl group which is substituted with a $C_5$-$C_6$-cycloalkyl group,
- a $C_3$-$C_4$-hydroxyalkyl group, a —($C_3$-$C_4$-alkyl)-N(R$^7$)(R$^8$) group, a CH$_3$CH$_2$CH—C(=O)NH$_2$ group, a 5- to 6-membered heterocycloalkyl group, a phenyl group, an indanyl group, and a monocyclic heteroaryl group,
  - wherein said 5- to 6-membered heterocycloalkyl group is selected from tetrahydrofuranyl, tetrahydro-2H-pyranyl and piperidinyl,
  - which 5- to 6-membered heterocycloalkyl group is optionally substituted one or two times, with a $C_1$-$C_3$-alkyl group,
  - and
  - wherein said 5- to 6-membered heterocycloalkyl group is connected to the rest of the molecule via a carbon atom of the said heterocycloalkyl group,
  - and
  - wherein said phenyl groups are optionally substituted, one, two or three times, each substituent independently selected from a halogen atom or a group selected from
    $C_1$-$C_4$-alkyl, $C_1$-$C_3$-haloalkyl, $C_1$-$C_3$-alkoxy, hydroxy, —C(=O)OR$^6$, —N(R$^7$)(R$^8$) and —($C_1$-$C_3$-alkyl)-N(R$^7$)(R$^8$),
  - and
  - wherein said monocyclic heteroaryl group is selected from
    oxazolyl, pyrazolyl, pyridinyl and pyrimidinyl,
  - which monocyclic heteroaryl group is optionally substituted one or two times, each substituent independently selected from a group selected from $C_1$-$C_3$-alkyl and $C_1$-$C_3$-alkoxy, $R^2$ represents a hydrogen atom or a fluorine atom,
$R^3$ represents a group selected from
- a $C_1$-$C_6$-alkyl group, a $C_3$-$C_6$-cycloalkyl group, a $C_1$-$C_6$-haloalkyl group, a $C_2$-$C_6$-alkenyl group and a phenyl group,
  - wherein said $C_1$-$C_6$-alkyl group is optionally substituted with a cyclopropyl group, $R^4$ represents a group selected from
- a $C_1$-$C_4$-alkyl group, a $C_3$-$C_8$-cycloalkyl group and a $C_2$-$C_3$-hydroxyalkyl group,
  - wherein said $C_1$-$C_4$-alkyl group is optionally substituted with a group selected from cyclopropyl and phenyl, $R^5$ represents a halogen atom or a group selected from
- a $C_1$-$C_4$-alkyl group, a $C_3$-$C_6$-cycloalkyl group, a $C_1$-haloalkyl group,
- a $C_1$-$C_3$-hydroxyalkyl group, a methoxy-($C_1$-$C_2$-alkyl)-group, a $C_1$-$C_3$-alkoxy group,
- a methylsulfanyl group, a —($C_1$-$C_2$-alkyl)-N(R$^7$)(R$^8$) group and a —N(R$^7$)(R$^8$) group, $R^6$ represents a hydrogen atom or a methyl group,
$R^7$ and $R^8$ represent, independently for each occurrence, a hydrogen atom or a $C_1$-$C_3$-alkyl group,
and tautomers, N-oxides, and salts thereof, and salts of tautomers or N-oxides.

In accordance with further embodiments, the present invention provides compounds of general formula (I), supra, in which:

$R^1$ represents a group selected from
- 3-pentyl, 2,2-dimethylpropyl, 4-heptyl, 4-fluorophenyl-cyclopropyl, cyclopentyl, cyclohexyl, cycloheptyl, cyclopentylmethyl, cyclohexylmethyl, 1-cyclohexylethyl, 1-hydroxypropan-2-yl,
- 2-hydroxypropyl, 1-hydroxybutan-2-yl, 1-cyanobutan-2-yl, 1-phenylbutan-2-yl, 1-amino-2-propyl, 1-amino-2-butyl, 1-amino-1-oxobutan-2-yl, indan-2-yl,
- a 5- to 6-membered heterocycloalkyl group, which is selected from tetrahydrofuran-3-yl, tetrahydro-2H-pyran-4-yl and piperidin-4-yl, and which is optionally substituted one or two times with a methyl group,
- a phenyl group, which is optionally substituted, one, two or three times, each substituent independently selected from a fluorine atom or a chlorine atom or a group selected from methyl, ethyl, propyl, isopropyl, difluoromethyl, trifluoromethyl, methoxy, —O—C(=O)-1,1-dimethylethyl, hydroxy, —C(=O)OCH$_3$, —C(=O)NH-cyclopropyl, amino, methylamino, aminomethyl, —S—CH$_3$, —S(=O)$_2$CH$_3$, and —S(=O)(NH)CH$_3$, and a monocyclic heteroaryl group, which is selected from
oxazol-2-yl, pyrazol-3-yl, pyrazol-5-yl, pyridin-2-yl, pyridin-3-yl, pyridin-4-yl, pyrimidin-2-yl, pyrimidin-4-yl, chinolin-5-yl, indazol-5-yl,
and which is optionally substituted one or two times, each substituent independently selected from methyl and methoxy, $R^2$ represents a hydrogen atom or a fluorine or chlorine atom, $R^3$ represents a group selected from
propyl, 2-methylpropyl, 3-pentyl, cyclopropylmethyl, cyclopropyl, cyclopropylmethyl, cyclobutyl, cyclopentyl, cyclohexyl, difluoromethyl, trifluoromethyl, 1,1-difluoroethyl, prop-2-en-1-yl, 2-methyl-prop-1-en-1-yl, N,N-dimethylaminoethyl, and phenyl, $R^4$ represents a group selected from
methyl, ethyl, propyl, isopropyl, 2-butyl, prop-2-en-1-yl, cyclopropylmethyl, benzyl, cyclopropyl, cyclobutyl, cyclopentyl, 2-hydroxyethyl, $R^5$ represents a chlorine atom or a group selected from
methyl, ethyl, propyl, isopropyl, 2-butyl, tert-butyl, cyclopropyl, cyclobutyl, cyclopentyl, trifluoromethyl, hydroxymethyl, 1-hydroxyethyl, 2-hydroxypropan-2-yl, 1-chloroethyl, 1-hydroxy-2,2,2-trifluoroethyl, 1-methoxyethyl, methoxy, isopropoxy, methylsulfanyl, aminomethyl, (methylamino)methyl, (dimethylamino)methyl, 1-aminoethyl, 2-aminoethyl, methylamino and ethyl(methyl)amino, —C(=O)OH, —C(=O)OCH$_3$, —C(=O)NH$_2$, —C(=O)NHCH$_3$, —C(=O)NHcyclopropyl, —C(=O)N(CH$_3$)$_2$, and —S(=O)(=NH)CH$_3$, or a tautomer, an N-oxide, a salt, a salt of a tautomer or a salt of an N-oxide thereof.

In accordance with further embodiments, the present invention provides compounds of general formula (I), supra, in which:

$R^1$ represents a group selected from
4-fluorophenylcyclopropyl, cyclopentyl, cyclohexyl, cycloheptyl, cyclohexylmethyl, 1-indan-2-yl,
a 5- to 6-membered heterocycloalkyl group, which is selected from tetrahydrofuran-3-yl, tetrahydro-2H-pyran-4-yl and piperidin-4-yl, and which is optionally substituted one or two times with a methyl group,
a phenyl group, which is optionally substituted, one, two or three times, each substituent independently selected from a fluorine atom or a chlorine atom or a group selected from
methyl, ethyl, propyl, isopropyl, difluoromethyl, trifluoromethyl, methoxy, —O—C(=O)-1,1-dimethylethyl, hydroxy, —C(=O)OCH$_3$, —C(=O)NH-cyclopropyl, amino, methylamino, aminomethyl, —S—CH$_3$, —S(=O)$_2$CH$_3$, and —S(=O)(NH)CH$_3$, and a monocyclic heteroaryl group, which is selected from
oxazol-2-yl, pyrazol-3-yl, pyrazol-5-yl, pyridin-2-yl, pyridin-3-yl, pyridin-4-yl, pyrimidin-2-yl, pyrimidin-4-yl, chinolin-5-yl, indazol-5-yl,
and which is optionally substituted one or two times, each substituent independently selected from methyl and methoxy, $R^2$ represents a hydrogen atom or a fluorine or chlorine atom, $R^3$ represents a group selected from
propyl, 2-methylpropyl, 3-pentyl, cyclopropylmethyl, cyclopropyl, cyclopropylmethyl, cyclobutyl, cyclopentyl, cyclohexyl, difluoromethyl, trifluoromethyl, 1,1-difluoroethyl, prop-2-en-1-yl, 2-methyl-prop-1-en-1-yl, N,N-dimethylaminoethyl, and phenyl, $R^4$ represents a group selected from
methyl, ethyl, propyl, isopropyl, 2-butyl, prop-2-en-1-yl, cyclopropylmethyl, benzyl, cyclopropyl, cyclobutyl, cyclopentyl, 2-hydroxyethyl, $R^5$ represents a chlorine atom or a group selected from
methyl, ethyl, propyl, isopropyl, 2-butyl, tert-butyl, cyclopropyl, cyclobutyl, cyclopentyl, trifluoromethyl, hydroxymethyl, hydroxy(trifluoromethyl)methyl, 1-hydroxyethyl, 2-hydroxypropan-2-yl, 1-chloroethyl, 1-hydroxy-2,2,2-trifluoroethyl, 1-methoxyethyl, methoxy, isopropoxy, methylsulfanyl, aminomethyl, (methylamino)methyl, (dimethylamino)methyl, 1-aminoethyl, 2-aminoethyl, methylamino and ethyl(methyl)amino, —C(=O)OH, —C(=O)OCH$_3$, —C(=O)NH$_2$, —C(=O)NHCH$_3$, —C(=O)NHcyclopropyl, —C(=O)N(CH$_3$)$_2$, and —S(=O)(=NH)CH$_3$, or a tautomer, an N-oxide, a salt, a salt of a tautomer or a salt of an N-oxide thereof.

In accordance with further embodiments, the present invention provides compounds of general formula (I), supra, in which:

$R^1$ represents a group selected from
3-pentyl, 2,2-dimethylpropyl, 4-heptyl, 4-fluorophenylcyclopropyl, cyclopentyl, cyclohexyl, cycloheptyl, cyclopentylmethyl, cyclohexylmethyl, 1-cyclohexylethyl, 1-hydroxypropan-2-yl,
2-hydroxypropyl, 1-hydroxybutan-2-yl, 1-cyanobutan-2-yl, 1-phenylbutan-2-yl, 1-amino-2-propyl, 1-amino-2-butyl, 1-amino-1-oxobutan-2-yl, indan-2-yl,
a 5- to 6-membered heterocycloalkyl group, which is selected from tetrahydrofuran-3-yl, tetrahydro-2H-pyran-4-yl and piperidin-4-yl, and which is optionally substituted one or two times with a methyl group,
a phenyl group, which is optionally substituted, one, two or three times, each substituent independently selected from a fluorine atom or a chlorine atom or a group selected from
methyl, ethyl, propyl, isopropyl, difluoromethyl, trifluoromethyl, methoxy, —O—C(=O)-1,1-dimethylethyl, hydroxy, —C(=O)OCH$_3$, —C(=O)NH-cyclopropyl, amino, methylamino, aminomethyl, —S—CH$_3$, —S(=O)$_2$CH$_3$, and —S(=O)(NH)CH$_3$, and a monocyclic heteroaryl group, which is selected from
oxazol-2-yl, pyrazol-3-yl, pyrazol-5-yl, pyridin-2-yl, pyridin-3-yl, pyridin-4-yl, pyrimidin-2-yl, pyrimidin-4-yl, chinolin-5-yl, indazol-5-yl,
and which is optionally substituted one or two times, each substituent independently selected from methyl and methoxy, $R^2$ represents a hydrogen atom or a fluorine atom, $R^3$ represents a group selected from
propyl, 2-methylpropyl, 3-pentyl, cyclopropylmethyl, cyclopropyl, cyclopropylmethyl, cyclobutyl, cyclopentyl, cyclohexyl, difluoromethyl, trifluoromethyl, 1,1-difluoroethyl, prop-2-en-1-yl, 2-methyl-prop-1-en-1-yl, N,N-dimethylaminoethyl, and phenyl, R⁴ represents a group selected from
methyl, ethyl, propyl, isopropyl, 2-butyl, prop-2-en-1-yl, cyclopropylmethyl, benzyl, cyclopropyl, cyclobutyl, cyclopentyl, 2-hydroxyethyl, —C(=O)OH, —C(=O)OCH₃, —C(=O)NH₂, —C(=O)NHCH₃, —C(=O)NHcyclopropyl, —C(=O)N(CH₃)₂, and —S(=O)(=NH)CH₃, R⁵ represents a chlorine atom or a group selected from
methyl, ethyl, propyl, isopropyl, 2-butyl, tert-butyl, cyclopropyl, cyclobutyl, cyclopentyl, trifluoromethyl, hydroxymethyl, hydroxy(trifluoromethyl)methyl, 1-hydroxyethyl, 2-hydroxypropan-2-yl, 1-chloroethyl, 1-hydroxy-2,2,2-trifluoroethyl, 1-methoxyethyl, methoxy, isopropoxy, methylsulfanyl, aminomethyl, (methylamino)methyl, (dimethylamino)methyl, 1-aminoethyl, 2-aminoethyl, methylamino and ethyl(methyl)amino, or a tautomer, an N-oxide, a salt, a salt of a tautomer or a salt of an N-oxide thereof.

In accordance with further embodiments, the present invention provides compounds of general formula (I), supra, in which:

R¹ represents a group selected from
4-fluorophenylcyclopropyl, cyclopentyl, cyclohexyl, cycloheptyl, indan-2-yl,
a 5- to 6-membered heterocycloalkyl group, which is selected from tetrahydrofuran-3-yl, tetrahydro-2H-pyran-4-yl and piperidin-4-yl, and which is optionally substituted one or two times with a methyl group,
a phenyl group, which is optionally substituted, one, two or three times, each substituent independently selected from a fluorine atom or a chlorine atom or a group selected from
methyl, ethyl, propyl, isopropyl, difluoromethyl, trifluoromethyl, methoxy, —O—C(=O)-1,1-dimethylethyl, hydroxy, —C(=O)OCH₃, —C(=O)NH-cyclopropyl, amino, methylamino, aminomethyl, —S—CH₃, —S(=O)₂CH₃, and —S(=O)(NH)CH₃, and
a monocyclic heteroaryl group, which is selected from oxazol-2-yl, pyrazol-3-yl, pyrazol-5-yl, pyridin-2-yl, pyridin-3-yl, pyridin-4-yl, pyrimidin-2-yl, pyrimidin-4-yl, chinolin-5-yl, indazol-5-yl,
and which is optionally substituted one or two times, each substituent independently selected from methyl and methoxy, R² represents a hydrogen atom or a fluorine atom,
R³ represents a group selected from
propyl, 2-methylpropyl, 3-pentyl, cyclopropylmethyl, cyclopropyl, cyclopropylmethyl, cyclobutyl, cyclopentyl, cyclohexyl, difluoromethyl, trifluoromethyl, 1,1-difluoroethyl, prop-2-en-1-yl, 2-methyl-prop-1-en-1-yl, N,N-dimethylaminoethyl, and phenyl, R⁴ represents a group selected from
methyl, ethyl, propyl, isopropyl, 2-butyl, prop-2-en-1-yl, cyclopropylmethyl, benzyl, cyclopropyl, cyclobutyl, cyclopentyl, 2-hydroxyethyl, R⁵ represents a chlorine atom or a group selected from
methyl, ethyl, propyl, isopropyl, 2-butyl, tert-butyl, cyclopropyl, cyclobutyl, cyclopentyl, trifluoromethyl, hydroxymethyl, hydroxy(trifluoromethyl)methyl, 1-hydroxyethyl, 2-hydroxypropan-2-yl, 1-chloroethyl, 1-hydroxy-2,2,2-trifluoroethyl, 1-methoxyethyl, methoxy, isopropoxy, methylsulfanyl, aminomethyl, (methylamino)methyl, (dimethylamino)methyl, 1-aminoethyl, 2-aminoethyl, methylamino and ethyl(methyl)amino, —C(=O)OH, —C(=O)OCH₃, —C(=O)NH₂, —C(=O)NHCH₃, —C(=O)NHcyclopropyl, —C(=O)N(CH₃)₂, and —S(=O)(=NH)CH₃, or a tautomer, an N-oxide, a salt, a salt of a tautomer or a salt of an N-oxide thereof.

In accordance with further embodiments, the present invention provides compounds of general formula (I), supra, in which:

R¹ represents a group selected from
3-pentyl, 2,2-dimethylpropyl, 4-heptyl, cyclopentyl, cyclohexyl, cycloheptyl, cyclopentylmethyl, cyclohexylmethyl, 1-cyclohexylethyl, 1-hydroxypropan-2-yl, 2-hydroxypropyl, 1-hydroxybutan-2-yl, 1-amino-2-propyl, 1-amino-2-butyl, CH₃CH₂CH—C(=O)NH₂, 5- to 6-membered heterocycloalkyl, phenyl, indan-2-yl and monocyclic heteroaryl,
wherein said 5- to 6-membered heterocycloalkyl group is selected from tetrahydrofuran-3-yl, tetrahydro-2H-pyran-4-yl and piperidin-4-yl,
which 5- to 6-membered heterocycloalkyl group is optionally substituted one or two times, with a methyl group,
and
wherein said phenyl groups are optionally substituted, one, two or three times, each substituent independently selected from a fluorine atom or a chlorine atom or a group selected from
methyl, ethyl, propyl, isopropyl, trifluoromethyl, methoxy, hydroxy, C(=O)OCH₃, amino, methylamino and aminomethyl,
and
wherein said monocyclic heteroaryl group is selected from oxazol-2-yl, pyrazol-3-yl, pyridin-2-yl, pyridin-3-yl, pyridin-4-yl, pyrimidin-2-yl and pyrimidin-4-yl,
which monocyclic heteroaryl group is optionally substituted one or two times, each substituent independently selected from a group selected from methyl and methoxy, R² represents a hydrogen atom or a fluorine atom,
R³ represents a group selected from
propyl, 2-methylpropyl, 3-pentyl, cyclopropylmethyl, cyclopropyl, cyclobutyl, cyclopentyl, cyclohexyl, trifluoromethyl, allyl, 2-methyl-prop1-enyl and phenyl, R⁴ represents a group selected from
methyl, ethyl, propyl, isopropyl, 2-butyl, cyclopropylmethyl, benzyl, cyclopropyl, cyclopentyl and 2-hydroxyethyl, R⁵ represents a chlorine atom or a group selected from
methyl, ethyl, propyl, isopropyl, 2-butyl, tert-butyl, cyclopropyl, cyclobutyl, cyclopentyl, trifluoromethyl, hydroxymethyl, 1-hydroxyethyl, 2-hydroxypropan-2-yl, 1-methoxyethyl, methoxy, isopropoxy, methylsulfanyl, aminomethyl, (methylamino)methyl, (dimethylamino)methyl, 1-aminoethyl, 2-aminoethyl, methylamino and ethyl(methyl)amino, and tautomers, N-oxides, and salts thereof, and salts of tautomers or N-oxides.

In accordance with further embodiments, the present invention provides compounds of general formula (I), supra, in which:
R¹ represents a group selected from
cyclopentyl, cyclohexyl, cycloheptyl, CH₃CH₂CH—C(=O)NH₂,
5- to 6-membered heterocycloalkyl, phenyl, indan-2-yl and monocyclic heteroaryl, wherein said 5- to 6-membered heterocycloalkyl group is selected from tetrahydrofuran-3-yl, tetrahydro-2H-pyran-4-yl and piperidin-4-yl,
  which 5- to 6-membered heterocycloalkyl group is optionally substituted one or two times, with a methyl group,
  and
  wherein said phenyl groups are optionally substituted, one, two or three times, each substituent independently selected from a fluorine atom or a chlorine atom or a group selected from
    methyl, ethyl, propyl, isopropyl, trifluoromethyl, methoxy, hydroxy, C(=O)OCH$_3$, amino, methylamino and aminomethyl,
  and
  wherein said monocyclic heteroaryl group is selected from oxazol-2-yl, pyrazol-3-yl, pyridin-2-yl, pyridin-3-yl, pyridin-4-yl, pyrimidin-2-yl and pyrimidin-4-yl,
    which monocyclic heteroaryl group is optionally substituted one or two times, each substituent independently selected from a group selected from methyl and methoxy,
$R^2$ represents a hydrogen atom or a fluorine atom,
$R^3$ represents a group selected from
  propyl, 2-methylpropyl, 3-pentyl, cyclopropylmethyl, cyclopropyl, cyclobutyl, cyclopentyl, cyclohexyl, trifluoromethyl, allyl, 2-methyl-prop1-enyl and phenyl,
$R^4$ represents a group selected from
  methyl, ethyl, propyl, isopropyl, 2-butyl, cyclopropylmethyl, benzyl, cyclopropyl, cyclopentyl and 2-hydroxyethyl,
$R^5$ represents a chlorine atom or a group selected from
  methyl, ethyl, propyl, isopropyl, 2-butyl, tert-butyl, cyclopropyl, cyclobutyl, cyclopentyl, trifluoromethyl, hydroxymethyl, 1-hydroxyethyl, 2-hydroxypropan-2-yl, 1-methoxyethyl, methoxy, isopropoxy, methylsulfanyl, aminomethyl, (methylamino)methyl, (dimethylamino)methyl, 1-aminoethyl, 2-aminoethyl, methylamino and ethyl(methyl)amino,
and tautomers, N-oxides, and salts thereof, and salts of tautomers or N-oxides.

In accordance with further embodiments, the present invention provides compounds of general formula (I), supra, selected from 5-fluoro-4-[3-methyl-5-oxo-4-(propan-2-yl)-4,5-dihydro-1H-1,2,4-triazol-1-yl]-N-(2-methylphenyl)-2-{[(2S)-1,1,1-trifluoropropan-2-yl]oxy}benzamide,
N-(2,6-difluorophenyl)-5-fluoro-4-[3-methyl-5-oxo-4-(propan-2-yl)-4,5-dihydro-1H-1,2,4-triazol-1-yl]-2-{[(2S)-1,1,1-trifluoropropan-2-yl]oxy}benzamide,
5-fluoro-N-(2-fluorophenyl)-4-[3-methyl-5-oxo-4-(propan-2-yl)-4,5-dihydro-1H-1,2,4-triazol-1-yl]-2-{[(2S)-1,1,1-trifluoropropan-2-yl]oxy}benzamide,
5-fluoro-4-[3-methyl-5-oxo-4-(propan-2-yl)-4,5-dihydro-1H-1,2,4-triazol-1-yl]-N-[3-(trifluoromethyl)phenyl]-2-{[(2S)-1,1,1-trifluoropropan-2-yl]oxy}benzamide,
5-fluoro-N-(2-fluoro-6-methylphenyl)-4-[3-methyl-5-oxo-4-(propan-2-yl)-4,5-dihydro-1H-1,2,4-triazol-1-yl]-2-{[(2S)-1,1,1-trifluoropropan-2-yl]oxy}benzamide,
5-fluoro-N-(2-fluorophenyl)-4-[3-methyl-5-oxo-4-(propan-2-yl)-4,5-dihydro-1H-1,2,4-triazol-1-yl]-2-[(1S)-1-phenylethoxy]benzamide,
5-fluoro-N-(2-fluoro-6-methylphenyl)-4-[3-methyl-5-oxo-4-(propan-2-yl)-4,5-dihydro-1H-1,2,4-triazol-1-yl]-2-[(1S)-1-phenylethoxy]benzamide,
N-(2,6-difluorophenyl)-5-fluoro-4-[3-methyl-5-oxo-4-(propan-2-yl)-4,5-dihydro-1H-1,2,4-triazol-1-yl]-2-[(1S)-1-phenylethoxy]benzamide,
5-fluoro-4-[3-methyl-5-oxo-4-(propan-2-yl)-4,5-dihydro-1H-1,2,4-triazol-1-yl]-2-[(1S)-1-phenylethoxy]-N-[3-(trifluoromethyl)phenyl]benzamide,
5-fluoro-4-[3-methyl-5-oxo-4-(propan-2-yl)-4,5-dihydro-1H-1,2,4-triazol-1-yl]-N-(2-methylphenyl)-2-[(1S)-1-phenylethoxy]benzamide,
5-fluoro-N-(2-fluoro-6-methylphenyl)-4-[3-methyl-5-oxo-4-(propan-2-yl)-4,5-dihydro-1H-1,2,4-triazol-1-yl]-2-[(2S)-pentan-2-yloxy]benzamide,
N-(2,6-difluorophenyl)-5-fluoro-4-[3-methyl-5-oxo-4-(propan-2-yl)-4,5-dihydro-1H-1,2,4-triazol-1-yl]-2-[(2S)-pentan-2-yloxy]benzamide,
5-fluoro-4-[3-methyl-5-oxo-4-(propan-2-yl)-4,5-dihydro-1H-1,2,4-triazol-1-yl]-N-(2-methylphenyl)-2-[(2S)-pentan-2-yloxy]benzamide,
5-fluoro-4-[3-methyl-5-oxo-4-(propan-2-yl)-4,5-dihydro-1H-1,2,4-triazol-1-yl]-2-[(2S)-pentan-2-yloxy]-N-[3-(trifluoromethyl)phenyl]benzamide,
5-fluoro-N-(2-fluorophenyl)-4-[3-methyl-5-oxo-4-(propan-2-yl)-4,5-dihydro-1H-1,2,4-triazol-1-yl]-2-[(2S)-pentan-2-yloxy]benzamide,
4-(3-ethyl-4-methyl-5-oxo-4,5-dihydro-1H-1,2,4-triazol-1-yl)-5-fluoro-N-(2-methylphenyl)-2-[(2S)-pentan-2-yloxy]benzamide,
4-(3-ethyl-4-methyl-5-oxo-4,5-dihydro-1H-1,2,4-triazol-1-yl)-5-fluoro-N-(2-fluoro-6-methylphenyl)-2-[(2S)-pentan-2-yloxy]benzamide,
N-(2,6-difluorophenyl)-4-(3-ethyl-4-methyl-5-oxo-4,5-dihydro-1H-1,2,4-triazol-1-yl)-5-fluoro-2-[(2S)-pentan-2-yloxy]benzamide,
4-(3-ethyl-4-methyl-5-oxo-4,5-dihydro-1H-1,2,4-triazol-1-yl)-5-fluoro-N-(2-fluorophenyl)-2-[(2S)-pentan-2-yloxy]benzamide,
4-(3-ethyl-4-methyl-5-oxo-4,5-dihydro-1H-1,2,4-triazol-1-yl)-5-fluoro-2-[(2S)-pentan-2-yloxy]-N-[3-(trifluoromethyl)phenyl]benzamide,
4-(3-ethyl-4-methyl-5-oxo-4,5-dihydro-1H-1,2,4-triazol-1-yl)-5-fluoro-N-(4-methoxyphenyl)-2-[(2S)-pentan-2-yloxy]benzamide,
4-(3-ethyl-4-methyl-5-oxo-4,5-dihydro-1H-1,2,4-triazol-1-yl)-5-fluoro-2-[(2S)-pentan-2-yloxy]-N-[4-(trifluoromethyl)phenyl]benzamide,
4-(3-ethyl-4-methyl-5-oxo-4,5-dihydro-1H-1,2,4-triazol-1-yl)-5-fluoro-2-[(2S)-pentan-2-yloxy]-N-[2-(trifluoromethyl)phenyl]benzamide,
N-(3-amino-2-methylphenyl)-4-(3-ethyl-4-methyl-5-oxo-4,5-dihydro-1H-1,2,4-triazol-1-yl)-5-fluoro-2-[(2S)-pentan-2-yloxy]benzamide,
N-(2-cyano-6-methylphenyl)-4-(3-ethyl-4-methyl-5-oxo-4,5-dihydro-1H-1,2,4-triazol-1-yl)-5-fluoro-2-[(2S)-pentan-2-yloxy]benzamide,
4-(3-ethyl-4-methyl-5-oxo-4,5-dihydro-1H-1,2,4-triazol-1-yl)-5-fluoro-N-(3-methylphenyl)-2-[(2S)-pentan-2-yloxy]benzamide,
N-(2,2-dimethylpropyl)-4-(3-ethyl-4-methyl-5-oxo-4,5-dihydro-1H-1,2,4-triazol-1-yl)-5-fluoro-2-[(2S)-pentan-2-yloxy]benzamide,
N-cycloheptyl-4-(3-ethyl-4-methyl-5-oxo-4,5-dihydro-1H-1,2,4-triazol-1-yl)-5-fluoro-2-[(2S)-pentan-2-yloxy]benzamide,
4-(3-ethyl-4-methyl-5-oxo-4,5-dihydro-1H-1,2,4-triazol-1-yl)-5-fluoro-N-(2-hydroxyphenyl)-2-[(2S)-pentan-2-yloxy]benzamide, N-(cyclohexylmethyl)-4-(3-ethyl-4-methyl-5-oxo-4,5-dihydro-1H-1,2,4-triazol-1-yl)-5-fluoro-2-[(2S)-pentan-2-yloxy]benzamide, N-(1-cyclohexylethyl)-4-(3-ethyl-4-methyl-5-oxo-4,5-dihydro-1H-1,2,4-triazol-1-yl)-5-fluoro-2-[(2S)-pentan-2-yloxy]benzamide, mixture of stereoisomers, N-(2,4-dimethylphenyl)-4-(3-ethyl-4-methyl-5-oxo-4,5-dihydro-1H-1,2,4-triazol-1-yl)-5-fluoro-2-[(2S)-pentan-2-yloxy]benzamide, 4-(3-ethyl-4-methyl-5-oxo-4,5-dihydro-1H-1,2,4-triazol-1-yl)-5-fluoro-N-[2-(methylamino)phenyl]-2-[(2S)-pentan-2-yloxy]benzamide, 4-(3-ethyl-4-methyl-5-oxo-4,5-dihydro-1H-1,2,4-triazol-1-yl)-5-fluoro-N-(2-methoxyphenyl)-2-[(2S)-pentan-2-yloxy]benzamide, 4-(3-ethyl-4-methyl-5-oxo-4,5-dihydro-1H-1,2,4-triazol-1-yl)-5-fluoro-N-(3-methoxyphenyl)-2-[(2S)-pentan-2-yloxy]benzamide, 4-(3-ethyl-4-methyl-5-oxo-4,5-dihydro-1H-1,2,4-triazol-1-yl)-N-(2-ethylphenyl)-5-fluoro-2-[(2S)-pentan-2-yloxy]benzamide, 4-(3-ethyl-4-methyl-5-oxo-4,5-dihydro-1H-1,2,4-triazol-1-yl)-5-fluoro-2-[(2S)-pentan-2-yloxy]-N-[2-(propan-2-yl)phenyl]benzamide, 4-(3-ethyl-4-methyl-5-oxo-4,5-dihydro-1H-1,2,4-triazol-1-yl)-5-fluoro-2-[(2S)-pentan-2-yloxy]-N-(2-propylphenyl)benzamide, 4-(3-ethyl-4-methyl-5-oxo-4,5-dihydro-1H-1,2,4-triazol-1-yl)-N-(4-ethylphenyl)-5-fluoro-2-[(2S)-pentan-2-yloxy]benzamide, 4-(3-ethyl-4-methyl-5-oxo-4,5-dihydro-1H-1,2,4-triazol-1-yl)-5-fluoro-2-[(2S)-pentan-2-yloxy]-N-[4-(propan-2-yl)phenyl]benzamide, N-(2,3-dihydro-1H-inden-2-yl)-4-(3-ethyl-4-methyl-5-oxo-4,5-dihydro-1H-1,2,4-triazol-1-yl)-5-fluoro-2-[(2S)-pentan-2-yloxy]benzamide, N-(cyclopentylmethyl)-4-(3-ethyl-4-methyl-5-oxo-4,5-dihydro-1H-1,2,4-triazol-1-yl)-5-fluoro-2-[(2S)-pentan-2-yloxy]benzamide, 4-(3-ethyl-4-methyl-5-oxo-4,5-dihydro-1H-1,2,4-triazol-1-yl)-5-fluoro-N-(4-methylphenyl)-2-[(2S)-pentan-2-yloxy]benzamide, N-(4-amino-2,6-dimethylphenyl)-4-(3-ethyl-4-methyl-5-oxo-4,5-dihydro-1H-1,2,4-triazol-1-yl)-5-fluoro-2-[(2S)-pentan-2-yloxy]benzamide, N-(2-amino-4,6-dimethylphenyl)-4-(3-ethyl-4-methyl-5-oxo-4,5-dihydro-1H-1,2,4-triazol-1-yl)-5-fluoro-2-[(2S)-pentan-2-yloxy]benzamide, N-[4-(aminomethyl)-3-methylphenyl]-4-(3-ethyl-4-methyl-5-oxo-4,5-dihydro-1H-1,2,4-triazol-1-yl)-5-fluoro-2-(pentan-2-yloxy)benzamide, 4-(3-cyclopropyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-cyclopropyl-4-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(3-cyclopropyl-4-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide, 4-(3-cyclobutyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-cyclobutyl-4-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(3-cyclobutyl-4-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide, 4-(3-cyclopropyl-4-ethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-cyclopropyl-4-ethyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(3-cyclopropyl-4-ethyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide, 4-(4-cyclopropyl-3-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(4-cyclopropyl-3-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(4-cyclopropyl-3-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide, N-(2,6-difluorophenyl)-5-fluoro-4-[4-methyl-5-oxo-3-(trifluoromethyl)-4,5-dihydro-1H-1,2,4-triazol-1-yl]-2-{[(2S)-1,1,1-trifluoropropan-2-yl]oxy}benzamide, 5-fluoro-N-(2-fluoro-6-methylphenyl)-4-[4-methyl-5-oxo-3-(trifluoromethyl)-4,5-dihydro-1H-1,2,4-triazol-1-yl]-2-{[(2S)-1,1,1-trifluoropropan-2-yl]oxy}benzamide, 5-fluoro-N-(2-fluorophenyl)-4-[4-methyl-5-oxo-3-(trifluoromethyl)-4,5-dihydro-1H-1,2,4-triazol-1-yl]-2-{[(2S)-1,1,1-trifluoropropan-2-yl]oxy}benzamide, 4-(4-cyclopropyl-3-ethyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(4-cyclopropyl-3-ethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(4-cyclopropyl-3-ethyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide, N-(2,6-difluorophenyl)-5-fluoro-4-[4-methyl-5-oxo-3-(propan-2-yl)-4,5-dihydro-1H-1,2,4-triazol-1-yl]-2-{[(2S)-1,1,1-trifluoropropan-2-yl]oxy}benzamide, 5-fluoro-N-(2-fluoro-6-methylphenyl)-4-[4-methyl-5-oxo-3-(propan-2-yl)-4,5-dihydro-1H-1,2,4-triazol-1-yl]-2-{[(2S)-1,1,1-trifluoropropan-2-yl]oxy}benzamide, 5-fluoro-N-(2-fluorophenyl)-4-[4-methyl-5-oxo-3-(propan-2-yl)-4,5-dihydro-1H-1,2,4-triazol-1-yl]-2-{[(2S)-1,1,1-trifluoropropan-2-yl]oxy}benzamide, 4-(3-ethyl-4-methyl-5-oxo-4,5-dihydro-1H-1,2,4-triazol-1-yl)-5-fluoro-N-(2-fluoro-6-methylphenyl)-2-[(1S)-1-phenylethoxy]benzamide, N-(2,6-difluorophenyl)-4-(3-ethyl-4-methyl-5-oxo-4,5-dihydro-1H-1,2,4-triazol-1-yl)-5-fluoro-2-[(1S)-1-phenylethoxy]benzamide, 4-(3-ethyl-4-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide, 4-(3-ethyl-4-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(3-ethyl-4-methyl-5-oxo-4,5-dihydro-1H-1,2,4-triazol-1-yl)-5-fluoro-N-(4-fluoro-2-methylphenyl)-2-{[(2S)-1,1,1-trifluoropropan-2-yl]oxy}benzamide, 5-fluoro-4-{3-[(1S)-1-hydroxyethyl]-4-methyl-5-oxo-4,5-dihydro-1H-1,2,4-triazol-1-yl}-N-(2-methylphenyl)-2-{[(2S)-1,1,1-trifluoropropan-2-yl]oxy}benzamide, 5-fluoro-N-[(2R)-1-hydroxypropan-2-yl]-4-[4-methyl-5-oxo-3-(propan-2-yl)-4,5-dihydro-1H-1,2,4-triazol-1-yl]-2-[(2S)-pentan-2-yloxy]benzamide, 5-fluoro-N-[(2R)-1-hydroxybutan-2-yl]-4-[4-methyl-5-oxo-3-(propan-2-yl)-4,5-dihydro-1H-1,2,4-triazol-1-yl]-2-[(2S)-pentan-2-yloxy]benzamide, N-[(2R)-1-amino-1-oxobutan-2-yl]-5-fluoro-4-[4-methyl-5-oxo-3-(propan-2-yl)-4,5-dihydro-1H-1,2,4-triazol-1-yl]-2-[(2S)-pentan-2-yloxy]benzamide, 5-fluoro-N-(heptan-4-yl)-4-[4-methyl-5-oxo-3-(propan-2-yl)-4,5-dihydro-1H-1,2,4-triazol-1-yl]-2-[(2S)-pentan-2-yloxy]benzamide, 2-(1-cyclohexylethoxy)-N-(2,4-dimethylphenyl)-5-fluoro-4-[3-(1-hydroxyethyl)-4-methyl-5-oxo-4,5-dihydro-1H-1,2,4-triazol-1-yl]benzamide, mixture of stereoisomers, N-(2-amino-6-methylphenyl)-2-(1-cyclohexylethoxy)-5-fluoro-4-[3-(1-hydroxyethyl)-4-methyl-5-oxo-4,5-dihydro-1H-1,2,4-triazol-1-yl]benzamide, mixture of stereoisomers, N-(4-amino-2-methylphenyl)-2-(1-cyclohexylethoxy)-5-fluoro-4-[3-(1-hydroxyethyl)-4-methyl-5-oxo-4,5-dihydro-1H-1,2,4-triazol-1-yl]benzamide, mixture of stereoisomers, 2-(1-cyclohexylethoxy)-N-(2,6-dimethylphenyl)-5-fluoro-4-[3-(1-hydroxyethyl)-4-methyl-5-oxo-4,5-dihydro-1H-1,2,4-triazol-1-yl]benzamide, mixture of stereoisomers, 5-fluoro-4-{3-[(1S)-1-hydroxyethyl]-4-methyl-5-oxo-4,5-dihydro-1H-1,2,4-triazol-1-yl}-N-(2-methylphenyl)-2-(pentan-2-yloxy)benzamide, mixture of stereoisomers, N-(2-amino-6-methylphenyl)-4-(3-ethyl-4-methyl-5-oxo-4,5-dihydro-1H-1,2,4-triazol-1-yl)-5-fluoro-2-(pent-4-en-2-yloxy)benzamide, mixture of stereoisomers, N-(2,6-dimethylphenyl)-5-fluoro-4-{3-[(1-hydroxyethyl]-4-methyl-5-oxo-4,5-dihydro-1H-1,2,4-triazol-1-yl}-2-[(2R)-pentan-2-yloxy]benzamide, mixture of stereoisomers, N-(4-amino-2-methylphenyl)-4-(3-ethyl-4-methyl-5-oxo-4,5-dihydro-1H-1,2,4-triazol-1-yl)-5-fluoro-2-[pent-4-en-2-yloxy]benzamide, mixture of stereoisomers, 5-fluoro-4-{4-methyl-3-[(methylamino)methyl]-5-oxo-4,5-dihydro-1H-1,2,4-triazol-1-yl}-N-(pentan-3-yl)-2-[(2S)-pentan-2-yloxy]benzamide, 2-(1-cyclohexylethoxy)-N-(2,6-dimethylphenyl)-5-fluoro-4-[3-(hydroxymethyl)-4-methyl-5-oxo-4,5-dihydro-1H-1,2,4-triazol-1-yl]benzamide, mixture of stereoisomers, 4-[3-(aminomethyl)-4-methyl-5-oxo-4,5-dihydro-1H-1,2,4-triazol-1-yl]-5-fluoro-N-(2-methylphenyl)-2-[(2S)-pentan-2-yloxy]benzamide, N-[4-amino-2-(trifluoromethyl)phenyl]-4-(3-ethyl-4-methyl-5-oxo-4,5-dihydro-1H-1,2,4-triazol-1-yl)-5-fluoro-2-[(2S)-pentan-2-yloxy]benzamide, N-[2-(aminomethyl)-6-methylphenyl]-4-(3-ethyl-4-methyl-5-oxo-4,5-dihydro-1H-1,2,4-triazol-1-yl)-5-fluoro-2-[(2S)-pentan-2-yloxy]benzamide, 4-{3-[(1R)-1-aminoethyl]-4-methyl-5-oxo-4,5-dihydro-1H-1,2,4-triazol-1-yl}-N-(4-amino-2-methylphenyl)-2-(1-cyclohexylethoxy)-5-fluorobenzamide, mixture of stereoisomers, 4-(4-cyclopentyl-3-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, N-(2,6-difluorophenyl)-4-{3-[ethyl(methyl)amino]-4-methyl-5-oxo-4,5-dihydro-1H-1,2,4-triazol-1-yl}-5-fluoro-2-{[(2S)-1,1,1-trifluoropropan-2-yl]oxy}benzamide, N-(2,6-difluorophenyl)-4-(3-ethyl-4-methyl-5-oxo-4,5-dihydro-1H-1,2,4-triazol-1-yl)-5-fluoro-2-{[(2S)-1,1,1-trifluoropropan-2-yl]oxy}benzamide, N-(2,6-difluorophenyl)-5-fluoro-4-[3-(1-hydroxyethyl)-4-methyl-5-oxo-4,5-dihydro-1H-1,2,4-triazol-1-yl]-2-{[(2S)-1,1,1-trifluoropropan-2-yl]oxy}benzamide, single stereoisomer, N-(2,6-difluorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide, N-(2,6-difluorophenyl)-4-{3-[(dimethylamino)methyl]-4-methyl-5-oxo-4,5-dihydro-1H-1,2,4-triazol-1-yl}-5-fluoro-2-{[(2S)-1,1,1-trifluoropropan-2-yl]oxy}benzamide, N-(2,6-difluorophenyl)-5-fluoro-4-(4-methyl-5-oxo-3-propyl-4,5-dihydro-1H-1,2,4-triazol-1-yl)-2-{[(2S)-1,1,1-trifluoropropan-2-yl]oxy}benzamide, N-(2,6-difluorophenyl)-5-fluoro-4-[4-methyl-3-(methylsulfanyl)-5-oxo-4,5-dihydro-1H-1,2,4-triazol-1-yl]-2-{[(2S)-1,1,1-trifluoropropan-2-yl]oxy}benzamide, 4-[3-(2-aminoethyl)-4-methyl-5-oxo-4,5-dihydro-1H-1,2,4-triazol-1-yl]-N-(2,6-difluorophenyl)-5-fluoro-2-{[(2S)-1,1,1-trifluoropropan-2-yl]oxy}benzamide, N-(2,6-difluorophenyl)-5-fluoro-4-[4-methyl-3-(methylamino)-5-oxo-4,5-dihydro-1H-1,2,4-triazol-1-yl]-2-{[(2S)-1,1,1-trifluoropropan-2-yl]oxy}benzamide, 4-(3-tert-butyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-chloro-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-[4-(cyclopropylmethyl)-3-methyl-5-oxo-4,5-dihydro-1H-1,2,4-triazol-1-yl]-N-(2,6-difluorophenyl)-5-fluoro-2-{[(2S)-1,1,1-trifluoropropan-2-yl]oxy}benzamide, N-(2,6-difluorophenyl)-5-fluoro-4-(3-methyl-5-oxo-4-propyl-4,5-dihydro-1H-1,2,4-triazol-1-yl)-2-{[(2S)-1,1,1-trifluoropropan-2-yl]oxy}benzamide, N-(2,6-difluorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, N-(2,6-difluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2,6-difluorophenyl)-4-[3-ethyl-4-(2-hydroxyethyl)-5-oxo-4,5-dihydro-1H-1,2,4-triazol-1-yl]-5-fluoro-2-{[(2S)-1,1,1-trifluoropropan-2-yl]oxy}benzamide, 4-(3,4-diethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(4-cyclopropyl-3-methoxy-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-chloro-4-ethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-cyclopentyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-[4-(butan-2-yl)-3-methyl-5-oxo-4,5-dihydro-1H-1,2,4-triazol-1-yl]-N-(2,6-difluorophenyl)-5-fluoro-2-{[(2S)-1,1,1-trifluoropropan-2-yl]oxy}benzamide, mixture of stereoisomers, 4-[3-(butan-2-yl)-4-methyl-5-oxo-4,5-dihydro-1H-1,2,4-triazol-1-yl]-N-(2,6-difluorophenyl)-5-fluoro-2-{[(2S)-1,1,1-trifluoropropan-2-yl]oxy}benzamide, mixture of stereoisomers, N-(2,6-difluorophenyl)-4-[4-ethyl-3-(methylsulfanyl)-5-oxo-4,5-dihydro-1H-1,2,4-triazol-1-yl]-5-fluoro-2-{[(2S)-1,1,1-trifluoropropan-2-yl]oxy}benzamide, N-(2,6-difluorophenyl)-5-fluoro-4-[3-(1-methoxyethyl)-4-methyl-5-oxo-4,5-dihydro-1H-1,2,4-triazol-1-yl]-2-{[(2S)-1,1,1-trifluoropropan-2-yl]oxy}benzamide, mixture of stereoisomers, N-(2,6-difluorophenyl)-4-[4-ethyl-5-oxo-3-(propan-2-yloxy)-4,5-dihydro-1H-1,2,4-triazol-1-yl]-5-fluoro-2-{[(2S)-1,1,1-trifluoropropan-2-yl]oxy}benzamide, 4-(4-benzyl-3-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, N-(2-chloro-6-fluorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide, N-(2-chloro-6-fluorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2-chloro-6-fluorophenyl)-5-fluoro-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide, 5-fluoro-4-[3-(hydroxymethyl)-4-methyl-5-oxo-4,5-dihydro-1H-1,2,4-triazol-1-yl]-N-(2-methoxy-4-methylpyridin-3-yl)-2-{[(2S)-1,1,1-trifluoropropan-2-yl]oxy}benzamide, 4-[4-ethyl-3-(hydroxymethyl)-5-oxo-4,5-dihydro-1H-1,2,4-triazol-1-yl]-5-fluoro-N-(2-methoxy-4-methylpyridin-3-yl)-2-{[(2S)-1,1,1-trifluoropropan-2-yl]oxy}benzamide, 5-fluoro-4-[3-(2-hydroxypropan-2-yl)-4-methyl-5-oxo-4,5-dihydro-1H-1,2,4-triazol-1-yl]-N-(2-methoxy-4-methylpyridin-3-yl)-2-{[(2S)-1,1,1-trifluoropropan-2-yl]oxy}benzamide, 5-fluoro-4-{3-[(1S)-1-hydroxyethyl]-4-methyl-5-oxo-4,5-dihydro-1H-1,2,4-triazol-1-yl}-N-(2-methoxy-4-methylpyridin-3-yl)-2-{[(2S)-1,1,1-trifluoropropan-2-yl]oxy}benzamide, 5-fluoro-N-(2-fluoro-6-methylphenyl)-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide, 4-[4-ethyl-3-(hydroxymethyl)-5-oxo-4,5-dihydro-1H-1,2,4-triazol-1-yl]-5-fluoro-N-(2-fluoro-6-methylphenyl)-2-{[(2S)-1,1,1-trifluoropropan-2-yl]oxy}benzamide, 5-fluoro-N-(2-fluoro-6-methylphenyl)-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, 5-fluoro-N-(2-fluoro-6-methylphenyl)-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide, N-(2,6-dichlorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide, N-(2,6-dichlorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2,6-dichlorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, N-(2,6-dichlorophenyl)-5-fluoro-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide, N-(2-chloro-6-fluorophenyl)-5-fluoro-4-[3-(hydroxymethyl)-4-methyl-5-oxo-4,5-dihydro-1H-1,2,4-triazol-1-yl]-2-[(2S)-pentan-2-yloxy]benzamide, N-(2-chloro-6-fluorophenyl)-5-fluoro-4-{3-[(1S)-1-hydroxyethyl]-4-methyl-5-oxo-4,5-dihydro-1H-1,2,4-triazol-1-yl}-2-[(2S)-pentan-2-yloxy]benzamide, N-(2-chloro-6-fluorophenyl)-5-fluoro-4-[3-(2-hydroxypropan-2-yl)-4-methyl-5-oxo-4,5-dihydro-1H-1,2,4-triazol-1-yl]-2-[(2S)-pentan-2-yloxy]benzamide, 5-fluoro-4-[3-(hydroxymethyl)-4-methyl-5-oxo-4,5-dihydro-1H-1,2,4-triazol-1-yl]-N-(2-methoxy-4-methylpyridin-3-yl)-2-[(2S)-pentan-2-yloxy]benzamide, 5-fluoro-4-{3-[(1S)-1-hydroxyethyl]-4-methyl-5-oxo-4,5-dihydro-1H-1,2,4-triazol-1-yl}-N-(2-methoxy-4-methylpyridin-3-yl)-2-[(2S)-pentan-2-yloxy]benzamide, 5-fluoro-4-[3-(2-hydroxypropan-2-yl)-4-methyl-5-oxo-4,5-dihydro-1H-1,2,4-triazol-1-yl]-N-(2-methoxy-4-methylpyridin-3-yl)-2-[(2S)-pentan-2-yloxy]benzamide, 5-fluoro-N-(2-fluoro-6-methylphenyl)-4-[3-(hydroxymethyl)-4-methyl-5-oxo-4,5-dihydro-1H-1,2,4-triazol-1-yl]-2-[(2S)-pentan-2-yloxy]benzamide, 5-fluoro-N-(2-fluoro-6-methylphenyl)-4-{3-[(1S)-1-hydroxyethyl]-4-methyl-5-oxo-4,5-dihydro-1H-1,2,4-triazol-1-yl}-2-[(2S)-pentan-2-yloxy]benzamide, 5-fluoro-N-(2-fluoro-6-methylphenyl)-4-[3-(2-hydroxypropan-2-yl)-4-methyl-5-oxo-4,5-dihydro-1H-1,2,4-triazol-1-yl]-2-[(2S)-pentan-2-yloxy]benzamide, 5-fluoro-4-[3-(hydroxymethyl)-4-methyl-5-oxo-4,5-dihydro-1H-1,2,4-triazol-1-yl]-N-(pentan-3-yl)-2-[(2S)-pentan-2-yloxy]benzamide, 5-fluoro-4-[3-(2-hydroxypropan-2-yl)-4-methyl-5-oxo-4,5-dihydro-1H-1,2,4-triazol-1-yl]-N-(pentan-3-yl)-2-[(2S)-pentan-2-yloxy]benzamide, N-(2,6-difluorophenyl)-4-(3-ethyl-4-methyl-5-oxo-4,5-dihydro-1H-1,2,4-triazol-1-yl)-2-{[(2S)-1,1,1-trifluoropropan-2-yl]oxy}benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(tetrahydrofuran-3-yl)benzamide, mixture of stereoisomers, 5-fluoro-N-[(2R)-1-hydroxypropan-2-yl]-4-[4-methyl-5-oxo-3-(propan-2-yl)-4,5-dihydro-1H-1,2,4-triazol-1-yl]-2-{[(2S)-4-methylpentan-2-yl]oxy}benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(1H-pyrazol-3-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyridin-2-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyridin-4-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(1-methylpiperidin-4-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(tetrahydro-2H-pyran-4-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyrimidin-4-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(1,3-oxazol-2-yl)benzamide, 5-fluoro-N-[(2R)-1-hydroxybutan-2-yl]-4-[4-methyl-5-oxo-3-(propan-2-yl)-4,5-dihydro-1H-1,2,4-triazol-1-yl]-2-{[(2S)-4-methylpentan-2-yl]oxy}benzamide, N-cyclopentyl-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide, N-cyclohexyl-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide, 5-fluoro-N-(2-hydroxypropyl)-4-[4-methyl-5-oxo-3-(propan-2-yl)-4,5-dihydro-1H-1,2,4-triazol-1-yl]-2-{[(2S)-4-methylpentan-2-yl]oxy}benzamide, mixture of stereoisomers, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-phenylbenzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyrimidin-2-yl)benzamide, N-[(2R)-1-aminopropan-2-yl]-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide, N-[(2R)-1-aminobutan-2-yl]-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(piperidin-4-yl)benzamide, 2-(1-cyclohexylethoxy)-4-(3-ethyl-4-methyl-5-oxo-4,5-dihydro-1H-1,2,4-triazol-1-yl)-5-fluoro-N-(pentan-3-yl)benzamide, mixture of stereoisomers, 2-[(1-cyclopropylpropan-2-yl)oxy]-4-(3-ethyl-4-methyl-5-oxo-4,5-dihydro-1H-1,2,4-triazol-1-yl)-5-fluoro-N-(pentan-3-yl)benzamide, mixture of stereoisomers, 2-(1-cyclopentylethoxy)-4-(3-ethyl-4-methyl-5-oxo-4,5-dihydro-1H-1,2,4-triazol-1-yl)-5-fluoro-N-(pentan-3-yl)benzamide, mixture of stereoisomers, 2-(1-cyclopropylethoxy)-4-(3-ethyl-4-methyl-5-oxo-4,5-dihydro-1H-1,2,4-triazol-1-yl)-5-fluoro-N-(pentan-3-yl)benzamide, mixture of stereoisomers, 4-(3-ethyl-4-methyl-5-oxo-4,5-dihydro-1H-1,2,4-triazol-1-yl)-5-fluoro-N-(pentan-3-yl)-2-(1-phenylethoxy)benzamide, mixture of stereoisomers, 4-(3-ethyl-4-methyl-5-oxo-4,5-dihydro-1H-1,2,4-triazol-1-yl)-2-[(3-ethylpentan-2-yl)oxy]-5-fluoro-N-(pentan-3-yl)benzamide, mixture of stereoisomers, 4-(3-ethyl-4-methyl-5-oxo-4,5-dihydro-1H-1,2,4-triazol-1-yl)-5-fluoro-2-[(4-methylpent-3-en-2-yl)oxy]-N-(pentan-3-yl)benzamide, mixture of stereoisomers, 4-(3-ethyl-4-methyl-5-oxo-4,5-dihydro-1H-1,2,4-triazol-1-yl)-5-fluoro-N-(pentan-3-yl)-2-(pent-4-en-2-yloxy)benzamide, mixture of stereoisomers, 2-(1-cyclobutylethoxy)-4-(3-ethyl-4-methyl-5-oxo-4,5-dihydro-1H-1,2,4-triazol-1-yl)-5-fluoro-N-(pentan-3-yl)benzamide, mixture of stereoisomers, 5-fluoro-4-[3-(1-hydroxyethyl)-4-methyl-5-oxo-4,5-dihydro-1H-1,2,4-triazol-1-yl]-N-(pentan-3-yl)-2-[(2S)-pentan-2-yloxy]benzamide, mixture of stereoisomers, and 5-fluoro-4-[3-(1-hydroxyethyl)-4-methyl-5-oxo-4,5-dihydro-1H-1,2,4-triazol-1-yl]-N-(2-methylphenyl)-2-(pentan-2-yloxy)benzamide, mixture of stereoisomers, or a tautomer, an N-oxide, a salt, a salt a tautomer or a salt of an N-oxide thereof.

In accordance with further embodiments, the present invention provides compounds of general formula (I), supra, selected from N-(2-chloro-6-fluorophenyl)-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, N-(2,6-difluorophenyl)-4-[4-ethyl-3-(hydroxymethyl)-5-oxo-4,5-dihydro-1H-1,2,4-triazol-1-yl]-2-{[(2S)-1,1,1-trifluoropropan-2-yl]oxy}benzamide, N-(2-chloro-6-fluorophenyl)-4-[4-ethyl-3-(hydroxymethyl)-5-oxo-4,5-dihydro-1H-1,2,4-triazol-1-yl]-2-{[(2S)-1,1,1-trifluoropropan-2-yl]oxy}benzamide, N-(2-chloro-6-fluorophenyl)-2-{[1,1-difluoropropan-2-yl]oxy}-4-[3-(2-hydroxypropan-2-yl)-4-methyl-5-oxo-4,5-dihydro-1H-1,2,4-triazol-1-yl]benzamide (Racemic)

N-(2-chloro-6-fluorophenyl)-2-{[1,1-difluoropropan-2-yl]oxy}-4-[4-ethyl-3-(hydroxymethyl)-5-oxo-4,5-dihydro-1H-1,2,4-triazol-1-yl]benzamide (Racemic)

N-(2-chloro-6-fluorophenyl)-4-[4-cyclopropyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide N-(2-chloro-6-fluorophenyl)-5-fluoro-4-[3-(hydroxymethyl)-5-oxo-4-propyl-4,5-dihydro-1H-1,2,4-triazol-1-yl]-2-{[(2S)-1,1,1-trifluoropropan-2-yl]oxy}benzamide, N-(2-chloro-6-fluorophenyl)-4-[4-cyclobutyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2-chloro-6-fluorophenyl)-5-fluoro-4-[3-(hydroxymethyl)-5-oxo-4-(prop-2-en-1-yl)-4,5-dihydro-1H-1,2,4-triazol-1-yl]-2-{[(2S)-1,1,1-trifluoropropan-2-yl]oxy}benzamide, N-(2-chloro-6-fluorophenyl)-2-{[3,3-difluorobutan-2-yl]oxy}-4-[4-ethyl-3-(hydroxymethyl)-5-oxo-4,5-dihydro-1H-1,2,4-triazol-1-yl]-5-fluorobenzamide (Racemic), 5-fluoro-4-[3-(hydroxymethyl)-5-oxo-4-propyl-4,5-dihydro-1H-1,2,4-triazol-1-yl]-N-(2-methoxy-4-methylpyridin-3-yl)-2-{[(2S)-1,1,1-trifluoropropan-2-yl]oxy}benzamide, N-(2-chloro-6-fluorophenyl)-4-[4-ethyl-3-(hydroxymethyl)-5-oxo-4,5-dihydro-1H-1,2,4-triazol-1-yl]-3-fluoro-2-{[(2S)-1,1,1-trifluoropropan-2-yl]oxy}benzamide N-(2-chloro-6-fluorophenyl)-3-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide N-(6-chloro-2-fluoro-3-methoxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(6-chloro-2-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide N-(6-chloro-2-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, 3-chloro-4-(4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamido)-5-fluorophenyl 2,2-dimethylpropanoate, N-(6-chloro-2-fluoro-4-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2-chloro-6-fluoro-3-methoxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2-chloro-6-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, 2-[(1S)-1-cyclohexylethoxy]-N-(1,4-dimethyl-1H-pyrazol-3-yl)-4-(3-ethyl-4-methyl-5-oxo-4,5-dihydro-1H-1,2,4-triazol-1-yl)-5-fluorobenzamide, 2-[(1S)-1-cyclohexylethoxy]-4-(3-ethyl-4-methyl-5-oxo-4,5-dihydro-1H-1,2,4-triazol-1-yl)-5-fluoro-N-[1-(4-fluorophenyl)cyclopropyl]benzamide 2-[(1S)-1-cyclohexylethoxy]-4-(3-ethyl-4-methyl-5-oxo-4,5-dihydro-1H-1,2,4-triazol-1-yl)-5-fluoro-N-(oxan-4-yl)benzamide 2-[(1S)-1-cyclohexylethoxy]-4-(3-ethyl-4-methyl-5-oxo-4,5-dihydro-1H-1,2,4-triazol-1-yl)-5-fluoro-N-(1-phenylbutan-2-yl)benzamide 2-[(1S)-1-cyclohexylethoxy]-4-(3-ethyl-4-methyl-5-oxo-4,5-dihydro-1H-1,2,4-triazol-1-yl)-5-fluoro-N-[3-(methanesulfonyl)phenyl]benzamide, 2-[(1S)-1-cyclohexylethoxy]-4-(3-ethyl-4-methyl-5-oxo-4,5-dihydro-1H-1,2,4-triazol-1-yl)-5-fluoro-N-(1-methyl-1H-pyrazol-5-yl)benzamide, N-(2-chloro-6-fluorophenyl)-4-[3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, 2-[(1S)-1-cyclohexylethoxy]-4-(3-ethyl-4-methyl-5-oxo-4,5-dihydro-1H-1,2,4-triazol-1-yl)-5-fluoro-N-[4-(methylsulfanyl)phenyl]benzamide, 4-(3-ethyl-4-methyl-5-oxo-4,5-dihydro-1H-1,2,4-triazol-1-yl)-5-fluoro-N-(4-methylpyridin-3-yl)-2-[(1S)-1-phenylethoxy]benzamide, 4-(3-ethyl-4-methyl-5-oxo-4,5-dihydro-1H-1,2,4-triazol-1-yl)-5-fluoro-N-(2-methylquinolin-5-yl)-2-[(1S)-1-phenylethoxy]benzamide, N-[3-(cyclopropylcarbamoyl)phenyl]-4-(3-ethyl-4-methyl-5-oxo-4,5-dihydro-1H-1,2,4-triazol-1-yl)-5-fluoro-2-[(1S)-1-phenylethoxy]benzamide, N-[2-(difluoromethyl)phenyl]-4-(3-ethyl-4-methyl-5-oxo-4,5-dihydro-1H-1,2,4-triazol-1-yl)-5-fluoro-2-[(1S)-1-phenylethoxy]benzamide, 4-(3-ethyl-4-methyl-5-oxo-4,5-dihydro-1H-1,2,4-triazol-1-yl)-5-fluoro-N-(6-methyl-1H-indazol-5-yl)-2-[(1S)-1-phenylethoxy]benzamide, N-(1-cyanobutan-2-yl)-4-(3-ethyl-4-methyl-5-oxo-4,5-dihydro-1H-1,2,4-triazol-1-yl)-5-fluoro-2-[(1S)-1-phenylethoxy]benzamide, 2-{[(2S)-1-(dimethylamino)propan-2-yl]oxy}-4-(3-ethyl-4-methyl-5-oxo-4,5-dihydro-1H-1,2,4-triazol-1-yl)-5-fluoro-N-(2-fluoro-6-methylphenyl)benzamide, 2-[(1S)-1-cyclohexylethoxy]-4-(3-ethyl-4-methyl-5-oxo-4,5-dihydro-1H-1,2,4-triazol-1-yl)-5-fluoro-N-[4-(S-methanesulfonimidoyl)phenyl]benzamide (mixture of stereoisomers), N-(2,6-difluorophenyl)-4-[4-ethyl-3-(S-methanesulfonimidoyl)-5-oxo-4,5-dihydro-1H-1,2,4-triazol-1-yl]-5-fluoro-2-{[(2S)-1,1,1-trifluoropropan-2-yl]oxy}benzamide (Mixture of stereoisomers), 1-(4-[(2-chloro-6-fluorophenyl)carbamoyl]-3-{[(2S)-1,1,1-trifluoropropan-2-yl]oxy}phenyl)-4-ethyl-5-oxo-4,5-dihydro-1H-1,2,4-triazole-3-carboxylic acid, 1-(4-[(2-chloro-6-fluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid, 1-(4-[(2,6-difluorophenyl)carbamoyl]-3-{[(2S)-1,1,1-trifluoropropan-2-yl]oxy}phenyl)-4-ethyl-5-oxo-4,5-dihydro-1H-1,2,4-triazole-3-carboxylic acid, 4-ethyl-1-(2-fluoro-4-[(2-fluoro-6-methylphenyl)carbamoyl]-5-{[(2S)-1,1,1-trifluoropropan-2-yl]oxy}phenyl)-5-oxo-4,5-dihydro-1H-1,2,4-triazole-3-carboxylic acid, 1-(4-[(2,6-dichlorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid, 1-(4-[(2-chloro-6-fluorophenyl)carbamoyl]-2-fluoro-3-{[(2S)-1,1,1-trifluoropropan-2-yl]oxy}phenyl)-4-ethyl-5-oxo-4,5-dihydro-1H-1,2,4-triazole-3-carboxylic acid, 1-(4-[(2-chloro-6-fluorophenyl)carbamoyl]-3-{[, 1-difluoropropan-2-yl]oxy}phenyl)-4-ethyl-5-oxo-4,5-dihydro-1H-1,2,4-triazole-3-carboxylic acid (Racemic), 1-(4-[(2-chloro-6-fluorophenyl)carbamoyl]-2-fluoro-5-{[(2S)-1,1,1-trifluoropropan-2-yl]oxy}phenyl)-4-methyl-5-oxo-4,5-dihydro-1H-1,2,4-triazole-3-carboxylic acid, 1-(2-fluoro-4-[(2-fluoro-6-methylphenyl)carbamoyl]-5-{[(2S)-1,1,1-trifluoropropan-2-yl]oxy}phenyl)-4-methyl-5-oxo-4,5-dihydro-1H-1,2,4-triazole-3-carboxylic acid, 1-(4-[(2,6-difluorophenyl)carbamoyl]-2-fluoro-5-{[(2S)-1,1,1-trifluoropropan-2-yl]oxy}phenyl)-4-methyl-5-oxo-4,5-dihydro-1H-1,2,4-triazole-3-carboxylic acid, 1-(4-[(2-chloro-6-fluorophenyl)carbamoyl]-2-fluoro-5-{[(2S)-1,1,1-trifluoropropan-2-yl]oxy}phenyl)-5-oxo-4-propyl-4,5-dihydro-1H-1,2,4-triazole-3-carboxylic acid, 1-(4-[(2-chloro-6-fluorophenyl)carbamoyl]-5-{[3,3-difluorobutan-2-yl]oxy}-2-fluorophenyl)-4-ethyl-5-oxo-4,5-dihydro-1H-1,2,4-triazole-3-carboxylic acid (racemic), 1-(4-[(2-chloro-6-fluorophenyl)carbamoyl]-2-fluoro-5-{[(2S)-1,1,1-trifluoropropan-2-yl]oxy}phenyl)-4-cyclopropyl-5-oxo-4,5-dihydro-1H-1,2,4-triazole-3-carboxylic acid, 1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid 1-(4-[(2-chloro-6-fluorophenyl)carbamoyl]-2-fluoro-5-{[(2S)-1,1,1-trifluoropropan-2-yl]oxy}phenyl)-5-oxo-4-(prop-2-en-1-yl)-4,5-dihydro-1H-1,2,4-triazole-3-carboxylic acid, 1-(4-[(2-chloro-6-fluorophenyl)carbamoyl]-2-fluoro-5-{[(2S)-1,1,1-trifluoropropan-2-yl]oxy}phenyl)-4-cyclobutyl-5-oxo-4,5-dihydro-1H-1,2,4-triazole-3-carboxylic acid, 1-(4-[(2,6-difluorophenyl)carbamoyl]-2-fluoro-5-{[(2S)-1,1,1-trifluoropropan-2-yl]oxy}phenyl)-4-methyl-5-oxo-4,5-dihydro-1H-1,2,4-triazole-3-carboxamide, 1-(4-[(2-chloro-6-fluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxamide, N-cyclopropyl-1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxamide, 1-(4-[(2,6-difluorophenyl)carbamoyl]-2-fluoro-5-{[(2S)-1,1,1-trifluoropropan-2-yl]oxy}phenyl)-N,4-dimethyl-5-oxo-4,5-dihydro-1H-1,2,4-triazole-3-carboxamide 1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxamide 1-(4-[(2,6-difluorophenyl)carbamoyl]-2-fluoro-5-{[(2S)-1,1,1-trifluoropropan-2-yl]oxy}phenyl)-4-ethyl-N,N-dimethyl-5-oxo-4,5-dihydro-1H-1,2,4-triazole-3-carboxamide Methyl 1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylate,
5-fluoro-4-{3-[1-hydroxyethyl]-4-methyl-5-oxo-4,5-dihydro-1H-1,2,4-triazol-1-yl}-N-(2-methylphenyl)-2-{[(2S)-1,1,1-trifluoropropan-2-yl]oxy}benzamide (Mixture of stereoisomers) and
4-{4-ethyl-5-oxo-3-[(1S)-2,2,2-trifluoro-1-hydroxyethyl]-4,5-dihydro-1H-1,2,4-triazol-1-yl}-5-fluoro-N-(2-methoxy-4-methylpyridin-3-yl)-2-{[(2S)-1,1,1-trifluoropropan-2-yl]oxy}benzamide (mixture of stereoisomers)
or a tautomer, an N-oxide, a salt, a salt a tautomer or a salt of an N-oxide thereof.

In accordance with further embodiments, the present invention provides the compounds of general formula (I), supra, which are exemplified in the experimental section.

In further embodiments, the present invention provides compounds of formula (I), supra, any compound selected from 4-(3-ethyl-4-methyl-5-oxo-4,5-dihydro-1H-1,2,4-triazol-1-yl)-5-fluoro-N-(2-methylphenyl)-2-[(2S)-pentan-2-yloxy]benzamide,
4-(3-ethyl-4-methyl-5-oxo-4,5-dihydro-1H-1,2,4-triazol-1-yl)-5-fluoro-N-(2-fluoro-6-methyl-phenyl)-2-[(2S)-pentan-2-yloxy]benzamide,
4-(3-cyclopropyl-4-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide,
4-(3-cyclopropyl-4-ethyl-5-oxo-4,5-dihydro-1H-1,2,4-triazol-1-yl)-5-fluoro-N-(2-fluoro-6-methyl-phenyl)-2-{[(2S)-1,1,1-trifluoropropan-2-yl]oxy}benzamide,
5-fluoro-N-(2-fluoro-6-methylphenyl)-4-[4-methyl-5-oxo-3-(propan-2-yl)-4,5-dihydro-1H-1,2,4-triazol-1-yl]-2-{[(2S)-1,1,1-trifluoropropan-2-yl]oxy}benzamide,
4-(3-ethyl-4-methyl-5-oxo-4,5-dihydro-1H-1,2,4-triazol-1-yl)-5-fluoro-N-(2-fluoro-6-methyl-phenyl)-2-{[(2S)-1,1,1-trifluoropropan-2-yl]oxy}benzamide,
N-(2-chloro-6-fluorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide,
N-(2-chloro-6-fluorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide,
N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide,
4-[4-ethyl-3-(hydroxymethyl)-5-oxo-4,5-dihydro-1H-1,2,4-triazol-1-yl]-5-fluoro-N-(2-fluoro-6-methylphenyl)-2-{[(2S)-1,1,1-trifluoropropan-2-yl]oxy}benzamide,
5-fluoro-N-(2-fluoro-6-methylphenyl)-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide,
N-(2,6-dichlorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide,
N-(2,6-dichlorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide,
N-(2,6-dichlorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide,
N-(2,6-dichlorophenyl)-5-fluoro-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide,
N-(2-chloro-6-fluorophenyl)-5-fluoro-4-[3-(hydroxymethyl)-4-methyl-5-oxo-4,5-dihydro-1H-1,2,4-triazol-1-yl]-2-[(2S)-pentan-2-yloxy]benzamide,
N-(2-chloro-6-fluorophenyl)-5-fluoro-4-{3-[(1S)-1-hydroxyethyl]-4-methyl-5-oxo-4,5-dihydro-1H-1,2,4-triazol-1-yl}-2-[(2S)-pentan-2-yloxy]benzamide,
N-(2-chloro-6-fluorophenyl)-5-fluoro-4-[3-(2-hydroxypropan-2-yl)-4-methyl-5-oxo-4,5-dihydro-1H-1,2,4-triazol-1-yl]-2-[(2S)-pentan-2-yloxy]benzamide,
5-fluoro-N-(2-fluoro-6-methylphenyl)-4-[3-(hydroxymethyl)-4-methyl-5-oxo-4,5-dihydro-1H-1,2,4-triazol-1-yl]-2-[(2S)-pentan-2-yloxy]benzamide,
5-fluoro-N-(2-fluoro-6-methylphenyl)-4-{3-[(1S)-1-hydroxyethyl]-4-methyl-5-oxo-4,5-dihydro-1H-1,2,4-triazol-1-yl}-2-[(2S)-pentan-2-yloxy]benzamide,
5-fluoro-N-(2-fluoro-6-methylphenyl)-4-[3-(2-hydroxypropan-2-yl)-4-methyl-5-oxo-4,5-dihydro-1H-1,2,4-triazol-1-yl]-2-[(2S)-pentan-2-yloxy]benzamide,
N-(2-chloro-6-fluorophenyl)-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide,
N-(2-chloro-6-fluorophenyl)-4-[4-ethyl-3-(hydroxymethyl)-5-oxo-4,5-dihydro-1H-1,2,4-triazol-1-yl]-2-{[(2S)-1,1,1-trifluoropropan-2-yl]oxy}benzamide,
N-(2-chloro-6-fluorophenyl)-5-fluoro-4-[3-(hydroxymethyl)-5-oxo-4-propyl-4,5-dihydro-1H-1,2,4-triazol-1-yl]-2-{[(2S)-1,1,1-trifluoropropan-2-yl]oxy}benzamide,
N-(2-chloro-6-fluorophenyl)-4-[4-cyclobutyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide,
N-(2-chloro-6-fluorophenyl)-5-fluoro-4-[3-(hydroxymethyl)-5-oxo-4-(prop-2-en-1-yl)-4,5-dihydro-1H-1,2,4-triazol-1-yl]-2-{[(2S)-1,1,1-trifluoropropan-2-yl]oxy}benzamide,
N-(6-chloro-2-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide,
N-(2-chloro-6-fluoro-4-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide,
N-(2-chloro-6-fluoro-3-methoxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide,
N-(2-chloro-6-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide,
1-(4-[(2-chloro-6-fluorophenyl)carbamoyl]-3-{[(2S)-1,1,1-trifluoropropan-2-yl]oxy}phenyl)-4-ethyl-5-oxo-4,5-dihydro-1H-1,2,4-triazole-3-carboxylic acid,
1-(4-[(2-chloro-6-fluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid,
1-(4-[(2,6-difluorophenyl)carbamoyl]-3-{[(2S)-1,1,1-trifluoropropan-2-yl]oxy}phenyl)-4-ethyl-5-oxo-4,5-dihydro-1H-1,2,4-triazole-3-carboxylic acid,
4-ethyl-1-(2-fluoro-4-[(2-fluoro-6-methylphenyl)carbamoyl]-5-{[(2S)-1,1,1-trifluoropropan-2-yl]oxy}phenyl)-5-oxo-4,5-dihydro-1H-1,2,4-triazole-3-carboxylic acid,
1-(4-[(2,6-dichlorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid, 1-(4-[(2-chloro-6-fluorophenyl)carbamoyl]-2-fluoro-5-{[(2S)-1,1,1-trifluoropropan-2-yl]oxy}phenyl)-4-methyl-5-oxo-4,5-dihydro-1H-1,2,4-triazole-3-carboxylic acid, 1-(4-[(2-chloro-6-fluorophenyl)carbamoyl]-2-fluoro-5-{[(2S)-1,1,1-trifluoropropan-2-yl]oxy}phenyl)-5-oxo-4-propyl-4,5-dihydro-1H-1,2,4-triazole-3-carboxylic acid, 1-(4-[(2-chloro-6-fluorophenyl)carbamoyl]-5-{[3,3-difluorobutan-2-yl]oxy}-2-fluorophenyl)-4-ethyl-5-oxo-4,5-dihydro-1H-1,2,4-triazole-3-carboxylic acid (racemic), 1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid 1-(4-[(2-chloro-6-fluorophenyl)carbamoyl]-2-fluoro-5-{[(2S)-1,1,1-trifluoropropan-2-yl]oxy}phenyl)-5-oxo-4-(prop-2-en-1-yl)-4,5-dihydro-1H-1,2,4-triazole-3-carboxylic acid, and 1-(4-[(2-chloro-6-fluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxamide, or a tautomer, an N-oxide, a salt, a salt a tautomer or a salt of an N-oxide thereof.

In further embodiments, the present invention provides compounds of formula (I), supra, any compound selected from 5-fluoro-4-[3-methyl-5-oxo-4-(propan-2-yl)-4,5-dihydro-1H-1,2,4-triazol-1-yl]-N-(2-methylphenyl)-2-{[(2S)-1,1,1-trifluoropropan-2-yl]oxy}benzamide N-(2,6-difluorophenyl)-5-fluoro-4-[3-methyl-5-oxo-4-(propan-2-yl)-4,5-dihydro-1H-1,2,4-triazol-1-yl]-2-{[(2S)-1,1,1-trifluoropropan-2-yl]oxy}benzamide 5-fluoro-N-(2-fluorophenyl)-4-[3-methyl-5-oxo-4-(propan-2-yl)-4,5-dihydro-1H-1,2,4-triazol-1-yl]-2-{[(2S)-1,1,1-trifluoropropan-2-yl]oxy}benzamide 5-fluoro-N-(2-fluoro-6-methylphenyl)-4-[3-methyl-5-oxo-4-(propan-2-yl)-4,5-dihydro-1H-1,2,4-triazol-1-yl]-2-{[(2S)-1,1,1-trifluoropropan-2-yl]oxy}benzamide 5-fluoro-4-{3-[(1S)-1-hydroxyethyl]-4-methyl-5-oxo-4,5-dihydro-1H-1,2,4-triazol-1-yl}-N-(2-methylphenyl)-2-{[(2S)-1,1,1-trifluoropropan-2-yl]oxy}benzamide N-(2,6-difluorophenyl)-5-fluoro-4-[3-(1-hydroxyethyl)-4-methyl-5-oxo-4,5-dihydro-1H-1,2,4-triazol-1-yl]-2-{[(2S)-1,1,1-trifluoropropan-2-yl]oxy}benzamide, single stereomer N-(2,6-difluorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide N-(2,6-difluorophenyl)-5-fluoro-4-(3-methyl-5-oxo-4-propyl-4,5-dihydro-1H-1,2,4-triazol-1-yl)-2-{[(2S)-1,1,1-trifluoropropan-2-yl]oxy}benzamide N-(2,6-difluorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide N-(2,6-difluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide N-(2-chloro-6-fluorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide, N-(2-chloro-6-fluorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2-chloro-6-fluorophenyl)-5-fluoro-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide 5-fluoro-N-(2-fluoro-6-methylphenyl)-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide 4-[4-ethyl-3-(hydroxymethyl)-5-oxo-4,5-dihydro-1H-1,2,4-triazol-1-yl]-5-fluoro-N-(2-fluoro-6-methylphenyl)-2-{[(2S)-1,1,1-trifluoropropan-2-yl]oxy}benzamide, 5-fluoro-N-(2-fluoro-6-methylphenyl)-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, 5-fluoro-N-(2-fluoro-6-methylphenyl)-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide N-(2,6-dichlorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide, N-(2,6-dichlorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2,6-dichlorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, N-(2,6-dichlorophenyl)-5-fluoro-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide, N-(2-chloro-6-fluorophenyl)-5-fluoro-4-[3-(hydroxymethyl)-5-oxo-4-propyl-4,5-dihydro-1H-1,2,4-triazol-1-yl]-2-{[(2S)-1,1,1-trifluoropropan-2-yl]oxy}benzamide, N-(6-chloro-2-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2-chloro-6-fluoro-4-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, and N-(2-chloro-6-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, or a tautomer, an N-oxide, a salt, a salt a tautomer or a salt of an N-oxide thereof.

In further embodiments, the present invention provides compounds of formula (I), supra, any compound selected from 5-fluoro-4-[3-methyl-5-oxo-4-(propan-2-yl)-4,5-dihydro-1H-1,2,4-triazol-1-yl]-N-(2-methylphenyl)-2-{[(2S)-1,1,1-trifluoropropan-2-yl]oxy}benzamide N-(2,6-difluorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide and N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, or a tautomer, an N-oxide, a salt, a salt a tautomer or a salt of an N-oxide thereof.

In another embodiment, the present invention provides a compound of formula (I), supra, which is 5-fluoro-4-[3-methyl-5-oxo-4-(propan-2-yl)-4,5-dihydro-1H-1,2,4-triazol-1-yl]-N-(2-methylphenyl)-2-{[(2S)-1,1,1-trifluoropropan-2-yl]oxy}benzamide or a tautomer, an N-oxide, a salt, a salt a tautomer or a salt of an N-oxide thereof.

In another embodiment, the present invention provides a compound of formula (I), supra, which is
N-(2,6-difluorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide and
or a tautomer, an N-oxide, a salt, a salt a tautomer or a salt of an N-oxide thereof.

In another embodiment, the present invention provides a compound of formula (I), supra, which is
N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide,
or a tautomer, an N-oxide, a salt, a salt a tautomer or a salt of an N-oxide thereof.

In further embodiments, the present invention provides compounds of formula (I), supra, selected from In further embodiments, the present invention provides compounds of formula (I), supra, in which:
$R^1$ represents a group selected from
  a $C_5$-$C_8$-alkyl group,
  a $C_2$-$C_8$-haloalkyl group,
  a $C_4$-$C_8$-cycloalkyl group,
    which is optionally substituted, one or two times, each substituent independently selected from a halogen atom or a group selected from hydroxy, phenyl and —N($R^7$)($R^8$),
    and wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
  a $C_1$-$C_6$-alkyl group which is substituted with a $C_3$-$C_8$-cycloalkyl group,
  a $C_2$-$C_6$-alkyl group which is substituted with a cyano group, a hydroxy group, a $C_3$-$C_8$-heterocycloalkyl group or a phenyl group,
  a $C_3$-$C_6$-alkyl group which is substituted with a monocyclic- or bicyclic heteroaryl group,
  a ($C_2$-$C_6$-hydroxyalkyl)-O—($C_2$-$C_6$-alky)- group,
  a —($C_3$-$C_6$-alkyl)-N($R^7$)($R^8$) group,
  a —($C_3$-$C_8$-cycloalkyl)-N($R^7$)($R^8$) group,
  a —($C_3$-$C_6$-alkyl)-C(═O)N($R^7$)($R^8$) group,
  a 4-7-membered heterocycloalkyl group, a 5- to 7-membered heterocycloalkenyl group, wherein said 4-7-membered heterocycloalkyl group and said 5- to 7-membered heterocycloalkenyl group are connected to the rest of the molecule via a carbon atom, and which is optionally substituted one or two times, each substituent independently selected from a group selected from
    $C_1$-$C_3$-alkyl, 5- to 6-membered heteroaryl, —C(═O)O($C_1$-$C_4$-alkyl), —C(═O)($C_1$-$C_6$-alkyl), —C(═O)($C_3$-$C_6$-cycloalkyl), —S(═O)$_2$($C_1$-$C_6$-alkyl) and oxo (═O),
    wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
  a phenyl group,
    which is optionally substituted, one, two, three, four or five times, each substituent independently selected from a halogen atom or a group selected from
      $C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), hydroxy, cyano, $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(═O)O$R^6$, —C(═O)N($R^7$)($R^8$), —N($R^7$)($R^8$), —($C_1$-$C_6$-alkyl)-N($R^7$)($R^8$), —($C_1$-$C_6$-alkyl)-C(═O)O$R^6$, —($C_1$-$C_6$-alkyl)-C(═O)N($R^7$)($R^8$), —O—C(═O)—($C_1$-$C_6$-alkyl)-, —SH, —S—($C_1$-$C_6$-alkyl), —S—($C_2$-$C_6$-alkenyl), —S(═O)$_2$N($R^7$)($R^8$), —S(═O)$_2$($C_1$-$C_6$-alkyl), —S(═O)$_2$—($C_2$-$C_6$-alkenyl), —S(═O)(═N$R^{11}$)($C_1$-$C_3$-alkyl), —N(O)$_2$, —P(═O)($C_1$-$C_3$-alkyl)$_2$ and SF$_5$,
    or
    wherein two vicinal substituents may form together a 5- or 6-membered, optionally heterocyclic, aromatic or non-aromatic ring, having optionally 1-3 heteroatoms independently selected from —N═, —NH—, —N($R^7$)—, —O—, —S—, and optionally containing a C(═O) group, and wherein the so formed ring is optionally substituted one or two times, each substituent independently selected from a halogen atom or a group selected from
      $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(═O)$_2$($C_1$-$C_6$-alkyl), —N(O)$_2$, and —N($R^7$)($R^8$) and
  a bicyclic aryl group,
  a partially saturated mono- or bicyclic aryl- or heteroaryl group,
  a monocyclic- or bicyclic heteroaryl group,
    which is optionally substituted one, two or three times, each substituent independently selected from a halogen atom or a group selected from
      $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, —O($C_2$-$C_6$-alkenyl), $C_3$-$C_8$-cycloalkoxy, aryl, —O-aryl, cyano, C(═O)O$R^6$, hydroxy, —SH, —S—($C_1$-$C_6$-alkyl), —S—($C_2$-$C_6$-alkenyl), —S(═O)$_2$($C_1$-$C_6$-alkyl), —S(═O)$_2$—($C_2$-$C_6$-alkenyl), —N(O)$_2$, and —N($R^7$)($R^8$),
or a tautomer, an N-oxide, a salt, a salt a tautomer or a salt of an N-oxide thereof.

In further embodiments, the present invention provides compounds of formula (I), supra, in which:
$R^1$ represents a group selected from
  a $C_5$-$C_8$-alkyl group, a $C_2$-$C_8$-haloalkyl group, a $C_4$-$C_8$-cycloalkyl group,
  a $C_1$-$C_6$-alkyl group which is substituted with a $C_3$-$C_8$-cycloalkyl group,
  a $C_2$-$C_6$-alkyl group which is substituted with a cyano group or a phenyl group,
  a $C_3$-$C_6$-alkyl group which is substituted with a monocyclic- or bicyclic heteroaryl group,
  a $C_2$-$C_6$-hydroxyalkyl group, a ($C_2$-$C_6$-hydroxyalkyl)-O—($C_2$-$C_6$-alky)- group,
  a —($C_3$-$C_6$-alkyl)-N($R^7$)($R^8$) group, a —($C_3$-$C_8$-cycloalkyl)-N($R^7$)($R^8$) group, a —($C_3$-$C_6$-alkyl)-C(=O)N($R^7$)($R^8$) group, a 4-7-membered, optionally unsaturated, heterocyclic group, a phenyl group, and a monocyclic- or bicyclic heteroaryl group,
wherein said cycloalkyl groups are optionally substituted, one or two times, each substituent independently selected from a halogen atom or a group selected from
hydroxy, phenyl and —N($R^7$)($R^8$),
wherein said phenyl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and
wherein said 4- to 7-membered heterocycloalkyl group and 5- to 7-membered heterocycloalkenyl group are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
and
wherein said 4-7-membered, optionally unsaturated, heterocyclic group is connected to the rest of the molecule via a carbon atom,
and
wherein said phenyl groups are optionally substituted, one, two, three, four or five times, each substituent independently selected from a halogen atom or a group selected from
$C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(O)OH, —C(=O)$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$), —SH, —S—($C_1$-$C_6$-alkyl), —S—($C_2$-$C_6$-alkenyl), —S(=O)$_2$($C_1$-$C_6$-alkyl), —S(=O)$_2$N($R^7$)($R^8$), —S(=O)$_2$($C_1$-$C_3$-alkyl), —S(=O)(=N$R^{11}$)($C_1$-$C_3$-alkyl), —N(O)$_2$, —P(=O)($C_1$-$C_3$-alkyl)$_2$ and SF$_5$,
or wherein two vicinal substituents of said phenyl groups may form together a 5- or 6-membered, optionally heterocyclic, aromatic or non-aromatic ring, having optionally 1-3 heteroatoms independently selected from —N=, —NH—, —N($R^7$)—, —O—, —S—, and optionally containing a C(=O) group, and wherein the so formed ring is optionally substituted one or two times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$)
and
wherein said monocyclic or bicyclic heteroaryl group is optionally substituted one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, —O($C_2$-$C_6$-alkenyl), $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$),
and tautomers, N-oxides, and salts thereof, and salts of tautomers or N-oxides.

In further embodiments, the present invention provides compounds of formula (I), supra, in which:
$R^1$ represents a group selected from
a $C_5$-$C_8$-alkyl group,
a $C_2$-$C_8$-haloalkyl group,
a $C_4$-$C_8$-cycloalkyl group,
wherein said cycloalkyl groups are optionally substituted, one or two times, each substituent independently selected from a halogen atom or a group selected from
hydroxy, phenyl and —N($R^7$)($R^8$),
wherein said phenyl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
a $C_1$-$C_6$-alkyl group which is substituted with a $C_3$-$C_8$-cycloalkyl group,
a $C_2$-$C_6$-alkyl group which is substituted with a cyano group, a hydroxy group or a phenyl group,
a $C_3$-$C_6$-alkyl group which is substituted with a monocyclic- or bicyclic heteroaryl group,
a $C_2$-$C_6$-cyanoalkyl- group,
a —($C_2$-$C_6$-alkyl)phenyl group,
a ($C_2$-$C_6$-hydroxyalkyl)-O—($C_2$-$C_6$-alky)- group,
a —($C_3$-$C_6$-alkyl)-N($R^7$)($R^8$) group,
a —($C_3$-$C_8$-cycloalkyl)-N($R^7$)($R^8$) group,
a —($C_3$-$C_6$-alkyl)-C(=O)N($R^7$)($R^8$) group,
a 4- to 7-membered heterocycloalkyl group,
which is optionally substituted one or two times, each substituent independently selected from a group selected from
$C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
wherein said 5- to 6-membered heteroaryl substituent is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and wherein said- to 7-membered heterocycloalkyl group is connected to the rest of the molecule via a carbon atom of the said heterocycloalkyl- or heterocycloalkenyl group,
a 5- to 7-membered heterocycloalkenyl group,
which is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
- wherein said 5- to 6-membered heteroaryl substituent is optionally substituted, one, two or three times, each substituent independently selected from a halogen atom or a group selected from
- $C_1$-$C_3$-alkyl, $C_1$-$C_4$-haloalkyl, $C_1$-$C_3$-alkoxy and hydroxy, and wherein said 5- to 7-membered heterocycloalkenyl group is connected to the rest of the molecule via a carbon atom of the said heterocycloalkyl- or heterocycloalkenyl group, a phenyl group, wherein said phenyl groups are optionally substituted, one, two, three, four or five times, each substituent independently selected from a halogen atom or a group selected from
- $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)OR$^6$, —C(=O)N(R$^7$)(R$^8$), —N(R$^7$)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{11}$)($C_1$-$C_3$-alkyl), —P(=O)($C_1$-$C_3$-alkyl)$_2$ and SF$_5$,
- or in which two substituents of said phenyl groups, when they are attached to adjacent ring atoms, are optionally linked to one another in such a way that they jointly form a group selected from
  —CH$_2$—N(R$^7$)—CH$_2$—, —CH$_2$—O—CH$_2$—, —O—CH$_2$—C(=O)—NH— and —NH—C(=O)—NH—, an indanyl group, a tetralinyl group, wherein said indanyl or tetralinyl group is optionally substituted one or two times, each substituent independently selected from a halogen atom or a group selected from
- $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N(R$^7$)(R$^8$), and a monocyclic- or bicyclic heteroaryl group,
- wherein said monocyclic or bicyclic heteroaryl group is optionally substituted one, two or three times, each substituent independently selected from a halogen atom or a group selected from
- $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N(R$^7$)(R$^8$), or a tautomer, an N-oxide, a salt, a salt a tautomer or a salt of an N-oxide thereof.

In further embodiments, the present invention provides compounds of formula (I), supra, in which:

R$^1$ represents a group selected from
- a $C_5$-$C_8$-alkyl group, a $C_2$-$C_8$-haloalkyl group, a $C_4$-$C_8$-cycloalkyl group,
- a $C_1$-$C_6$-alkyl group which is substituted with a $C_3$-$C_8$-cycloalkyl group,
- a $C_2$-$C_6$-alkyl group which is substituted with a cyano group or a phenyl group,
- a $C_3$-$C_6$-alkyl group which is substituted with a monocyclic- or bicyclic heteroaryl group,
- a $C_2$-$C_6$-hydroxyalkyl group, a ($C_2$-$C_6$-hydroxyalkyl)-O—($C_2$-$C_6$-alky)- group,
- a —($C_3$-$C_6$-alkyl)-N(R$^7$)(R$^8$) group, a —($C_3$-$C_8$-cycloalkyl)-N(R$^7$)(R$^8$) group,
- a —($C_3$-$C_6$-alkyl)-C(=O)N(R$^7$)(R$^8$) group, a 4- to 7-membered heterocycloalkyl group, a 5- to 7-membered heterocycloalkenyl group, a phenyl group, an indanyl group, a tetralinyl group and a monocyclic- or bicyclic heteroaryl group, wherein said cycloalkyl groups are optionally substituted, one or two times, each substituent independently selected from a halogen atom or a group selected from
hydroxy, phenyl and —N(R$^7$)(R$^8$),
- wherein said phenyl substituent is optionally substituted, one, two or three times, each substituent independently selected from a halogen atom or a group selected from
- $C_1$-$C_3$-alkyl, $C_1$-$C_4$-haloalkyl, $C_1$-$C_3$-alkoxy and hydroxy, and
wherein said 4- to 7-membered heterocycloalkyl group and 5- to 7-membered heterocycloalkenyl group are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
- wherein said 5- to 6-membered heteroaryl substituent is optionally substituted, one, two or three times, each substituent independently selected from a halogen atom or a group selected from
- $C_1$-$C_3$-alkyl, $C_1$-$C_4$-haloalkyl, $C_1$-$C_3$-alkoxy and hydroxy, and
wherein said 4- to 7-membered heterocycloalkyl group and said 5- to 7-membered heterocycloalkenyl group are connected to the rest of the molecule via a carbon atom of the said heterocycloalkyl- or heterocycloalkenyl group, and
wherein said phenyl groups are optionally substituted, one, two, three, four or five times, each substituent independently selected from a halogen atom or a group selected from
- $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)OR$^6$, —C(=O)N(R$^7$)(R$^8$), —N(R$^7$)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{11}$)($C_1$-$C_3$-alkyl), —P(=O)($C_1$-$C_3$-alkyl)$_2$ and SF$_5$,
- or in which two substituents of said phenyl groups, when they are attached to adjacent ring atoms, are optionally linked to one another in such a way that they jointly form a group selected from
  —CH$_2$—N(R$^7$)—CH$_2$—, —CH$_2$—O—CH$_2$—, —O—CH$_2$—C(=O)—NH— and —NH—C(=O)—NH—, and
wherein said indanyl or tetralinyl group is optionally substituted one or two times, each substituent independently selected from a halogen atom or a group selected from
- $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N(R$^7$)(R$^8$), and
wherein said monocyclic or bicyclic heteroaryl group is optionally substituted one, two or three times, each substituent independently selected from a halogen atom or a group selected from
C$_1$-C$_6$-alkyl, C$_1$-C$_6$-haloalkyl, C$_3$-C$_8$-cycloalkyl, C$_1$-C$_6$-alkoxy, C$_1$-C$_6$-haloalkoxy, C$_3$-C$_8$-cycloalkoxy, cyano, hydroxy and —N(R$^7$)(R$^8$), and tautomers, N-oxides, and salts thereof, and salts of tautomers or N-oxides.

In further embodiments, the present invention provides compounds of formula (I), supra, in which:

R$^1$ represents a group selected from
a C$_5$-C$_8$-alkyl group,
a C$_2$-C$_8$-haloalkyl group,
a C$_4$-C$_8$-cycloalkyl group,
  which is optionally substituted, one or two times, each substituent independently selected from a halogen atom or a group selected from
  hydroxy, phenyl and —N(R$^7$)(R$^8$),
    wherein said phenyl substituent is optionally substituted, one, two or three times, each substituent independently selected from a halogen atom or a group selected from
    C$_1$-C$_3$-alkyl, C$_1$-C$_3$-haloalkyl, C$_1$-C$_3$-alkoxy and hydroxy,
a C$_1$-C$_3$-alkyl group which is substituted with a C$_3$-C$_6$-cycloalkyl group,
a C$_2$-C$_6$-alkyl group which is substituted with a cyano group, a hydroxy group or a phenyl group,
a C$_3$-C$_6$-alkyl group which is substituted with a monocyclic or bicyclic heteroaryl group,
a C$_2$-C$_6$-cyanoalkyl- group,
a —(C$_2$-C$_6$-alkyl)phenyl group,
a (C$_2$-C$_3$-hydroxyalkyl)-O—(C$_2$-C$_6$-alky)- group,
a —(C$_3$-C$_6$-alkyl)-N(R$^7$)(R$^8$) group,
a —(C$_3$-C$_6$-cycloalkyl)-N(R$^7$)(R$^8$) group,
a —(C$_3$-C$_6$-alkyl)-C(=O)N(R$^7$)(R$^8$) group,
a 4- to 6-membered heterocycloalkyl group,
  which is optionally substituted one or two times, each substituent independently selected from a group selected from
  C$_1$-C$_3$-alkyl, 5- to 6-membered heteroaryl, —C(=O)O(C$_1$-C$_4$-alkyl), —C(=O)(C$_1$-C$_3$-alkyl), —C(=O)(C$_3$-C$_6$-cycloalkyl), —S(=O)$_2$(C$_1$-C$_3$-alkyl) and oxo (=O),
    wherein said 5- to 6-membered heteroaryl group is optionally substituted, one, two or three times, each substituent independently selected from a halogen atom or a group selected from
    C$_1$-C$_3$-alkyl, C$_1$-C$_3$-haloalkyl, C$_1$-C$_3$-alkoxy and hydroxy,
  wherein said 4- to 6-membered heterocycloalkyl group is connected to the rest of the molecule via a carbon atom or nitrogen atom of the said heterocycloalkyl- or heterocycloalkenyl group,
a 5- to 6-membered heterocycloalkenyl group,
  which is optionally substituted one or two times, each substituent independently selected from a group selected from
  C$_1$-C$_3$-alkyl, 5- to 6-membered heteroaryl, —C(=O)O(C$_1$-C$_4$-alkyl), —C(=O)(C$_1$-C$_3$-alkyl), —C(=O)(C$_3$-C$_6$-cycloalkyl), —S(=O)$_2$(C$_1$-C$_3$-alkyl) and oxo (=O),
    wherein said 5- to 6-membered heteroaryl group is optionally substituted, one, two or three times, each substituent independently selected from a halogen atom or a group selected from
    C$_1$-C$_3$-alkyl, C$_1$-C$_3$-haloalkyl, C$_1$-C$_3$-alkoxy and hydroxy,
  wherein said 5- to 6-membered heterocycloalkenyl group is connected to the rest of the molecule via a carbon atom or nitrogen atom of the said heterocycloalkyl- or heterocycloalkenyl group,
a phenyl group,
  which is optionally substituted, one, two, three, four or five times, each substituent independently selected from a halogen atom or a group selected from
  C$_1$-C$_4$-alkyl, C$_3$-C$_6$-cycloalkyl, C$_1$-C$_3$-haloalkyl, C$_1$-C$_3$-hydroxyalkyl, C$_1$-C$_3$-alkoxy, C$_1$-C$_3$-haloalkoxy, C$_3$-C$_6$-cycloalkoxy, hydroxy, cyano, —C(=O)OR$^6$, —C(=O)N(R$^7$)(R$^8$), —N(R$^7$)(R$^8$), —(C$_1$-C$_3$-alkyl)-N(R$^7$)(R$^8$), —(C$_1$-C$_3$-alkyl)-C(=O)OR$^6$, —(C$_1$-C$_3$-alkyl)-C(=O)N(R$^7$)(R$^8$), —S(=O)$_2$N(R$^7$)(R$^8$), —S(=O)$_2$(C$_1$-C$_3$-alkyl), —S(=O)(=NR$^{11}$)(C$_1$-C$_3$-alkyl), —P(=O)(C$_1$-C$_3$-alkyl)$_2$ and SF$_5$, or in which two substituents of said phenyl groups, when they are attached to adjacent ring atoms, are optionally linked to one another in such a way that they jointly form a group selected from
  —CH$_2$—N(R$^7$)—CH$_2$—, —CH$_2$—O—CH$_2$—, —O—CH$_2$—C(=O)—NH— and —NH—C(=O)—NH—,
an indanyl group,
  which is optionally substituted one or two times, each substituent independently selected from a halogen atom or a group selected from
  C$_1$-C$_3$-alkyl, C$_1$-C$_3$-haloalkyl, C$_3$-C$_6$-cycloalkyl, C$_1$-C$_3$-alkoxy, C$_1$-C$_3$-haloalkoxy, C$_3$-C$_6$-cycloalkoxy, cyano, hydroxy and —N(R$^7$)(R$^8$),
a tetralinyl group and
  which is optionally substituted one or two times, each substituent independently selected from a halogen atom or a group selected from
  C$_1$-C$_3$-alkyl, C$_1$-C$_3$-haloalkyl, C$_3$-C$_6$-cycloalkyl, C$_1$-C$_3$-alkoxy, C$_1$-C$_3$-haloalkoxy, C$_3$-C$_6$-cycloalkoxy, cyano, hydroxy and —N(R$^7$)(R$^8$),
a monocyclic- or bicyclic heteroaryl group,
  which is optionally substituted one, two or three times, each substituent independently selected from a halogen atom or a group selected from
  C$_1$-C$_3$-alkyl, C$_1$-C$_3$-haloalkyl, C$_3$-C$_6$-cycloalkyl, C$_1$-C$_3$-alkoxy, C$_1$-C$_3$-haloalkoxy, C$_3$-C$_6$-cycloalkoxy, cyano, hydroxy and —N(R$^7$)(R$^8$), or a tautomer, an N-oxide, a salt, a salt of a tautomer or a salt of an N-oxides thereof.

In further embodiments, the present invention provides compounds of formula (I), supra, in which:

R$^1$ represents a group selected from
a C$_5$-C$_8$-alkyl group, a C$_2$-C$_8$-haloalkyl group, a C$_4$-C$_8$-cycloalkyl group,
a C$_1$-C$_3$-alkyl group which is substituted with a C$_3$-C$_6$-cycloalkyl group,
a C$_2$-C$_6$-alkyl group which is substituted with a cyano group or a phenyl group,
a C$_3$-C$_6$-alkyl group which is substituted with a monocyclic or bicyclic heteroaryl group,
a C$_2$-C$_6$-hydroxyalkyl group, a (C$_2$-C$_3$-hydroxyalkyl)-O—(C$_2$-C$_6$-alky)- group,
a —(C$_3$-C$_6$-alkyl)-N(R$^7$)(R$^8$) group, a —(C$_3$-C$_6$-cycloalkyl)-N(R$^7$)(R$^8$) group,
a —(C$_3$-C$_6$-alkyl)-C(=O)N(R$^7$)(R$^8$) group, a 4- to 6-membered heterocycloalkyl group, a 5- to 6-membered heterocycloalkenyl group, a phenyl group, an indanyl group, a tetralinyl group and a monocyclic- or bicyclic heteroaryl group, wherein said cycloalkyl groups are optionally substituted, one or two times, each substituent independently selected from a halogen atom or a group selected from hydroxy, phenyl and —N($R^7$)($R^8$), wherein said phenyl substituent is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, and wherein said 4- to 6-membered heterocycloalkyl group and 5- to 6-membered heterocycloalkenyl group are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), wherein said 5- to 6-membered heteroaryl group is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, and wherein said 4- to 6-membered heterocycloalkyl group and 5- to 6-membered heterocycloalkenyl group are connected to the rest of the molecule via a carbon atom of the said heterocycloalkyl- or heterocyclalkenyl group, and wherein said phenyl groups are optionally substituted, one, two, three, four or five times, each substituent independently selected from a halogen atom or a group selected from $C_1$-$C_4$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(=O)O$R^6$, —C(=O)N($R^7$)($R^8$), —N($R^7$)($R^8$), —($C_1$-$C_3$-alkyl)-N($R^7$)($R^8$), —($C_1$-$C_3$-alkyl)-C(=O)O$R^6$, —($C_1$-$C_3$-alkyl)-C(=O)N($R^7$)($R^8$), —S(=O)$_2$N($R^7$)($R^8$), —S(=O)$_2$($C_1$-$C_3$-alkyl), —S(=O)(=N$R^{11}$)($C_1$-$C_3$-alkyl), —P(=O)($C_1$-$C_3$-alkyl)$_2$ and SF$_5$, or in which two substituents of said phenyl groups, when they are attached to adjacent ring atoms, are optionally linked to one another in such a way that they jointly form a group selected from —CH$_2$—N($R^7$)—CH$_2$—, —CH$_2$—O—CH$_2$—, —O—CH$_2$—C(=O)—NH— and —NH—C(=O)—NH—, wherein said indanyl- or tetralinyl group is optionally substituted one or two times, each substituent independently selected from a halogen atom or a group selected from $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), and wherein said monocyclic or bicyclic heteroaryl group is optionally substituted one, two or three times, each substituent independently selected from a halogen atom or a group selected from $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), and tautomers, N-oxides, and salts thereof, and salts of tautomers or N-oxides.

In further embodiments, the present invention provides compounds of formula (I), supra, in which:

$R^1$ represents a group selected from a $C_5$-$C_8$-alkyl group, a $C_4$-$C_8$-cycloalkyl group, which is optionally substituted, one or two times, with a phenyl group, wherein said phenyl substituent is optionally substituted, one, two or three times, each substituent independently selected from a halogen atom, a $C_1$-$C_3$-alkyl group which is substituted with a $C_3$-$C_6$-cycloalkyl group, a $C_2$-$C_6$-alkyl group which is substituted with a hydroxy group or a phenyl group, a $C_3$-$C_6$-alkyl group which is substituted with a monocyclic or bicyclic heteroaryl group, a $C_2$-$C_6$-cyanoalkyl- group, a —($C_2$-$C_6$-alkyl)phenyl group, a —($C_3$-$C_6$-alkyl)-N($R^7$)($R^8$) group, a —($C_3$-$C_6$-alkyl)-C(=O)N($R^7$)($R^8$) group, a 4- to 6-membered heterocycloalkyl group, which is optionally substituted one or two times, each substituent independently selected from a $C_1$-$C_3$-alkyl group, and which is connected to the rest of the molecule via a carbon atom of the said heterocycloalkyl group, a phenyl group, which is optionally substituted, one, two, three or four times, each substituent independently selected from a halogen atom or a group selected from $C_1$-$C_4$-alkyl, $C_1$-$C_3$-haloalkyl, $C_1$-$C_3$-hydroxyalkyl, $C_1$-$C_3$-alkoxy, hydroxy, —C(=O)O$R^6$, —C(=O)N($R^7$)($R^8$), N($R^7$)($R^8$), —($C_1$-$C_3$-alkyl)-N($R^7$)($R^8$), —O—C(=O)—($C_1$-$C_4$-alkyl), —S—$C_1$-$C_3$-alkyl, —S(=O)$_2$($C_1$-$C_3$-alkyl), —S(=O)(=N$R^{11}$)($C_1$-$C_3$-alkyl) and —P(=O)($C_1$-$C_3$-alkyl)$_2$, an indanyl group and a monocyclic- or bicyclic heteroaryl group, which are optionally substituted one, two or three times, each substituent independently selected from a halogen atom or a group selected from $C_1$-$C_3$-alkyl and $C_1$-$C_3$-alkoxy, and tautomers, N-oxides, and salts thereof, and salts of tautomers or N-oxides.

In further embodiments, the present invention provides compounds of formula (I), supra, in which:

$R^1$ represents a group selected from a $C_5$-$C_8$-alkyl group, a $C_4$-$C_8$-cycloalkyl group, a $C_1$-$C_3$-alkyl group which is substituted with a $C_3$-$C_6$-cycloalkyl group, a $C_2$-$C_6$-alkyl group which is substituted with a phenyl group, a $C_3$-$C_6$-alkyl group which is substituted with a monocyclic or bicyclic heteroaryl group, a $C_2$-$C_6$-hydroxyalkyl group, a —($C_3$-$C_6$-alkyl)-N($R^7$)($R^8$) group, a —($C_3$-$C_6$-alkyl)-C(=O)N($R^7$)($R^8$) group, a 4- to 6-membered heterocycloalkyl group, a phenyl group, an indanyl group and a monocyclic- or bicyclic heteroaryl group, wherein said cycloalkyl groups are optionally substituted, one or two times, with a phenyl group, wherein said phenyl substituent is optionally substituted, one, two or three times, each substituent independently selected from a halogen atom,
and
wherein said 4- to 6-membered heterocycloalkyl group is optionally substituted one or two times, each substituent independently selected from a $C_1$-$C_3$-alkyl group,
and
wherein said 4- to 6-membered heterocycloalkyl group is connected to the rest of the molecule via a carbon atom of the said heterocycloalkyl group,
and
wherein said phenyl groups are optionally substituted, one, two, three or four times, each substituent independently selected from a halogen atom or a group selected from
$C_1$-$C_4$-alkyl, $C_1$-$C_3$-haloalkyl, $C_1$-$C_3$-hydroxyalkyl, $C_1$-$C_3$-alkoxy, hydroxy, —C(=O)OR$^6$, —N(R$^7$)(R$^8$), —($C_1$-$C_3$-alkyl)-N(R$^7$)(R$^8$), —S(=O)$_2$($C_1$-$C_3$-alkyl), —S(=O)(=NR$^{11}$)($C_1$-$C_3$-alkyl) and —P(=O)($C_1$-$C_3$-alkyl)$_2$,
and
wherein said monocyclic or bicyclic heteroaryl group is optionally substituted one, two or three times, each substituent independently selected from a halogen atom or a group selected from
$C_1$-$C_3$-alkyl and $C_1$-$C_3$-alkoxy,
and tautomers, N-oxides, and salts thereof, and salts of tautomers or N-oxides.

In further embodiments, the present invention provides compounds of formula (I), supra, in which:
$R^1$ represents a group selected from
a $C_5$-$C_7$-alkyl group,
a $C_5$-$C_7$-cycloalkyl group,
a $C_1$-$C_2$-alkyl group which is substituted with a $C_5$-$C_7$-cycloalkyl group,
a $C_2$-$C_5$-alkyl group which is substituted with a cyano group a hydroxy group or a phenyl group,
a —($C_3$-$C_8$-alkyl)-N(R$^7$)(R$^8$) group,
a —($C_3$-$C_8$-alkyl)-C(=O)N(R$^7$)(R$^8$) group,
a 5- to 6-membered heterocycloalkyl group,
which is optionally substituted one or two times, with a $C_1$-$C_3$-alkyl group, and which is connected to the rest of the molecule via a carbon atom,
a phenyl group,
which is optionally substituted, one, two or three times, each substituent independently selected from a halogen atom or a group selected from $C_1$-$C_3$-alkyl, $C_1$-$C_3$-haloalkyl, $C_1$-$C_3$-alkoxy, hydroxy, —C(=O)OR$^6$, —C(=O)N(R$^7$)(R$^8$), —N(R$^7$)(R$^8$), —($C_1$-$C_3$-alkyl)-N(R$^7$)(R$^8$), —O—C(=O)—($C_1$-$C_4$-alkyl), —S—$C_1$-$C_3$-alkyl, —S(=O)$_2$—$C_1$-$C_3$-alkyl, —S(=O)(=NH)($C_1$-$C_3$-alkyl) and
an indanyl group, and
a monocyclic heteroaryl group,
which is optionally substituted one or two times, each substituent independently selected from a group selected from
$C_1$-$C_3$-alkyl and $C_1$-$C_3$-alkoxy,
or a tautomer, an N-oxide, a salt, a salt of a tautomer or a salt of an N-oxide thereof.

In further embodiments, the present invention provides compounds of formula (I), supra, in which:
$R^1$ represents a group selected from
a $C_5$-$C_7$-alkyl group, a $C_5$-$C_7$-cycloalkyl group,
a $C_1$-$C_2$-alkyl group which is substituted with a $C_5$-$C_7$-cycloalkyl group,
a $C_2$-$C_5$-hydroxyalkyl group, a —($C_3$-$C_8$-alkyl)-N(R$^7$)(R$^8$) group,
a —($C_3$-$C_8$-alkyl)-C(=O)N(R$^7$)(R$^8$) group, a 5- to 6-membered heterocycloalkyl group,
a phenyl group, an indanyl group, and a monocyclic heteroaryl group,
which 5- to 6-membered heterocycloalkyl group is optionally substituted one or two times, with a $C_1$-$C_3$-alkyl group,
and
wherein said 5- to 6-membered heterocycloalkyl group is connected to the rest of the molecule via a carbon atom of the said heterocycloalkyl group,
and
wherein said phenyl groups are optionally substituted, one, two or three times, each substituent independently selected from a halogen atom or a group selected from
$C_1$-$C_4$-alkyl, $C_1$-$C_3$-haloalkyl, $C_1$-$C_3$-alkoxy, hydroxy, —C(=O)OR$^6$, —N(R$^7$)(R$^8$) and —($C_1$-$C_3$-alkyl)-N(R$^7$)(R$^8$),
and
which monocyclic heteroaryl group is optionally substituted one or two times, each substituent independently selected from a group selected from
$C_1$-$C_3$-alkyl and $C_1$-$C_3$-alkoxy,
and tautomers, N-oxides, and salts thereof, and salts of tautomers or N-oxides.

In further embodiments, the present invention provides compounds of formula (I), supra, in which:
$R^1$ represents a group selected from
a $C_5$-$C_7$-alkyl group,
a $C_5$-$C_7$-cycloalkyl group,
a $C_1$-$C_2$-alkyl group which is substituted with a $C_5$-$C_6$-cycloalkyl group,
a $C_3$-$C_4$-hydroxyalkyl group,
a $C_3$-$C_4$-phenylalkyl group,
a —($C_3$-$C_4$-alkyl)-N(R$^7$)(R$^8$) group,
a CH$_3$CH$_2$CH—C(=O)NH$_2$ group,
a 5- to 6-membered heterocycloalkyl group,
which is optionally substituted one or two times, with a $C_1$-$C_3$-alkyl group, and
which is connected to the rest of the molecule via a carbon atom,
a phenyl group,
which is optionally substituted, one, two or three times, each substituent independently selected from a halogen atom or a group selected from $C_1$-$C_3$-alkyl, $C_1$-$C_3$-haloalkyl, $C_1$-$C_3$-alkoxy, hydroxy, —C(=O)OR$^6$, —C(=O)N(R$^7$)(R$^8$), —N(R$^7$)(R$^8$), —O—C(=O)—($C_1$-$C_4$-alkyl), —S—$C_1$-$C_3$-alkyl, —S(=O)$_2$—$C_1$-$C_3$-alkyl, —S(=O)(=NH)($C_1$-$C_3$-alkyl) and —($C_1$-$C_3$-alkyl)-N(R$^7$)(R$^8$),
an indanyl group, and
a monocyclic heteroaryl group,
which is optionally substituted one or two times, each substituent independently selected from a group selected from
$C_1$-$C_3$-alkyl and $C_1$-$C_3$-alkoxy,
or a tautomer, an N-oxide, a salt, a salt of a tautomer or a salt of an N-oxide thereof.

In further embodiments, the present invention provides compounds of formula (I), supra, in which:

$R^1$ represents a group selected from
a $C_5$-$C_7$-alkyl group, a $C_5$-$C_7$-cycloalkyl group,
a $C_1$-$C_2$-alkyl group which is substituted with a $C_5$-$C_6$-cycloalkyl group,
a $C_3$-$C_4$-hydroxyalkyl group, a —($C_3$-$C_4$-alkyl)-N($R^7$)($R^8$) group, a $CH_3CH_2CH$—C(=O)$NH_2$ group, a 5- to 6-membered heterocycloalkyl group, a phenyl group, an indanyl group, and a monocyclic heteroaryl group,
wherein said 5- to 6-membered heterocycloalkyl group is selected from tetrahydrofuranyl, tetrahydro-2H-pyranyl and piperidinyl,
which 5- to 6-membered heterocycloalkyl group is optionally substituted one or two times, with a $C_1$-$C_3$-alkyl group,
and
wherein said 5- to 6-membered heterocycloalkyl group is connected to the rest of the molecule via a carbon atom of the said heterocycloalkyl group,
and
wherein said phenyl groups are optionally substituted, one, two or three times, each substituent independently selected from a halogen atom or a group selected from
$C_1$-$C_4$-alkyl, $C_1$-$C_3$-haloalkyl, $C_1$-$C_3$-alkoxy, hydroxy, —C(=O)$OR^6$, —N($R^7$)($R^8$) and —($C_1$-$C_3$-alkyl)-N($R^7$)($R^8$),
and
wherein said monocyclic heteroaryl group is selected from oxazolyl, pyrazolyl, pyridinyl and pyrimidinyl,
which monocyclic heteroaryl group is optionally substituted one or two times, each substituent independently selected from a group selected from
$C_1$-$C_3$-alkyl and $C_1$-$C_3$-alkoxy,
and tautomers, N-oxides, and salts thereof, and salts of tautomers or N-oxides.

In further embodiments, the present invention provides compounds of formula (I), supra, in which:
$R^1$ represents a group selected from
3-pentyl, 2,2-dimethylpropyl, 4-heptyl, 4-fluorophenyl-cyclopropyl, cyclopentyl, cyclohexyl, cycloheptyl, cyclopentylmethyl, cyclohexylmethyl, 1-cyclohexyl-ethyl, 1-hydroxypropan-2-yl, 2-hydroxypropyl, 1-hydroxybutan-2-yl, 1-cyanobutan-2-yl, 1-phenylbutan-2-yl, 1-amino-2-propyl, 1-amino-2-butyl, 1-amino-1-oxobutan-2-yl, indan-2-yl,
a 5- to 6-membered heterocycloalkyl group, which is selected from tetrahydrofuran-3-yl, tetrahydro-2H-pyran-4-yl and piperidin-4-yl, and which is optionally substituted one or two times with a methyl group,
a phenyl group, which is optionally substituted, one, two or three times, each substituent independently selected from a fluorine atom or a chlorine atom or a group selected from
methyl, ethyl, propyl, isopropyl, difluoromethyl, trifluoromethyl, methoxy, —O—C(=O)-1,1-dimethylethyl, hydroxy, —C(=O)$OCH_3$, —C(=O)NH-cyclopropyl, amino, methylamino, aminomethyl, —S—$CH_3$, —S(=O)$_2CH_3$, and —S(=O)(NH)$CH_3$, and
a monocyclic heteroaryl group, which is selected from oxazol-2-yl, pyrazol-3-yl, pyrazol-5-yl, pyridin-2-yl, pyridin-3-yl, pyridin-4-yl, pyrimidin-2-yl, pyrimidin-4-yl, chinolin-5-yl, indazol-5-yl,
and which is optionally substituted one or two times, each substituent independently selected from methyl and methoxy,
or a tautomer, an N-oxide, a salt, a salt of a tautomer or a salt of an N-oxide thereof.

In further embodiments, the present invention provides compounds of formula (I), supra, in which:
$R^1$ represents a group selected from
3-pentyl, 2,2-dimethylpropyl, 4-heptyl, 4-fluorophenyl-cyclopropyl, cyclopentyl, cyclohexyl, cycloheptyl, cyclopentylmethyl, cyclohexylmethyl, 1-cyclohexylethyl, 1-hydroxypropan-2-yl, 2-hydroxypropyl, 1-hydroxybutan-2-yl,
2-hydroxypropyl, 1-hydroxybutan-2-yl, 1-amino-2-propyl, 1-amino-2-butyl, $CH_3CH_2CH$—C(=O)$NH_2$,
5- to 6-membered heterocycloalkyl, phenyl, indanyl and monocyclic heteroaryl,
wherein said 5- to 6-membered heterocycloalkyl group is selected from tetrahydrofuranyl, tetrahydro-2H-pyranyl and piperidinyl,
which 5- to 6-membered heterocycloalkyl group is optionally substituted one or two times, with a methyl group,
and
wherein said phenyl groups are optionally substituted, one, two or three times, each substituent independently selected from a fluorine atom or a chlorine atom or a group selected from
methyl, ethyl, propyl, isopropyl, trifluoromethyl, methoxy, hydroxy, C(=O)$OCH_3$, amino, methylamino and aminomethyl,
and
wherein said monocyclic heteroaryl group is selected from oxazolyl, pyrazolyl, pyridinyl and pyrimidinyl,
which monocyclic heteroaryl group is optionally substituted one or two times, each substituent independently selected from a group selected from methyl and methoxy,
and tautomers, N-oxides, and salts thereof, and salts of tautomers or N-oxides.

In further embodiments, the present invention provides compounds of formula (I), supra, in which:
$R^1$ represents a group selected from
  3-pentyl, 2,2-dimethylpropyl, 4-heptyl, cyclopentyl, cyclohexyl, cycloheptyl, cyclopentylmethyl, cyclohexylmethyl, 1-cyclohexylethyl, 1-hydroxypropan-2-yl, 2-hydroxypropyl, 1-hydroxybutan-2-yl, 1-amino-2-propyl, 1-amino-2-butyl, $CH_3CH_2CH$—$C(=O)NH_2$, 5- to 6-membered heterocycloalkyl, phenyl, indan-2-yl and monocyclic heteroaryl,
    wherein said 5- to 6-membered heterocycloalkyl group is selected from tetrahydrofuran-3-yl, tetrahydro-2H-pyran-4-yl and piperidin-4-yl,
    which 5- to 6-membered heterocycloalkyl group is optionally substituted one or two times, with a methyl group,
    and
    wherein said phenyl groups are optionally substituted, one, two or three times, each substituent independently selected from a fluorine atom or a chlorine atom or a group selected from
      methyl, ethyl, propyl, isopropyl, trifluoromethyl, methoxy, hydroxy, $C(=O)OCH_3$, amino, methylamino and aminomethyl,
    and
    wherein said monocyclic heteroaryl group is selected from oxazol-2-yl, pyrazol-3-yl, pyridin-2-yl, pyridin-3-yl, pyridin-4-yl, pyrimidin-2-yl and pyrimidin-4-yl,
      which monocyclic heteroaryl group is optionally substituted one or two times, each substituent independently selected from a group selected from methyl and methoxy,
and tautomers, N-oxides, and salts thereof, and salts of tautomers or N-oxides.

In accordance with further embodiments, the present invention provides compounds of general formula (I), in which
$R^1$ represents a phenyl group which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —$C(=O)OR^6$, —$C(=O)N(R^7)(R^8)$, —$N(R^7)(R^8)$, —$(C_1$-$C_6$-alkyl)-$N(R^7)(R^8)$, —$(C_1$-$C_6$-alkyl)-$C(=O)OR^6$, —$(C_1$-$C_6$-alkyl)-$C(=O)N(R^7)(R^8)$, —$S(=O)_2N(R^7)(R^8)$, —$S(=O)_2(C_1$-$C_3$-alkyl), —$S(=O)(=NR^{11})(C_1$-$C_3$-alkyl), —$P(=O)(C_1$-$C_3$-alkyl)$_2$ and $SF_5$,
  or in which two substituents of said phenyl groups, when they are attached to adjacent ring atoms, are optionally linked to one another in such a way that they jointly form a group selected from
    —$CH_2$—$N(R^7)$—$CH_2$—, —$CH_2$—O—$CH_2$—, —O—$CH_2$—$C(=O)$—NH— and —NH—$C(=O)$—NH—,
and tautomers, N-oxides, and salts thereof, and salts of tautomers or N-oxides.

In accordance with further embodiments, the present invention provides compounds of general formula (I), in which $R^1$ represents a phenyl group, which is optionally substituted, one or two times, each substituent independently selected from a hydroxy group, a fluorine atom, a chlorine atom and a methyl group and tautomers, N-oxides, and salts thereof, and salts of tautomers or N-oxides.

In accordance with further embodiments, the present invention provides compounds of general formula (I), in which
$R^1$ represents a phenyl group, which is optionally substituted, one or two times, each substituent independently selected from a fluorine atom, a chlorine atom and a methyl group.

In accordance with further embodiments, the present invention provides compounds of general formula (I), in which
$R^1$ represents a $C_4$-$C_8$-cycloalkyl group or a —$(C_3$-$C_8$-cycloalkyl)-$N(R^7)(R^8)$ group which are optionally substituted, one or two times, each substituent independently selected from a halogen atom or a group selected from hydroxy, phenyl and —$N(R^7)(R^8)$,
  wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy.

In accordance with further embodiments, the present invention provides compounds of general formula (I), in which
$R^1$ represents a 4- to 7-membered heterocycloalkyl group or a 5- to 7-membered heterocycloalkenyl group, wherein said 4- to 7-membered heterocycloalkyl group and 5- to 7-membered heterocycloalkenyl group are optionally substituted one or two times, each substituent independently selected from a group selected from $C_1$-$C_3$-alkyl, 5- to 6-membered heteroaryl,
—$C(=O)O(C_1$-$C_4$-alkyl), —$C(=O)(C_1$-$C_6$-alkyl), —$C(=O)(C_3$-$C_6$-cycloalkyl), —$S(=O)_2(C_1$-$C_6$-alkyl) and oxo (=O),
and wherein said 4- to 7-membered heterocycloalkyl group and 5- to 7-membered heterocycloalkenyl group are connected to the rest of the molecule via a carbon atom of the said heterocycloalkyl- or heterocyclalkenyl group.

In accordance with further embodiments, the present invention provides compounds of general formula (I), in which $R^1$ represents a indanyl group, a tetralinyl group and a monocyclic- or bicyclic heteroaryl group
  wherein said indanyl or tetralinyl group is optionally substituted one or two times, each substituent independently selected from a halogen atom or a group selected from $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —$N(R^7)(R^8)$,
  wherein said monocyclic or bicyclic heteroaryl group is optionally substituted one, two or three times, each substituent independently selected from a halogen atom or a group selected from
$C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —$N(R^7)(R^8)$ and tautomers, N-oxides, and salts thereof, and salts of tautomers or N-oxides.

In further embodiments, the present invention provides compounds of formula (I), supra, in which:
$R^1$ represents a group selected from
  a $C_5$-$C_8$-alkyl group,
  a $C_2$-$C_8$-haloalkyl group,
  a $C_4$-$C_8$-cycloalkyl group,
    which is optionally substituted, one or two times, each substituent independently selected from a halogen atom or a group selected from hydroxy, phenyl and —$N(R^7)(R^8)$,
    and wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a —($C_3$-$C_8$-cycloalkyl)-N($R^7$)($R^8$) group, a —($C_3$-$C_6$-alkyl)-C(=O)N($R^7$)($R^8$) group, a 4-7-membered heterocycloalkyl group, a 5- to 7-membered heterocycloalkenyl group, wherein said 4-7-membered heterocycloalkyl group and said 5- to 7-membered heterocycloalkenyl group are connected to the rest of the molecule via a carbon atom, and which is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), hydroxy, $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$), —O—C(=O)—($C_1$-$C_6$-alkyl)-, —SH, —S—($C_1$-$C_6$-alkyl), —S—($C_2$-$C_6$-alkenyl), —S(=O)$_2$N($R^7$)($R^8$), —S(=O)$_2$($C_1$-$C_6$-alkyl), —S(=O)$_2$—($C_2$-$C_6$-alkenyl), —S(=O)(=N$R^{11}$)($C_1$-$C_3$-alkyl), —N(O)$_2$, —P(=O)($C_1$-$C_3$-alkyl)$_2$ and SF$_5$, or wherein two vicinal substituents may form together a 5- or 6-membered, optionally heterocyclic, aromatic or non-aromatic ring, having optionally 1-3 heteroatoms independently selected from —N=, —NH—, —N($R^7$)—, —O—, —S—, and optionally containing a C(=O) group, and wherein the so formed ring is optionally substituted one or two times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$) and a monocyclic- or bicyclic heteroaryl group, which is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, —O($C_2$-$C_6$-alkenyl), $C_3$-$C_8$-cycloalkoxy, aryl, —O-aryl, cyano, C(=O)O$R^6$, hydroxy, —SH, —S—($C_1$-$C_6$-alkyl), —S—($C_2$-$C_6$-alkenyl), —S(=O)$_2$($C_1$-$C_6$-alkyl), —S(=O)$_2$—($C_2$-$C_6$-alkenyl), —N(O)$_2$, and —N($R^7$)($R^8$), and tautomers, N-oxides, and salts thereof, and salts of tautomers or N-oxides.

In further embodiments, the present invention provides compounds of formula (I), supra, in which:

$R^1$ represents a group selected from a $C_5$-$C_8$-alkyl group, a $C_4$-$C_8$-cycloalkyl group, a —($C_3$-$C_8$-cycloalkyl)-N($R^7$)($R^8$) group, a 4-7-membered, optionally unsaturated, heterocyclic group, a phenyl group, and a monocyclic- or bicyclic heteroaryl group, wherein said cycloalkyl groups are optionally substituted, one or two times, each substituent independently selected from a halogen atom or a group selected from hydroxy, phenyl and —N($R^7$)($R^8$), wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said 4- to 7-membered heterocycloalkyl group and 5- to 7-membered heterocycloalkenyl group are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said 4-7-membered, optionally unsaturated, heterocyclic group is connected to the rest of the molecule via a carbon atom, and wherein said phenyl groups are optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(O)OH, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$), —SH, —S—($C_1$-$C_6$-alkyl), —S—($C_2$-$C_6$-alkenyl), —S(=O)$_2$($C_1$-$C_6$-alkyl), —S(=O)$_2$N($R^7$)($R^8$), —S(=O)$_2$($C_1$-$C_3$-alkyl), —S(=O)(=N$R^{11}$)($C_1$-$C_3$-alkyl), —N(O)$_2$, —P(=O)($C_1$-$C_3$-alkyl)$_2$ and SF$_5$, or wherein two vicinal substituents of said phenyl groups may form together a 5- or 6-membered, optionally heterocyclic, aromatic or non-aromatic ring, having optionally 1-3 heteroatoms independently selected from —N=, —NH—, —N($R^7$)—, —O—, —S—, and optionally containing a C(=O)

group, and wherein the so formed ring is optionally substituted one or two times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$) and wherein said monocyclic or bicyclic heteroaryl group is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, —O($C_2$-$C_6$-alkenyl), $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$), and tautomers, N-oxides, and salts thereof, and salts of tautomers or N-oxides.

In further embodiments, the present invention provides compounds of formula (I), supra, in which:

$R^1$ represents a group selected from a $C_5$-$C_8$-alkyl group, a $C_4$-$C_8$-cycloalkyl group, a —($C_3$-$C_8$-cycloalkyl)-N($R^7$)($R^8$) group, a 4-7-membered, optionally unsaturated, heterocyclic group, a phenyl group, and a monocyclic- or bicyclic heteroaryl group, wherein said cycloalkyl groups are optionally substituted, one or two times, each substituent independently selected from a halogen atom or a group selected from hydroxy, phenyl and —N($R^7$)($R^8$), wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said 4- to 7-membered heterocycloalkyl group and 5- to 7-membered heterocycloalkenyl group are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$ and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said 4-7-membered, optionally unsaturated, heterocyclic group is connected to the rest of the molecule via a carbon atom, and wherein said phenyl groups are optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(O)OH, —C(=O)$OR^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)$OR^6$, —($C_1$-$C_6$-alkyl)-C(=O)N($R^7$)($R^8$), —SH, —S—($C_1$-$C_6$-alkyl), —S—($C_2$-$C_6$-alkenyl), —S(=O)$_2$($C_1$-$C_6$-alkyl), —S(=O)$_2$N($R^7$)($R^8$), —S(=O)$_2$, —S(=O)(=$NR^{11}$)($C_1$-$C_3$-alkyl), —N(O)$_2$, —P(=O)($C_1$-$C_3$-alkyl)$_2$ and $SF_5$, or wherein two vicinal substituents of said phenyl groups may form together a 5- or 6-membered, optionally heterocyclic, aromatic or non-aromatic ring, having optionally 1-3 heteroatoms independently selected from —N=, —NH—, —N($R^7$)—, —O—, —S—, and optionally containing a C(=O) group, and wherein the so formed ring is optionally substituted one or two times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$, —N(O)$_2$, and —N($R^7$)($R^8$) and wherein said monocyclic or bicyclic heteroaryl group is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, —O($C_2$-$C_6$-alkenyl), $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$, —N(O)$_2$, and —N($R^7$)($R^8$), and tautomers, N-oxides, and salts thereof, and salts of tautomers or N-oxides.

In further embodiments, the present invention provides compounds of formula (I), supra, in which:

$R^1$ represents a group selected from a $C_4$-$C_8$-cycloalkyl group, which is optionally substituted, one or two times, each substituent independently selected from a halogen atom or a group selected from hydroxy, phenyl and —N($R^7$)($R^8$), and wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a —($C_3$-$C_8$-cycloalkyl)-N($R^7$)($R^8$) group, a 4-7-membered heterocycloalkyl group a 5- to 7-membered heterocycloalkenyl group, wherein said 4-7-membered heterocycloalkyl group and said 5- to 7-membered heterocycloalkenyl group are connected to the rest of the molecule via a carbon atom, and which is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), hydroxy, $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR$^6$, —C(=O)N(R$^7$)(R$^8$), —N(R$^7$)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$), —O—C(=O)—($C_1$-$C_6$-alkyl)-, —SH, —S—($C_1$-$C_6$-alkyl), —S—($C_2$-$C_6$-alkenyl), —S(=O)$_2$N(R$^7$)(R$^8$), —S(=O)$_2$($C_1$-$C_6$-alkyl), —S(=O)$_2$—($C_2$-$C_6$-alkenyl), —S(=O)(=NR$^{11}$)($C_1$-$C_3$-alkyl), —N(O)$_2$, —P(=O)($C_1$-$C_3$-alkyl)$_2$ and SF$_5$, or wherein two vicinal substituents may form together a 5- or 6-membered, optionally heterocyclic, aromatic or non-aromatic ring, having optionally 1-3 heteroatoms independently selected from —N=, —NH—, —N(R$^7$)—, —O—, —S—, and optionally containing a C(=O) group, and wherein the so formed ring is optionally substituted one or two times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N(R$^7$)(R$^8$) and a monocyclic- or bicyclic heteroaryl group, which is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, —O($C_2$-$C_6$-alkenyl), $C_3$-$C_8$-cycloalkoxy, aryl, —O-aryl, cyano, C(=O)OR$^6$, hydroxy, —SH, —S—($C_1$-$C_6$-alkyl), —S—($C_2$-$C_6$-alkenyl), —S(=O)$_2$($C_1$-$C_6$-alkyl), —S(=O)$_2$—($C_2$-$C_6$-alkenyl), —N(O)$_2$, and —N(R$^7$)(R$^8$), and tautomers, N-oxides, and salts thereof, and salts of tautomers or N-oxides.

In further embodiments, the present invention provides compounds of formula (I), supra, in which R$^1$ represents a group selected from a $C_4$-$C_8$-cycloalkyl group, wherein said cycloalkyl groups are optionally substituted, one or two times, each substituent independently selected from a halogen atom or a group selected from hydroxy, phenyl and —N(R$^7$)(R$^8$), wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a —($C_3$-$C_8$-cycloalkyl)-N(R$^7$)(R$^8$) group, a 4- to 7-membered heterocycloalkyl group, which is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said- to 7-membered heterocycloalkyl group is connected to the rest of the molecule via a carbon atom of the said heterocycloalkyl- or heterocycloalkenyl group, a 5- to 7-membered heterocycloalkenyl group, which is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and wherein said 5- to 7-membered heterocycloalkenyl group is connected to the rest of the molecule via a carbon atom of the said heterocycloalkyl- or heterocycloalkenyl group, a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)OR$^6$, —C(=O)N(R$^7$)(R$^8$), —N(R$^7$)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{11}$)($C_1$-$C_3$-alkyl), —P(=O)($C_1$-$C_3$-alkyl)$_2$ and SF$_5$, or in which two substituents of said phenyl group, when they are attached to adjacent ring atoms, are optionally linked to one another in such a way that they jointly form a group selected from —CH$_2$—N(R$^7$)—CH$_2$—, —CH$_2$—O—CH$_2$—, —O—CH$_2$—C(=O)—NH— and —NH—C(=O)—NH—, an indanyl group, a tetralinyl group
  wherein said indanyl or tetralinyl group is optionally substituted one or two times, each substituent independently selected from a halogen atom or a group selected from
    $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$),
  and
  a monocyclic- or bicyclic heteroaryl group,
    which is optionally substituted one, two or three times, each substituent independently selected from a halogen atom or a group selected from $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$),
and tautomers, N-oxides, and salts thereof, and salts of tautomers or N-oxides.

In further embodiments, the present invention provides compounds of formula (I), supra, in which
$R^1$ represents a group selected from
  a $C_4$-$C_8$-cycloalkyl group, a —($C_3$-$C_8$-cycloalkyl)-N($R^7$)($R^8$) group,
  a 4- to 7-membered heterocycloalkyl group, a 5- to 7-membered heterocycloalkenyl group, a phenyl group, an indanyl group, a tetralinyl group and a monocyclic- or bicyclic heteroaryl group,
    wherein said cycloalkyl groups are optionally substituted, one or two times, each substituent independently selected from a halogen atom or a group selected from
      hydroxy, phenyl and —N($R^7$)($R^8$),
        wherein said phenyl substituent is optionally substituted, one, two or three times, each substituent independently selected from a halogen atom or a group selected from
          $C_1$-$C_3$-alkyl, $C_1$-$C_4$-haloalkyl, $C_1$-$C_3$-alkoxy and hydroxy,
    and
    wherein said 4- to 7-membered heterocycloalkyl group and 5- to 7-membered heterocycloalkenyl group are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O),
      wherein said 5- to 6-membered heteroaryl substituent is optionally substituted, one, two or three times, each substituent independently selected from a halogen atom or a group selected from
        $C_1$-$C_3$-alkyl, $C_1$-$C_4$-haloalkyl, $C_1$-$C_3$-alkoxy and hydroxy,
      and
      wherein said 4- to 7-membered heterocycloalkyl group and 5- to 7-membered heterocycloalkenyl group are connected to the rest of the molecule via a carbon atom of the said heterocycloalkyl- or heterocycloalkenyl group,
    and
    wherein said phenyl groups are optionally substituted, one, two, three, four or five times, each substituent independently selected from a halogen atom or a group selected from
      $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_8$-cycloalkoxy, hydroxy, cyano, —C(=O)O$R^6$, —C(=O)N($R^7$)($R^8$), —N($R^7$)($R^8$), —($C_1$-$C_6$-alkyl)-N($R^7$)($R^8$), —($C_1$-$C_6$-alkyl)-C(=O)O$R^6$, —($C_1$-$C_6$-alkyl)-C(=O)N($R^7$)($R^8$), —S(=O)$_2$N($R^7$)($R^8$), —S(=O)$_2$($C_1$-$C_3$-alkyl), —S(=O)(=N$R^{11}$)($C_1$-$C_3$-alkyl), —P(=O)($C_1$-$C_3$-alkyl)$_2$ and SF$_5$,
    or in which two substituents of said phenyl groups, when they are attached to adjacent ring atoms, are optionally linked to one another in such a way that they jointly form a group selected from
      —CH$_2$—N($R^7$)—CH$_2$—, —CH$_2$—O—CH$_2$—, —O—CH$_2$—C(=O)—NH— and —NH—C(=O)—NH—,
    and
    wherein said indanyl or tetralinyl group is optionally substituted one or two times, each substituent independently selected from a halogen atom or a group selected from
      $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$),
    and
    wherein said monocyclic or bicyclic heteroaryl group is optionally substituted one, two or three times, each substituent independently selected from a halogen atom or a group selected from
      $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —N($R^7$)($R^8$),
and tautomers, N-oxides, and salts thereof, and salts of tautomers or N-oxides.

In further embodiments, the present invention provides compounds of formula (I), supra, in which:
$R^1$ represents a group selected from
  a $C_4$-$C_8$-cycloalkyl group,
    which is optionally substituted, one or two times, each substituent independently selected from a halogen atom or a group selected from hydroxy, phenyl and —N($R^7$)($R^8$),
      wherein said phenyl substituent is optionally substituted, one, two or three times, each substituent independently selected from a halogen atom or a group selected from
        $C_1$-$C_3$-alkyl, $C_1$-$C_3$-haloalkyl, $C_1$-$C_3$-alkoxy and hydroxy,
  a —($C_3$-$C_6$-cycloalkyl)-N($R^7$)($R^8$) group,
  a 4- to 6-membered heterocycloalkyl group,
    which is optionally substituted one or two times, each substituent independently selected from a group selected from
      $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
        wherein said 5- to 6-membered heteroaryl group is optionally substituted, one, two or three times, each substituent independently selected from a halogen atom or a group selected from
          $C_1$-$C_3$-alkyl, $C_1$-$C_3$-haloalkyl, $C_1$-$C_3$-alkoxy and hydroxy,
    wherein said 4- to 6-membered heterocycloalkyl group is connected to the rest of the molecule via a carbon atom or nitrogen atom of the said heterocycloalkyl- or heterocycloalkenyl group,
  a 5- to 6-membered heterocycloalkenyl group, which is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), wherein said 5- to 6-membered heteroaryl group is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, wherein said 5- to 6-membered heterocycloalkenyl group is connected to the rest of the molecule via a carbon atom of the said heterocycloalkyl- or heterocycloalkenyl group, a phenyl group, which is optionally substituted, one, two, three, four or five times, each substituent independently selected from a halogen atom or a group selected from $C_1$-$C_4$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(=O)O$R^6$, —C(=O)N($R^7$)($R^8$), —N($R^7$)($R^8$), —($C_1$-$C_3$-alkyl)-N($R^7$)($R^8$), —($C_1$-$C_3$-alkyl)-C(=O)O$R^6$, —($C_1$-$C_3$-alkyl)-C(=O)N($R^7$)($R^8$), —S(=O)$_2$N($R^7$)($R^8$), —S(=O)$_2$($C_1$-$C_3$-alkyl), —S(=O)(=N$R^{11}$)($C_1$-$C_3$-alkyl), —P(=O)($C_1$-$C_3$-alkyl)$_2$ and SF$_5$, or in which two substituents of said phenyl groups, when they are attached to adjacent ring atoms, are optionally linked to one another in such a way that they jointly form a group selected from —CH$_2$—N($R^7$)—CH$_2$—, —CH$_2$—O—CH$_2$—, —O—CH$_2$—C(=O)—NH— and —NH—C(=O)—NH—, an indanyl group, which is optionally substituted one or two times, each substituent independently selected from a halogen atom or a group selected from $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), a tetralinyl group and which is optionally substituted one or two times, each substituent independently selected from a halogen atom or a group selected from $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), a monocyclic- or bicyclic heteroaryl group, which is optionally substituted one, two or three times, each substituent independently selected from a halogen atom or a group selected from $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), or a tautomer, an N-oxide, a salt, a salt of a tautomer or a salt of an N-oxide thereof.

In further embodiments, the present invention provides compounds of formula (I), supra, in which:

$R^1$ represents a group selected from a $C_4$-$C_8$-cycloalkyl group, a —($C_3$-$C_6$-cycloalkyl)-N($R^7$)($R^8$) group, a 4- to 6-membered heterocycloalkyl group, a 5- to 6-membered heterocycloalkenyl group a phenyl group, an indanyl group, a tetralinyl group and a monocyclic- or bicyclic heteroaryl group, wherein said cycloalkyl groups are optionally substituted, one or two times, each substituent independently selected from a halogen atom or a group selected from hydroxy, phenyl and —N($R^7$)($R^8$), wherein said phenyl substituent is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, and wherein said 4- to 6-membered heterocycloalkyl group and 5- to 6-membered heterocycloalkenyl group are optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O), wherein said 5- to 6-membered heteroaryl group is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, and wherein said 4- to 6-membered heterocycloalkyl group and 5- to 6-membered heterocycloalkenyl group are connected to the rest of the molecule via a carbon atom of the said heterocycloalkyl- or heterocycloalkenyl group, and wherein said phenyl groups are optionally substituted, one, two, three, four or five times, each substituent independently selected from a halogen atom or a group selected from $C_1$-$C_4$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(=O)O$R^6$, —C(=O)N($R^7$)($R^8$), —N($R^7$)($R^8$), —($C_1$-$C_3$-alkyl)-N($R^7$)($R^8$), —($C_1$-$C_3$-alkyl)-C(=O)O$R^6$, —($C_1$-$C_3$-alkyl)-C(=O)N($R^7$)($R^8$), —S(=O)$_2$N($R^7$)($R^8$), —S(=O)$_2$($C_1$-$C_3$-alkyl), —S(=O)(=N$R^{11}$)($C_1$-$C_3$-alkyl), —P(=O)($C_1$-$C_3$-alkyl)$_2$ and SF$_5$, or in which two substituents of said phenyl groups, when they are attached to adjacent ring atoms, are optionally linked to one another in such a way that they jointly form a group selected from —CH$_2$—N($R^7$)—CH$_2$—, —CH$_2$—O—CH$_2$—, —O—CH$_2$—C(=O)—NH— and —NH—C(=O)—NH—, and wherein said indanyl- or tetralinyl group is optionally substituted one or two times, each substituent independently selected from a halogen atom or a group selected from $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N($R^7$)($R^8$), and wherein said monocyclic or bicyclic heteroaryl group is optionally substituted one, two or three times, each substituent independently selected from a halogen atom or a group selected from
$C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —$N(R^7)(R^8)$,
and tautomers, N-oxides, and salts thereof, and salts of tautomers or N-oxides.

In further embodiments, the present invention provides compounds of formula (I), supra, in which:
$R^1$ represents a group selected from
a $C_4$-$C_8$-cycloalkyl group,
which is optionally substituted, one or two times, with a phenyl group,
wherein said phenyl substituent is optionally substituted, one, two or three times, each substituent independently selected from a halogen atom,
a 4- to 6-membered heterocycloalkyl group,
which is optionally substituted one or two times, each substituent independently selected from a $C_1$-$C_3$-alkyl group,
and
which is connected to the rest of the molecule via a carbon atom of the said heterocycloalkyl group,
a phenyl group,
which is optionally substituted, one, two, three or four times, each substituent independently selected from a halogen atom or a group selected from $C_1$-$C_4$-alkyl, $C_1$-$C_3$-haloalkyl, $C_1$-$C_3$-hydroxyalkyl, $C_1$-$C_3$-alkoxy, hydroxy, —C(=O)O$R^6$, —C(=O)N($R^7$)($R^8$), N($R^7$)($R^8$), —($C_1$-$C_3$-alkyl)-N($R^7$)($R^8$), —O—C(=O)—($C_1$-$C_4$-alkyl), —S—$C_1$-$C_3$-alkyl, —S(=O)$_2$($C_1$-$C_3$-alkyl), —S(=O)(=N$R^{11}$)($C_1$-$C_3$-alkyl) and —P(=O)($C_1$-$C_3$-alkyl)$_2$,
an indanyl group and
a monocyclic- or bicyclic heteroaryl group,
which are optionally substituted one, two or three times, each substituent independently selected from a halogen atom or a group selected from $C_1$-$C_3$-alkyl and $C_1$-$C_3$-alkoxy,
and tautomers, N-oxides, and salts thereof, and salts of tautomers or N-oxides.

In further embodiments, the present invention provides compounds of formula (I), supra, in which:
$R^1$ represents a group selected from
a $C_4$-$C_8$-cycloalkyl group, a 4- to 6-membered heterocycloalkyl group,
a phenyl group, an indanyl group and a monocyclic- or bicyclic heteroaryl group,
wherein said cycloalkyl groups are optionally substituted, one or two times, with a phenyl group,
wherein said phenyl substituent is optionally substituted, one, two or three times, each substituent independently selected from a halogen atom,
and
wherein said 4- to 6-membered heterocycloalkyl group is optionally substituted one or two times, each substituent independently selected from a $C_1$-$C_3$-alkyl group,
and
wherein said 4- to 6-membered heterocycloalkyl group is connected to the rest of the molecule via a carbon atom of the said heterocycloalkyl group,
and
wherein said phenyl groups are optionally substituted, one, two, three or four times, each substituent independently selected from a halogen atom or a group selected from
$C_1$-$C_4$-alkyl, $C_1$-$C_3$-haloalkyl, $C_1$-$C_3$-hydroxyalkyl, $C_1$-$C_3$-alkoxy, hydroxy, —C(=O)O$R^6$, —N($R^7$)($R^8$), —($C_1$-$C_3$-alkyl)-N($R^7$)($R^8$), —S(=O)$_2$($C_1$-$C_3$-alkyl), —S(=O)(=N$R^{11}$)($C_1$-$C_3$-alkyl) and —P(=O)($C_1$-$C_3$-alkyl)$_2$,
and
wherein said monocyclic or bicyclic heteroaryl group is optionally substituted one, two or three times, each substituent independently selected from a halogen atom or a group selected from
$C_1$-$C_3$-alkyl and $C_1$-$C_3$-alkoxy,
and tautomers, N-oxides, and salts thereof, and salts of tautomers or N-oxides.

In further embodiments, the present invention provides compounds of formula (I), supra, in which:
$R^1$ represents a group selected from
a $C_5$-$C_7$-cycloalkyl group,
a 5- to 6-membered heterocycloalkyl group,
which is optionally substituted one or two times, with a $C_1$-$C_3$-alkyl group, and
which is connected to the rest of the molecule via a carbon atom,
a phenyl group,
which is optionally substituted, one, two or three times, each substituent independently selected from a halogen atom or a group selected from $C_1$-$C_3$-alkyl, $C_1$-$C_3$-haloalkyl, $C_1$-$C_3$-alkoxy, hydroxy, —C(=O)O$R^6$, —C(=O)N($R^7$)($R^8$), —N($R^7$)($R^8$), —($C_1$-$C_3$-alkyl)-N($R^7$)($R^8$), —O—C(=O)—($C_1$-$C_4$-alkyl), —S—$C_1$-$C_3$-alkyl, —S(=O)$_2$—$C_1$-$C_3$-alkyl, —S(=O)(=NH)($C_1$-$C_3$-alkyl) and
an indanyl group, and
a monocyclic heteroaryl group,
which is optionally substituted one or two times, each substituent independently selected from a group selected from
$C_1$-$C_3$-alkyl and $C_1$-$C_3$-alkoxy,
or a tautomer, an N-oxide, a salt, a salt of a tautomer or a salt of an N-oxide thereof.

In further embodiments, the present invention provides compounds of formula (I), supra, in which:
$R^1$ represents a group selected from
a $C_5$-$C_7$-cycloalkyl group, a 5- to 6-membered heterocycloalkyl group,
a phenyl group, an indanyl group, and a monocyclic heteroaryl group,
which 5- to 6-membered heterocycloalkyl group is optionally substituted one or two times, with a $C_1$-$C_3$-alkyl group,
and
wherein said 5- to 6-membered heterocycloalkyl group is connected to the rest of the molecule via a carbon atom of the said heterocycloalkyl group,
and
wherein said phenyl groups are optionally substituted, one, two or three times, each substituent independently selected from a halogen atom or a group selected from
$C_1$-$C_4$-alkyl, $C_1$-$C_3$-haloalkyl, $C_1$-$C_3$-alkoxy, hydroxy, —C(=O)O$R^6$, —N($R^7$)($R^8$) and —($C_1$-$C_3$-alkyl)-N($R^7$)($R^8$), and
which monocyclic heteroaryl group is optionally substituted one or two times, each substituent independently selected from a group selected from
$C_1$-$C_3$-alkyl and $C_1$-$C_3$-alkoxy,
and tautomers, N-oxides, and salts thereof, and salts of tautomers or N-oxides.

In further embodiments, the present invention provides compounds of formula (I), supra, in which:
$R^1$ represents a group selected from
a $C_5$-$C_7$-cycloalkyl group,
a 5- to 6-membered heterocycloalkyl group,
which is optionally substituted one or two times, with a $C_1$-$C_3$-alkyl group, and which is connected to the rest of the molecule via a carbon atom,
a phenyl group,
which is optionally substituted, one, two or three times, each substituent independently selected from a halogen atom or a group selected from $C_1$-$C_3$-alkyl, $C_1$-$C_3$-haloalkyl, $C_1$-$C_3$-alkoxy, hydroxy, —C(=O)OR$^6$, —C(=O)N(R$^7$)(R$^8$), —N(R$^7$)(R$^8$), —O—C(=O)—(C$_1$-$C_4$-alkyl), —S—C$_1$-$C_3$-alkyl, —S(=O)$_2$—C$_1$-$C_3$-alkyl, —S(=O)(=NH)(C$_1$-$C_3$-alkyl) and —(C$_1$-$C_3$-alkyl)-N(R$^7$)(R$^8$),
an indanyl group, and
a monocyclic heteroaryl group,
which is optionally substituted one or two times, each substituent independently selected from a group selected from
$C_1$-$C_3$-alkyl and $C_1$-$C_3$-alkoxy,
or a tautomer, an N-oxide, a salt, a salt of a tautomer or a salt of an N-oxide thereof.

In further embodiments, the present invention provides compounds of formula (I), supra, in which:
$R^1$ represents a group selected from
a phenyl group,
which is optionally substituted, one, two or three times, each substituent independently selected from a halogen atom or a group selected from $C_1$-$C_3$-alkyl, $C_1$-$C_3$-haloalkyl, $C_1$-$C_3$-alkoxy, hydroxy, —C(=O)OR$^6$, —C(=O)N(R$^7$)(R$^8$), —N(R$^7$)(R$^8$), —O—C(=O)—(C$_1$-$C_4$-alkyl), —S—C$_1$-$C_3$-alkyl, —S(=O)$_2$—C$_1$-$C_3$-alkyl, —S(=O)(=NH)(C$_1$-$C_3$-alkyl) and —(C$_1$-$C_3$-alkyl)-N(R$^7$)(R$^8$),
or a tautomer, an N-oxide, a salt, a salt of a tautomer or a salt of an N-oxide thereof.

In yet further embodiments, the present invention provides compounds of formula (I), supra, in which:
$R^1$ represents a group selected from
a phenyl group,
which is optionally substituted, one, two or three times, each substituent independently selected from a halogen atom or a group selected from
$C_1$-$C_3$-alkyl, $C_1$-$C_3$-haloalkyl, $C_1$-$C_3$-alkoxy, hydroxy,
or a tautomer, an N-oxide, a salt, a salt of a tautomer or a salt of an N-oxide thereof.

In other embodiments, the present invention provides compounds of formula (I), supra, in which:
$R^1$ represents a group selected from
a phenyl group,
which is optionally substituted, one or two times, each substituent independently selected from a halogen atom or a group selected from
$C_1$-$C_3$-haloalkyl, $C_1$-$C_3$-alkoxy, hydroxy,
or a tautomer, an N-oxide, a salt, a salt of a tautomer or a salt of an N-oxide thereof.

In other embodiments, the present invention provides compounds of formula (I), supra, in which:
$R^1$ represents a group selected from
a phenyl group,
which is optionally substituted, one or two times, each substituent independently selected from a halogen atom or a tautomer, an N-oxide, a salt, a salt of a tautomer or a salt of an N-oxide thereof.

In further embodiments, the present invention provides compounds of formula (I), supra, in which:
$R^1$ represents a group selected from
a $C_5$-$C_7$-cycloalkyl group, a 5- to 6-membered heterocycloalkyl group, a phenyl group,
an indanyl group, and a monocyclic heteroaryl group,
wherein said 5- to 6-membered heterocycloalkyl group is selected from tetrahydrofuranyl, tetrahydro-2H-pyranyl and piperidinyl,
which 5- to 6-membered heterocycloalkyl group is optionally substituted one or two times, with a $C_1$-$C_3$-alkyl group,
and
wherein said 5- to 6-membered heterocycloalkyl group is connected to the rest of the molecule via a carbon atom of the said heterocycloalkyl group,
and
wherein said phenyl groups are optionally substituted, one, two or three times, each substituent independently selected from a halogen atom or a group selected from
$C_1$-$C_4$-alkyl, $C_1$-$C_3$-haloalkyl, $C_1$-$C_3$-alkoxy, hydroxy, —C(=O)OR$^6$, —N(R$^7$)(R$^8$) and —(C$_1$-$C_3$-alkyl)-N(R$^7$)(R$^8$),
and
wherein said monocyclic heteroaryl group is selected from oxazolyl, pyrazolyl, pyridinyl and pyrimidinyl,
which monocyclic heteroaryl group is optionally substituted one or two times, each substituent independently selected from a group selected from
$C_1$-$C_3$-alkyl and $C_1$-$C_3$-alkoxy,
and tautomers, N-oxides, and salts thereof, and salts of tautomers or N-oxides.

In further embodiments, the present invention provides compounds of formula (I), supra, in which:
$R^1$ represents a group selected from
4-fluorophenylcyclopropyl, cyclopentyl, cyclohexyl, cycloheptyl, indan-2-yl,
a 5- to 6-membered heterocycloalkyl group, which is selected from tetrahydrofuran-3-yl, tetrahydro-2H-pyran-4-yl and piperidin-4-yl,
and which is optionally substituted one or two times with a methyl group,
a phenyl group, which is optionally substituted, one, two or three times, each substituent independently selected from a fluorine atom or a chlorine atom or a group selected from
methyl, ethyl, propyl, isopropyl, difluoromethyl, trifluoromethyl, methoxy, —O—C(=O)-1,1-dimethylethyl, hydroxy, —C(=O)OCH$_3$, —C(=O)NH-cyclopropyl, amino, methylamino, aminomethyl, —S—CH$_3$, —S(=O)$_2$CH$_3$, and —S(=O)(NH)CH$_3$, and
a monocyclic heteroaryl group, which is selected from oxazolyl, pyrazolyl, pyridinyl, pyrimidinyl, chinolinyl, indazolyl, and which is optionally substituted one or two times, each substituent independently selected from methyl and methoxy,
or a tautomer, an N-oxide, a salt, a salt of a tautomer or a salt of an N-oxide thereof.

In further embodiments, the present invention provides compounds of formula (I), supra, in which:

R¹ represents a group selected from
cyclopentyl, cyclohexyl, cycloheptyl, 5- to 6-membered heterocycloalkyl, phenyl, indan-2-yl and monocyclic heteroaryl,
wherein said 5- to 6-membered heterocycloalkyl group is selected from tetrahydrofuran-3-yl, tetrahydro-2H-pyran-4-yl and piperidin-4-yl, which 5- to 6-membered heterocycloalkyl group is optionally substituted one or two times, with a methyl group,
and
wherein said phenyl groups are optionally substituted, one, two or three times, each substituent independently selected from a fluorine atom or a chlorine atom or a group selected from
methyl, ethyl, propyl, isopropyl, trifluoromethyl, methoxy, hydroxy, $C(=O)OCH_3$, amino, methylamino and aminomethyl,
and
wherein said monocyclic heteroaryl group is selected from oxazolyl, pyrazolyl, pyridinyl and pyrimidinyl,
which monocyclic heteroaryl group is optionally substituted one or two times, each substituent independently selected from a group selected from methyl and methoxy,
and tautomers, N-oxides, and salts thereof, and salts of tautomers or N-oxides.

In further embodiments, the present invention provides compounds of formula (I), supra, in which:
R¹ represents a group selected from
4-fluorophenylcyclopropyl, cyclopentyl, cyclohexyl, cycloheptyl, indan-2-yl,
a 5- to 6-membered heterocycloalkyl group, which is selected from tetrahydrofuran-3-yl, tetrahydro-2H-pyran-4-yl and piperidin-4-yl, and which is optionally substituted one or two times with a methyl group,
a phenyl group, which is optionally substituted, one, two or three times, each substituent independently selected from a fluorine atom or a chlorine atom or a group selected from
methyl, ethyl, propyl, isopropyl, difluoromethyl, trifluoromethyl, methoxy, —O—C(=O)-1,1-dimethylethyl, hydroxy, —C(=O)OCH₃, —C(=O)NH-cyclopropyl, amino, methylamino, aminomethyl, —S—CH₃, —S(=O)₂CH₃, and —S(=O)(NH)CH₃, and
a monocyclic heteroaryl group, which is selected from oxazol-2-yl, pyrazol-3-yl, pyrazol-5-yl, pyridin-2-yl, pyridin-3-yl, pyridin-4-yl, pyrimidin-2-yl, pyrimidin-4-yl, chinolin-5-yl, indazol-5-yl,
and which is optionally substituted one or two times, each substituent independently selected from methyl and methoxy,
or a tautomer, an N-oxide, a salt, a salt of a tautomer or a salt of an N-oxide thereof.

In further embodiments, the present invention provides compounds of formula (I), supra, in which:
R¹ represents a group selected from
cyclopentyl, cyclohexyl, cycloheptyl, 5- to 6-membered heterocycloalkyl, phenyl, indan-2-yl and monocyclic heteroaryl,
wherein said 5- to 6-membered heterocycloalkyl group is selected from tetrahydrofuran-3-yl, tetrahydro-2H-pyran-4-yl and piperidin-4-yl, which 5- to 6-membered heterocycloalkyl group is optionally substituted one or two times, with a methyl group,
and
wherein said phenyl groups are optionally substituted, one, two or three times, each substituent independently selected from a fluorine atom or a chlorine atom or a group selected from
methyl, ethyl, propyl, isopropyl, trifluoromethyl, methoxy, hydroxy, $C(=O)OCH_3$, amino, methylamino and aminomethyl,
and
wherein said monocyclic heteroaryl group is selected from
oxazol-2-yl, pyrazol-3-yl, pyridin-2-yl, pyridin-3-yl, pyridin-4-yl, pyrimidin-2-yl and pyrimidin-4-yl,
which monocyclic heteroaryl group is optionally substituted one or two times, each substituent independently selected from a group selected from methyl and methoxy,
and tautomers, N-oxides, and salts thereof, and salts of tautomers or N-oxides.

In further embodiments, the present invention provides compounds of formula (I), supra, in which:
R² represents a hydrogen atom or a fluorine atom,
and tautomers, N-oxides, and salts thereof, and salts of tautomers or N-oxides.

In further embodiments, the present invention provides compounds of formula (I), supra, in which:
R² represents a hydrogen atom or a halogen atom,
or a tautomer, an N-oxide, a salt, a salt of a tautomer or a salt of an N-oxide thereof.

In further embodiments, the present invention provides compounds of formula (I), supra, in which:
R² represents a hydrogen atom or a fluorine atom,
and tautomers, N-oxides, and salts thereof, and salts of tautomers or N-oxides.

In further embodiments, the present invention provides compounds of formula (I), supra, in which:
R² represents a hydrogen atom, a fluorine atom or a chlorine atom,
or a tautomer, an N-oxide, a salt, a salt of a tautomer or a salt of an N-oxide thereof.

In further embodiments, the present invention provides compounds of formula (I), supra, in which:
R² represents a fluorine atom or a chlorine atom,
or a tautomer, an N-oxide, a salt, a salt of a tautomer or a salt of an N-oxide thereof.

In further embodiments, the present invention provides compounds of formula (I), supra, in which:
R² represents a fluorine atom,
and tautomers, N-oxides, and salts thereof, and salts of tautomers or N-oxides.

In further embodiments, the present invention provides compounds of formula (I), supra, in which:
R² represents a hydrogen atom,
and tautomers, N-oxides, and salts thereof, and salts of tautomers or N-oxides.

In further embodiments, the present invention provides compounds of formula (I), supra, in which:
R³ represents a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a $C_2$-$C_6$-alkenyl group, a $C_2$-$C_6$-alkynyl group,
a $C_4$-$C_8$-cycloalkenyl group, a $(C_1$-$C_6$-alkyl)-N(R⁷)R⁸ group,
a —($C_1$-$C_6$-alkyl)-(4- to 7-membered nitrogen containing heterocycloalkyl) group and
a phenyl group,
wherein said $C_1$-$C_6$-alkyl group is optionally substituted with a $C_3$-$C_8$-cycloalkyl group,
and wherein said 4- to 7-membered nitrogen containing heterocycloalkyl group is optionally substituted with a $C_1$-$C_3$-alkyl group,
and
wherein said 4- to 7-membered nitrogen containing heterocycloalkyl group is connected to the alkyl group via a carbon atom of the heterocycloalkyl group,
and
wherein said phenyl group is optionally substituted, one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N(R$^7$)(R$^8$)
or a tautomer, an N-oxide, a salt, a salt of a tautomer or a salt of an N-oxide thereof.

In further embodiments, the present invention provides compounds of formula (I), supra, in which:
R$^3$ represents a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a $C_2$-$C_6$-alkenyl group, a $C_2$-$C_6$-alkynyl group,
a $C_4$-$C_8$-cycloalkenyl group, a ($C_1$-$C_6$-alkyl)-N(R$^7$)R$^8$ group,
a —($C_1$-$C_6$-alkyl)-(4- to 7-membered nitrogen containing heterocycloalkyl) group and
a phenyl group,
wherein said $C_1$-$C_6$-alkyl group is optionally substituted with a $C_3$-$C_8$-cycloalkyl group,
and
wherein said 4- to 7-membered nitrogen containing heterocycloalkyl group is optionally substituted with a $C_1$-$C_3$-alkyl group,
and
wherein said 4- to 7-membered nitrogen containing heterocycloalkyl group is connected to the alkyl group via a carbon atom of the heterocycloalkyl group,
and
wherein said phenyl group is optionally substituted, one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$, —N(O)$_2$, and —N(R$^7$)(R$^8$)
and tautomers, N-oxides, and salts thereof, and salts of tautomers or N-oxides.

In further embodiments, the present invention provides compounds of formula (I), supra, in which:
R$^3$ represents a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a $C_2$-$C_6$-alkenyl group, a $C_2$-$C_6$-alkynyl group, a $C_4$-$C_8$-cycloalkenyl group, a ($C_1$-$C_6$-alkyl)-N(R$^7$)R$^8$ group,
a —($C_1$-$C_6$-alkyl)-(4- to 7-membered nitrogen containing heterocycloalkyl) group and
a phenyl group,
wherein said $C_1$-$C_6$-alkyl group is optionally substituted with a $C_3$-$C_8$-cycloalkyl group,
and
wherein said 4- to 7-membered nitrogen containing heterocycloalkyl group is optionally substituted with a $C_1$-$C_3$-alkyl group,
and
wherein said 4- to 7-membered nitrogen containing heterocycloalkyl group is connected to the alkyl group via a carbon atom of the heterocycloalkyl group,
and
wherein said phenyl group is optionally substituted, one, two or three times, each substituent independently selected from a halogen atom or a group selected from
$C_1$-$C_3$-alkyl, $C_1$-$C_4$-haloalkyl, $C_1$-$C_3$-alkoxy and hydroxy,
and tautomers, N-oxides, and salts thereof, and salts of tautomers or N-oxides.

In further embodiments, the present invention provides compounds of formula (I), supra, in which:
R$^3$ represents a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a $C_2$-$C_6$-alkenyl group, a $C_2$-$C_6$-alkynyl group,
a $C_4$-$C_6$-cycloalkenyl group, a ($C_1$-$C_6$-alkyl)-N(R$^7$)R$^8$ group,
a —($C_1$-$C_6$-alkyl)-(4- to 6-membered nitrogen containing heterocycloalkyl) group and
a phenyl group,
wherein said $C_1$-$C_6$-alkyl group is optionally substituted with a $C_3$-$C_6$-cycloalkyl group,
and
wherein said 4- to 6-membered nitrogen containing heterocycloalkyl group is optionally substituted with a $C_1$-$C_3$-alkyl group,
and
wherein said 4- to 6-membered nitrogen containing heterocycloalkyl group is connected to the alkyl group via a carbon atom of the heterocycloalkyl group,
and
wherein said phenyl group is optionally substituted, one, two or three times, each substituent independently selected from a halogen atom or a group selected from
$C_1$-$C_3$-alkyl, $C_1$-$C_3$-haloalkyl, $C_1$-$C_3$-alkoxy and hydroxy,
and tautomers, N-oxides, and salts thereof, and salts of tautomers or N-oxides.

In further embodiments, the present invention provides compounds of formula (I), supra, in which:
R$^3$ represents a group selected from
a $C_1$-$C_6$-alkyl group, a $C_3$-$C_8$-cycloalkyl group, a $C_1$-$C_6$-haloalkyl group, a $C_2$-$C_6$-alkenyl group and a phenyl group,
wherein said $C_1$-$C_6$-alkyl group is optionally substituted with a $C_3$-$C_6$-cycloalkyl group,
and tautomers, N-oxides, and salts thereof, and salts of tautomers or N-oxides.

In further embodiments, the present invention provides compounds of formula (I), supra, in which:
$R^3$ represents a group selected from
a $C_1$-$C_6$-alkyl group, a $C_3$-$C_6$-cycloalkyl group, a $C_1$-$C_6$-haloalkyl group, a $C_2$-$C_6$-alkenyl group and a phenyl group,
wherein said $C_1$-$C_6$-alkyl group is optionally substituted with a cyclopropyl group,
and tautomers, N-oxides, and salts thereof, and salts of tautomers or N-oxides.

In further embodiments, the present invention provides compounds of formula (I), supra, in which:
$R^3$ represents a group selected from
a $C_1$-$C_3$-alkyl group, a $C_3$-$C_6$-cycloalkyl group, a $C_1$-$C_3$-haloalkyl group, and a $C_2$-$C_3$-alkenyl group
or a tautomer, an N-oxide, a salt, a salt of a tautomer or a salt of an N-oxide thereof.

In further embodiments, the present invention provides compounds of formula (I), supra, in which:
$R^3$ represents a group selected from
a $C_1$-$C_3$-alkyl group, a $C_1$-$C_3$-haloalkyl group, and a $C_2$-$C_3$-alkenyl group
or a tautomer, an N-oxide, a salt, a salt of a tautomer or a salt of an N-oxide thereof.

In further embodiments, the present invention provides compounds of formula (I), supra, in which:
$R^3$ represents a group selected from
a $C_1$-$C_3$-alkyl group, and a $C_1$-$C_3$-haloalkyl group,
or a tautomer, an N-oxide, a salt, a salt of a tautomer or a salt of an N-oxide thereof.

In further embodiments, the present invention provides compounds of formula (I), supra, in which:
$R^3$ represents a group selected from
a $C_1$-$C_3$-alkyl group,
or a tautomer, an N-oxide, a salt, a salt of a tautomer or a salt of an N-oxide thereof.

In further embodiments, the present invention provides compounds of formula (I), supra, in which:
$R^3$ represents a group selected from
a $C_1$-$C_3$-haloalkyl group,
or a tautomer, an N-oxide, a salt, a salt of a tautomer or a salt of an N-oxide thereof.

In further embodiments, the present invention provides compounds of formula (I), supra, in which:
$R^3$ represents a group selected from
propyl, 2-methylpropyl, 3-pentyl, cyclopropylmethyl, cyclopropyl, cyclobutyl, cyclopentyl, cyclohexyl, trifluoromethyl, allyl, 2-methyl-prop1-enyl and phenyl,
and tautomers, N-oxides, and salts thereof, and salts of tautomers or N-oxides.

In further embodiments, the present invention provides compounds of formula (I), supra, in which:
$R^4$ represents a group selected from,
a $C_1$-$C_6$-alkyl group,
which is optionally substituted with a group selected from $C_3$-$C_8$-cycloalkyl and phenyl,
wherein said phenyl group is optionally substituted, one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)OR$^6$, hydroxy, —SH, —S—($C_1$-$C_6$-alkyl), —S—($C_2$-$C_6$-alkenyl), S(=O)$_2$($C_1$-$C_6$-alkyl), —S(=O)$_2$—($C_2$-$C_6$-alkenyl), —N(O)$_2$, and —N($R^7$)($R^8$)
a $C_2$-$C_6$-alkenyl group,
a $C_3$-$C_8$-cycloalkyl group,
a $C_2$-$C_6$-haloalkyl group,
a $C_2$-$C_6$-hydroxyalkyl group,
a —($C_2$-$C_6$-alkyl)-N($R^7$)($R^8$) group,
a —C(=O)OR$^6$ group,
a —C(=O)NR$^7$R$^8$ group, and
a —S(=O)(=NR$^{11}$)($C_1$-$C_3$-alkyl) group,
or a tautomer, an N-oxide, a salt, a salt of a tautomer or a salt of an N-oxide thereof.

In further embodiments, the present invention provides compounds of formula (I), supra, in which:
$R^4$ represents a group selected from
a $C_1$-$C_6$-alkyl group, a $C_3$-$C_8$-cycloalkyl group, a $C_2$-$C_6$-haloalkyl group,
a $C_2$-$C_6$-hydroxyalkyl group and a —($C_2$-$C_6$-alkyl)-N($R^7$)($R^8$) group,
wherein said $C_1$-$C_6$-alkyl group is optionally substituted with a group selected from
$C_3$-$C_8$-cycloalkyl and phenyl,
wherein said phenyl group is optionally substituted, one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$)

In further embodiments, the present invention provides compounds of formula (I), supra, in which:
$R^4$ represents a group selected from
a $C_1$-$C_6$-alkyl group, a $C_3$-$C_8$-cycloalkyl group, a $C_2$-$C_6$-haloalkyl group,
a $C_2$-$C_6$-hydroxyalkyl group and a —($C_2$-$C_6$-alkyl)-N($R^7$)($R^8$) group,
wherein said $C_1$-$C_6$-alkyl group is optionally substituted with a group selected from
$C_3$-$C_8$-cycloalkyl and phenyl,
wherein said phenyl group is optionally substituted, one, two or three times, each substituent independently selected from a halogen atom or a group selected from
$C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$)
or a tautomer, an N-oxide, a salt, a salt of a tautomer or a salt of an N-oxide thereof.

In further embodiments, the present invention provides compounds of formula (I), supra, in which:
$R^4$ represents a group selected from
a $C_1$-$C_6$-alkyl group, a $C_3$-$C_8$-cycloalkyl group, a $C_2$-$C_6$-haloalkyl group,
a $C_2$-$C_6$-hydroxyalkyl group and a —($C_2$-$C_6$-alkyl)-N($R^7$)($R^8$) group,
wherein said $C_1$-$C_6$-alkyl group is optionally substituted with a group selected from
$C_3$-$C_8$-cycloalkyl and phenyl, wherein said phenyl group is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(═O)$_2$, —N(O)$_2$, and —N($R^7$)($R^8$)

and tautomers, N-oxides, and salts thereof, and salts of tautomers or N-oxides.

In further embodiments, the present invention provides compounds of formula (I), supra, in which:

$R^4$ represents a group selected from a $C_2$-$C_6$-alkylenyl group, a $C_3$-$C_8$-cycloalkyl group, a $C_2$-$C_6$-haloalkyl group, a —C(═O)$OR^6$ group, a C(═O)$NR^7R^8$ group, a —S(═O)(═$NR^{11}$)($C_1$-$C_3$-alkyl) group, a $C_2$-$C_6$-hydroxyalkyl group and a —($C_2$-$C_6$-alkyl)-N($R^7$)($R^8$) group, a $C_1$-$C_6$-alkyl group, which is optionally substituted with a group selected from $C_3$-$C_8$-cycloalkyl and phenyl, wherein said phenyl group is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, or a tautomer, an N-oxide, a salt, a salt of a tautomer or a salt of an N-oxide thereof.

In further embodiments, the present invention provides compounds of formula (I), supra, in which:

$R^4$ represents a group selected from a $C_1$-$C_6$-alkyl group, a $C_3$-$C_8$-cycloalkyl group, a $C_2$-$C_6$-haloalkyl group, a $C_2$-$C_6$-hydroxyalkyl group and a —($C_2$-$C_6$-alkyl)-N($R^7$)($R^8$) group, wherein said $C_1$-$C_6$-alkyl group is optionally substituted with a group selected from $C_3$-$C_8$-cycloalkyl and phenyl, wherein said phenyl group is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, and tautomers, N-oxides, and salts thereof, and salts of tautomers or N-oxides.

In further embodiments, the present invention provides compounds of formula (I), supra, in which:

$R^4$ represents a group selected from a $C_2$-$C_6$-alkylenyl group, a $C_3$-$C_6$-cycloalkyl group, a $C_2$-$C_6$-haloalkyl group, a —C(═O)$OR^6$ group, a C(═O)$NR^7R^8$ group, a —S(═O)(═$NR^{11}$)($C_1$-$C_3$-alkyl) group, a $C_2$-$C_6$-hydroxyalkyl group and a —($C_2$-$C_6$-alkyl)-N($R^7$)($R^8$) group, a $C_1$-$C_6$-alkyl group, which is optionally substituted with a group selected from $C_3$-$C_6$-cycloalkyl and phenyl, wherein said phenyl substituent is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy, or a tautomer, an N-oxide, a salt, a salt of a tautomer or a salt of an N-oxide thereof.

In further embodiments, the present invention provides compounds of formula (I), supra, in which:

$R^4$ represents a group selected from a $C_1$-$C_6$-alkyl group, a $C_3$-$C_6$-cycloalkyl group, a $C_2$-$C_6$-haloalkyl group, a $C_2$-$C_6$-hydroxyalkyl group and a —($C_2$-$C_6$-alkyl)-N($R^7$)($R^8$) group, wherein said $C_1$-$C_6$-alkyl group is optionally substituted with a group selected from $C_3$-$C_6$-cycloalkyl and phenyl, wherein said phenyl group is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy and tautomers, N-oxides, and salts thereof, and salts of tautomers or N-oxides.

In further embodiments, the present invention provides compounds of formula (I), supra, in which:

$R^4$ represents a group selected from a $C_2$-$C_6$-alkenyl group, a $C_3$-$C_6$-cycloalkyl group and a $C_2$-$C_6$-hydroxyalkyl group, a —C(═O)$OR^6$ group, a C(═O)$NR^7R^8$ group, a —S(═O)(═$NR^{11}$)($C_1$-$C_3$-alkyl) group, a $C_1$-$C_6$-alkyl group, which is optionally substituted with a group selected from $C_3$-$C_6$-cycloalkyl and phenyl, or a tautomer, an N-oxide, a salt, a salt of a tautomer or a salt of an N-oxide thereof.

In further embodiments, the present invention provides compounds of formula (I), supra, in which:

$R^4$ represents a group selected from a $C_1$-$C_6$-alkyl group, a $C_3$-$C_6$-cycloalkyl group and a $C_2$-$C_6$-hydroxyalkyl group, wherein said $C_1$-$C_6$-alkyl group is optionally substituted with a group selected from $C_3$-$C_6$-cycloalkyl and phenyl, and tautomers, N-oxides, and salts thereof, and salts of tautomers or N-oxides.

In further embodiments, the present invention provides compounds of formula (I), supra, in which:

$R^4$ represents a group selected from a $C_2$-$C_4$-alkenyl group, a $C_3$-$C_6$-cycloalkyl group and a $C_2$-$C_3$-hydroxyalkyl group, a —C(═O)$OR^6$ group, a C(═O)$NR^7R^8$ group, a —S(═O)(═NH)($C_1$-$C_3$-alkyl) group, a $C_1$-$C_5$-alkyl group, which is optionally substituted with a group selected from cyclopropyl and phenyl, or a tautomer, an N-oxide, a salt, a salt of a tautomer or a salt of an N-oxide thereof.

In further embodiments, the present invention provides compounds of formula (I), supra, in which:

$R^4$ represents a group selected from a $C_1$-$C_5$-alkyl group, a $C_3$-$C_6$-cycloalkyl group and a $C_2$-$C_3$-hydroxyalkyl group,- wherein said $C_1$-$C_4$-alkyl group is optionally substituted with a group selected from
cyclopropyl and phenyl,
and tautomers, N-oxides, and salts thereof, and salts of tautomers or N-oxides.

In further embodiments, the present invention provides compounds of formula (I), supra, in which:
$R^4$ represents a group selected from
a $C_2$-$C_3$-alkenyl group, a $C_3$-$C_8$-cycloalkyl group and a $C_2$-$C_3$-hydroxyalkyl group, a —C(=O)O$R^6$ group, a C(=O)N$R^7R^8$ group, a —S(=O)(=NH)($C_1$-$C_3$-alkyl) group, and
a $C_1$-$C_4$-alkyl group,
said alkyl group is optionally substituted with a group selected from cyclopropyl and phenyl,
or a tautomer, an N-oxide, a salt, a salt of a tautomer or a salt of an N-oxide thereof.

In further embodiments, the present invention provides compounds of formula (I), supra, in which:
$R^4$ represents a group selected from
a $C_2$-$C_4$-alkenyl group,
a $C_3$-$C_8$-cycloalkyl group,
a $C_1$-$C_3$-hydroxyalkyl group,
a $C_1$-$C_4$-alkyl group,
which is optionally substituted with a group selected from cyclopropyl and phenyl,
or a tautomer, an N-oxide, a salt, a salt of a tautomer or a salt of an N-oxide thereof.

In further embodiments, the present invention provides compounds of formula (I), supra, in which:
$R^4$ represents a group selected from
a $C_1$-$C_4$-alkyl group, a $C_3$-$C_8$-cycloalkyl group and a $C_1$-$C_3$-hydroxyalkyl group,
wherein said $C_1$-$C_4$-alkyl group is optionally substituted with a group selected from
cyclopropyl and phenyl,
or a tautomer, an N-oxide, a salt, a salt of a tautomer or a salt of an N-oxide thereof.

In further embodiments, the present invention provides compounds of formula (I), supra, in which:
$R^4$ represents a group selected from
a $C_1$-$C_4$-alkyl group, a $C_3$-$C_8$-cycloalkyl group and a $C_2$-$C_3$-hydroxyalkyl group,
wherein said $C_1$-$C_4$-alkyl group is optionally substituted with a group selected from
cyclopropyl and phenyl,
and tautomers, N-oxides, and salts thereof, and salts of tautomers or N-oxides.

In further embodiments, the present invention provides compounds of formula (I), supra, in which:
$R^4$ represents a $C_1$-$C_4$-alkyl group,
or a tautomer, an N-oxide, a salt, a salt of a tautomer or a salt of an N-oxide thereof.

In further embodiments, the present invention provides compounds of formula (I), supra, in which:
$R^4$ represents a group selected from
methyl, ethyl, propyl, isopropyl, 2-butyl, prop-2-en-1-yl, cyclopropylmethyl, benzyl, cyclopropyl, cyclobutyl, cyclopentyl, 2-hydroxyethyl,
or a tautomer, an N-oxide, a salt, a salt of a tautomer or a salt of an N-oxide thereof.

In further embodiments, the present invention provides compounds of formula (I), supra, in which:
$R^4$ represents a group selected from
methyl, ethyl, propyl, isopropyl, 2-butyl, prop-2-en-1-yl, cyclopropylmethyl, cyclopropyl, cyclobutyl, cyclopentyl, 2-hydroxyethyl,
or a tautomer, an N-oxide, a salt, a salt of a tautomer or a salt of an N-oxide thereof.

In further embodiments, the present invention provides compounds of formula (I), supra, in which:
$R^4$ represents a group selected from
methyl, ethyl, propyl, isopropyl, 2-butyl, prop-2-en-1-yl, cyclopropylmethyl, 2-hydroxyethyl,
or a tautomer, an N-oxide, a salt, a salt of a tautomer or a salt of an N-oxide thereof.

In further embodiments, the present invention provides compounds of formula (I), supra, in which:
$R^4$ represents a group selected from
methyl, ethyl, propyl, isopropyl, 2-butyl, prop-2-en-1-yl
or a tautomer, an N-oxide, a salt, a salt of a tautomer or a salt of an N-oxide thereof.

In further embodiments, the present invention provides compounds of formula (I), supra, in which:
$R^4$ represents a group selected from
methyl, ethyl, propyl, isopropyl, 2-butyl,
or a tautomer, an N-oxide, a salt, a salt of a tautomer or a salt of an N-oxide thereof.

In further embodiments, the present invention provides compounds of formula (I), supra, in which:
$R^4$ represents a group selected from
methyl, ethyl, propyl, isopropyl,
or a tautomer, an N-oxide, a salt, a salt of a tautomer or a salt of an N-oxide thereof.

In further embodiments, the present invention provides compounds of formula (I), supra, in which:
$R^4$ represents a group selected from
methyl, ethyl, propyl,
or a tautomer, an N-oxide, a salt, a salt of a tautomer or a salt of an N-oxide thereof.

In further embodiments, the present invention provides compounds of formula (I), supra, in which:
$R^4$ represents a group selected from
benzyl, cyclopropyl, cyclobutyl, cyclopentyl,
or a tautomer, an N-oxide, a salt, a salt of a tautomer or a salt of an N-oxide thereof.

In further embodiments, the present invention provides compounds of formula (I), supra, in which:
$R^4$ represents a group selected from
methyl, ethyl, propyl, isopropyl, 2-butyl, cyclopropylmethyl, benzyl, cyclopropyl, cyclopentyl and 2-hydroxyethyl,
and tautomers, N-oxides, and salts thereof, and salts of tautomers or N-oxides.

In further embodiments, the present invention provides compounds of formula (I), supra, in which:
$R^4$ represents a group selected from
benzyl, cyclopropyl, cyclobutyl, cyclopentyl and —S(=O)(=NH)CH$_3$,
or a tautomer, an N-oxide, a salt, a salt of a tautomer or a salt of an N-oxide thereof.

In further embodiments, the present invention provides compounds of formula (I), supra, in which:
$R^5$ represents a halogen atom or a group selected from
a $C_1$-$C_6$-alkyl group,
a $C_3$-$C_8$-cycloalkyl group,
a $C_1$-$C_6$-haloalkyl group which is optionally substituted with a hydroxy group,
a $C_1$-$C_6$-hydroxyalkyl group,
a —($C_1$-$C_6$-alkyl)-N($R^7$)($R^8$) group,
a —($C_1$-$C_6$-alkyl)-O—($C_1$-$C_6$-alkyl) group,
a $C_2$-$C_6$-alkenyl group,
a $C_2$-$C_6$-alkynyl group,
a $C_1$-$C_6$-alkoxy group,
a $C_1$-$C_6$-alkylsulfanyl group, and
a —N($R^7$)($R^8$) group, a —C(=O)OR$^6$ group,
a —C(=O)N(R$^7$)(R$^8$) group,
a —S(=O)(=NR$^{11}$)(C$_1$-C$_3$-alkyl) group, and
a phenyl group
which is optionally substituted one, two or three times, each substituent independently selected from a halogen atom or a group selected from C$_1$-C$_6$-alkyl, C$_1$-C$_6$-haloalkyl, C$_2$-C$_6$-alkenyl, C$_2$-C$_6$-alkynyl, aryl, —(C$_1$-C$_6$-alkyl)-aryl, -aryl-(C$_1$-C$_6$-alkyl), C$_3$-C$_8$-cycloalkyl, C$_1$-C$_6$-alkoxy, —O(C$_2$-C$_6$-alkenyl), C$_1$-C$_6$-haloalkoxy, C$_3$-C$_8$-cycloalkoxy, aryl, —O-aryl, cyano, —C(=O)OR$^6$, hydroxy, —SH, —S—(C$_1$-C$_6$-alkyl), —S—(C$_2$-C$_6$-alkenyl), S(=O)$_2$(C$_1$-C$_6$-alkyl), —S(=O)$_2$—(C$_2$-C$_6$-alkenyl), —N(O)$_2$, and —N(R$^7$)(R$^8$)

or a tautomer, an N-oxide, a salt, a salt of a tautomer or a salt of an N-oxide thereof.

In further embodiments, the present invention provides compounds of formula (I), supra, in which:
R$^5$ represents a halogen atom or a group selected from
a C$_1$-C$_6$-alkyl group, a C$_3$-C$_8$-cycloalkyl group, a C$_1$-C$_6$-haloalkyl group,
a C$_1$-C$_6$-hydroxyalkyl group, a (C$_1$-C$_3$-alkoxy)-(C$_1$-C$_6$-alkyl)- group,
a C$_2$-C$_6$-alkenyl group, a C$_2$-C$_6$-alkynyl group, a C$_1$-C$_6$-alkoxy group,
a C$_1$-C$_6$-alkylsulfanyl group, a —(C$_1$-C$_6$-alkyl)-N(R$^7$)(R$^8$) group and a —N(R$^7$)(R$^8$) group,
and tautomers, N-oxides, and salts thereof, and salts of tautomers or N-oxides.

In further embodiments, the present invention provides compounds of formula (I), supra, in which: R$^5$ represents a halogen atom or a group selected from
a C$_1$-C$_6$-alkyl group,
a C$_3$-C$_8$-cycloalkyl group,
a C$_1$-C$_6$-haloalkyl group,
a C$_1$-C$_6$-hydroxyalkyl group, which is optionally substituted with a hydroxy group,
a (C$_1$-C$_3$-alkoxy)-(C$_1$-C$_6$-alkyl)- group,
a C$_2$-C$_6$-alkenyl group, a C$_2$-C$_6$-alkynyl group,
a C$_1$-C$_6$-alkoxy group,
a C$_1$-C$_6$-alkylsulfanyl group,
a —(C$_1$-C$_6$-alkyl)-N(R$^7$)(R$^8$) group,
a —N(R$^7$)(R$^8$) group,
a —C(=O)OR$^6$ group,
a —C(=O)N(R$^7$)(R$^8$) group, and a —S(=O)(=NR$^{11}$)(C$_1$-C$_3$-alkyl) group,
or a tautomer, an N-oxide, a salt, a salt of a tautomer or a salt of an N-oxide thereof.

In further embodiments, the present invention provides compounds of formula (I), supra, in which: R$^5$ represents a halogen atom or a group selected from
a C$_1$-C$_6$-alkyl group,
a C$_3$-C$_6$-cycloalkyl group,
a C$_1$-C$_6$-haloalkyl group, which is optionally substituted with a hydroxy group,
a C$_1$-C$_6$-hydroxyalkyl group,
a (C$_1$-C$_3$-alkoxy)-(C$_1$-C$_6$-alkyl)- group,
a C$_2$-C$_6$-alkenyl group, a C$_2$-C$_6$-alkynyl group,
a C$_1$-C$_6$-alkoxy group,
a C$_1$-C$_6$-alkylsulfanyl group,
a —(C$_1$-C$_6$-alkyl)-N(R$^7$)(R$^8$) group,
a —N(R$^7$)(R$^8$) group,
a —C(=O)OR$^6$ group,
a —C(=O)N(R$^7$)(R$^8$) group, and a —S(=O)(=NR$^{11}$)(C$_1$-C$_3$-alkyl) group or a tautomer, an N-oxide, a salt, a salt of a tautomer or a salt of an N-oxide thereof.

In further embodiments, the present invention provides compounds of formula (I), supra, in which:
R$^5$ represents a halogen atom or a group selected from
a C$_1$-C$_6$-alkyl group,
a C$_3$-C$_6$-cycloalkyl group,
a C$_1$-C$_6$-haloalkyl group, which is optionally substituted with a hydroxy group,
a C$_1$-C$_6$-hydroxyalkyl group,
a (C$_1$-C$_3$-alkoxy)-(C$_1$-C$_6$-alkyl)- group,
a C$_1$-C$_6$-alkoxy group,
C$_1$-C$_6$-alkylsulfanyl group,
—(C$_1$-C$_6$-alkyl)-N(R$^7$)(R$^8$) group,
a —N(R$^7$)(R$^8$) group,
a —C(=O)OR$^6$ group,
a —C(=O)N(R$^7$)(R$^8$) group, and a —S(=O)(=NR$^{11}$)(C$_1$-C$_3$-alkyl) group or a tautomer, an N-oxide, a salt, a salt of a tautomer or a salt of an N-oxide thereof.

In further embodiments, the present invention provides compounds of formula (I), supra, in which:
R$^5$ represents a halogen atom or a group selected from
a C$_1$-C$_6$-alkyl group, a C$_3$-C$_6$-cycloalkyl group, a C$_1$-C$_6$-haloalkyl group,
a C$_1$-C$_6$-hydroxyalkyl group, a (C$_1$-C$_3$-alkoxy)-(C$_1$-C$_6$-alkyl)- group, a C$_1$-C$_6$-alkoxy group, a C$_1$-C$_6$-alkylsulfanyl group, a —(C$_1$-C$_6$-alkyl)-N(R$^7$)(R$^8$) group and a —N(R$^7$)(R$^8$) group,
and tautomers, N-oxides, and salts thereof, and salts of tautomers or N-oxides.

In further embodiments, the present invention provides compounds of formula (I), supra, in which:
R$^5$ represents a halogen atom or a group selected from
a C$_1$-C$_4$-alkyl group,
a C$_3$-C$_6$-cycloalkyl group,
a C$_1$-C$_3$-haloalkyl group, which is optionally substituted with a hydroxy group,
a C$_1$-C$_3$-hydroxyalkyl group,
(C$_1$-C$_3$-alkyl)-O—(C$_1$-C$_3$-alkyl)- group,
a C$_1$-C$_4$-alkoxy group,
a C$_1$-C$_3$-alkylsulfanyl group,
a —(C$_1$-C$_3$-alkyl)-N(R$^7$)(R$^8$) group,
a —N(R$^7$)(R$^8$) group,
a —C(=O)OR$^6$ group,
a —C(=O)N(R$^7$)(R$^8$) group, and a —S(=O)(=NR$^{11}$)(C$_1$-C$_3$-alkyl) group or a tautomer, an N-oxide, a salt, a salt of a tautomer or a salt of an N-oxide thereof.

In further embodiments, the present invention provides compounds of formula (I), supra, in which:
R$^5$ represents a halogen atom or a group selected from
a C$_1$-C$_4$-alkyl group, a C$_3$-C$_6$-cycloalkyl group, a C$_1$-C$_3$-haloalkyl group,
a C$_1$-C$_3$-hydroxyalkyl group, (C$_1$-C$_3$-alkyl)-O—(C$_1$-C$_3$-alkyl)- group, a C$_1$-C$_4$-alkoxy group,
a C$_1$-C$_3$-alkylsulfanyl group, a —(C$_1$-C$_3$-alkyl)-N(R$^7$)(R$^8$) group and a —N(R$^7$)(R$^8$) group,
and tautomers, N-oxides, and salts thereof, and salts of tautomers or N-oxides.

In further embodiments, the present invention provides compounds of formula (I), supra, in which:
R$^5$ represents a halogen atom or a group selected from
a C$_1$-C$_4$-alkyl group, a C$_3$-C$_6$-cycloalkyl group, a C$_1$-C$_3$-haloalkyl group which is optionally substituted with a hydroxy group, a C$_1$-C$_3$-hydroxyalkyl group, a CH$_3$O—(C$_1$-C$_2$-alkyl)- group, a C$_1$-C$_3$-alkoxy group, a methylsulfanyl group, a —($C_1$-$C_2$-alkyl)-N($R^7$)($R^8$) group and a —N($R^7$)($R^8$) group, or a tautomer, an N-oxide, a salt, a salt of a tautomer or a salt of an N-oxide thereof.

In further embodiments, the present invention provides compounds of formula (I), supra, in which:

$R^5$ represents a halogen atom or a group selected from
a $C_1$-$C_4$-alkyl group, a $C_3$-$C_6$-cycloalkyl group, a $C_1$-haloalkyl group,
a $C_1$-$C_3$-hydroxyalkyl group, a methoxy-($C_1$-$C_2$-alkyl)- group, a $C_1$-$C_3$-alkoxy group,
a methylsulfanyl group, a —($C_1$-$C_2$-alkyl)-N($R^7$)($R^8$) group and a —N($R^7$)($R^8$) group, and tautomers, N-oxides, and salts thereof, and salts of tautomers or N-oxides.

In further embodiments, the present invention provides compounds of formula (I), supra, in which:

$R^5$ represents a chlorine atom or a group selected from
methyl, ethyl, propyl, isopropyl, 2-butyl, tert-butyl, cyclopropyl, cyclobutyl, cyclopentyl, trifluoromethyl, hydroxymethyl, hydroxy(trifluoromethyl)methyl, 1-hydroxyethyl, 2-hydroxypropan-2-yl, 1-chloroethyl, 1-hydroxy-2,2,2-trifluoroethyl, 1-methoxyethyl, methoxy, isopropoxy, methylsulfanyl, aminomethyl, (methylamino)methyl, (dimethylamino)methyl, 1-aminoethyl, 2-aminoethyl, methylamino and ethyl(methyl)amino, —C(=O)OH, —C(=O)OCH$_3$, —C(=O)NH$_2$, —C(=O)NHCH$_3$, —C(=O)NHcyclopropyl, —C(=O)N(CH$_3$)$_2$, and —S(=O)(=NH)CH$_3$, or a tautomer, an N-oxide, a salt, a salt of a tautomer or a salt of an N-oxide thereof.

In further embodiments, the present invention provides compounds of formula (I), supra, in which:

$R^5$ represents a chlorine atom or a group selected from
methyl, ethyl, propyl, isopropyl, 2-butyl, tert-butyl, cyclopropyl, cyclobutyl, cyclopentyl, trifluoromethyl, hydroxymethyl, 1-hydroxyethyl, 2-hydroxypropan-2-yl, 1-methoxyethyl, methoxy, isopropoxy, methylsulfanyl, aminomethyl, (methylamino)methyl, (dimethylamino)methyl, 1-aminoethyl, 2-aminoethyl, methylamino and ethyl(methyl)amino, and tautomers, N-oxides, and salts thereof, and salts of tautomers or N-oxides.

In further embodiments, the present invention provides compounds of formula (I), supra, in which:

$R^5$ represents a group selected from
methyl, ethyl, propyl, isopropyl, 2-butyl, tert-butyl, cyclopropyl, cyclobutyl, cyclopentyl, trifluoromethyl, hydroxymethyl, hydroxy(trifluoromethyl)methyl, 1-hydroxyethyl, 2-hydroxypropan-2-yl, 1-methoxyethyl, methoxy, isopropoxy, methylsulfanyl, aminomethyl, (methylamino)methyl, (dimethylamino)methyl, 1-aminoethyl, 2-aminoethyl, methylamino and ethyl(methyl)amino, or a tautomer, an N-oxide, a salt, a salt of a tautomer or a salt of an N-oxide thereof.

In further embodiments, the present invention provides compounds of formula (I), supra, in which:

$R^5$ represents a chlorine atom or a group selected from
—C(=O)OH, —C(=O)OCH$_3$, —C(=O)NH$_2$, —C(=O)NHCH$_3$, —C(=O)NHcyclopropyl, —C(=O)N(CH$_3$)$_2$, and —S(=O)(=NH)CH$_3$, or a tautomer, an N-oxide, a salt, a salt of a tautomer or a salt of an N-oxide thereof.

In further embodiments, the present invention provides compounds of formula (I), supra, in which:

$R^5$ represents a group selected from
methyl, ethyl, propyl, isopropyl, 2-butyl, tert-butyl, trifluoromethyl, hydroxymethyl, hydroxy(trifluoromethyl)methyl, 1-hydroxyethyl, 2-hydroxypropan-2-yl, 1-methoxyethyl, methoxy, isopropoxy, aminomethyl, (methylamino)methyl, (dimethylamino)methyl, 1-aminoethyl, 2-aminoethyl, methylamino and ethyl(methyl)amino, or a tautomer, an N-oxide, a salt, a salt of a tautomer or a salt of an N-oxide thereof.

In further embodiments, the present invention provides compounds of formula (I), supra, in which:

$R^5$ represents a group selected from
methyl, ethyl, propyl, isopropyl, 2-butyl, tert-butyl, trifluoromethyl, hydroxymethyl, 1-hydroxyethyl, 2-hydroxypropan-2-yl, 1-methoxyethyl, methoxy, isopropoxy or a tautomer, an N-oxide, a salt, a salt of a tautomer or a salt of an N-oxide thereof.

In further embodiments, the present invention provides compounds of formula (I), supra, in which:

$R^5$ represents a group selected from
trifluoromethyl, hydroxymethyl, 1-hydroxyethyl, 2-hydroxypropan-2-yl, 1-methoxyethyl, methoxy, isopropoxy or a tautomer, an N-oxide, a salt, a salt of a tautomer or a salt of an N-oxide thereof.

In further embodiments, the present invention provides compounds of formula (I), supra, in which:

$R^5$ represents a group selected from
methyl, ethyl, propyl, isopropyl, 2-butyl, tert-butyl, or a tautomer, an N-oxide, a salt, a salt of a tautomer or a salt of an N-oxide thereof.

In further embodiments, the present invention provides compounds of formula (I), supra, in which:

$R^5$ represents a group selected from
trifluoromethyl, or a tautomer, an N-oxide, a salt, a salt of a tautomer or a salt of an N-oxide thereof.

In further embodiments, the present invention provides compounds of formula (I), supra, in which:

$R^5$ represents a group selected from
hydroxymethyl, 1-hydroxyethyl, 2-hydroxypropan-2-yl, 1-methoxyethyl, methoxy, isopropoxy or a tautomer, an N-oxide, a salt, a salt of a tautomer or a salt of an N-oxide thereof.

In further embodiments, the present invention provides compounds of formula (I), supra, in which:

$R^5$ represents a group selected from
$C_1$-$C_3$-hydroxyalkyl, $C_1$-$C_3$-alkoxy and $C_1$-$C_3$-alkoxy-($C_1$-$C_3$)alkyl, or a tautomer, an N-oxide, a salt, a salt of a tautomer or a salt of an N-oxide thereof.

In further embodiments, the present invention provides compounds of formula (I), supra, in which:

$R^5$ represents a group selected from
$C_1$-$C_5$-hydroxyalkyl and $C_1$-$C_5$-alkoxy, or a tautomer, an N-oxide, a salt, a salt of a tautomer or a salt of an N-oxide thereof.

In further embodiments, the present invention provides compounds of formula (I), supra, in which:

$R^5$ represents a $C_1$-$C_5$-hydroxyalkyl group or a tautomer, an N-oxide, a salt, a salt of a tautomer or a salt of an N-oxide thereof.

In further embodiments, the present invention provides compounds of formula (I), supra, in which:

$R^5$ represents a group selected from
C$_1$-C$_4$-hydroxyalkyl and C$_1$-C$_4$-alkoxy,
or a tautomer, an N-oxide, a salt, a salt of a tautomer or a salt of an N-oxide thereof.

In further embodiments, the present invention provides compounds of formula (I), supra, in which:
$R^5$ represents a C$_1$-C$_4$-hydroxyalky group,
or a tautomer, an N-oxide, a salt, a salt of a tautomer or a salt of an N-oxide thereof.

In further embodiments, the present invention provides compounds of formula (I), supra, in which:
$R^5$ represents a C$_1$-C$_4$-alkoxy group,
or a tautomer, an N-oxide, a salt, a salt of a tautomer or a salt of an N-oxide thereof.

In further embodiments, the present invention provides compounds of formula (I), supra, in which:
$R^5$ represents a group selected from
C$_1$-C$_3$-hydroxyalkyl and C$_1$-C$_3$-alkoxy,
or a tautomer, an N-oxide, a salt, a salt of a tautomer or a salt of an N-oxide thereof.

In further embodiments, the present invention provides compounds of formula (I), supra, in which:
$R^5$ represents a C$_1$-C$_3$-hydroxyalkyl group,
or a tautomer, an N-oxide, a salt, a salt of a tautomer or a salt of an N-oxide thereof.

In further embodiments, the present invention provides compounds of formula (I), supra, in which:
$R^5$ represents a group selected from
hydroxymethyl, 1-hydroxyethyl, 2-hydroxypropan-2-yl,
or a tautomer, an N-oxide, a salt, a salt of a tautomer or a salt of an N-oxide thereof.

In further embodiments, the present invention provides compounds of formula (I), supra, in which:
$R^5$ represents a group selected from
hydroxymethyl,
or a tautomer, an N-oxide, a salt, a salt of a tautomer or a salt of an N-oxide thereof.

In further embodiments, the present invention provides compounds of formula (I), supra, in which:
$R^5$ represents a group selected from
1-hydroxyethyl,
or a tautomer, an N-oxide, a salt, a salt of a tautomer or a salt of an N-oxide thereof.

In further embodiments, the present invention provides compounds of formula (I), supra, in which:
$R^5$ represents a group selected from
2-hydroxypropan-2-yl,
or a tautomer, an N-oxide, a salt, a salt of a tautomer or a salt of an N-oxide thereof.

In further embodiments, the present invention provides compounds of formula (I), supra, in which:
$R^5$ represents a group selected from
1-methoxyethyl, methoxy, isopropoxy
or a tautomer, an N-oxide, a salt, a salt of a tautomer or a salt of an N-oxide thereof.

In further embodiments, the present invention provides compounds of formula (I), supra, in which:
$R^6$ represents a hydrogen atom or a group selected from
a C$_1$-C$_6$-alkyl group and a benzyl group,
and tautomers, N-oxides, and salts thereof, and salts of tautomers or N-oxides.

In further embodiments, the present invention provides compounds of formula (I), supra, in which:
$R^6$ represents a hydrogen atom or a group selected from
a C$_1$-C$_4$-alkyl group and a benzyl group,
and tautomers, N-oxides, and salts thereof, and salts of tautomers or N-oxides.

In further embodiments, the present invention provides compounds of formula (I), supra, in which:
$R^6$ represents a hydrogen atom or a C$_1$-C$_4$-alkyl group,
and tautomers, N-oxides, and salts thereof, and salts of tautomers or N-oxides.

In further embodiments, the present invention provides compounds of formula (I), supra, in which:
$R^6$ represents a hydrogen atom or a C$_1$-C$_3$-alkyl group,
and tautomers, N-oxides, and salts thereof, and salts of tautomers or N-oxides.

In further embodiments, the present invention provides compounds of formula (I), supra, in which:
$R^6$ represents a hydrogen atom or a methyl group,
and tautomers, N-oxides, and salts thereof, and salts of tautomers or N-oxides.

In further embodiments, the present invention provides compounds of formula (I), supra, in which:
$R^7$ and $R^8$ represent, independently for each occurrence, a hydrogen atom or a group selected from
a C$_1$-C$_6$-alkyl group, a C$_2$-C$_6$-hydroxyalkyl group, a C$_3$-C$_6$-cycloalkyl group, and a —(C$_2$-C$_6$-alkyl)-N(R$^9$)(R$^{10}$) group,
or
$R^7$ and $R^8$ together with the nitrogen to which they are attached represent a nitrogen containing
4- to 7-membered heterocycloalkyl group,
which is optionally substituted with a group selected from
C$_1$-C$_3$-alkyl, —S(=O)$_2$(C$_1$-C$_3$-alkyl) and —C(=O)O (C$_1$-C$_4$-alkyl),
or a tautomer, an N-oxide, a salt, a salt of a tautomer or a salt of an N-oxide thereof.

In further embodiments, the present invention provides compounds of formula (I), supra, in which:
$R^7$ and $R^8$ represent, independently for each occurrence, a hydrogen atom or a group selected from
a C$_1$-C$_6$-alkyl group, a C$_2$-C$_6$-hydroxyalkyl group and a —(C$_2$-C$_6$-alkyl)-N(R$^9$)(R$^{10}$) group,
or
$R^7$ and $R^8$ together with the nitrogen to which they are attached represent a
nitrogen containing 4- to 7-membered heterocycloalkyl group,
wherein said 4- to 7-membered nitrogen containing heterocycloalkyl group is optionally substituted with a group selected from
C$_1$-C$_3$-alkyl, —S(=O)$_2$(C$_1$-C$_3$-alkyl) and —C(=O)O (C$_1$-C$_4$-alkyl),
and tautomers, N-oxides, and salts thereof, and salts of tautomers or N-oxides.

In further embodiments, the present invention provides compounds of formula (I), supra, in which:
$R^7$ and $R^8$ represent, independently for each occurrence, a hydrogen atom or a group selected from
a C$_1$-C$_6$-alkyl group, a C$_2$-C$_6$-hydroxyalkyl group, a C$_3$-C$_6$-cycloalkyl group, and a —(C$_2$-C$_6$-alkyl)-N(R$^9$)(R$^{10}$) group,
or a tautomer, an N-oxide, a salt, a salt of a tautomer or a salt of an N-oxide thereof.

In further embodiments, the present invention provides compounds of formula (I), supra, in which:
$R^7$ and $R^8$ represent, independently for each occurrence, a hydrogen atom or a group selected from
a C$_1$-C$_6$-alkyl group, a C$_2$-C$_6$-hydroxyalkyl group and a —(C$_2$-C$_6$-alkyl)-N(R$^9$)(R$^{10}$) group,
and tautomers, N-oxides, and salts thereof, and salts of tautomers or N-oxides.

In further embodiments, the present invention provides compounds of formula (I), supra, in which:
$R^7$ and $R^8$ together with the nitrogen to which they are attached represent a nitrogen containing 4- to 7-membered heterocycloalkyl group,
wherein said 4- to 7-membered nitrogen containing heterocycloalkyl group is optionally substituted with a group selected from
$C_1$-$C_3$-alkyl, —S(=O)$_2$($C_1$-$C_3$-alkyl) and —C(=O)O ($C_1$-$C_4$-alkyl),
and tautomers, N-oxides, and salts thereof, and salts of tautomers or N-oxides.

In further embodiments, the present invention provides compounds of formula (I), supra, in which:
$R^7$ and $R^8$ represent, independently for each occurrence, a hydrogen atom or a group selected from a $C_1$-$C_3$-alkyl group, a $C_2$-$C_3$-hydroxyalkyl group, a —($C_2$-$C_3$-alkyl)-N($R^9$)($R^{10}$) group and $C_3$-$C_6$-cycloalkyl group,
or
$R^7$ and $R^8$ together with the nitrogen to which they are attached represent a nitrogen containing 4- to 6-membered heterocycloalkyl group,
wherein said 4- to 6-membered nitrogen containing heterocycloalkyl group is optionally substituted with a group selected from
$C_1$-$C_3$-alkyl, —S(=O)$_2$($C_1$-$C_3$-alkyl) and —C(=O)O ($C_1$-$C_4$-alkyl),
or a tautomer, an N-oxide, a salt, a salt of a tautomer or a salt of an N-oxide thereof.

In further embodiments, the present invention provides compounds of formula (I), supra, in which:
$R^7$ and $R^8$ represent, independently for each occurrence, a hydrogen atom or a group selected from
a $C_1$-$C_3$-alkyl group, a $C_2$-$C_3$-hydroxyalkyl group and a —($C_2$-$C_3$-alkyl)-N($R^9$)($R^{10}$) group,
or
$R^7$ and $R^8$ together with the nitrogen to which they are attached represent a
nitrogen containing 4- to 6-membered heterocycloalkyl group,
wherein said 4- to 6-membered nitrogen containing heterocycloalkyl group is optionally substituted with a group selected from
$C_1$-$C_3$-alkyl, —S(=O)$_2$($C_1$-$C_3$-alkyl) and —C(=O)O ($C_1$-$C_4$-alkyl),
and tautomers, N-oxides, and salts thereof, and salts of tautomers or N-oxides.

In further embodiments, the present invention provides compounds of formula (I), supra, in which:
$R^7$ and $R^8$ represent, independently for each occurrence, a hydrogen atom or a group selected from a $C_1$-$C_3$-alkyl group, a $C_2$-$C_3$-hydroxyalkyl group, a —($C_2$-$C_3$-alkyl)-N($R^9$)($R^{10}$) group and $C_3$-$C_6$-cycloalkyl group,
or a tautomer, an N-oxide, a salt, a salt of a tautomer or a salt of an N-oxide thereof.

In further embodiments, the present invention provides compounds of formula (I), supra, in which:
$R^7$ and $R^8$ represent, independently for each occurrence, a hydrogen atom or a group selected from
a $C_1$-$C_3$-alkyl group, a $C_2$-$C_3$-hydroxyalkyl group and a —($C_2$-$C_3$-alkyl)-N($R^9$)($R^{10}$) group,
and tautomers, N-oxides, and salts thereof, and salts of tautomers or N-oxides.

In further embodiments, the present invention provides compounds of formula (I), supra, in which:
$R^7$ and $R^8$ together with the nitrogen to which they are attached represent a nitrogen containing 4- to 6-membered heterocycloalkyl group,
wherein said 4- to 6-membered nitrogen containing heterocycloalkyl group is optionally substituted with a group selected from
$C_1$-$C_3$-alkyl, —S(=O)$_2$($C_1$-$C_3$-alkyl) and —C(=O)O ($C_1$-$C_4$-alkyl),
and tautomers, N-oxides, and salts thereof, and salts of tautomers or N-oxides.

In further embodiments, the present invention provides compounds of formula (I), supra, in which:
$R^7$ and $R^8$ represent, independently for each occurrence, a hydrogen atom or a $C_1$-$C_3$-alkyl group or a cyclopropyl group,
or a tautomer, an N-oxide, a salt, a salt of a tautomer or a salt of an N-oxide thereof.

In further embodiments, the present invention provides compounds of formula (I), supra, in which:
$R^7$ and $R^8$ represent, independently for each occurrence, a hydrogen atom or a $C_1$-$C_3$-alkyl group,
and tautomers, N-oxides, and salts thereof, and salts of tautomers or N-oxides.

In further embodiments, the present invention provides compounds of formula (I), supra, in which:
$R^9$ and $R^{10}$ represent, independently for each occurrence, a hydrogen atom or a $C_1$-$C_3$-alkyl group,
or
$R^9$ and $R^{10}$ together with the nitrogen to which they are attached represent a nitrogen containing 4- to 7-membered heterocycloalkyl group,
and tautomers, N-oxides, and salts thereof, and salts of tautomers or N-oxides.

In further embodiments, the present invention provides compounds of formula (I), supra, in which:
$R^9$ and $R^{10}$ represent, independently for each occurrence, a hydrogen atom or a $C_1$-$C_3$-alkyl group,
and tautomers, N-oxides, and salts thereof, and salts of tautomers or N-oxides.

In further embodiments, the present invention provides compounds of formula (I), supra, in which:
$R^9$ and $R^{10}$ together with the nitrogen to which they are attached represent a nitrogen containing 4- to 7-membered heterocycloalkyl group,
and tautomers, N-oxides, and salts thereof, and salts of tautomers or N-oxides.

In further embodiments, the present invention provides compounds of formula (I), supra, in which:
$R^9$ and $R^{10}$ represent, identically or differently, a hydrogen atom or a $C_1$-$C_3$-alkyl group,
or
$R^9$ and $R^{10}$ together with the nitrogen to which they are attached represent a nitrogen containing 4- to 6-membered heterocycloalkyl group,
and tautomers, N-oxides, and salts thereof, and salts of tautomers or N-oxides.

In further embodiments, the present invention provides compounds of formula (I), supra, in which:
$R^9$ and $R^{10}$ together with the nitrogen to which they are attached represent a nitrogen containing 4- to 6-membered heterocycloalkyl group,
and tautomers, N-oxides, and salts thereof, and salts of tautomers or N-oxides.

In further embodiments, the present invention provides compounds of formula (I), supra, in which:
$R^{11}$ represents a hydrogen atom or a group selected from a cyano group and a —C(=O)($C_1$-$C_3$-haloalkyl) group, and tautomers, N-oxides, and salts thereof, and salts of tautomers or N-oxides.

In further embodiments, the present invention provides compounds of formula (I), supra, in which:
$R^{11}$ represents a hydrogen atom,
and tautomers, N-oxides, and salts thereof, and salts of tautomers or N-oxides.

In accordance with further embodiments, the present invention provides compounds of general formula (Ia),

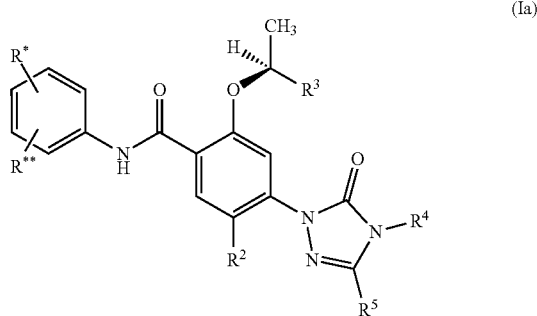

(Ia)

in which
$R^2$-$R^{11}$ have the meanings as in any of claims 1-6 unless specified below and R* and R** are independently selected from a halogen atom or a group selected from $C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(O)OH, —C(=O)OR$^6$, —C(=O)N(R$^7$)(R$^8$), —N(R$^7$)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$), —SH, —S—($C_1$-$C_6$-alkyl), —S—($C_2$-$C_6$-alkenyl), —S(=O)$_2$($C_1$-$C_6$-alkyl), —S(=O)$_2$N(R$^7$)(R$^8$), —S(=O)$_2$($C_1$-$C_3$-alkyl),
—S(=O)(=NR$^{11}$)($C_1$-$C_3$-alkyl), —N(O)$_2$, —P(=O)($C_1$-$C_3$-alkyl)$_2$ and SF$_5$,
or wherein, in case R* and R** do have vicinal position in the phenyl group, they may form together a 5- or 6-membered, optionally heterocyclic, aromatic or non-aromatic ring, having optionally 1-3 heteroatoms independently selected from —N=, —NH—, —N(R$^7$)—, —O—, —S—, and optionally containing a C(=O) group, and wherein the so formed ring is optionally substituted one or two times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N(R$^7$)(R$^8$)
and
$R^3$ represents a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a $C_2$-$C_6$-alkenyl group, a $C_2$-$C_6$-alkynyl group,
a $C_4$-$C_8$-cycloalkenyl group, a ($C_1$-$C_6$-alkyl)-N(R$^7$)R$^8$ group,
a —($C_1$-$C_6$-alkyl)-(4- to 7-membered nitrogen containing heterocycloalkyl) group and
a phenyl group,
wherein said $C_1$-$C_6$-alkyl group is optionally substituted with a $C_3$-$C_8$-cycloalkyl group,
and
wherein said 4- to 7-membered nitrogen containing heterocycloalkyl group is optionally substituted with a $C_1$-$C_3$-alkyl group,
and
wherein said 4- to 7-membered nitrogen containing heterocycloalkyl group is connected to the alkyl group via a carbon atom of the heterocycloalkyl group,
and
wherein said phenyl group is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N(R$^7$)(R$^8$),
more specifically $R^3$ representing a $C_1$-$C_6$-alkyl group, a $C_3$-$C_8$-cycloalkyl group, a $C_1$-$C_6$-haloalkyl group, a $C_2$-$C_6$-alkenyl group, a phenyl group which is optionally substituted with a $C_3$-$C_8$-cycloalkyl group, even further more specifically $R^3$ represents a CF$_3$ group,
or a tautomer, an N-oxide, a salt, a salt of a tautomer or a salt of an N-oxide thereof.

In accordance with further embodiments, the present invention provides compounds of general formula (Ia),

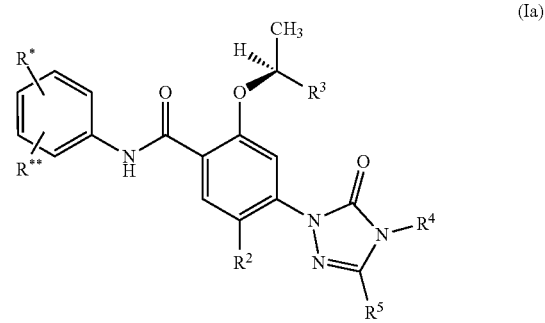

(Ia)

in which
$R^2$-$R^{11}$ have the meanings as in claim 1 unless specified below
and R* and R** are independently selected from a halogen atom or a group selected from $C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, hydroxy, aryl, —O-aryl, cyano, —C(O)OH, —C(=O)OR$^6$, —C(=O)N(R$^7$)(R$^8$), —N(R$^7$)(R$^8$), —($C_1$-$C_6$-alkyl)-N(R$^7$)(R$^8$), —($C_1$-$C_6$-alkyl)-C(=O)OR$^6$, —($C_1$-$C_6$-alkyl)-C(=O)N(R$^7$)(R$^8$), —SH, —S—($C_1$-$C_6$-alkyl), —S—($C_2$-$C_6$-alkenyl), —S(=O)$_2$N(R$^7$)(R$^8$), —S(=O)$_2$($C_1$-$C_3$-alkyl), —S(=O)(=NR$^{11}$)($C_1$-$C_3$-alkyl), —N(O)$_2$, —P(=O)($C_1$-$C_3$-alkyl)$_2$ and SF$_5$,
or wherein, in case R* and R** do have vicinal position in the phenyl group, they may form together a 5- or 6-membered, optionally heterocyclic, aromatic or non-aromatic ring, having optionally 1-3 heteroatoms independently selected from —N=, —NH—, —N(R$^7$)—, —O—, —S—, and optionally containing a C(=O) group, and wherein the so formed ring is optionally substituted one or two times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —N(O)$_2$, and —N($R^7$)($R^8$)
and
$R^3$ represents a group selected from
a $C_1$-$C_6$-alkyl group, a $C_3$-$C_8$-cycloalkyl group, a $C_1$-$C_6$-haloalkyl group,
a $C_1$-$C_6$-hydroxyalkyl group, a $C_2$-$C_6$-alkenyl group, a $C_2$-$C_6$-alkynyl group,
a $C_4$-$C_8$-cycloalkenyl group, a ($C_1$-$C_6$-alkyl)-N($R^7$)$R^8$ group,
a —($C_1$-$C_6$-alkyl)-(4- to 7-membered nitrogen containing heterocycloalkyl) group and
a phenyl group,
  wherein said $C_1$-$C_6$-alkyl group is optionally substituted with a
  $C_3$-$C_8$-cycloalkyl group,
  and
  wherein said 4- to 7-membered nitrogen containing heterocycloalkyl group is optionally substituted with a $C_1$-$C_3$-alkyl group,
  and
  wherein said 4- to 7-membered nitrogen containing heterocycloalkyl group is connected to the alkyl group via a carbon atom of the heterocycloalkyl group,
  and
  wherein said phenyl group is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —N(O)$_2$, and —N($R^7$)($R^8$),
more specifically $R^3$ representing a $C_1$-$C_6$-alkyl group, a $C_3$-$C_8$-cycloalkyl group, a $C_1$-$C_6$-haloalkyl group, a $C_2$-$C_6$-alkenyl group, a phenyl group which is optionally substituted with a $C_3$-$C_8$-cycloalkyl group, even further more specifically $R^3$ represents a $CF_3$ group,
and tautomers, N-oxides, and salts thereof, and salts of tautomers or N-oxides.

In accordance with further embodiments, the present invention provides compounds of general formula (I),
in which
$R^1$ represents a phenyl group,
which phenyl group is optionally substituted, one or two times, each substituent independently selected from a halogen atom, a $C_1$-$C_3$-alkyl group, a trifluoromethyl group, a amino group or a —NH($C_1$-$C_3$-alkyl) group, or more specifically selected from a fluorine atom, a chlorine atom, a methyl group, a ethyl group, a propyl group, a propan-2-yl group, a trifluoromethyl group, a amino group, a —NH(CH$_3$) group, or even more specifically selected from a fluorine atom, a chlorine atom and a methyl group,
and
$R^3$ represents a trifluoromethyl group and tautomers, N-oxides, and salts thereof, and salts of tautomers or N-oxides.

In accordance with further embodiments, the present invention provides compounds of general formula (I),
in which
$R^1$ represents a phenyl group,
which phenyl group is optionally substituted, one or two times, each substituent independently selected from a halogen atom, a $C_1$-$C_3$-alkyl group, a trifluoromethyl group, a amino group or a —NH($C_1$-$C_3$-alkyl) group, or more specifically selected from a fluorine atom, a chlorine atom, a methyl group, a ethyl group, a propyl group, a propan-2-yl group, a trifluoromethyl group, a amino group, a —NH(CH$_3$) group, or even more specifically selected from a fluorine atom, a chlorine atom and a methyl group,
and
$R^2$ represents a hydrogen atom or a fluorine atom and tautomers, N-oxides, and salts thereof, and salts of tautomers or N-oxides.

In accordance with further embodiments, the present invention provides compounds of general formula (I),
in which
$R^1$ represents a phenyl group,
which phenyl group is optionally substituted, one or two times, each substituent independently selected from a halogen atom, a $C_1$-$C_3$-alkyl group, a trifluoromethyl group, a amino group or a —NH($C_1$-$C_3$-alkyl) group, or more specifically selected from a fluorine atom, a chlorine atom, a methyl group, a ethyl group, a propyl group, a propan-2-yl group, a trifluoromethyl group, a amino group, a —NH(CH$_3$) group, or even more specifically selected from a fluorine atom, a chlorine atom and a methyl group,
and
$R^2$ represents a fluorine atom and tautomers, N-oxides, and salts thereof, and salts of tautomers or N-oxides.

In accordance with further embodiments, the present invention provides compounds of general formula (I),
in which
$R^1$ represents a phenyl group, which is optionally substituted, one or two times, each substituent independently selected from a halogen atom, a $C_1$-$C_3$-alkyl group, a trifluoromethyl group, or more specifically selected from a fluorine atom, a chlorine atom, a methyl group, a ethyl group, a propyl group, a propan-2-yl group, a trifluoromethyl group,
$R^2$ represents a hydrogen atom, a fluorine atom, or a chlorine atom, more specifically a hydrogen atom or a fluorine atom,
$R^3$ represents a group selected from propyl, 2-methylpropyl, 3-pentyl, cyclopropylmethyl, cyclopropyl, cyclobutyl, cyclopentyl, cyclohexyl, difluoromethyl, trifluoromethyl, allyl, 2-methyl-prop-1-enyl
$R^4$ represents a group selected from
  a $C_1$-$C_4$-alkyl group, a $C_3$-$C_8$-cycloalkyl group and a $C_2$-$C_3$-hydroxyalkyl group, wherein said $C_1$-$C_4$-alkyl group is optionally substituted with a group selected from cyclopropyl and phenyl,
$R^5$ represents a halogen atom or a group selected from
  a $C_1$-$C_4$-alkyl group, a $C_3$-$C_6$-cycloalkyl group, a $C_1$-$C_3$-haloalkyl group,
  a $C_1$-$C_3$-hydroxyalkyl group, a CH$_3$O—($C_1$-$C_2$-alkyl)- group, a $C_1$-$C_3$-alkoxy group,
  a methylsulfanyl group, a —($C_1$-$C_2$-alkyl)-N($R^7$)($R^8$) group and a —N($R^7$)($R^8$) group,
$R^6$ represents a hydrogen atom or a $C_1$-$C_3$-alkyl group,
$R^7$ and $R^8$ represent, independently for each occurrence, a hydrogen atom or a group selected from a $C_1$-$C_3$-alkyl group, a $C_2$-$C_3$-hydroxyalkyl group, a —($C_2$-$C_3$-alkyl)-N($R^9$)($R^{10}$) group and $C_3$-$C_6$-cycloalkyl group,
or a tautomer, an N-oxide, a salt, a salt of a tautomer or a salt of an N-oxide thereof.

In accordance with further embodiments, the present invention provides compounds of general formula (I),
in which
$R^1$ represents a phenyl group, which is optionally substituted, one, two or three times, each substituent independently selected from a halogen atom, a hydroxy group, a $C_1$-$C_3$-alkyl group, a trifluoromethyl group, or more specifically selected from a hydroxy group, a fluorine atom, a chlorine atom, a methyl group, a ethyl group, a propyl group, a propan-2-yl group, a trifluoromethyl group,
$R^2$ represents a hydrogen atom, a fluorine atom, or a chlorine atom, more specifically a hydrogen atom or a fluorine atom,
$R^3$ represents a group selected from propyl, 2-methylpropyl, 3-pentyl, cyclopropylmethyl, cyclopropyl, cyclobutyl, cyclopentyl, cyclohexyl, difluoromethyl, trifluoromethyl, allyl, 2-methyl-prop-1-enyl
$R^4$ represents a group selected from
    a $C_1$-$C_4$-alkyl group, a $C_2$-$C_3$-alkenyl group, a $C_3$-$C_8$-cycloalkyl group and a $C_2$-$C_3$-hydroxyalkyl group,
    wherein said $C_1$-$C_4$-alkyl group is optionally substituted with a group selected from cyclopropyl and phenyl,
$R^5$ represents a halogen atom or a group selected from
    a $C_1$-$C_4$-alkyl group, a $C_3$-$C_6$-cycloalkyl group, a $C_1$-$C_3$-haloalkyl group,
    a $C_1$-$C_3$-hydroxyalkyl group, a $CH_3O$—($C_1$-$C_2$-alkyl)- group, a $C_1$-$C_3$-alkoxy group,
    a methylsulfanyl group, a —($C_1$-$C_2$-alkyl)-N($R^7$)($R^8$) group, a —N($R^7$)($R^8$) group, a C(=O)O$R^6$ group and a C(=O)N$R^7R^8$ group,
$R^6$ represents a hydrogen atom or a $C_1$-$C_3$-alkyl group,
$R^7$ and $R^8$ represent, independently for each occurrence, a hydrogen atom or a group selected from a $C_1$-$C_3$-alkyl group, a $C_2$-$C_3$-hydroxyalkyl group, a —($C_2$-$C_3$-alkyl)-N($R^9$)($R^{10}$) group and $C_3$-$C_6$-cycloalkyl group,
or a tautomer, an N-oxide, a salt, a salt of a tautomer or a salt of an N-oxide thereof.

In accordance with further embodiments, the present invention provides compounds of general formula (I),
in which
$R^1$ represents a phenyl group, which is optionally substituted, one, two or three times, each substituent independently selected from a hydroxy group, a fluorine atom, a chlorine atom, a methyl group, a ethyl group, a propyl group, a propan-2-yl group, a trifluoromethyl group,
$R^2$ represents a hydrogen atom or a fluorine atom,
$R^3$ represents a group selected from propyl, 2-methylpropyl, 3-pentyl, difluoromethyl, trifluoromethyl, allyl, 2-methyl-prop-1-enyl
$R^4$ represents a group selected from
    a $C_1$-$C_4$-alkyl group, a $C_2$-$C_3$-alkenyl group, a $C_3$-$C_8$-cycloalkyl group and a $C_2$-$C_3$-hydroxyalkyl group,
    wherein said $C_1$-$C_4$-alkyl group is optionally substituted with a group selected from cyclopropyl and phenyl,
$R^5$ represents a halogen atom or a group selected from
    a $C_1$-$C_4$-alkyl group, a $C_3$-$C_6$-cycloalkyl group, a $C_1$-$C_3$-haloalkyl group,
    a $C_1$-$C_3$-hydroxyalkyl group, a $CH_3O$—($C_1$-$C_2$-alkyl)- group, a $C_1$-$C_3$-alkoxy group,
    a methylsulfanyl group, a —($C_1$-$C_2$-alkyl)-N($R^7$)($R^8$) group, a —N($R^7$)($R^8$) group, a C(=O)O$R^6$ group and a C(=O)N$R^7R^8$ group,
$R^6$ represents a hydrogen atom or a $C_1$-$C_3$-alkyl group,
$R^7$ and $R^8$ represent, independently for each occurrence, a hydrogen atom or a group selected from a $C_1$-$C_3$-alkyl group, a $C_2$-$C_3$-hydroxyalkyl group, a —($C_2$-$C_3$-alkyl)-N($R^9$)($R^{10}$) group and $C_3$-$C_6$-cycloalkyl group,
or a tautomer, an N-oxide, a salt, a salt of a tautomer or a salt of an N-oxide thereof.

In accordance with further embodiments, the present invention provides compounds of general formula (I),
in which
$R^1$ represents a phenyl group, which is optionally substituted, one, two or three times, each substituent independently selected from a hydroxy group, a fluorine atom, a chlorine atom, a methyl group,
$R^2$ represents a fluorine atom,
$R^3$ represents a trifluoromethyl group,
$R^4$ represents a group selected from methyl, ethyl, propyl, and isopropyl,
$R^5$ represents a group selected from methyl, hydroxymethyl, hydroxyethyl, hydroxypropyl, a C(=O)O$R^6$ group and a C(=O)N$R^7R^8$ group
$R^6$ represents a hydrogen atom or a $C_1$-$C_3$-alkyl group,
$R^7$ and $R^8$ represent, independently for each occurrence, a hydrogen atom or a $C_1$-$C_3$-alkyl group,
or a tautomer, an N-oxide, a salt, a salt of a tautomer or a salt of an N-oxide thereof.

In accordance with further embodiments, the present invention provides compounds of general formula (I),
in which
$R^1$ represents a phenyl group, which is optionally substituted, one or two times, each substituent independently selected from a fluorine atom, a chlorine atom, a methyl group,
$R^2$ represents a fluorine atom,
$R^3$ represents a trifluoromethyl group,
$R^4$ represents a group selected from methyl, ethyl, propyl, isopropyl,
$R^5$ represents a group selected from methyl, hydroxymethyl, hydroxyethyl, hydroxypropyl,
or a tautomer, an N-oxide, a salt, a salt of a tautomer or a salt of an N-oxide thereof.

In accordance with further embodiments, the present invention provides compounds of general formula (I),

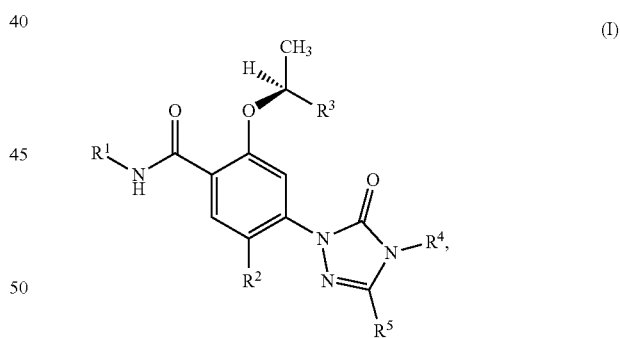

in which
$R^1$ represents a group selected from
    $C_3$-$C_6$-alkyl, $C_5$-$C_6$-cycloalkyl, a pyridyl group which is substituted with methyl and/or methoxy, or phenyl which is substituted one or more times with a group independently selected from fluorine atom, a chlorine atom, a $C_1$-$C_3$-alkyl group, a trifluoromethyl group, a amino group or a —NH($C_1$-$C_3$-alkyl) group.
$R^2$ represents a fluorine atom,
$R^3$ represents a group selected from
    a propyl group, a cyclobutyl group, a trifluoromethyl group, a allyl group and a phenyl group,
$R^4$ represents a group selected from
    a $C_1$-$C_4$-alkyl group and a cyclopropyl group, $R^5$ represents a chlorine atom or a group selected from
$C_1$-$C_3$-alkyl, $C_4$-$C_6$-cycloalkyl, trifluoromethyl, $C_1$-$C_3$-hydroxyalkyl,
and tautomers, N-oxides, and salts thereof, and salts of tautomers or N-oxides.

In accordance with further embodiments, the present invention provides compounds of general formula (I),

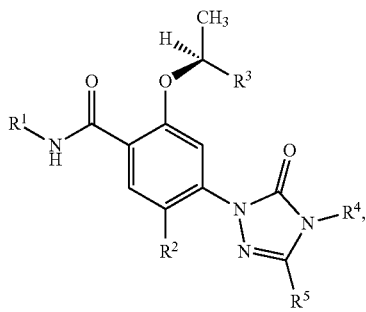

(I)

in which
$R^1$ represents a group selected from
3-pentyl, cycloheptyl, 2-methoxy-4-methylpyridin-3-yl, 2,6-dichlorophenyl, 2-chloro-6-fluorophenyl, 2,6-difluorophenyl, 2-fluoro-6-methylphenyl, 4-fluoro-2-methylphenyl, 2-methylphenyl, 2-ethylphenyl, 2-propylphenyl, 2-(propan-2-yl)phenyl, 2-(trifluoromethyl)phenyl, 2-(methylamino)phenyl and 3-amino-2-methylphenyl,
$R^2$ represents a fluorine atom,
$R^3$ represents a group selected from
propyl, cyclobutyl, trifluoromethyl, allyl and phenyl,
$R^4$ represents a group selected from
methyl, ethyl, propyl, isopropyl and cyclopropyl,
$R^5$ represents a chlorine atom or a group selected from
methyl, ethyl, isopropyl, cyclopropyl, cyclobutyl, trifluoromethyl, hydroxymethyl, 1-hydroxyethyl and 2-hydroxypropan-2-yl,
and tautomers, N-oxides, and salts thereof, and salts of tautomers or N-oxides.

In accordance with further embodiments, the present invention provides compounds of general formula (I),

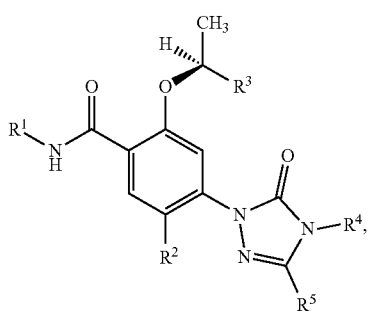

(I)

in which
$R^1$ represents a group selected from
2,6-dichlorophenyl, 2-chloro-6-fluorophenyl, 2-fluoro-6-methylphenyl and 2-methylphenyl,
$R^2$ represents a fluorine atom,
$R^3$ represents a group selected from
propyl and trifluoromethyl,
$R^4$ represents a group selected from
methyl, ethyl and propyl,
$R^5$ represents a chlorine atom or a group selected from
ethyl, isopropyl, cyclopropyl, hydroxymethyl, 1-hydroxyethyl and 2-hydroxypropan-2-yl,
and tautomers, N-oxides, and salts thereof, and salts of tautomers or N-oxides.

In accordance with further embodiments, the present invention provides compounds of general formula (I),

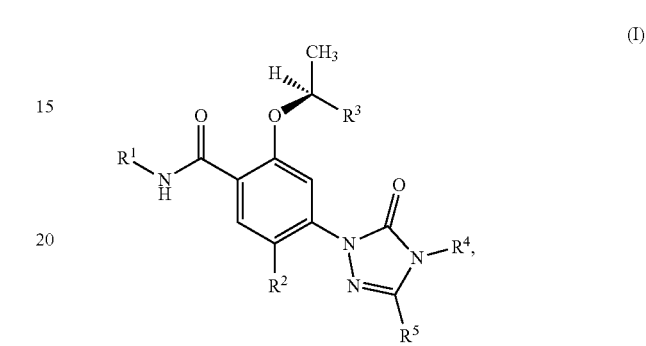

(I)

in which
$R^1$ represents a group selected from
2,6-dichlorophenyl, 2-chloro-6-fluorophenyl, 2-fluoro-6-methylphenyl, 2,6-difluorophenyl, 2-chloro-6-fluoro-5-hydroxyphenyl, 2-chloro-6-fluoro-4-hydroxyphenyl, 2-chloro-6-fluoro-3-hydroxyphenyl, 2-chloro-6-fluoro-3-methoxyphenyl and 2-methylphenyl,
$R^2$ represents a fluorine atom,
$R^3$ represents a group selected from
propyl and trifluoromethyl,
$R^4$ represents a group selected from
methyl, ethyl, propyl, 2-propenyl and cyclobutyl,
$R^5$ represents a chlorine atom or a group selected from
ethyl, isopropyl, cyclopropyl, hydroxymethyl, 1-hydroxyethyl and 2-hydroxypropan-2-yl, COOH, CONR$^7$R$^8$, and
$R^7$ and $R^8$ represent, independently for each occurrence, a hydrogen atom or a group selected from a $C_1$-$C_3$-alkyl group, a $C_2$-$C_3$-hydroxyalkyl group, a —($C_2$-$C_3$-alkyl)-N(R$^9$)(R$^{10}$) group and $C_3$-$C_6$-cycloalkyl group
$R^9$ and $R^{10}$ represent, identically or differently, a hydrogen atom or a $C_1$-$C_3$-alkyl group,
or
$R^9$ and $R^{10}$ together with the nitrogen to which they are attached represent a nitrogen containing 4- to 6-membered heterocycloalkyl group,
or a tautomer, an N-oxide, a salt, a salt of a tautomer or a salt of an N-oxide thereof.

In accordance with further embodiments, the present invention provides the compounds of general formula (I), in which
$R^1$ represents a phenyl group which is optionally substituted, one, two or three times, each substituent independently selected from a halogen atom, a $C_1$-$C_3$-alkyl group and a $C_1$-$C_3$-alkoxy group,
$R^2$ represents a fluorine or chlorine atom,
$R^3$ represents a group selected from
$C_1$-$C_4$-alkyl group or a $C_1$-$C_4$-haloalkyl group,
$R^4$ represents a group selected from
a $C_1$-$C_4$-alkyl group, a $C_2$-$C_3$-alkenyl group and a $C_4$-$C_5$-cycloalkyl group R⁵ represents a chlorine atom or a group selected from
C₁-C₄-alkyl group, C₃-C₈ cycloalkyl group, cyclopropyl, C₁-C₄-hydroxyalkyl group, COOH, and CONR⁷R⁸,
R⁷ and R⁸ represent, independently for each occurrence, a hydrogen atom or a group selected from a C₁-C₃-alkyl group, a C₂-C₃-hydroxyalkyl group, a —(C₂-C₃-alkyl)-N(R⁹)(R¹⁰) group and C₃-C₆-cycloalkyl group
or a tautomer, an N-oxide, a salt, a salt of a tautomer or a salt of an N-oxide thereof.

In accordance with further embodiments, the present invention provides the compounds of general formula (I), in which
R¹ represents a phenyl group which is optionally substituted, one, two or three times, each substituent independently selected from a fluorine atom, a chlorine atom, a methyl group and a methoxy group,
R² represents a fluorine atom,
R³ represents a group selected from
propyl and trifluoromethyl,
R⁴ represents a group selected from
methyl, ethyl, propyl, 2-propenyl and cyclobutyl,
R⁵ represents a chlorine atom or a group selected from
ethyl, isopropyl, cyclopropyl, hydroxymethyl, 1-hydroxyethyl and 2-hydroxypropan-2-yl, COOH, CONR⁷R⁸, and
R⁷ and R⁸ represent, independently for each occurrence, a hydrogen atom or a group selected from a C₁-C₃-alkyl group, a C₂-C₃-hydroxyalkyl group, a —(C₂-C₃-alkyl)-N(R⁹)(R¹⁰) group and C₃-C₆-cycloalkyl group
or a tautomer, an N-oxide, a salt, a salt of a tautomer or a salt of an N-oxide thereof.

In accordance with further embodiments, the present invention provides the compounds of general formula (I), in which
R¹ represents a phenyl group which is optionally substituted, one, two or three times, each substituent independently selected from a fluorine atom, a chlorine atom, a methyl group and a methoxy group,
R² represents a fluorine atom,
R³ represents a group selected from
propyl and trifluoromethyl,
R⁴ represents a group selected from
methyl, ethyl, propyl, 2-propenyl and cyclobutyl,
R⁵ represents a chlorine atom or a group selected from
ethyl, isopropyl, cyclopropyl, hydroxymethyl, 1-hydroxyethyl and 2-hydroxypropan-2-yl, COOH, CONR⁷R⁸, and
R⁷ and R⁸ represent, independently for each occurrence, a hydrogen atom or a C₁-C₃-alkyl group
or a tautomer, an N-oxide, a salt, a salt of a tautomer or a salt of an N-oxide thereof.

In accordance with further embodiments, the present invention provides compounds of general formula (I),

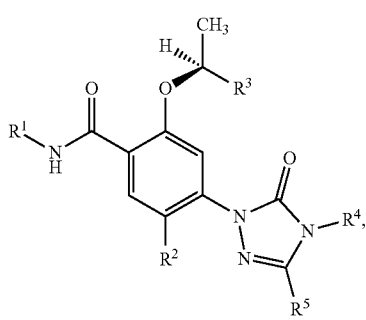

(I)

in which
R¹ represents a phenyl group,
which phenyl group is optionally substituted, one or two times, each substituent independently selected from a fluorine atom, a chlorine atom and a methyl group,
R² represents a fluorine atom,
R³ represents a group selected from
propyl and trifluoromethyl,
R⁴ represents a group selected from
methyl, ethyl and propyl,
R⁵ represents a chlorine atom or a group selected from
ethyl, isopropyl, cyclopropyl, hydroxymethyl, 1-hydroxyethyl and 2-hydroxypropan-2-yl,
and tautomers, N-oxides, and salts thereof, and salts of tautomers or N-oxides.

In accordance with further embodiments, the present invention provides compounds of general formula (I),

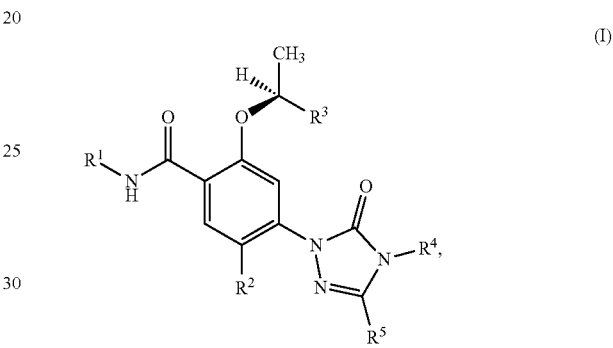

(I)

in which
R¹ represents a phenyl group,
which phenyl group is optionally substituted, one or two times, each substituent independently selected from a fluorine atom, a chlorine atom and a methyl group,
R² represents a fluorine atom,
R³ represents a group selected from
propyl and trifluoromethyl,
R⁴ represents a group selected from
methyl, ethyl and propyl,
R⁵ represents a chlorine atom or a group selected from
ethyl, isopropyl, cyclopropyl and C₁-C₃-hydroxyalkyl,
and tautomers, N-oxides, and salts thereof, and salts of tautomers or N-oxides.

In accordance with further embodiments, the present invention provides the compounds of general formula (I), in which
R¹ represents a phenyl group,
which phenyl group is optionally substituted, one or two times, each substituent independently selected from a hydroxy group, a fluorine atom, a chlorine atom and a methyl group,
R² represents a fluorine atom,
R³ represents a group selected from
propyl and trifluoromethyl,
R⁴ represents a group selected from
methyl, ethyl and propyl,
R⁵ represents a chlorine atom or a group selected from
ethyl, isopropyl, cyclopropyl and C₁-C₃-hydroxyalkyl,
or a tautomer, an N-oxide, a salt, a salt of a tautomer or a salt of an N-oxide thereof.

In accordance with further embodiments, the present invention provides the compounds of general formula (I), in which R$^1$ represents a phenyl group,
which phenyl group is optionally substituted, one or two times, each substituent independently selected from a hydroxy group, a fluorine atom, a chlorine atom and a methyl group, R$^2$ represents a fluorine atom or a chlorine atom, R$^3$ represents a group selected from
propyl and trifluoromethyl, R$^4$ represents a group selected from
methyl, ethyl and propyl, R$^5$ represents a chlorine atom or a group selected from
ethyl, isopropyl, cyclopropyl and C$_1$-C$_3$-hydroxyalkyl, or a tautomer, an N-oxide, a salt, a salt of a tautomer or a salt of an N-oxide thereof.

In accordance with further embodiments, the present invention provides compounds of general formula (I),

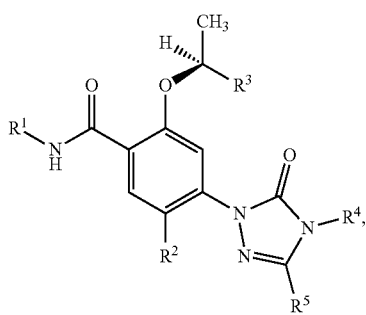

(I)

in which

R$^1$ represents a group selected from
cycloheptyl, 2-methoxy-4-methylpyridin-3-yl, 2,6-dichlorophenyl, 2-chloro-6-fluorophenyl, 2,6-difluorophenyl, 2-fluoro-6-methylphenyl, 4-fluoro-2-methylphenyl, 2-methylphenyl, 2-ethylphenyl, 2-propylphenyl, 2-(propan-2-yl)phenyl, 2-(trifluoromethyl)phenyl, 2-(methylamino)phenyl and 3-amino-2-methylphenyl, R$^2$ represents a fluorine atom, R$^3$ represents a group selected from
propyl, trifluoromethyl, allyl and phenyl, R$^4$ represents a group selected from
methyl, ethyl, propyl, isopropyl and cyclopropyl, R$^5$ represents a chlorine atom or a group selected from
methyl, ethyl, isopropyl, cyclopropyl, cyclobutyl, trifluoromethyl, hydroxymethyl, 1-hydroxyethyl and 2-hydroxypropan-2-yl, and tautomers, N-oxides, and salts thereof, and salts of tautomers or N-oxides.

In further embodiments, the present invention provides compounds of formula (I), supra, in which:

R$^1$ represents a group selected from
3-pentyl, cycloheptyl, 2-methoxy-4-methylpyridin-3-yl, 2,6-dichlorophenyl, 2-chloro-6-fluorophenyl, 2,6-difluorophenyl, 2-fluoro-6-methylphenyl, 4-fluoro-2-methylphenyl, 2-methylphenyl, 2-ethylphenyl, 2-propylphenyl, 2-(propan-2-yl)phenyl, 2-(trifluoromethyl)phenyl, 2-(methylamino)phenyl and 3-amino-2-methylphenyl, and tautomers, N-oxides, and salts thereof, and salts of tautomers or N-oxides.

In accordance with further embodiments, the present invention provides compounds of general formula (I), R$^1$ represents a group selected from
cycloheptyl, 2-methoxy-4-methylpyridin-3-yl, 2,6-dichlorophenyl, 2-chloro-6-fluorophenyl, 2,6-difluorophenyl, 2-fluoro-6-methylphenyl, 4-fluoro-2-methylphenyl, 2-methylphenyl, 2-ethylphenyl, 2-propylphenyl, 2-(propan-2-yl)phenyl, 2-(trifluoromethyl)phenyl, 2-(methylamino)phenyl and 3-amino-2-methylphenyl, and tautomers, N-oxides, and salts thereof, and salts of tautomers or N-oxides.

In further embodiments, the present invention provides compounds of formula (I), supra, in which:

R$^3$ represents a group selected from
propyl, cyclobutyl, trifluoromethyl, allyl and phenyl, and tautomers, N-oxides, and salts thereof, and salts of tautomers or N-oxides.

R$^3$ represents a group selected from
propyl, trifluoromethyl, allyl and phenyl, and tautomers, N-oxides, and salts thereof, and salts of tautomers or N-oxides.

In further embodiments, the present invention provides compounds of formula (I), supra, in which:

R$^4$ represents a group selected from
methyl, ethyl, propyl, isopropyl and cyclopropyl, and tautomers, N-oxides, and salts thereof, and salts of tautomers or N-oxides.

In further embodiments, the present invention provides compounds of formula (I), supra, in which:

R$^5$ represents a chlorine atom or a group selected from
methyl, ethyl, isopropyl, cyclopropyl, cyclobutyl, trifluoromethyl, hydroxymethyl, 1-hydroxyethyl and 2-hydroxypropan-2-yl, and tautomers, N-oxides, and salts thereof, and salts of tautomers or N-oxides.

In further embodiments, the present invention provides compounds of formula (I), supra, in which:

R$^1$ represents a phenyl group,
which phenyl group is optionally substituted, one or two times, each substituent independently selected from a fluorine atom, a chlorine atom and a methyl group, and tautomers, N-oxides, and salts thereof, and salts of tautomers or N-oxides.

In further embodiments, the present invention provides compounds of formula (I), supra, in which:

R$^1$ represents a group selected from
2,6-dichlorophenyl, 2-chloro-6-fluorophenyl, 2-fluoro-6-methylphenyl and 2-methylphenyl, and tautomers, N-oxides, and salts thereof, and salts of tautomers or N-oxides.

In further embodiments, the present invention provides compounds of formula (I), supra, in which:

R$^3$ represents a group selected from
propyl and trifluoromethyl, and tautomers, N-oxides, and salts thereof, and salts of tautomers or N-oxides.

In further embodiments, the present invention provides compounds of formula (I), supra, in which:

R$^3$ represents a group selected from
propyl, or a tautomer, an N-oxide, a salt, a salt of a tautomer or a salt of an N-oxide thereof.

In further embodiments, the present invention provides compounds of formula (I), supra, in which:

R$^3$ represents trifluoromethyl group, or a tautomer, an N-oxide, a salt, a salt of a tautomer or a salt of an N-oxide thereof.

In further embodiments, the present invention provides compounds of formula (I), supra, in which:

$R^4$ represents a group selected from
methyl, ethyl and propyl,
and tautomers, N-oxides, and salts thereof, and salts of tautomers or N-oxides.

In further embodiments, the present invention provides compounds of formula (I), supra, in which:
$R^5$ represents a chlorine atom or a group selected from
ethyl, isopropyl, cyclopropyl and $C_1$-$C_3$-hydroxyalkyl,
and tautomers, N-oxides, and salts thereof, and salts of tautomers or N-oxides.

In further embodiments, the present invention provides compounds of formula (I), supra, in which:
$R^5$ represents a $C_1$-$C_5$-hydroxyalkyl group,
and tautomers, N-oxides, and salts thereof, and salts of tautomers or N-oxides.

In further embodiments, the present invention provides compounds of formula (I), supra, in which:
$R^5$ represents a $C_1$-$C_4$-hydroxyalkyl group,
and tautomers, N-oxides, and salts thereof, and salts of tautomers or N-oxides.

In further embodiments, the present invention provides compounds of formula (I), supra, in which:
$R^5$ represents a $C_1$-$C_3$-hydroxyalkyl group,
and tautomers, N-oxides, and salts thereof, and salts of tautomers or N-oxides.

In further embodiments, the present invention provides compounds of formula (I), supra, in which:
$R^5$ represents a chlorine atom or a group selected from
ethyl, isopropyl, cyclopropyl, hydroxymethyl, 1-hydroxyethyl and 2-hydroxypropan-2-yl,
and tautomers, N-oxides, and salts thereof, and salts of tautomers or N-oxides.

The present invention provides any sub-combination within any embodiment or aspect of the present invention of compounds of general formula (I), supra.

The present invention provides any sub-combination within any embodiment or aspect of the present invention of intermediate compounds of general formulae (IV), (VI), (VIII), (IX), (X), (XV), (XVIII), (XIX), (X) and (XXI).

The present invention provides the compounds of general formula (I) which are disclosed in the Example Section of this text, infra.

The compounds according to the invention of general formula (I) can be prepared according to the following schemes 1, 2, 3, 4 and 5. The schemes and procedures described below illustrate synthetic routes to the compounds of general formula (I) of the invention and are not intended to be limiting. It is clear to the person skilled in the art that the order of transformations as exemplified in schemes 1, 2, 3, 4 and 5 can be modified in various ways. The order of transformations exemplified in these schemes is therefore not intended to be limiting. In addition, interconversion of any of the substituents, $R^1$, $R^2$, $R^3$, $R^4$ or $R^5$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999). Specific examples are described in the subsequent paragraphs.

Synthetic Routes

Five routes for the preparation of compounds of general formula (I) are described in schemes 1, 2, 3, 4 and 5.

Synthetic Route 1

Scheme 1: Route for the preparation of compounds of general formula (I) in which $R^1$, $R^2$, $R^3$, $R^4$ and $R^5$ have the meaning as given for general formula (I), supra.

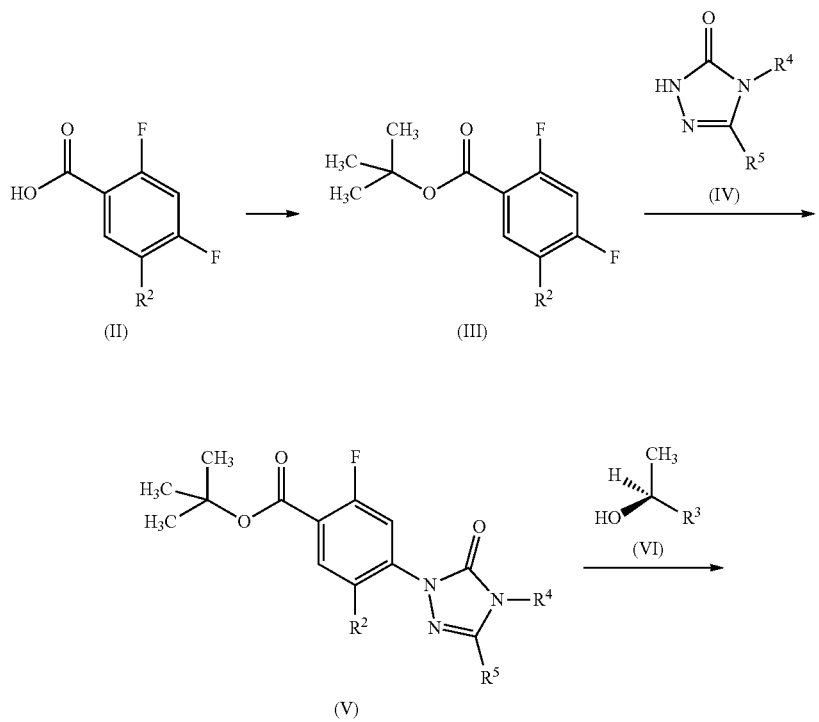

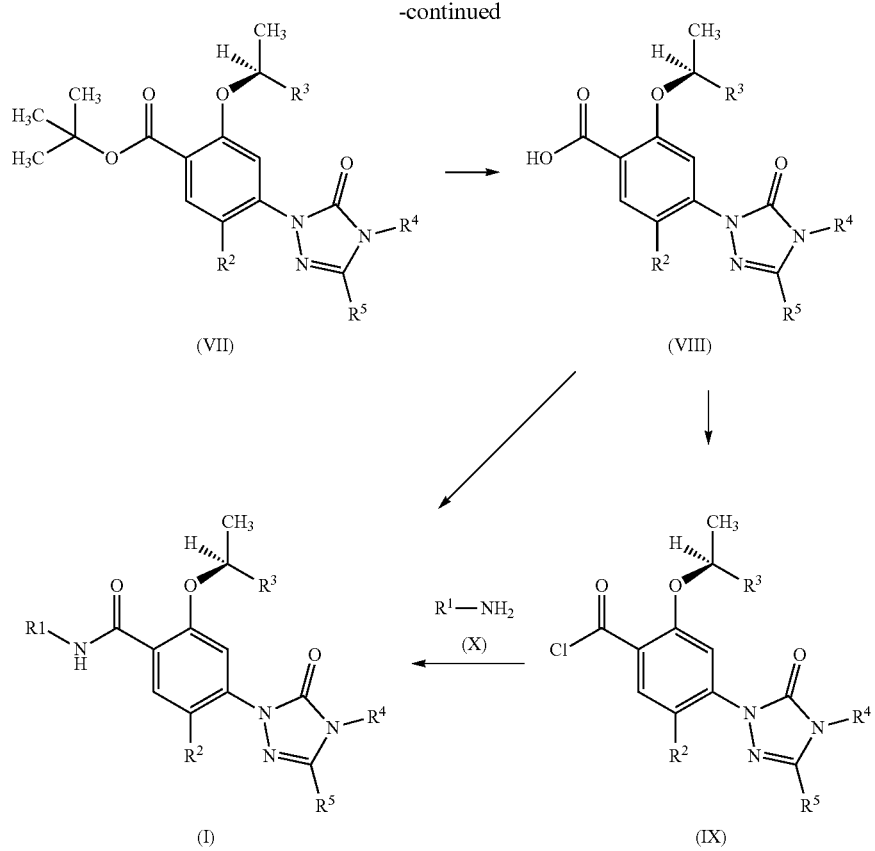

Compounds of general formulae (II), (IV), (VI) and (X) are either commercially available or can be prepared according to procedures available from the public domain, as understandable to the person skilled in the art. Specific examples are described in the Experimental Section.

(II)→(III):

tert-Butyl benzoates of general formula (III) can be prepared from benzoic acid derivatives of general formula (II) according to procedures available from the public domain, as understandable to the person skilled in the art.

In connection with the method of the invention, the use of di-tert-butyl-dicarbonate in tert-butanol was preferable.

Alternatively, the tert-butyl benzoates of general formula (III) can be prepared from benzoic acid derivatives of general formula (II) by in situ formation of the corresponding acid chlorides and subsequent reaction with tert-butanol.

In situ formation of acid chlorides from benzoic acids of general formula (II) can be accomplished, for example by using oxalyl chloride or thionyl chloride, both reagents used in the presence of catalytic amount of N,N-dimethylformamide.

(III)+(IV)→(V):

The formation of tert-butyl benzoates of general formula (V) can be accomplished by the reaction of triazolinones of general formula (IV) with tert-butyl benzoates of general formula (III) in the presence of a base. In connection with the method of the invention, the use of 1,8-diazabicyclo[5.4.0]undec-7-ene as organic base in acetonitrile at 80° C. was preferable.

(V)+(VI)→(VII)→(VIII):

The formation of benzoic acids of general formula (VIII) can be accomplished by reaction of tert-butyl benzoates of general formula (V) with alcohols of general formula (VI) in the presence of a base, and subsequent saponification of the resulting ester of general formula (VII).

Bases that can be employed for the reaction of tert-butyl benzoates of general formula (V) with alcohols of general formula (VI) are for example sodium hydride, sodium tert-butanolate, potassium tert-butanolate, or cesium carbonate. In connection with the method of the invention, potassium hexamethyldisilazide solution in tetrahydrofuran was preferably used as organic base.

Solvents that can be used for the reactions of tert-butyl benzoates of general formula (V) with alcohols of general formula (VI) are for example tetrahydrofuran, dimethyl sulfoxide and N,N-dimethylformamide. In connection with the method according to the invention tertahydrofuran was preferably used as solvent.

Reaction temperatures for the reactions of tert-butyl benzoates of general formula (V) with alcohols of general formula (VI) are for example ranging from room temperature to 130° C.

Cooling of the reaction mixture is optionally necessary on adding the reactants or bases. In connection with the method of the invention, cooling the reaction to −10° C. prior addition of potassium hexamethyldisilazide solution in tetrahydrofuran and subsequent running the reaction at room temperature was preferable.

Suitable reaction times for the reaction of tert-butyl benzoates of general formula (V) with alcohols of general formula (VI) are ranging from 1 h several days.

The reaction of tert-butyl benzoates of general formula (V) with alcohols of general formula (VI) can also result in transesterification, such as the tert-butoxide moiety of the tert-butyl benzoates of general formula (V) can be replaced by the alkoxide R³CH(CH₃)O moiety of the alcohols of general formula (VI). In order to obtain the benzoic acids of general formula (VIII), subsequent ester hydrolysis is required.

Ester hydrolysis can be achieved by various methods which are well known to the person skilled in the art, for example by treatment of the esters with lithium hydroxide, sodium hydroxide or potassium hydroxide, in solvents, such as, for example water, 1,4-dioxane, ethanol or tetrahydrofuran or mixtures thereof. The reactions can be carried out at temperatures ranging from room temperature to the boiling point of the respective solvent or solvent mixture.

In connection with the method of the invention, use of lithium hydroxide in water/dioxane was preferable. (VIII)→(IX), (VIII)/((IX)+(X)→(I):

The compounds of general formula (I) can be prepared by the reaction of the benzoic acids of general formula (VIII) with amines of general formula (X) either by
  in situ formation of the corresponding acid chlorides of general formula (IX) and subsequent reaction with amines of general formula (X),
or by
  amide coupling of the benzoic acids of general formula (VIII) with amines of general formula (X).

In situ formation of acid chlorides of general formula (IX) from benzoic acids of general formula (VIII) can be accomplished, for example by using oxalyl chloride or thionyl chloride, both reagents used in the presence of catalytic amount of N,N-dimethylformamide. In connection with the method according to the invention, oxalyl chloride is preferably used in the presence of N,N-dimethylformamide.

Suitable solvents for the in situ formation of acid chlorides of general formula (IX) from benzoic acids of general formula (VIII) include aprotic nonpolar solvents such as for example dichloromethane or toluene. In connection with the method according to the invention, dichloromethane is preferably used as solvent.

Suitable reaction temperatures for the in situ formation of acid chlorides of general formula (IX) from benzoic acids of general formula (VIII) mostly reflect the boiling point of the solvents used in the reaction. In connection with the method according to the invention, adding of oxalyl chloride was carried out at 0° C. and the reaction mixture was subsequently allowed to warm up to room temperature.

Subsequent reactions of the in situ formed acid chlorides of general formula (IX) with amines of general formula (X) can be carried out in the presence of an organic base. Suitable organic bases are for example triethylamine, pyridine or N-ethyl-N,N-diisopropylamine. In connection with the method according to the invention, triethylamine was preferably used as organic base.

Suitable solvents for the reaction of acid chlorides of general formula (IX) with amines of general formula (X) include aprotic polar solvents such as for example acetonitrile, N,N-dimethylformamide or aprotic nonpolar solvents such as dichloromethane. In connection with the method according to the invention dichloromethane was used as solvent.

Suitable coupling reagents for the reaction of benzoic acids of general formula (VIII) with amines of general formula (X) are for example O-(7-aza-1H-benzotriazol-1-yl)-N,N,N',N'-tetramethyluronium hexafluorophosphate (HATU), dicyclohexylcarbodiimide or a combination of 1H-benzotria-1-ol and 1-ethyl-3-[3-(diemthylaminopropyl] carbodiimide hydrochloride.

Suitable organic bases for the amide coupling of benzoic acids of general formula (VIII) with amines of general formula (X) are for example 4-(dimethylamino)pyridine, N-ethyl-N,N-diisopropylamine or triethylamine.

Suitable solvents for the for the amide coupling of benzoic acids of general formula (VIII) with amines of general formula (X) are for example N,N-dimethylformamide, dichloromethane or tetrahydrofuran.

For coupling of the amide bond, other methods which are well known to the person skilled in the art are also suitable, such as a condensation between amine and acid using propanephosphonic acid anhydride (T3P) as coupling reagent.

In connection with the invention, formation of the compounds according to the invention of general formula (I) were preferrably accomplished by in situ formation of acid chlorides of general formula (IX) from benzoic acids of general formula (VIII) and subsequent reaction with amines of general formula (X).

Synthetic Route 2

Scheme 2: Route for the preparation of compounds of general formula (I) in which R¹, R², R³, R⁴ and R⁵ have the meaning as given for general formula (I), supra, and A represents a chlorine, bromine or iodine atom.

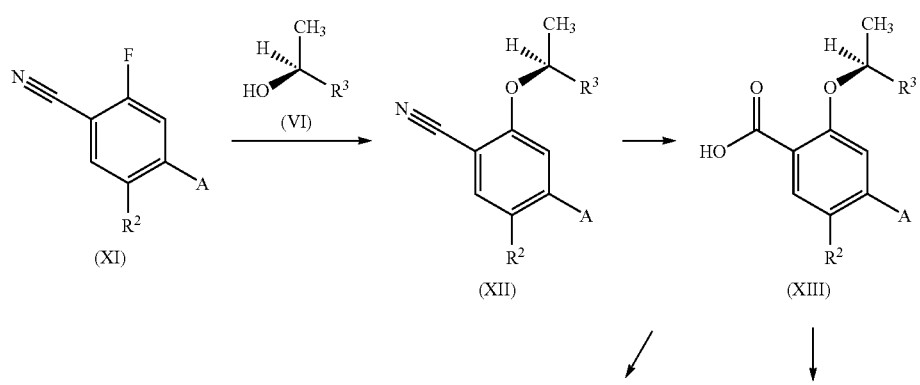

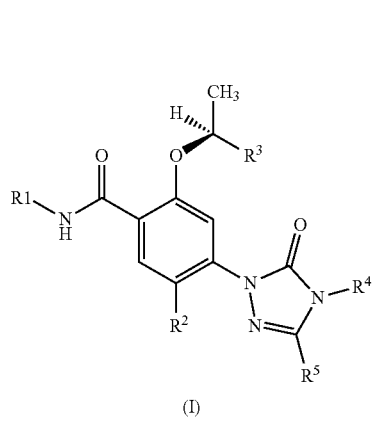
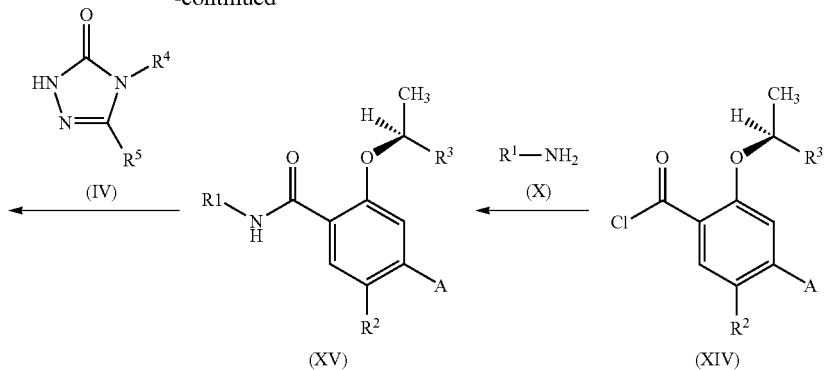

Compounds of general formulae (XI), (IV), (VI) and (X) are either commercially available or can be prepared according to procedures available from the public domain, as understandable to the person skilled in the art. Specific examples are described in the Experimental Section.

(XI)+(VI)→(XII):

Nitriles of general formula (XII) can be prepared from nitriles of general formula (XI) and with alcohols of general formula (VI) according to procedures available from the public domain, as understandable to the person skilled in the art.

In connection with the method of the invention, the use of sodium hydride in DMF was preferable.

Alternatively, for alcohols of sufficiently high acidity the use of potassium carbonate was preferable.

(XII)→(XIII):

The formation of benzoates of general formula (XIII) can be accomplished by hydrolysis of nitriles of general formula XII using strong acids or bases.

In connection with the method of the invention, the use of sodium hydroxide in ethanol at 90° C. was preferable.

(XIII)→(XIV)+(X)→(XV):

The compounds of general formula (XV) can be prepared by the reaction of the benzoic acids of general formula (XIII) with amines of general formula (X) either by in situ formation of the corresponding acid chlorides of general formula (XIV) and subsequent reaction with amines of general formula (X), or by amide coupling of the benzoic acids of general formula (XV) with amines of general formula (X).

In situ formation of acid chlorides of general formula (XIV) from benzoic acids of general formula (XIII) can be accomplished, for example by using oxalyl chloride or thionyl chloride, both reagents used in the presence of catalytic amount of N,N-dimethylformamide. In connection with the method according to the invention, oxalyl chloride is preferably used in the presence of N,N-dimethylformamide.

Suitable solvents for the in situ formation of acid chlorides of general formula (XIV) from benzoic acids of general formula (XIII) include aprotic nonpolar solvents such as for example dichloromethane or toluene. In connection with the method according to the invention, dichloromethane is preferably used as solvent.

Suitable reaction temperatures for the in situ formation of acid chlorides of general formula (XIV) from benzoic acids of general formula (XIII) mostly reflect the boiling point of the solvents used in the reaction. In connection with the method according to the invention, adding of oxalyl chloride was carried out at 0° C. and the reaction mixture was subsequently allowed to warm up to room temperature.

Subsequent reactions of the in situ formed acid chlorides of general formula (XIV) with amines of general formula (X) can be carried out in the presence of an organic base. Suitable organic bases are for example triethylamine, pyridine or N-ethyl-N,N-diisopropylamine. In connection with the method according to the invention, triethylamine was preferably used as organic base.

Suitable solvents for the reaction of acid chlorides of general formula (XIV) with amines of general formula (X) include aprotic polar solvents such as for example acetonitrile, N,N-dimethylformamide or aprotic nonpolar solvents such as dichloromethane. In connection with the method according to the invention dichloromethane was used as solvent.

Suitable coupling reagents for the reaction of benzoic acids of general formula (XIII) with amines of general formula (X) are for example O-(7-aza-1H-benzotriazol-1-yl)-N,N,N,N'-tetramethyluronium hexafluorophosphate (HATU), dicyclohexylcarbodiimide or a combination of 1H-benzotria-1-ol and 1-ethyl-3-[3-(diemthylaminopropyl]carbodiimide hydrochloride.

Suitable organic bases for the amide coupling of benzoic acids of general formula (XIII) with amines of general formula (X) are for example 4-(dimethylamino)pyridine, N-ethyl-N,N-diisopropylamine or triethylamine.

Suitable solvents for the for the amide coupling of benzoic acids of general formula (XIII) with amines of general formula (X) are for example N,N-dimethylformamide, dichloromethane or tetrahydrofuran.

For coupling of the amide bond, other methods which are well known to the person skilled in the art are also suitable, such as a condensation between amine and acid using propanephosphonic acid anhydride (T3P) as coupling reagent.

In connection with the invention, formation of the compounds according to the invention of general formula (XV) were preferrably accomplished by in situ formation of acid chlorides of general formula (XIV) from benzoic acids of general formula (XIII) and subsequent reaction with amines of general formula (X).

(XV)+(IV)→(I):

Compounds according to the invention of general formula (I) can be prepared from halides of general formula (XV) and from triazolones of general formula (IV) using transition metals as catalysts.

Intermediates of general formula (XV) can be reacted with a suitable triazolone of general formula (IV), such as, for example 3-ethyl-4-methyl-1H-1,2,4-triazol-5(4H)-one, in the presence of a suitable base, such as, for example cesium carbonate, and a suitable palladium catalyst, such as for example (1E,4E)-1,5-diphenylpenta-1,4-dien-3-one-palladium, in the presence of a suitable ligand, such as for example (9,9-dimethyl-9H-xanthene-4,5-diyl)bis(diphenylphosphine), in a suitable solvent system, such as, for example, dioxane, in a temperature range from room temperature to the boiling point of the respective solvent, preferably the reaction is carried out at 100° C. to furnish compounds of general formula (I). Alternatively the following palladium catalysts can be used:

allylpalladium chloride dimer, dichlorobis(benzonitrile) palladium (II), palladium (II) acetate, palladium (II) chloride, tetrakis(triphenylphosphine)palladium (0), tris(dibenzylideneacetone)dipalladium (0), chloro(2'-amino-1,1'-biphenyl-2-yl)palladium(II) dimer, (2'-amino-1,1'-biphenyl-2-yl)methanesulfonatopalladium (II) dimer, trans-di(µ-acetato)bis[o-(di-o-tolylphosphino)benzyl]dipalladium(II) [cataCXium® C], allylchloro[1,3-bis(2,4,6-trimethylphenyl)imidazol-2-ylidene]palladium(II), allylchloro[1,3-bis(2,6-diisopropylphenyl)imidazol-2-ylidene]palladium(II), chloro[(1,3-dimesitylimidazol-[1,3-bis(2,4,6-trimethylphenyl)-1,3-dihydro-2H-imidazol-2-ylidene](chloro){2-[(dimethylamino)methyl]phenyl}palladium, chloro[(1,2,3-N)-3-phenyl-2-propenyl][1,3-bis(2,6-di-isopropylphenyl)imidazol-2-ylidene]palladium(II), [2-(acetylamino)phenyl]{1,3-bis[2,6-di(propan-2-yl)phenyl]-1,3-dihydro-2H-imidazol-2-ylidene}chloropalladium, {1,3-bis[2,6-di(propan-2-yl)phenyl]-1,3-dihydro-2H-imidazol-2-ylidene}(chloro){2-[(dimethylamino)methyl]phenyl} palladium, {1,3-bis[2,6-di(propan-2-yl)phenyl]-2,3-dihydro-1H-imidazol-2-yl}(dichloro)(3-chloropyridine-kappaN) palladium, [1,3-bis(2,6-diisopropylphenyl) imidazol-2-ylidene](3-chloropyridyl)palladium(II) dichloride, [2-(acetylamino)-4-methoxyphenyl]{1,3-bis[2,6-di(propan-2-yl)phenyl]-1,3-dihydro-2H-imidazol-2-ylidene}chloropalladium, {1,3-bis[2,6-di(propan-2-yl)phenyl]-1,3-dihydro-2H-imidazol-2-ylidene}(chloro){2-[(dimethylamino)methyl]-3,5-dimethoxyphenyl}palladium, dichloro[1,3-bis(2,6-di-3-pentylphenyl)imidazol-2-ylidene](3-chloropyridyl)palladium(II), dichloro(di-µ-chloro)bis[1,3-bis(2,6-di-iso-propylphenyl) imidazol-2-ylidene]dipalladium(II), 2-(2'-di-tert-butylphosphine)biphenylpalladium(II) acetate, chloro[dicyclohexyl(2',6'-dimethoxybiphenyl-2-yl)-lambda5-phosphanyl][2-(phenyl-kappaC2)ethanaminato-kappaN]palladium, [2-(2-aminoethyl)phenyl](chloro)palladium-di-tert-butyl[2',4',6'-tri(propan-2-yl)biphenyl-2-yl]phosphane, {dicyclohexyl[2',4',6'-tri(propan-2-yl)biphenyl-2-yl]phosphane}{2-[2-(methylazanidyl-kappaN)ethyl]phenyl-kappaC1}palladium, chloro(2-dicyclohexylphosphino-2',6'-dimethoxy-1,1'-biphenyl)(2'-amino-1,1'-biphenyl-2-yl)palladium(II), [2',6'-bis(propan-2-yloxy)biphenyl-2-yl](dicyclohexyl)phosphane-[2-(2-aminoethyl)phenyl](chloro)palladium, [2-(2-aminoethyl)phenyl](chloro){dicyclohexyl[2',4',6'-tri(propan-2-yl)biphenyl-2-yl]-lambda5-phosphanylidene}palladium, 2'-(dicyclohexylphosphanyl)-N,N,N',N'-tetramethylbiphenyl-2,6-diamine-(2'-aminobiphenyl-2-yl)(chloro)palladium, chloro(2-dicyclohexylphosphino-2',6'-di-iso-propoxy-1,1'-biphenyl)(2'-amino-1,1'-biphenyl-2-yl)palladium(II), [2'-(azanidyl-kappaN) biphenyl-2-yl-kappaC2](chloro){dicyclohexyl [2',4',6'-tri(propan-2-yl)biphenyl-2-yl]-lambda5-phosphanyl}palladium, (2'-aminobi-phenyl-2-yl)(methanesulfonato-kappaO)palladium-di-tert-butyl[2',4',6'-tri(propan-2-yl)biphenyl-2-yl]phosphane, (2'-aminobiphenyl-2-yl)palladium(1+) methanesulfonate-di-tert-butyl[2',4',6'-tri(propan-2-yl)biphenyl-2-yl] phosphane, dicyclohexyl[3,6-dimethoxy-2',4',6'-tri(propan-2-yl)biphenyl-2-yl]phosphane-[2-(2-aminoethyl) phenyl](chloro)palladium, (2'-aminobiphenyl-2-yl)palladium(1+) methanesulfonate-2'-(dicyclohexylphosphanyl)-N,N,N',N'-tetramethylbiphenyl-2,6-diamine, sodium 2'-(dicyclohexylphosphanyl)-2,6-dimethoxybiphenyl-3-sulfonate-(2'-aminobiphenyl-2-yl)(chloro)palladium, chloro(2-dicyclohexylphosphino-2',4',6'-tri-iso-propyl-1,1'-biphenyl)[2-(2-aminoethyl)phenyl]palladium(II), (2'-aminobiphenyl-2-yl)(methane-sulfonato-kappaO) palladium-[2',6'-bis(propan-2-yloxy)biphenyl-2-yl](dicyclohexyl) phosphane, (2'-aminobiphenyl-2-yl)(methanesulfonato-kappaO)palladium-dicyclohexyl[2',4',6'-tri(propan-2-yl)biphenyl-2-yl]phosphane, (2'-aminobiphenyl-2-yl)palladium(1+) methanesulfonate-dicyclohexyl[2',4',6'-tri(propan-2-yl)biphenyl-2-yl] phosphane, dicyclohexyl[3,6-dimethoxy-2',4',6'-tri(propan-2-yl)biphenyl-2-yl]phosphane-(2'-aminobiphenyl-2-yl)(chloro)palladium, (2'-aminobiphenyl-2-yl)(methanesulfonato-kappaO) palladium-di-tert-butyl[3,6-dimethoxy-2',4',6'-tri(propan-2-yl)biphenyl-2-yl]phosphane, (2'-aminobiphenyl-2-yl)(methanesulfonato-kappaO) palladium dicyclohexyl[3,6-dimethoxy-2',4',6'-tri(propan-2-yl)biphenyl-2-yl]phosphane or the following ligands:

racemic-2,2'-bis(diphenylphosphino)-1,1'-binaphthyl, rac-BINAP, 1,1'-bis(diphenyl-phosphino)ferrocene, bis(2-diphenylphosphinophenyl)ether, di-tert-butylmethylphosphonium tetrafluoroborate, 2-(di-tert-butylphosphino)biphenyl, tri-tert-butylphosphonium tetrafluoroborate, tri-2-furylphosphine, tris(2,4-di-tert-butylphenyl)phosphite, tri-o-tolylphosphine, (9,9-dimethyl-9H-xanthene-4,5-diyl)bis(diphenylphosphine), dicyclohexyl(2',4',6'-triisopropyl-3,6-dimethoxybiphenyl-2-yl)phosphine, di-tert-butyl (2',4',6'-triisopropyl-3,6-dimethoxybiphenyl-2-yl)phosphine, di-tert-butyl(2',4',6'-triisopropylbiphenyl-2-yl)phosphine, dicyclohexyl(2',4,6-triisopropylbiphenyl-2-yl) phosphine, di-tert-butyl(2',4',6'-triisopropyl-3-methoxy-6-methylbiphenyl-2-yl)phos-phine, di-tert-butyl(2',4',6'-triisopropyl-3,4,5,6-tetramethylbiphenyl-2-yl) phosphine, adamantan-1-yl (adamantan-2-yl)(2',4',6'-triisopropyl-3,6-dimethoxybiphenyl-2-yl) phosphine, dicyclohexyl(2',6'-dimethoxybiphenyl-2-yl)phosphine, dicyclohexyl(2',6'-diisopropoxybiphenyl-2-yl)phosphine, 2'-(dicyclohexylphosphino)-N,N-dimethyl-biphenyl-2-amine, 2'-(di-tert-butylphosphino)-N,N-dimethylbiphenyl-2-amine, 2'-(di-phenylphosphino)-N,N,N',N'-tetramethylbiphenyl-2,6-diamine, di-tert-butyl(2',4',6'-tricyclohexyl-3,6-dimethoxybiphenyl-2-yl)phosphine, bis[3,5-bis(trifluoromethyl phe-nyl] (2',4',6'-triisopropyl-3,6-dimethoxybiphenyl-2-yl) phosphine, biphenyl-2-yl(di-tert-butyl)phosphine, dicyclohexyl(2'-methylbiphenyl-2-yl)phosphine, biphenyl-2-yl (dicyclohexyl)phosphine, 2'-(dicyclohexylphosphino)-N,N-dimethylphenyl-2-amine, 2'-(dicyclohexylphosphino)-N,N',N'-tetramethylbiphenyl-2,6-diamine, sodium 2'-(dicyclohexylphosphino)-2,6-diisopropylbiphenyl-4- sulfonate, sodium 2'-(dicyclohexylphosphino)-2,6-dimethoxybiphenyl-3-sulfonate, 1,1'-binaphthalen-2-yl(di-tert-butyl)phosphine, 1,3-bis(2,4,6-trimethylphenyl)-1,3-dihydro-2H-imidazol-2-ylidene, 1,3-bis[2,6-di(propan-2-yl)phenyl]-1,3-dihydro-2H-imidazol-2-ylidene.

Synthetic Route 3

Scheme 3: Route for the preparation of compounds of general formula (I) in which $R^1$, $R^2$, $R^3$, $R^4$ and $R^5$ have the meaning as given for general formula (I), supra.

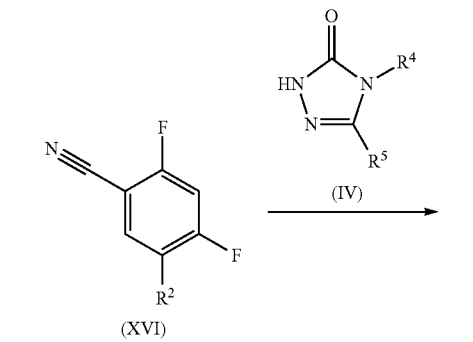

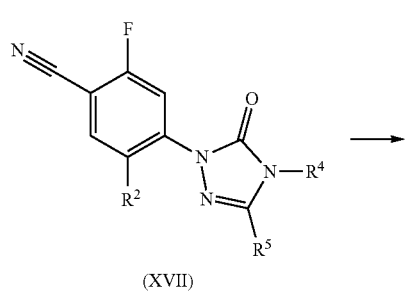

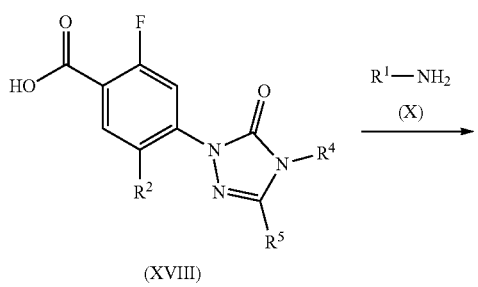

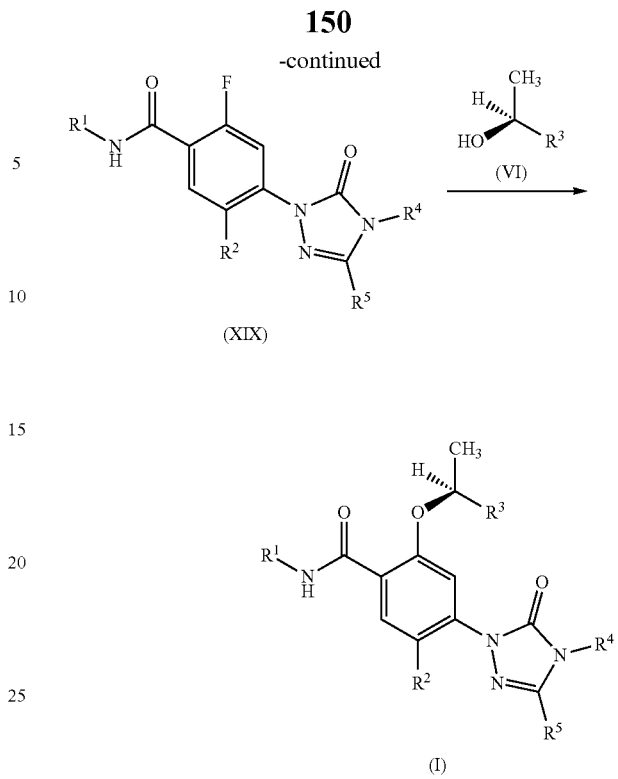

Compounds of general formulae (XVI), (IV), (VI) and (X) are either commercially available or can be prepared according to procedures available from the public domain, as understandable to the person skilled in the art. Specific examples are described in the Experimental Section.

Nitriles of general formula (XVII) can be prepared from nitriles of general formula (XVI) and triazolinones of general formula (IV) in the presence of a base. In connection with the method of the invention, the use of potassium carbonate as base in acetonitrile at 80° C. was preferable.

The formation of benzoates of general formula (XVIII) can be accomplished by hydrolysis of nitriles of general formula XVII using strong acids or bases. In connection with the method of the invention, the use of sodium hydroxide in ethanol at 85° C. was preferable.

The compounds of general formula (XIX) can be prepared by the reaction of the benzoic acids of general formula (XVIII) with amines of general formula (X) by amide coupling.

Suitable coupling reagents for the reaction of benzoic acids of general formula (XVIII) with amines of general formula (X) are for example O-(7-aza-1H-benzotriazol-1-yl)-N,N,N,N'-tetramethyluronium hexafluorophosphate (HATU), dicyclohexylcarbodiimide or a combination of 1H-benzotria-1-ol and 1-ethyl-3-[3-(diemthylaminopropyl] carbodiimide hydrochloride.

Suitable organic bases for the amide coupling of benzoic acids of general formula (XVIII) with amines of general formula (X) are for example 4-(dimethylamino)pyridine, N-ethyl-N,N-diisopropylamine, N-methylpyrollidine, or triethylamine.

Suitable solvents for the for the amide coupling of benzoic acids of general formula (XVIII) with amines of general formula (X) are for example N,N-dimethylformamide, dichloromethane or tetrahydrofuran.

For coupling of the amide bond, other methods which are well known to the person skilled in the art are also suitable, such as a condensation between amine and acid using propanephosphonic acid anhydride (T3P) as coupling reagent, or transformation of benzoic acids of general formula (XVIII) into their respective acid chlorides and subsequent reaction with amines of general formula (X) as described above.

In connection with the invention, formation of the compounds of general formula (XIX) were preferrably accomplished by HATU mediated amide coupling of benzoic acids of general formula (XVIII) and amines of general formula (X).

The formation of compounds of general formula (I) can be accomplished by reaction of amides of general formula (XIX) and alcohols of general formula (VI) in the presence of a base. Bases that can be employed for the reaction of amides of general formula (XIX) with alcohols of general formula (VI) are for example sodium hydride, sodium tert-butanolate, potassium tert-butanolate, or cesium carbonate. In connection with the method of the invention, sodium hydride was preferrably used as organic base.

Solvents that can be used for the reactions of tert-butyl benzoates of general formula (V) with alcohols of general formula (VI) are for example tetrahydrofuran, dimethyl sulfoxide and N,N-dimethylformamide. In connection with the method according to the invention N,N-dimethylformamide was preferrably used as solvent.

Reaction temperatures for the reactions of tert-butyl benzoates of general formula (V) with alcohols of general formula (VI) are for example ranging from room temperature to 80° C. In connection with the method of the invention, the reaction of alcohols of general formula (VI) with sodium hydride was preferrably performed at room temperature for 1 h before addition of amides of formula (XIX) and subsequent heating of the reaction mixture to 80° C.

Suitable reaction times for the reaction of tert-butyl benzoates of general formula (V) with alcohols of general formula (VI) are ranging from 3 h to several days.

Synthetic Route 4

Scheme 4: Route for the preparation of compounds of general formula (I) in which $R^1$, $R^2$, $R^3$, $R^4$ and $R^5$ have the meaning as given for general formula (I), supra.

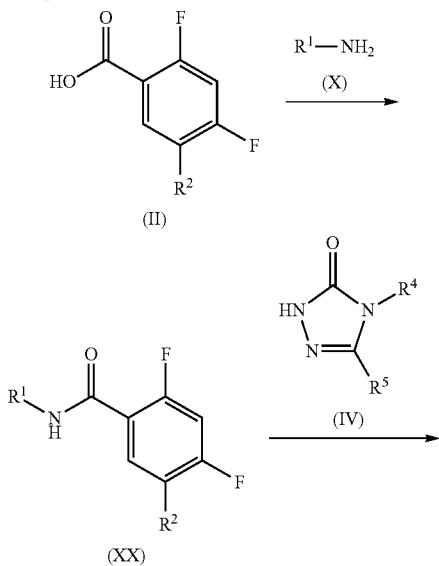

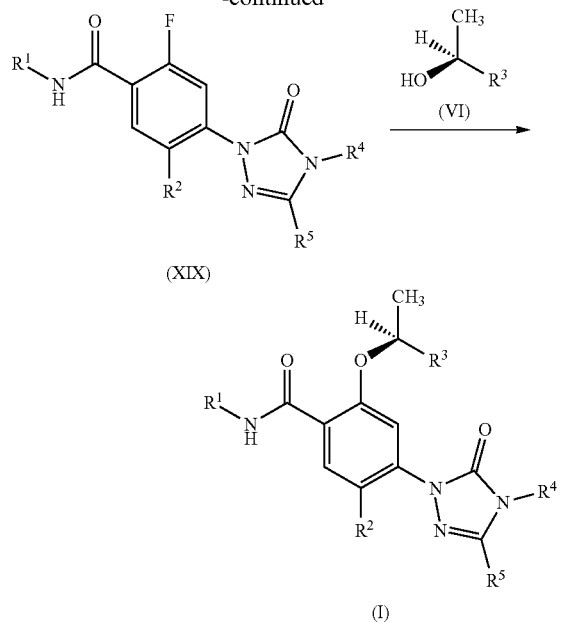

Compounds of general formulae (II), (IV), (VI) and (X) are either commercially available or can be prepared according to procedures available from the public domain, as understandable to the person skilled in the art. Specific examples are described in the Experimental Section.

Amides of general formula (XX) can be prepared by the reaction of the benzoic acids of general formula (II) with amines of general formula (X) by amide coupling.

Suitable coupling reagents for the reaction of benzoic acids of general formula (II) with amines of general formula (X) are for example O-(7-aza-1H-benzotriazol-1-yl)-N,N,N,N'-tetramethyluronium hexafluorophosphate (HATU), dicyclohexylcarbodiimide or a combination of 1H-benzotria-1-ol and 1-ethyl-3-[3-(diemthylaminopropyl]carbodiimide hydrochloride.

Suitable organic bases for the amide coupling of benzoic acids of general formula (II) with amines of general formula (X) are for example 4-(dimethylamino)pyridine, N-ethyl-N,N-diisopropylamine, N-methylpyrollidine, or triethylamine.

Suitable solvents for the for the amide coupling of benzoic acids of general formula (II) with amines of general formula (X) are for example N,N-dimethylformamide, dichloromethane or tetrahydrofuran.

For coupling of the amide bond, other methods which are well known to the person skilled in the art are also suitable, such as a condensation between amine and acid using propanephosphonic acid anhydride (T3P) as coupling reagent, or transformation of benzoic acids of general formula (II) into their respective acid chlorides and subsequent reaction with amines of general formula (X) as described above.

In connection with the invention, formation of the compounds of general formula (XX) were preferrably accomplished by HATU mediated amide coupling of benzoic acids of general formula (II) and amines of general formula (X).

Alternatively, amides of general formula (XX) can be prepared from benzoic acid derivatives of general formula (II) by in situ formation of the corresponding acid chlorides and subsequent reaction with amines of general formula (X).

In situ formation of acid chlorides from benzoic acids of general formula (II) can be accomplished, for example by using oxalyl chloride or thionyl chloride, both reagents used in the presence of catalytic amount of N,N-dimethylformamide.

(XX)+(IV)→(XIX):

The formation of compounds of general formula (XIX) can be accomplished by the reaction of triazolinones of general formula (IV) with amides of general formula (XX) in the presence of a base, such as potassium carbonate. In connection with the method of the invention, the use of 1,8-diazabicyclo[5.4.0]undec-7-ene as organic base in acetonitrile at 80° C. was preferable.

The formation of compounds of general formula (I) can be accomplished by reaction of amides of general formula (XIX) and alcohols of general formula (VI) in the presence of a base. Bases that can be employed for the reaction of amides of general formula (XIX) with alcohols of general formula (VI) are for example sodium hydride, sodium tert-butanolate, potassium tert-butanolate, or cesium carbonate. In connection with the method of the invention, sodium hydride was preferrably used as organic base.

Solvents that can be used for the reactions of amides of general formula (XIX) with alcohols of general formula (VI) are for example tetrahydrofuran, dimethyl sulfoxide and N,N-dimethylformamide. In connection with the method according to the invention N,N-dimethylformamide was preferrably used as solvent.

Reaction temperatures for the reactions of amides of general formula (XIX) with alcohols of general formula (VI) are for example ranging from room temperature to 140° C. In connection with the method of the invention, the reaction of alcohols of general formula (VI) with sodium hydride was preferrably performed at room temperature for 1 h before addition of amides of formula (XIX) and subsequent heating of the reaction mixture to 80° C.

Suitable reaction times for the reaction of amides of general formula (XIX) with alcohols of general formula (VI) are ranging from 3 h to several days.

Synthetic Route 5

Scheme 5: Alternative route for the preparation of compounds of general formula (VIII) in which $R^2$, $R^3$, $R^4$ and $R^5$ have the meaning as given for general formula (I), supra. and A represents a chlorine, bromine or iodine atom.

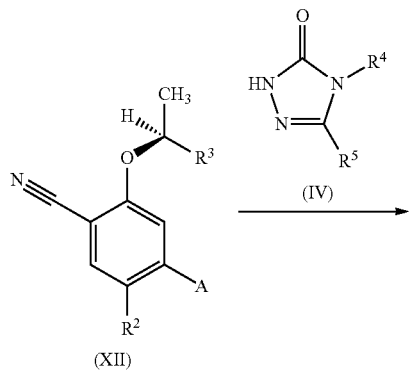

(XII)

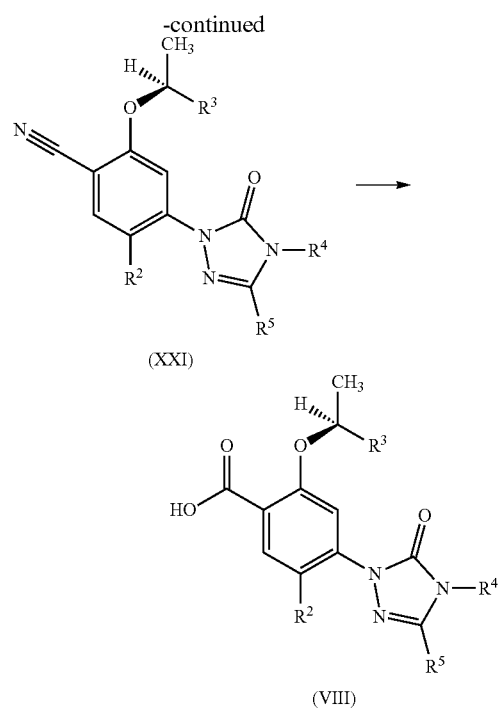

(XXI)

(VIII)

An alternative synthesis of compounds of formula (VIII) is described in scheme 5.

Compounds of general formula (XXI) can be prepared from halides of general formula (XII) and from triazolones of general formula (IV) using transition metals as catalysts.

The formation of benzoates of general formula (VIII) can be accomplished by hydrolysis of nitriles of general formula XXI using strong acids or bases. In connection with the method of the invention, the use of sulphuric acid, acetic acid and water at 120° C. was preferable.

The synthesis of compounds of general formula (XII) and the synthesis of compounds of general formula (I) from compounds of general formula (VIII) is described above.

The order of transformations exemplified in these schemes is therefore not intended to be limiting. In addition, interconversion of any of the substituents, $R^1$, $R^2$, $R^3$, $R^4$ or $R^5$ can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in *Protective Groups in Organic Synthesis*, $3^{rd}$ edition, Wiley 1999). Specific examples are described in the subsequent paragraphs.

The resulting compounds of general formula (I) are optionally converted with corresponding (i) solvents and/or (ii) bases or acids to their solvates, salts and/or solvates of the salts, in which $R^1$, $R^2$, $R^3$, $R^4$ and $R^5$ have the meaning as given for general formula (I), supra.

In accordance with another aspect, the present invention provides methods of preparing compounds of general formula (I) as defined supra, said methods comprising the step of allowing an intermediate compound of general formula (VIII):

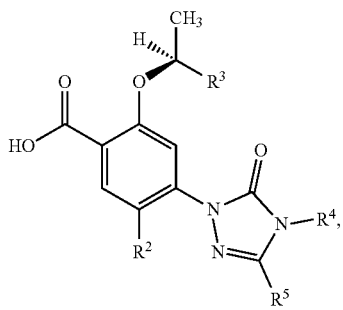

(VIII)

in which $R^2$, $R^3$, $R^4$ and $R^5$ are as defined for the compound of general formula (I) as defined supra,
to react with a compound of general formula (X):

$$R^1\text{—NH}_2 \quad (X),$$

in which $R^1$ is as defined for the compound of general formula (I) as defined supra, thereby giving a compound of general formula (I):

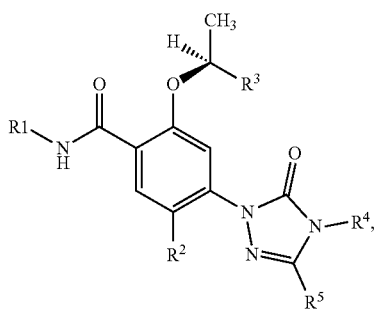

(I)

in which $R^1$, $R^2$, $R^3$, $R^4$ and $R^5$ are as defined supra.

In accordance with certain embodiments, the present invention provides methods of preparing compounds of general formula (I) as defined supra, said methods comprising the step of allowing an intermediate compound of general formula (IX):

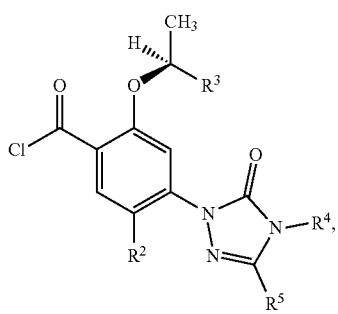

(IX)

in which $R^2$, $R^3$, $R^4$ and $R^5$ are as defined for the compound of general formula (I) as defined supra,
to react with a compound of general formula (X):

$$R^1\text{—NH}_2 \quad (X),$$

in which $R^1$ is as defined for the compound of general formula (I) as defined supra, thereby giving a compound of general formula (I):

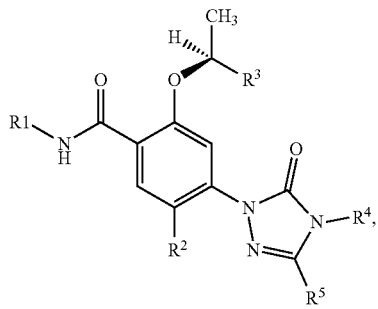

(I)

in which $R^1$, $R^2$, $R^3$, $R^4$ and $R^5$ are as defined supra.

In accordance with further embodiments, the present invention provides methods of preparing compounds of general formula (I) as defined supra, said methods comprising the step of allowing an intermediate compound of general formula (XV):

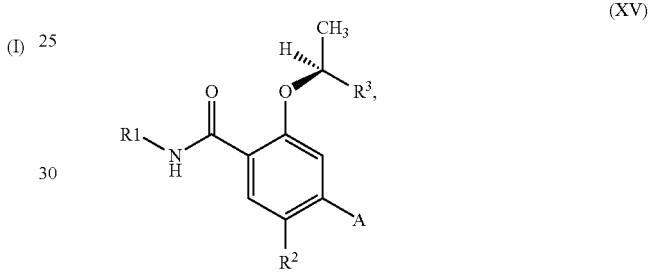

(XV)

in which $R^1$, $R^2$ and $R^3$ are as defined for the compound of general formula (I) as defined supra, and A represents a chlorine, bromine or iodine atom,
to react with a compound of general formula (IV):

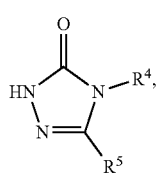

(IV)

in which $R^4$ and $R^5$ are as defined for the compound of general formula (I) as defined supra, thereby giving a compound of general formula (I):

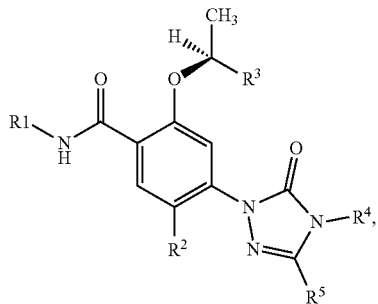

(I)

in which $R^1$, $R^2$, $R^3$, $R^4$ and $R^5$ are as defined supra.

In accordance with other embodiments, the present invention provides methods of preparing compounds of general formula (I) as defined supra, said methods comprising the step of allowing an intermediate compound of general formula (XVIII):

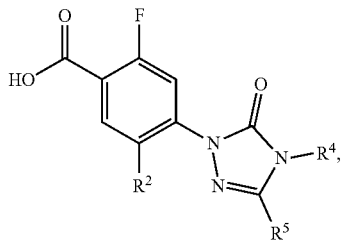

(XVIII)

in which $R^2$, $R^4$ and $R^5$ are as defined for the compound of general formula (I) as defined supra, to react with a compound of general formula (X):

 (X), in which $R^1$ is as defined for the compound of general formula (I) as defined supra, thereby giving a compound of general formula (XIX):

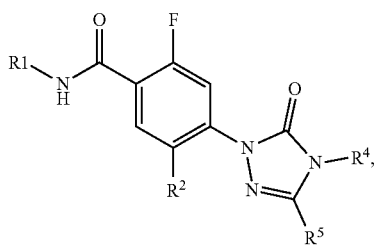

(XIX)

in which $R^1$, $R^2$, $R^4$ and $R^5$ are as defined supra.

In accordance with other embodiments, the present invention provides methods of preparing compounds of general formula (I) as defined supra, said methods comprising the step of allowing an intermediate compound of general formula (XX):

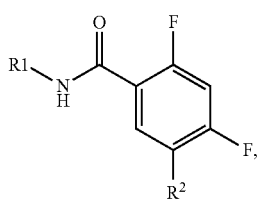

(XX)

in which $R^1$ and $R^2$ are as defined for the compound of general formula (I) as defined supra, to react with a compound of general formula (IV):

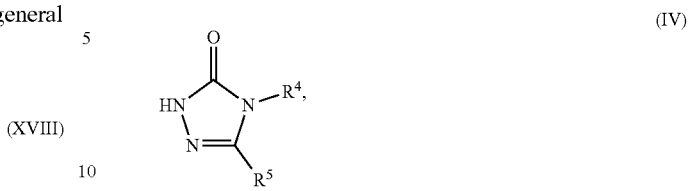

(IV)

in which $R^4$ and $R^5$ are as defined for the compound of general formula (I) as defined supra, thereby giving a compound of general formula (XIX):

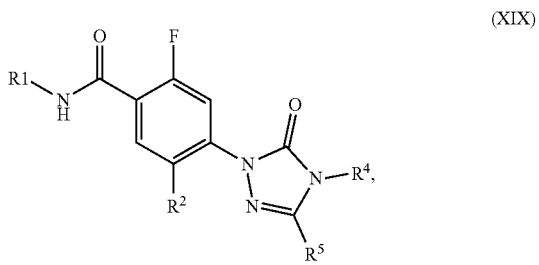

(XIX)

in which $R^1$, $R^2$, $R^4$ and $R^5$ are as defined for the compound of general formula (I) as defined supra.

In accordance with further embodiments, the present invention provides methods of preparing compounds of general formula (I) as defined supra, said methods comprising the step of allowing an intermediate compound of general formula (XIX):

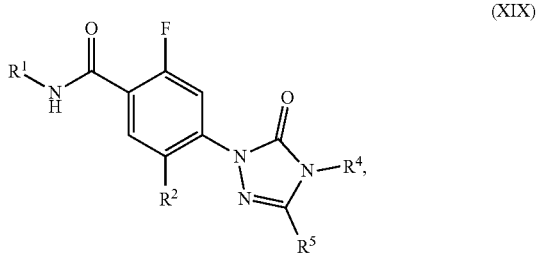

(XIX)

in which $R^1$, $R^2$, $R^4$ and $R^5$ are as defined for the compound of general formula (I) as defined supra, to react with a compound of general formula (VI):

(VI)

in which $R^3$ is as defined for the compound of general formula (I) as defined supra, thereby giving a compound of general formula (I):

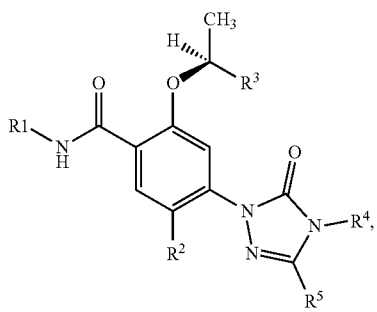
(I)

in which $R^1$, $R^2$, $R^3$, $R^4$ and $R^5$ are as defined supra.

In accordance with another aspect, the present invention provides methods of preparing compounds of general formula (I) as defined supra,
said methods comprise the step of allowing an intermediate compound of general formula (VIII):

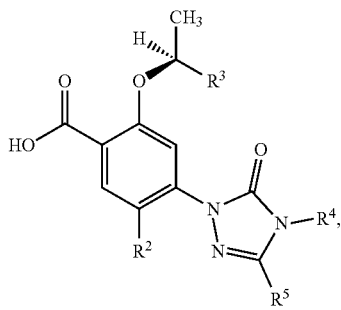
(VIII)

in which $R^2$, $R^3$, $R^4$ and $R^5$ are as defined for the compound of general formula (I) as defined supra,
to react with a compound of general formula (X):

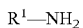 (X), in which $R^1$ is as defined for the compound of general formula (I) as defined supra,
thereby giving a compound of general formula (I):

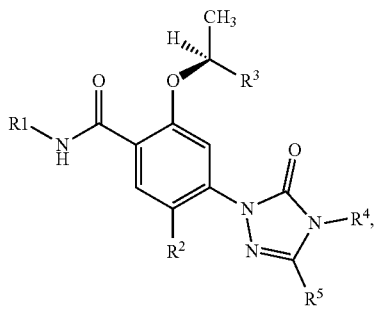
(I)

in which $R^1$, $R^2$, $R^3$, $R^4$ and $R^5$ are as defined supra,
then optionally converting said compound into solvates, salts and/or solvates of such salts using the corresponding (i) solvents and/or (ii) bases or acids.

In accordance with certain embodiments, the present invention provides methods of preparing compounds of general formula (I) as defined supra, said methods comprising the step of allowing an intermediate compound of general formula (IX):

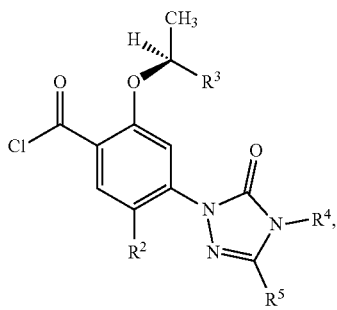
(IX)

in which $R^2$, $R^3$, $R^4$ and $R^5$ are as defined for the compound of general formula (I) as defined supra,
to react with a compound of general formula (X):

 (X), in which $R^1$ is as defined for the compound of general formula (I) as defined supra,
thereby giving a compound of general formula (I):

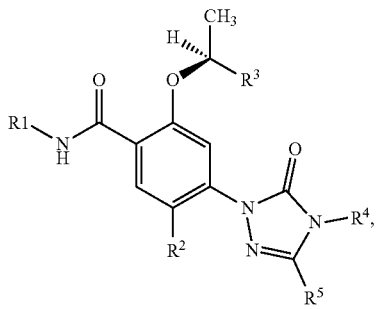
(I)

in which $R^1$, $R^2$, $R^3$, $R^4$ and $R^5$ are as defined supra,
then optionally converting said compound into solvates, salts and/or solvates of such salts using the corresponding (i) solvents and/or (ii) bases or acids.

In accordance with further embodiments, the present invention provides methods of preparing compounds of general formula (I) as defined supra, said methods comprising the step of allowing an intermediate compound of general formula (XV)

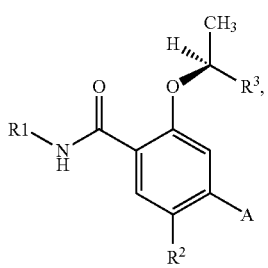
(XV)

in which R¹, R² and R³ are as defined for the compound of general formula (I) as defined supra, and A represents a chlorine, bromine or iodine atom,
to react with a compound of general formula (IV):

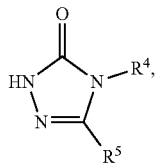
(IV)

in which R⁴ and R⁵ are as defined for the compound of general formula (I) as defined supra,
thereby giving a compound of general formula (I):

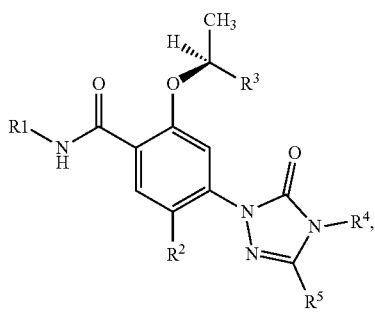
(I)

in which R¹, R², R³, R⁴ and R⁵ are as defined supra,
then optionally converting said compound into solvates, salts and/or solvates of such salts using the corresponding (i) solvents and/or (ii) bases or acids.

In accordance with other embodiments, the present invention provides methods of preparing compounds of general formula (I) as defined supra, said methods comprising the step of allowing an intermediate compound of general formula (XIX)

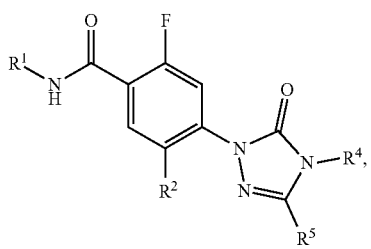
(XIX)

in which R¹, R², R⁴ and R⁵ are as defined for the compound of general formula (I) as defined supra,
to react with a compound of general formula (VI):

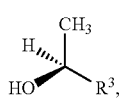
(VI)

in which R³ is as defined for the compound of general formula (I) as defined supra,
thereby giving a compound of general formula (I):

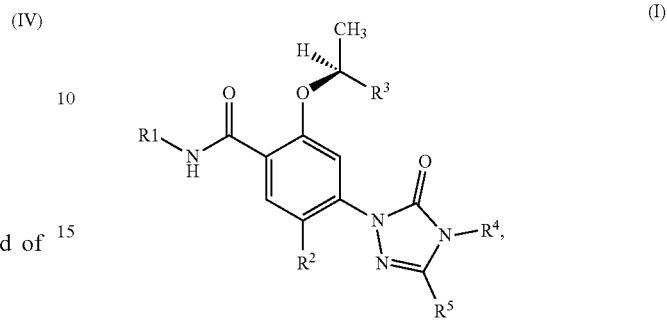
(I)

in which R¹, R², R³, R⁴ and R⁵ are as defined supra,
then optionally converting said compound into solvates, salts and/or solvates of such salts using the corresponding (i) solvents and/or (ii) bases or acids.

The present invention provides methods of preparing compounds of the present invention of general formula (I), said methods comprising the steps as described in the Experimental Section herein.

In accordance with a further aspect, the present invention provides intermediate compounds which are useful for the preparation of the compounds of general formula (I), supra.

Particularly, the invention provides the intermediate compounds of general formula (IV)

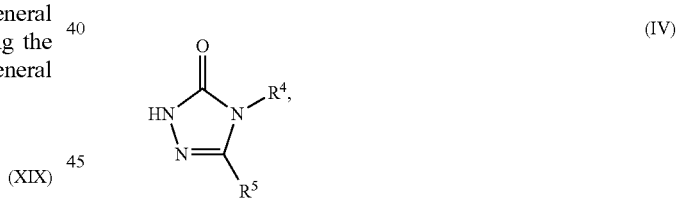
(IV)

in which R⁴ and R⁵ are as defined for the compound of general formula (I) supra.

Particularly, the invention provides the intermediate compounds of general formula (VI)

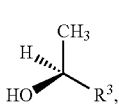
(VI)

in which R³ is as defined for the compound of general formula (I) supra.

Particularly, the invention provides the intermediate compounds of general formula (VIII)

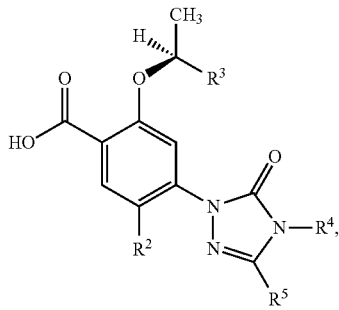

(VIII)

in which $R^2$, $R^3$, $R^4$ and $R^5$ are as defined for the compound of general formula (I) supra.

Particularly, the inventions provides the intermediate compounds of general formula (IX)

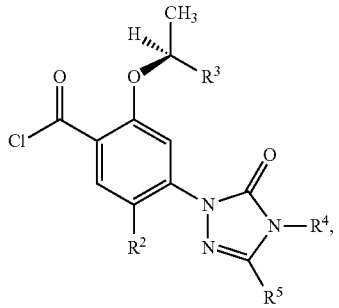

(IX)

in which $R^2$, $R^3$, $R^4$ and $R^5$ are as defined for the compound of general formula (I) supra.

Particularly, the inventions provides the intermediate compounds of general formula (XV)

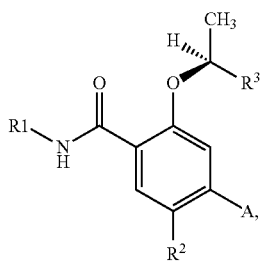

(XV)

in which $R^1$, $R^2$ and $R^3$ are as defined for the compound of general formula (I) supra, and A represents a chlorine, bromine or iodine atom.

Particularly, the inventions provides the intermediate compounds of general formula (XVIII):

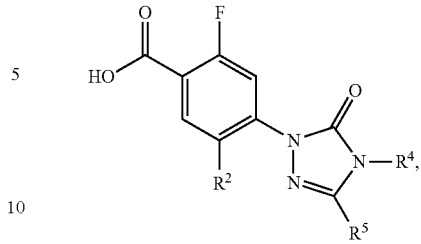

(XVIII)

in which $R^2$, $R^4$ and $R^5$ are as defined for the compound of general formula (I) supra.

Particularly, the invention provides the intermediate compounds of general formula (XIX)

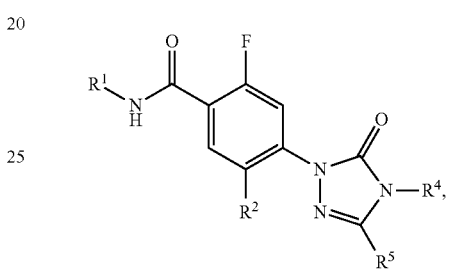

(XIX)

in which $R^1$, $R^2$, $R^4$ and $R^5$ are as defined for the compound of general formula (I) supra.

Particularly, the invention provides the intermediate compounds of general formula (XXI)

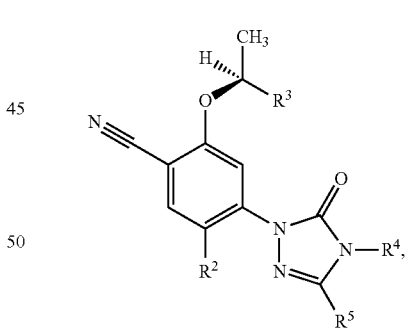

(XXI)

in which $R^2$, $R^3$, $R^4$ and $R^5$ are as defined for the compound of general formula (I) supra.

In accordance with another aspect, the present invention provides the use of said intermediate compounds for the preparation of a compound of general formula (I) as defined supra.

Particularly, the invention provides the use of intermediate compounds of general formula (IV):

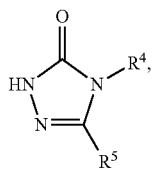
(IV)

in which R⁴ and R⁵ are as defined for the compound of general formula (I) supra, for the preparation of a compound of general formula (I) as defined supra.

Particularly, the invention provides the use of intermediate compounds of general formula (VI):

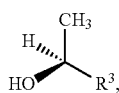
(VI)

in which R³ is as defined for the compound of general formula (I) supra, for the preparation of a compound of general formula (I) as defined supra.

Particularly, the invention provides the use of intermediate compounds of general formula (VIII):

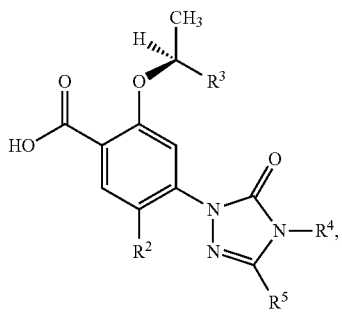
(VIII)

in which R², R³, R⁴ and R⁵ are as defined for the compound of general formula (I) supra, for the preparation of a compound of general formula (I) as defined supra.

Particularly, the invention provides the use of intermediate compounds of general formula (IX):

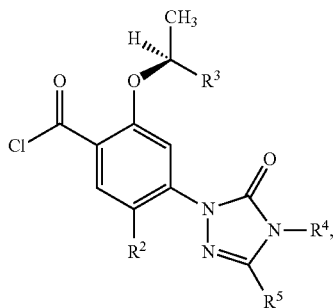
(IX)

in which R², R³, R⁴ and R⁵ are as defined for the compound of general formula (I) supra, for the preparation of a compound of general formula (I) as defined supra.

Particularly, the invention provides the use of intermediate compounds of general formula (X):

(X), in which R¹ is as defined for the compound of general formula (I) as defined supra, for the preparation of a compound of general formula (I) as defined supra.

Particularly, the invention provides the use of intermediate compounds of general formula (XV):

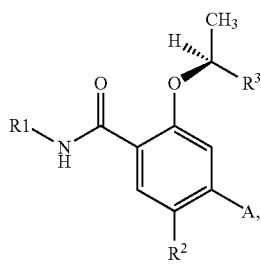
(XV)

in which R¹, R² and R³ are as defined for the compound of general formula (I) supra, and A represents a chlorine, bromine or iodine atom, for the preparation of a compound of general formula (I) as defined supra.

Particularly, the invention provides the use of intermediate compounds of general formula (XVIII):

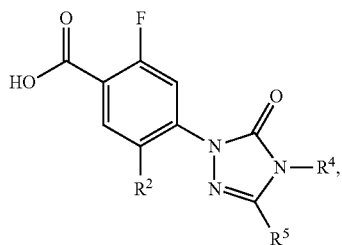
(XVIII)

in which R², R⁴ and R⁵ are as defined for the compound of general formula (I) supra, for the preparation of a compound of general formula (I) as defined supra.

Particularly, the invention provides the use of intermediate compounds of general formula (XIX):

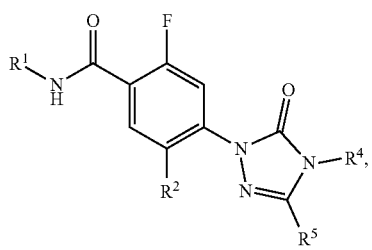
(XIX)

in which R¹, R², R⁴ and R⁵ are as defined for the compound of general formula (I) supra, for the preparation of a compound of general formula (I) as defined supra.

Particularly, the invention provides the use of intermediate compounds of general formula (XX):

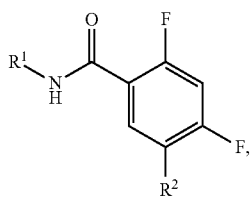

(XX)

in which R¹ and R² are as defined for the compound of general formula (I) as defined supra, for the preparation of a compound of general formula (I) as defined supra.

Particularly, the invention provides the use of intermediate compounds of general formula (XXI):

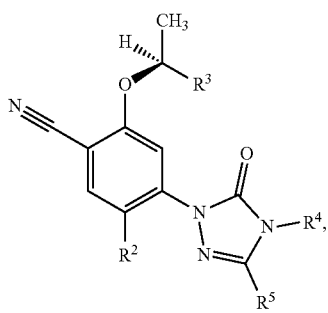

(XXI)

in which R², R³, R⁴ and R⁵ are as defined for the compound of general formula (I) supra, for the preparation of a compound of general formula (I) as defined supra.

The present invention provides the use of the intermediate compounds of general formula (IV), (VI), (VIII), (IX), (X), (XV), (XVIII), (XIX) and (XXI) which are disclosed in the Example Section of this text, infra.

The present invention provides the intermediate compounds which are disclosed in the Example Section of this text, infra.

The present invention provides the intermediate compounds of general formula (IV), (VI), (VIII), (IX), (X), (XV), (XVIII), (XIX) and (XXI) which are disclosed in the Example Section of this text, infra.

The present invention provides any sub-combination within any embodiment or aspect of the present invention of intermediate compounds of general formula (IV), (VI), (VIII), (IX), (X), (XV), (XVIII), (XIX) and (XXI), supra.

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

Compounds of general formula (I) of the present invention demonstrate a valuable pharmacological spectrum of action, which could not have been predicted. Compounds of the present invention have surprisingly been found to effectively inhibit DHODH and it is possible therefore that said compounds be used for the treatment or prophylaxis of diseases, preferably hyperproliferative and/or inflammatory disorders in humans and animals.

Compounds of the present invention can be utilized to inhibit the activity of DHODH. This method comprises administering to a mammal in need thereof, including a human, an effective amount of a compound of general formula (I) of the present invention, or a pharmaceutically acceptable salt, polymorph, metabolite, hydrate, solvate or ester thereof, for the treatment of hyperproliferative and/or inflammatory disorders.

Another aspect of the invention is a method of inhibiting proliferation of a cell, comprising contacting the cell with a compound of formula (I).

Hyperproliferative disorders include, but are not limited to, for example: psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include sarcomas, and haematological malignancies including but not limited to leukemias, lymphomas, multiple myeolomas.

One aspect of the invention is the use of the compounds of formula (I) for the treatment of cancer, the compounds of formula (I) for use in the treatment of cancer as well as a method of treatment of cancer diseases comprising administering a specific amount of a compound of formula (I).

Examples of breast cancers include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumour.

Tumours of the male reproductive organs include, but are not limited to, prostate and testicular cancer.

Tumours of the female reproductive organs include, but are not limited to, endometrial, cervical, ovarian, vaginal, and vulvar cancer, as well as sarcoma of the uterus.

Tumours of the digestive tract include, but are not limited to, anal, colon, colorectal, oesophageal, gallbladder, gastric, pancreatic, rectal, small-intestine, and salivary gland cancers.

Tumours of the urinary tract include, but are not limited to, bladder, penile, kidney, renal pelvis, ureter, urethral and human papillary renal cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, oropharyngeal cancer, lip and oral cavity cancer and squamous cell.

Lymphomas include, but are not limited to, AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell lymphoma DLBCL, double-hit lymphoma and double-expressor lymphoma; anaplastic large cell lymphoma, B-cell lymphoma, cutaneous T-cell lymphoma, Burkitt's lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma and Sezary syndrome.

Sarcomas include, but are not limited to, sarcoma of the soft tissue, gliosarcoma, osteosarcoma, malignant fibrous histiocytoma, lymphosarcoma, and rhabdomyosarcoma.

Leukemias include, but are not limited to acute lymphoblastic leukemia, acute myeloid leukemia, (acute) T-cell leukemia, acute lymphoblastic leukemia, acute lymphocytic leukemia (ALL), acute monocytic leukemia (AML), acute promyelocytic leukemia (APL), bisphenotypic B myelomonocytic leukemia, chronic lymphocytic leukemia, chronic myelogenous leukemia, chronic myeloid leukemia (CML), chronic myelomonocytic leukemia (CMML), large granular lymphocytic leukemia, plasma cell leukemia, and also myelodysplastic syndrome (MDS), which can develop into an acute myeloid leukemia.

Inhibition of DHODH can also lead to differentiation of tumor initiating cells in hematological and solid cancers, especially leukemias.

The present invention also provides methods of treating angiogenic disorders including diseases associated with excessive and/or abnormal angiogenesis.

Inappropriate and ectopic expression of angiogenesis can be deleterious to an organism. A number of pathological conditions are associated with the growth of extraneous blood vessels. These include, for example, diabetic retinopathy, ischemic retinal-vein occlusion, and retinopathy of prematurity [Aiello et al., New Engl. J. Med., 1994, 331, 1480; Peer et al., Lab. Invest., 1995, 72, 638], age-related macular degeneration (AMD) [Lopez et al., Invest. Opthalmol. Vis. Sci., 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of general formula (I) of the present invention can be utilized to treat and/or prevent any of the aforementioned angiogenesis disorders, for example by inhibiting and/or reducing blood vessel formation; by inhibiting, blocking, reducing, decreasing, etc. endothelial cell proliferation, or other types involved in angiogenesis, as well as causing cell death or apoptosis of such cell types.

Another aspect of the invention is a method for controlling cancer (e.g., through treatment, prophylaxis, etc.) in a subject (e.g., human, rat, etc.) by administering an effective amount of at least one compound of general formula (I), or a pharmaceutically acceptable salt, polymorph, metabolite, hydrate, solvate or ester thereof to the subject.

In some embodiments, the subject may be administered a medicament, comprising at least one compound of general formula (I) of the present invention and one or more pharmaceutically acceptable carriers, excipients and/or diluents.

In some embodiments, the method of treatment and/or prophylaxis of a hyperproliferative disorder in a subject may comprise administering to the subject an effective amount of a compound of general formula (I). The hyperproliferative disorder may be, for example, cancer (the cancer types as defined supra, more particularly leukemia, lymphoma, solid tumors, such as e.g. colorectal carcinoma, lung cancer, ovarian cancer, pancreatic cancer, renal cancer, even more particularly e.g. acute myeloid leukemia, colorectal carcinoma, leukemia, lung cancer, lymphoma, multiple myeloma, ovarian cancer, pancreatic cancer and renal cell carcinoma).

In some embodiments, the method of treatment and/or prophylaxis of a hyperproliferative disorder in a subject may comprise administering to the subject an effective amount of a compound of general formula (I). The hyperproliferative disorder may be, for example, cancer (e.g., lung cancer, acute myeloid leukemia, acute promyelocytic leukemia (APL), mixed-lineage leukemia (MLL), chronic myeloid leukemia (CML), myelodysplastic syndrome (MDS), lymphoma, glioblastoma, prostate cancer, or any other cancer indication as defined herein).

In another aspect, the present invention provides the use of a compound of general formula (I) of the present invention, or a pharmaceutically acceptable salt, polymorph, metabolite, hydrate, solvate or ester thereof, for the preparation of a medicament for the treatment or prophylaxis of a disease.

In another aspect, the present invention provides the use of a compound of general formula (I) of the present invention, or a pharmaceutically acceptable salt, polymorph, metabolite, hydrate, solvate or ester thereof, for the treatment of cancer, which cancer is selected from acute myeloid leukemia, colorectal carcinoma, leukemia, lung cancer, lymphoma, multiple myeloma, ovarian cancer, pancreatic cancer and renal cell carcinoma.

In another aspect the invention provides methods of treatment of cancer comprising administering a compound of general formula (I) or a pharmaceutically acceptable salt, polymorph, metabolite, hydrate, solvate or ester thereof, where the cancer is selected from acute myeloid leukemia, colorectal carcinoma, leukemia, lung cancer, lymphoma, multiple myeloma, ovarian cancer, pancreatic cancer and renal cell carcinoma.

In another aspect, the present invention provides the use of a compound of general formula (I) of the present invention, or a pharmaceutically acceptable salt, polymorph, metabolite, hydrate, solvate or ester thereof, for the treatment of cancer, which cancer is selected from acute myeloid leukemia, breast cancer, colorectal carcinoma, gastric cancer, gliosarcoma, head & neck cancer, hepatocellular carcinoma, leukemia, lung cancer, lymphoma, multiple myeloma, neuroblastoma, ovarian cancer, pancreatic cancer, prostate cancer, renal cell carcinoma, and sarcoma.

In another aspect the invention provides methods for the treatment of cancer comprising administering a compound of general formula (I) or a pharmaceutically acceptable salt, polymorph, metabolite, hydrate, solvate or ester thereof, where the cancer is selected from acute myeloid leukemia, breast cancer, colorectal carcinoma, gastric cancer, gliosarcoma, head & neck cancer, hepatocellular carcinoma, leukemia, lung cancer, lymphoma, multiple myeloma, neuroblastoma, ovarian cancer, pancreatic cancer, prostate cancer, renal cell carcinoma, and sarcoma.

In another aspect, the present invention provides the use of a compound of general formula (I) of the present invention, or a pharmaceutically acceptable salt, polymorph, metabolite, hydrate, solvate or ester thereof, for the treatment of cancer, which cancer is selected from acute T-cell lymphoblastic leukemia, acute promyelocytic leukemia, acute myeloid leukemia, anaplastic large cell lymphoma, biphenotypic B myelomonocytic leukemia, B-cell lymphoma, breast cancer, Burkitt lymphoma, chronic myeloid leukemia, colorectal carcinoma, gastric cancer, gliosarcoma, head & neck cancer, hepatocellular carcinoma, lung cancer, multiple myeloma, neuroblastoma, ovarian cancer, pancreatic cancer, prostate cancer, renal cell carcinoma, sarcoma and T-cell lymphoma. In another aspect the invention provides methods of treatment of cancer comprising administering a compound of general formula (I) or a pharmaceutically acceptable salt, polymorph, metabolite, hydrate, solvate or ester thereof, where the cancer is selected from acute T-cell lymphoblastic leukemia, acute promyelocytic leukemia, acute myeloid leukemia, anaplastic large cell lymphoma, biphenotypic B myelomonocytic leukemia, B-cell lymphoma, breast cancer, Burkitt lymphoma, chronic myeloid leukemia, colorectal carcinoma, gastric cancer, gliosarcoma, head & neck cancer, hepatocellular carcinoma, lung cancer, multiple myeloma, neuroblastoma, ovarian cancer, pancreatic cancer, prostate cancer, renal cell carcinoma, sarcoma and T-cell lymphoma.

In another aspect, the present invention provides methods of treating cancer, which cancer is selected from lung cancer, leukemia, acute myeloid leukemia, gliosarcoma, colorectal carcinoma, head & neck cancer, hepatocellular carcinoma, multiple myeloma, lymphoma, breast cancer, neuroblastoma, ovarian cancer, gastric cancer, pancreatic cancer, prostate cancer, renal cell carcinoma, and sarcoma.

In another aspect, the present invention provides the use of a compound of general formula (I) of the present invention, or a pharmaceutically acceptable salt, polymorph, metabolite, hydrate, solvate or ester thereof, for the treatment of cancer, which cancer is selected from lung cancer, leukemia, acute myeloid leukemia, gliosarcoma, colorectal carcinoma, head & neck cancer, hepatocellular carcinoma, multiple myeloma, lymphoma, breast cancer, neuroblastoma, ovarian cancer, gastric cancer, pancreatic cancer, prostate cancer, renal cell carcinoma, and sarcoma.

In another aspect, the present invention provides the use of a compound of general formula (I) of the present invention, or a pharmaceutically acceptable salt, polymorph, metabolite, hydrate, solvate or ester thereof, for the treatment of cancer, which cancer is selected from leukemias, lymphomas, sarcomas and solid tumors.

In another aspect the invention provides methods for the treatment of cancer comprising administering a compound of general formula (I) or a pharmaceutically acceptable salt, polymorph, metabolite, hydrate, solvate or ester thereof, wherein the cancer is selected from leukemias, lymphomas, sarcomas and solid tumors.

In another aspect, the present invention provides methods for use of a compound of general formula (I) of the present invention, or a pharmaceutically acceptable salt, polymorph, metabolite, hydrate, solvate or ester thereof, for the treatment of cancer and methods of treating cancer, which cancer is selected from colorectal cancer, leukemia and lymphoma. In another aspect the invention provides methods for the treatment of cancer comprising administering a compound of general formula (I) or a pharmaceutically acceptable salt, polymorph, metabolite, hydrate, solvate or ester thereof, wherein the cancer is selected from colorectal cancer, leukemia and lymphoma.

In another aspect, the present invention provides the use of a compound of general formula (I) of the present invention, or a pharmaceutically acceptable salt, polymorph, metabolite, hydrate, solvate or ester thereof, for the treatment of cancer and methods of treating cancer, which cancer is selected from colorectal cancer, leukemia and lymphoma. In another aspect the invention provides methods of treatment of cancer comprising administering a compound of general formula (I) or a pharmaceutically acceptable salt, polymorph, metabolite, hydrate, solvate or ester thereof, wherein the cancer is selected from colorectal cancer, leukemia and lymphoma.

In another aspect, the present invention provides the use of a compound of general formula (I) of the present invention, or a pharmaceutically acceptable salt, polymorph, metabolite, hydrate, solvate or ester thereof, for the treatment of one or more cancer types and methods of treating one or more cancer types, where cancer is selected from ALL, AML, APL, CMML, DLBCL, MDS, MCL, T-NHL, colorectal cancer, melanoma and ovarian cancer.

In another aspect the invention provides methods for the treatment of cancer comprising administering a compound of general formula (I) or a pharmaceutically acceptable salt, polymorph, metabolite, hydrate, solvate or ester thereof, where the cancer is selected from ALL, AML, APL, CMML, DLBCL, MDS, MCL, T-NHL, colorectal cancer, melanoma and ovarian cancer.

In another aspect, the present invention provides the use of a compound of general formula (I) of the present invention, or a pharmaceutically acceptable salt, polymorph, metabolite, hydrate, solvate or ester thereof, for the treatment of one or more cancer types, where cancer is selected from leukemias including but not limited to acute lymphoblastic leukemia (ALL), acute myeloid leukemia (AML), acute T-cell leukemia, acute monocytic leukemia, acute promyelocytic leukemia (APL), bisphenotypic B myelomonocytic leukemia, chronic myelogenous leukemia, chronic myeloid leukemia, chronic myelomonocytic leukemia (CMML), large granular lymphocytic leukemia, and myelodysplastic syndrome (MDS), which can develop into an acute myeloid leukemia, lymphomas including but not limited to AIDS-related lymphoma, chronic lymphocytic lymphoma, non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma and double-expressor lymphoma; anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma;

sarcomas including but not limited to sarcoma of the soft tissue, gliosarcoma, osteosarcoma, malignant fibrous histiocytoma, lymphosarcoma, and rhabdomyosarcoma;

and solid tumors including but not limited to breast cancer, colorectal carcinoma, gastric cancer, gliosarcoma, head & neck cancer, hepatocellular carcinoma, lung cancer, multiple myeloma, neuroblastoma, ovarian cancer, pancreatic cancer, prostate cancer, renal cell carcinoma and sarcoma.

In another aspect the invention provides method for the treatment of cancer comprising administering an effective amount of a compound of general formula (I) where the cancer is selected from leukemias including but not limited to acute lymphoblastic leukemia (ALL), acute myeloid leukemia (AML), acute T-cell leukemia, acute monocytic leukemia, acute promyelocytic leukemia, bisphenotypic B myelomonocytic leukemia, chronic myelogenous leukemia, chronic myeloid leukemia, chronic myelomonocytic leukemia (CMML), large granular lymphocytic leukemia, and myelodysplastic syndrome (MDS), which can develop into an acute myeloid leukemia, lymphomas including but not limited to AIDS-related lymphoma, chronic lymphocytic lymphoma, non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma and double-expressor lymphoma; anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma;

sarcomas including but not limited to sarcoma of the soft tissue, gliosarcoma, osteosarcoma, malignant fibrous histiocytoma, lymphosarcoma, and rhabdomyosarcoma; and solid tumors including but not limited to breast cancer, colorectal carcinoma, gastric cancer, gliosarcoma, head & neck cancer, hepatocellular carcinoma, lung cancer, multiple myeloma, neuroblastoma, ovarian cancer, pancreatic cancer, prostate cancer, renal cell carcinoma and sarcoma.

In another aspect, the present invention provides a method for inhibiting cell proliferation or viability in a cancer cell, the method comprising contacting the cell with any compound of any claim, aspect or embodiment disclosed herein, thereby inhibiting cell proliferation or viability.

In a further aspect the present invention provides a method for inhibiting Dihydroorotate Dehydrogenase (DHODH) enzymatic activity, the method comprising contacting DHODH with any compound of any claim, aspect or embodiment disclosed herein, thereby inhibiting DHODH enzymatic activity.

In yet a further aspect the present invention provides a method for treating lymphoma in a subject, the method comprising administering to the subject an effective amount of any compound of any claim, aspect or embodiment disclosed herein, thereby treating the lymphoma.

In yet a further aspect the present invention provides a method for treating lymphoma mentioned above in a subject, wherein the lymphoma is selected from the group AIDS-related lymphoma, chronic lymphocytic lymphoma (CLL), non-Hodgkin's lymphoma (NHL), T-non-Hodgkin lymphoma (T-NHL), subtypes of NHL such as Diffuse Large Cell Lymphoma (DLBCL), activated B-cell DLBCL, germinal center B-cell DLBCL, double-hit lymphoma and double-expressor lymphoma; anaplastic large cell lymphoma, B-cell lymphoma, cutaneous T-cell lymphoma, Burkitt lymphoma, follicular lymphoma, hairy cell lymphoma, Hodgkin's disease, mantle cell lymphoma (MCL), lymphoma of the central nervous system, small lymphocytic lymphoma and chronic lymphocytic lymphoma.

In another aspect, the present invention provides a method for treating leukemia in a subject, the method comprising administering to the subject an effective amount of any compound of any claim, aspect or embodiment disclosed herein, thereby treating the leukemia.

In yet a further aspect the present invention provides a method for treating leukemia mentioned above, wherein the leukemia is selected from the group acute lymphoblastic leukemia, acute myeloid leukemia, (acute) T-cell leukemia, acute lymphoblastic leukemia, acute lymphocytic leukemia, acute monocytic leukemia, acute promyelocytic leukemia, bisphenotypic B myelomonocytic leukemia, chronic lymphocytic leukemia, chronic myelogenous leukemia, chronic myeloid leukemia, chronic myelomonocytic leukemia, large granular lymphocytic leukemia, plasma cell leukemia, and also myelodysplastic syndrome, which can develop into an acute myeloid leukemia.

In another aspect, the present invention provides methods for treating or preventing a disease or condition associated with inflammation, a metabolic disorder, infection or an immune disease or condition by administering to a subject having such condition or disease, a therapeutically effective amount of a compound or composition of the invention.

In further embodiments, diseases or conditions, including chronic diseases, of humans or other species can be treated or prevented by inhibition of DHODH. These diseases or conditions include (1) inflammatory or allergic diseases such as systemic anaphylaxis and hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis and urticaria, (5) vasculitis, (6) spondyloarthropathies, (7) scleroderma, (8) asthma and respiratory allergic diseases such as allergic asthma, allergic rhinitis, allergic conjunctivitis, hypersensitivity lung diseases and the like, and (9) autoimmune diseases, such as arthritis (including rheumatoid and psoriatic), systemic lupus erythematosus, type I diabetes, glomerulonephritis and the like, (10) graft rejection (including allograft rejection and graft-v-host disease), (11) other diseases in which undesired inflammatory responses are to be inhibited, e.g., atherosclerosis, myositis, neurological disorders such as stroke, ischemic reperfusion injury, traumatic brain injury and closed-head injuries, neurodegenerative diseases (e.g., Parkinson's disease), multiple sclerosis, Alzheimer's disease, encephalitis, meningitis, osteoporosis, gout, hepatitis, nephritis, gall bladder disease, sepsis, sarcoidosis, conjunctivitis, otitis, chronic obstructive pulmonary disease, sinusitis and Behcet's syndrome, and (12) immune diseases or conditions.

In another aspect, the present invention provides methods for treating or preventing viral infections in a subject, the methods comprising administering to a subject having or at risk of developing a viral infection a therapeutically effective amount of a compound of the invention.

In yet another aspect, the present invention provides methods of treating or preventing Malaria, the method comprising administering to a subject having or at risk of developing Malaria a therapeutically effective amount of a compound of the invention.

These disorders have been well characterized in humans, but also exist with a similar etiology in other mammals, and can be treated by administering pharmaceutical compositions of the present invention.

If it is stated "preventing or treating" or "treatment or prophylaxis" or the like, treating/treatment is preferred.

The term "treating" or "treatment" as stated throughout this document is used conventionally, for example the management or care of a subject for the purpose of combating, alleviating, reducing, relieving, improving the condition of a disease or disorder, such as a carcinoma.

The compounds of the present invention can be used in particular in therapy and prevention, i.e. prophylaxis, of tumour growth and metastases, especially in solid tumours of all indications and stages with or without pre-treatment of the tumour growth.

Generally, the use of chemotherapeutic agents and/or anti-cancer agents in combination with a compound or pharmaceutical composition of the present invention will serve to:
1. yield better efficacy in reducing the growth of a tumour or even eliminate the tumour as compared to administration of either agent alone,
2. provide for the administration of lesser amounts of the administered chemotherapeutic agents,
3. provide for a chemotherapeutic treatment that is well tolerated in the patient with fewer deleterious pharmacological complications than observed with single agent chemotherapies and certain other combined therapies,
4. provide for treating a broader spectrum of different cancer types in mammals, especially humans,
5. provide for a higher response rate among treated patients,
6. provide for a longer survival time among treated patients compared to standard chemotherapy treatments,
7. provide a longer time for tumour progression, and/or
8. yield efficacy and tolerability results at least as good as those of the agents used alone, compared to known instances where other cancer agent combinations produce antagonistic effects.

In addition, the compounds of general formula (I) of the present invention can also be used in combination with radiotherapy and/or surgical intervention.

In a further embodiment of the present invention, the compounds of general formula (I) of the present invention may be used to sensitize a cell to radiation, i.e. treatment of a cell with a compound of the present invention prior to radiation treatment of the cell renders the cell more susceptible to DNA damage and cell death than the cell would be in the absence of any treatment with a compound of the present invention. In one aspect, the cell is treated with at least one compound of general formula (I) of the present invention.

Thus, the present invention also provides a method of killing a cell, wherein a cell is administered one or more compounds of the present invention in combination with conventional radiation therapy.

The present invention also provides a method of rendering a cell more susceptible to cell death, wherein the cell is treated with one or more compounds of general formula (I) of the present invention prior to the treatment of the cell to cause or induce cell death. In one aspect, after the cell is treated with one or more compounds of general formula (I) of the present invention, the cell is treated with at least one compound, or at least one method, or a combination thereof, in order to cause DNA damage for the purpose of inhibiting the function of the normal cell or killing the cell.

In other embodiments the invention relates to a method for the treatment of cancer comprising contacting a cell with at least one DNA damaging agent and a compound of the invention, thereby treating the cancer. In one embodiment, the DNA damaging agent contacts the cell prior to, during, or concurrently with a compound of the invention. In another embodiment, contacting the cell with one or more compounds of general formula (I) of the present invention sensitizes the cell to cell death.

In other embodiments of the present invention, a cell is killed by treating the cell with at least one DNA damaging agent, i.e. after treating a cell with one or more compounds of general formula (I) of the present invention to sensitize the cell to cell death, the cell is treated with at least one DNA damaging agent to kill the cell. DNA damaging agents useful in the present invention include, but are not limited to, chemotherapeutic agents (e.g. cis platin), ionizing radiation (X-rays, ultraviolet radiation), carcinogenic agents, and mutagenic agents.

In other embodiments, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of general formula (I) of the present invention is administered to a cell prior to the radiation or other induction of DNA damage in the cell.

Thus in other embodiments of the invention the invention relates to a method for the treatment of cancer in a subject comprising administering to the subject an effective amount of a compound of formula (I) prior to, during, or concurrently with exposing the subject to radiation and/or administration of a DNA damaging agent.

In another aspect of the invention, a compound of general formula (I) of the present invention is administered to a cell concomitantly with the radiation or other induction of DNA damage in the cell.

In yet another aspect of the invention, a compound of general formula (I) of the present invention is administered to a cell immediately after radiation or other induction of DNA damage in the cell has begun.

In another aspect, the cell is in vitro. In another embodiment, the cell is in vivo.

In accordance with a further aspect, the present invention provides compounds of general formula (I), as described supra, or tautomers, N-oxides, and salts thereof, or salts of tautomers or N-oxides, particularly pharmaceutically acceptable salts thereof, or mixtures of same, for use in the treatment or prophylaxis of diseases, in particular hyperproliferative and/or inflammatory disorders.

In accordance with a further aspect, the present invention provides compounds of general formula (I), as described supra, or tautomers, N-oxides, and salts thereof, or salts of tautomers or N-oxides, particularly pharmaceutically acceptable salts thereof, or mixtures of same, for use in the treatment or prophylaxis of diseases, in particular inflammatory disorders.

In accordance with a further aspect, the present invention provides compounds of general formula (I), as described supra, or tautomers, N-oxides, and salts thereof, or salts of tautomers or N-oxides, for use in the treatment or prophylaxis of diseases, in particular hyperproliferative disorders, particularly benign hyperproliferative disorders, more particularly cancer.

The pharmaceutical activity of the compounds according to the invention can be explained by their activity as DHODH inhibitors.

In accordance with a further aspect, the present invention provides the use of compounds of general formula (I), as described supra, or tautomers, N-oxides, and salts thereof, or salts of tautomers or N-oxides, particularly pharmaceutically acceptable salts thereof, or mixtures of same, for the treatment or prophylaxis of diseases, in particular hyperproliferative and/or inflammatory disorders.

In accordance with a further aspect, the present invention provides the use of compounds of general formula (I), as described supra, or tautomers, N-oxides, and salts thereof, or salts of tautomers or N-oxides, particularly pharmaceutically acceptable salts thereof, or mixtures of same, for the treatment or prophylaxis of diseases, in particular hyperproliferative disorders, particularly benign hyperproliferative disorders, more particularly cancer.

In accordance with a further aspect, the present invention provides the use of compounds of general formula (I), as described supra, or tautomers, N-oxides, and salts thereof, or salts of tautomers or N-oxides, particularly pharmaceutically acceptable salts thereof, or mixtures of same, in a method of treatment or prophylaxis of diseases, in particular hyperproliferative and/or inflammatory disorders, particularly cancer.

In accordance with a further aspect, the present invention provides the use of compounds of general formula (I), as described supra, or tautomers, N-oxides, and salts thereof, or salts of tautomers or N-oxides, particularly pharmaceutically acceptable salts thereof, or mixtures of same, in a method of treatment or prophylaxis of diseases, in particular hyperproliferative disorders, particularly benign hyperproliferative disorders, more particularly cancer.

In accordance with a further aspect, the present invention provides the use of a compound of general formula (I), as described supra, or a tautomer, an N-oxide, and a salt thereof, or a salt of a tautomer or an N-oxide, particularly a pharmaceutically acceptable salt thereof, or a mixture of same, for the preparation of a medicament, for the prophylaxis or treatment of diseases, in particular hyperproliferative disorders, particularly benign hyperproliferative disorders, more particularly cancer.

In accordance with a further aspect, the present invention provides use of a compound of general formula (I), as described supra, or a tautomer, an N-oxide, and a salt thereof, or a salt of a tautomer or an N-oxide, particularly a pharmaceutically acceptable salt thereof, or a mixture of same, for the preparation of a pharmaceutical composition, for the prophylaxis or treatment of diseases, in particular hyperproliferative and/or inflammatory disorders.

In accordance with a further aspect, the present invention provides use of a compound of general formula (I), as described supra, or a tautomer, an N-oxide, and a salt thereof, or a salt of a tautomer or an N-oxide, particularly a pharmaceutically acceptable salt thereof, or a mixture of same, for the preparation of a pharmaceutical composition, preferably a medicament, for the prophylaxis or treatment of diseases, in particular hyperproliferative disorders, particularly benign hyperproliferative disorders, more particularly cancer.

In accordance with a further aspect, the present invention provides a method for the treatment or prophylaxis of diseases, in particular hyperproliferative and/or inflammatory disorders, comprising administering to a subject in need thereof an effective amount of a compound of general formula (I), as described supra, or a tautomer, an N-oxide, and a salt thereof, or a salt of a tautomer or an N-oxide, particularly a pharmaceutically acceptable salt thereof, or a mixture of same.

In accordance with a further aspect, the present invention provides a method for the treatment or prophylaxis of diseases, in particular hyperproliferative disorders, particularly benign hyperproliferative disorders, more particularly cancer, comprising administering to a subject in need thereof an effective amount of a compound of general formula (I), as described supra, or a tautomer, an N-oxide, and a salt thereof, or a salt of a tautomer or an N-oxide, particularly a pharmaceutically acceptable salt thereof, or a mixture of same.

In accordance with a further aspect, the present invention provides pharmaceutical compositions, in particular a medicament, comprising a compound of general formula (I), as described supra, or a tautomer, an N-oxide, and a salt thereof, or a salt of a tautomer or an N-oxide, particularly a pharmaceutically acceptable salt, or a mixture of same, and one or more excipients), in particular one or more pharmaceutically acceptable excipient(s). Conventional procedures for preparing such pharmaceutical compositions in appropriate dosage forms can be utilized.

The present invention furthermore provides pharmaceutical compositions, in particular medicaments, which comprise at least one compound according to the invention, conventionally together with one or more pharmaceutically suitable excipients, and to their use for the above mentioned purposes.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia, fillers and carriers (for example cellulose, microcrystalline cellulose (such as, for example, Avicel®), lactose, mannitol, starch, calcium phosphate (such as, for example, Di-Cafos®)),
ointment bases (for example petroleum jelly, paraffins, triglycerides, waxes, wool wax, wool wax alcohols, lanolin, hydrophilic ointment, polyethylene glycols),
bases for suppositories (for example polyethylene glycols, cacao butter, hard fat),
solvents (for example water, ethanol, isopropanol, glycerol, propylene glycol, medium chain-length triglycerides fatty oils, liquid polyethylene glycols, paraffins),
surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxethylene fatty acid esters, polyoxyethylene fatty alcohol ethers, glycerol fatty acid esters, poloxamers (such as, for example, Pluronic®),
buffers, acids and bases (for example phosphates, carbonates, citric acid, acetic acid, hydrochloric acid, sodium hydroxide solution, ammonium carbonate, trometamol, triethanolamine),
isotonicity agents (for example glucose, sodium chloride),
adsorbents (for example highly-disperse silicas),
viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine),
disintegrants (for example modified starch, carboxymethylcellulose-sodium, sodium starch glycolate (such as, for example, Explotab®), cross-linked polyvinylpyrrolidone, croscarmellose-sodium (such as, for example, AcDiSol®)),
flow regulators, lubricants, glidants and mould release agents (for example magnesium stearate, stearic acid, talc, highly-disperse silicas (such as, for example, Aerosil®)),
coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)),
capsule materials (for example gelatine, hydroxypropylmethylcellulose),
synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers),
plasticizers (for example polyethylene glycols, propylene glycol, glycerol, triacetine, triacetyl citrate, dibutyl phthalate),
penetration enhancers,
stabilisers (for example antioxidants such as, for example, ascorbic acid, ascorbyl palmitate, sodium ascorbate, butylhydroxyanisole, butylhydroxytoluene, propyl gallate),
preservatives (for example parabens, sorbic acid, thiomersal, benzalkonium chloride, chlorhexidine acetate, sodium benzoate),
colourants (for example inorganic pigments such as, for example, iron oxides, titanium dioxide),
flavourings, sweeteners, flavour- and/or odour-masking agents.

The present invention furthermore relates to a pharmaceutical composition which comprise at least one compound according to the invention, conventionally together with one or more pharmaceutically suitable excipient(s), and to their use according to the present invention.

In accordance with another aspect, the present invention provides pharmaceutical combinations, in particular medicaments, comprising at least one compound of general formula (I) of the present invention and at least one or more further active ingredients, in particular for the treatment and/or prophylaxis of a hyperproliferative disorder, particularly cancer.

Particularly, the present invention provides a pharmaceutical combination, which comprises:
one or more first active ingredients, in particular compounds of general formula (I) as defined supra, and
one or more further active ingredients, in particular anti-cancer agents.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also provides such pharmaceutical combinations. For example, the compounds of the present invention can be combined with known anti-cancer agents.

Examples of anti-cancer agents include:
131I-chTNT, abarelix, abiraterone, aclarubicin, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumabpentetreotide, nilotinib, nilutamide, nimorazole, nimotuzumab, nimustine, nintedanib, nitracrine, nivolumab, obinutuzumab, octreotide, ofatumumab, olaparib, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Based upon standard laboratory techniques known to evaluate compounds useful for the treatment of hyperproliferative and/or inflammatory disorders, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg (e.g. about 0.5 mg to about 5 mg, about 5 mg to about 50 mg, about 50 mg to about 500 mg, about 500 mg to about 1500 mg, etc.) of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

In other embodiments of the invention the total amount of the active ingredient to be administered will generally range from 0.001 mg/kg to 200 mg/kg body weight per day, and preferably from 0.01 mg/kg to 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from 0.5 mg to 1500 mg of active ingredient, and can be administered one or more times per day or less than once a day.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

EXPERIMENTAL SECTION

NMR peak forms are stated as they appear in the spectra, possible higher order effects have not been considered.

The $^1$H-NMR data of selected examples are listed in the form of $^1$H-NMR peaklists. For each signal peak the δ value in ppm is given, followed by the signal intensity, reported in round brackets. The δ value-signal intensity pairs from different peaks are separated by commas. Therefore, a peaklist is described by the general form: $\delta_1$ (intensity$_1$), $\delta_2$ (intensity$_2$), . . . , $\delta_i$ (intensity$_i$), . . . , $\delta_n$ (intensity$_n$).

The intensity of a sharp signal correlates with the height (in cm) of the signal in a printed NMR spectrum. When compared with other signals, this data can be correlated to the real ratios of the signal intensities. In the case of broad signals, more than one peak, or the center of the signal along with their relative intensity, compared to the most intense signal displayed in the spectrum, are shown. A $^1$H-NMR peaklist is similar to a classical $^1$H-NMR readout, and thus usually contains all the peaks listed in a classical NMR interpretation. Moreover, similar to classical $^1$H-NMR printouts, peaklists can show solvent signals, signals derived from stereoisomers of target compounds (also the subject of the invention), and/or peaks of impurities. The peaks of stereoisomers, and/or peaks of impurities are typically displayed with a lower intensity compared to the peaks of the target compounds (e.g., with a purity of >90%). Such stereoisomers and/or impurities may be typical for the particular manufacturing process, and therefore their peaks may help to identify the reproduction of our manufacturing process on the basis of "by-product fingerprints". An expert who calculates the peaks of the target compounds by known methods (MestReC, ACD simulation, or by use of empirically evaluated expectation values), can isolate the peaks of target compounds as required, optionally using additional intensity filters. Such an operation would be similar to peak-picking in classical $^1$H-NMR interpretation. A detailed description of the reporting of NMR data in the form of peaklists can be found in the publication "Citation of NMR Peaklist Data within Patent Applications" (cf. Research Disclosure Database Number 605005, 2014, 1 Aug. 2014, or http://www.researchdisclosure.com/searching-disclosures). In the peak picking routine, as described in the Research Disclosure Database Number 605005, the parameter "MinimumHeight" can be adjusted between 1% and 4%. Depending on the chemical structure and/or depending on the concentration of the measured compound it may be reasonable to set the parameter "MinimumHeight"<1%.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

| Abbreviation | Meaning |
|---|---|
| aq. | aqueous |
| ACN | acetonitrile |
| br | broad ($^1$H-NMR signal) |
| cat. | catalytic |
| CDI | 1,1'-carbonyldiimidazole |
| CI | chemical ionisation |
| conc. | concentrated |
| d | doublet |
| DAD | diode array detector |
| DCM | dichloromethane |
| dd | double-doublet |
| ddd | double-doublet-doublet |
| DIPEA | diisopropylethylamine |
| DMAP | 4-dimethylaminopyridine |
| DMF | N,N-dimethylformamide |
| DMSO | dim ethylsulfoxide |
| eq. | equivalent |
| ESI | electrospray (ES) ionisation |
| h | hour(s) |
| HATU | 1-[bis(dimethylamino)methylene]-1H-1,2,3-triazolo[4,5-b]pyridinium 3-oxid hexafluorophosphate |
| HBTU | (o-benzotriazole-10-yl)-N,N,N',N,-tetramethyluronium hexafluorophosphate |
| HCl | hydrochloric acid |
| HPLC | high performance liquid chromatography |
| LC-MS | liquid chromatography mass spectrometry |
| m | multiplet |
| min | minute(s) |
| MeOH | methanol |
| Mp. | melting point |
| MS | mass spectrometry |
| Abbreviation | Meaning |
| NMR | nuclear magnetic resonance spectroscopy: chemical shifts (δ) are given in ppm. The chemical shifts were corrected by setting the DMSO signal to 2.50 ppm unless otherwise stated. |
| MTP | microtiter plate |
| q | quartet |
| quin | quintet |
| r.t. or rt or RT | room temperature |
| Rt | retention time (as measured either with HPLC or UPLC) in minutes |
| s | singlet |
| sxt | sextet |
| sep | septet |
| t | triplet |
| td | triple-doublet |

TABLE 1-continued

Abbreviations

| Abbreviation | Meaning |
|---|---|
| THF | tetrahydrofuran |
| TLC | thin-layer chromatography |
| UPLC | ultra performance liquid chromatography |

Other abbreviations have their meanings customary per se to the skilled person.

The various aspects and embodiments of the invention described in this application are illustrated by the following examples which are not meant to limit the invention in any way.

The example testing experiments described herein serve to illustrate the present invention and the invention is not limited to the examples given.

Experimental Section—General Part

All reagents, for which the synthesis is not described in the experimental part, are either commercially available, or are known compounds or may be formed from known compounds by known methods by a person skilled in the art. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

UPLC-MS Standard Procedures

Analytical UPLC-MS was performed as described below. The masses (m/z) are reported from the positive mode electrospray ionisation unless the negative mode is indicated (ESI−).

Method A (HPLC-MS):
Instrument: Waters Acquity UPLCMS SingleQuad; Column: Acquity UPLC BEH C18 1.7 μm, 50×2.1 mm; eluent A: water+0.1 vol % formic acid (99%), eluent B: acetonitrile; gradient: 0-1.6 min 1-99% B, 1.6-2.0 min 99% B; flow 0.8 ml/min; temperature: 60° C.; DAD scan: 210-400 nm.

Method B (HPLC-MS):
Instrument: Waters Acquity UPLCMS SingleQuad; Column: Acquity UPLC BEH C18 1.7 μm, 50×2.1 mm; eluent A: water+0.2 Vol-% aq. ammonia (32%), eluent B: acetonitrile; gradient: 0-1.6 min 1-99% B, 1.6-2.0 min 99% B; flow 0.8 ml/min; temperature: 60° C.; DAD scan: 210-400 nm.

Experimental Section—Intermediates

Intermediate 1 tert-butyl 2,4,5-trifluorobenzoate

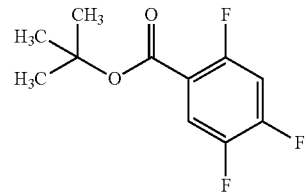 [SMILES: CC(C)(C)OC(=O)c1cc(F)c(F)cc1F]

To stirred solution of 2,4,5-trifluorobenzoic acid (28.4 g, 161 mmol, 1.00 eq.) in tert-butanol (806 mL, 0.20 mol/L) was successively added di-tert-butyl-dicarbonate (70.4 g, 323 mmol, 2.00 eq.) and DMAP (1.97 g, 16.1 mmol, 0.10 eq.). The resulting mixture was stirred 30° C. overnight and concentrated under reduced pressure. The residue was diluted with ethyl acetate and washed with aqueous 1.0 M hydrochloric acid (2×), saturated aqueous sodium bicarbonate (2×), brine (2×), dried (sodium sulfate) and concentrated under reduced pressure. The residue was purified by column chromatography (hexanes/ethyl acetate) to give the desired product (27.4 g, 73%).

$^1$H NMR (300 MHz, CDCl$_3$) δ [ppm] 1.58 (s, 9H), 6.91-7.02 (m, 1H), 7.71 (ddd, 1H).

Triazolone Intermediates (IV)

Triazolones were obtained commercially or synthesized according to the literature unless specified below.

The following intermediates can be synthesized using the procedures outlined in Chemische Berichte (1969), 102(3), 755-66: 3-chloro-4-methyl-1H-1,2,4-triazol-5(4H)-one, 3-ethyl-4-methyl-1H-1,2,4-triazol-5(4H)-one, The following intermediates were previously described in Chimica acta Turcica (1975), Vol. 2, Issue 3, page 113: 4-methyl-3-propyl-1H-1,2,4-triazol-5(4H)-one, 3-ethyl-4-(2-hydroxyethyl)-1H-1,2,4-triazol-5(4H)-one The following intermediates can be synthesized using the procedures outlined in EP 0422469 A2 (Example numbers refer to the original publication):
4-isopropyl-3-methyl-1H-1,2,4-triazol-5(4H)-one (Ex. II-5), 3-cyclopropyl-4-methyl-1H-1,2,4-triazol-5(4H)-one (Ex. II-33), 3-cyclopropyl-4-ethyl-1H-1,2,4-triazol-5(4H)-one (Ex. II-34), 4-cyclopropyl-3-methyl-1H-1,2,4-triazol-5 (4H)-one (Ex. II-18), 4-cyclopropyl-3-ethyl-1H-1,2,4-triazol-5(4H)-one (Ex. II-24), 3-isopropyl-4-methyl-1H-1,2,4-triazol-5(4H)-one (Ex. II-13), 4-cyclopentyl-3-methyl-1H-1,2,4-triazol-5(4H)-one (Ex. II-46), 3-cyclobutyl-4-methyl-1H-1,2,4-triazol-5(4H)-one, 3-tert-butyl-4-methyl-1H-1,2, 4-triazol-5(4H)-one, 4-cyclopropylmethyl-3-methyl-1H-1,2,4-triazol-5(4H)-one, 3,4-diethyl-1H-1,2,4-triazol-5(4H)-one, 3-cyclopentyl-4-methyl-1H-1,2,4-triazol-5(4H)-one, 4-butan-2-yl-3-methyl-1H-1,2,4-triazol-5(4H)-one, 3-butan-2-yl-4-methyl-1H-1,2,4-triazol-5(4H)-one, The following intermediates can be synthesized using the procedures outlined in DE 3709574 A1: 3-dimethylamino-4-methyl-1H-1,2,4-triazol-5(4H)-one (Ex IV-1), 3-[ethyl(methyl)amino]-4-methyl-1H-1,2,4-triazol-5(4H)-one.

4-methyl-3-methylsulfanyl-1H-1,2,4-triazol-5-one can be synthesized using the procedures outlined in U.S. Pat. No. 4,098,896.

4-methyl-5-(trifluoromethyl)-2,4-dihydro-3H-1,2,4-triazol-3-one can be synthesized using the procedures outlined in U.S. Pat. No. 5,508,420.

4-methyl-3-methylamino-1H-1,2,4-triazol-5-one can be synthesized using the procedures outlined in DE 3916208.

The following intermediates can be synthesized using the procedures outlined in DE 3934081: 3-methyl-4-propyl-1H-1,2,4-triazol-5-one, 4-cyclopentyl-1H-1,2,4-triazol-5-one.

The following intermediates can be synthesized using the procedures outlined in EP 507171/DE 4110795: 4-cyclopropyl-3-methoxy-1H-1,2,4-triazol-5(4H)-one (Ex. II-5), 4-methyl-3-phenoxy-1H-1,2,4-triazol-5(4H)-one (Ex. II-3), 3-chloro-4-ethyl-1H-1,2,4-triazol-5(4H)-one can be synthesized using the procedures outlined in EP 0425948/DE 3936622

4-ethyl-3-methylsulfanyl-1H-1,2,4-triazol-5-one can be synthesized using the procedures outlined in EP 431291/DE 3936623

4-ethyl-3-isopropoxy-1H-1,2,4-triazol-5(4H)-one can be synthesized using the procedures outlined in EP 703224/DE 4433968

Intermediate 2 tert-butyl [(1R)-1-(4-methyl-5-oxo-4,5-dihydro-1H-1,2,4-triazol-3-yl)ethyl]carbamate

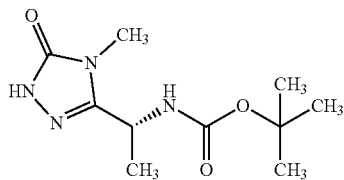 [SMILES: C[C@@H](NC(=O)OC(C)(C)C)c1n[nH]c(=O)n1C]

Methyl N-(tert-butoxycarbonyl)-D-alaninate (8.00 g, 39.4 mmol) was dissolved in ethanol (10 mL), followed by hydrazine hydrate (20 mL, 410 mmol). The mixture was stirred at 100° C. for 30 min (Caution! Use appropriate safety measures). The solvent was removed to obtain tert-butyl [(2R)-1-hydrazinyl-1-oxopropan-2-yl]carbamate (8.00 g, 39.4 mmol).

The crude intermediate was dissolved in dichloromethane (50 ml) and treated with triethylamine (7.6 ml, 54 mmol), 1,1′-Carbonyldiimidazol (8.40 g, 51.8 mmol). The mixture was stirred at room temperature overnight. The mixture was washed with water, organic solvent was dried and concentrated to obtain tert-butyl [(1R)-1-(5-oxo-4,5-dihydro-1,3,4-oxadiazol-2-yl)ethyl]carbamate The crude intermediate was dissolved in methylamine solution (27 mL, 40% solution in water, 380 mmol) and the mixture was heated to reflux overnight. The solvent was removed to yield tert-butyl [(1R)-1-(4-methyl-5-oxo-4,5-dihydro-1H-1,2,4-triazol-3-yl)ethyl]carbamate which was sufficiently pure to be used for further reactions.

Intermediate 3 tert-butyl [(4-methyl-5-oxo-4,5-dihydro-1H-1,2,4-triazol-3-yl)methyl]carbamate

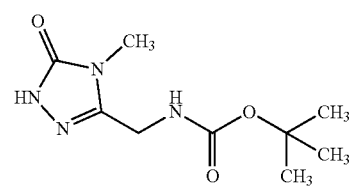 [SMILES: Cn1c(CNC(=O)OC(C)(C)C)n[nH]c1=O]

Synthesized from N-(tert-butoxycarbonyl)-glycine methyl ester analogously to Intermediate 2.

Intermediate 4

5-[1-(1-ethoxyethoxy)ethyl]-4-methyl-2,4-dihydro-3H-1,2,4-triazol-3-one

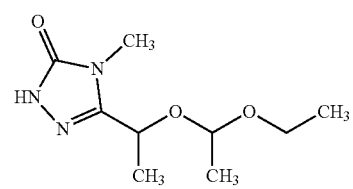

Synthesized from ethyl 2-(1-ethoxyethoxy)propanoate (Bulletin of the Chemical Society of Japan, 1987, vol. 60, p. 2127-2138) analogously to Intermediate 2.

Intermediate 5

5-[(benzyloxy)methyl]-4-methyl-2,4-dihydro-3H-1,2,4-triazol-3-one

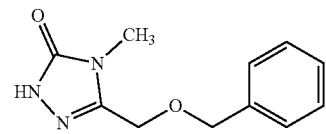 [SMILES: Cn1c(COCc2ccccc2)n[nH]c1=O]

Synthesized from methyl (benzyloxy)acetate analogously to Intermediate 2.

Intermediate 6

4-ethyl-5-(hydroxymethyl)-2,4-dihydro-3H-1,2,4-triazol-3-one

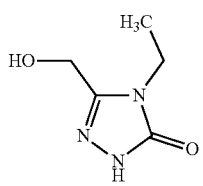

2-hydroxyacetohydrazide (50.0 g, 555 mmol) was dissolved in water (125 mL) and cooled to 0° C. Ethyl isocyanate (44 ml, 560 mmol) was added (very exotherm!) and the resulting mixture was stirred at room temperature overnight. The resulting suspension was treated with sodium hydroxide solution (64 g, 50 wt % in water) (exotherm). The resulting solution was heated to 95° C. overnight. The yellow reaction mixture was neutralized with concentrated hydrochloric acid and the resulting cloudy solution was concentrated to dryness. The solids were triturated with a mixture of dichloromethane and isopropanol (4:1, 750 mL), the solution was filtered off and concentrated to dryness again to yield~78 g of crude product. The product was recrystallized from ethyl acetate to yield the desired product (56.2 g, 71% yield).

$^1$H-NMR (400 MHz, DMSO-d6) δ [ppm]: 1.156 (6.88), 1.174 (16.00), 1.192 (7.02), 2.518 (0.48), 3.606 (2.02), 3.623 (6.84), 3.641 (6.79), 3.659 (1.96), 4.316 (4.51), 5.540 (0.94).

Intermediate 7

3-(1-hydroxy-1-methyl-ethyl)-4-methyl-1H-1,2,4-triazol-5-one

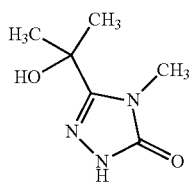

Hydrazine Hydrate (201 g, 4.03 mol) was added dropwise to methyl 2-hydroxy-2-methylpropanoate (500.0 g, 4.03 mol) over 2 h (exotherm!). The rate of addition was controlled to maintain a temperature between 45-55° C. The mixture was slowly heated to 80° C. to distill off methanol. The crude hydrazide was dissolved in water (500 mL) and cooled to 0° C. Methyl isocyanate (230 g, 4.03 mol) was added (very exotherm!) and the resulting mixture was stirred at room temperature overnight. The resulting mixture was treated with sodium hydroxide solution (480 g, 50 wt % in water, 6 mol) (exotherm). The resulting solution was heated to 95° C. overnight. The yellow reaction mixture was neutralized with concentrated hydrochloric acid (716 g, 30.6%, 6 mol). The resulting cloudy solution was heated to 80° C., filtered hot, and cooled to room temperature. The product crystallized directly from the solution to yield 470 g, 74% yield).

Mp. 186° C.

$^1$H-NMR (400 MHz, DMSO-d6) δ [ppm]: 1.43 (s, 6H) 3.28 (s, 3H) 5.47 (s, 1H) 11.45 (s, 1H).

Intermediate 8

3-(hydroxymethyl)-4-methyl-1H-1,2,4-triazol-5-one

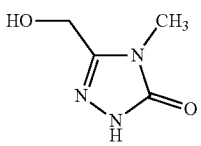

Hydrazine Hydrate (150 g, 3 mol) was added dropwise to butyl hydroxyacetate (417 g, 3 mol) (exotherm!). The mixture was slowly heated to 50° C. for 1 h. N-Butanol was azeotroped with water. The crude hydrazide was dissolved in water (750 mL) and cooled to -10° C. Methyl isocyanate (171 g, 3 mol) was added (very exotherm!) and the resulting mixture was stirred at room temperature overnight. The resulting mixture was treated with sodium hydroxide solution (360 g, 50 wt % in water, 4.5 mol) (exotherm). The resulting solution was heated to 95° C. overnight. The reaction mixture was neutralized with concentrated hydrochloric acid (555 g, 30%, 4.5 mol). The resulting mixture was concentrated to dryness and extracted with DMF (1 L). The DMF was removed under vacuum and the product was crystallized from ethyleneglycol (700 mL) to yield 250 g, 74% yield).

Mp. 144-145° C.

Intermediate 9

3-[(1S)-1-hydroxyethyl]-4-methyl-1H-1,2,4-triazol-5-one

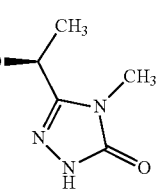

Synthesized analogous to Intermediate 7 from ethyl-(2S)-hydroxypropanoate. The product crystallized directly from the solution to yield 465 g, which was recrystallized again from water (400 mL) to yield 438 g of product (contained 8.5% water, 70% yield).

Mp. 100-103° C.

Optical rotation (MeOH) 18.8°+/−0.09°

$^1$H NMR (400 MHz, DMSO-d6) Shift=11.47 (br s, 1H), 5.55 (br d, J=5.6 Hz, 1H), 4.61 (quin, J=6.2 Hz, 1H), 3.17 (s, 3H), 1.38 (d, J=6.6 Hz, 3H).

Intermediate 10

5-[(dimethylamino)methyl]-4-methyl-2,4-dihydro-3H-1,2,4-triazol-3-one

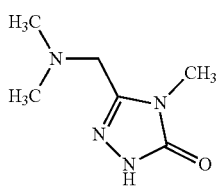

Synthesized analogously to Intermediate 7. After neutralization the aqueous solution was concentrated and the product was extracted from the resulting solids with ethoxythanol. The solvent was removed and the product was distilled. The product was then re-crystallized from butyl acetate. Mp. 115° C.

Intermediate 11

5-(1-methoxyethyl)-4-methyl-2,4-dihydro-3H-1,2,4-triazol-3-one, Mixture of Stereoisomers

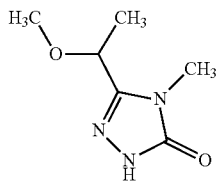

Synthesized analogously to Intermediate 7. After neutralization the aqueous solution was concentrated and the product was extracted from the resulting solids with butyl acetate and isopropanol. The solvent was removed and the product was distilled. The product was then re-crystallized from butyl acetate.

Intermediate 12

5-[(1S)-1-(benzyloxy)ethyl]-1,3,4-oxadiazol-2(3H)-one

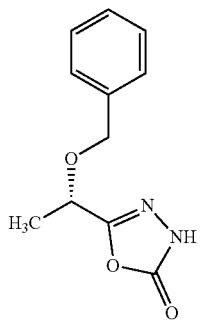 [SMILES: C[C@H](OCc1ccccc1)c1n[nH]c(=O)o1]

(2S)-2-(benzyloxy)propanehydrazide (synthesis is described in WO2010/71813, 7.10 g, 36.6 mmol) was dissolved in THF (43 ml), CDI (7.11 g, 43.9 mmol) was added and the mixture was cooled to 0° C. Triethylamine (10 ml, 73 mmol) was added dropwise. The mixture was stirred at room temperature overnight. The mixture was concentrated and purified using silica gel chromatography (DCM/MeOH 0-50%) to yield the desired intermediate (6.94 g, 86% yield).

$^1$H NMR (400 MHz, CHLOROFORM-d) δ ppm 1.46 (d, 3H), 4.34 (q, 1H), 4.41-4.50 (m, 1H), 4.52-4.60 (m, 1H), 7.17 (s, 1H), 7.19-7.31 (m, 4H).

Intermediate 13

5-[(1S)-1-(benzyloxy)ethyl]-4-methyl-2,4-dihydro-3H-1,2,4-triazol-3-one

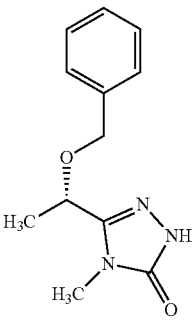

5-[(1S)-1-(benzyloxy)ethyl]-1,3,4-oxadiazol-2(3H)-one (Intermediate 12, 6.94 g, 31.5 mmol) was dissolved in methylamine (27 ml, 40% in water, 380 mmol) and stirred at 100° C. for 5 h. The mixture was concentrated to yield the desired product in sufficient purity (7.4 g).

LC-MS (Method A): Rt=0.85 min; MS (ESIpos): m/z=234 [M+H]$^+$

Intermediate 14 tert-butyl 2,5-difluoro-4-(4-isopropyl-3-methyl-5-oxo-1,2,4-triazol-1-yl)benzoate

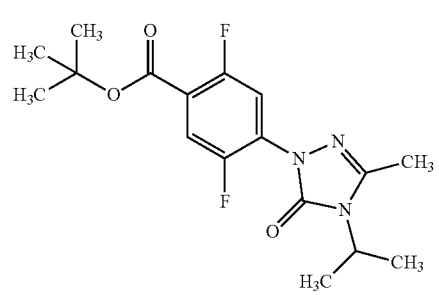 [SMILES: Cc1nn(-c2cc(F)c(C(=O)OC(C)(C)C)cc2F)c(=O)n1C(C)C]

To a stirred solution of tert-butyl 2,4,5-trifluorobenzoate (4.99 g, 21.5 mmol, 1.00 eq.) and 4-isopropyl-3-methyl-1H-1,2,4-triazol-5(4H)-one (3.19 g, 22.6 mmol, 1.05 eq.) in anhydrous acetonitrile (53.8 mL, 0.40 mol/L) was added 1,8-diazabicyclo[5.4.0]undec-7-ene (3.89 mL, 25.8 mmol, 1.20 eq.). The resulting mixture was heated at 80° C. overnight, cooled to room temperature and concentrated under reduced pressure. The residue was purified by column chromatography (hexanes/ethyl acetate) to give the desired product (4.56 g, 60%).

¹H NMR (300 MHz, CDCl₃) δ [ppm] 1.54 (d, 6H), 1.59 (s, 9H), 2.35 (s, 3H), 4.32 (sep, 1H), 7.47 (dd, 1H), 7.69 (dd, 1H).

MS (ESIpos): m/z=354 (M+H)⁺.

Intermediate 15 tert-butyl 4-(3-ethyl-4-methyl-5-oxo-4,5-dihydro-1H-1,2,4-triazol-1-yl)-2,5-difluorobenzoate

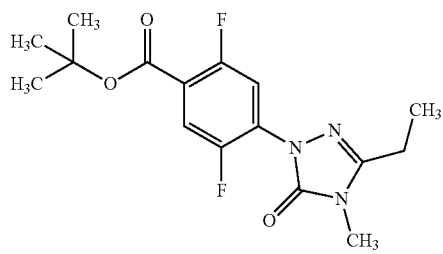 [SMILES: CCc1nn(-c2cc(F)c(C(=O)OC(C)(C)C)cc2F)c(=O)n1C]

Synthesized analogously to Intermediate 14 from 3-ethyl-4-methyl-1H-1,2,4-triazol-5(4H)-one. Potassium carbonate was used as a base instead of 1,8-diazabicyclo[5.4.0]undec-7-ene.

Intermediate 16 tert-butyl 4-(3-cyclopropyl-4-methyl-5-oxo-4,5-dihydro-1H-1,2,4-triazol-1-yl)-2,5-difluorobenzoate

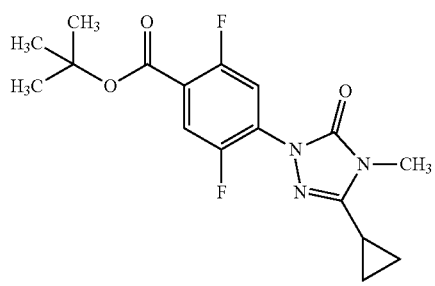 [SMILES: Cn1c(C2CC2)nn(-c2cc(F)c(C(=O)OC(C)(C)C)cc2F)c1=O]

Synthesized analogously to Intermediate 14 from 3-cyclopropyl-4-methyl-1H-1,2,4-triazol-5(4H)-one. Potassium carbonate was used as a base instead of 1,8-diazabicyclo[5.4.0]undec-7-ene.

LC-MS (Method A): R$_t$=1.29 min; MS (ESIpos): m/z=352 [M+H]⁺.

Intermediate 17 tert-butyl 4-(3-cyclopropyl-4-ethyl-5-oxo-4,5-dihydro-1H-1,2,4-triazol-1-yl)-2,5-difluorobenzoate

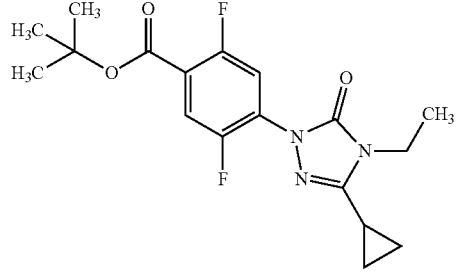 [SMILES: CCn1c(C2CC2)nn(-c2cc(F)c(C(=O)OC(C)(C)C)cc2F)c1=O]

Synthesized analogously to Intermediate 14 from 3-cyclopropyl-4-ethyl-1H-1,2,4-triazol-5(4H)-one. Potassium carbonate was used as a base instead of 1,8-diazabicyclo[5.4.0]undec-7-ene.

LC-MS (Method A): R$_t$=1.37 min; MS (ESIpos): m/z=366 [M+H]⁺.

Intermediate 18 tert-butyl 4-(4-cyclopropyl-3-methyl-5-oxo-4,5-dihydro-1H-1,2,4-triazol-1-yl)-2,5-difluorobenzoate

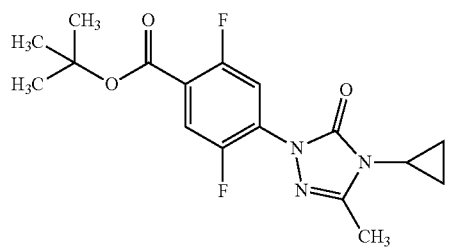 [SMILES: Cc1nn(-c2cc(F)c(C(=O)OC(C)(C)C)cc2F)c(=O)n1C1CC1]

Synthesized analogously to Intermediate 14 from 4-cyclopropyl-3-methyl-1H-1,2,4-triazol-5(4H)-one. Potassium carbonate was used as a base instead of 1,8-diazabicyclo[5.4.0]undec-7-ene.

LC-MS (Method A): R$_t$=1.25 min; MS (ESIpos): m/z=352 [M+H]⁺.

Intermediate 19 tert-butyl 4-(4-cyclopropyl-3-ethyl-5-oxo-4,5-dihydro-1H-1,2,4-triazol-1-yl)-2,5-difluorobenzoate

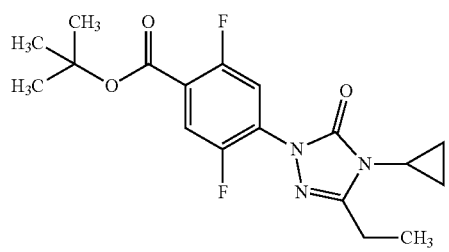 [SMILES: CCc1nn(-c2cc(F)c(C(=O)OC(C)(C)C)cc2F)c(=O)n1C1CC1]

Synthesized analogously to Intermediate 14 from 4-cyclopropyl-3-ethyl-1H-1,2,4-triazol-5(4H)-one. Potassium carbonate was used as a base instead of 1,8-diazabicyclo[5.4.0]undec-7-ene.

LC-MS (Method A): R$_t$=1.32 min; MS (ESIpos): m/z=366 [M+H]$^+$.

Intermediate 20 tert-butyl 4-(3-cyclobutyl-4-methyl-5-oxo-4,5-dihydro-1H-1,2,4-triazol-1-yl)-2,5-difluorobenzoate

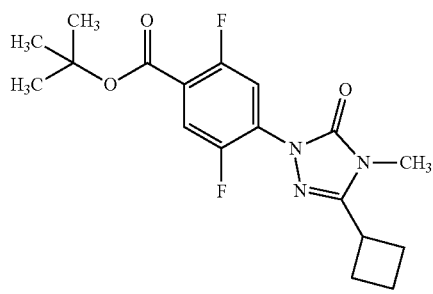 [SMILES: Cn1c(C2CCC2)nn(-c2cc(F)c(C(=O)OC(C)(C)C)cc2F)c1=O]

Synthesized analogously to Intermediate 14 from 3-cyclobutyl-4-methyl-1H-1,2,4-triazol-5(4H)-one. Potassium carbonate was used as a base instead of 1,8-diazabicyclo[5.4.0]undec-7-ene.

LC-MS (Method A): R$_t$=1.39 min; MS (ESIpos): m/z=366 [M+H]$^+$.

Intermediate 21 tert-butyl 2,5-difluoro-4-[4-methyl-5-oxo-3-(trifluoromethyl)-4,5-dihydro-1H-1,2,4-triazol-1-yl]benzoate

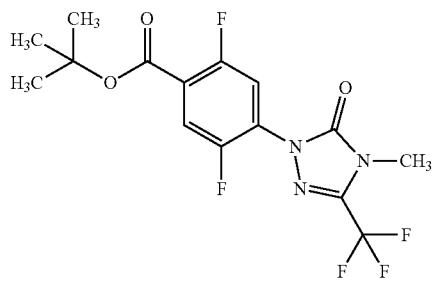 [SMILES: Cn1c(C(F)(F)F)nn(-c2cc(F)c(C(=O)OC(C)(C)C)cc2F)c1=O]

Synthesized analogously to Intermediate 14 from 4-methyl-5-(trifluoromethyl)-2,4-dihydro-3H-1,2,4-triazol-3-one. Potassium carbonate was used as a base instead of 1,8-diazabicyclo[5.4.0]undec-7-ene.

LC-MS (Method A): R$_t$=1.39 min; MS (ESIpos): m/z=324 [M+H−tBu]$^+$.

Intermediate 22 tert-butyl 2,5-difluoro-4-[4-methyl-5-oxo-3-(propan-2-yl)-4,5-dihydro-1H-1,2,4-triazol-1-yl]benzoate

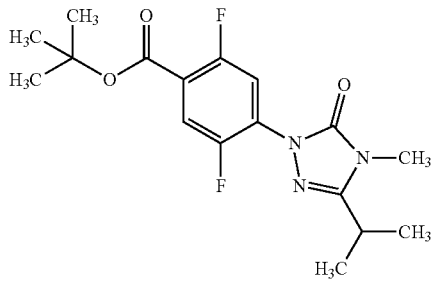 [SMILES: CC(C)c1nn(-c2cc(F)c(C(=O)OC(C)(C)C)cc2F)c(=O)n1C]

Synthesized analogously to Intermediate 14 from 3-isopropyl-4-methyl-1H-1,2,4-triazol-5(4H)-one. Potassium carbonate was used as a base instead of 1,8-diazabicyclo[5.4.0]undec-7-ene.

LC-MS (Method A): R$_t$=1.34 min; MS (ESIpos): m/z=354 [M+H]$^+$.

Intermediate 23 tert-butyl 4-{3-[(1S)-1-(benzyloxy)ethyl]-4-methyl-5-oxo-4,5-dihydro-1H-1,2,4-triazol-1-yl}-2,5-difluorobenzoate

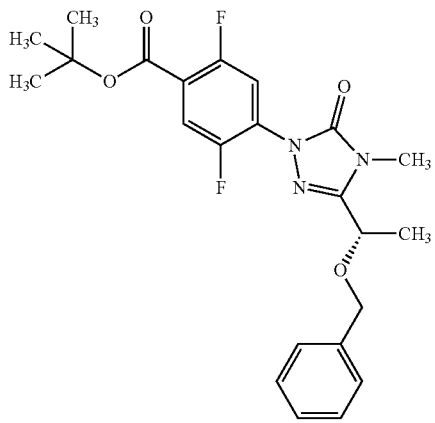 [SMILES: C[C@H](OCc1ccccc1)c1nn(-c2cc(F)c(C(=O)OC(C)(C)C)cc2F)c(=O)n1C]

Synthesized analogously to Intermediate 14 from Intermediate 13. Potassium carbonate was used as a base instead of 1,8-diazabicyclo[5.4.0]undec-7-ene.

$^1$H NMR (400 MHz, CHLOROFORM-d) δ=7.72 (dd, J=6.3, 10.6 Hz, 1H), 7.43 (dd, J=5.8, 10.6 Hz, 1H), 7.40-7.27 (m, 5H), 4.63 (q, J=6.8 Hz, 1H), 4.59-4.48 (m, 2H), 3.39 (s, 3H), 1.64 (d, J=6.8 Hz, 3H), 1.60 (s, 9H).

Intermediate 24 tert-butyl 4-{3-[1-(1-ethoxyethoxy)ethyl]-4-methyl-5-oxo-4,5-dihydro-1H-1,2,4-triazol-1-yl}-2,5-difluorobenzoate, Mixture of Diastereomers

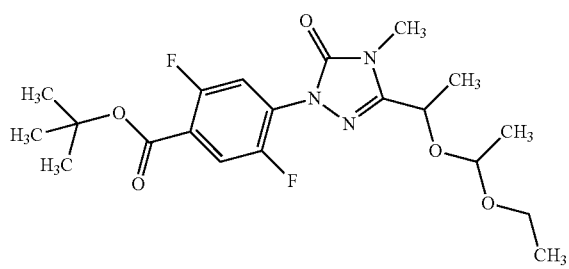 [SMILES: CCOC(C)OC(C)c1nn(-c2cc(F)c(C(=O)OC(C)(C)C)cc2F)c(=O)n1C]

Synthesized analogously to Intermediate 14 from Intermediate 4. Potassium carbonate was used as a base instead of 1,8-diazabicyclo[5.4.0]undec-7-ene.

Intermediate 25 tert-butyl 4-(3-{(1R)-1-[(tert-butoxycarbonyl)amino]ethyl}-4-methyl-5-oxo-4,5-dihydro-1H-1,2,4-triazol-1-yl)-2,5-difluorobenzoate

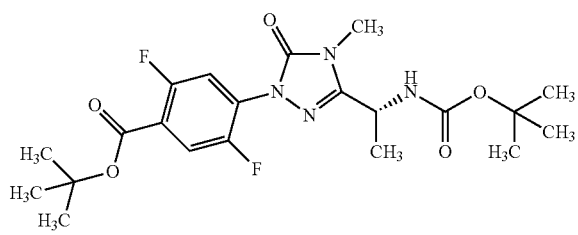 [SMILES: C[C@@H](NC(=O)OC(C)(C)C)c1nn(-c2cc(F)c(C(=O)OC(C)(C)C)cc2F)c(=O)n1C]

Synthesized analogously to Intermediate 14 from Intermediate 2. Potassium carbonate was used as a base instead of 1,8-diazabicyclo[5.4.0]undec-7-ene. DMF was used as solvent instead of acetonitrile.

Intermediate 26 tert-butyl 4-{3-[(benzyloxy)methyl]-4-methyl-5-oxo-4,5-dihydro-1H-1,2,4-triazol-1-yl}-2,5-difluorobenzoate

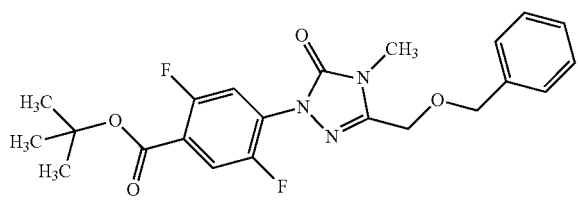 [SMILES: Cn1c(COCc2ccccc2)nn(-c2cc(F)c(C(=O)OC(C)(C)C)cc2F)c1=O]

Synthesized analogously to Intermediate 14 from Intermediate 5. Potassium carbonate was used as a base instead of 1,8-diazabicyclo[5.4.0]undec-7-ene. DMF was used as solvent instead of acetonitrile.

Intermediate 27 tert-butyl 4-(3-{[(tert-butoxycarbonyl)amino]methyl}-4-methyl-5-oxo-4,5-dihydro-1H-1,2,4-triazol-1-yl)-2,5-difluorobenzoate

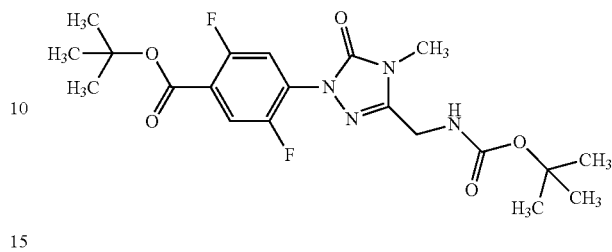

Synthesized analogously to Intermediate 14 from Intermediate 3. Potassium carbonate was used as a base instead of 1,8-diazabicyclo[5.4.0]undec-7-ene. DMF was used as solvent instead of acetonitrile.

Intermediate 28 tert-butyl 4-(3-{[(tert-butoxycarbonyl)(methyl)amino]methyl}-4-methyl-5-oxo-4,5-dihydro-1H-1,2,4-triazol-1-yl)-2,5-difluorobenzoate

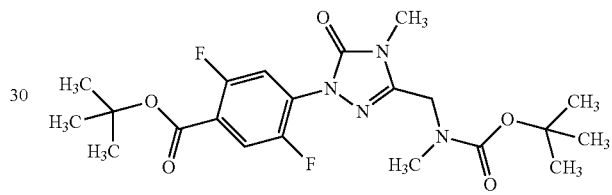

tert-butyl 4-(3-{[(tert-butoxycarbonyl)amino]methyl}-4-methyl-5-oxo-4,5-dihydro-1H-1,2,4-triazol-1-yl)-2,5-difluorobenzoate (Intermediate 27, 400 mg, 908 µmol) was dissolved in DMF (10 mL). Sodium hydride (60% in mineral oil, 54.5 mg, 1.36 mmol), was added and the mixture was stirred at room temperature for 15 min. Methyl iodide (193 mg, 1.36 mmol) was added and the mixture was stirred at room temperature for 15 min. The reaction was quenched with brine (20 ml), extracted with ethyl acetate (2×20 ml), washed with brine (2×20 ml), dried and concentrated. The compound was purified using silica gel column chromatography (petrol ether:ethyl acetate 5:1) to yield the desired intermediate (150 mg, 36% yield).

Intermediate 29 tert-butyl 4-{3-[(1R)-1-aminoethyl]-4-methyl-5-oxo-4,5-dihydro-1H-1,2,4-triazol-1-yl}-2,5-difluorobenzoate, Salt with Hydrochloric Acid

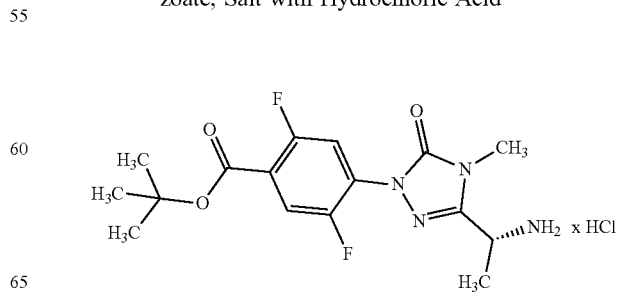

tert-butyl 4-(3-{(1R)-1-[(tert-butoxycarbonyl)amino]ethyl}-4-methyl-5-oxo-4,5-dihydro-1H-1,2,4-triazol-1-yl)-2,5-difluorobenzoate (Intermediate 25, 1.80 g, 3.96 mmol) was dissolved in THF (30 ml). Hydrogen chloride gas was bubbled through the solution for 30 minutes. The reaction mixture was stirred at room temperature for another 2 h. The mixture was concentrated to yield the desired product in sufficient purity (1.4 g, 90% yield).

Intermediate 30 tert-butyl 4-{3-[(1R)-1-(dibenzylamino)ethyl]-4-methyl-5-oxo-4,5-dihydro-1H-1,2,4-triazol-1-yl}-2,5-difluorobenzoate

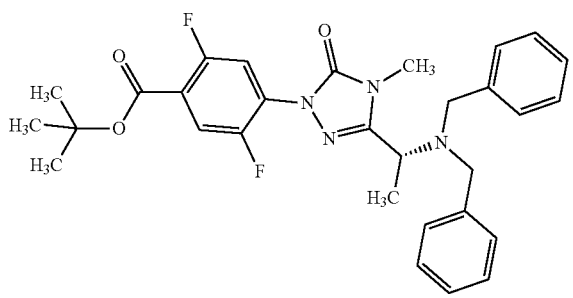 [SMILES: C[C@H](c1nn(-c2cc(F)c(C(=O)OC(C)(C)C)cc2F)c(=O)n1C)N(Cc1ccccc1)Cc1ccccc1]

tert-butyl 4-{3-[(1R)-1-aminoethyl]-4-methyl-5-oxo-4,5-dihydro-1H-1,2,4-triazol-1-yl}-2,5-difluorobenzoate hydrochloride (1:1) (Intermediate 29, 1.40 g, 3.58 mmol) was dissolved in DMF (30 ml). Sodium hydride (640 mg, 60% in mineral oil, 16.0 mmol) was added slowly. The mixture was cooled to 0° C. and benzyl bromide (1.2 ml, 9.9 mmol) was added dropwise. The mixture was stirred at room temperature overnight, quenched with ammonium chloride solution (300 ml), and extracted with ethyl acetate (200 ml). The organic layer was washed with 200 ml brine. Column chromatography (petrol ether:ethyl acetate 10:1) yields the product (800 mg, 41% yield).

Intermediate 31 tert-butyl 4-(3-cyclopropyl-4-methyl-5-oxo-4,5-dihydro-1H-1,2,4-triazol-1-yl)-5-fluoro-2-{[(2S)-1,1,1-trifluoropropan-2-yl]oxy}benzoate

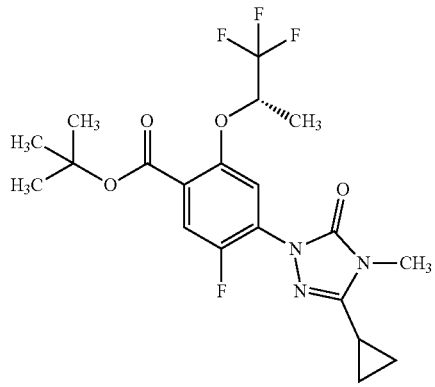 [SMILES: C[C@H](Oc1cc(-n2nc(C3CC3)n(C)c2=O)c(F)cc1C(=O)OC(C)(C)C)C(F)(F)F]

(2S)-1,1,1-trifluoropropan-2-ol (520 µl, 5.8 mmol) was dissolved in THF (5.8 mL) and cooled to −10° C. Potassium bis(trimethylsilyl)amide (1M solution in THF, 3.2 ml, 3.2 mmol) was added dropwise and the mixture was stirred at −10° C. for 1 h. tert-butyl 4-(3-cyclopropyl-4-methyl-5-oxo-4,5-dihydro-1H-1,2,4-triazol-1-yl)-2,5-difluorobenzoate (Intermediate 16, 926 mg, 2.64 mmol) was added as a solution in THF (2.6 mL). The mixture was slowly warmed to room temperature and stirred at room temperature overnight. The reaction was quenched with water and the mixture was extracted with DCM. The aqueous layer was extracted once more with water and the combined organic layers were washed with brine. The resulting solution was dried over magnesium sulfate and concentrated to yield the desired product (888 mg, 76% yield).

LC-MS (Method A): $R_t$=1.40 min; MS (ESIpos): m/z=446 [M+H]$^+$.

$^1$H-NMR (400 MHz, DMSO-d6) δ [ppm]: 0.000 (0.64), 1.384 (1.34), 1.400 (1.41), 1.479 (0.87), 1.500 (16.00), 3.303 (5.18), 3.322 (13.59), 7.563 (0.83), 7.588 (0.79).

Intermediate 32 tert-butyl 4-(3-cyclobutyl-4-methyl-5-oxo-4,5-dihydro-1H-1,2,4-triazol-1-yl)-5-fluoro-2-{[(2S)-1,1,1-trifluoropropan-2-yl]oxy}benzoate

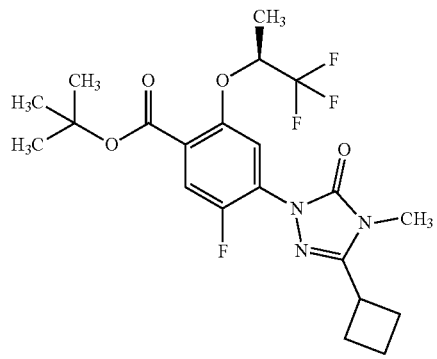 [SMILES: C[C@H](Oc1cc(-n2nc(C3CCC3)n(C)c2=O)c(F)cc1C(=O)OC(C)(C)C)C(F)(F)F]

Synthesized analogously to Intermediate 31 from Intermediate 20 and (2S)-1,1,1-trifluoropropan-2-ol LC-MS (Method A): $R_t$=1.47 min; MS (ESIpos): m/z=460 [M+H]$^+$.

Intermediate 33 tert-butyl 4-(4-cyclopropyl-3-methyl-5-oxo-4,5-dihydro-1H-1,2,4-triazol-1-yl)-5-fluoro-2-{[(2S)-1,1,1-trifluoropropan-2-yl]oxy}benzoate

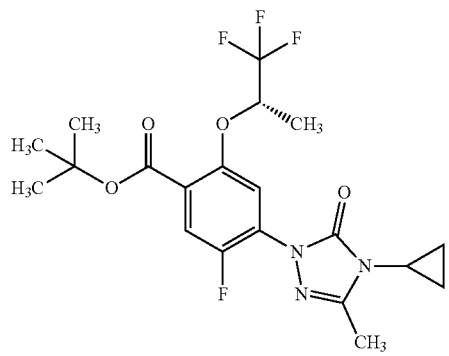 [SMILES: Cc1nn(-c2cc(O[C@@H](C)C(F)(F)F)c(C(=O)OC(C)(C)C)cc2F)c(=O)n1C1CC1]

Synthesized analogously to Intermediate 31 from Intermediate 18 and (2S)-1,1,1-trifluoropropan-2-ol.

Intermediate 34 tert-butyl 4-(4-cyclopropyl-3-ethyl-5-oxo-4,5-dihydro-1H-1,2,4-triazol-1-yl)-5-fluoro-2-{[(2S)-1,1,1-trifluoropropan-2-yl]oxy}benzoate

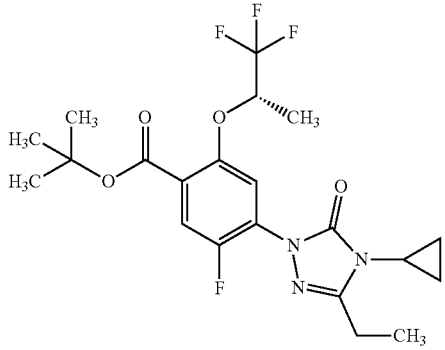 [SMILES: CCc1nn(-c2cc(O[C@@H](C)C(F)(F)F)c(C(=O)OC(C)(C)C)cc2F)c(=O)n1C1CC1]

Synthesized analogously to Intermediate 31 from Intermediate 19 and (2S)-1,1,1-trifluoropropan-2-ol.

Intermediate 35 tert-butyl 4-(3-cyclopropyl-4-ethyl-5-oxo-4,5-dihydro-1H-1,2,4-triazol-1-yl)-5-fluoro-2-{[(2S)-1,1,1-trifluoropropan-2-yl]oxy}benzoate

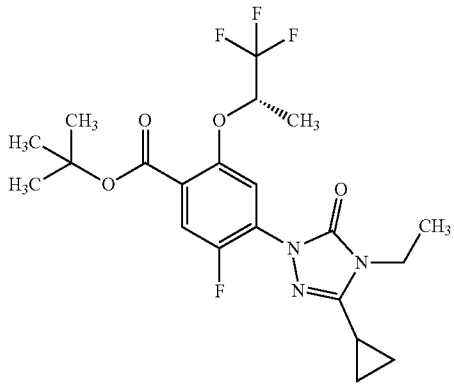 [SMILES: CCn1c(C2CC2)nn(-c2cc(O[C@@H](C)C(F)(F)F)c(C(=O)OC(C)(C)C)cc2F)c1=O]

Synthesized analogously to Intermediate 31 from Intermediate 17 and (2S)-1,1,1-trifluoropropan-2-ol.

Intermediate 36 tert-butyl 5-fluoro-4-[4-methyl-5-oxo-3-(trifluoromethyl)-4,5-dihydro-1H-1,2,4-triazol-1-yl]-2-{[(2S)-1,1,1-trifluoropropan-2-yl]oxy}benzoate

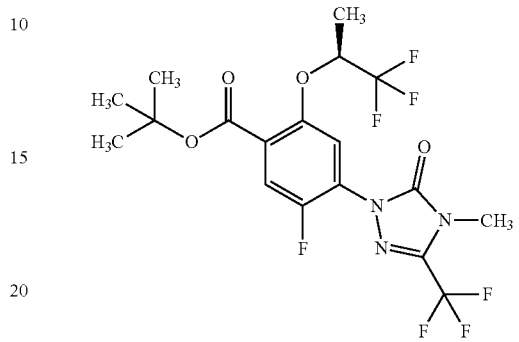

Synthesized analogously to Intermediate 31 from Intermediate 21 and (2S)-1,1,1-trifluoropropan-2-ol.

LC-MS (Method A): $R_t$=1.49 min; MS (ESIpos): m/z=418 [M+H-tBu]$^+$.

$^1$H-NMR (400 MHz, DMSO-d6) δ [ppm]: 1.404 (1.48), 1.420 (1.48), 1.510 (16.00), 3.382 (2.80), 7.669 (0.85), 7.694 (0.84).

Intermediate 37 tert-butyl 5-fluoro-4-[4-methyl-5-oxo-3-(propan-2-yl)-4,5-dihydro-1H-1,2,4-triazol-1-yl]-2-{[(2S)-1,1,1-trifluoropropan-2-yl]oxy}benzoate

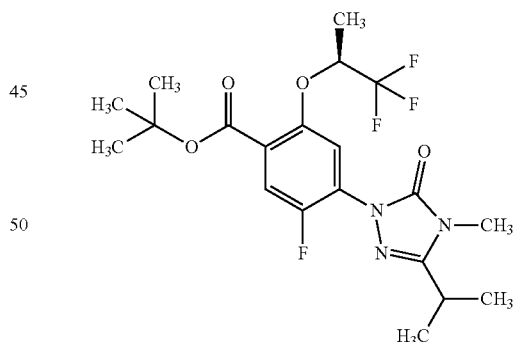

Synthesized analogously to Intermediate 31 from Intermediate 22 and (2S)-1,1,1-trifluoropropan-2-ol.

The crude product was triturated with a 1:1 mixture of water and ethanol, washed with water and dried in a vacuum oven.

LC-MS (Method A): $R_t$=1.42 min; MS (ESIpos): m/z=392 [M+H-tBu]$^+$.

$^1$H-NMR (400 MHz, DMSO-d6) δ [ppm]: 1.239 (4.32), 1.256 (4.42), 1.401 (1.43), 1.417 (1.43), 1.514 (16.00), 1.546 (0.64), 3.261 (5.15), 7.587 (0.85), 7.613 (0.82).

Intermediate 38 tert-butyl 4-{3-[(1S)-1-(benzyloxy)ethyl]-4-methyl-5-oxo-4,5-dihydro-1H-1,2,4-triazol-1-yl}-5-fluoro-2-{[(2S)-1,1,1-trifluoropropan-2-yl]oxy}benzoate

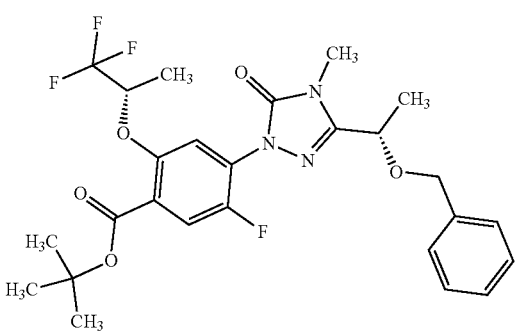 [SMILES: C[C@H](OCc1ccccc1)c1nn(-c2cc(O[C@@H](C)C(F)(F)F)c(C(=O)OC(C)(C)C)cc2F)c(=O)n1C]

Synthesized analogously to Intermediate 31 from Intermediate 23 and (2S)-1,1,1-trifluoropropan-2-ol.

LC-MS (Method A): Rt=1.52 min; MS (ESIpos): m/z=540 [M+H]$^+$.

Intermediate 39

5-fluoro-4-(4-isopropyl-3-methyl-5-oxo-1,2,4-triazol-1-yl)-2-[(1S)-2,2,2-trifluoro-1-methyl-ethoxy]benzoic acid

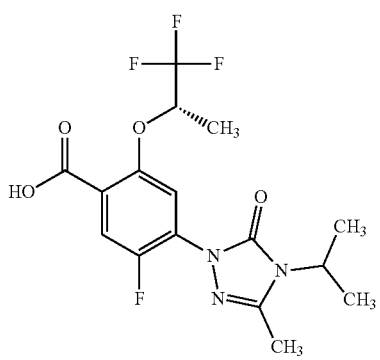 [SMILES: Cc1nn(-c2cc(O[C@@H](C)C(F)(F)F)c(C(=O)O)cc2F)c(=O)n1C(C)C]

To a −10° C. stirred solution of (S)-1,1,1-trifluoropropan-2-ol (702 mg, 6.15 mmol, 2.05 eq.) in anhydrous THF (6.15 mL, 1.00 mol/L) was added a 1.0 M solution of potassium hexamethyldisilazide in THF (3.30 mL, 3.30 mmol, 1.10 eq.) dropwise. The mixture was stirred at −10° C. for 1 h, after which the mixture was added dropwise to a −10° C. stirred solution of tert-butyl 2,5-difluoro-4-(4-isopropyl-3-methyl-5-oxo-4,5-dihydro-1H-1,2,4-triazol-1-yl)benzoate (1.06 g, 3.00 mmol, 1.00 eq.). The solution was stirred for 2 h at −10° C. followed by 2 days at room temperature and then concentrated under reduced pressure. Following column chromatography (hexanes/ethyl acetate), the residue was resuspended in a 4:1 mixture of dioxane:water (15.0 mL, 0.20 mol/L) and lithium hydroxide (1.08 g, 45.0 mmol, 15.0 eq.) was added. The resulting suspension was stirred at 70° C. for 2 d and cooled to room temperature. Water was added to the mixture wand washed with diethyl ether (2×). The aqueous layer was acidified to pH 2 with 1.0 M aqueous hydrochloric acid and extracted with diethyl ether (3×). The combined organic extracts were washed with brine, dried (magnesium sulfate) and concentrated under reduced pressure. The residue was purified by column chromatography (dichloromethane/methanol) to give the desired product (957 mg, 82%).

$^1$H NMR (400 MHz, CDCl$_3$) δ [ppm] 1.56 (d, 6H), 1.63 (d, 3H), 2.37 (s, 3H), 4.32 (sep, 1H), 4.89 (q, 1H), 7.53 (d, 1H), 8.00 (d, 1H).

MS (ESIpos): m/z=392 (M+H)$^+$.

Intermediate 40

4-(3-ethyl-4-methyl-5-oxo-4,5-dihydro-1H-1,2,4-triazol-1-yl)-5-fluoro-2-{[(2S)-1,1,1-trifluoro-propan-2-yl]oxy}benzoic acid

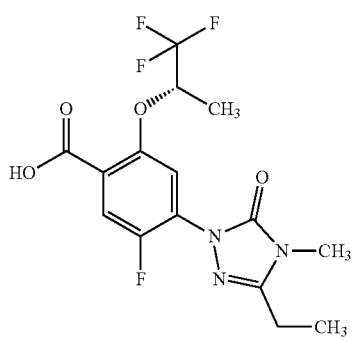 [SMILES: CCc1nn(-c2cc(O[C@@H](C)C(F)(F)F)c(C(=O)O)cc2F)c(=O)n1C]

Synthesized analogously to Intermediate 39 from Intermediate 15 and (S)-1,1,1-trifluoropropan-2-ol.

LC-MS (Method A): R$_t$=0.93 min; MS (ESIpos): m/z=378.5 [M+H]$^+$.

Intermediate 41

5-fluoro-4-(4-isopropyl-3-methyl-5-oxo-1,2,4-triazol-1-yl)-2-[(1S)-1-phenylethoxy]benzoic acid

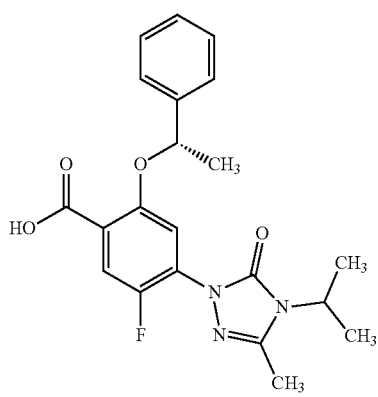 [SMILES: Cc1nn(-c2cc(O[C@@H](C)c3ccccc3)c(C(=O)O)cc2F)c(=O)n1C(C)C]

Synthesized analogously to Intermediate 39 from Intermediate 14 and (1S)-1-phenylethanol.

$^1$H NMR (300 MHz, CDCl$_3$) δ [ppm] 1.53 (d, 3H), 1.80 (d, 3H), 2.33 (s, 3H), 4.30 (sep, 1H), 5.61 (q, 1H), 7.30-7.40 (m, 5H), 7.45 (d, 1H), 7.97 (d, 1H), 11.1 (b, 1H).

MS (ESIpos): m/z=400 (M+H)$^+$.

Intermediate 42

5-fluoro-4-(4-isopropyl-3-methyl-5-oxo-1,2,4-tri-azol-1-yl)-2-[(1S)-1-methylbutoxy]benzoic acid

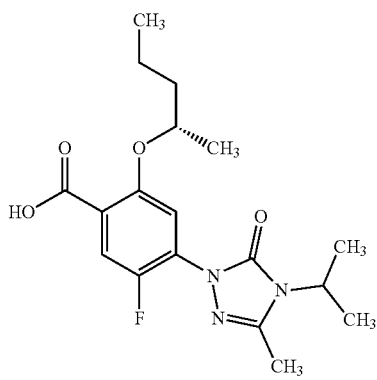 [SMILES: CCC[C@H](C)Oc1cc(-n2nc(C)n(C(C)C)c2=O)c(F)cc1C(=O)O]

Synthesized analogously to Intermediate 39 from Intermediate 14 and (2S)-pentan-2-ol.

$^1$H NMR (300 MHz, CDCl$_3$) € [ppm] 0.97 (t, 3H), 1.37-1.54 (m, 2H), 1.44 (d, 3H), 1.55 (d, 6H), 1.64-1.92 (m, 2H), 2.37 (s, 3H), 4.33 (sep, 1H), 4.64-4.77 (m, 1H), 7.45 (d, 1H), 8.01 (d, 1H), 11.1 (b, 1H).

MS (ESIpos): m/z=366 (M+H)$^+$.

Intermediate 43

4-(3-ethyl-4-methyl-5-oxo-4,5-dihydro-1H-1,2,4-triazol-1-yl)-5-fluoro-2-[(1S)-1-phenylethoxy]ben-zoic acid

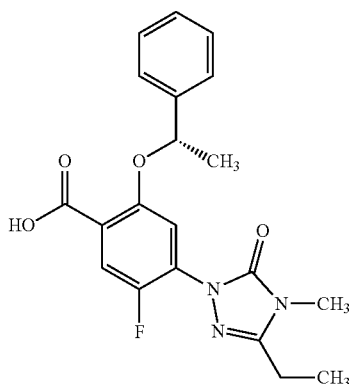

Synthesized analogously to Intermediate 39 from Intermediate 15 and (1S)-1-phenylethanol.

LC-MS (Method A): R$_t$=1.03 min.
MS (ESIpos): m/z=386 [M+H]$^+$.

Intermediate 44

4-(3-ethyl-4-methyl-5-oxo-1,2,4-triazol-1-yl)-5-fluoro-2-[(1S)-1-methylbutoxy]benzoic acid

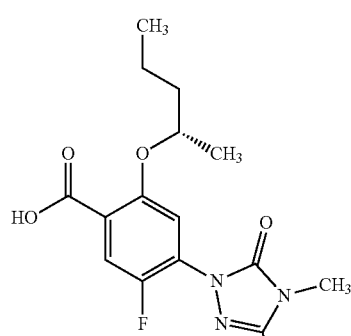

Synthesized analogously to Intermediate 39 from Intermediate 15 and (2S)-pentan-2-ol.

$^1$H NMR (400 MHz, CDCl$_3$) δ [ppm] 0.97 (t, 3H), 1.35 (t, 3H), 1.39-1.58 (m, 2H), 1.43 (d, 3H), 1.66-1.77 (m, 1H), 1.79-1.91 (m, 1H), 2.64 (q, 2H), 3.32 (s, 3H), 4.64-4.73 (m, 1H), 7.43 (d, 1H), 8.02 (d, 1H), 11.1 (b, 1H).

MS (ESIpos): m/z=352 (M+H)$^+$.

Intermediate 45

4-(3-ethyl-4-methyl-5-oxo-1,2,4-triazol-1-yl)-5-fluoro-2-[(1S)-1-methylbutoxy]benzoic acid

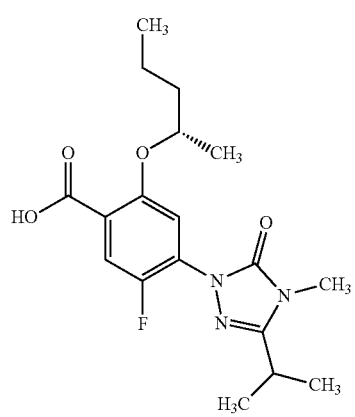 [SMILES: CCC[C@H](C)Oc1cc(-n2nc(C(C)C)n(C)c2=O)c(F)cc1C(=O)O]

Synthesized analogously to Intermediate 39 from Intermediate 22 and (2S)-pentan-2-ol using sodium hydride as a base and DMF as the solvent.

Intermediate 46

4-(3-ethyl-4-methyl-5-oxo-4,5-dihydro-1H-1,2,4-triazol-1-yl)-5-fluoro-2-[(2S)-pent-4-en-2-yloxy]benzoic acid

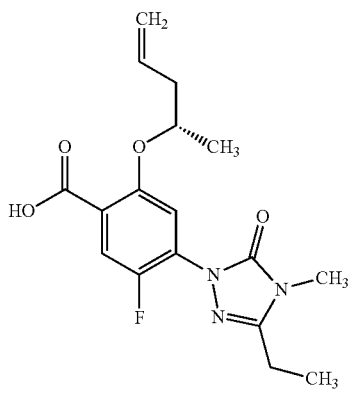 [SMILES: C=CC[C@H](C)Oc1cc(-n2nc(CC)n(C)c2=O)c(F)cc1C(=O)O]

Synthesized analogously to Intermediate 39 from Intermediate 15 and (2S)-pent-4-en-2-ol using sodium hydride as a base and DMF as the solvent.

Intermediate 47

2-(1-cyclohexylethoxy)-4-{3-[1-(1-ethoxyethoxy)ethyl]-4-methyl-5-oxo-4,5-dihydro-1H-1,2,4-triazol-1-yl}-5-fluorobenzoic acid, Mixture of Stereoisomers

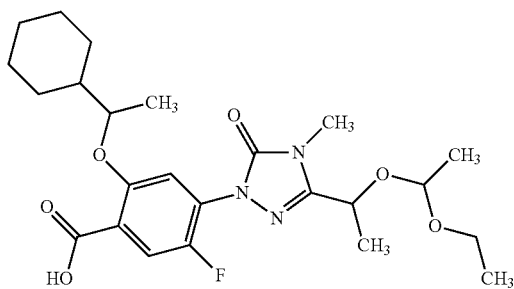 [SMILES: CCOC(C)OC(C)c1nn(-c2cc(OC(C)C3CCCCC3)c(C(=O)O)cc2F)c(=O)n1C]

Synthesized analogously to Intermediate 39 from Intermediate 24 and 1-cyclohexylethanol using sodium hydride as a base and DMF as the solvent.

Intermediate 48

4-{3-[(benzyloxy)methyl]-4-methyl-5-oxo-4,5-dihydro-1H-1,2,4-triazol-1-yl}-2-(1-cyclohexylethoxy)-5-fluorobenzoic acid, Mixture of Stereoisomers

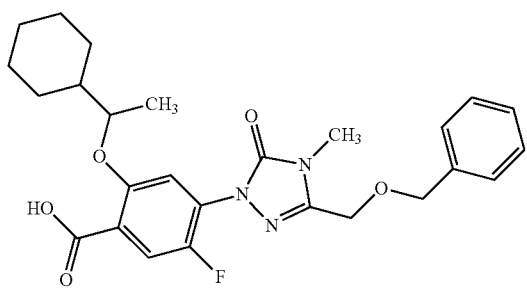 [SMILES: CC(Oc1cc(-n2nc(COCc3ccccc3)n(C)c2=O)c(F)cc1C(=O)O)C1CCCCC1]

Synthesized analogously to Intermediate 39 from Intermediate 26 and 1-cyclohexylethanol using sodium hydride as a base and DMF as the solvent.

Intermediate 49

4-(3-{[(tert-butoxycarbonyl)(methyl)amino]methyl}-4-methyl-5-oxo-4,5-dihydro-1H-1,2,4-triazol-1-yl)-5-fluoro-2-[(2S)-pentan-2-yloxy]benzoic acid

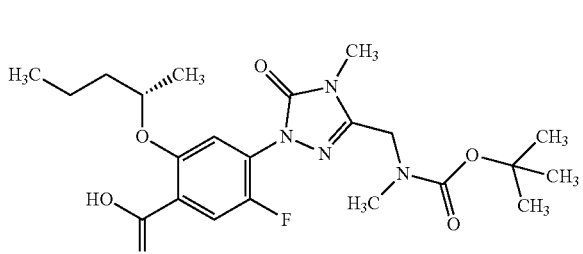

Synthesized analogously to Intermediate 39 from Intermediate 28 and (2S)-pentan-2-ol using sodium hydride as a base and DMF as the solvent.

Intermediate 50

4-{3-[(dibenzylamino)methyl]-4-methyl-5-oxo-4,5-dihydro-1H-1,2,4-triazol-1-yl}-5-fluoro-2-[(2S)-pentan-2-yloxy]benzoic acid

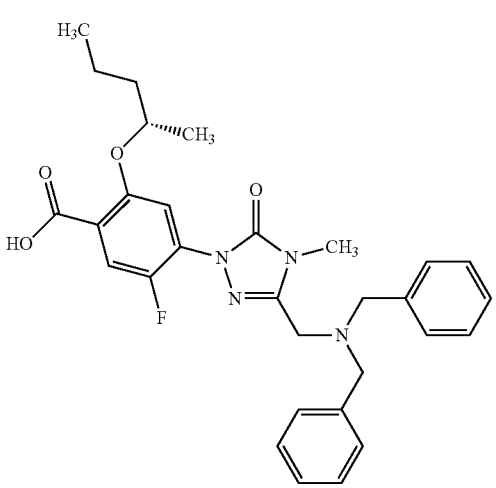 [SMILES: CCC[C@H](C)Oc1cc(-n2nc(CN(Cc3ccccc3)Cc3ccccc3)n(C)c2=O)c(F)cc1C(=O)O]

Synthesized analogously to Intermediate 39 from Intermediate 30 and (2S)-pentan-2-ol using sodium hydride as a base and DMF as the solvent.

MS: m/z=533 (M+H)$^+$.

Intermediate 51

4-{3-[1-(1-ethoxyethoxy)ethyl]-4-methyl-5-oxo-4,5-dihydro-1H-1,2,4-triazol-1-yl}-5-fluoro-2-[(2S)-pentan-2-yloxy]benzoic acid, Mixture of Stereoisomers

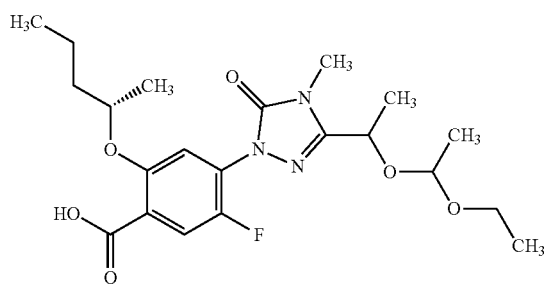 [SMILES: CCC[C@H](C)Oc1cc(-n2nc(C(C)OC(C)OCC)n(C)c2=O)c(F)cc1C(=O)O]

Synthesized analogously to Intermediate 39 from Intermediate 24 and (2S)-pentan-2-ol using sodium hydride as a base and DMF as the solvent.

Intermediate 52

2-(1-cyclohexylethoxy)-4-{3-[(1R)-1-(dibenzylamino)ethyl]-4-methyl-5-oxo-4,5-dihydro-1H-1,2,4-triazol-1-yl}-5-fluorobenzoic acid, Mixture of Stereoisomers

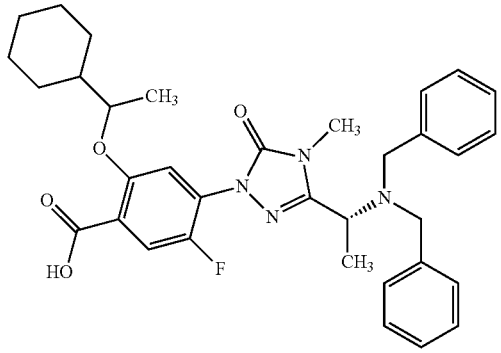 [SMILES: CC(Oc1cc(-n2nc([C@@H](C)N(Cc3ccccc3)Cc3ccccc3)n(C)c2=O)c(F)cc1C(=O)O)C1CCCCC1]

tert-butyl 4-{3-[(1R)-1-(dibenzylamino)ethyl]-4-methyl-5-oxo-4,5-dihydro-1H-1,2,4-triazol-1-yl}-2,5-difluorobenzoate (Intermediate 30, 334 mg, 625 µmol) and (1S)-1-cyclohexylethanol (130 mg, 1.12 mmol) were dissolved in DMF (10 ml), sodium hydride (45.0 mg, 60% in mineral oil, 1.12 mmol) was added, and the mixture was stirred at 100° C. for 6 h. The solvent was removed and the product was purified using prepTLC to yield 120 mg (60% yield).

Intermediate 53

4-(3-cyclopropyl-4-ethyl-5-oxo-4,5-dihydro-1H-1,2,4-triazol-1-yl)-5-fluoro-2-{[(2S)-1,1,1-trifluoropropan-2-yl]oxy}benzoic acid

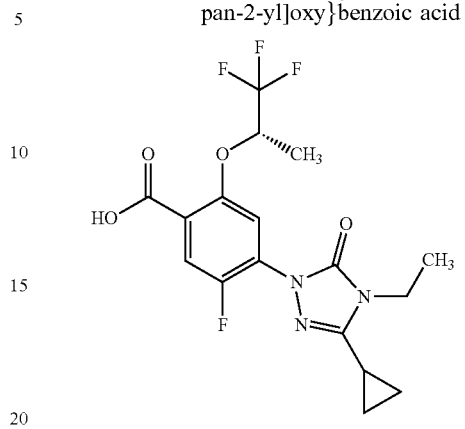

tert-butyl 4-(3-cyclopropyl-4-ethyl-5-oxo-4,5-dihydro-1H-1,2,4-triazol-1-yl)-5-fluoro-2-{[(2S)-1,1,1-trifluoropropan-2-yl]oxy}benzoate (Intermediate 35, 3.84 g, 8.36 mmol) was dissolved in dichloromethane (12 ml). Trifluoroacetic acid (12 ml, 160 mmol) was added dropwise and the mixture was stirred at room temperature for 1 h. The reaction mixture was concentrated and the crude product was purified by column chromatography (dichloromethane/methanol) to give the desired product (2.02 g, 60% yield).

LC-MS (Method A): $R_t$=1.06 min; MS (ESIpos): m/z=404 [M+H]$^+$.

$^1$H-NMR (400 MHz, DMSO-d6) δ [ppm]: 0.761 (0.65), 0.766 (0.71), 0.779 (0.69), 0.866 (0.78), 0.887 (2.00), 0.898 (4.51), 0.904 (5.19), 0.911 (4.78), 0.916 (4.67), 0.925 (1.99), 0.976 (1.92), 0.984 (4.42), 0.991 (3.32), 0.996 (2.93), 1.005 (4.74), 1.011 (3.26), 1.023 (1.17), 1.165 (1.17), 1.184 (2.45), 1.201 (1.21), 1.260 (7.20), 1.278 (16.00), 1.296 (7.20), 1.394 (12.36), 1.410 (12.63), 1.422 (1.25), 1.469 (0.96), 1.486 (0.95), 1.996 (0.78), 2.009 (1.52), 2.017 (1.65), 2.029 (2.86), 2.038 (1.16), 2.042 (1.56), 2.050 (1.36), 2.063 (0.62), 2.326 (0.75), 2.522 (2.24), 2.668 (0.79), 3.654 (1.12), 3.671 (1.09), 3.787 (2.10), 3.805 (6.60), 3.823 (6.47), 3.841 (1.95), 5.190 (0.84), 5.206 (2.04), 5.222 (2.61), 5.238 (1.94), 5.253 (0.87), 5.757 (0.82), 7.466 (4.81), 7.481 (4.73), 7.621 (5.56), 7.648 (5.36).

Intermediate 54

4-(3-cyclopropyl-4-methyl-5-oxo-4,5-dihydro-1H-1,2,4-triazol-1-yl)-5-fluoro-2-{[(2S)-1,1,1-trifluoropropan-2-yl]oxy}benzoic acid

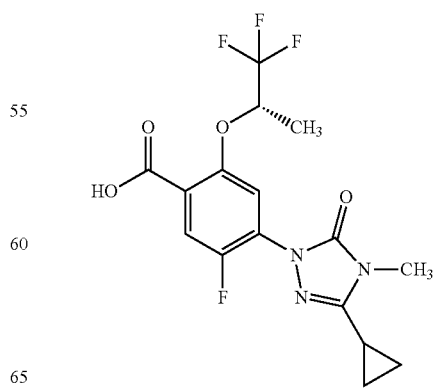

Synthesized analogously to Intermediate 53 from Intermediate 31.

LC-MS (Method A): $R_t$=1.98 min; MS (ESIpos): m/z=390 [M+H]$^+$.

$^1$H-NMR (500 MHz, DMSO-d6) δ [ppm]: 0.874 (1.67), 0.884 (5.75), 0.888 (6.08), 0.893 (5.75), 0.898 (6.38), 0.905 (2.85), 0.966 (2.38), 0.974 (6.11), 0.979 (4.77), 0.983 (3.45), 0.990 (6.25), 0.995 (4.79), 1.005 (1.73), 1.038 (2.63), 1.052 (5.18), 1.066 (2.47), 1.234 (1.15), 1.291 (1.86), 1.305 (3.84), 1.320 (1.73), 1.395 (15.07), 1.408 (16.00), 1.420 (0.93), 1.471 (0.74), 1.484 (0.71), 1.508 (0.88), 1.957 (1.10), 1.967 (2.05), 1.974 (2.30), 1.977 (1.23), 1.984 (4.03), 1.990 (1.40), 1.994 (1.97), 2.000 (2.03), 2.010 (0.93), 2.514 (7.45), 2.518 (6.08), 2.522 (4.52), 3.159 (1.01), 3.275 (0.82), 3.416 (0.99), 3.430 (2.88), 3.444 (2.77), 3.457 (0.93), 3.857 (2.96), 4.398 (0.58), 4.412 (1.42), 4.426 (1.34), 5.182 (0.93), 5.194 (2.27), 5.207 (3.10), 5.220 (2.19), 5.233 (0.85), 5.758 (2.14), 7.454 (6.19), 7.466 (6.19), 7.633 (7.34), 7.654 (6.99).

Intermediate 55

4-(3-cyclobutyl-4-methyl-5-oxo-4,5-dihydro-1H-1,2,4-triazol-1-yl)-5-fluoro-2-{[(2S)-1,1,1-trifluoropropan-2-yl]oxy}benzoic acid

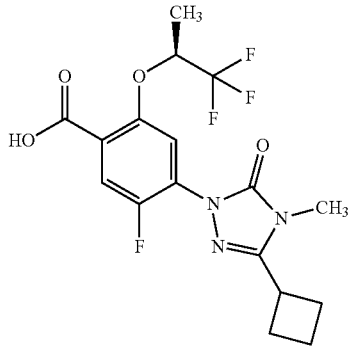 [SMILES: C[C@H](Oc1cc(-n2nc(C3CCC3)n(C)c2=O)c(F)cc1C(=O)O)C(F)(F)F]

Synthesized analogously to Intermediate 53 from Intermediate 32.

LC-MS (Method A): $R_t$=1.08 min; MS (ESIpos): m/z=404 [M+H]$^+$.

$^1$H-NMR (400 MHz, DMSO-d6) δ [ppm]: 1.405 (4.83), 1.421 (4.84), 1.515 (0.81), 1.531 (4.45), 2.046 (0.89), 2.068 (0.80), 2.073 (0.81), 2.292 (2.66), 2.301 (1.18), 2.304 (1.38), 2.313 (3.23), 2.327 (1.01), 2.331 (1.15), 2.334 (1.16), 2.338 (0.93), 3.138 (16.00), 3.597 (0.80), 3.599 (0.84), 3.618 (1.18), 3.620 (1.26), 3.638 (0.74), 3.641 (0.79), 5.213 (0.89), 5.229 (1.13), 5.245 (0.83), 7.511 (2.12), 7.526 (2.10), 7.652 (2.70), 7.678 (2.58).

Intermediate 56

4-(4-cyclopropyl-3-methyl-5-oxo-4,5-dihydro-1H-1,2,4-triazol-1-yl)-5-fluoro-2-{[(2S)-1,1,1-trifluoropropan-2-yl]oxy}benzoic acid

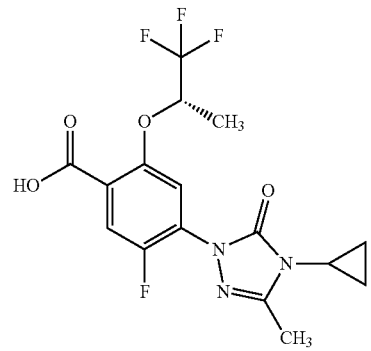 [SMILES: Cc1nn(-c2cc(O[C@@H](C)C(F)(F)F)c(C(=O)O)cc2F)c(=O)n1C1CC1]

Synthesized analogously to Intermediate 53 from Intermediate 33.

LC-MS (Method A): $R_t$=0.95 min; MS (ESIpos): m/z=389 [M+H]$^+$.

Intermediate 57

5-fluoro-4-[4-methyl-5-oxo-3-(trifluoromethyl)-4,5-dihydro-1H-1,2,4-triazol-1-yl]-2-{[(2S)-1,1,1-trifluoropropan-2-yl]oxy}benzoic acid

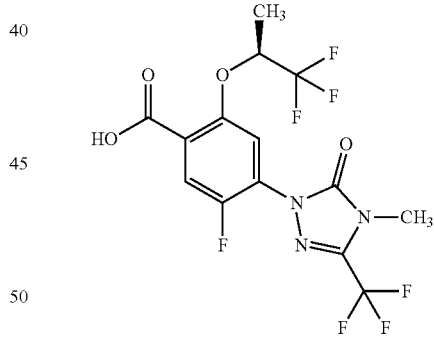

Synthesized analogously to Intermediate 53 from Intermediate 36.

LC-MS (Method A): $R_t$=1.11 min; MS (ESIpos): m/z=418 [M+H]$^+$.

$^1$H-NMR (400 MHz, DMSO-d6) δ [ppm]: 0.000 (1.09), 1.406 (8.28), 1.421 (8.32), 1.510 (0.82), 1.522 (3.20), 2.510 (1.29), 2.514 (0.89), 3.382 (16.00), 5.177 (0.57), 5.193 (1.41), 5.209 (1.84), 5.225 (1.33), 5.747 (0.96), 6.957 (1.06), 7.085 (1.16), 7.213 (1.05), 7.574 (3.58), 7.590 (3.55), 7.716 (4.50), 7.741 (4.39).

Intermediate 58

4-(4-cyclopropyl-3-ethyl-5-oxo-4,5-dihydro-1H-1,2,4-triazol-1-yl)-5-fluoro-2-{[(2S)-1,1,1-trifluoropropan-2-yl]oxy}benzoic acid

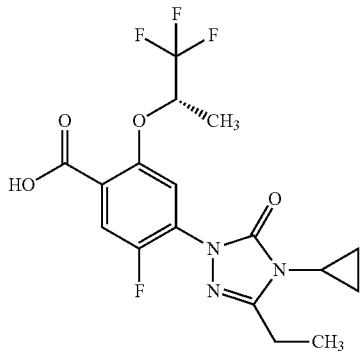 [SMILES: CCc1nn(-c2cc(O[C@@H](C)C(F)(F)F)c(C(=O)O)cc2F)c(=O)n1C1CC1]

Synthesized analogously to Intermediate 53 from Intermediate 34.

LC-MS (Method A): $R_t$=1.04 min; MS (ESIpos): m/z=403 [M+H]$^+$.

Intermediate 59

5-fluoro-4-[4-methyl-5-oxo-3-(propan-2-yl)-4,5-dihydro-1H-1,2,4-triazol-1-yl]-2-{[(2S)-1,1,1-trifluoropropan-2-yl]oxy}benzoic acid

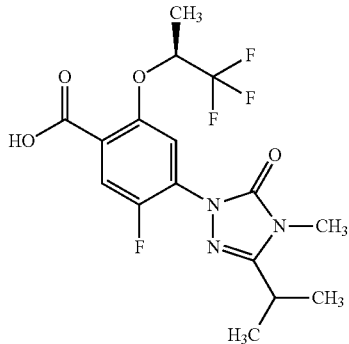 [SMILES: CC(C)c1nn(-c2cc(O[C@@H](C)C(F)(F)F)c(C(=O)O)cc2F)c(=O)n1C]

Synthesized analogously to Intermediate 53 from Intermediate 37.

LC-MS (Method A): $R_t$=1.03 min; MS (ESIpos): m/z=392 [M+H]$^+$.

$^1$H-NMR (400 MHz, DMSO-d6) δ [ppm]: 1.171 (0.92), 1.224 (3.60), 1.232 (1.87), 1.237 (15.86), 1.249 (2.00), 1.254 (16.00), 1.403 (4.62), 1.418 (4.66), 1.735 (1.21), 1.986 (1.58), 2.083 (1.04), 3.015 (1.16), 3.032 (1.58), 3.050 (1.12), 3.254 (1.33), 5.204 (0.80), 5.220 (1.04), 5.237 (0.74), 5.756 (0.69), 7.492 (2.08), 7.507 (2.06), 7.648 (2.70), 7.674 (2.59), 8.132 (4.73).

Intermediate 60

4-{3-[(1S)-1-(benzyloxy)ethyl]-4-methyl-5-oxo-4,5-dihydro-1H-1,2,4-triazol-1-yl}-5-fluoro-2-{[(2S)-1,1,1-trifluoropropan-2-yl]oxy}benzoic acid

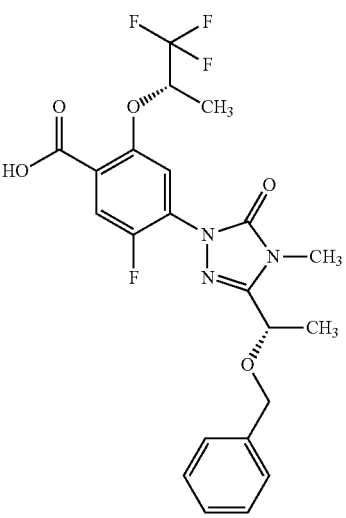 [SMILES: C[C@H](OCc1ccccc1)c1nn(-c2cc(O[C@@H](C)C(F)(F)F)c(C(=O)O)cc2F)c(=O)n1C]

Synthesized analogously to Intermediate 53 from Intermediate 38.

LC-MS (Method A): Rt=1.21 min; MS (ESIpos): m/z=484 [M+H]$^+$.

Intermediate 61

5-fluoro-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzoic acid

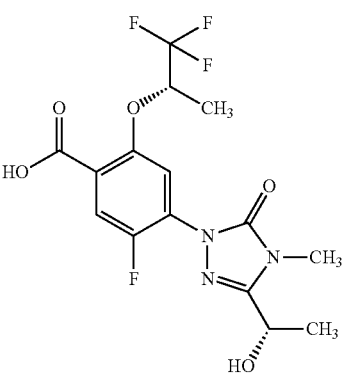 [SMILES: C[C@H](O)c1nn(-c2cc(O[C@@H](C)C(F)(F)F)c(C(=O)O)cc2F)c(=O)n1C]

4-{3-[(1S)-1-(benzyloxy)ethyl]-4-methyl-5-oxo-4,5-dihydro-1H-1,2,4-triazol-1-yl}-5-fluoro-2-{[(2S)-1,1,1-trifluoropropan-2-yl]oxy}benzoic acid (Intermediate 60, 866 mg, 1.79 mmol) was dissolved in ethanol (20 mL). Palladium (10% on carbon, 191 mg, 179 μmol) and ammonium formate (1.69 g, 26.9 mmol) was added and the mixture was stirred at 80° C. for 3 h. The mixture was filtered and concentrated. The residue was purified by flash column chromatography (DCM/MeOH 0-90%) to yield the desired product (540 mg, 76% yield).

LC-MS (Method A): Rt=0.80 min; MS (ESIpos): m/z=394 [M+H]⁺.

Intermediate 62

4-bromo-5-fluoro-2-{[(2S)-1,1,1-trifluoropropan-2-yl]oxy}benzonitrile

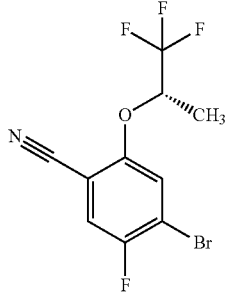 [SMILES: C[C@H](Oc1cc(Br)c(F)cc1C#N)C(F)(F)F]

To a stirred suspension of 4-bromo-2,5-difluorobenzonitrile (91 g, 417 mmol) and potassium carbonate (173 g, 1.25 mol) in N,N-dimethylformamide (910 ml) was added (S)-1,1,1-trifluoropropanol [CAS 3539-97-7] dropwise (52.4 g, 460 mmol). The resulting mixture was heated at 70° C. for 15 hours and cooled to room temperature. The reaction was concentrated and the residue was diluted with water. The aqueous solution was extracted with DCM (3×). The combined organic washes were washed with brine, dried over sodium sulfate, filtered, and concentrated under reduced pressure to give an oil (136.6 g). The residue was triturated with a mixture of hexanes and toluene (9:1, 200 mL) to give the desired product as a white solid (90.3 g, 93% purity, 64% yield).

LC-MS (Method A): $R_t$=1.29 min; MS (ESIpos): m/z=312.0 [M+H]⁺.

¹H-NMR (400 MHz, CHLOROFORM-d) δ [ppm]: 1.511 (4.41), 1.531 (15.64), 1.533 (16.00), 1.548 (15.84), 1.550 (15.83), 4.566 (1.08), 4.581 (2.68), 4.597 (3.18), 4.612 (2.62), 4.626 (1.01), 7.194 (5.27), 7.207 (7.60), 7.220 (7.57).

Intermediate 63

4-bromo-5-fluoro-2-[(2S)-pentan-2-yloxy]benzonitrile

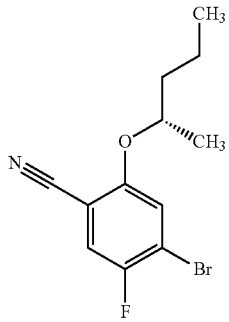 [SMILES: CCC[C@H](C)Oc1cc(Br)c(F)cc1C#N]

Synthesized analogously to Intermediate 62 from 4-bromo-2,5-difluorobenzonitrile and (S)-2-pentanol.

¹H NMR (400 MHz, DMSO-d6) δ=7.92 (d, J=8.1 Hz, 1H), 7.70 (d, J=5.6 Hz, 1H), 4.70 (sxt, J=6.0 Hz, 1H), 1.71-1.49 (m, 2H), 1.46-1.31 (m, 2H), 1.25 (d, J=5.8 Hz, 3H), 0.90 (t, J=7.4 Hz, 3H).

Intermediate 64

4-bromo-2-{[(2S)-1,1,1-trifluoropropan-2-yl]oxy}benzonitrile

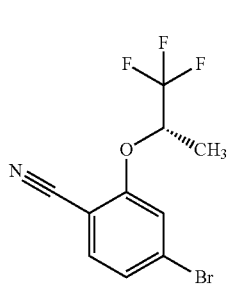 [SMILES: C[C@H](Oc1cc(Br)ccc1C#N)C(F)(F)F]

Synthesized analogously to Intermediate 62 from 4-bromo-2-fluorobenzonitrile and (S)-1,1,1-trifluoropropanol.

LC-MS (Method A): $R_t$=1.27 min; MS (ESIpos): m/z=294 [M+H]⁺.

¹H-NMR (500 MHz, CHLOROFORM-d) δ [ppm]: 1.368 (3.65), 1.415 (15.76), 1.427 (16.00), 1.428 (15.81), 1.984 (0.94), 4.525 (1.13), 4.538 (2.65), 4.550 (3.35), 4.562 (2.58), 4.574 (1.03), 7.019 (7.92), 7.022 (8.28), 7.073 (9.59), 7.089 (5.49), 7.092 (5.57), 7.105 (7.20), 7.108 (6.95).

Intermediate 65

4-bromo-5-fluoro-2-{[(2S)-1,1,1-trifluoropropan-2-yl]oxy}benzoic acid

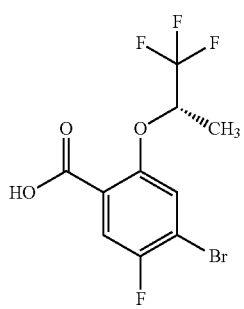 [SMILES: C[C@H](Oc1cc(Br)c(F)cc1C(=O)O)C(F)(F)F]

To a solution of 4-bromo-5-fluoro-2-{[(2S)-1,1,1-trifluoropropan-2-yl]oxy}benzonitrile (Intermediate 62, 27.4 g, 87.9 mmol) in ethanol (90 ml) was added aqueous sodium hydroxide (2 N, 140 ml) and the resulting mixture was heated to 90° C. for 20 hours. The resulting solution was cooled to room temperature, diluted with water, and extracted with dichloromethane. The aqueous phase was acidified with 2 N aqueous hydrochloric acid (pH 2) upon which a white solid precipitated. The suspension was stirred for further 15 minutes, the solid was filtered off, washed with water and dried in vacuo. to yield an off-white solid (25.97 g, 89%), which was used for the next step without further purification.

LC-MS (Method A): $R_t$=1.16 min; MS (ESIpos): m/z=331 [M+H]$^+$.

$^1$H-NMR (400 MHz, DMSO-d6) δ [ppm]: 1.396 (15.96), 1.411 (16.00), 1.469 (0.69), 1.484 (0.45), 2.518 (3.48), 2.523 (2.36), 5.288 (1.19), 5.304 (2.89), 5.320 (3.73), 5.336 (2.70), 5.352 (1.05), 7.612 (11.35), 7.634 (11.12), 7.743 (7.88), 7.757 (7.91).

Intermediate 66

4-bromo-5-fluoro-2-[(2S)-pentan-2-yloxy]benzoic acid

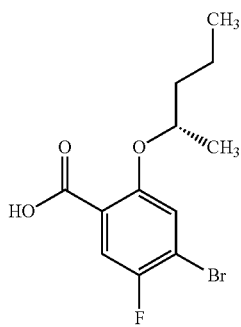 [SMILES: CCC[C@H](C)Oc1cc(Br)c(F)cc1C(=O)O]

Synthesized analogously to Intermediate 65 from Intermediate 63.

LC-MS (Method A): $R_t$=1.33 min; MS (ESIneg): m/z=303 [M−H]$^-$.

$^1$H-NMR (400 MHz, DMSO-d6) δ [ppm]: 0.858 (6.86), 0.876 (16.00), 0.894 (8.19), 1.192 (14.64), 1.208 (14.81), 1.322 (0.52), 1.339 (1.03), 1.346 (0.95), 1.363 (2.02), 1.381 (2.40), 1.397 (2.08), 1.418 (1.35), 1.437 (0.69), 1.464 (0.71), 1.478 (0.92), 1.486 (0.48), 1.497 (1.30), 1.512 (1.59), 1.520 (1.07), 1.526 (1.00), 1.534 (1.18), 1.549 (0.63), 1.570 (0.87), 1.585 (1.27), 1.594 (0.98), 1.600 (1.20), 1.609 (1.21), 1.619 (0.91), 1.624 (0.96), 1.633 (0.59), 1.643 (0.65), 4.519 (1.19), 4.534 (2.20), 4.549 (2.18), 4.564 (1.14), 7.466 (4.77), 7.480 (4.70), 7.524 (5.49), 7.545 (5.40).

Intermediate 67

4-bromo-2-{[(2S)-1,1,1-trifluoropropan-2-yl]oxy}benzoic acid

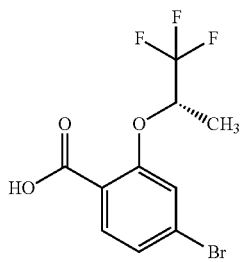 [SMILES: C[C@H](Oc1cc(Br)ccc1C(=O)O)C(F)(F)F]

To a solution of 4-bromo-2-{[(2S)-1,1,1-trifluoropropan-2-yl]oxy}benzonitrile (Intermediate 64, 5.00 g, 17.0 mmol) in ethanol (18 ml) was added aqueous sodium hydroxide (2 N, 28 ml) and the resulting mixture was heated to 90° C. for 21 hours. The resulting solution was cooled to room temperature, diluted with water, and extracted with dichloromethane. The aqueous phase was acidified with 2 N aqueous hydrochloric acid (pH 2) upon which a white solid precipitated. The suspension was stirred for further 15 minutes, the solid was filtered off, washed with water and dried in vacuo. to yield white solid 4.76 g (89%), which was used for the next step without further purification.

LC-MS (Method A): $R_t$=1.15 min; MS (ESIneg): m/z=311 [M−H]$^-$.

$^1$H-NMR (400 MHz, DMSO-d6) δ [ppm]: 1.403 (15.87), 1.419 (16.00), 2.518 (2.74), 2.523 (1.80), 5.352 (1.13), 5.368 (2.86), 5.383 (3.71), 5.400 (2.72), 5.416 (1.03), 7.299 (6.49), 7.304 (6.51), 7.320 (6.97), 7.324 (7.05), 7.584 (13.85), 7.596 (8.97), 7.600 (8.84), 7.605 (12.52).

Intermediate 68

4-bromo-5-fluoro-2-{[(2S)-1,1,1-trifluoropropan-2-yl]oxy}benzoyl chloride

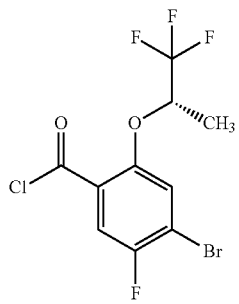 [SMILES: C[C@H](Oc1cc(Br)c(F)cc1C(=O)Cl)C(F)(F)F]

To a solution of 4-bromo-5-fluoro-2-{[(2S)-1,1,1-trifluoropropan-2-yl]oxy}benzoic acid (Intermediate 65, 15.0 g, 45.3 mmol) in dichloromethane (230 ml) was added N,N-dimethylformamide (350 μl), followed by dropwise addition of ethanedioyl dichloride (4.7 ml, 54 mmol). The reaction mixture was stirred at room temperature for one hour, and concentrated under reduced pressure. The title compound was obtained as brown oil (15.84 g, quantitative), which was used for the next step without purification. For analytic, a small amount of the product was treated with methanol, to yield the corresponding methyl ester, which was detected by LC-MS.

LC-MS (Method A) [methyl ester]: $R_t$=1.36 min; MS (ESIpos): m/z=345 [M+H]$^+$.

Intermediate 69

4-bromo-2-{[(2S)-1,1,1-trifluoropropan-2-yl]oxy}benzoyl chloride

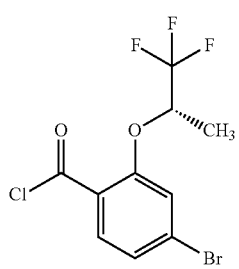 [SMILES: C[C@H](Oc1cc(Br)ccc1C(=O)Cl)C(F)(F)F]

To a solution of 4-bromo-2-{[(2S)-1,1,1-trifluoropropan-2-yl]oxy}benzoic acid (2.6 g, 8.3 mmol) in dichloromethane (42 ml) was added N,N-dimethylformamide (870 µl), followed by dropwise addition of ethanedioyl dichloride (870 µl, 10 mmol). The reaction mixture was stirred at room temperature for one hour, and concentrated under reduced pressure. The title compound was obtained as brown oil (15.84 g, quantitative), which was used for the next step without purification. For analytic, a small amount of the product was treated with methanol, to yield the corresponding methyl ester, which was detected by LC-MS.

LC-MS (Method A) [methyl ester]: $R_t$=1.33 min; MS (ESIpos): m/z=327 $[M+H]^+$.

Intermediate 70

4-bromo-N-(2,6-difluorophenyl)-5-fluoro-2-{[(2S)-1,1,1-trifluoropropan-2-yl]oxy}benzamide

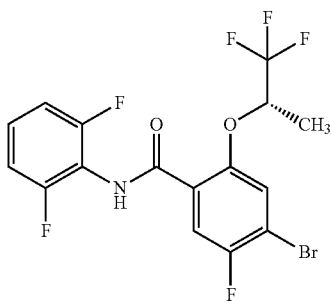 [SMILES: C[C@H](Oc1cc(Br)c(F)cc1C(=O)Nc1c(F)cccc1F)C(F)(F)F]

4-Bromo-5-fluoro-2-{[(2S)-1,1,1-trifluoropropan-2-yl]oxy}benzoyl chloride (Intermediate 68, 17.0 g, 48.6 mmol) was dissolved in DCM (200 mL) and added to a solution of 2,6-difluoroaniline (5.8 ml, 54 mmol) and triethylamine (7.5 ml, 54 mmol) in DCM (350 mL). The mixture was stirred at room temperature for 1 h. The mixture was concentrated to yield 29.3 g of crude product. The crude product was dissolved in ethanol (150 mL) and water (300 mL) was added slowly. The resulting precipitate was filtered off, the solids were washed with water and dried to yield the desired product (20.6 g, 96% yield).

LC-MS (Method A): $R_t$=1.40 min; MS (ESIneg): m/z=440 $[M-H]^-$.

$^1$H-NMR (400 MHz, DMSO-d6) δ [ppm]: 1.147 (1.01), 1.165 (1.91), 1.184 (1.01), 1.339 (0.56), 1.356 (0.62), 1.394 (0.97), 1.411 (1.35), 1.430 (16.00), 1.446 (15.69), 1.486 (0.42), 2.331 (0.97), 2.518 (4.44), 2.522 (3.02), 2.673 (0.97), 5.366 (1.11), 5.383 (2.64), 5.399 (3.30), 5.415 (2.46), 5.430 (1.04), 7.183 (4.93), 7.203 (10.41), 7.224 (6.52), 7.367 (1.18), 7.382 (2.50), 7.403 (3.68), 7.419 (1.98), 7.424 (1.91), 7.440 (0.83), 7.555 (7.05), 7.576 (6.98), 7.808 (6.25), 7.822 (6.18), 9.886 (0.42), 9.918 (10.17).

Intermediate 71

4-bromo-N-(2-chloro-6-fluorophenyl)-5-fluoro-2-{[(2S)-1,1,1-trifluoropropan-2-yl]oxy}benzamide

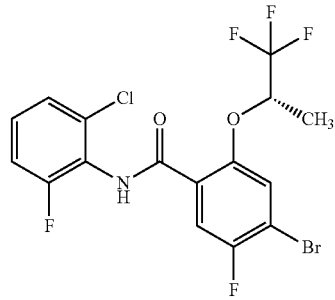 [SMILES: C[C@H](Oc1cc(Br)c(F)cc1C(=O)Nc1c(F)cccc1Cl)C(F)(F)F]

4-Bromo-5-fluoro-2-{[(2S)-1,1,1-trifluoropropan-2-yl]oxy}benzoyl chloride (Intermediate 68, 31.9 g, 91.3 mmol) was dissolved in DCM (300 mL) and added to a solution of 2-chloro-6-fluoroaniline (14.6 g, 100.4 mmol) and triethylamine (14 ml, 100 mmol) in DCM (400 mL). The mixture was stirred at room temperature for 30 min. The mixture was concentrated to yield 47.9 g of crude product. The crude product was dissolved in ethanol (250 mL) and water (500 mL) was added slowly. The resulting precipitate was filtered off, the solids were washed with water and dried to yield the desired product (39.3 g, 84.5% yield).

Synthesized analogously to Intermediate 70 from Intermediate 68 and 2-chloro-6-fluoroaniline.

LC-MS (Method A): $R_t$=1.44 min; MS (ESIpos): m/z=458 $[M+H]^+$.

$^1$H-NMR (400 MHz, DMSO-d6) δ [ppm]: 1.343 (1.46), 1.359 (1.66), 1.387 (0.50), 1.437 (16.00), 1.452 (15.88), 1.475 (0.73), 1.495 (0.82), 1.513 (0.53), 1.907 (0.67), 2.332 (1.23), 2.518 (7.59), 2.523 (4.64), 2.673 (1.20), 5.400 (1.28), 5.416 (2.77), 5.432 (3.47), 5.448 (2.51), 5.464 (1.02), 7.323 (1.55), 7.328 (1.69), 7.347 (3.94), 7.354 (2.01), 7.363 (2.31), 7.371 (2.98), 7.383 (2.19), 7.395 (1.78), 7.402 (3.88), 7.416 (5.31), 7.425 (9.08), 7.431 (9.78), 7.445 (2.16), 7.481 (0.67), 7.502 (0.44), 7.528 (6.83), 7.549 (6.80), 7.665 (0.44), 7.680 (0.70), 7.694 (0.41), 7.820 (5.90), 7.833 (5.87), 9.977 (11.65).

Intermediate 72

4-bromo-5-fluoro-N-(2-methoxy-4-methylpyridin-3-yl)-2-{[(2S)-1,1,1-trifluoropropan-2-yl]oxy}benzamide

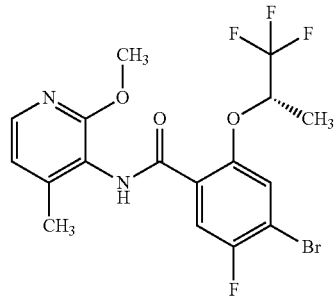 [SMILES: COc1nccc(C)c1NC(=O)c1cc(F)c(Br)cc1O[C@@H](C)C(F)(F)F]

Synthesized analogously to Intermediate 70 from Intermediate 68 and 2-methoxy-4-methylpyridin-3-amine.

LC-MS (Method A): R$_t$=1.38 min; MS (ESIpos): m/z=451 [M+H]$^+$.

$^1$H-NMR (400 MHz, DMSO-d6) δ [ppm]: 1.446 (5.62), 1.462 (5.58), 2.200 (13.29), 3.850 (16.00), 5.449 (0.89), 5.465 (1.15), 5.481 (0.85), 6.924 (2.33), 6.937 (2.44), 7.546 (2.69), 7.568 (2.65), 7.799 (2.29), 7.813 (2.29), 7.962 (2.81), 7.975 (2.74), 9.581 (2.51).

Intermediate 73

4-bromo-5-fluoro-N-(2-fluoro-6-methylphenyl)-2-{[(2S)-1,1,1-trifluoropropan-2-yl]oxy}benzamide

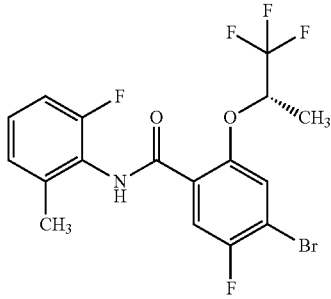 [SMILES: Cc1cccc(F)c1NC(=O)c1cc(F)c(Br)cc1O[C@@H](C)C(F)(F)F]

Synthesized analogously to Intermediate 70 from Intermediate 68 and 2-fluoro-6-methylaniline LC-MS (Method A): R$_t$=1.43 min; MS (ESIneg): m/z=436 [M−H]$^−$.

$^1$H-NMR (400 MHz, DMSO-d6) δ [ppm]: 1.430 (6.96), 1.446 (6.97), 2.253 (16.00), 2.306 (0.44), 2.518 (1.84), 2.523 (1.21), 5.408 (0.47), 5.424 (1.14), 5.441 (1.50), 5.456 (1.11), 5.473 (0.45), 7.093 (0.94), 7.109 (2.52), 7.113 (2.43), 7.126 (2.63), 7.135 (1.55), 7.222 (1.09), 7.236 (1.25), 7.241 (1.61), 7.256 (1.27), 7.261 (0.81), 7.275 (0.64), 7.538 (4.25), 7.559 (4.17), 7.802 (3.13), 7.816 (3.11), 9.747 (3.41).

Intermediate 74

4-bromo-N-(2,6-dichlorophenyl)-5-fluoro-2-{[(2S)-1,1,1-trifluoropropan-2-yl]oxy}benzamide

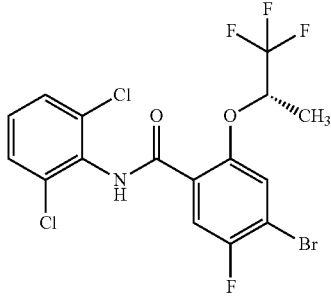

Synthesized analogously to Intermediate 70 from Intermediate 68 and 2,6-dichloroaniline. The product was purified using reverse phase chromatography.

LC-MS (Method A): R$_t$=1.47 min; MS (ESIpos): m/z=473 [M+H]$^+$.

$^1$H-NMR (400 MHz, DMSO-d6) δ [ppm]: 1.435 (14.34), 1.451 (14.01), 2.084 (7.26), 2.323 (1.25), 2.327 (1.62), 2.332 (1.20), 2.518 (6.10), 2.523 (3.75), 2.665 (1.16), 2.669 (1.53), 2.673 (1.11), 5.421 (1.02), 5.437 (2.36), 5.453 (3.01), 5.469 (2.17), 5.485 (0.83), 7.376 (2.87), 7.397 (4.86), 7.417 (3.98), 7.497 (7.26), 7.518 (7.31), 7.572 (16.00), 7.592 (11.84), 7.818 (5.18), 7.832 (5.04), 10.140 (6.89).

Intermediate 75

4-bromo-N-(2,6-difluorophenyl)-2-{[(2S)-1,1,1-trifluoropropan-2-yl]oxy}benzamide

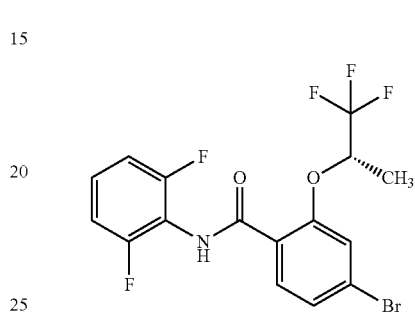

Synthesized analogously to Intermediate 70 from Intermediate 69 and 2,6-difluoroaniline LC-MS (Method A): R$_t$=1.36 min; MS (ESIpos): m/z=424 [M+H]$^+$.

$^1$H-NMR (400 MHz, DMSO-d6) δ [ppm]: 1.054 (0.42), 1.350 (0.40), 1.365 (0.42), 1.445 (16.00), 1.461 (15.92), 2.518 (4.30), 2.523 (2.73), 5.433 (1.17), 5.449 (2.71), 5.465 (3.50), 5.481 (2.57), 5.497 (1.09), 7.176 (4.91), 7.197 (10.19), 7.217 (6.29), 7.362 (4.96), 7.365 (4.80), 7.382 (7.32), 7.385 (6.93), 7.395 (4.03), 7.411 (2.04), 7.433 (0.82), 7.493 (7.91), 7.514 (5.84), 7.667 (8.70), 9.794 (12.87).

Intermediate 76

4-bromo-N-(2-chloro-6-fluorophenyl)-5-fluoro-2-[(2S)-pentan-2-yloxy]benzamide

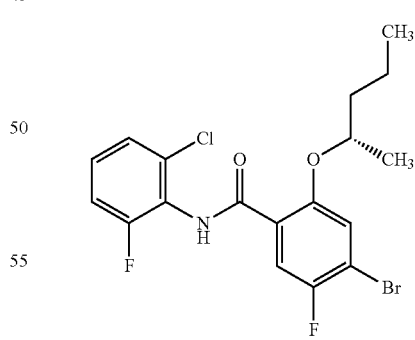

4-bromo-5-fluoro-2-[(2S)-pentan-2-yloxy]benzoic acid (Intermediate 66, 1.16 g, 3.80 mmol) was suspended in DCM (5 mL). 1-Chlor-1-dimethylamino-2-methyl-1-propen (1.5 ml, 11 mmol) was added and the mixture was stirred at room temperature for 30 minutes. Pyridine (1.5 ml, 19 mmol) and 2-chloro-6-fluoroaniline (830 mg, 5.70 mmol) was added as a solution in DCM (5 mL). The mixture was stirred at room temperature for 1 h. The reaction mixture was concentrated and purified using column chromatography (hexanes/ethyl acetate: 0-70%) to yield 1.31 g (98% purity, 78% yield) of desired product.

LC-MS (Method A): $R_t$=1.61 min; MS (ESIneg): m/z=430 [M–H]⁻.

¹H-NMR (400 MHz, DMSO-d6) δ [ppm]: 0.863 (7.04), 0.882 (16.00), 0.900 (8.01), 1.291 (9.46), 1.307 (9.57), 1.345 (1.10), 1.369 (1.27), 1.386 (1.19), 1.402 (1.14), 1.420 (1.08), 1.437 (1.19), 1.455 (1.10), 1.472 (0.67), 1.488 (0.41), 1.542 (0.54), 1.556 (0.95), 1.578 (1.10), 1.590 (1.38), 1.602 (1.06), 1.614 (0.97), 1.629 (0.48), 1.720 (0.60), 1.736 (0.97), 1.752 (1.10), 1.795 (0.63), 2.327 (0.93), 2.669 (0.97), 4.724 (0.99), 4.738 (1.73), 4.753 (1.71), 4.767 (0.93), 7.327 (1.06), 7.348 (2.53), 7.372 (1.84), 7.379 (1.34), 7.399 (2.18), 7.413 (2.33), 7.433 (4.92), 7.454 (1.49), 7.631 (4.99), 7.640 (3.63), 7.653 (3.41), 9.784 (4.77).

Intermediate 77

4-bromo-5-fluoro-N-(2-methoxy-4-methylpyridin-3-yl)-2-[(2S)-pentan-2-yloxy]benzamide

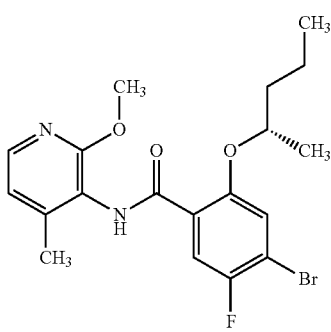 [SMILES: CCC[C@H](C)Oc1cc(Br)c(F)cc1C(=O)Nc1c(C)ccnc1OC]

Synthesized analogously to Intermediate 76 from Intermediate 66 and 2-methoxy-4-methylpyridin-3-amine.

LC-MS (Method A): $R_t$=1.56 min; MS (ESIneg): m/z=423 [M–H]⁻.

¹H-NMR (400 MHz, DMSO-d6) δ [ppm]: 0.876 (3.55), 0.894 (7.83), 0.913 (3.92), 1.172 (0.61), 1.298 (7.01), 1.313 (7.15), 1.363 (0.58), 1.387 (0.78), 1.405 (0.87), 1.422 (0.91), 1.445 (0.73), 1.464 (0.64), 1.483 (0.45), 1.578 (0.53), 1.597 (0.64), 1.612 (0.86), 1.621 (0.62), 1.636 (0.62), 1.722 (0.65), 1.737 (0.65), 1.746 (0.66), 1.988 (1.14), 2.188 (13.60), 2.327 (0.81), 2.669 (0.77), 3.867 (16.00), 4.757 (0.62), 4.773 (1.19), 4.788 (1.18), 4.803 (0.61), 6.935 (2.45), 6.948 (2.45), 7.628 (2.37), 7.642 (2.38), 7.660 (2.73), 7.683 (2.67), 7.960 (2.69), 7.973 (2.58), 9.587 (2.92).

Intermediate 78

4-bromo-5-fluoro-N-(2-fluoro-6-methylphenyl)-2-[(2S)-pentan-2-yloxy]benzamide

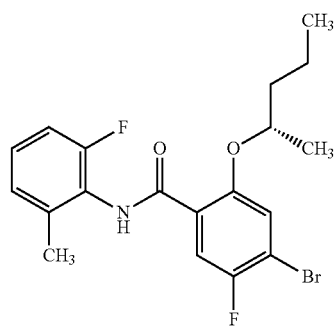 [SMILES: CCC[C@H](C)Oc1cc(Br)c(F)cc1C(=O)Nc1c(C)cccc1F]

Synthesized analogously to Intermediate 76 from Intermediate 66 and 2-fluoro-6-methylaniline LC-MS (Method A): $R_t$=1.60 min; MS (ESIpos): m/z=412 [M+H]⁺.

¹H-NMR (400 MHz, DMSO-d6) δ [ppm]: 0.863 (4.41), 0.882 (9.67), 0.900 (4.96), 1.154 (0.51), 1.172 (1.00), 1.190 (0.52), 1.276 (8.57), 1.291 (8.62), 1.322 (0.59), 1.331 (0.67), 1.340 (0.78), 1.358 (0.83), 1.365 (0.92), 1.372 (0.79), 1.382 (0.96), 1.398 (0.92), 1.414 (0.84), 1.427 (0.92), 1.446 (0.87), 1.464 (0.48), 1.526 (0.42), 1.539 (0.71), 1.559 (0.80), 1.574 (1.06), 1.584 (0.78), 1.598 (0.77), 1.681 (0.50), 1.696 (0.77), 1.711 (0.82), 1.721 (0.80), 1.755 (0.47), 1.988 (1.85), 2.257 (16.00), 2.303 (0.44), 4.018 (0.45), 4.035 (0.45), 4.684 (0.76), 4.700 (1.44), 4.715 (1.41), 4.729 (0.74), 7.098 (1.05), 7.119 (3.75), 7.136 (3.06), 7.224 (1.05), 7.238 (1.32), 7.243 (1.63), 7.257 (1.32), 7.277 (0.61), 7.583 (5.97), 7.599 (3.30), 7.605 (3.58), 9.600 (3.47).

Intermediate 79

4-bromo-5-fluoro-N-(pentan-3-yl)-2-[(2S)-pentan-2-yloxy]benzamide

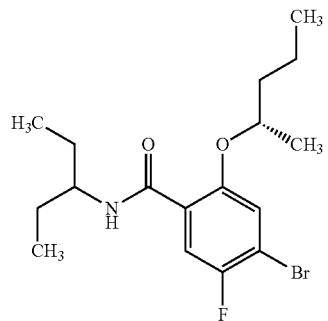 [SMILES: CCC[C@H](C)Oc1cc(Br)c(F)cc1C(=O)NC(CC)CC]

Synthesized analogously to Intermediate 76 from Intermediate 66 and pentan-3-amine.

LC-MS (Method A): $R_t$=1.62 min; MS (ESIneg): m/z=372 [M–H]⁻.

¹H-NMR (400 MHz, DMSO-d6) δ [ppm]: 0.849 (6.80), 0.868 (16.00), 0.889 (13.47), 0.908 (4.47), 1.236 (7.73), 1.251 (7.64), 1.354 (1.75), 1.372 (2.45), 1.391 (2.90), 1.410 (2.75), 1.429 (1.79), 1.494 (0.58), 1.512 (1.53), 1.526 (2.19), 1.544 (2.51), 1.559 (2.27), 1.571 (1.81), 1.596 (1.55), 1.612 (1.25), 1.626 (0.97), 1.638 (0.97), 3.761 (1.08), 3.780 (1.28), 4.681 (0.79), 4.696 (1.44), 4.711 (1.42), 4.726 (0.75), 7.524 (2.62), 7.538 (2.63), 7.564 (2.68), 7.587 (2.65), 7.851 (1.45), 7.873 (1.44).

Intermediate 80

2,5-difluoro-4-[4-methyl-5-oxo-3-(propan-2-yl)-4,5-dihydro-1H-1,2,4-triazol-1-yl]benzonitrile

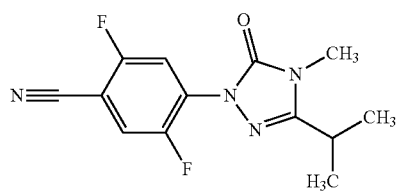 [SMILES: CC(C)c1nn(-c2cc(F)c(C#N)cc2F)c(=O)n1C]

4-methyl-5-(propan-2-yl)-2,4-dihydro-3H-1,2,4-triazol-3-one (2.91 g, 20.6 mmol) and potassium carbonate (5.70 g, 41.2 mmol) were suspended in acetonitrile (50 ml). 2,4,5-trifluorobenzonitrile (2.4 ml, 21 mmol) was added and the mixture was refluxed overnight. The mixture was cooled and the precipitate was filtered off. The solids were was washed with acetonitrile and the combined washes were concentrated. The resulting solid was washed, triturated with hexanes, and filtered. The solids were washed with hexanes and dried to yield the desired product (5.3 g, 91% yield).

Intermediate 81

5-fluoro-4-[4-methyl-5-oxo-3-(propan-2-yl)-4,5-dihydro-1H-1,2,4-triazol-1-yl]-2-{[(2S)-4-methyl-pentan-2-yl]oxy}benzonitrile

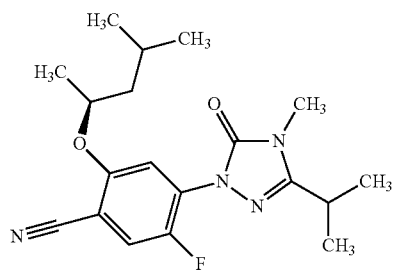 [SMILES: CC(C)C[C@H](C)Oc1cc(-n2nc(C(C)C)n(C)c2=O)c(F)cc1C#N]

Sodium hydride (115 mg, 60% purity, 2.87 mmol) was suspended in acetonitrile (10 mL). (2S)-4-methylpentan-2-ol (230 µl, 1.8 mmol) was added as a solution in acetonitrile (5 mL). The mixture was stirred at room temperature for 30 minutes. 2,5-difluoro-4-[4-methyl-5-oxo-3-(propan-2-yl)-4,5-dihydro-1H-1,2,4-triazol-1-yl]benzonitrile (Intermediate 80, 400 mg, 1.44 mmol) was added and the mixture was stirred at room temperature overnight. The reaction was quenched with methanol (5 mL) and water (2 mL) and concentrated. The resulting residue was dissolved in ethyl acetate, washed with water (2×), dried, and concentrated. The crude product was purified using reverse phase preparative HPLC to yield the desired product (358 mg, 69% yield).

Intermediate 82

5-fluoro-4-[4-methyl-5-oxo-3-(propan-2-yl)-4,5-dihydro-1H-1,2,4-triazol-1-yl]-2-{[(2S)-4-methyl-pentan-2-yl]oxy}benzoic acid

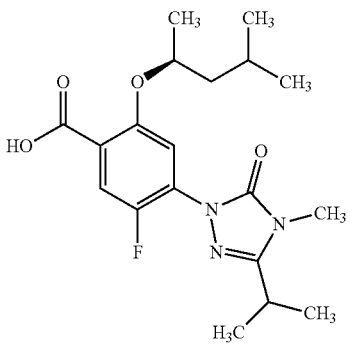 [SMILES: CC(C)C[C@H](C)Oc1cc(-n2nc(C(C)C)n(C)c2=O)c(F)cc1C(=O)O]

5-fluoro-4-[4-methyl-5-oxo-3-(propan-2-yl)-4,5-dihydro-1H-1,2,4-triazol-1-yl]-2-{[(2S)-4-methyl-pentan-2-yl]oxy}benzonitrile (Intermediate 81, 328 mg, 910 µmol) was dissolved in ethanol (3 mL). Sodium hydroxide solution (22% in water, 3 mL) was added and the mixture was stirred at 90° C. overnight. The mixture was cooled to room temperature and concentrated. The residue was diluted with water and extracted with ethyl acetate (3×). The aqueous layer was acidified to pH 3 using 1N hydrochloric acid. The aqueous phase was extracted with ethyl acetate (3×) and the combined organic fractions were dried and concentrated. Preparative reverse phase chromatography yield the desired product (262 mg, 75% yield).

Intermediate 83

2,4,5-trifluoro-N-(2-methylphenyl)benzamide

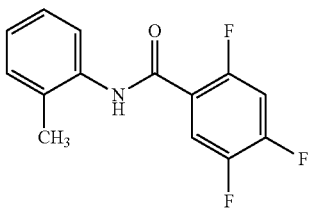 [SMILES: Cc1ccccc1NC(=O)c1cc(F)c(F)cc1F]

2,4,5-trifluorobenzoic acid (6.00 g, 34.1 mmol) and 2-methylaniline (5.48 g, 51.1 mmol) were dissolved in dichloromethane (100 ml). Triethylamine (6.88 g, 68.1 mmol) and HATU (19.4 g, 51.1 mmol) were added. The mixture was stirred at room temperature for 1 h. The reaction mixture was washed with aqueous hydrochloric acid (1N), saturated sodium carbonate solution, and brine. The organic layer was dried and concentrated to yield 7.6 g of the desired product (84% yield).

Intermediate 84

2,4,5-trifluoro-N-(pentan-3-yl)benzamide

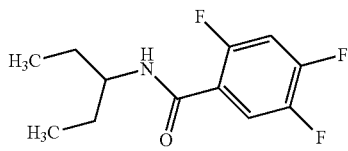 [SMILES: CCC(CC)NC(=O)c1cc(F)c(F)cc1F]

Synthesized analogously to Intermediate 83 using 2,4,5-trifluorobenzoic acid and pentan-3-amine.

Intermediate 85

4-{3-[1-(1-ethoxyethoxy)ethyl]-4-methyl-5-oxo-4,5-dihydro-1H-1,2,4-triazol-1-yl}-2,5-difluoro-N-(pentan-3-yl)benzamide

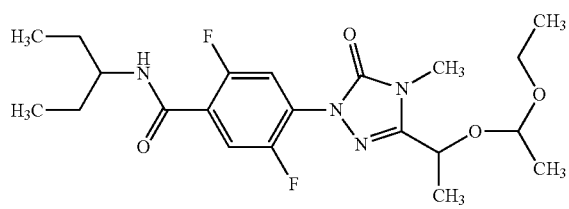 [SMILES: CCOC(C)OC(C)c1nn(-c2cc(F)c(C(=O)NC(CC)CC)cc2F)c(=O)n1C]

2,4,5-trifluoro-N-(pentan-3-yl)benzamide (Intermediate 84, 1.00 g, 4.08 mmol) and 5-[1-(1-ethoxyethoxy)ethyl]-4-methyl-2,4-dihydro-3H-1,2,4-triazol-3-one (Intermediate 4, 1.00 g, 4.65 mmol) were dissolved in acetonitrile (20 mL). Potassium carbonate (1.00 g, 7.24 mmol) was added and the mixture was stirred at 80° C. overnight. The mixture was concentrated, suspended in water and extracted with ethyl acetate. The organic layer was dried and concentrated. The crude product was purified using column chromatography to yield the desired product (300 mg, 16% yield).

Intermediate 86

4-{3-[1-(1-ethoxyethoxy)ethyl]-4-methyl-5-oxo-4,5-dihydro-1H-1,2,4-triazol-1-yl}-2,5-difluoro-N-(2-methylphenyl)benzamide

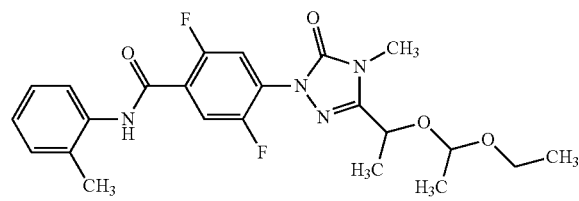 [SMILES: CCOC(C)OC(C)c1nn(-c2cc(F)c(C(=O)Nc3ccccc3C)cc2F)c(=O)n1C]

Synthesized analogously to Intermediate 83 using and Intermediate 4.

Intermediate 87

4-(3-ethyl-4-methyl-5-oxo-4,5-dihydro-1H-1,2,4-triazol-1-yl)-2,5-difluoro-N-(pentan-3-yl)benzamide

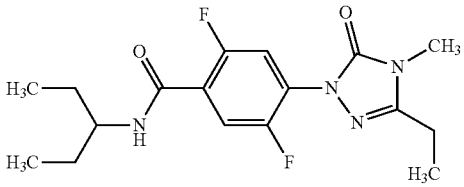 [SMILES: CCc1nn(-c2cc(F)c(C(=O)NC(CC)CC)cc2F)c(=O)n1C]

Synthesized analogously to Intermediate 85 using Intermediate 84 and 3-ethyl-4-methyl-1H-1,2,4-triazol-5(4H)-one.

Intermediate 88

4-(3-ethyl-4-methyl-5-oxo-4,5-dihydro-1H-1,2,4-triazol-1-yl)-2,5-difluorobenzonitrile

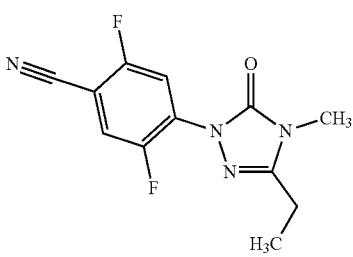 [SMILES: CCc1nn(-c2cc(F)c(C#N)cc2F)c(=O)n1C]

5-ethyl-4-methyl-2,4-dihydro-3H-1,2,4-triazol-3-one (3.00 g, 23.6 mmol) and potassium carbonate (6.52 g, 47.2 mmol) were suspended in acetonitrile (50 ml). The mixture was stirred at reflux overnight. The mixture was filtered and the filter cake was washed with acetonitrile. The solvent was concentrated and the residue was triturated with hexanes to yield the desired intermediate.

LC-MS (Method A): $R_t$=0.93 min; MS (ESIpos): m/z=265 [M+H]$^+$

Intermediate 89

4-bromo-2-{[1,1-difluoropropan-2-yl]oxy}benzonitrile (Racemic)

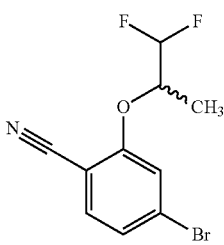

Synthesized analogously to Intermediate 62 from 4-bromo-2-fluorobenzonitrile and 1,1-difluoropropan-2-ol.

LC-MS (Method A): R*t*=1.23 min; MS (ESIpos): m/z=276 [M+H]+

¹H-NMR (400 MHz, DMSO-d6) δ [ppm]: 1.331 (16.00), 1.344 (9.60), 1.347 (15.75), 2.518 (2.46), 2.522 (1.72), 2.673 (0.49), 3.350 (3.94), 3.380 (4.43), 3.387 (1.48), 3.401 (1.35), 3.404 (1.72), 3.409 (0.49), 3.414 (0.49), 3.416 (0.49), 5.072 (0.74), 5.080 (0.86), 5.088 (0.86), 5.096 (0.98), 5.100 (1.48), 5.108 (1.60), 5.116 (1.48), 5.124 (1.60), 5.136 (0.86), 5.144 (0.74), 5.152 (0.62), 6.108 (2.58), 6.115 (2.46), 6.245 (4.80), 6.252 (4.92), 6.381 (2.22), 6.389 (2.34), 7.362 (8.25), 7.366 (7.51), 7.383 (8.12), 7.386 (8.86), 7.707 (15.14), 7.727 (13.54), 7.740 (9.60), 7.744 (9.48).

Intermediate 90

4-bromo-2-{[3,3-difluorobutan-2-yl]oxy}-5-fluorobenzonitrile (Racemic)

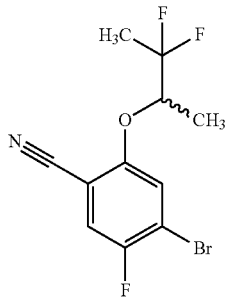 [SMILES: CC(Oc1cc(Br)c(F)cc1C#N)C(C)(F)F]

Synthesized analogously to Intermediate 62 from 4-bromo-2,5-difluorobenzonitrile and 3,3-difluorobutan-2-ol ¹H-NMR (400 MHz, DMSO-d6) δ [ppm]: 1.343 (12.26), 1.359 (12.22), 1.665 (8.25), 1.692 (0.75), 1.714 (16.00), 1.763 (7.25), 2.518 (1.70), 2.522 (1.10), 2.727 (2.33), 2.888 (2.89), 3.318 (0.56), 3.347 (0.56), 5.009 (0.92), 5.016 (0.51), 5.025 (1.05), 5.031 (1.32), 5.040 (0.76), 5.047 (1.30), 5.055 (1.04), 5.062 (0.52), 5.071 (0.91), 5.756 (1.06), 7.896 (6.28), 7.910 (6.32), 7.972 (9.05), 7.993 (8.72), 8.149 (0.67), 8.162 (0.72), 8.166 (0.75), 8.170 (0.72), 8.179 (0.72), 8.184 (0.83), 8.186 (0.81), 8.200 (0.68).

Intermediate 91

4-bromo-3-fluoro-2-{[(2S)-1,1,1-trifluoropropan-2-yl]oxy}benzonitrile

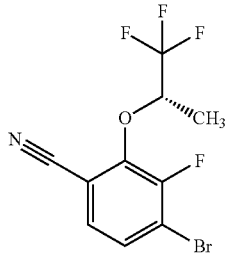 [SMILES: C[C@H](Oc1c(C#N)ccc(Br)c1F)C(F)(F)F]

Synthesized analogously to Intermediate 62 from 4-bromo-2,3-difluorobenzonitrile and (S)-1,1,1-trifluoropropanol.

¹H-NMR (400 MHz, DMSO-d6) δ [ppm]: 1.378 (1.16), 1.395 (1.13), 1.437 (1.13), 1.453 (1.16), 1.525 (15.67), 1.541 (16.00), 2.518 (1.82), 2.523 (1.27), 2.728 (4.04), 2.888 (4.76), 5.172 (1.31), 5.189 (3.21), 5.205 (4.23), 5.221 (3.08), 5.236 (1.19), 7.656 (4.97), 7.661 (5.29), 7.678 (9.93), 7.682 (11.32), 7.719 (9.88), 7.734 (9.24), 7.741 (5.13), 7.756 (4.79), 7.763 (0.86), 7.950 (0.58).

Intermediate 92

2-{[(2S)-1-(dimethylamino)propan-2-yl]oxy}-4-(3-ethyl-4-methyl-5-oxo-4,5-dihydro-1H-1,2,4-triazol-1-yl)-5-fluorobenzonitrile

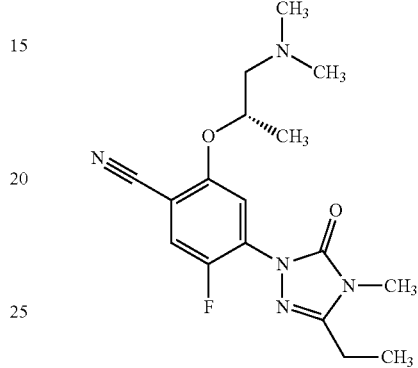

To a solution of (2S)-1-(dimethylamino)propan-2-ol (234 mg, 2.27 mmol) in THF (16 ml, 200 mmol), cooled to 0° C., was slowly added sodium hydride (90.8 mg, 60% in mineral oil, 2.27 mmol). 4-(3-ethyl-4-methyl-5-oxo-4,5-dihydro-1H-1,2,4-triazol-1-yl)-2,5-difluorobenzonitrile (Intermediate 88, 500 mg, 1.89 mmol) was added as a solution in THF (3 mL). The mixture was stirred at 0° C. for 30 min, and was warmed to room temperature overnight. The reaction was quenched with brine and the mixture was extracted with ethyl acetate. The organic phase was dried over sodium sulfate, filtered, and concentrated to yield the desired intermediate (600 mg, 91% yield).

LC-MS (Method A): R*t*=0.63 min; MS (ESIpos): m/z=349 [M+H]+

Intermediate 93

2-{[(2S)-1-(dimethylamino)propan-2-yl]oxy}-4-(3-ethyl-4-methyl-5-oxo-4,5-dihydro-1H-1,2,4-triazol-1-yl)-5-fluorobenzoic acid

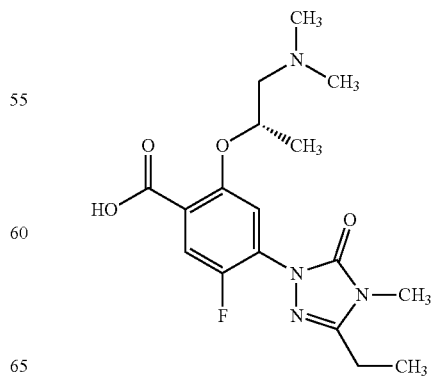

To a solution of 2-{[(2S)-1-(dimethylamino)propan-2-yl]oxy}-4-(3-ethyl-4-methyl-5-oxo-4,5-dihydro-1H-1,2,4-triazol-1-yl)-5-fluorobenzonitrile (Intermediate 92, 600 mg, 1.73 mmol) in ethanol (20 ml) was added aqueous sodium hydroxide (2 N, 20 ml) and the resulting mixture was heated to 90° C. for 2 hours. The resulting solution was cooled to room temperature and diluted with water. The aqueous phase was washed with ethyl acetate, acidified with hydrochloric acid (1N) and washed with dichloromethane. The aqueous phase was concentrated and the residue was purified using prepHPLC to yield the desired intermediate (230 mg, 36% yield)

LC-MS (Method A): $R_t$=0.60 min; MS (ESIpos): m/z=367 [M+H]$^+$

Intermediate 94

4-bromo-2-{[1,1-difluoropropan-2-yl]oxy}benzoic acid (Racemic)

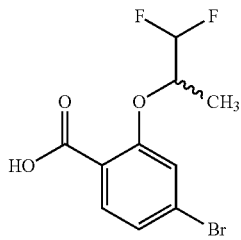 [SMILES: CC(Oc1cc(Br)ccc1C(=O)O)C(F)F]

Synthesized analogously to Intermediate 65 from Intermediate 89.

LC-MS (Method A): $R_t$=1.09 min; MS (ESIpos): m/z=295 [M+H]$^+$ $^1$H-NMR (400 MHz, DMSO-d6) δ [ppm]: 1.281 (15.80), 1.297 (16.00), 2.518 (2.76), 2.523 (1.90), 4.864 (0.72), 4.873 (0.92), 4.880 (0.96), 4.892 (1.38), 4.901 (1.40), 4.909 (1.37), 4.918 (1.44), 4.928 (0.93), 4.936 (0.86), 4.944 (0.67), 6.017 (2.51), 6.026 (2.42), 6.155 (3.98), 6.163 (3.96), 6.292 (2.14), 6.300 (2.21), 7.252 (7.16), 7.256 (7.23), 7.272 (7.63), 7.277 (7.92), 7.517 (10.22), 7.521 (9.92), 7.559 (15.54), 7.580 (13.27).

Intermediate 95

4-bromo-2-{[3,3-difluorobutan-2-yl]oxy}-5-fluorobenzoic acid (Racemic)

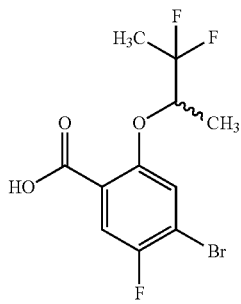 [SMILES: CC(Oc1cc(Br)c(F)cc1C(=O)O)C(C)(F)F]

Synthesized analogously to Intermediate 65 from Intermediate 90.

LC-MS (Method A): $R_t$=1.16 min; MS (ESIpos): m/z=327 [M+H]$^+$ $^1$H-NMR (400 MHz, DMSO-d6) δ [ppm]: 1.282 (13.39), 1.298 (13.29), 1.346 (0.58), 1.362 (0.57), 1.644 (0.63), 1.654 (8.31), 1.693 (1.28), 1.703 (16.00), 1.751 (7.31), 2.518 (2.11), 2.522 (1.44), 4.847 (0.98), 4.854 (0.65), 4.863 (1.13), 4.870 (1.87), 4.878 (0.76), 4.886 (1.91), 4.893 (1.06), 4.901 (0.70), 4.908 (0.93), 7.587 (10.62), 7.610 (9.76), 7.670 (6.89), 7.684 (7.00), 7.751 (0.69), 7.766 (0.70), 7.772 (0.68), 7.788 (0.66), 7.866 (0.68), 7.880 (0.68), 7.890 (0.69), 7.904 (0.66).

Intermediate 96

4-bromo-3-fluoro-2-{[(2S)-1,1,1-trifluoropropan-2-yl]oxy}benzoic acid

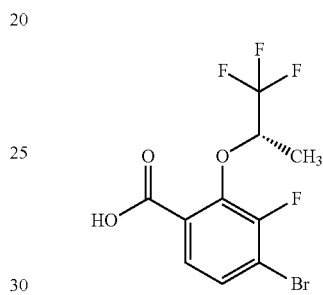

Synthesized analogously to Intermediate 65 from Intermediate 91.

LC-MS (Method A): $R_t$=1.20 min; MS (ESIneg): m/z=329 [M−H]

$^1$H-NMR (400 MHz, DMSO-d6) δ [ppm]: 1.303 (0.76), 1.343 (1.08), 1.353 (1.37), 1.360 (1.30), 1.368 (1.19), 1.443 (15.98), 1.458 (16.00), 2.518 (2.59), 2.523 (1.81), 4.910 (1.21), 4.926 (3.04), 4.942 (3.93), 4.958 (2.92), 4.974 (1.23), 5.758 (1.44), 7.535 (4.20), 7.539 (4.02), 7.557 (8.36), 7.561 (10.33), 7.584 (8.25), 7.588 (1.84), 7.599 (7.64), 7.605 (3.10), 7.609 (0.89), 7.620 (3.90), 13.488 (0.63).

Intermediate 97

4-bromo-2-{[1,1-difluoropropan-2-yl]oxy}benzoyl chloride (Racemic)

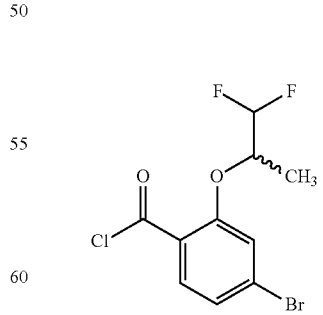

Synthesized analogously to Intermediate 68 from Intermediate 94.

LC-MS (Method A) [methyl ester]: MS (ESIpos): m/z=308 [M+H]$^+$.

Intermediate 98

4-bromo-2-{[3,3-difluorobutan-2-yl]oxy}-5-fluorobenzoyl chloride (Racemic)

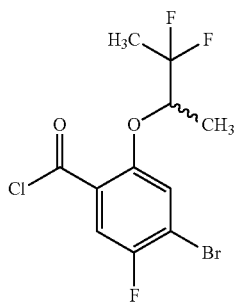 [SMILES: CC(Oc1cc(Br)c(F)cc1C(=O)Cl)C(C)(F)F]

Synthesized analogously to Intermediate 68 from Intermediate 95.

LC-MS (Method A) [methyl ester]: MS (ESIpos): m/z=340 [M+H]⁺.

Intermediate 99

4-bromo-3-fluoro-2-{[(2S)-1,1,1-trifluoropropan-2-yl]oxy}benzoyl chloride

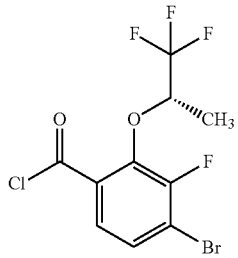 [SMILES: C[C@H](Oc1c(C(=O)Cl)ccc(Br)c1F)C(F)(F)F]

Synthesized analogously to Intermediate 68 from Intermediate 96.

LC-MS (Method A) [methyl ester]: MS (ESIpos): m/z=344 [M+H]⁺.

Intermediate 100

4-bromo-N-(2-chloro-6-fluorophenyl)-2-{[(2S)-1,1,1-trifluoropropan-2-yl]oxy}benzamide

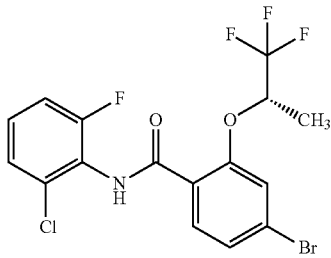

Synthesized analogously to Intermediate 70 from Intermediate 69 and 2-chloro-6-fluoroaniline LC-MS (Method A): $R_t$=1.41 min; MS (ESIpos): m/z=440 [M+H]⁺

¹H-NMR (400 MHz, DMSO-d6) δ [ppm]: 1.448 (6.01), 1.464 (6.02), 2.085 (16.00), 2.518 (1.99), 2.523 (1.32), 5.477 (0.92), 5.492 (1.19), 5.509 (0.89), 5.758 (5.07), 7.320 (0.62), 7.340 (1.42), 7.357 (0.90), 7.364 (1.25), 7.374 (2.05), 7.394 (3.12), 7.408 (1.65), 7.419 (2.92), 7.425 (3.65), 7.440 (0.76), 7.504 (2.49), 7.524 (1.85), 7.674 (2.93), 9.864 (4.29).

Intermediate 101

4-bromo-N-(2-chloro-6-fluorophenyl)-2-{[1,1-difluoropropan-2-yl]oxy}benzamide (Racemic)

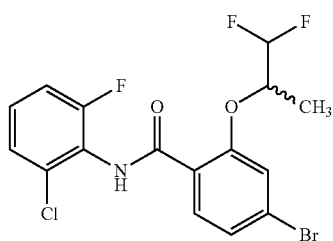 [SMILES: CC(Oc1cc(Br)ccc1C(=O)Nc1c(F)cccc1Cl)C(F)F]

Synthesized analogously to Intermediate 70 from Intermediate 97 and 2-chloro-6-fluoroaniline.

LC-MS (Method A): $R_t$=1.37 min; MS (ESIpos): m/z=422 [M+H]⁺

¹H-NMR (400 MHz, DMSO-d6) δ [ppm]: 1.363 (16.00), 1.378 (16.00), 2.518 (7.70), 2.523 (5.05), 3.300 (0.84), 3.377 (0.60), 5.075 (1.92), 5.085 (1.86), 5.091 (1.86), 5.101 (1.92), 5.758 (1.50), 6.127 (1.92), 6.136 (1.86), 6.265 (3.61), 6.273 (3.67), 6.403 (1.80), 6.411 (1.80), 7.319 (1.86), 7.323 (2.17), 7.342 (9.50), 7.362 (7.76), 7.367 (9.08), 7.378 (2.59), 7.392 (2.11), 7.398 (4.63), 7.411 (4.93), 7.418 (4.03), 7.427 (9.26), 7.432 (10.89), 7.447 (2.59), 7.452 (2.05), 7.632 (12.15), 7.653 (7.34), 9.699 (11.49).

Intermediate 102

4-bromo-N-(2-chloro-6-fluorophenyl)-2-{[3,3-difluorobutan-2-yl]oxy}-5-fluorobenzamide (Racemic)

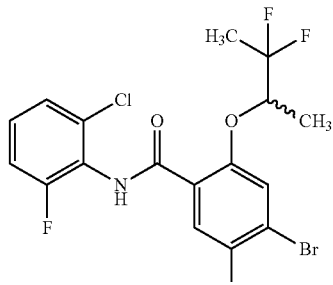

Synthesized analogously to Intermediate 70 from Intermediate 98 and 2-chloro-6-fluoroaniline.

LC-MS (Method A): $R_t$=1.42 min; MS (ESIpos): m/z=454 [M+H]⁺

¹H-NMR (400 MHz, DMSO-d6) δ [ppm]: 1.154 (4.72), 1.172 (9.81), 1.190 (4.75), 1.237 (1.07), 1.332 (12.43), 1.347 (12.37), 1.383 (0.42), 1.642 (8.41), 1.691 (16.00), 1.712 (0.70), 1.739 (7.28), 1.987 (15.86), 2.084 (11.61), 2.518 (7.06), 2.522 (4.84), 4.000 (1.15), 4.017 (3.46), 4.035 (3.49), 4.053 (1.15), 4.988 (0.84), 5.011 (1.60), 5.028 (1.60), 5.050 (0.76), 7.327 (1.21), 7.331 (1.32), 7.347 (2.53), 7.350 (3.15), 7.357 (1.57), 7.367 (1.91), 7.374 (2.36), 7.383 (1.55), 7.397 (1.29), 7.403 (2.98), 7.417 (3.37), 7.423 (3.04), 7.429 (6.16), 7.435 (8.69), 7.449 (1.74), 7.455 (1.27), 7.543 (5.01), 7.564 (5.06), 7.763 (4.44), 7.777 (4.44), 9.933 (5.48).

Intermediate 103

4-bromo-N-(2-chloro-6-fluorophenyl)-3-fluoro-2-{[(2S)-1,1,1-trifluoropropan-2-yl]oxy}benzamide

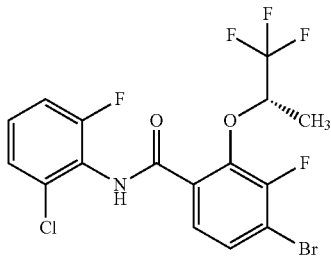 [SMILES: C[C@H](Oc1c(C(=O)Nc2c(F)cccc2Cl)ccc(Br)c1F)C(F)(F)F]

Synthesized analogously to Intermediate 70 from Intermediate 99 and 2-chloro-6-fluoroaniline.

LC-MS (Method A): $R_t$=1.43 min; MS (ESIpos): m/z=458 [M+H]$^+$ $^1$H-NMR (400 MHz, DMSO-d6) δ [ppm]: 1.053 (0.80), 1.330 (0.50), 1.348 (0.50), 1.363 (0.57), 1.378 (0.46), 1.418 (15.92), 1.434 (16.00), 2.518 (4.32), 2.523 (3.05), 4.945 (1.22), 4.961 (2.98), 4.977 (3.86), 4.993 (2.79), 5.010 (1.07), 7.345 (5.00), 7.348 (4.93), 7.365 (7.33), 7.369 (7.98), 7.376 (2.18), 7.385 (2.29), 7.393 (3.02), 7.400 (1.87), 7.414 (1.37), 7.421 (3.63), 7.434 (4.35), 7.443 (8.10), 7.450 (8.78), 7.464 (1.83), 7.469 (1.03), 7.660 (3.78), 7.675 (4.09), 7.681 (3.63), 7.696 (3.32), 10.345 (6.42).

Intermediate 104

2-[(1S)-1-cyclohexylethoxy]-4-(3-ethyl-4-methyl-5-oxo-4,5-dihydro-1H-1,2,4-triazol-1-yl)-5-fluorobenzoic acid

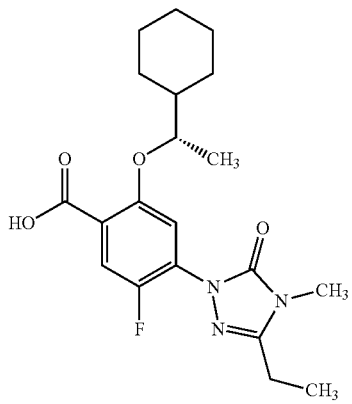 [SMILES: CCc1nn(-c2cc(O[C@@H](C)C3CCCCC3)c(C(=O)O)cc2F)c(=O)n1C]

Synthesized analogously to Intermediate 39 from Intermediate 15 and (1S)-1-cyclohexylethanol LC-MS (Method A): $R_t$=1.25 min; MS (ESIpos): m/z=392 [M+H]$^+$

EXPERIMENTAL SECTION—EXAMPLES

Example 1

5-fluoro-4-[3-methyl-5-oxo-4-(propan-2-yl)-4,5-dihydro-1H-1,2,4-triazol-1-yl]-N-(2-methylphenyl)-2-{[(2S)-1,1,1-trifluoropropan-2-yl]oxy}benzamide

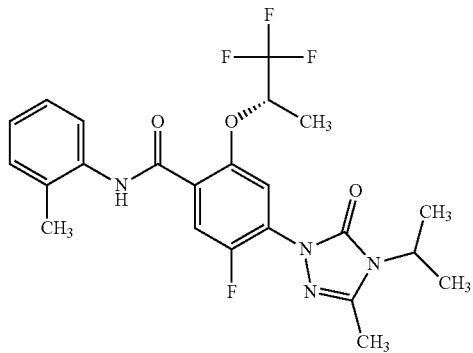 [SMILES: Cc1ccccc1NC(=O)c1cc(F)c(-n2nc(C)n(C(C)C)c2=O)cc1O[C@@H](C)C(F)(F)F]

To a 0° C. stirred solution of 5-fluoro-4-[3-methyl-5-oxo-4-(propan-2-yl)-4,5-dihydro-1H-1,2,4-triazol-1-yl]-2-{[(2S)-1,1,1-trifluoropropan-2-yl]oxy}benzoic acid (Intermediate 39, 98.0 mg, 0.25 mmol, 1.00 eq.) and catalytic DMF in anhydrous DCM (0.65 mL, 0.40 mol/L) was added oxalyl chloride (34.9 mg, 0.28 mmol, 1.10 eq.) dropwise. The resulting mixture was warmed to room temperature, stirred for 1 h and concentrated under reduced pressure. A solution of the residue in anhydrous DCM (0.83 mL, 0.30 mol/L) was added dropwise to a 0° C. stirred solution of o-toluidine (29.5 mg, 0.28 mmol, 1.10 eq.) and triethylamine (27.8 mg, 0.28 mmol, 1.10 eq.) in anhydrous DCM (0.92 mL, 0.30 mol/L). Following complete addition, the mixture was warmed to room temperature and stirred for 1 h. Aqueous 1.0 M hydrochloric acid was added to the mixture and extracted with DCM (3×). The combined organic extracts were washed with brine, dried (magnesium sulfate) and concentrated under reduced pressure. The residue was purified by flash column chromatography (hexanes/ethyl acetate) to give the desired product (103 mg, 86%).

$^1$H NMR (300 MHz, CDCl$_3$) δ [ppm] 1.56 (d, 6H), 1.62 (d, 3H), 2.31 (s, 3H), 2.38 (s, 3H), 4.34 (sep, 1H), 4.83-4.98 (q, 1H), 7.13 (t, 1H), 7.21-7.30 (m, 2H), 7.46 (d, 1H), 7.89 (d, 1H), 8.14 (d, 1H), 9.03 (s, 1H).

MS (ESIpos): m/z=481 (M+H)$^+$.

Example 2

N-(2,6-difluorophenyl)-5-fluoro-4-[3-methyl-5-oxo-4-(propan-2-yl)-4,5-dihydro-1H-1,2,4-triazol-1-yl]-2-{[(2S)-1,1,1-trifluoropropan-2-yl]oxy}benzamide

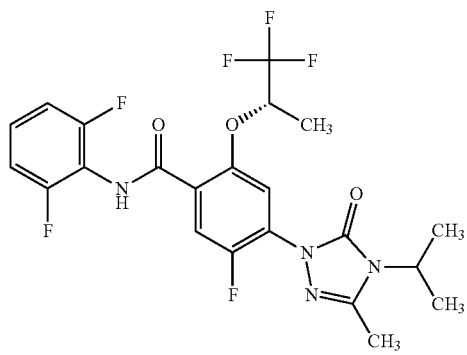 [SMILES: Cc1nn(-c2cc(O[C@@H](C)C(F)(F)F)c(C(=O)Nc3c(F)cccc3F)cc2F)c(=O)n1C(C)C]

Synthesized analogous to Example 1 from Intermediate 39 and 2,6-difluoroaniline.

$^1$H NMR (300 MHz, CDCl$_3$) δ [ppm] 1.56 (d, 6H), 1.64 (d, 3H), 2.38 (s, 3H), 4.34 (sep, 1H), 4.85-4.99 (m, 1H), 6.94-7.05 (m, 2H), 7.19-7.30 (m, 1H), 7.49 (d, 1H), 8.15 (d, 1H), 8.98 (s, 1H).

MS (ESIpos): m/z=503 (M+H)$^+$.

Example 3

5-fluoro-N-(2-fluorophenyl)-4-[3-methyl-5-oxo-4-(propan-2-yl)-4,5-dihydro-1H-1,2,4-triazol-1-yl]-2-{[(2S)-1,1,1-trifluoropropan-2-yl]oxy}benzamide

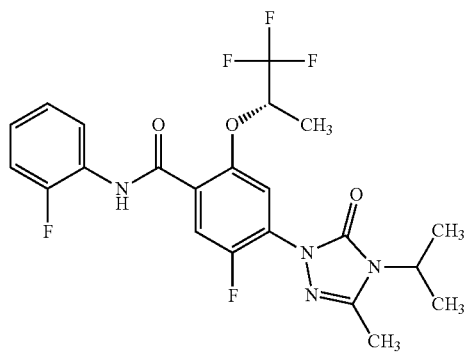 [SMILES: Cc1nn(-c2cc(O[C@@H](C)C(F)(F)F)c(C(=O)Nc3ccccc3F)cc2F)c(=O)n1C(C)C]

Synthesized analogous to Example 1 from Intermediate 39 and 2-fluoroaniline.

$^1$H NMR (300 MHz, CDCl$_3$) δ [ppm] 1.56 (d, 6H), 1.66 (d, 3H), 2.38 (s, 3H), 4.34 (sep, 1H), 4.86-5.01 (m, 1H), 7.04-7.23 (m, 3H), 7.48 (d, 1H), 8.16 (d, 1H), 8.54 (td, 1H), 9.77 (s, 1H).

MS (ESIpos): m/z=485 (M+H)$^+$.

Example 4

5-fluoro-4-[3-methyl-5-oxo-4-(propan-2-yl)-4,5-dihydro-1H-1,2,4-triazol-1-yl]-N-[3-(trifluoromethyl)phenyl]-2-{[(2S)-1,1,1-trifluoropropan-2-yl]oxy}benzamide

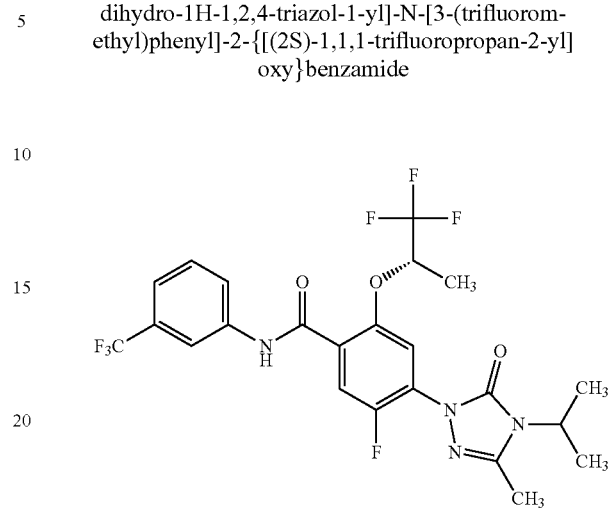

Synthesized analogous to Example 1 from Intermediate 39 and 3-(trifluoromethyl)aniline.

$^1$H NMR (300 MHz, CDCl$_3$) δ [ppm] 1.56 (d, 6H), 1.66 (d, 3H), 2.38 (s, 3H), 4.33 (sep, 1H), 4.88-5.01 (m, 1H), 7.40 (d, 1H), 7.45-7.52 (m, 2H), 7.79 (d, 1H), 8.04 (s, 1H), 8.17 (d, 1H), 9.62 (s, 1H).

MS (ESIpos): m/z=535 (M+H)$^+$.

Example 5

5-fluoro-N-(2-fluoro-6-methylphenyl)-4-[3-methyl-5-oxo-4-(propan-2-yl)-4,5-dihydro-1H-1,2,4-triazol-1-yl]-2-{[(2S)-1,1,1-trifluoropropan-2-yl]oxy}benzamide

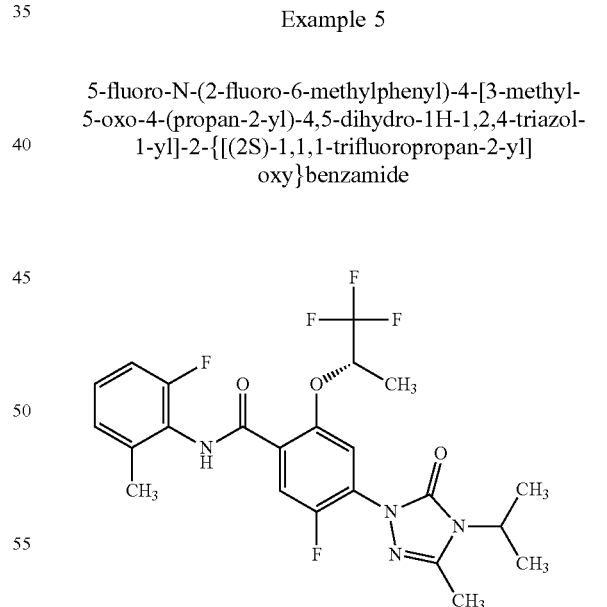

Synthesized analogous to Example 1 from Intermediate 39 and 2-fluoro-6-methylaniline.

$^1$H NMR (300 MHz, CDCl$_3$) δ [ppm] 1.56 (d, 6H), 1.64 (d, 3H), 2.30 (s, 3H), 2.38 (s, 3H), 4.34 (sep, 1H), 4.87-5.00 (m, 1H), 6.96-7.09 (m, 2H), 7.19 (dd, 1H), 7.47 (d, 1H), 8.15 (d, 1H), 8.87 (s, 1H).

MS (ESIpos): m/z=499 (M+H)$^+$.

Example 6

5-fluoro-N-(2-fluorophenyl)-4-[3-methyl-5-oxo-4-(propan-2-yl)-4,5-dihydro-1H-1,2,4-triazol-1-yl]-2-[(1S)-1-phenylethoxy]benzamide

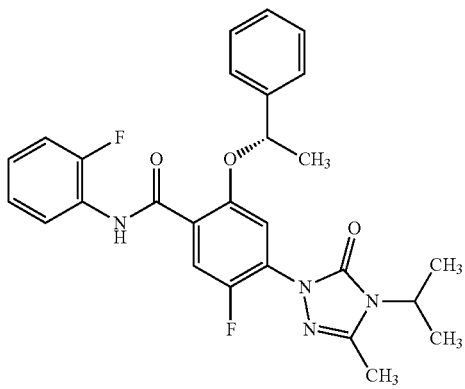 [SMILES: Cc1nn(-c2cc(O[C@@H](C)c3ccccc3)c(C(=O)Nc3ccccc3F)cc2F)c(=O)n1C(C)C]

Synthesized analogous to Example 1 from Intermediate 41 and 2-fluoroaniline ¹H NMR (300 MHz, CDCl₃) δ [ppm] 1.52 (d, 6H), 1.84 (d, 3H), 2.32 (s, 3H), 4.30 (sep, 1H), 5.61 (q, 1H), 7.04-7.44 (m, 9H), 8.11 (d, 1H) 8.64 (d, 1H), 10.5 (s, 1H).

MS (ESIpos): m/z=493 (M+H)⁺.

Example 7

5-fluoro-N-(2-fluoro-6-methylphenyl)-4-[3-methyl-5-oxo-4-(propan-2-yl)-4,5-dihydro-1H-1,2,4-triazol-1-yl]-2-[(1S)-1-phenylethoxy]benzamide

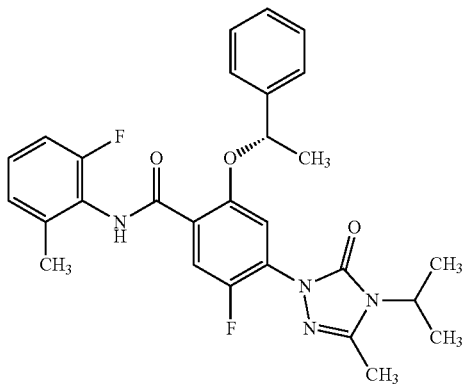 [SMILES: Cc1cccc(F)c1NC(=O)c1cc(F)c(-n2nc(C)n(C(C)C)c2=O)cc1O[C@@H](C)c1ccccc1]

Synthesized analogous to Example 1 from Intermediate 41 and 2-fluoro-6-methylaniline.

¹H NMR (300 MHz, CDCl₃) δ [ppm] 1.53 (d, 6H), 1.78 (d, 3H), 2.29 (s, 3H), 2.33 (s, 3H), 4.32 (sep, 1H), 5.61 (q, 1H), 6.97-7.08 (m, 2H), 7.13-7.22 (m, 1H), 7.28-7.45 (m, 6H), 8.10 (d, 1H), 9.59 (s, 1H).

MS (ESIneg): m/z=505 (M−H)⁻.

Example 8

N-(2,6-difluorophenyl)-5-fluoro-4-[3-methyl-5-oxo-4-(propan-2-yl)-4,5-dihydro-1H-1,2,4-triazol-1-yl]-2-[(1S)-1-phenylethoxy]benzamide

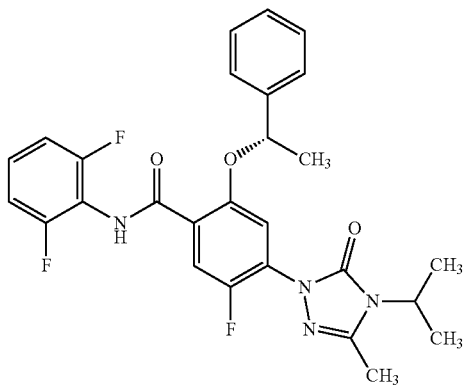 [SMILES: Cc1nn(-c2cc(O[C@@H](C)c3ccccc3)c(C(=O)Nc3c(F)cccc3F)cc2F)c(=O)n1C(C)C]

Synthesized analogous to Example 1 from Intermediate 41 and 2,6-difluoroaniline.

¹H NMR (300 MHz, CDCl₃) δ [ppm] 1.53 (d, 6H), 1.80 (d, 3H), 2.33 (s, 3H), 4.31 (sep, 1H), 5.61 (q, 1H), 6.96-7.05 (m, 2H), 7.17-7.46 (m, 7H), 8.10 (d, 1H) 9.72 (s, 1H).

MS (ESIpos): m/z=511 (M+H)⁺.

Example 9

5-fluoro-4-[3-methyl-5-oxo-4-(propan-2-yl)-4,5-dihydro-1H-1,2,4-triazol-1-yl]-2-[(1S)-1-phenylethoxy]-N-[3-(trifluoromethyl)phenyl]benzamide

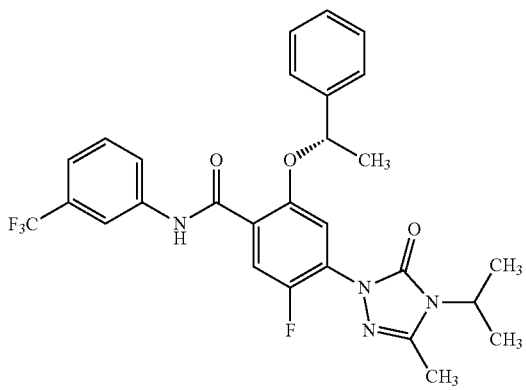 [SMILES: Cc1nn(-c2cc(O[C@@H](C)c3ccccc3)c(C(=O)Nc3cccc(C(F)(F)F)c3)cc2F)c(=O)n1C(C)C]

Synthesized analogous to Example 1 from Intermediate 41 and 3-(trifluoromethyl)aniline.

¹H NMR (300 MHz, CDCl₃) δ [ppm] 1.55 (d, 6H), 1.86 (s, 3H), 2.36 (s, 3H), 4.33 (sep, 1H), 5.61 (q, 1H), 7.32-7.49 (m, 8H), 7.64 (s, 1H), 7.76 (d, 1H), 8.12 (d, 1H), 10.2 (s, 1H).

MS (ESIneg): m/z=541 (M−H)⁻.

Example 10

5-fluoro-4-[3-methyl-5-oxo-4-(propan-2-yl)-4,5-dihydro-1H-1,2,4-triazol-1-yl]-N-(2-methyl-phenyl)-2-[(1S)-1-phenylethoxy]benzamide

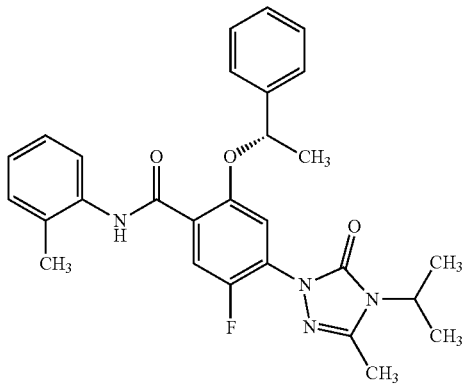 [SMILES: Cc1ccccc1NC(=O)c1cc(F)c(-n2nc(C)n(C(C)C)c2=O)cc1O[C@@H](C)c1ccccc1]

Synthesized analogous to Example 1 from Intermediate 41 and 2-methylaniline.

$^1$H NMR (300 MHz, CDCl$_3$) δ [ppm] 1.53 (d, 6H), 1.79 (d, 3H), 2.18 (s, 3H), 2.34 (s, 3H), 4.32 (sep, 1H), 5.62 (q, 1H), 7.06-7.42 (m, 9H), 8.02 (d, 1H) 8.14 (d, 1H), 9.64 (s, 1H).

MS (ESIpos): m/z=489 (M+H)$^+$.

Example 11

5-fluoro-N-(2-fluoro-6-methylphenyl)-4-[3-methyl-5-oxo-4-(propan-2-yl)-4,5-dihydro-1H-1,2,4-triazol-1-yl]-2-[(2S)-pentan-2-yloxy]benzamide

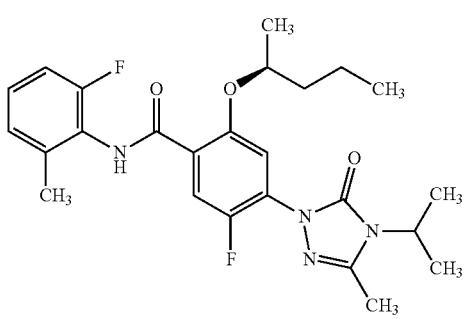 [SMILES: CCC[C@H](C)Oc1cc(-n2nc(C)n(C(C)C)c2=O)c(F)cc1C(=O)Nc1c(C)cccc1F]

Synthesized analogous to Example 1 from Intermediate 42 and 2-fluoro-6-methylaniline.

$^1$H NMR (300 MHz, CDCl$_3$) δ [ppm] 0.95 (t, 3H), 1.38-1.54 (m, 2H), 1.43 (d, 3H), 1.56 (d, 6H), 1.62-1.76 (m, 1H), 1.77-1.91 (m, 1H), 2.32 (s, 3H), 2.38 (s, 3H), 4.35 (sep, 1H), 4.61-4.71 (m, 1H), 6.95-7.09 (m, 2H), 7.17 (dd, 1H), 7.39 (d, 1H), 8.13 (d, 1H), 9.56 (s, 1H).

MS (ESIpos): m/z=473 (M+H)$^+$.

Example 12

N-(2,6-difluorophenyl)-5-fluoro-4-[3-methyl-5-oxo-4-(propan-2-yl)-4,5-dihydro-1H-1,2,4-triazol-1-yl]-2-[(2S)-pentan-2-yloxy]benzamide

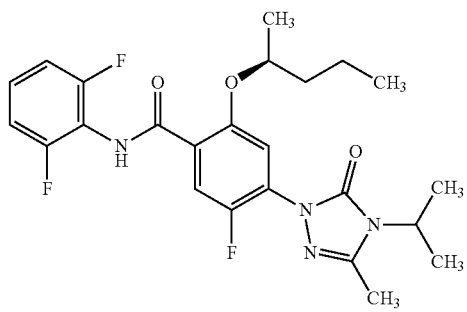 [SMILES: CCC[C@H](C)Oc1cc(-n2nc(C)n(C(C)C)c2=O)c(F)cc1C(=O)Nc1c(F)cccc1F]

Synthesized analogous to Example 1 from Intermediate 42 and 2,6-difluoroaniline.

$^1$H NMR (300 MHz, CDCl$_3$) δ [ppm] 0.96 (t, 3H), 1.38-1.55 (m, 2H), 1.43 (d, 3H), 1.56 (d, 6H), 1.62-1.77 (m, 1H), 1.79-1.93 (m, 1H), 2.37 (s, 3H), 4.35 (sep, 1H), 4.60-4.73 (m, 1H), 6.95-7.04 (m, 2H), 7.16-7.29 (m, 1H), 7.40 (d, 1H), 8.13 (d, 1H), 9.69 (s, 1H).

MS (ESIpos): m/z=477 (M+H)$^+$.

Example 13

5-fluoro-4-[3-methyl-5-oxo-4-(propan-2-yl)-4,5-dihydro-1H-1,2,4-triazol-1-yl]-N-(2-methyl-phenyl)-2-[(2S)-pentan-2-yloxy]benzamide

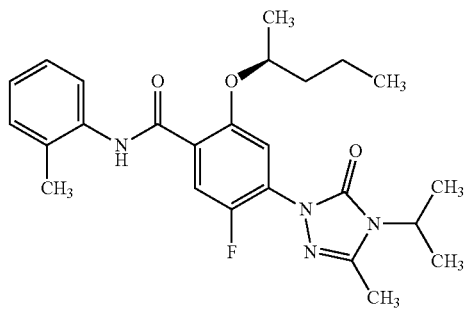 [SMILES: CCC[C@H](C)Oc1cc(-n2nc(C)n(C(C)C)c2=O)c(F)cc1C(=O)Nc1ccccc1C]

Synthesized analogous to Example 1 from Intermediate 42 and 2-methylaniline.

$^1$H NMR (300 MHz, CDCl$_3$) δ [ppm] 0.94 (t, 3H), 1.37-1.53 (m, 2H), 1.42 (d, 3H), 1.56 (d, 6H), 1.60-1.74 (m, 1H), 1.77-1.93 (m, 1H), 2.34 (s, 3H), 2.37 (s, 3H), 4.35 (sep, 1H), 4.59-4.72 (m, 1H), 7.11 (t, 1H), 7.19-7.30 (m, 2H), 7.39 (d, 1H), 8.01 (d, 1H), 8.16 (d, 1H), 9.66 (s 1H).

MS (ESIpos): m/z=455 (M+H)$^+$.

Example 14

5-fluoro-4-[3-methyl-5-oxo-4-(propan-2-yl)-4,5-dihydro-1H-1,2,4-triazol-1-yl]-2-[(2S)-pentan-2-yloxy]-N-[3-(trifluoromethyl)phenyl]benzamide

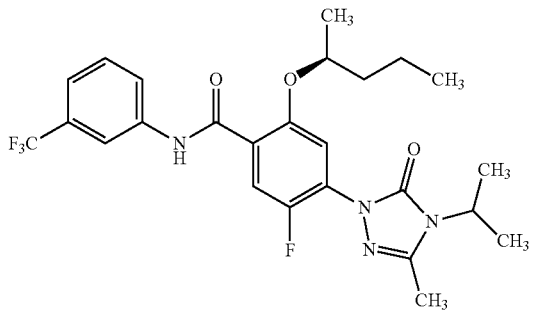 [SMILES: CCC[C@H](C)Oc1cc(-n2nc(C)n(C(C)C)c2=O)c(F)cc1C(=O)Nc1cccc(C(F)(F)F)c1]

Synthesized analogous to Example 1 from Intermediate 42 and 3-(trifluoromethyl)aniline.

$^1$H NMR (300 MHz, CDCl$_3$) δ [ppm] 1.00 (t, 3H), 1.41-1.61 (m, 2H), 1.47 (d, 3H), 1.55 (d, 6H), 1.70-1.98 (m, 2H), 2.37 (s, 3H), 4.34 (sep, 1H), 4.61-4.74 (m, 1H), 7.35-7.41 (m, 2H), 7.48 (t, 1H), 7.84 (d, 1H), 7.94 (s, 1H), 8.13 (d, 1H), 10.4 (s, 1H).

MS (ESIpos): m/z=509 (M+H)$^+$.

Example 15

5-fluoro-N-(2-fluorophenyl)-4-[3-methyl-5-oxo-4-(propan-2-yl)-4,5-dihydro-1H-1,2,4-triazol-1-yl]-2-[(2S)-pentan-2-yloxy]benzamide

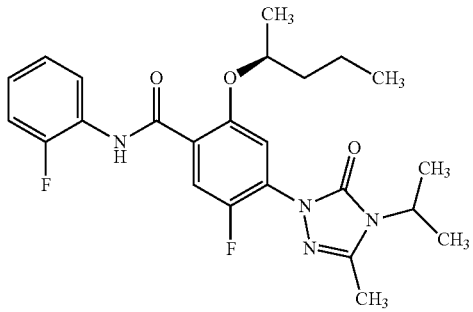 [SMILES: CCC[C@H](C)Oc1cc(-n2nc(C)n(C(C)C)c2=O)c(F)cc1C(=O)Nc1ccccc1F]

Synthesized analogous to Example 1 from Intermediate 42 and 2-fluoroaniline.

$^1$H NMR (300 MHz, CDCl$_3$) δ [ppm] 0.96 (t, 3H), 1.35-1.53 (m, 2H), 1.44 (d, 3H), 1.56 (d, 6H), 1.63-1.79 (m, 1H), 1.86-2.01 (m, 1H), 2.37 (s, 3H), 4.35 (sep, 1H), 4.61-4.73 (m, 1H), 7.01-7.22 (m, 3H), 7.38 (d, 1H), 8.16 (d, 1H), 8.62 (td, 1H), 10.5 (s, 1H).

MS (ESIpos): m/z=457 (M+H)$^+$.

Example 16

4-(3-ethyl-4-methyl-5-oxo-4,5-dihydro-1H-1,2,4-triazol-1-yl)-5-fluoro-N-(2-methylphenyl)-2-[(2S)-pentan-2-yloxy]benzamide

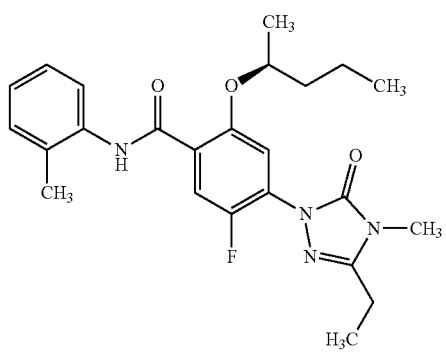 [SMILES: CCC[C@H](C)Oc1cc(-n2nc(CC)n(C)c2=O)c(F)cc1C(=O)Nc1ccccc1C]

Synthesized analogous to Example 1 from Intermediate 44 and 2-methylaniline.

$^1$H NMR (300 MHz, CDCl$_3$) 5 [ppm] 0.94 (t, 3H), 1.36 (t, 3H), 1.40-1.54 (m, 2H), 1.43 (d, 3H), 1.60-1.74 (m, 1H), 1.79-1.89 (m, 1H), 2.34 (s, 3H), 2.65 (q, 2H), 3.33 (s, 3H), 4.59-4.70 (m, 1H), 7.11 (td, 1H), 7.20-7.30 (m, 2H), 7.36 (d, 1H), 8.02 (d, 1H), 8.17 (d, 1H), 9.65 (s, 1H).

MS (ESIpos): m/z=441 (M+H)$^+$.

Example 17

4-(3-ethyl-4-methyl-5-oxo-4,5-dihydro-1H-1,2,4-triazol-1-yl)-5-fluoro-N-(2-fluoro-6-methylphenyl)-2-[(2S)-pentan-2-yloxy]benzamide

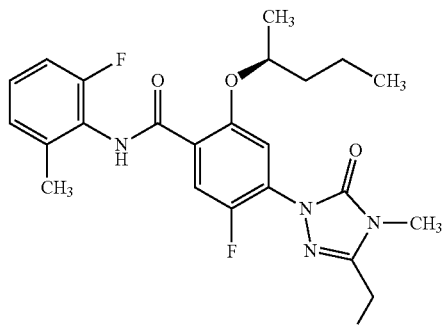

Synthesized analogous to Example 1 from Intermediate 44 and 2-fluoro-6-methylaniline.

$^1$H NMR (300 MHz, CDCl$_3$) δ [ppm] 0.95 (t, 3H), 1.36 (t, 3H), 1.43 (d, 3H), 1.43-1.58 (m, 2H), 1.62-1.75 (m, 1H), 1.77-1.92 (m, 1H), 2.31 (s, 3H), 2.65 (q, 2H), 3.33 (s, 3H), 4.59-4.71 (m, 1H), 6.95-7.09 (m, 2H), 7.17 (dd, 1H), 7.36 (d, 1H), 8.13 (d, 1H), 9.55 (s, 1H).

MS (ESIpos): m/z=459 (M+H)$^+$.

Example 18

N-(2,6-difluorophenyl)-4-(3-ethyl-4-methyl-5-oxo-4,5-dihydro-1H-1,2,4-triazol-1-yl)-5-fluoro-2-[(2S)-pentan-2-yloxy]benzamide

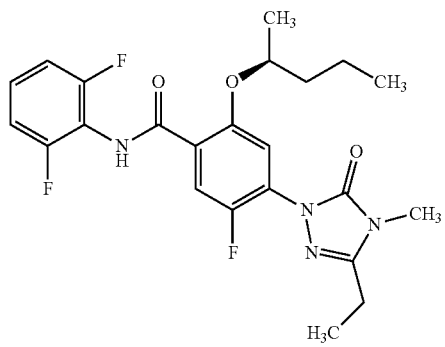 [SMILES: CCC[C@H](C)Oc1cc(-n2nc(CC)n(C)c2=O)c(F)cc1C(=O)Nc1c(F)cccc1F]

Synthesized analogous to Example 1 from Intermediate 44 and 2,6-difluoroaniline.

$^1$H NMR (300 MHz, CDCl$_3$) δ [ppm] 0.92 (t, 3H), 1.36 (t, 3H), 1.38-1.59 (m, 2H), 1.43 (d, 3H), 1.63-1.77 (m, 1H), 1.79-1.93 (m, 1H), 2.65 (q, 2H), 3.32 (s, 3H), 4.59-4.71 (m, 1H), 6.94-7.05 (m, 2H), 7.16-7.25 (m, 1H), 7.37 (d, 1H), 8.13 (d, 1H), 9.68 (s, 1H).

MS (ESIpos): m/z=463 (M+H)$^+$.

Example 19

4-(3-ethyl-4-methyl-5-oxo-4,5-dihydro-1H-1,2,4-triazol-1-yl)-5-fluoro-N-(2-fluorophenyl)-2-[(2S)-pentan-2-yloxy]benzamide

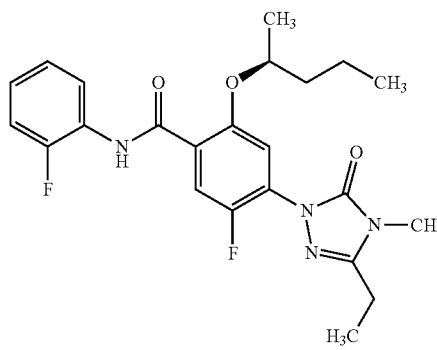

Synthesized analogous to Example 1 from Intermediate 44 and 2-fluoroaniline.

$^1$H NMR (300 MHz, CDCl$_3$) δ [ppm] 0.96 (t, 3H), 1.36 (t, 3H), 1.38-1.59 (m, 2H), 1.45 (d, 3H), 1.64-1.78 (m, 1H), 1.86-2.01 (m, 1H), 2.65 (q, 2H), 3.33 (s, 3H), 4.59-4.72 (m, 1H), 7.02-7.22 (m, 3H), 7.35 (d, 1H), 8.16 (d, 1H), 8.62 (td, 1H), 10.5 (s, 1H).

MS (ESIpos): m/z=445 (M+H)$^+$.

Example 20

4-(3-ethyl-4-methyl-5-oxo-4,5-dihydro-1H-1,2,4-triazol-1-yl)-5-fluoro-2-[(2S)-pentan-2-yloxy]-N-[3-(trifluoromethyl)phenyl]benzamide

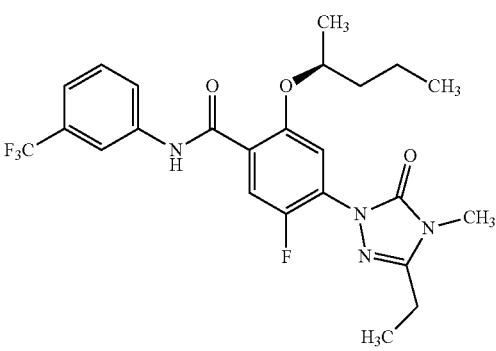 [SMILES: CCC[C@H](C)Oc1cc(-n2nc(CC)n(C)c2=O)c(F)cc1C(=O)Nc1cccc(C(F)(F)F)c1]

Synthesized analogous to Example 1 from Intermediate 44 and 3-(trifluoromethyl)aniline.

$^1$H NMR (300 MHz, CDCl$_3$) δ [ppm] 0.99 (t, 3H), 1.36 (t, 3H), 1.40-1.64 (m, 2H), 1.47 (d, 3H), 1.70-1.99 (m, 2H), 2.65 (q, 2H), 3.33 (s, 3H), 4.60-4.72 (m, 1H), 7.34-7.41 (m, 2H), 7.49 (t, 1H), 7.85 (d, 1H), 7.93 (s, 1H), 8.14 (d, 1H), 10.3 (s, 1H).

MS (ESIpos): m/z=495 (M+H)$^+$.

Example 21

4-(3-ethyl-4-methyl-5-oxo-4,5-dihydro-1H-1,2,4-triazol-1-yl)-5-fluoro-N-(4-methoxyphenyl)-2-[(2S)-pentan-2-yloxy]benzamide

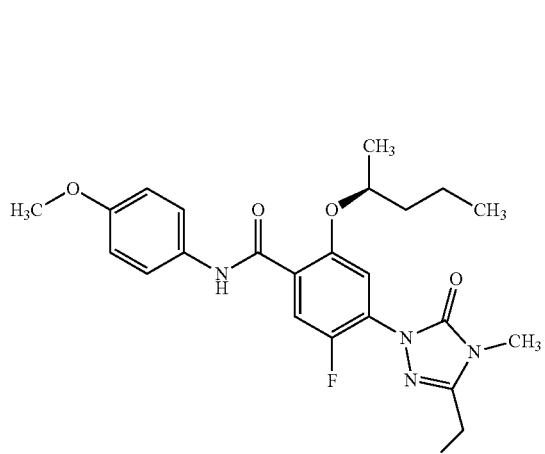

Synthesized analogous to Example 1 from Intermediate 44 and 4-methoxyaniline.

Example 22

4-(3-ethyl-4-methyl-5-oxo-4,5-dihydro-1H-1,2,4-triazol-1-yl)-5-fluoro-2-[(2S)-pentan-2-yloxy]-N-[4-(trifluoromethyl)phenyl]benzamide

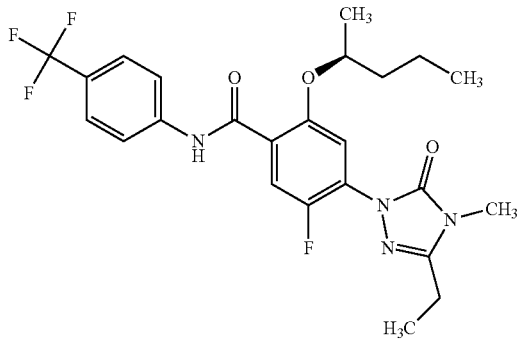 [SMILES: CCC[C@H](C)Oc1cc(-n2nc(CC)n(C)c2=O)c(F)cc1C(=O)Nc1ccc(C(F)(F)F)cc1]

Synthesized analogous to Example 1 from Intermediate 44 and 4-(trifluoromethyl)aniline.

Example 23

4-(3-ethyl-4-methyl-5-oxo-4,5-dihydro-1H-1,2,4-triazol-1-yl)-5-fluoro-2-[(2S)-pentan-2-yloxy]-N-[2-(trifluoromethyl)phenyl]benzamide

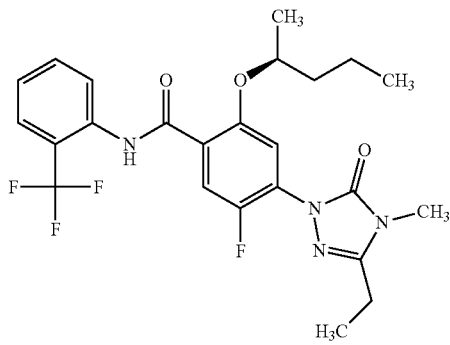 [SMILES: CCC[C@H](C)Oc1cc(-n2nc(CC)n(C)c2=O)c(F)cc1C(=O)Nc1ccccc1C(F)(F)F]

Synthesized analogous to Example 1 from Intermediate 44 and 2-(trifluoromethyl)aniline.

Example 24

N-(3-amino-2-methylphenyl)-4-(3-ethyl-4-methyl-5-oxo-4,5-dihydro-1H-1,2,4-triazol-1-yl)-5-fluoro-2-[(2S)-pentan-2-yloxy]benzamide

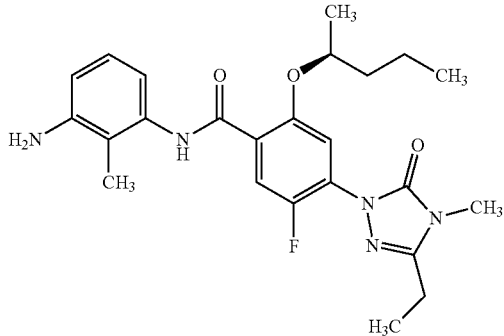 [SMILES: CCC[C@H](C)Oc1cc(-n2nc(CC)n(C)c2=O)c(F)cc1C(=O)Nc1cccc(N)c1C]

Synthesized analogous to Example 1 from Intermediate 44 and 2-methylbenzene-1,3-diamine.

Example 25

N-(2-cyano-6-methylphenyl)-4-(3-ethyl-4-methyl-5-oxo-4,5-dihydro-1H-1,2,4-triazol-1-yl)-5-fluoro-2-[(2S)-pentan-2-yloxy]benzamide

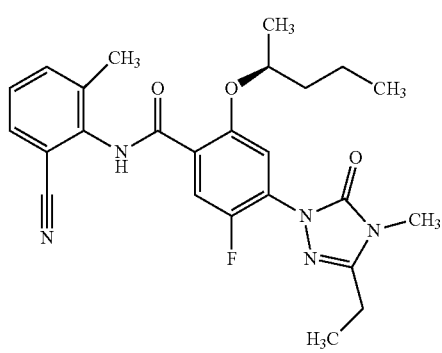 [SMILES: CCC[C@H](C)Oc1cc(-n2nc(CC)n(C)c2=O)c(F)cc1C(=O)Nc1c(C)cccc1C#N]

Synthesized analogous to Example 1 from Intermediate 44 and 2-amino-3-methylbenzonitrile.

Example 26

4-(3-ethyl-4-methyl-5-oxo-4,5-dihydro-1H-1,2,4-triazol-1-yl)-5-fluoro-N-(3-methylphenyl)-2-[(2S)-pentan-2-yloxy]benzamide

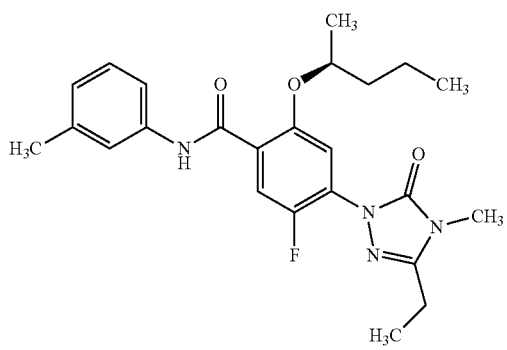

Synthesized analogous to Example 1 from Intermediate 44 and m-toluidine.

Example 27

N-(2,2-dimethylpropyl)-4-(3-ethyl-4-methyl-5-oxo-4,5-dihydro-1H-1,2,4-triazol-1-yl)-5-fluoro-2-[(2S)-pentan-2-yloxy]benzamide

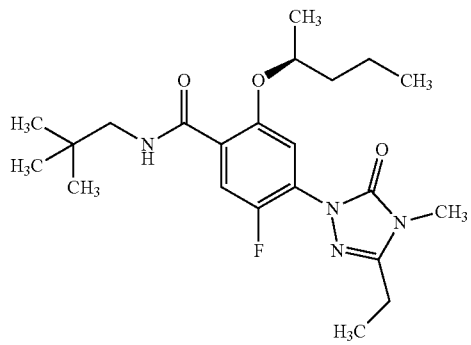 [SMILES: CCC[C@H](C)Oc1cc(-n2nc(CC)n(C)c2=O)c(F)cc1C(=O)NCC(C)(C)C]

Synthesized analogous to Example 1 from Intermediate 44 and 2,2-dimethylpropan-1-amine.

Example 28

N-cycloheptyl-4-(3-ethyl-4-methyl-5-oxo-4,5-dihydro-1H-1,2,4-triazol-1-yl)-5-fluoro-2-[(2S)-pentan-2-yloxy]benzamide

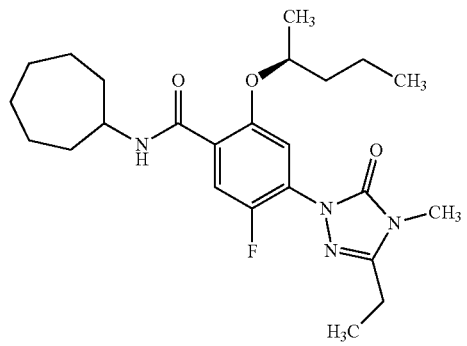 [SMILES: CCC[C@H](C)Oc1cc(-n2nc(CC)n(C)c2=O)c(F)cc1C(=O)NC1CCCCCC1]

Synthesized analogous to Example 1 from Intermediate 44 and cycloheptanamine.

Example 29

4-(3-ethyl-4-methyl-5-oxo-4,5-dihydro-1H-1,2,4-triazol-1-yl)-5-fluoro-N-(2-hydroxyphenyl)-2-[(2S)-pentan-2-yloxy]benzamide

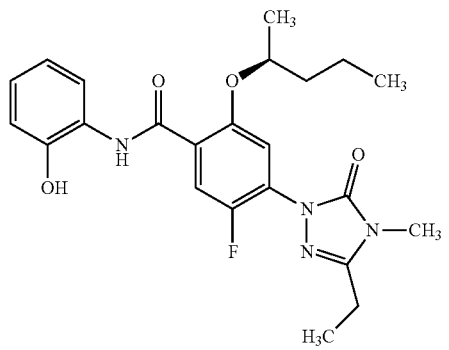 [SMILES: CCC[C@H](C)Oc1cc(-n2nc(CC)n(C)c2=O)c(F)cc1C(=O)Nc1ccccc1O]

Synthesized analogous to Example 1 from Intermediate 44 and 2-aminophenol.

Example 30

N-(cyclohexylmethyl)-4-(3-ethyl-4-methyl-5-oxo-4,5-dihydro-1H-1,2,4-triazol-1-yl)-5-fluoro-2-[(2S)-pentan-2-yloxy]benzamide

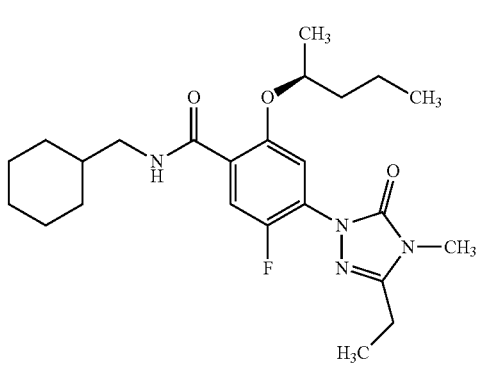 [SMILES: CCC[C@H](C)Oc1cc(-n2nc(CC)n(C)c2=O)c(F)cc1C(=O)NCC1CCCCC1]

Synthesized analogous to Example 1 from Intermediate 44 and 1-cyclohexylmethanamine.

Example 31

N-(1-cyclohexylethyl)-4-(3-ethyl-4-methyl-5-oxo-4,5-dihydro-1H-1,2,4-triazol-1-yl)-5-fluoro-2-[(2S)-pentan-2-yloxy]benzamide, Mixture of Stereoisomers

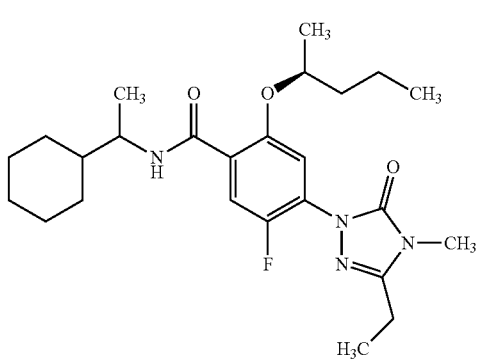 [SMILES: CCC[C@H](C)Oc1cc(-n2nc(CC)n(C)c2=O)c(F)cc1C(=O)NC(C)C1CCCCC1]

Synthesized analogous to Example 1 from Intermediate 44 and 1-cyclohexylethanamine.

Example 32

N-(2,4-dimethylphenyl)-4-(3-ethyl-4-methyl-5-oxo-4,5-dihydro-1H-1,2,4-triazol-1-yl)-5-fluoro-2-[(2S)-pentan-2-yloxy]benzamide

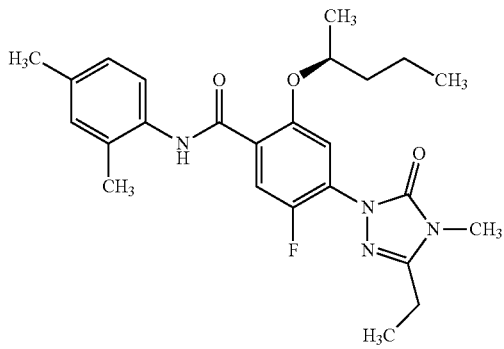

Synthesized analogous to Example 1 from Intermediate 44 and 2,4-dimethylaniline.

Example 33

4-(3-ethyl-4-methyl-5-oxo-4,5-dihydro-1H-1,2,4-triazol-1-yl)-5-fluoro-N-[2-(methylamino)-phenyl]-2-[(2S)-pentan-2-yloxy]benzamide

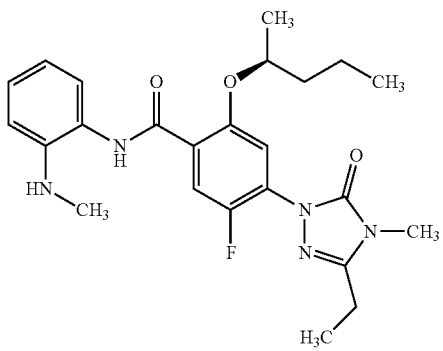 [SMILES: CCC[C@H](C)Oc1cc(-n2nc(CC)n(C)c2=O)c(F)cc1C(=O)Nc1ccccc1NC]

Synthesized analogous to Example 1 from Intermediate 44 and N-methylbenzene-1,2-diamine.

Example 34

4-(3-ethyl-4-methyl-5-oxo-4,5-dihydro-1H-1,2,4-triazol-1-yl)-5-fluoro-N-(2-methoxyphenyl)-2-[(2S)-pentan-2-yloxy]benzamide

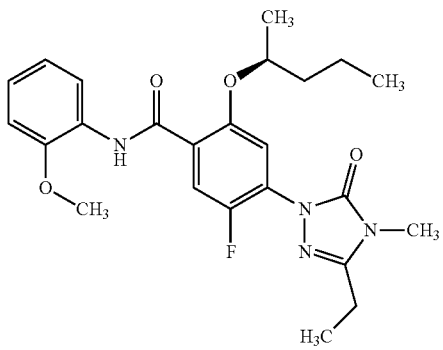 [SMILES: CCC[C@H](C)Oc1cc(-n2nc(CC)n(C)c2=O)c(F)cc1C(=O)Nc1ccccc1OC]

Synthesized analogous to Example 1 from Intermediate 44 and 2-methoxyaniline.

Example 35

4-(3-ethyl-4-methyl-5-oxo-4,5-dihydro-1H-1,2,4-triazol-1-yl)-5-fluoro-N-(3-methoxyphenyl)-2-[(2S)-pentan-2-yloxy]benzamide

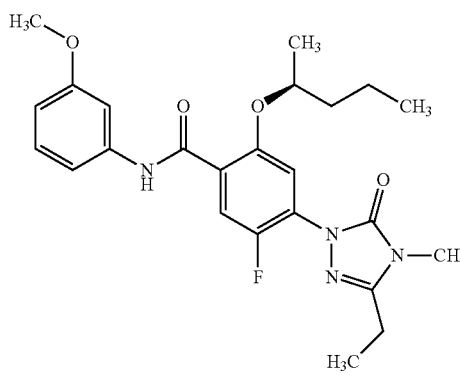 [SMILES: CCC[C@H](C)Oc1cc(-n2nc(CC)n(C)c2=O)c(F)cc1C(=O)Nc1cccc(OC)c1]

Synthesized analogous to Example 1 from Intermediate 44 and 3-methoxyaniline.

Example 36

4-(3-ethyl-4-methyl-5-oxo-4,5-dihydro-1H-1,2,4-triazol-1-yl)-N-(2-ethylphenyl)-5-fluoro-2-[(2S)-pentan-2-yloxy]benzamide

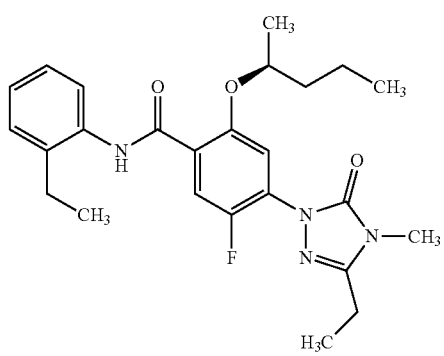 [SMILES: CCC[C@H](C)Oc1cc(-n2nc(CC)n(C)c2=O)c(F)cc1C(=O)Nc1ccccc1CC]

Synthesized analogous to Example 1 from Intermediate 44 and 2-ethylaniline.

Example 37

4-(3-ethyl-4-methyl-5-oxo-4,5-dihydro-1H-1,2,4-triazol-1-yl)-5-fluoro-2-[(2S)-pentan-2-yloxy]-N-[2-(propan-2-yl)phenyl]benzamide

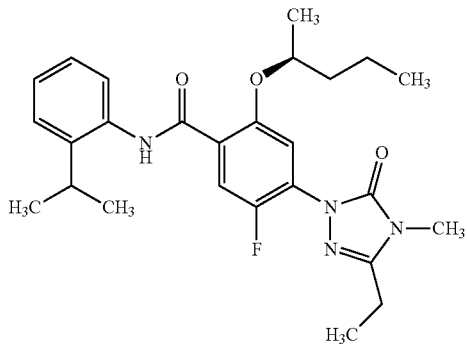 [SMILES: CCC[C@H](C)Oc1cc(-n2nc(CC)n(C)c2=O)c(F)cc1C(=O)Nc1ccccc1C(C)C]

Synthesized analogous to Example 1 from Intermediate 44 and 2-isopropylaniline.

Example 38

4-(3-ethyl-4-methyl-5-oxo-4,5-dihydro-1H-1,2,4-triazol-1-yl)-5-fluoro-2-[(2S)-pentan-2-yloxy]-N-(2-propylphenyl)benzamide

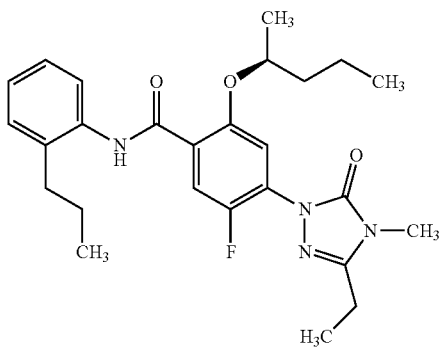 [SMILES: CCCc1ccccc1NC(=O)c1cc(F)c(-n2nc(CC)n(C)c2=O)cc1O[C@@H](C)CCC]

Synthesized analogous to Example 1 from Intermediate 44 and 2-propylaniline.

Example 39

4-(3-ethyl-4-methyl-5-oxo-4,5-dihydro-1H-1,2,4-triazol-1-yl)-N-(4-ethylphenyl)-5-fluoro-2-[(2S)-pentan-2-yloxy]benzamide

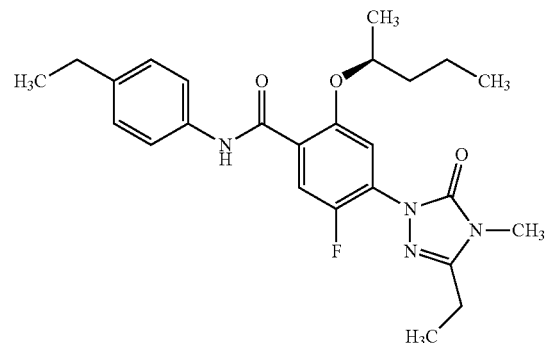

Synthesized analogous to Example 1 from Intermediate 44 and 4-ethylaniline.

Example 40

4-(3-ethyl-4-methyl-5-oxo-4,5-dihydro-1H-1,2,4-triazol-1-yl)-5-fluoro-2-[(2S)-pentan-2-yloxy]-N-[4-(propan-2-yl)phenyl]benzamide

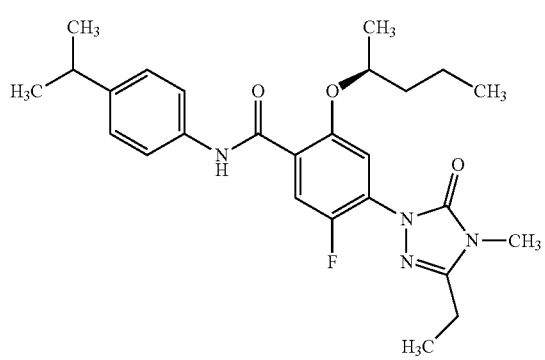 [SMILES: CCC[C@H](C)Oc1cc(-n2nc(CC)n(C)c2=O)c(F)cc1C(=O)Nc1ccc(C(C)C)cc1]

Synthesized analogous to Example 1 from Intermediate 44 and 4-isopropylaniline.

Example 41

N-(2,3-dihydro-1H-inden-2-yl)-4-(3-ethyl-4-methyl-5-oxo-4,5-dihydro-1H-1,2,4-triazol-1-yl)-5-fluoro-2-[(2S)-pentan-2-yloxy]benzamide

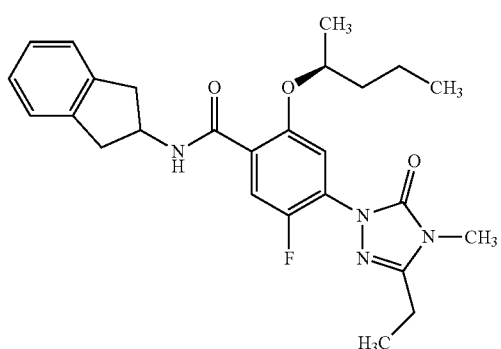

Synthesized analogous to Example 1 from Intermediate 44 and indan-2-amine.

Example 42

N-(cyclopentylmethyl)-4-(3-ethyl-4-methyl-5-oxo-4,5-dihydro-1H-1,2,4-triazol-1-yl)-5-fluoro-2-[(2S)-pentan-2-yloxy]benzamide

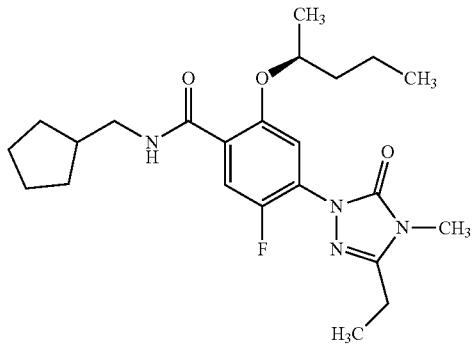 [SMILES: CCC[C@H](C)Oc1cc(-n2nc(CC)n(C)c2=O)c(F)cc1C(=O)NCC1CCCC1]

Synthesized analogous to Example 1 from Intermediate 44 and 1-cyclopentylmethanamine.

Example 43

4-(3-ethyl-4-methyl-5-oxo-4,5-dihydro-1H-1,2,4-triazol-1-yl)-5-fluoro-N-(4-methylphenyl)-2-[(2S)-pentan-2-yloxy]benzamide

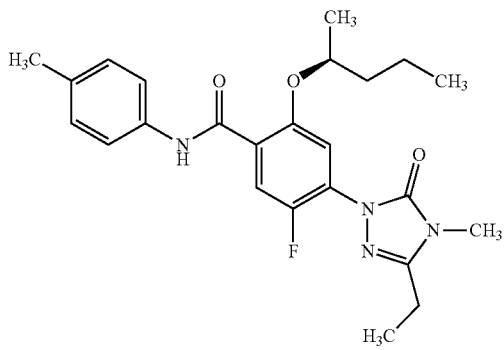

Synthesized analogous to Example 1 from Intermediate 44 and p-toluidine.

Example 44

N-(4-amino-2,6-dimethylphenyl)-4-(3-ethyl-4-methyl-5-oxo-4,5-dihydro-1H-1,2,4-triazol-1-yl)-5-fluoro-2-[(2S)-pentan-2-yloxy]benzamide

Step A tert-butyl [4-({4-(3-ethyl-4-methyl-5-oxo-4,5-dihydro-1H-1,2,4-triazol-1-yl)-5-fluoro-2-[(2S)-pentan-2-yloxy]benzoyl}amino)-3,5-dimethylphenyl]carbamate

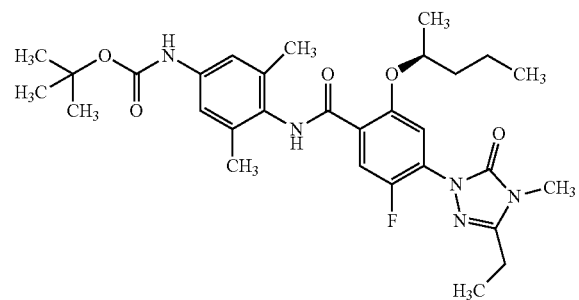 [SMILES: CCC[C@H](C)Oc1cc(-n2nc(CC)n(C)c2=O)c(F)cc1C(=O)Nc1c(C)cc(NC(=O)OC(C)(C)C)cc1C]

Synthesized analogous to Example 1 from Intermediate 44 and tert-butyl (4-amino-3,5-dimethylphenyl)carbamate.

Step B

N-(4-amino-2,6-dimethylphenyl)-4-(3-ethyl-4-methyl-5-oxo-4,5-dihydro-1H-1,2,4-triazol-1-yl)-5-fluoro-2-[(2S)-pentan-2-yloxy]benzamide

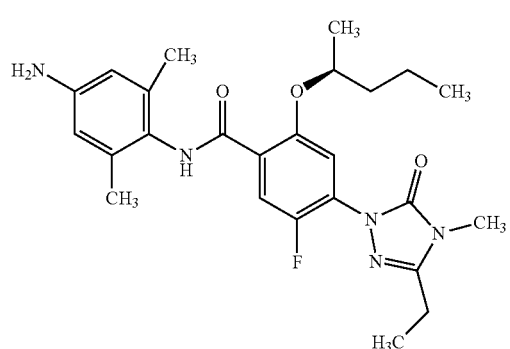

The intermediate from STEP A was dissolved in methanol and hydrogen chloride gas was bubbled through the reaction for 20 minutes. The solvent was evaporated to yield pure product.

Example 45

N-(2-amino-4,6-dimethylphenyl)-4-(3-ethyl-4-methyl-5-oxo-4,5-dihydro-1H-1,2,4-triazol-1-yl)-5-fluoro-2-[(2S)-pentan-2-yloxy]benzamide

Step A

N-(2,4-dimethyl-6-nitrophenyl)-4-(3-ethyl-4-methyl-5-oxo-4,5-dihydro-1H-1,2,4-triazol-1-yl)-5-fluoro-2-[(2S)-pentan-2-yloxy]benzamide

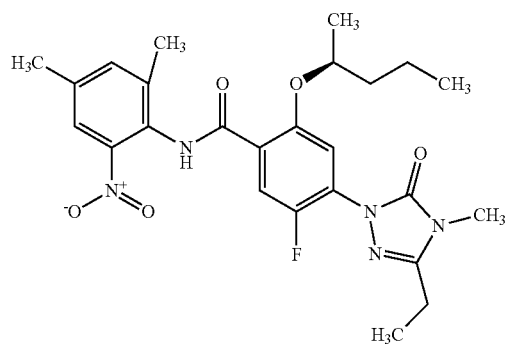

4-(3-ethyl-4-methyl-5-oxo-4,5-dihydro-1H-1,2,4-triazol-1-yl)-5-fluoro-2-[(2S)-pentan-2-yloxy]-benzoic acid (Intermediate 44, 100 mg, 285 µmol) and 2,4-dimethyl-6-nitroaniline (47.0 mg, 283 µmol) were dissolved in THF (10 mL) and pyridine (1 mL). Phosphoryl chloride (500 µl, 5.4 mmol) was added and the mixture was stirred overnight. The reaction mixture was concentrated and the crude product was purified using preparative TLC to yield the desired intermediate (70 mg, 49% yield).

Step B

N-(2-amino-4,6-dimethylphenyl)-4-(3-ethyl-4-methyl-5-oxo-4,5-dihydro-1H-1,2,4-triazol-1-yl)-5-fluoro-2-[(2S)-pentan-2-yloxy]benzamide

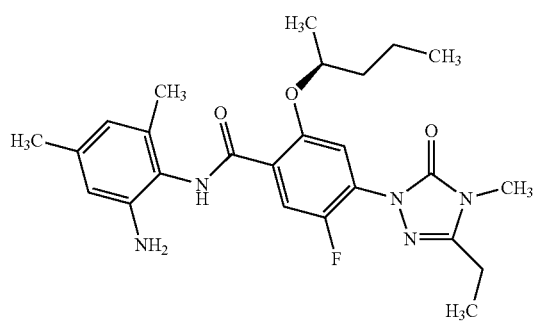

N-(2,4-dimethyl-6-nitrophenyl)-4-(3-ethyl-4-methyl-5-oxo-4,5-dihydro-1H-1,2,4-triazol-1-yl)-5-fluoro-2-[(2S)-pentan-2-yloxy]benzamide (Intermediate from STEP A, 70.0 mg, 140 µmol) was dissolved in methanol (20 mL). Raney-Nickel (10 mg) was added and the mixture was stirred under an atmosphere of hydrogen overnight. The reaction mixture was filtered and concentrated and the crude product was purified using preparative TLC to yield the desired intermediate (22 mg, 33% yield).

Example 46

N-[4-(aminomethyl)-3-methylphenyl]-4-(3-ethyl-4-methyl-5-oxo-4,5-dihydro-1H-1,2,4-triazol-1-yl)-5-fluoro-2-(pentan-2-yloxy)benzamide Step A N-(4-cyano-3-methylphenyl)-4-(3-ethyl-4-methyl-5-oxo-4,5-dihydro-1H-1,2,4-triazol-1-yl)-5-fluoro-2-[(2S)-pentan-2-yloxy]benzamide

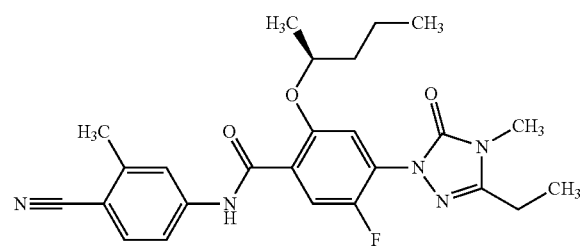 [SMILES: CCC[C@H](C)Oc1cc(-n2nc(CC)n(C)c2=O)c(F)cc1C(=O)Nc1ccc(C#N)c(C)c1]

Synthesized analogously to Example 45 (STEP A) from Intermediate 44 and 4-amino-3-methylbenzonitrile.

Step B

N-[4-(aminomethyl)-3-methylphenyl]-4-(3-ethyl-4-methyl-5-oxo-4,5-dihydro-1H-1,2,4-triazol-1-yl)-5-fluoro-2-(pentan-2-yloxy)benzamide

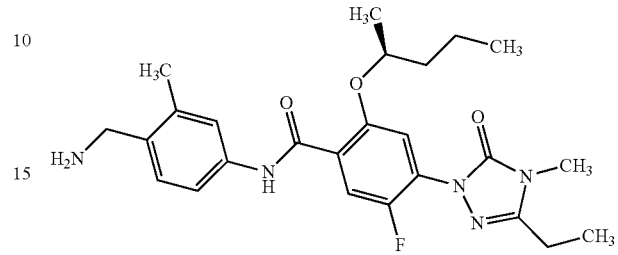

Synthesized analogously to Example 45 (STEP B) from Intermediate 44.

Example 47

4-(3-cyclopropyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

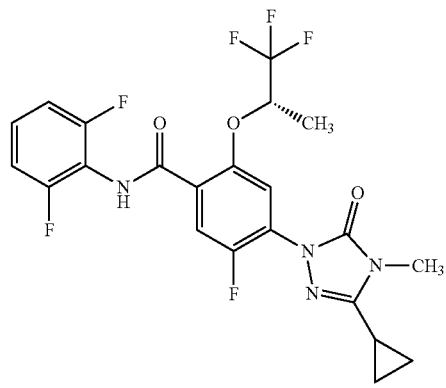 [SMILES: C[C@H](Oc1cc(-n2nc(C3CC3)n(C)c2=O)c(F)cc1C(=O)Nc1c(F)cccc1F)C(F)(F)F]

Step A:
4-(3-Cyclopropyl-4-methyl-5-oxo-4,5-dihydro-1H-1,2,4-triazol-1-yl)-5-fluoro-2-{[(2S)-1,1,1-tri-fluoropropan-2-yl]oxy}benzoic acid (Intermediate 54, 699 mg, 1.80 mmol) was dissolved DCM (9 mL). DMF (14 µl, 180 µmol) was added followed by oxalyl chloride (190 µl, 2.2 mmol). The mixture was stirred at room temperature for 2 h. The reaction was concentrated to yield the desired acid chloride (648 mg, 88%) which was used directly in the next step.
Step B:
4-(3-Cyclopropyl-4-methyl-5-oxo-4,5-dihydro-1H-1,2,4-triazol-1-yl)-5-fluoro-2-{[(2S)-1,1,1-tri-fluoropropan-2-yl]oxy}benzoyl chloride (Intermediate from STEP A, 143 mg, 351 µmol) was dissolved in DCM (2 mL) and added to a solution of 2,6-difluoroaniline (42 µl, 390 µmol) and triethylamine (54 µl, 390 µmol) in DCM (3 mL). The mixture was stirred at room temperature for 1 h. The reaction was concentrated and purified using preparative chromatography (water+0.1% formic acid/acetonitrile gradient) to yield the desired product (63.5 mg, 97% purity, 35% yield).

LC-MS (Method A): $R_t$=1.24 min; MS (ESIpos): m/z=501 [M+H]$^+$.

$^1$H-NMR (400 MHz, DMSO-d6) δ [ppm]: 0.893 (1.75), 0.899 (1.96), 0.906 (1.85), 0.911 (1.88), 0.920 (0.81), 0.972 (0.81), 0.981 (1.83), 0.987 (1.37), 0.992 (1.24), 1.002 (1.96), 1.007 (1.37), 1.424 (3.81), 1.439 (3.78), 1.975 (0.61), 1.983 (0.69), 1.995 (1.17), 2.008 (0.63), 2.327 (0.71), 2.518 (3.02), 2.523 (2.03), 2.669 (0.74), 3.324 (16.00), 5.279 (0.61), 5.294 (0.81), 7.189 (1.14), 7.210 (2.39), 7.230 (1.50), 7.407 (0.81), 7.514 (1.45), 7.529 (1.47), 7.549 (1.63), 7.573 (1.57), 9.963 (3.50).

Example 48

4-(3-cyclopropyl-4-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide

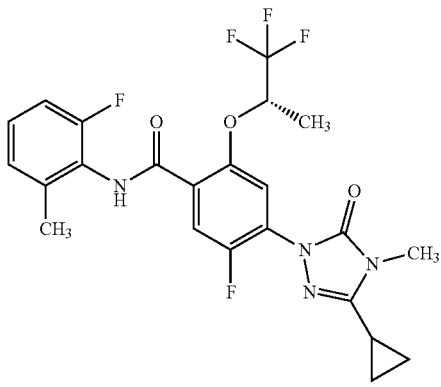 [SMILES: Cc1cccc(F)c1NC(=O)c1cc(F)c(-n2nc(C3CC3)n(C)c2=O)cc1O[C@@H](C)C(F)(F)F]

Synthesized from Intermediate 54 and 2-fluoro-6-methylaniline.

LC-MS (Method A): $R_t$=1.28 min; MS (ESIpos): m/z=497 [M+H]$^+$.

Example 49

4-(3-cyclopropyl-4-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide

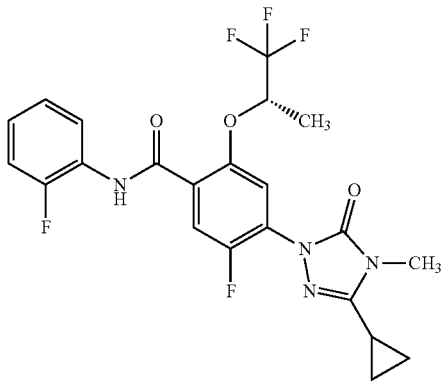 [SMILES: C[C@H](Oc1cc(-n2nc(C3CC3)n(C)c2=O)c(F)cc1C(=O)Nc1ccccc1F)C(F)(F)F]

Synthesized from Intermediate 54 and 2-fluoroaniline.

LC-MS (Method A): $R_t$=1.25 min; MS (ESIpos): m/z=483 [M+H]$^+$.

$^1$H-NMR (400 MHz, CHLOROFORM-d) δ [ppm]: 0.990 (1.13), 0.996 (2.27), 0.999 (1.38), 1.002 (1.74), 1.006 (1.83), 1.010 (1.47), 1.015 (5.11), 1.018 (2.51), 1.186 (1.84), 1.499 (1.43), 1.581 (3.60), 1.596 (3.60), 1.657 (1.14), 3.359 (16.00), 7.030 (0.99), 7.039 (0.79), 7.044 (1.46), 7.071 (0.95), 7.341 (1.58), 7.354 (1.57), 8.059 (2.00), 8.088 (2.04), 8.465 (0.91), 8.470 (0.98).

Example 50

4-(3-cyclobutyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

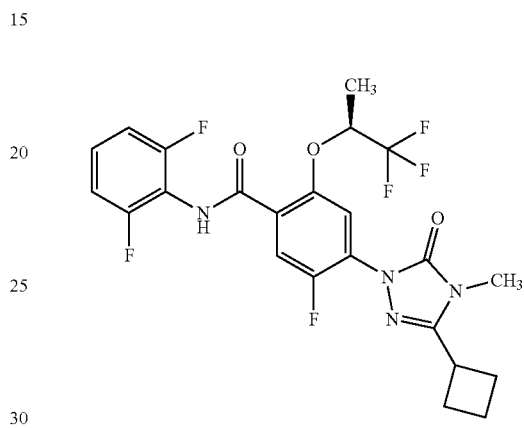

Synthesized from Intermediate 55 and 2,6-difluoroaniline.

LC-MS (Method A): $R_t$=1.31 min; MS (ESIpos): m/z=515 [M+H]$^+$.

$^1$H-NMR (400 MHz, DMSO-d6) δ [ppm]: 1.232 (0.96), 1.434 (4.95), 1.450 (4.91), 1.914 (0.75), 2.034 (0.66), 2.055 (1.18), 2.078 (1.01), 2.083 (1.01), 2.105 (0.66), 2.280 (0.92), 2.285 (1.05), 2.296 (1.36), 2.304 (3.86), 2.317 (2.41), 2.325 (5.35), 2.337 (1.62), 2.346 (1.71), 2.518 (5.39), 2.523 (3.55), 2.665 (0.88), 2.669 (1.18), 2.674 (0.83), 3.152 (16.00), 3.613 (1.05), 3.634 (1.58), 3.654 (1.01), 5.300 (0.79), 5.317 (1.01), 5.332 (0.75), 7.191 (1.40), 7.212 (2.89), 7.232 (1.75), 7.407 (0.92), 7.568 (3.51), 7.583 (1.88), 7.592 (2.10), 9.982 (2.72).

Example 51

4-(3-cyclobutyl-4-methyl-5-oxo-4,5-dihydro-1H-1,2,4-triazol-1-yl)-5-fluoro-N-(2-fluoro-6-methyl-phenyl)-2-{[(2S)-1,1,1-trifluoropropan-2-yl]oxy}benzamide

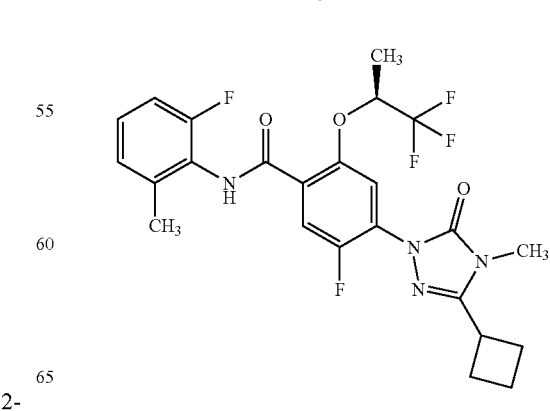

Synthesized from Intermediate 55 and 2-fluoro-6-methylaniline.

LC-MS (Method A): $R_t$=1.30 min; MS (ESIpos): m/z=511 [M+H]$^+$.

$^1$H-NMR (400 MHz, DMSO-d6) δ [ppm]: 1.434 (4.63), 1.450 (4.60), 2.057 (0.89), 2.080 (0.80), 2.084 (0.80), 2.273 (11.08), 2.305 (2.80), 2.313 (1.22), 2.317 (1.56), 2.326 (4.06), 2.347 (1.13), 2.351 (0.90), 2.518 (2.48), 2.522 (1.65), 2.668 (0.69), 3.154 (16.00), 3.611 (0.78), 3.614 (0.81), 3.633 (1.19), 3.635 (1.16), 3.654 (0.77), 3.656 (0.75), 5.360 (0.96), 7.119 (1.50), 7.124 (1.44), 7.136 (1.64), 7.145 (0.92), 7.228 (0.75), 7.242 (0.80), 7.249 (1.05), 7.549 (2.62), 7.563 (2.05), 7.574 (3.13), 7.577 (2.32), 9.803 (2.69).

Example 52

4-(3-cyclobutyl-4-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide

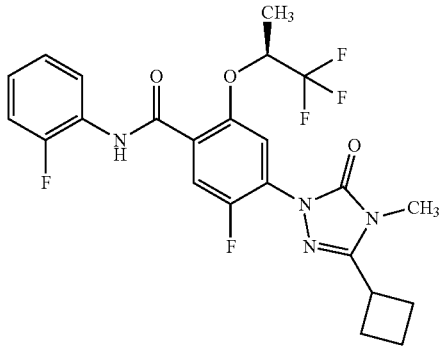 [SMILES: C[C@H](Oc1cc(-n2nc(C3CCC3)n(C)c2=O)c(F)cc1C(=O)Nc1ccccc1F)C(F)(F)F]

Synthesized from Intermediate 55 and 2-fluoroaniline.

LC-MS (Method A): $R_t$=1.37 min; MS (ESIpos): m/z=497 [M+H]$^+$.

$^1$H-NMR (400 MHz, DMSO-d6) δ [ppm]: 1.478 (4.55), 1.494 (4.51), 2.056 (1.02), 2.078 (0.88), 2.083 (0.88), 2.297 (1.08), 2.305 (3.20), 2.313 (1.47), 2.318 (1.84), 2.326 (4.39), 2.337 (1.09), 2.347 (1.31), 2.351 (1.01), 2.518 (2.20), 2.523 (1.41), 3.154 (16.00), 3.613 (0.88), 3.615 (0.91), 3.634 (1.26), 3.636 (1.35), 3.655 (0.85), 3.658 (0.80), 5.432 (0.96), 7.211 (0.78), 7.216 (0.97), 7.219 (1.54), 7.223 (1.72), 7.226 (1.41), 7.230 (2.19), 7.238 (1.50), 7.244 (1.38), 7.299 (0.79), 7.305 (0.71), 7.326 (0.83), 7.617 (1.81), 7.631 (1.76), 7.738 (2.06), 7.765 (2.03), 8.083 (1.05), 8.088 (0.87), 10.021 (2.26).

Example 53

4-(3-cyclopropyl-4-ethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

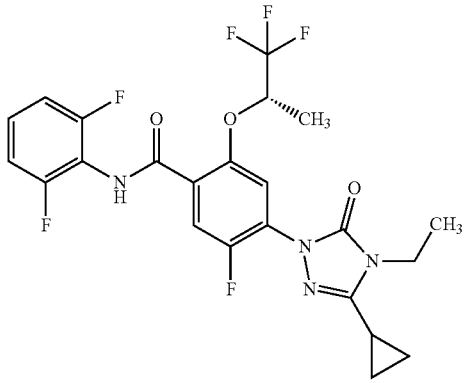 [SMILES: CCn1c(C2CC2)nn(-c2cc(O[C@@H](C)C(F)(F)F)c(C(=O)Nc3c(F)cccc3F)cc2F)c1=O]

Synthesized from Intermediate 53 and 2,6-difluoroaniline.

LC-MS (Method A): $R_t$=1.30 min; MS (ESIpos): m/z=515 [M+H]$^+$.

$^1$H-NMR (400 MHz, DMSO-d6) δ [ppm]: 0.897 (1.19), 0.909 (4.05), 0.915 (4.68), 0.922 (4.54), 0.927 (4.40), 0.936 (2.17), 0.985 (1.82), 0.994 (4.26), 1.000 (3.21), 1.005 (2.93), 1.015 (4.61), 1.021 (3.28), 1.033 (1.19), 1.272 (6.85), 1.290 (16.00), 1.308 (7.06), 1.425 (9.15), 1.440 (9.15), 2.009 (0.70), 2.022 (1.40), 2.030 (1.61), 2.035 (0.98), 2.042 (2.79), 2.050 (1.05), 2.055 (1.47), 2.063 (1.33), 2.332 (1.54), 2.336 (0.70), 2.518 (8.31), 2.523 (5.66), 3.800 (1.89), 3.818 (6.01), 3.836 (5.94), 3.854 (1.75), 5.295 (1.47), 5.311 (1.89), 5.326 (1.40), 7.190 (2.79), 7.210 (5.87), 7.230 (3.63), 7.386 (1.33), 7.407 (1.96), 7.423 (0.98), 7.428 (1.05), 7.533 (3.63), 7.546 (6.71), 7.571 (3.84), 9.958 (8.87).

Example 54

4-(3-cyclopropyl-4-ethyl-5-oxo-4,5-dihydro-1H-1,2,4-triazol-1-yl)-5-fluoro-N-(2-fluoro-6-methyl-phenyl)-2-{[(2S)-1,1,1-trifluoropropan-2-yl]oxy}benzamide

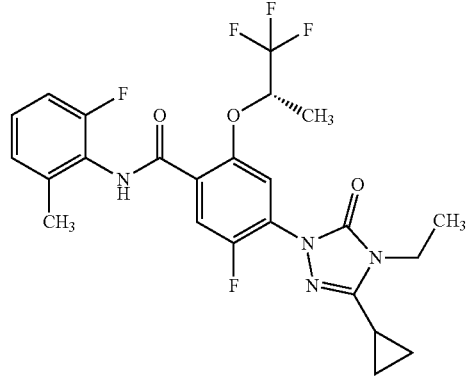 [SMILES: CCn1c(C2CC2)nn(-c2cc(O[C@@H](C)C(F)(F)F)c(C(=O)Nc3c(C)cccc3F)cc2F)c1=O]

Synthesized from Intermediate 53 and 2-fluoro-6-methylaniline.

LC-MS (Method A): $R_t$=1.33 min; MS (ESIpos): m/z=511 [M+H]$^+$.

$^1$H-NMR (400 MHz, DMSO-d6) δ [ppm]: 0.896 (0.75), 0.908 (2.62), 0.914 (2.86), 0.920 (2.62), 0.927 (2.78), 0.935 (1.23), 0.986 (1.11), 0.995 (2.60), 1.001 (1.90), 1.006 (1.75), 1.015 (2.78), 1.021 (1.98), 1.033 (0.75), 1.275 (4.37), 1.292 (10.11), 1.311 (4.40), 1.424 (6.95), 1.440 (6.95), 2.023 (0.90), 2.031 (1.00), 2.043 (1.77), 2.052 (0.64), 2.055 (0.95), 2.064 (0.87), 2.266 (16.00), 2.332 (1.11), 2.518 (6.61), 2.523 (4.22), 2.673 (1.13), 3.802 (1.16), 3.820 (3.83), 3.838 (3.78), 3.856 (1.08), 5.338 (1.08), 5.354 (1.41), 5.369 (1.03), 7.099 (0.87), 7.116 (2.32), 7.120 (2.24), 7.132 (2.47), 7.141 (1.41), 7.225 (1.05), 7.240 (1.16), 7.245 (1.59), 7.260 (1.18), 7.265 (0.80), 7.279 (0.64), 7.524 (3.83), 7.527 (4.78), 7.539 (3.04), 7.551 (3.70), 9.784 (4.09).

Example 55

4-(3-cyclopropyl-4-ethyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide

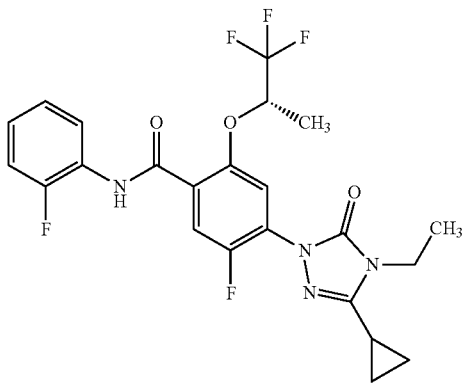 [SMILES: CCn1c(C2CC2)nn(-c2cc(O[C@@H](C)C(F)(F)F)c(C(=O)Nc3ccccc3F)cc2F)c1=O]

Synthesized from Intermediate 53 and 2-fluoroaniline.
LC-MS (Method A): $R_t$=1.40 min; MS (ESIpos): m/z=497 [M+H]$^+$.

$^1$H-NMR (400 MHz, DMSO-d6) δ [ppm]: 0.900 (1.23), 0.912 (4.19), 0.918 (4.67), 0.925 (4.36), 0.930 (4.44), 0.939 (1.94), 0.989 (1.86), 0.997 (4.24), 1.003 (3.15), 1.009 (2.89), 1.018 (4.58), 1.024 (3.18), 1.036 (1.16), 1.274 (7.04), 1.291 (16.00), 1.310 (7.11), 1.470 (9.74), 1.486 (9.70), 2.013 (0.75), 2.026 (1.44), 2.033 (1.61), 2.038 (0.94), 2.046 (2.82), 2.054 (1.05), 2.059 (1.49), 2.067 (1.32), 2.518 (3.16), 2.523 (2.19), 3.803 (1.92), 3.821 (6.23), 3.839 (6.06), 3.858 (1.79), 5.414 (1.57), 5.430 (2.03), 5.446 (1.48), 7.202 (1.36), 7.207 (1.61), 7.213 (2.02), 7.216 (3.19), 7.219 (3.64), 7.222 (3.01), 7.226 (4.64), 7.237 (3.22), 7.240 (3.13), 7.253 (0.84), 7.296 (1.68), 7.302 (1.52), 7.315 (1.21), 7.320 (1.52), 7.324 (1.79), 7.331 (1.02), 7.334 (1.02), 7.348 (1.03), 7.579 (3.85), 7.594 (3.81), 7.719 (4.45), 7.745 (4.44), 8.059 (1.25), 8.065 (1.13), 8.079 (2.23), 8.085 (1.83), 8.093 (1.08), 8.104 (1.08), 10.001 (4.27).

Example 56

4-(4-cyclopropyl-3-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

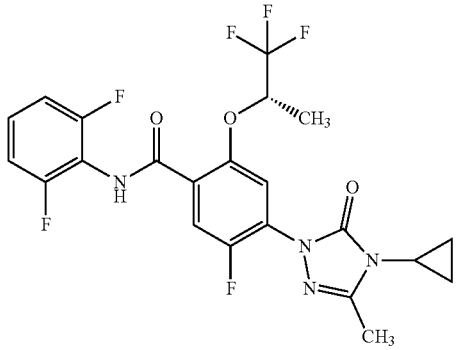 [SMILES: Cc1nn(-c2cc(O[C@@H](C)C(F)(F)F)c(C(=O)Nc3c(F)cccc3F)cc2F)c(=O)n1C1CC1]

Synthesized from Intermediate 56 and 2,6-difluoroaniline.
LC-MS (Method A): $R_t$=1.21 min; MS (ESIpos): m/z=501 [M+H]$^+$.

$^1$H-NMR (400 MHz, DMSO-d6) δ [ppm]: 0.967 (1.74), 0.972 (3.20), 0.982 (3.59), 0.990 (8.16), 1.425 (4.50), 1.442 (4.51), 2.084 (1.22), 2.327 (1.22), 2.337 (16.00), 2.518 (2.48), 2.523 (1.66), 2.669 (0.61), 2.894 (0.78), 2.909 (1.37), 5.278 (0.73), 5.295 (0.95), 5.758 (1.12), 7.188 (1.41), 7.209 (2.92), 7.229 (1.81), 7.406 (0.99), 7.520 (1.75), 7.534 (1.78), 7.547 (2.01), 7.573 (1.90), 9.977 (4.24).

Example 57

4-(4-cyclopropyl-3-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide

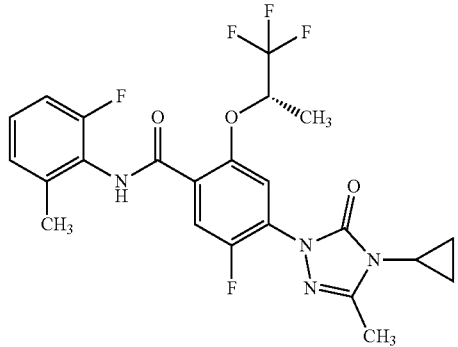 [SMILES: Cc1cccc(F)c1NC(=O)c1cc(F)c(-n2nc(C)n(C3CC3)c2=O)cc1O[C@@H](C)C(F)(F)F]

Synthesized from Intermediate 56 and 2-fluoro-6-methylaniline.
LC-MS (Method A): $R_t$=1.25 min; MS (ESIpos): m/z=497 [M+H]$^+$.

$^1$H-NMR (400 MHz, DMSO-d6) δ [ppm]: 0.968 (1.57), 0.974 (3.00), 0.983 (3.36), 0.992 (7.39), 1.425 (5.20), 1.441 (5.20), 2.267 (11.89), 2.326 (1.03), 2.331 (1.55), 2.338 (16.00), 2.518 (2.46), 2.522 (1.62), 2.910 (1.28), 5.322 (0.83), 5.338 (1.08), 5.354 (0.77), 5.758 (0.60), 7.114 (1.82), 7.119 (1.72), 7.131 (1.89), 7.141 (1.06), 7.224 (0.79), 7.238 (0.87), 7.245 (1.15), 7.259 (0.91), 7.511 (2.15), 7.525 (2.46), 7.530 (2.96), 7.554 (2.57), 9.802 (3.10).

Example 58

4-(4-cyclopropyl-3-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide

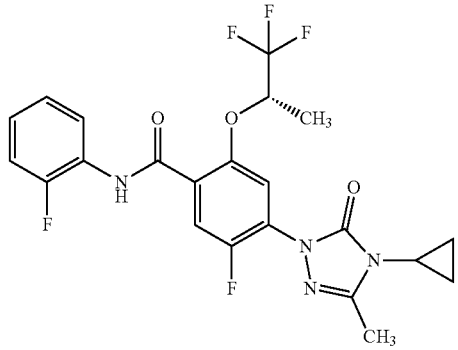 [SMILES: Cc1nn(-c2cc(O[C@@H](C)C(F)(F)F)c(C(=O)Nc3ccccc3F)cc2F)c(=O)n1C1CC1]

Synthesized from Intermediate 56 and 2-fluoroaniline.
LC-MS (Method A): $R_t$=1.31 min; MS (ESIpos): m/z=483 [M+H]$^+$.
$^1$H-NMR (400 MHz, DMSO-d6) δ [ppm]: 0.970 (1.58), 0.975 (3.12), 0.984 (3.26), 0.992 (8.02), 1.469 (4.52), 1.484 (4.50), 2.340 (16.00), 2.912 (1.27), 5.411 (0.94), 7.215 (1.46), 7.219 (1.71), 7.226 (2.10), 7.234 (1.39), 7.236 (1.45), 7.239 (1.50), 7.294 (0.77), 7.322 (0.82), 7.565 (1.78), 7.580 (1.76), 7.716 (2.09), 7.743 (2.00), 8.072 (1.01), 8.078 (0.85), 10.017 (2.23).

Example 59

N-(2,6-difluorophenyl)-5-fluoro-4-[4-methyl-5-oxo-3-(trifluoromethyl)-4,5-dihydro-1H-1,2,4-triazol-1-yl]-2-{[(2S)-1,1,1-trifluoropropan-2-yl]oxy}benzamide

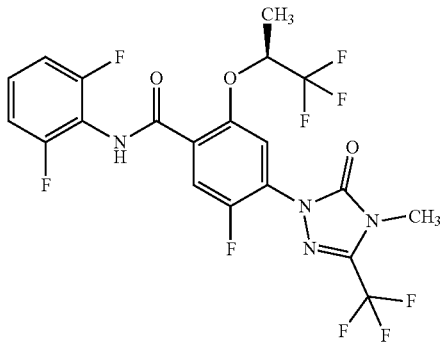 [SMILES: C[C@H](Oc1cc(-n2nc(C(F)(F)F)n(C)c2=O)c(F)cc1C(=O)Nc1c(F)cccc1F)C(F)(F)F]

Synthesized from Intermediate 57 and 2,6-difluoroaniline.
LC-MS (Method A): $R_t$=1.33 min; MS (ESIneg): m/z=527 [M−H]$^−$.
$^1$H-NMR (400 MHz, DMSO-d6) δ [ppm]: 1.439 (7.13), 1.454 (7.49), 2.323 (0.63), 2.327 (0.99), 2.332 (0.92), 2.523 (11.15), 2.665 (0.63), 2.669 (0.97), 2.673 (0.91), 3.406 (16.00), 5.267 (1.18), 5.283 (1.55), 5.299 (1.21), 7.193 (1.99), 7.214 (4.22), 7.234 (2.64), 7.392 (1.08), 7.408 (1.49), 7.428 (0.99), 7.637 (2.69), 7.646 (3.96), 7.651 (4.01), 7.670 (2.75), 10.084 (3.43).

Example 60

5-fluoro-N-(2-fluoro-6-methylphenyl)-4-[4-methyl-5-oxo-3-(trifluoromethyl)-4,5-dihydro-1H-1,2,4-triazol-1-yl]-2-{[(2S)-1,1,1-trifluoropropan-2-yl]oxy}benzamide

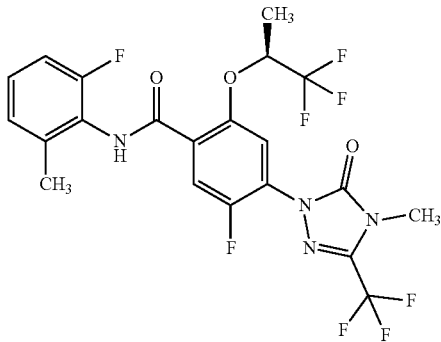 [SMILES: Cc1cccc(F)c1NC(=O)c1cc(F)c(-n2nc(C(F)(F)F)n(C)c2=O)cc1O[C@@H](C)C(F)(F)F]

Synthesized from Intermediate 57 and 2-fluoro-6-methylaniline.
LC-MS (Method A): $R_t$=1.31 min; MS (ESIpos): m/z=525 [M+H]$^+$.
$^1$H-NMR (400 MHz, DMSO-d6) δ [ppm]: 1.439 (6.82), 1.455 (6.86), 2.278 (16.00), 2.518 (2.40), 2.522 (1.70), 3.408 (13.33), 5.292 (0.44), 5.309 (1.08), 5.324 (1.43), 5.340 (1.04), 5.356 (0.40), 7.104 (0.87), 7.120 (2.02), 7.126 (2.10), 7.137 (2.42), 7.147 (1.33), 7.231 (1.08), 7.245 (1.18), 7.250 (1.58), 7.265 (1.19), 7.270 (0.77), 7.284 (0.66), 7.631 (3.93), 7.637 (3.04), 7.652 (3.46), 7.655 (4.24), 9.891 (3.85).

Example 61

5-fluoro-N-(2-fluorophenyl)-4-[4-methyl-5-oxo-3-(trifluoromethyl)-4,5-dihydro-1H-1,2,4-triazol-1-yl]-2-{[(2S)-1,1,1-trifluoropropan-2-yl]oxy}benzamide

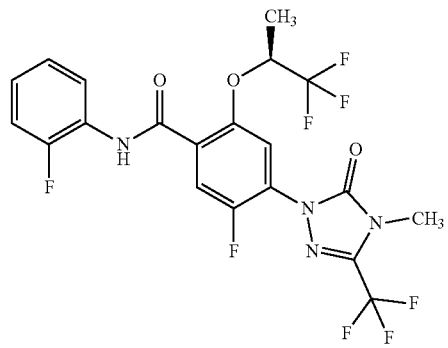 [SMILES: C[C@H](Oc1cc(-n2nc(C(F)(F)F)n(C)c2=O)c(F)cc1C(=O)Nc1ccccc1F)C(F)(F)F]

Synthesized from Intermediate 57 and 2-fluoroaniline.
LC-MS (Method A): $R_t$=1.38 min; MS (ESIpos): m/z=511 [M+H]$^+$.
$^1$H-NMR (400 MHz, DMSO-d6) δ [ppm]: 1.470 (7.46), 1.486 (7.50), 2.518 (2.27), 2.523 (1.68), 3.408 (16.00), 5.331 (0.51), 5.347 (1.22), 5.363 (1.60), 5.379 (1.17), 5.395 (0.45), 7.212 (0.98), 7.222 (2.82), 7.229 (3.48), 7.237 (2.90), 7.240 (2.38), 7.246 (3.34), 7.258 (0.66), 7.295 (1.35), 7.302 (0.93), 7.311 (0.73), 7.314 (0.82), 7.322 (1.40), 7.331 (0.86), 7.336 (0.65), 7.340 (0.59), 7.347 (0.77), 7.666 (3.06), 7.681 (3.04), 7.784 (3.78), 7.810 (3.74), 8.014 (1.04), 8.019 (0.75), 8.022 (0.76), 8.034 (1.54), 8.039 (1.25), 8.048 (0.85), 8.059 (0.94), 10.097 (4.20).

Example 62

4-(4-cyclopropyl-3-ethyl-5-oxo-4,5-dihydro-1H-1,2,4-triazol-1-yl)-5-fluoro-N-(2-fluoro-6-methyl-phenyl)-2-{[(2S)-1,1,1-trifluoropropan-2-yl]oxy}benzamide

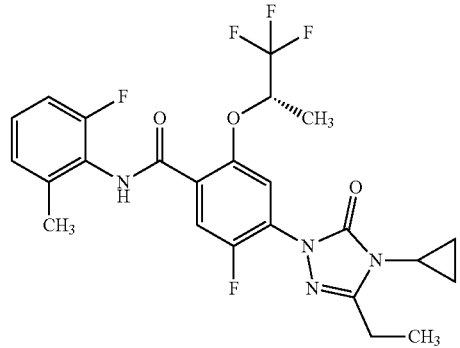 [SMILES: CCc1nn(-c2cc(O[C@@H](C)C(F)(F)F)c(C(=O)Nc3c(C)cccc3F)cc2F)c(=O)n1C1CC1]

Synthesized from Intermediate 58 and 2-fluoro-6-methylaniline.

LC-MS (Method A): $R_t$=1.32 min; MS (ESIpos): m/z=511 [M+H]⁺.

¹H-NMR (400 MHz, DMSO-d6) δ [ppm]: 0.972 (2.01), 0.978 (3.38), 0.981 (2.92), 0.990 (5.04), 0.996 (7.00), 1.005 (1.83), 1.235 (5.68), 1.254 (12.83), 1.273 (5.66), 1.428 (7.03), 1.444 (7.04), 2.269 (16.00), 2.518 (2.22), 2.523 (1.55), 2.720 (1.66), 2.739 (5.55), 2.757 (5.26), 2.776 (1.52), 2.897 (0.91), 2.905 (0.85), 2.912 (1.74), 2.919 (0.84), 2.923 (0.89), 2.928 (0.77), 5.319 (1.10), 5.335 (1.44), 5.352 (1.03), 7.100 (0.91), 7.116 (2.37), 7.121 (2.25), 7.133 (2.54), 7.143 (1.44), 7.226 (1.12), 7.240 (1.21), 7.246 (1.59), 7.261 (1.24), 7.266 (0.78), 7.280 (0.66), 7.517 (2.99), 7.533 (6.26), 7.558 (3.68), 9.796 (4.21).

Example 63

4-(4-cyclopropyl-3-ethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

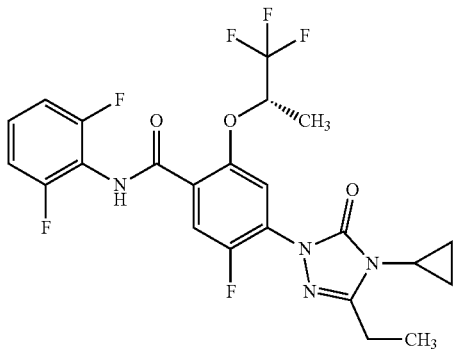 [SMILES: CCc1nn(-c2cc(O[C@@H](C)C(F)(F)F)c(C(=O)Nc3c(F)cccc3F)cc2F)c(=O)n1C1CC1]

Synthesized from Intermediate 58 and 2,6-difluoroaniline.

LC-MS (Method A): $R_t$=1.29 min; MS (ESIpos): m/z=515 [M+H]⁺.

¹H-NMR (400 MHz, DMSO-d6) δ [ppm]: 0.971 (3.22), 0.977 (5.28), 0.980 (4.55), 0.989 (7.78), 0.995 (10.76), 1.234 (7.62), 1.252 (16.00), 1.271 (7.54), 1.429 (8.50), 1.444 (8.34), 2.331 (1.01), 2.518 (6.33), 2.523 (4.27), 2.674 (1.01), 2.719 (2.30), 2.737 (7.09), 2.756 (6.85), 2.775 (2.06), 2.896 (1.37), 2.903 (1.37), 2.911 (2.42), 2.922 (1.37), 2.926 (1.13), 5.275 (1.37), 5.292 (1.77), 5.308 (1.25), 7.191 (2.58), 7.211 (5.28), 7.231 (3.26), 7.388 (1.29), 7.408 (1.81), 7.424 (0.97), 7.429 (0.93), 7.526 (3.18), 7.541 (3.35), 7.551 (3.67), 7.576 (3.43), 9.972 (7.86).

Example 64

4-(4-cyclopropyl-3-ethyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide

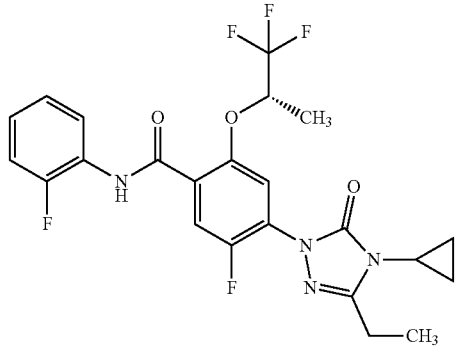 [SMILES: CCc1nn(-c2cc(O[C@@H](C)C(F)(F)F)c(C(=O)Nc3ccccc3F)cc2F)c(=O)n1C1CC1]

Synthesized from Intermediate 58 and 2-fluoroaniline.

LC-MS (Method A): $R_t$=1.39 min; MS (ESIpos): m/z=497 [M+H]⁺.

¹H-NMR (400 MHz, DMSO-d6) δ [ppm]: 0.973 (2.62), 0.979 (4.41), 0.982 (3.76), 0.990 (6.29), 0.997 (9.11), 1.004 (2.36), 1.234 (7.22), 1.253 (16.00), 1.271 (7.41), 1.471 (7.47), 1.487 (7.48), 2.518 (3.96), 2.522 (2.63), 2.721 (2.14), 2.739 (6.79), 2.758 (6.64), 2.777 (1.93), 2.898 (1.17), 2.906 (1.07), 2.913 (2.18), 2.921 (1.07), 2.924 (1.11), 2.928 (0.93), 5.391 (1.20), 5.407 (1.57), 5.423 (1.13), 7.202 (1.05), 7.208 (1.26), 7.214 (1.64), 7.216 (2.39), 7.220 (2.80), 7.223 (2.29), 7.227 (3.61), 7.235 (2.32), 7.238 (2.42), 7.241 (2.42), 7.296 (1.31), 7.302 (1.16), 7.315 (0.93), 7.320 (1.20), 7.324 (1.40), 7.334 (0.84), 7.348 (0.80), 7.571 (3.00), 7.585 (2.97), 7.721 (3.60), 7.747 (3.51), 8.056 (0.98), 8.075 (1.67), 8.082 (1.35), 8.101 (0.84), 10.010 (3.22).

Example 65

N-(2,6-difluorophenyl)-5-fluoro-4-[4-methyl-5-oxo-3-(propan-2-yl)-4,5-dihydro-1H-1,2,4-triazol-1-yl]-2-{[(2S)-1,1,1-trifluoropropan-2-yl]oxy}benzamide

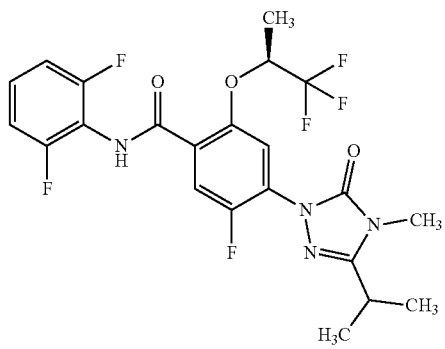 [SMILES: CC(C)c1nn(-c2cc(O[C@@H](C)C(F)(F)F)c(C(=O)Nc3c(F)cccc3F)cc2F)c(=O)n1C]

Synthesized from Intermediate 59 and 2,6-difluoroaniline.

LC-MS (Method A): $R_t$=1.24 min; MS (ESIpos): m/z=503 [M+H]⁺.

¹H-NMR (400 MHz, DMSO-d6) δ [ppm]: 1.251 (15.90), 1.268 (16.00), 1.431 (3.86), 1.447 (3.84), 2.518 (1.83), 2.523 (1.32), 3.012 (0.42), 3.030 (1.12), 3.047 (1.52), 3.064 (1.09), 3.081 (0.41), 3.274 (14.97), 5.294 (0.63), 5.309 (0.81), 5.326 (0.60), 7.192 (1.14), 7.212 (2.41), 7.232 (1.51), 7.386 (0.55), 7.407 (0.80), 7.428 (0.42), 7.550 (1.45), 7.564 (2.76), 7.588 (1.59), 9.976 (2.43).

Example 66

5-fluoro-N-(2-fluoro-6-methylphenyl)-4-[4-methyl-5-oxo-3-(propan-2-yl)-4,5-dihydro-1H-1,2,4-triazol-1-yl]-2-{[(2S)-1,1,1-trifluoropropan-2-yl]oxy}benzamide

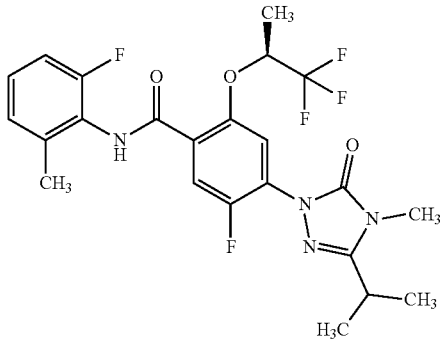 [SMILES: Cc1cccc(F)c1NC(=O)c1cc(F)c(-n2nc(C(C)C)n(C)c2=O)cc1O[C@@H](C)C(F)(F)F]

Synthesized from Intermediate 59 and 2-fluoro-6-methylaniline.
LC-MS (Method A): $R_t$=1.26 min; MS (ESIpos): m/z=499 [M+H]$^+$.
$^1$H-NMR (400 MHz, DMSO-d6) δ [ppm]: 1.252 (15.82), 1.270 (16.00), 1.432 (4.75), 1.447 (4.76), 2.273 (11.02), 2.518 (1.09), 2.523 (0.75), 3.014 (0.42), 3.031 (1.15), 3.048 (1.53), 3.065 (1.08), 3.276 (15.10), 5.337 (0.75), 5.354 (0.97), 5.369 (0.71), 7.103 (0.61), 7.119 (1.55), 7.123 (1.52), 7.136 (1.70), 7.145 (0.94), 7.228 (0.73), 7.242 (0.80), 7.249 (1.07), 7.263 (0.83), 7.268 (0.52), 7.282 (0.44), 7.545 (4.28), 7.559 (2.07), 7.570 (2.55), 9.798 (2.78).

Example 67

5-fluoro-N-(2-fluorophenyl)-4-[4-methyl-5-oxo-3-(propan-2-yl)-4,5-dihydro-1H-1,2,4-triazol-1-yl]-2-{[(2S)-1,1,1-trifluoropropan-2-yl]oxy}benzamide

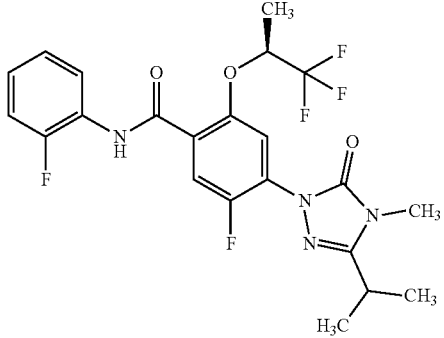 [SMILES: CC(C)c1nn(-c2cc(O[C@@H](C)C(F)(F)F)c(C(=O)Nc3ccccc3F)cc2F)c(=O)n1C]

Synthesized from Intermediate 59 and 2-fluoroaniline.
LC-MS (Method A): $R_t$=1.34 min; MS (ESIpos): m/z=485 [M+H]$^+$.
$^1$H-NMR (400 MHz, DMSO-d6) δ [ppm]: 1.251 (15.85), 1.268 (16.00), 1.475 (4.00), 1.491 (4.00), 2.518 (1.61), 2.523 (1.16), 3.015 (0.42), 3.032 (1.11), 3.050 (1.49), 3.067 (1.08), 3.277 (15.50), 5.408 (0.64), 5.424 (0.85), 5.440 (0.61), 7.205 (0.56), 7.211 (0.66), 7.219 (1.31), 7.223 (1.47), 7.226 (1.16), 7.230 (1.96), 7.238 (1.31), 7.244 (1.31), 7.299 (0.71), 7.304 (0.64), 7.317 (0.47), 7.326 (0.74), 7.333 (0.41), 7.336 (0.42), 7.350 (0.43), 7.596 (1.61), 7.611 (1.58), 7.734 (1.91), 7.759 (1.90), 8.061 (0.53), 8.066 (0.44), 8.080 (0.92), 8.086 (0.75), 8.092 (0.41), 8.105 (0.48), 10.016 (2.07).

Example 68

4-(3-ethyl-4-methyl-5-oxo-4,5-dihydro-1H-1,2,4-triazol-1-yl)-5-fluoro-N-(2-fluoro-6-methyl-phenyl)-2-[(1S)-1-phenylethoxy]benzamide

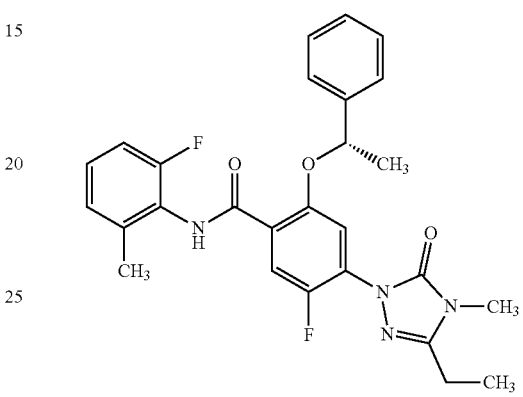

Synthesized from Intermediate 43 and 2-fluoro-6-methylaniline.
LC-MS (Method A): $R_t$=1.33 min; MS (ESIneg): m/z=492 [M−H]$^-$.
$^1$H-NMR (400 MHz, CHLOROFORM-d) δ [ppm]: 1.313 (3.69), 1.331 (7.67), 1.350 (3.85), 1.591 (1.61), 1.790 (5.27), 1.806 (5.23), 2.309 (9.88), 2.583 (1.18), 2.602 (3.74), 2.621 (3.37), 2.639 (1.04), 3.292 (16.00), 5.593 (1.08), 5.609 (1.07), 7.024 (0.96), 7.082 (1.17), 7.181 (0.91), 7.195 (0.90), 7.285 (2.08), 7.301 (2.64), 7.319 (1.21), 7.345 (1.36), 7.360 (1.17), 7.364 (2.82), 7.381 (1.52), 7.385 (0.98), 7.411 (2.32), 7.414 (2.60), 7.417 (1.20), 7.431 (1.57), 7.435 (1.03), 8.102 (2.23), 8.131 (2.22), 9.620 (1.35).

Example 69

N-(2,6-difluorophenyl)-4-(3-ethyl-4-methyl-5-oxo-4,5-dihydro-1H-1,2,4-triazol-1-yl)-5-fluoro-2-[(1S)-1-phenylethoxy]benzamide

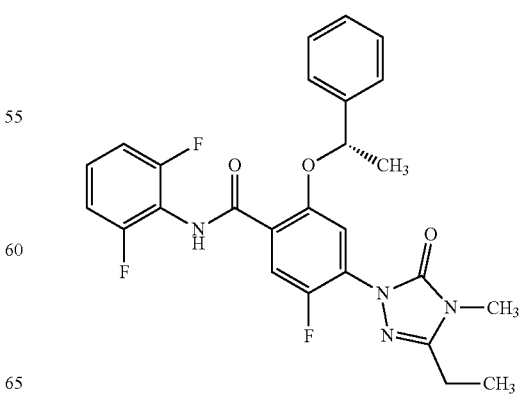

Synthesized from Intermediate 43 and 2,6-difluoroaniline.

LC-MS (Method A): R$_t$=1.30 min; MS (ESIneg): m/z=495 [M–H]$^-$.

$^1$H-NMR (400 MHz, CHLOROFORM-d) [ppm]: 1.312 (3.65), 1.331 (7.68), 1.350 (3.81), 1.574 (3.67), 1.803 (4.93), 1.819 (5.08), 2.582 (1.18), 2.601 (3.61), 2.620 (3.37), 2.639 (1.01), 3.291 (16.00), 5.590 (1.01), 5.606 (1.02), 7.003 (1.23), 7.023 (2.54), 7.043 (1.76), 7.242 (0.98), 7.299 (1.89), 7.302 (1.55), 7.313 (1.82), 7.321 (1.16), 7.349 (1.29), 7.364 (1.08), 7.368 (2.69), 7.386 (1.44), 7.388 (0.98), 7.417 (2.19), 7.419 (2.49), 7.423 (1.19), 7.437 (1.50), 7.441 (1.03), 8.100 (2.02), 8.129 (2.01), 9.743 (1.22).

Example 70

4-(3-ethyl-4-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy}benzamide

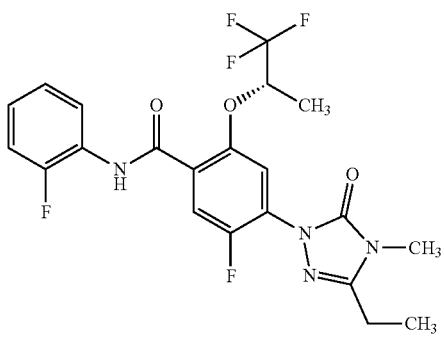 [SMILES: CCc1nn(-c2cc(O[C@@H](C)C(F)(F)F)c(C(=O)Nc3ccccc3F)cc2F)c(=O)n1C]

Synthesized from Intermediate 40 and 2-fluoroaniline.

LC-MS (Method A): R$_t$=1.29 min; MS (ESIpos): m/z=471 [M+H]$^+$.

$^1$H-NMR (400 MHz, CHLOROFORM-d) δ [ppm]: 1.356 (3.69), 1.375 (7.75), 1.394 (3.90), 1.594 (1.02), 1.664 (3.49), 1.679 (3.50), 2.635 (1.21), 2.654 (3.71), 2.673 (3.46), 2.692 (1.05), 3.338 (16.00), 7.109 (1.02), 7.118 (0.80), 7.122 (1.44), 7.150 (0.92), 7.450 (1.55), 7.464 (1.56), 8.155 (2.04), 8.184 (2.00), 8.546 (0.94), 8.550 (0.98).

Example 71

4-(3-ethyl-4-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide

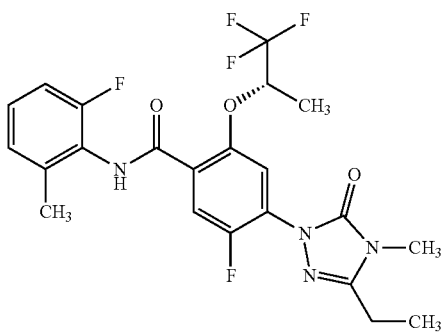 [SMILES: CCc1nn(-c2cc(O[C@@H](C)C(F)(F)F)c(C(=O)Nc3c(C)cccc3F)cc2F)c(=O)n1C]

Synthesized from Intermediate 40 and 2-fluoro-6-methylaniline.

LC-MS (Method A): R$_t$=1.21 min; MS (ESIpos): m/z=486 [M+H]$^+$.

$^1$H-NMR (400 MHz, CHLOROFORM-d) δ [ppm]: 1.357 (3.92), 1.376 (8.19), 1.394 (4.10), 1.592 (1.03), 1.644 (3.91), 1.660 (4.02), 2.312 (10.10), 2.637 (1.28), 2.656 (3.75), 2.675 (3.80), 2.694 (1.13), 3.339 (16.00), 4.929 (0.85), 7.011 (0.99), 7.081 (1.18), 7.188 (0.90), 7.202 (0.88), 7.434 (1.79), 7.448 (1.77), 8.144 (2.20), 8.172 (2.18), 8.872 (1.20).

Example 72

4-(3-ethyl-4-methyl-5-oxo-4,5-dihydro-1H-1,2,4-triazol-1-yl)-5-fluoro-N-(4-fluoro-2-methyl-phenyl)-2-{[(2S)-1,1,1-trifluoropropan-2-yl]oxy}benzamide

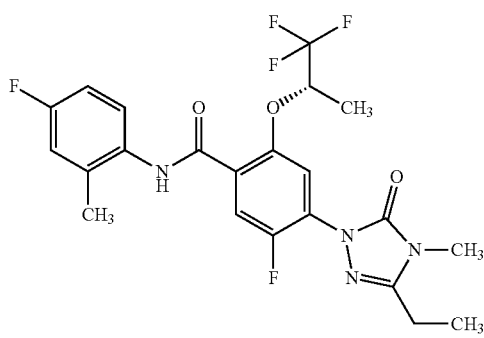 [SMILES: CCc1nn(-c2cc(O[C@@H](C)C(F)(F)F)c(C(=O)Nc3ccc(F)cc3C)cc2F)c(=O)n1C]

Synthesized from Intermediate 40 and 4-fluoro-2-methylaniline.

LC-MS (Method A): R$_t$=1.26 min; MS (ESIpos): m/z=486 [M+H]$^+$.

$^1$H-NMR (400 MHz, CHLOROFORM-d) [ppm]: 1.356 (3.86), 1.375 (8.22), 1.394 (4.01), 1.625 (4.50), 1.642 (4.35), 2.297 (10.31), 2.637 (1.27), 2.656 (3.73), 2.675 (3.77), 2.694 (1.13), 3.339 (16.00), 4.909 (0.90), 6.953 (2.09), 6.974 (1.80), 7.428 (1.85), 7.442 (1.83), 8.128 (2.26), 8.157 (2.28), 8.962 (1.11).

Example 73

5-fluoro-4-{3-[(1S)-1-hydroxyethyl]-4-methyl-5-oxo-4,5-dihydro-1H-1,2,4-triazol-1-yl}-N-(2-methylphenyl)-2-{[(2S)-1,1,1-trifluoropropan-2-yl]oxy}benzamide

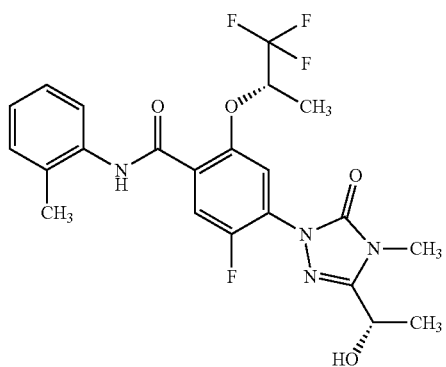 [SMILES: Cc1ccccc1NC(=O)c1cc(F)c(-n2nc([C@H](C)O)n(C)c2=O)cc1O[C@@H](C)C(F)(F)F]

5-fluoro-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzoic acid (Intermediate 61, 100 mg, 254 μmol) was dissolved in DMF (1 mL), HATU was added (193 mg, 509 μmol) and the mixture was stirred at room temperature for 15 min. 2-methylaniline (54.5 mg, 509 μmol) was added, followed by N,N-diisopropylethylamine (130 μl, 760 μmol). The mixture was stirred for 2 h at room temperature. The reaction mixture was purified using reverse phase HPLC (X-Bridge Prep C18 5 μm OBD Solvent: Water (+0.1% NH₃)/ACN Gradient: 5%-95% ACN in 10 min at 30 ml/min) to yield the desired product (48.0 mg (99% purity, 39% yield).

LC-MS (Method A): $R_t$=1.15 min; MS (ESIpos): m/z=483 [M+H]⁺.

¹H-NMR (400 MHz, CHLOROFORM-d) [ppm]: 1.585 (2.22), 1.624 (4.48), 1.640 (4.47), 1.683 (7.65), 1.700 (7.81), 2.227 (0.60), 2.319 (10.89), 3.478 (16.00), 4.868 (0.43), 4.884 (1.10), 4.899 (1.45), 4.914 (1.05), 7.128 (0.49), 7.131 (0.51), 7.149 (1.29), 7.165 (0.97), 7.167 (0.92), 7.244 (1.58), 7.251 (1.02), 7.289 (0.56), 7.435 (1.73), 7.449 (1.71), 7.884 (1.38), 7.903 (1.20), 8.133 (2.28), 8.162 (2.25), 9.031 (1.27).

Example 74

5-fluoro-N-[(2R)-1-hydroxypropan-2-yl]-4-[4-methyl-5-oxo-3-(propan-2-yl)-4,5-dihydro-1H-1,2,4-triazol-1-yl]-2-[(2S)-pentan-2-yloxy]benzamide

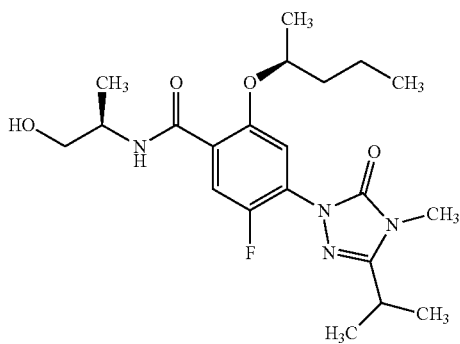 [SMILES: CCC[C@H](C)Oc1cc(-n2nc(C(C)C)n(C)c2=O)c(F)cc1C(=O)N[C@H](C)CO]

Synthesized from Intermediate 45 and (2R)-2-aminopropan-1-ol.

Example 75

5-fluoro-N-[(2R)-1-hydroxybutan-2-yl]-4-[4-methyl-5-oxo-3-(propan-2-yl)-4,5-dihydro-1H-1,2,4-triazol-1-yl]-2-[(2S)-pentan-2-yloxy]benzamide

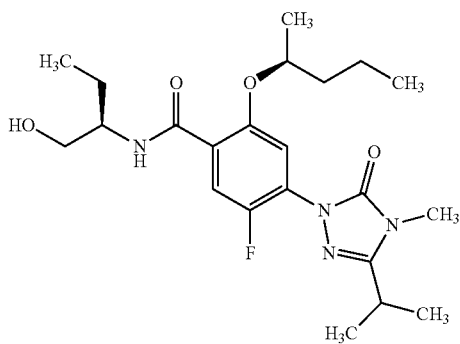 [SMILES: CCC[C@H](C)Oc1cc(-n2nc(C(C)C)n(C)c2=O)c(F)cc1C(=O)N[C@H](CC)CO]

Synthesized from Intermediate 45 and (2R)-2-aminobutan-1-ol.

Example 76

N-[(2R)-1-amino-1-oxobutan-2-yl]-5-fluoro-4-[4-methyl-5-oxo-3-(propan-2-yl)-4,5-dihydro-1H-1,2,4-triazol-1-yl]-2-[(2S)-pentan-2-yloxy]benzamide

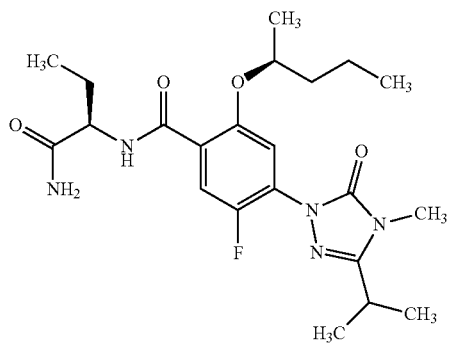 [SMILES: CCC[C@H](C)Oc1cc(-n2nc(C(C)C)n(C)c2=O)c(F)cc1C(=O)N[C@H](CC)C(N)=O]

Synthesized from Intermediate 45 and (2R)-2-aminobutanamide.

Example 77

5-fluoro-N-(heptan-4-yl)-4-[4-methyl-5-oxo-3-(propan-2-yl)-4,5-dihydro-1H-1,2,4-triazol-1-yl]-2-[(2S)-pentan-2-yloxy]benzamide

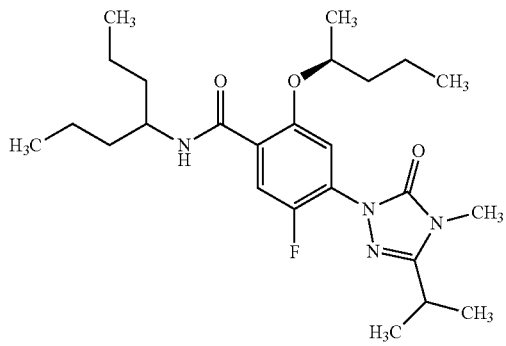 [SMILES: CCCC(CCC)NC(=O)c1cc(F)c(-n2nc(C(C)C)n(C)c2=O)cc1O[C@@H](C)CCC]

Synthesized from Intermediate 45 and heptan-4-amine.

Example 78

2-(1-cyclohexylethoxy)-N-(2,4-dimethylphenyl)-5-fluoro-4-[3-(1-hydroxyethyl)-4-methyl-5-oxo-4,5-dihydro-1H-1,2,4-triazol-1-yl]benzamide, Mixture of Stereoisomers Step A 2-(1-cyclohexylethoxy)-N-(2,4-dimethylphenyl)-4-{3-[1-(1-ethoxyethoxy)ethyl]-4-methyl-5-oxo-4,5-dihydro-1H-1,2,4-triazol-1-yl}-5-fluorobenzamide, Mixture of Stereoisomers

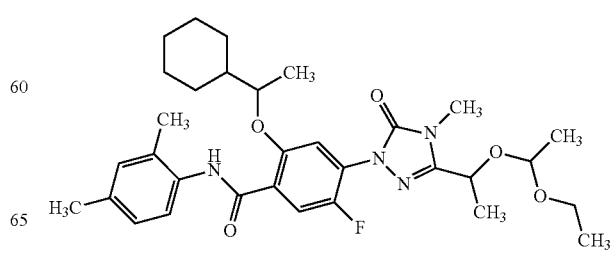

Synthesized from Intermediate 47 and 2,4-dimethylaniline.

Step B 2-(1-cyclohexylethoxy)-N-(2,4-dimethylphenyl)-5-fluoro-4-[3-(1-hydroxyethyl)-4-methyl-5-oxo-4,5-dihydro-1H-1,2,4-triazol-1-yl]benzamide, Mixture of Stereoisomers

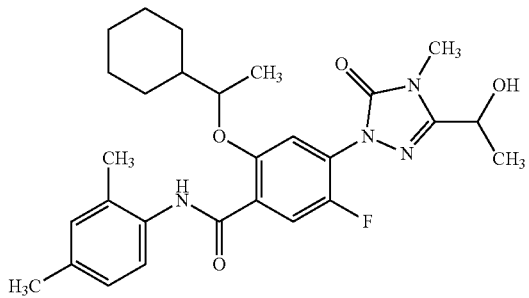 [SMILES: Cc1ccc(NC(=O)c2cc(F)c(-n3nc(C(C)O)n(C)c3=O)cc2OC(C)C2CCCCC2)c(C)c1]

2-(1-cyclohexylethoxy)-N-(2,4-dimethylphenyl)-4-{3-[1-(1-ethoxyethoxy)ethyl]-4-methyl-5-oxo-4,5-dihydro-1H-1,2,4-triazol-1-yl}-5-fluorobenzamide (Intermediate from STEP A above, 120 mg, 206 μmol) was dissolved in methanol (5 mL). 5 drops of hydrochloric acid (0.1N in water) were added. The mixture was stirred at room temperature until TLC showed complete conversion. Solid sodium carbonate was added and the mixture was concentrated. The product was purified using column chromatography to yield the desired product as a mixture of diastereomers.

Example 79

N-(2-amino-6-methylphenyl)-2-(1-cyclohexylethoxy)-5-fluoro-4-[3-(1-hydroxyethyl)-4-methyl-5-oxo-4,5-dihydro-1H-1,2,4-triazol-1-yl]benzamide, Mixture of Stereoisomers Step A tert-butyl {2-[(2-(1-cyclohexylethoxy)-4-{3-[1-(1-ethoxyethoxy)ethyl]-4-methyl-5-oxo-4,5-dihydro-1H-1,2,4-triazol-1-yl}-5-fluorobenzoyl)amino]-3-methylphenyl}carbamate, mixture of stereoisomers

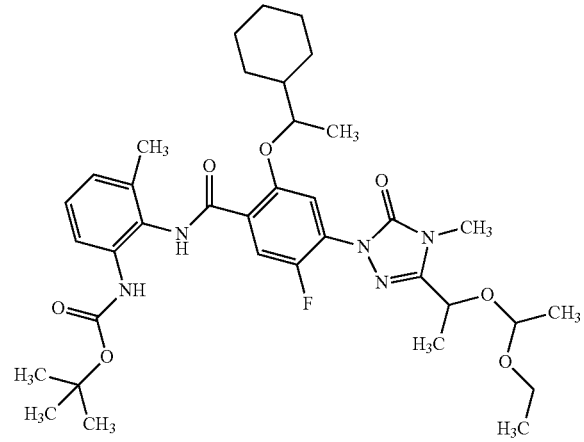 [SMILES: CCOC(C)OC(C)c1nn(-c2cc(OC(C)C3CCCCC3)c(C(=O)Nc3c(C)cccc3NC(=O)OC(C)(C)C)cc2F)c(=O)n1C]

Synthesized from Intermediate 47 and tert-butyl (2-amino-3-methylphenyl)carbamate.

Step B

N-(2-amino-6-methylphenyl)-2-(1-cyclohexylethoxy)-5-fluoro-4-[3-(1-hydroxyethyl)-4-methyl-5-oxo-4,5-dihydro-1H-1,2,4-triazol-1-yl]benzamide, Mixture of Stereoisomers

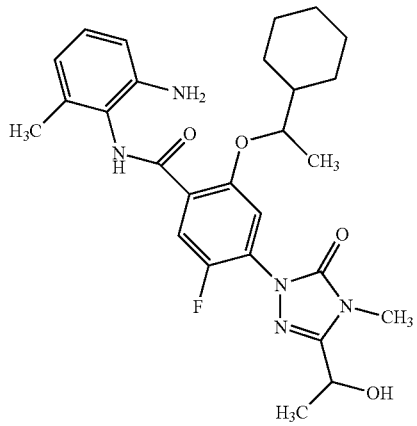

tert-butyl {2-[(2-(1-cyclohexylethoxy)-4-{3-[1-(1-ethoxyethoxy)ethyl]-4-methyl-5-oxo-4,5-dihydro-1H-1,2,4-triazol-1-yl}-5-fluorobenzoyl)amino]-3-methylphenyl}carbamate (160 mg, 234 μmol) was dissolved in DCM (5.0 ml). Hydrochloric acid (0.4N, 1 mL) was added and the mixture was stirred vigorously overnight. The mixture was concentrated and purified using preparative TLC to yield the desired product as a mixture of stereoisomers.

Example 80

N-(4-amino-2-methylphenyl)-2-(1-cyclohexylethoxy)-5-fluoro-4-[3-(1-hydroxyethyl)-4-methyl-5-oxo-4,5-dihydro-1H-1,2,4-triazol-1-yl]benzamide, Mixture of Stereoisomers Step A tert-butyl {4-[(2-(1-cyclohexylethoxy)-4-{3-[1-(1-ethoxyethoxy)ethyl]-4-methyl-5-oxo-4,5-dihydro-1H-1,2,4-triazol-1-yl}-5-fluorobenzoyl)amino]-3-methylphenyl}carbamate, Mixture of Stereoisomers

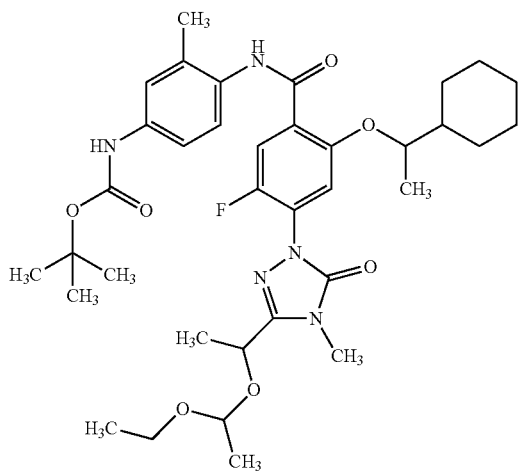 [SMILES: CCOC(C)OC(C)c1nn(-c2cc(OC(C)C3CCCCC3)c(C(=O)Nc3ccc(NC(=O)OC(C)(C)C)cc3C)cc2F)c(=O)n1C]

Synthesized from Intermediate 47 and tert-butyl (4-amino-3-methylphenyl)carbamate.

Step B

N-(4-amino-2-methylphenyl)-2-(1-cyclohexylethoxy)-5-fluoro-4-[3-(1-hydroxyethyl)-4-methyl-5-oxo-4,5-dihydro-1H-1,2,4-triazol-1-yl]benzamide, Mixture of Stereoisomers

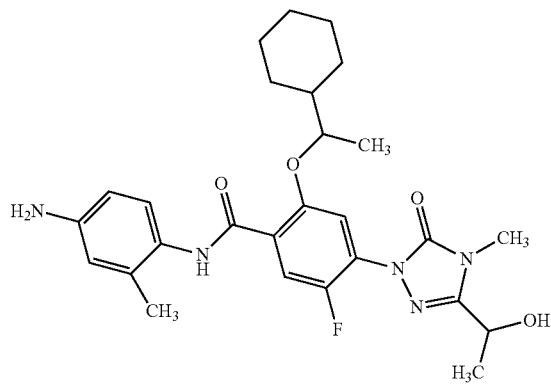 [SMILES: Cc1cc(N)ccc1NC(=O)c1cc(F)c(-n2nc(C(C)O)n(C)c2=O)cc1OC(C)C1CCCCC1]

Synthesized analogously to Example 79 from the intermediate above.

Example 81

2-(1-cyclohexylethoxy)-N-(2,6-dimethylphenyl)-5-fluoro-4-[3-(1-hydroxyethyl)-4-methyl-5-oxo-4,5-dihydro-1H-1,2,4-triazol-1-yl]benzamide, Mixture of Stereoisomers Step A 2-(1-cyclohexylethoxy)-N-(2,6-dimethylphenyl)-4-{3-[1-(1-ethoxyethoxy)ethyl]-4-methyl-5-oxo-4,5-dihydro-1H-1,2,4-triazol-1-yl}-5-fluorobenzamide, Mixture of Stereoisomers

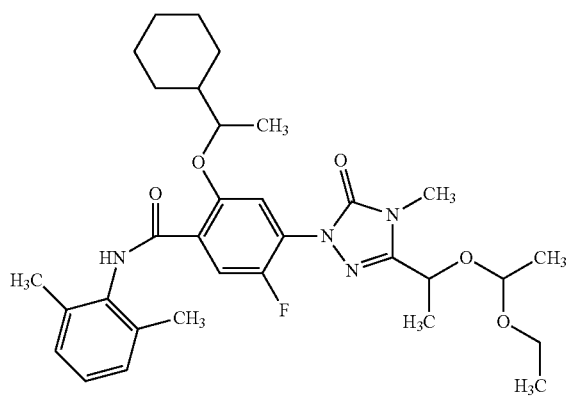 [SMILES: CCOC(C)OC(C)c1nn(-c2cc(OC(C)C3CCCCC3)c(C(=O)Nc3c(C)cccc3C)cc2F)c(=O)n1C]

Synthesized from Intermediate 47 and 2,6-dimethylaniline.

Step B 2-(1-cyclohexylethoxy)-N-(2,6-dimethylphenyl)-5-fluoro-4-[3-(1-hydroxyethyl)-4-methyl-5-oxo-4,5-dihydro-1H-1,2,4-triazol-1-yl]benzamide, Mixture of Stereoisomers

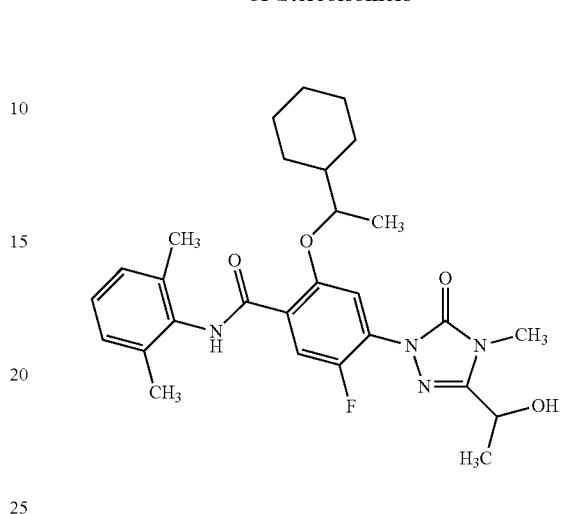

Synthesized analogously to Example 79 from the intermediate above.

$^1$H-NMR (400 MHz, DMSO-d6) delta [ppm]: 1.002 (0.45), 1.063 (0.51), 1.087 (0.67), 1.125 (0.81), 1.148 (0.76), 1.179 (0.67), 1.231 (4.24), 1.247 (4.06), 1.355 (1.22), 1.455 (4.38), 1.471 (4.40), 1.606 (0.76), 1.628 (0.68), 1.695 (1.34), 1.720 (0.91), 1.898 (0.45), 1.928 (0.42), 2.241 (16.00), 2.368 (0.40), 3.312 (2.57), 4.354 (0.56), 4.369 (0.85), 4.384 (0.54), 4.764 (0.78), 4.780 (1.10), 4.796 (0.74), 5.799 (1.81), 5.814 (1.75), 7.120 (7.86), 7.301 (1.33), 7.316 (1.32), 7.558 (1.58), 7.584 (1.54), 9.554 (2.02).

Example 82

5-fluoro-4-{3-[(1S)-1-hydroxyethyl]-4-methyl-5-oxo-4,5-dihydro-1H-1,2,4-triazol-1-yl}-N-(2-methylphenyl)-2-(pentan-2-yloxy)benzamide, Mixture of Stereoisomers Step A 4-{3-[(1S)-1-(1-ethoxyethoxy)ethyl]-4-methyl-5-oxo-4,5-dihydro-1H-1,2,4-triazol-1-yl}-5-fluoro-N-(2-methylphenyl)-2-(pentan-2-yloxy)benzamide, Mixture of Stereoisomers

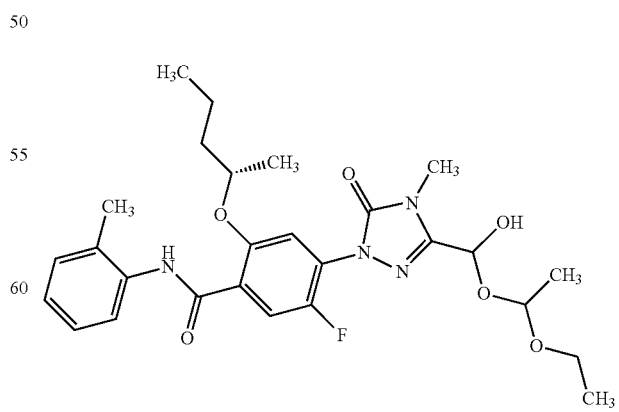

Synthesized from Intermediate 51 and o-toluidine.

Step B 5-fluoro-4-{3-[(1S)-1-hydroxyethyl]-4-methyl-5-oxo-4,5-dihydro-1H-1,2,4-triazol-1-yl}-N-(2-methylphenyl)-2-(pentan-2-yloxy)benzamide, Mixture of Stereoisomers

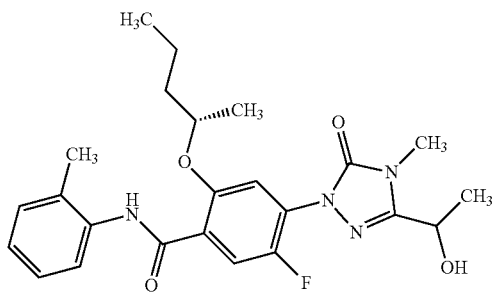 [SMILES: CCC[C@H](C)Oc1cc(-n2nc(C(C)O)n(C)c2=O)c(F)cc1C(=O)Nc1ccccc1C]

Synthesized analogously to Example 78 from the intermediate above.

Example 83

N-(2-amino-6-methylphenyl)-4-(3-ethyl-4-methyl-5-oxo-4,5-dihydro-1H-1,2,4-triazol-1-yl)-5-fluoro-2-(pent-4-en-2-yloxy)benzamide, Mixture of Stereoisomers Step A tert-butyl [2-({4-(3-ethyl-4-methyl-5-oxo-4,5-dihydro-1H-1,2,4-triazol-1-yl)-5-fluoro-2-(pent-4-en-2-yloxy)benzoyl}amino)-3-methylphenyl]carbamate, Mixture of Stereoisomers

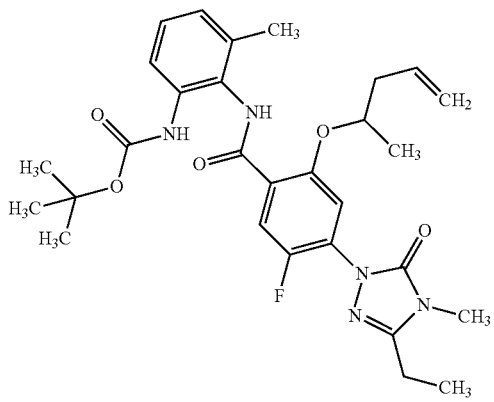 [SMILES: C=CCC(C)Oc1cc(-n2nc(CC)n(C)c2=O)c(F)cc1C(=O)Nc1c(C)cccc1NC(=O)OC(C)(C)C]

Synthesized from Intermediate 46 and tert-butyl (2-amino-3-methylphenyl)carbamate.

Step B

N-(2-amino-6-methylphenyl)-4-(3-ethyl-4-methyl-5-oxo-4,5-dihydro-1H-1,2,4-triazol-1-yl)-5-fluoro-2-(pent-4-en-2-yloxy)benzamide, Mixture of Stereoisomers

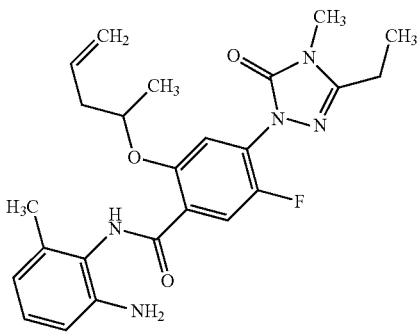 [SMILES: C=CCC(C)Oc1cc(-n2nc(CC)n(C)c2=O)c(F)cc1C(=O)Nc1c(C)cccc1N]

Synthesized analogously to Example 78 from the intermediate above.

Example 84

N-(2,6-dimethylphenyl)-5-fluoro-4-{3-[(1-hydroxyethyl]-4-methyl-5-oxo-4,5-dihydro-1H-1,2,4-triazol-1-yl}-2-[(2R)-pentan-2-yloxy]benzamide, Mixture of Stereoisomers Step A N-(2,6-dimethylphenyl)-4-{3-[1-(1-ethoxyethoxy)ethyl]-4-methyl-5-oxo-4,5-dihydro-1H-1,2,4-triazol-1-yl}-5-fluoro-2-[(2R)-pentan-2-yloxy]benzamide, Mixture of Stereoisomers

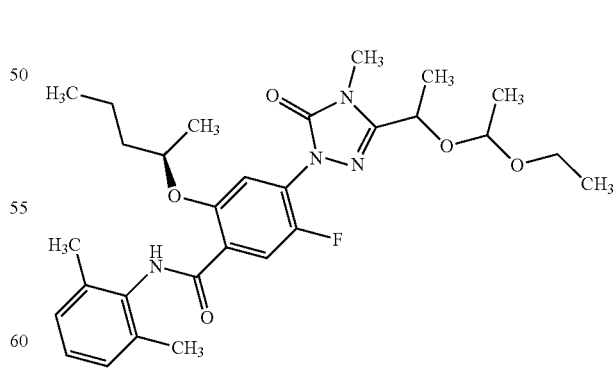

Synthesized from Intermediate 51 and 2,6-dimethylaniline.

Step B

N-(2,6-dimethylphenyl)-5-fluoro-4-{3-[(1-hydroxy-ethyl]-4-methyl-5-oxo-4,5-dihydro-1H-1,2,4-triazol-1-yl}-2-[(2R)-pentan-2-yloxy]benzamide, Mixture of Stereoisomers

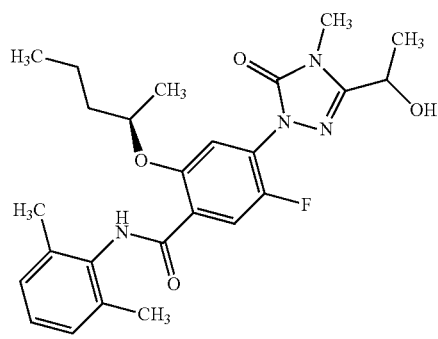 [SMILES: CCC[C@@H](C)Oc1cc(-n2nc(C(C)O)n(C)c2=O)c(F)cc1C(=O)Nc1c(C)cccc1C]

Synthesized analogously to Example 78 from the intermediate above.

Example 85

N-(4-amino-2-methylphenyl)-4-(3-ethyl-4-methyl-5-oxo-4,5-dihydro-1H-1,2,4-triazol-1-yl)-5-fluoro-2-[pent-4-en-2-yloxy]benzamide, Mixture of Stereoisomers Step A tert-butyl [4-({4-(3-ethyl-4-methyl-5-oxo-4,5-dihydro-1H-1,2,4-triazol-1-yl)-5-fluoro-2-[pent-4-en-2-yloxy]benzoyl}amino)-3-methylphenyl]carbamate, Mixture of Stereoisomers

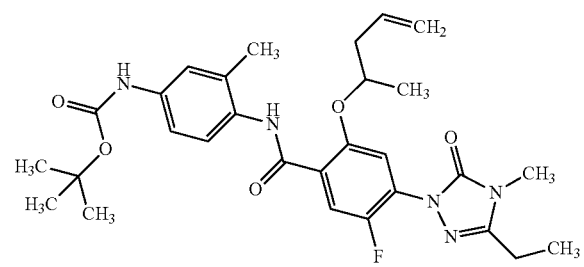 [SMILES: C=CCC(C)Oc1cc(-n2nc(CC)n(C)c2=O)c(F)cc1C(=O)Nc1ccc(NC(=O)OC(C)(C)C)cc1C]

Synthesized from Intermediate 46 and tert-butyl (4-amino-3-methylphenyl)carbamate.

Step B

N-(4-amino-2-methylphenyl)-4-(3-ethyl-4-methyl-5-oxo-4,5-dihydro-1H-1,2,4-triazol-1-yl)-5-fluoro-2-[pent-4-en-2-yloxy]benzamide, Mixture of Stereoisomers

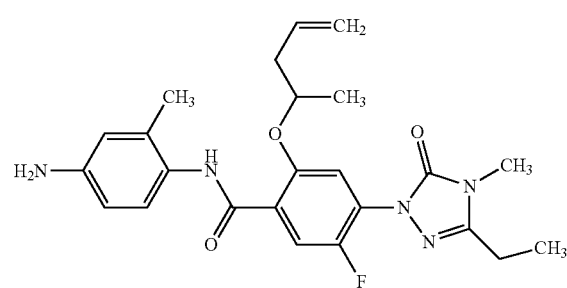 [SMILES: C=CCC(C)Oc1cc(-n2nc(CC)n(C)c2=O)c(F)cc1C(=O)Nc1ccc(N)cc1C]

Synthesized analogously to Example 78 from the intermediate above. THF was used instead of methanol.

Example 86

5-fluoro-4-{4-methyl-3-[(methylamino)methyl]-5-oxo-4,5-dihydro-1H-1,2,4-triazol-1-yl}-N-(pentan-3-yl)-2-[(2S)-pentan-2-yloxy]benzamide Step A tert-butyl [(1-{2-fluoro-4-(pentan-3-ylcarbamoyl)-5-[(2S)-pentan-2-yloxy]phenyl}-4-methyl-5-oxo-4,5-dihydro-1H-1,2,4-triazol-3-yl)methyl]methylcarbamate

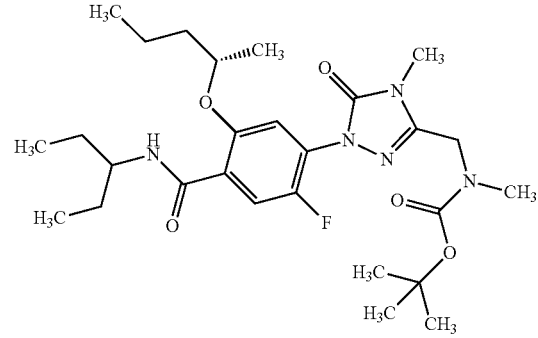 [SMILES: CCC[C@H](C)Oc1cc(-n2nc(CN(C)C(=O)OC(C)(C)C)n(C)c2=O)c(F)cc1C(=O)NC(CC)CC]

Synthesized from Intermediate 49 and pentan-3-amine.

283

Step B 5-fluoro-4-{4-methyl-3-[(methylamino)methyl]-5-oxo-4,5-dihydro-1H-1,2,4-triazol-1-yl}-N-(pentan-3-yl)-2-[(2S)-pentan-2-yloxy]benzamide

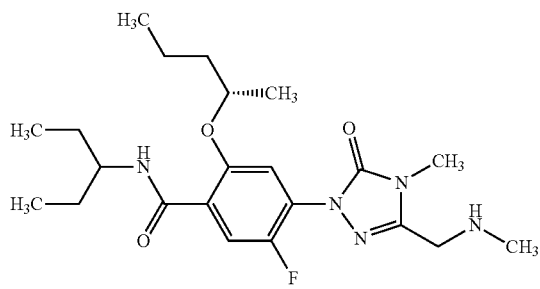 [SMILES: CCC[C@H](C)Oc1cc(-n2nc(CNC)n(C)c2=O)c(F)cc1C(=O)NC(CC)CC]

Synthesized analogously to Example 78 from the intermediate above.

Example 87

2-(1-cyclohexylethoxy)-N-(2,6-dimethylphenyl)-5-fluoro-4-[3-(hydroxymethyl)-4-methyl-5-oxo-4,5-dihydro-1H-1,2,4-triazol-1-yl]benzamide, Mixture of Stereoisomers Step A 4-{3-[(benzyloxy)methyl]-4-methyl-5-oxo-4,5-dihydro-1H-1,2,4-triazol-1-yl}-2-(1-cyclohexyl-ethoxy)-N-(2,6-dimethylphenyl)-5-fluorobenzamide, Mixture of Stereoisomers

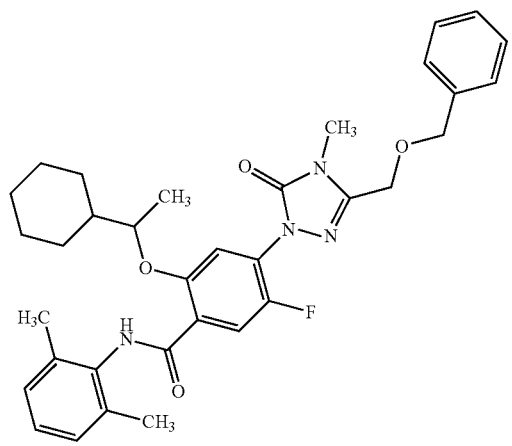 [SMILES: Cc1cccc(C)c1NC(=O)c1cc(F)c(-n2nc(COCc3ccccc3)n(C)c2=O)cc1OC(C)C1CCCCC1]

Synthesized from Intermediate 48 and 2,6-dimethylaniline.

Step B 2-(1-cyclohexylethoxy)-N-(2,6-dimethylphenyl)-5-fluoro-4-[3-(hydroxymethyl)-4-methyl-5-oxo-4,5-dihydro-1H-1,2,4-triazol-1-yl]benzamide, Mixture of Stereoisomers

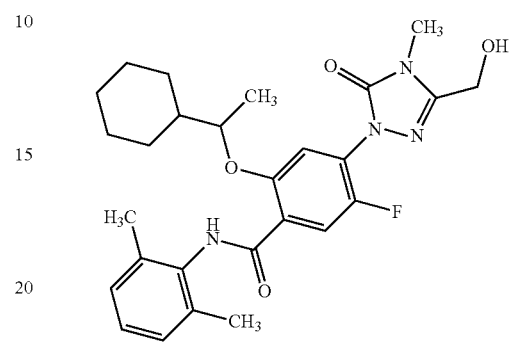

4-{3-[(benzyloxy)methyl]-4-methyl-5-oxo-4,5-dihydro-1H-1,2,4-triazol-1-yl}-2-(1-cyclohexyl-ethoxy)-N-(2,6-dimethylphenyl)-5-fluorobenzamide (Intermediate from above, 57.0 mg, 97.2 μmol) was dissolved in methanol (10 mL). The vessel was purged with nitrogen and palladium (10% on carbon, 20 mg) was added. The vessel was purged with hydrogen and the mixture was stirred under an atmosphere of hydrogen overnight. The mixture was filtered through a plug of celite and concentrated. Column chromatography yielded the desired product (20 mg, 41% yield).

Example 88

4-[3-(aminomethyl)-4-methyl-5-oxo-4,5-dihydro-1H-1,2,4-triazol-1-yl]-5-fluoro-N-(2-methyl-phenyl)-2-[(2S)-pentan-2-yloxy]benzamide Step A 4-{3-[(dibenzylamino)methyl]-4-methyl-5-oxo-4,5-dihydro-1H-1,2,4-triazol-1-yl}-5-fluoro-N-(2-methylphenyl)-2-[(2S)-pentan-2-yloxy]benzamide

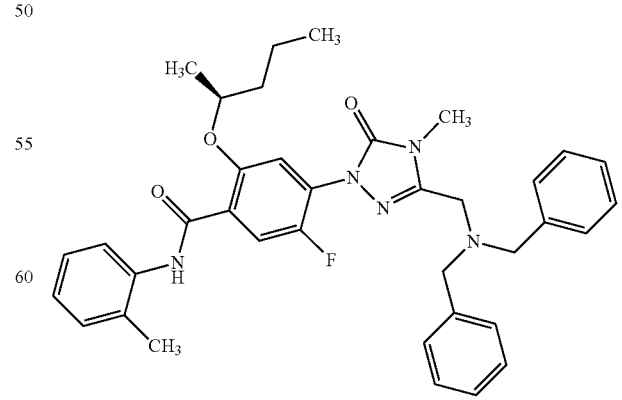

Synthesized from Intermediate 50 and o-toluidine.

Step B

4-[3-(aminomethyl)-4-methyl-5-oxo-4,5-dihydro-1H-1,2,4-triazol-1-yl]-5-fluoro-N-(2-methyl-phenyl)-2-[(2S)-pentan-2-yloxy]benzamide

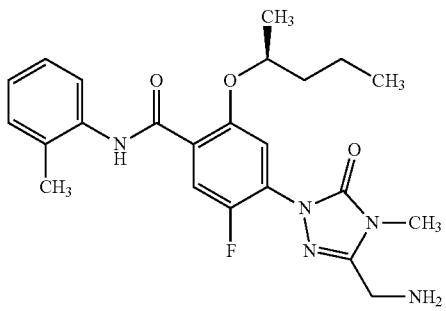 [SMILES: CCC[C@H](C)Oc1cc(-n2nc(CN)n(C)c2=O)c(F)cc1C(=O)Nc1ccccc1C]

Synthesized analogously to Example 87 from the intermediate above.

Example 89

N-[4-amino-2-(trifluoromethyl)phenyl]-4-(3-ethyl-4-methyl-5-oxo-4,5-dihydro-1H-1,2,4-triazol-1-yl)-5-fluoro-2-[(2S)-pentan-2-yloxy]benzamide Step A 4-(3-ethyl-4-methyl-5-oxo-4,5-dihydro-1H-1,2,4-triazol-1-yl)-5-fluoro-N-[4-nitro-2-(trifluoro-methyl)phenyl]-2-[(2S)-pentan-2-yloxy]benzamide

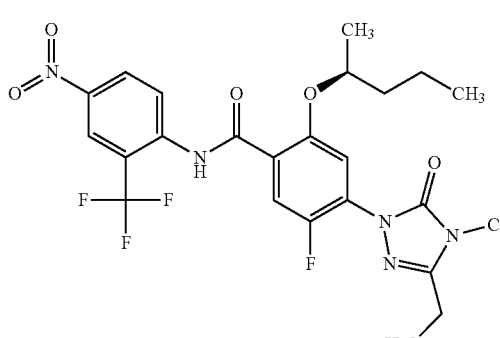

Synthesized from Intermediate 44 and 4-nitro-2-(trifluoromethyl)aniline.

LC-MS: m/z=540 [M+H]$^+$.

Step B

N-[4-amino-2-(trifluoromethyl)phenyl]-4-(3-ethyl-4-methyl-5-oxo-4,5-dihydro-1H-1,2,4-triazol-1-yl)-5-fluoro-2-[(2S)-pentan-2-yloxy]benzamide

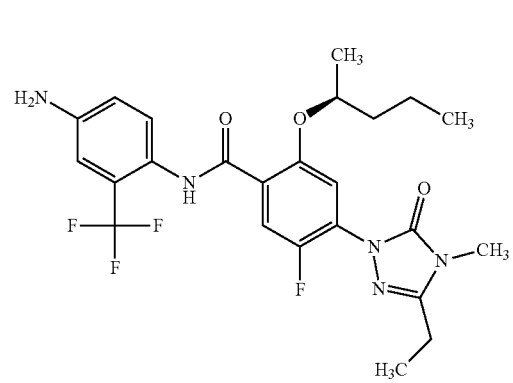 [SMILES: CCC[C@H](C)Oc1cc(-n2nc(CC)n(C)c2=O)c(F)cc1C(=O)Nc1ccc(N)cc1C(F)(F)F]

Synthesized analogously to Example 87 from the intermediate above.

Example 90

N-[2-(aminomethyl)-6-methylphenyl]-4-(3-ethyl-4-methyl-5-oxo-4,5-dihydro-1H-1,2,4-triazol-1-yl)-5-fluoro-2-[(2S)-pentan-2-yloxy]benzamide

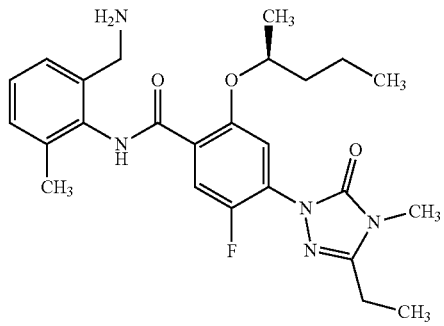 [SMILES: CCC[C@H](C)Oc1cc(-n2nc(CC)n(C)c2=O)c(F)cc1C(=O)Nc1c(C)cccc1CN]

N-(2-cyano-6-methylphenyl)-4-(3-ethyl-4-methyl-5-oxo-4,5-dihydro-1H-1,2,4-triazol-1-yl)-5-fluoro-2-[(2S)-pentan-2-yloxy]benzamide (Example 25, 50.0 mg, 107 µmol) was dissolved in methanol (10 mL). The vessel was purged with nitrogen and Raney-Nickel (5 mg) was added. The vessel was purged with hydrogen and the mixture was stirred under an atmosphere of hydrogen overnight. The mixture was filtered through a plug of celite and concentrated. Preparative TLC yielded the desired product (8 mg, 19% yield).

Example 91

4-{3-[(1R)-1-aminoethyl]-4-methyl-5-oxo-4,5-dihydro-1H-1,2,4-triazol-1-yl}-N-(4-amino-2-methylphenyl)-2-(1-cyclohexylethoxy)-5-fluorobenzamide, Mixture of Stereoisomers

Step A tert-butyl {4-[(2-(1-cyclohexylethoxy)-4-{3-[(1R)-1-(dibenzylamino)ethyl]-4-methyl-5-oxo-4,5-dihydro-1H-1,2,4-triazol-1-yl}-5-fluorobenzoyl)amino]-3-methylphenyl}carbamate, mixture of stereoisomers

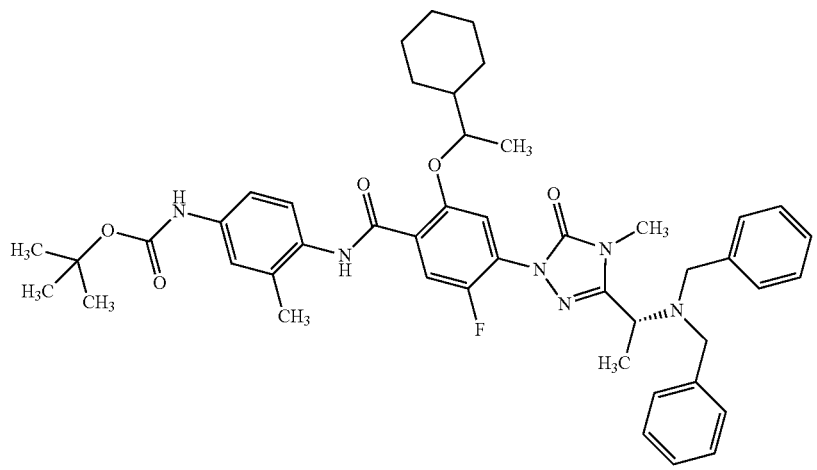 [SMILES: Cc1cc(NC(=O)OC(C)(C)C)ccc1NC(=O)c1cc(F)c(-n2nc([C@@H](C)N(Cc3ccccc3)Cc3ccccc3)n(C)c2=O)cc1OC(C)C1CCCCC1]

Synthesized from Intermediate 52 and tert-butyl (4-amino-3-methylphenyl)carbamate.

Step B

N-(4-amino-2-methylphenyl)-2-(1-cyclohexylethoxy)-4-{3-[(1R)-1-(dibenzylamino)ethyl]-4-methyl-5-oxo-4,5-dihydro-1H-1,2,4-triazol-1-yl}-5-fluorobenzamide, Mixture of Stereoisomers

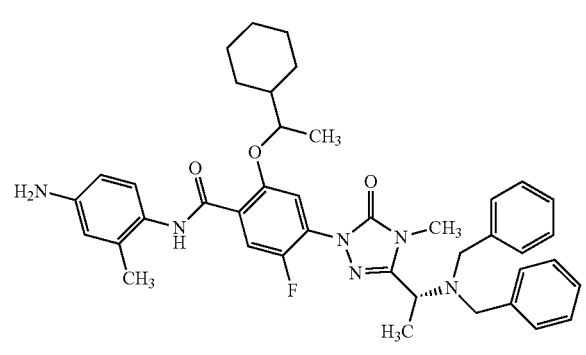 [SMILES: Cc1cc(N)ccc1NC(=O)c1cc(F)c(-n2nc([C@@H](C)N(Cc3ccccc3)Cc3ccccc3)n(C)c2=O)cc1OC(C)C1CCCCC1]

Synthesized analogously to Example 78 (STEP B) from the intermediate above.

Step C

4-{3-[(1R)-1-aminoethyl]-4-methyl-5-oxo-4,5-dihydro-1H-1,2,4-triazol-1-yl}-N-(4-amino-2-methylphenyl)-2-(1-cyclohexylethoxy)-5-fluorobenzamide, Mixture of Stereoisomers

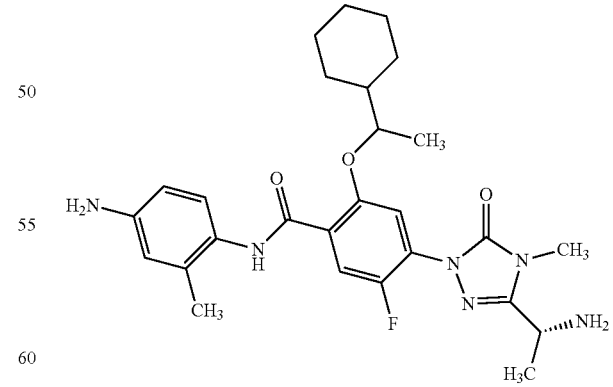

Synthesized analogously to Example 87 (STEP B) from the intermediate above.

Example 92

4-(4-cyclopentyl-3-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

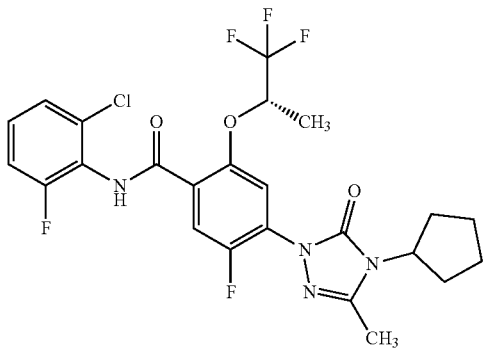 [SMILES: Cc1nn(-c2cc(O[C@@H](C)C(F)(F)F)c(C(=O)Nc3c(F)cccc3Cl)cc2F)c(=O)n1C1CCCC1]

4-bromo-N-(2,6-difluorophenyl)-5-fluoro-2-{[(2S)-1,1,1-trifluoropropan-2-yl]oxy}benzamide (Intermediate 70, 100 mg, 226 μmol), 4-cyclopentyl-5-methyl-2,4-dihydro-3H-1,2,4-triazol-3-one (56.7 mg, 339 μmol), tris(dibenzylideneacetone)dipalladium(0) (20.7 mg, 22.6 μmol), 4,5-bis(diphenylphosphino)-9,9-dimethylxanthene (39.3 mg, 67.8 μmol), and cesium carbonate (147 mg, 452 μmol) were loaded into a microwave vial. The vial was purged with argon, dioxane (2 mL, degassed) was added, and the vial was sealed. The mixture was stirred for 17 h at 110° C. after which LCMS indicated full conversion. The resulting suspension was filtered over Celite, washed with ethyl acetate and concentrated. Mass triggered preparative chromatography yielded the desired product (88.0 mg, 66% yield).

LC-MS (Method A): $R_t$=1.35 min; MS (ESIpos): m/z=529 [M+H]$^+$.

$^1$H-NMR (400 MHz, DMSO-d6) δ [ppm]: 1.426 (4.94), 1.442 (4.94), 1.581 (1.48), 1.594 (1.48), 1.610 (1.09), 1.643 (0.59), 1.810 (1.09), 1.822 (1.58), 1.828 (1.58), 1.843 (0.99), 1.861 (0.40), 1.919 (0.49), 1.947 (1.19), 1.968 (1.28), 2.030 (0.49), 2.048 (1.19), 2.069 (1.28), 2.078 (0.99), 2.099 (0.69), 2.171 (1.09), 2.330 (16.00), 2.518 (2.37), 2.522 (1.48), 2.668 (0.49), 3.310 (0.59), 3.317 (0.89), 3.321 (1.19), 3.326 (0.89), 3.332 (1.58), 3.337 (2.17), 3.344 (3.65), 3.350 (6.22), 3.352 (7.01), 3.387 (2.47), 3.391 (1.28), 3.394 (1.09), 3.399 (0.89), 3.404 (1.09), 4.346 (0.99), 4.367 (1.58), 4.389 (0.99), 5.304 (0.79), 5.320 (0.99), 5.336 (0.79), 7.188 (1.58), 7.208 (3.16), 7.228 (1.98), 7.337 (0.49), 7.345 (0.79), 7.369 (0.49), 7.384 (1.38), 7.391 (0.99), 7.406 (1.19), 7.422 (0.89), 7.426 (0.79), 7.438 (0.40), 7.459 (0.69), 7.463 (0.69), 7.476 (0.49), 7.548 (3.85), 7.564 (2.17), 7.572 (2.27), 9.977 (4.15).

Example 93

N-(2,6-difluorophenyl)-4-{3-[ethyl(methyl)amino]-4-methyl-5-oxo-4,5-dihydro-1H-1,2,4-triazol-1-yl}-5-fluoro-2-{[(2S)-1,1,1-trifluoropropan-2-yl]oxy}benzamide

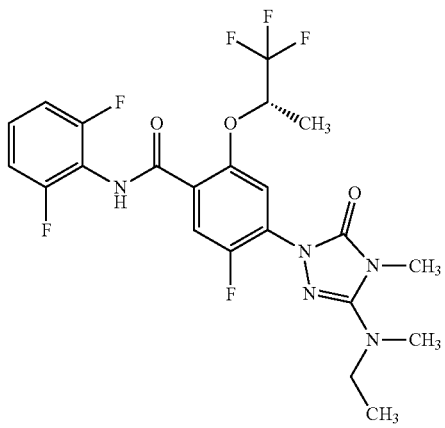 [SMILES: CCN(C)c1nn(-c2cc(O[C@@H](C)C(F)(F)F)c(C(=O)Nc3c(F)cccc3F)cc2F)c(=O)n1C]

Synthesized analogously to Example 92 from Intermediate 70 and 3-[ethyl(methyl)amino]-4-methyl-1H-1,2,4-triazol-5(4H)-one.

LC-MS (Method A): $R_t$=1.29 min; MS (ESIpos): m/z=518 [M+H]$^+$.

$^1$H-NMR (400 MHz, DMSO-d6) δ [ppm]: 1.135 (3.49), 1.153 (7.77), 1.171 (3.60), 1.433 (3.84), 1.449 (3.86), 2.085 (16.00), 2.518 (4.47), 2.523 (2.85), 2.789 (14.49), 3.138 (1.00), 3.155 (3.02), 3.173 (3.04), 3.191 (1.23), 3.204 (13.66), 5.273 (0.63), 5.289 (0.82), 5.305 (0.61), 7.191 (1.20), 7.212 (2.46), 7.231 (1.55), 7.387 (0.72), 7.408 (0.88), 7.424 (0.49), 7.428 (0.49), 7.532 (1.61), 7.540 (2.09), 7.547 (1.77), 7.566 (1.59), 9.932 (3.65).

Example 94

N-(2,6-difluorophenyl)-4-(3-ethyl-4-methyl-5-oxo-4,5-dihydro-1H-1,2,4-triazol-1-yl)-5-fluoro-2-{[(2S)-1,1,1-trifluoropropan-2-yl]oxy}benzamide

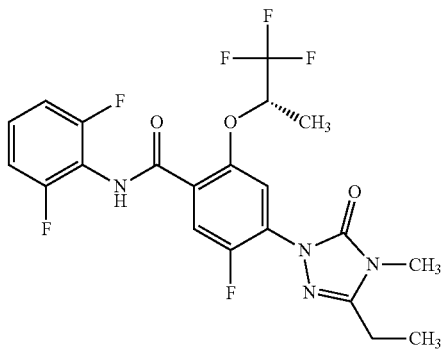 [SMILES: CCc1nn(-c2cc(O[C@@H](C)C(F)(F)F)c(C(=O)Nc3c(F)cccc3F)cc2F)c(=O)n1C]

Synthesized analogously to Example 92 from Intermediate 70 and 3-ethyl-4-methyl-1H-1,2,4-triazol-5(4H)-one.

LC-MS (Method A): Rt=1.20 min; MS (ESIpos): m/z=489 [M+H]$^+$.

¹H-NMR (400 MHz, CHLOROFORM-d) [ppm]: 1.358 (3.49), 1.377 (8.19), 1.396 (3.72), 1.561 (5.96), 1.645 (3.60), 1.662 (3.62), 2.640 (1.14), 2.658 (3.70), 2.677 (3.49), 2.695 (1.02), 3.340 (16.00), 4.906 (0.57), 4.922 (0.72), 4.937 (0.55), 6.992 (1.24), 7.006 (0.80), 7.012 (2.38), 7.032 (1.69), 7.231 (0.60), 7.237 (0.44), 7.247 (0.40), 7.253 (1.06), 7.259 (0.52), 7.454 (1.56), 7.468 (1.52), 8.150 (1.65), 8.178 (1.63), 8.977 (1.03).

Example 95

N-(2,6-difluorophenyl)-5-fluoro-4-[3-(1-hydroxyethyl)-4-methyl-5-oxo-4,5-dihydro-1H-1,2,4-triazol-1-yl]-2-{[(2S)-1,1,1-trifluoropropan-2-yl]oxy}benzamide, Single Stereomer

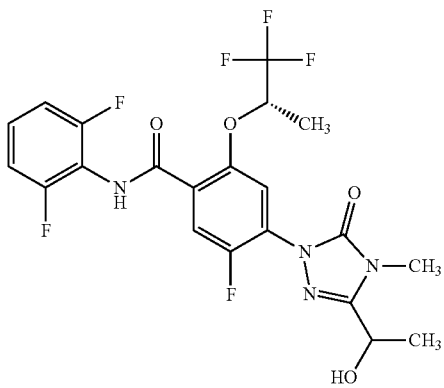 [SMILES: CC(O)c1nn(-c2cc(O[C@@H](C)C(F)(F)F)c(C(=O)Nc3c(F)cccc3F)cc2F)c(=O)n1C]

Synthesized analogously to Example 92 from Intermediate 70 and 3-ethyl-4-methyl-1H-1,2,4-triazol-5(4H)-one.

LC-MS (Method A): Rt=1.08 min; MS (ESIpos): m/z=505 [M+H]⁺.

¹H-NMR (400 MHz, CHLOROFORM-d) [ppm]: 1.573 (6.88), 1.650 (3.45), 1.666 (3.48), 1.689 (6.76), 1.706 (6.92), 2.109 (0.45), 2.125 (0.44), 3.487 (16.00), 4.891 (0.75), 4.906 (1.27), 4.922 (1.06), 4.937 (0.58), 6.994 (1.25), 7.006 (0.41), 7.015 (2.29), 7.034 (1.63), 7.236 (0.60), 7.242 (0.41), 7.257 (0.96), 7.278 (0.57), 7.460 (1.50), 7.474 (1.48), 8.150 (1.60), 8.178 (1.58), 8.974 (1.04).

Example 96

N-(2,6-difluorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide

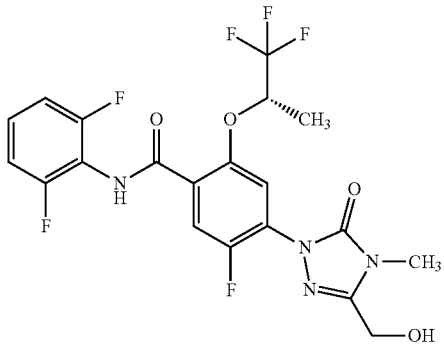 [SMILES: C[C@H](Oc1cc(-n2nc(CO)n(C)c2=O)c(F)cc1C(=O)Nc1c(F)cccc1F)C(F)(F)F]

Synthesized analogously to Example 92 from Intermediate 70 and Intermediate 8.

LC-MS (Method A): R_f=1.05 min; MS (ESIpos): m/z=491 [M+H]⁺

¹H-NMR (400 MHz, DMSO-d6) δ [ppm]: 1.429 (4.59), 1.444 (4.56), 2.083 (7.38), 2.331 (0.53), 2.518 (3.16), 2.522 (2.11), 2.673 (0.53), 3.309 (16.00), 4.465 (4.29), 4.480 (4.29), 5.297 (0.75), 5.313 (0.98), 5.329 (0.72), 5.741 (1.36), 5.755 (2.97), 5.770 (1.24), 7.191 (1.43), 7.211 (2.90), 7.231 (1.81), 7.388 (0.72), 7.408 (0.98), 7.424 (0.56), 7.429 (0.56), 7.563 (1.81), 7.578 (3.61), 7.603 (1.92), 10.004 (4.07).

Example 97

N-(2,6-difluorophenyl)-4-{3-[(dimethylamino)methyl]-4-methyl-5-oxo-4,5-dihydro-1H-1,2,4-triazol-1-yl}-5-fluoro-2-{[(2S)-1,1,1-trifluoropropan-2-yl]oxy}benzamide

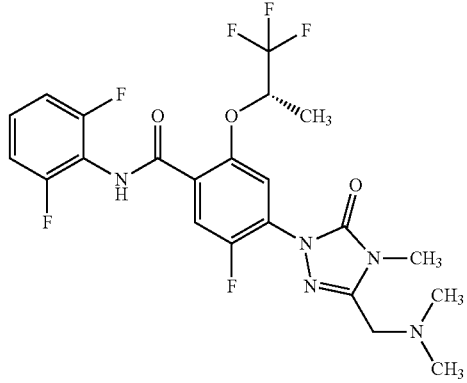 [SMILES: C[C@H](Oc1cc(-n2nc(CN(C)C)n(C)c2=O)c(F)cc1C(=O)Nc1c(F)cccc1F)C(F)(F)F]

Synthesized analogously to Example 92 from Intermediate 70 and Intermediate 10.

LC-MS (Method A): R_f=0.91 min; MS (ESIneg): m/z=516 [M−H]⁻.

¹H-NMR (400 MHz, DMSO-d6) δ [ppm]: 1.433 (2.90), 1.448 (2.89), 2.084 (0.94), 2.240 (16.00), 2.518 (2.15), 2.523 (1.43), 2.729 (0.95), 2.888 (1.16), 3.298 (10.16), 3.446 (4.62), 5.292 (0.46), 5.307 (0.60), 5.323 (0.45), 7.192 (0.88), 7.212 (1.85), 7.233 (1.15), 7.388 (0.44), 7.410 (0.63), 7.573 (1.70), 7.591 (1.32), 7.596 (1.42), 9.992 (2.69).

Example 98

N-(2,6-difluorophenyl)-5-fluoro-4-(4-methyl-5-oxo-3-propyl-4,5-dihydro-1H-1,2,4-triazol-1-yl)-2-{[(2S)-1,1,1-trifluoropropan-2-yl]oxy}benzamide

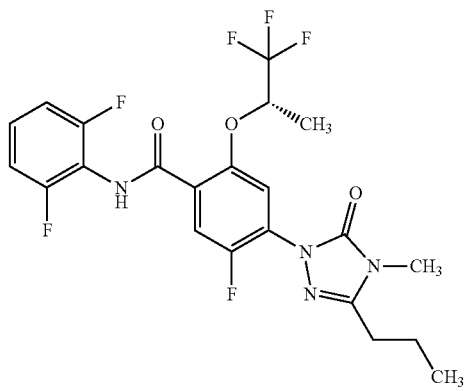 [SMILES: CCCc1nn(-c2cc(O[C@@H](C)C(F)(F)F)c(C(=O)Nc3c(F)cccc3F)cc2F)c(=O)n1C]

Synthesized analogously to Example 92 from Intermediate 70 and 4-methyl-3-propyl-1H-1,2,4-triazol-5(4H)-one LC-MS (Method A): $R_t$=1.28 min; MS (ESIpos): m/z=503 [M+H]$^+$.

$^1$H-NMR (400 MHz, DMSO-d6) δ [ppm]: 0.979 (3.95), 0.997 (9.01), 1.016 (4.32), 1.137 (0.83), 1.232 (0.55), 1.429 (3.95), 1.445 (3.95), 1.660 (1.29), 1.678 (2.39), 1.696 (2.39), 1.715 (1.29), 2.331 (2.76), 2.337 (1.20), 2.518 (16.00), 2.523 (10.85), 2.602 (2.30), 2.621 (3.49), 2.639 (2.11), 2.674 (2.85), 2.678 (1.29), 3.233 (14.62), 5.288 (0.64), 5.304 (0.83), 5.320 (0.55), 7.190 (1.01), 7.210 (2.02), 7.231 (1.20), 7.407 (0.64), 7.541 (1.10), 7.561 (1.93), 7.586 (1.47), 9.977 (2.94).

Example 99

N-(2,6-difluorophenyl)-5-fluoro-4-[4-methyl-3-(methylsulfanyl)-5-oxo-4,5-dihydro-1H-1,2,4-triazol-1-yl]-2-{[(2S)-1,1,1-trifluoropropan-2-yl]oxy}benzamide

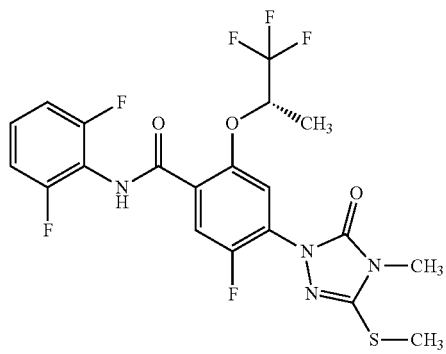 [SMILES: CSc1nn(-c2cc(O[C@@H](C)C(F)(F)F)c(C(=O)Nc3c(F)cccc3F)cc2F)c(=O)n1C]

Synthesized analogously to Example 92 from Intermediate 70 and 4-methyl-3-methylsulfanyl-1H-1,2,4-triazol-5-one.

LC-MS (Method A): $R_t$=1.26 min; MS (ESIpos): m/z=507 [M+H]$^+$.

$^1$H-NMR (400 MHz, DMSO-d6) δ [ppm]: 1.435 (3.55), 1.451 (3.52), 2.458 (0.77), 2.518 (3.76), 2.523 (2.67), 2.593 (16.00), 2.674 (0.70), 2.888 (0.42), 3.207 (12.62), 5.278 (0.56), 5.294 (0.74), 5.310 (0.56), 7.192 (1.05), 7.212 (2.15), 7.232 (1.34), 7.387 (0.56), 7.408 (0.70), 7.425 (0.46), 7.582 (2.04), 7.601 (1.51), 7.606 (1.72), 9.986 (2.74).

Example 100

4-[3-(2-aminoethyl)-4-methyl-5-oxo-4,5-dihydro-1H-1,2,4-triazol-1-yl]-N-(2,6-difluorophenyl)-5-fluoro-2-{[(2S)-1,1,1-trifluoropropan-2-yl]oxy}benzamide

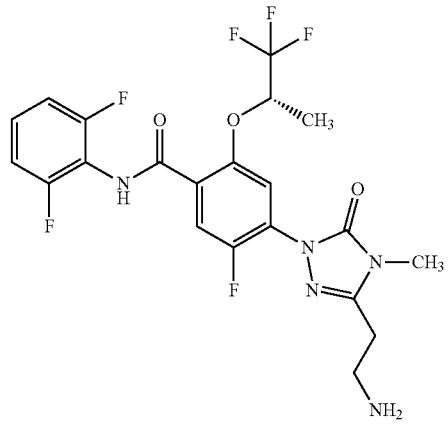 [SMILES: C[C@H](Oc1cc(-n2nc(CCN)n(C)c2=O)c(F)cc1C(=O)Nc1c(F)cccc1F)C(F)(F)F]

Synthesized analogously to Example 92 from Intermediate 70 and 5-(2-aminoethyl)-4-methyl-2,4-dihydro-3H-1,2,4-triazol-3-one hydrochloride.

LC-MS (Method A): $R_t$=0.90 min; MS (ESIpos): m/z=504 [M+H]$^+$.

$^1$H-NMR (400 MHz, DMSO-d6) δ [ppm]: 1.021 (0.44), 1.066 (1.47), 1.137 (0.59), 1.232 (0.81), 1.435 (10.86), 1.451 (10.57), 1.805 (1.69), 1.900 (0.51), 1.921 (1.32), 2.075 (1.10), 2.084 (16.00), 2.096 (0.44), 2.336 (1.25), 2.518 (15.49), 2.522 (11.08), 2.539 (1.61), 2.673 (3.16), 2.678 (1.54), 2.699 (0.37), 2.729 (0.59), 2.810 (2.79), 2.827 (6.09), 2.845 (3.60), 2.888 (0.88), 2.900 (0.59), 2.914 (0.81), 2.930 (0.51), 3.001 (3.52), 3.017 (5.58), 3.034 (2.72), 3.080 (1.69), 3.102 (2.64), 3.276 (3.74), 3.390 (2.50), 3.808 (0.59), 5.251 (0.73), 5.267 (1.61), 5.283 (2.13), 5.299 (1.61), 5.313 (0.73), 5.758 (1.10), 7.193 (3.52), 7.213 (7.41), 7.233 (4.70), 7.336 (0.51), 7.346 (0.44), 7.355 (0.81), 7.374 (0.95), 7.390 (1.83), 7.411 (2.57), 7.426 (1.83), 7.433 (1.76), 7.442 (0.81), 7.447 (0.73), 7.460 (0.44), 7.464 (0.44), 7.554 (3.96), 7.572 (6.09), 7.597 (4.40), 8.285 (6.31), 9.986 (1.47).

Example 101

N-(2,6-difluorophenyl)-5-fluoro-4-[4-methyl-3-(methylamino)-5-oxo-4,5-dihydro-1H-1,2,4-triazol-1-yl]-2-{[(2S)-1,1,1-trifluoropropan-2-yl]oxy}benzamide

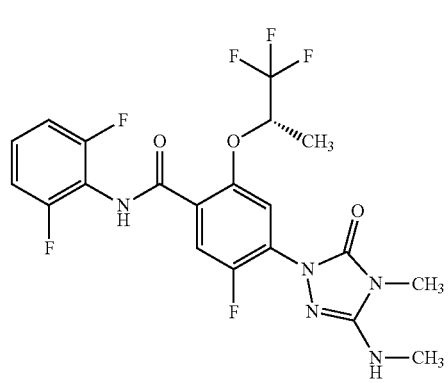 [SMILES: CNc1nn(-c2cc(O[C@@H](C)C(F)(F)F)c(C(=O)Nc3c(F)cccc3F)cc2F)c(=O)n1C]

Synthesized analogously to Example 92 from Intermediate 70 and 4-methyl-3-methylamino-1H-1,2,4-triazol-5-one.

LC-MS (Method A): $R_t$=1.12 min; MS (ESIpos): m/z=490 [M+H]$^+$.

$^1$H-NMR (400 MHz, DMSO-d6) δ [ppm]: 1.433 (4.32), 1.449 (4.30), 2.085 (1.54), 2.518 (2.84), 2.523 (1.99), 2.737 (7.94), 2.749 (7.88), 2.938 (0.68), 3.095 (16.00), 5.267 (0.70), 5.282 (0.92), 5.298 (0.68), 5.759 (0.95), 6.556 (1.32), 6.568 (1.32), 6.579 (0.45), 7.189 (1.34), 7.210 (2.76), 7.231 (1.71), 7.386 (0.69), 7.406 (0.97), 7.427 (0.67), 7.516 (2.44), 7.526 (1.78), 7.542 (1.75), 9.894 (4.18).

Example 102

4-(3-tert-butyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

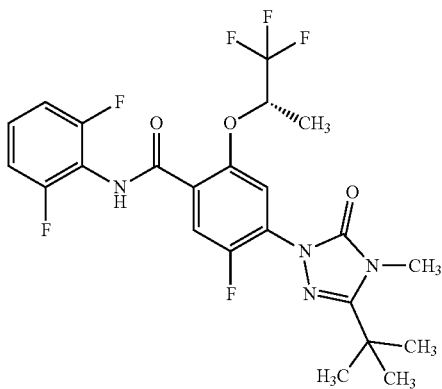 [SMILES: C[C@H](Oc1cc(-n2nc(C(C)(C)C)n(C)c2=O)c(F)cc1C(=O)Nc1c(F)cccc1F)C(F)(F)F]

Synthesized analogously to Example 92 from Intermediate 70 and 5-tert-butyl-4-methyl-2,4-dihydro-3H-1,2,4-triazol-3-one.

LC-MS (Method A): $R_t$=1.35 min; MS (ESIpos): m/z=517 [M+H]$^+$.

$^1$H-NMR (400 MHz, DMSO-d6) δ [ppm]: 1.372 (16.00), 1.432 (1.55), 1.448 (1.53), 2.518 (1.06), 2.523 (0.73), 3.415 (5.48), 7.193 (0.47), 7.213 (0.97), 7.233 (0.60), 7.566 (1.20), 7.581 (0.62), 7.591 (0.68), 9.975 (1.30).

Example 103

4-(3-chloro-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

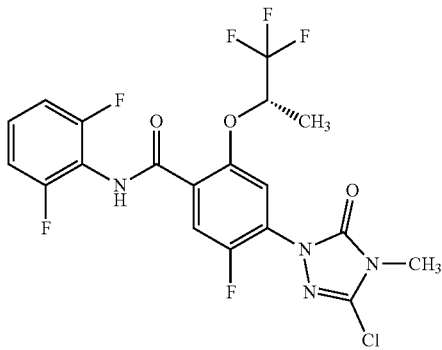 [SMILES: C[C@H](Oc1cc(-n2nc(Cl)n(C)c2=O)c(F)cc1C(=O)Nc1c(F)cccc1F)C(F)(F)F]

Synthesized analogously to Example 92 from Intermediate 70 and 3-chloro-4-methyl-1H-1,2,4-triazol-5(4H)-one.

LC-MS (Method A): $R_t$=1.24 min; MS (ESIpos): m/z=495 [M+H]$^+$.

$^1$H-NMR (400 MHz, DMSO-d6) δ [ppm]: 1.432 (4.98), 1.447 (4.96), 1.646 (1.03), 2.084 (1.12), 2.518 (3.17), 2.522 (2.18), 3.262 (0.44), 3.283 (16.00), 5.280 (0.79), 5.296 (1.02), 5.312 (0.74), 7.192 (1.69), 7.212 (3.24), 7.232 (2.14), 7.367 (1.00), 7.384 (1.51), 7.395 (1.81), 7.410 (1.46), 7.431 (0.77), 7.446 (0.41), 7.582 (1.92), 7.597 (2.07), 7.604 (2.37), 7.629 (2.10), 10.033 (3.81).

Example 104

4-[4-(cyclopropylmethyl)-3-methyl-5-oxo-4,5-dihydro-1H-1,2,4-triazol-1-yl]-N-(2,6-difluoro-phenyl)-5-fluoro-2-{[(2S)-1,1,1-trifluoropropan-2-yl]oxy}benzamide

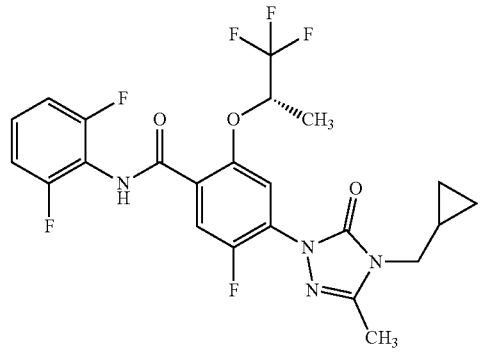 [SMILES: Cc1nn(-c2cc(O[C@@H](C)C(F)(F)F)c(C(=O)Nc3c(F)cccc3F)cc2F)c(=O)n1CC1CC1]

Synthesized analogously to Example 92 from Intermediate 70 and 4-cyclopropylmethyl-3-methyl-1H-1,2,4-triazol-5(4H)-one.

LC-MS (Method A): $R_t$=1.27 min; MS (ESIneg): m/z=513 [M–H]$^-$.

$^1$H-NMR (400 MHz, DMSO-d6) δ [ppm]: 0.362 (0.81), 0.373 (3.14), 0.386 (3.31), 0.399 (1.07), 0.500 (1.07), 0.511 (2.62), 0.514 (2.62), 0.520 (1.62), 0.530 (2.81), 0.546 (0.76), 1.146 (0.40), 1.158 (0.74), 1.165 (0.71), 1.177 (1.02), 1.188 (0.69), 1.196 (0.69), 1.425 (5.50), 1.441 (5.43), 2.318 (1.00), 2.323 (1.33), 2.327 (1.19), 2.345 (16.00), 2.518 (3.55), 2.535 (0.69), 2.660 (0.79), 2.665 (1.07), 2.669 (0.79), 3.550 (4.36), 3.568 (4.21), 5.318 (0.88), 5.335 (1.14), 5.351 (0.83), 7.187 (1.71), 7.207 (3.43), 7.228 (2.14), 7.367 (0.52), 7.383 (1.05), 7.404 (1.26), 7.420 (0.71), 7.559 (2.48), 7.568 (2.33), 7.583 (4.12), 9.975 (4.83).

Example 105

N-(2,6-difluorophenyl)-5-fluoro-4-(3-methyl-5-oxo-4-propyl-4,5-dihydro-1H-1,2,4-triazol-1-yl)-2-{[(2S)-1,1,1-trifluoropropan-2-yl]oxy}benzamide

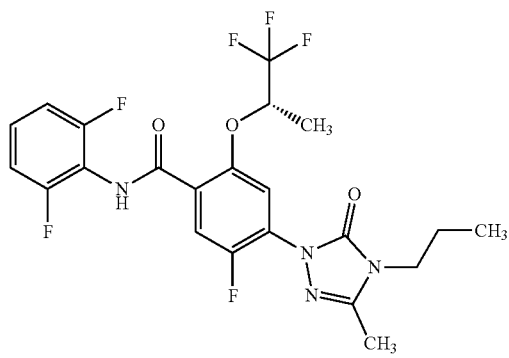 [SMILES: CCCn1c(C)nn(-c2cc(O[C@@H](C)C(F)(F)F)c(C(=O)Nc3c(F)cccc3F)cc2F)c1=O]

Synthesized analogously to Example 92 from Intermediate 70 and 3-methyl-4-propyl-1H-1,2,4-triazol-5-one.

LC-MS (Method A): $R_t$=1.25 min; MS (ESIpos): m/z=503 [M+H]$^+$.

$^1$H-NMR (400 MHz, DMSO-d6) δ [ppm]: 0.891 (4.07), 0.909 (8.88), 0.928 (4.31), 1.429 (5.60), 1.444 (5.51), 1.629 (1.44), 1.648 (2.78), 1.666 (2.52), 1.684 (1.32), 2.313 (16.00), 2.326 (1.53), 2.539 (0.82), 2.669 (1.03), 3.603 (2.30), 3.621 (3.59), 3.640 (2.11), 5.295 (0.41), 5.311 (0.91), 5.327 (1.17), 5.343 (0.86), 7.191 (1.73), 7.211 (3.45), 7.231 (2.11), 7.370 (0.52), 7.387 (1.05), 7.408 (1.25), 7.424 (0.74), 7.560 (3.64), 7.577 (2.49), 7.583 (2.52), 9.979 (4.65).

Example 106

N-(2,6-difluorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide

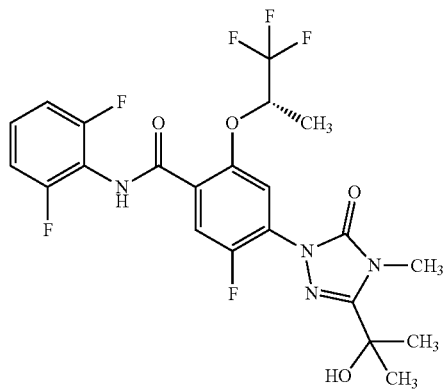 [SMILES: C[C@H](Oc1cc(-n2nc(C(C)(C)O)n(C)c2=O)c(F)cc1C(=O)Nc1c(F)cccc1F)C(F)(F)F]

4-Bromo-N-(2,6-difluorophenyl)-5-fluoro-2-{[(2S)-1,1,1-trifluoropropan-2-yl]oxy}benzamide (Intermediate 70, 100 mg, 226 μmol), 5-(2-hydroxypropan-2-yl)-4-methyl-2,4-dihydro-3H-1,2,4-triazol-3-one (Intermediate 7, 53 mg, 339 μmol), tris(dibenzylideneacetone)dipalladium(0) (21 mg, 23 μmol), 4,5-bis(diphenylphosphino)-9,9-dimethylxanthene (39 mg, 68 μmol), and cesium carbonate (147 mg, 452 μmol) were loaded into a microwave vial. The vial was purged with argon, dioxane (2 mL, degassed) was added, and the vial was sealed. The mixture was stirred for 17 h at 110° C. overnight. The resulting suspension was filtered over Celite, washed with ethyl acetate and concentrated. Mass triggered preparative chromatography yielded the desired product (56 mg, 46% yield).

LC-MS (Method A): $R_t$=1.16 min; MS (ESIpos): m/z=519 [M+H]$^+$.

$^1$H-NMR (400 MHz, DMSO-d6) δ [ppm]: 1.432 (2.83), 1.447 (2.81), 1.525 (16.00), 2.084 (1.68), 2.518 (1.87), 2.522 (1.28), 3.452 (9.33), 5.297 (0.45), 5.312 (0.58), 5.328 (0.42), 5.748 (4.50), 5.758 (0.55), 7.193 (0.85), 7.214 (1.77), 7.233 (1.12), 7.390 (0.43), 7.410 (0.61), 7.562 (1.11), 7.575 (1.96), 7.599 (1.17), 9.982 (2.69).

Example 107

N-(2,6-difluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide

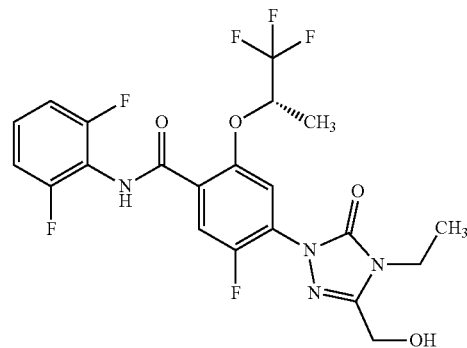 [SMILES: CCn1c(CO)nn(-c2cc(O[C@@H](C)C(F)(F)F)c(C(=O)Nc3c(F)cccc3F)cc2F)c1=O]

Synthesized analogously to Example 92 from Intermediate 70 and Intermediate 6.

LC-MS (Method A): $R_t$=1.10 min; MS (ESIpos): m/z=505 [M+H]$^+$.

$^1$H-NMR (400 MHz, DMSO-d6) δ [ppm]: 1.138 (0.94), 1.234 (0.65), 1.263 (7.12), 1.281 (16.00), 1.299 (7.00), 1.430 (10.06), 1.446 (10.00), 1.907 (0.53), 2.085 (2.12), 2.337 (0.94), 2.518 (10.88), 2.523 (7.71), 2.537 (0.47), 2.674 (2.06), 2.679 (0.88), 3.764 (1.88), 3.781 (6.00), 3.800 (5.94), 3.817 (1.76), 4.478 (9.24), 4.492 (9.29), 5.301 (0.65), 5.318 (1.59), 5.333 (2.06), 5.349 (1.53), 5.365 (0.65), 5.759 (3.12), 5.787 (3.12), 5.801 (7.24), 5.816 (2.88), 7.192 (3.12), 7.212 (6.47), 7.233 (4.06), 7.373 (0.71), 7.389 (1.59), 7.410 (2.18), 7.426 (1.18), 7.431 (1.29), 7.446 (0.53), 7.577 (7.29), 7.594 (4.35), 7.601 (4.65), 10.000 (9.41).

Example 108

N-(2,6-difluorophenyl)-4-[3-ethyl-4-(2-hydroxyethyl)-5-oxo-4,5-dihydro-1H-1,2,4-triazol-1-yl]-5-fluoro-2-{[(2S)-1,1,1-trifluoropropan-2-yl]oxy}benzamide

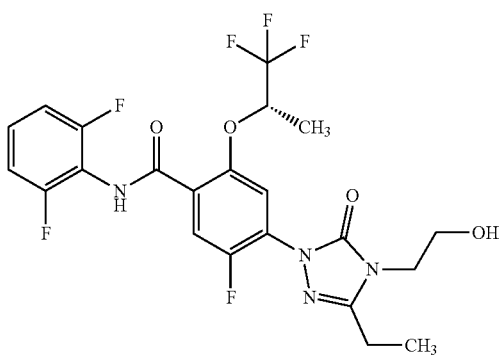 [SMILES: CCc1nn(-c2cc(O[C@@H](C)C(F)(F)F)c(C(=O)Nc3c(F)cccc3F)cc2F)c(=O)n1CCO]

Synthesized analogously to Example 92 from Intermediate 70 and 3-ethyl-4-(2-hydroxyethyl)-1H-1,2,4-triazol-5(4H)-one.

LC-MS (Method A): $R_t$=1.13 min; MS (ESIpos): m/z=519 [M+H]$^+$.

$^1$H-NMR (400 MHz, DMSO-d6) δ [ppm]: 1.104 (0.43), 1.201 (7.34), 1.220 (16.00), 1.239 (7.60), 1.433 (8.50), 1.449 (8.45), 2.331 (0.73), 2.518 (4.21), 2.522 (2.93), 2.673 (0.83), 2.695 (2.27), 2.713 (6.98), 2.732 (6.68), 2.751 (2.06), 3.594 (1.33), 3.607 (4.09), 3.620 (4.85), 3.633 (2.13), 3.700 (3.97), 3.713 (5.49), 3.727 (2.27), 5.037 (2.35), 5.050 (5.35), 5.063 (2.27), 5.292 (0.57), 5.308 (1.37), 5.324 (1.77), 5.340 (1.28), 5.355 (0.50), 7.193 (2.60), 7.214 (5.42), 7.234 (3.39), 7.355 (0.50), 7.373 (0.62), 7.389 (1.32), 7.410 (1.85), 7.431 (1.11), 7.447 (0.47), 7.562 (4.03), 7.567 (4.69), 7.576 (3.55), 7.592 (3.58), 9.973 (8.24).

Example 109

4-(3,4-diethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

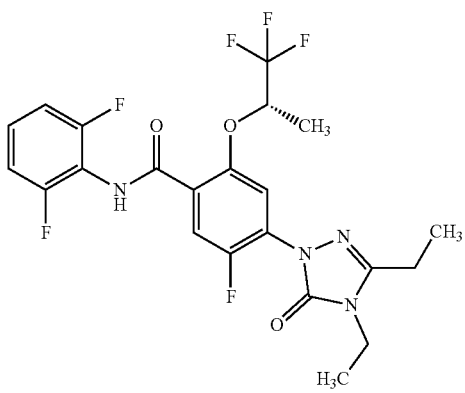 [SMILES: CCc1nn(-c2cc(O[C@@H](C)C(F)(F)F)c(C(=O)Nc3c(F)cccc3F)cc2F)c(=O)n1CC]

Synthesized analogously to Example 92 from Intermediate 70 and 3,4-diethyl-1H-1,2,4-triazol-5(4H)-one.

LC-MS (Method A): $R_t$=1.26 min; MS (ESIpos): m/z=503 [M+H]$^+$.

$^1$H-NMR (400 MHz, DMSO-d6) δ [ppm]: 1.213 (6.77), 1.232 (16.00), 1.251 (8.02), 1.432 (4.95), 1.448 (4.93), 2.323 (0.77), 2.327 (1.06), 2.331 (0.75), 2.518 (4.18), 2.523 (2.95), 2.665 (0.89), 2.669 (1.33), 2.674 (2.10), 2.692 (4.33), 2.711 (4.16), 2.729 (1.25), 3.676 (1.01), 3.694 (3.19), 3.712 (3.10), 3.730 (0.94), 5.307 (0.80), 5.323 (1.04), 5.339 (0.75), 7.193 (1.54), 7.214 (3.19), 7.234 (2.01), 7.373 (0.46), 7.389 (0.92), 7.395 (0.90), 7.410 (1.11), 7.431 (0.60), 7.564 (2.73), 7.583 (2.32), 7.588 (2.49), 9.974 (4.64).

Example 110

4-(4-cyclopropyl-3-methoxy-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

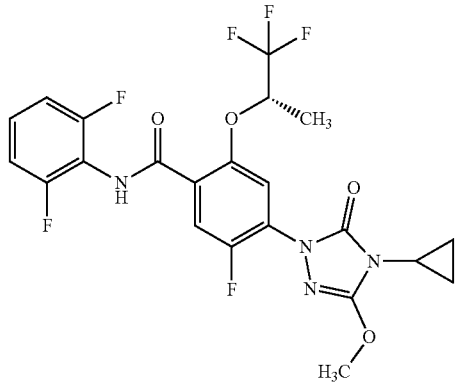 [SMILES: COc1nn(-c2cc(O[C@@H](C)C(F)(F)F)c(C(=O)Nc3c(F)cccc3F)cc2F)c(=O)n1C1CC1]

Synthesized analogously to Example 92 from Intermediate 70 and 4-cyclopropyl-3-methoxy-1H-1,2,4-triazol-5(4H)-one.

LC-MS (Method A): $R_t$=1.27 min; MS (ESIpos): m/z=517 [M+H]$^+$.

$^1$H-NMR (400 MHz, DMSO-d6) δ [ppm]: 0.927 (8.00), 0.940 (7.45), 1.232 (0.82), 1.434 (3.56), 1.450 (3.49), 2.322 (2.94), 2.326 (3.97), 2.331 (2.80), 2.336 (1.23), 2.518 (16.00), 2.522 (10.67), 2.664 (3.01), 2.668 (4.03), 2.673 (2.87), 2.678 (1.30), 2.801 (1.03), 2.814 (1.37), 2.827 (0.96), 3.274 (0.82), 3.932 (1.09), 3.993 (14.70), 5.249 (0.55), 5.266 (0.68), 5.281 (0.55), 5.759 (1.78), 7.189 (1.03), 7.210 (2.05), 7.231 (1.23), 7.387 (0.48), 7.407 (0.68), 7.530 (1.23), 7.544 (2.53), 7.569 (1.44), 9.949 (3.01).

Example 111

4-(3-chloro-4-ethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

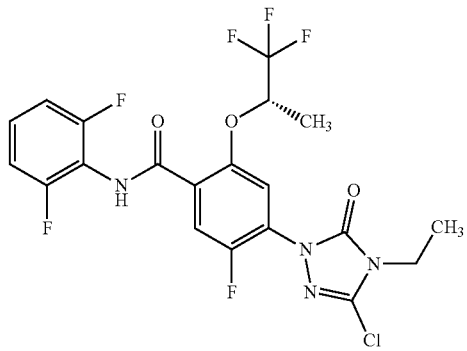 [SMILES: CCn1c(Cl)nn(-c2cc(O[C@@H](C)C(F)(F)F)c(C(=O)Nc3c(F)cccc3F)cc2F)c1=O]

Synthesized analogously to Example 92 from Intermediate 70 and 3-chloro-4-ethyl-1H-1,2,4-triazol-5(4H)-one.

LC-MS (Method A): $R_t$=1.30 min; MS (ESIpos): m/z=509 [M+H]$^+$.

$^1$H-NMR (400 MHz, DMSO-d6) δ [ppm]: 1.232 (0.55), 1.252 (2.69), 1.270 (6.14), 1.288 (2.69), 1.433 (3.38), 1.448 (3.38), 1.647 (0.48), 2.326 (4.21), 2.331 (2.97), 2.336 (1.31), 2.518 (16.00), 2.522 (10.76), 2.539 (4.90), 2.668 (4.14), 2.673 (2.97), 2.678 (1.31), 3.747 (0.76), 3.765 (2.28), 3.783 (2.28), 3.801 (0.69), 5.289 (0.55), 5.305 (0.69), 5.320 (0.55), 7.189 (0.83), 7.209 (1.52), 7.230 (0.90), 7.367 (0.48), 7.384 (0.83), 7.395 (0.76), 7.600 (1.52), 7.624 (1.72), 10.032 (2.07).

Example 112

4-(3-cyclopentyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

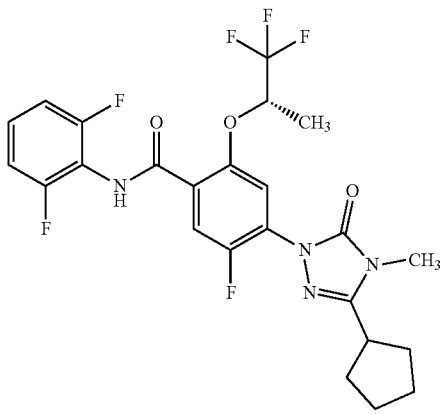 [SMILES: C[C@H](Oc1cc(-n2nc(C3CCCC3)n(C)c2=O)c(F)cc1C(=O)Nc1c(F)cccc1F)C(F)(F)F]

Synthesized analogously to Example 92 from Intermediate 70 and 3-cyclopentyl-4-methyl-1H-1,2,4-triazol-5(4H)-one.

LC-MS (Method A): $R_t$=1.36 min; MS (ESIneg): m/z=527 [M−H]$^−$.

$^1$H-NMR (400 MHz, DMSO-d6) δ [ppm]: 1.430 (4.79), 1.446 (4.74), 1.605 (0.52), 1.614 (0.84), 1.634 (1.50), 1.643 (1.45), 1.652 (1.64), 1.672 (1.22), 1.693 (1.36), 1.698 (1.31), 1.710 (1.41), 1.731 (0.99), 1.768 (0.56), 1.786 (0.89), 1.798 (1.03), 1.815 (1.36), 1.833 (0.94), 1.976 (0.56), 2.004 (1.41), 2.024 (1.13), 2.035 (0.80), 2.327 (0.75), 2.331 (0.56), 2.518 (3.24), 2.523 (2.21), 2.669 (0.75), 2.673 (0.52), 3.103 (0.42), 3.166 (1.17), 3.186 (1.64), 3.205 (1.08), 3.225 (0.42), 3.257 (16.00), 5.286 (0.75), 5.301 (0.99), 5.317 (0.70), 7.192 (1.50), 7.212 (3.05), 7.233 (1.92), 7.346 (0.66), 7.372 (0.52), 7.386 (1.31), 7.394 (0.94), 7.409 (1.13), 7.425 (0.66), 7.429 (0.66), 7.460 (0.70), 7.465 (0.70), 7.478 (0.47), 7.545 (1.88), 7.559 (3.66), 7.585 (1.92), 7.783 (0.42), 9.972 (4.04).

Example 113

4-[4-(butan-2-yl)-3-methyl-5-oxo-4,5-dihydro-1H-1,2,4-triazol-1-yl]-N-(2,6-difluorophenyl)-5-fluoro-2-{[(2S)-1,1,1-trifluoropropan-2-yl]oxy}benzamide, Mixture of Stereoisomers

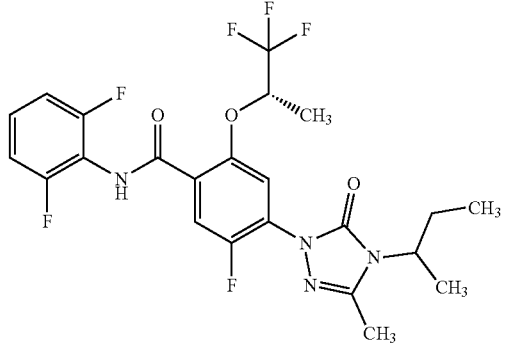 [SMILES: CCC(C)n1c(C)nn(-c2cc(O[C@@H](C)C(F)(F)F)c(C(=O)Nc3c(F)cccc3F)cc2F)c1=O]

Synthesized analogously to Example 92 from Intermediate 70 and 4-butan-2-yl-3-methyl-1H-1,2,4-triazol-5(4H)-one.

LC-MS (Method A): Rt=1.31 min; MS (ESIpos): m/z=517 [M+H]$^+$.

$^1$H-NMR (400 MHz, DMSO-d6) δ [ppm]: 0.833 (3.02), 0.852 (6.79), 0.870 (3.25), 1.233 (0.75), 1.428 (10.34), 1.446 (10.26), 1.714 (0.60), 1.732 (0.91), 1.750 (0.68), 1.766 (0.45), 1.959 (0.45), 1.977 (0.53), 2.000 (0.53), 2.017 (0.45), 2.312 (13.21), 2.323 (3.09), 2.327 (4.00), 2.332 (2.79), 2.336 (1.28), 2.518 (16.00), 2.523 (11.09), 2.539 (2.57), 2.660 (1.21), 2.665 (2.72), 2.669 (3.85), 2.673 (2.72), 2.678 (1.21), 3.288 (0.45), 3.372 (0.53), 3.962 (0.45), 3.979 (0.68), 4.002 (0.60), 5.331 (0.60), 5.346 (0.75), 5.363 (0.60), 7.188 (0.91), 7.208 (1.74), 7.228 (1.06), 7.405 (0.60), 7.548 (1.58), 7.572 (2.19), 9.974 (2.04).

Example 114

4-[3-(butan-2-yl)-4-methyl-5-oxo-4,5-dihydro-1H-1,2,4-triazol-1-yl]-N-(2,6-difluorophenyl)-5-fluoro-2-{[(2S)-1,1,1-trifluoropropan-2-yl]oxy}benzamide, Mixture of Stereoisomers

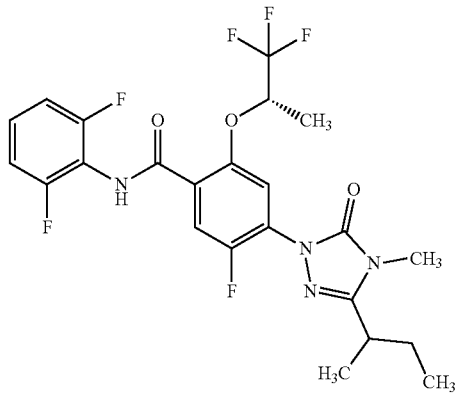 [SMILES: CCC(C)c1nn(-c2cc(O[C@@H](C)C(F)(F)F)c(C(=O)Nc3c(F)cccc3F)cc2F)c(=O)n1C]

Synthesized analogously to Example 92 from Intermediate 70 and 3-butan-2-yl-4-methyl-1H-1,2,4-triazol-5(4H)-one.

LC-MS (Method A): $R_t$=1.33 min; MS (ESIpos): m/z=517 [M+H]$^+$.

$^1$H-NMR (400 MHz, DMSO-d6) δ [ppm]: 0.920 (3.85), 0.939 (8.54), 0.957 (4.16), 1.228 (8.26), 1.246 (8.38), 1.432 (5.29), 1.448 (5.20), 1.517 (0.61), 1.534 (0.98), 1.552 (1.19), 1.569 (1.19), 1.587 (0.73), 1.646 (1.74), 1.737 (0.70), 1.753 (1.04), 1.771 (1.16), 1.789 (0.83), 1.806 (0.49), 2.323 (0.67), 2.327 (0.89), 2.331 (0.67), 2.665 (0.70), 2.669 (0.92), 2.840 (0.83), 2.857 (1.53), 2.874 (1.47), 2.891 (0.73), 3.112 (0.58), 3.265 (16.00), 5.290 (0.89), 5.306 (1.13), 5.322 (0.83), 7.193 (1.80), 7.214 (3.46), 7.234 (2.11), 7.339 (0.49), 7.350 (0.46), 7.367 (1.38), 7.384 (2.20), 7.395 (2.26), 7.410 (1.41), 7.426 (0.86), 7.549 (2.17), 7.564 (4.07), 7.588 (2.11), 9.975 (4.19).

Example 115

N-(2,6-difluorophenyl)-4-[4-ethyl-3-(methylsulfanyl)-5-oxo-4,5-dihydro-1H-1,2,4-triazol-1-yl]-5-fluoro-2-{[(2S)-1,1,1-trifluoropropan-2-yl]oxy}benzamide

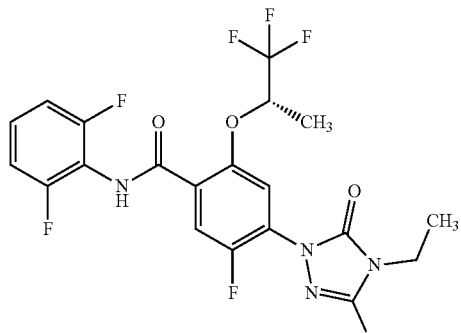

Synthesized analogously to Example 92 from Intermediate 70 and 4-ethyl-3-methylsulfanyl-1H-1,2,4-triazol-5-one.

LC-MS (Method A): $R_t$=1.32 min; MS (ESIpos): m/z=521 [M+H]$^+$.

$^1$H-NMR (400 MHz, DMSO-d6) δ [ppm]: 1.227 (2.93), 1.244 (6.69), 1.263 (2.90), 1.437 (3.81), 1.453 (3.78), 2.479 (1.22), 2.518 (2.19), 2.523 (1.52), 2.606 (16.00), 3.647 (0.78), 3.665 (2.50), 3.683 (2.45), 3.701 (0.74), 5.297 (0.60), 5.313 (0.79), 5.329 (0.59), 7.193 (1.16), 7.214 (2.43), 7.234 (1.53), 7.373 (0.47), 7.390 (0.65), 7.395 (0.63), 7.411 (0.86), 7.431 (0.52), 7.582 (1.62), 7.607 (1.95), 7.611 (1.74), 7.627 (1.43), 9.980 (3.30).

Example 116

N-(2,6-difluorophenyl)-5-fluoro-4-[3-(1-methoxyethyl)-4-methyl-5-oxo-4,5-dihydro-1H-1,2,4-triazol-1-yl]-2-{[(2S)-1,1,1-trifluoropropan-2-yl]oxy}benzamide, Mixture of Stereoisomers

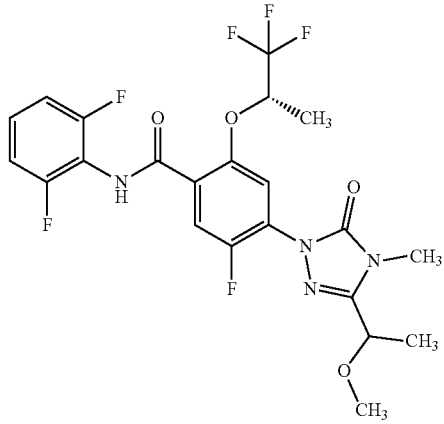 [SMILES: COC(C)c1nn(-c2cc(O[C@@H](C)C(F)(F)F)c(C(=O)Nc3c(F)cccc3F)cc2F)c(=O)n1C]

Synthesized analogously to Example 92 from Intermediate 70 and Intermediate 11.

LC-MS (Method A): $R_t$=1.23 min; MS (ESIpos): m/z=519 [M+H]$^+$.

Example 117

N-(2,6-difluorophenyl)-4-[4-ethyl-5-oxo-3-(propan-2-yloxy)-4,5-dihydro-1H-1,2,4-triazol-1-yl]-5-fluoro-2-{[(2S)-1,1,1-trifluoropropan-2-yl]oxy}benzamide

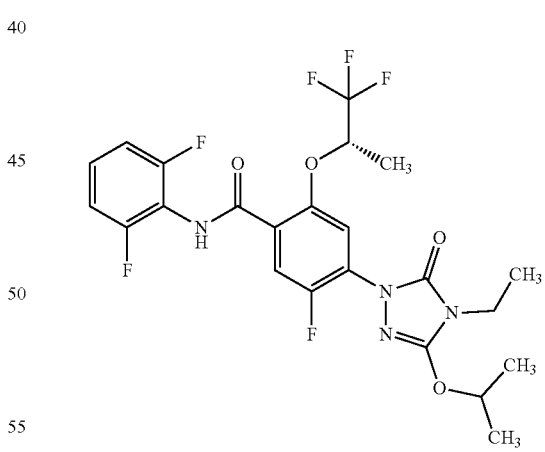

Synthesized analogously to Example 92 from Intermediate 70 and 4-ethyl-3-isopropoxy-1H-1,2,4-triazol-5(4H)-one.

LC-MS (Method A): $R_t$=1.40 min; MS (ESIpos): m/z=533 [M+H]$^+$.

$^1$H-NMR (400 MHz, DMSO-d6) δ [ppm]: 1.193 (2.96), 1.211 (6.72), 1.229 (3.18), 1.396 (15.67), 1.411 (16.00), 1.437 (3.84), 1.453 (3.75), 2.518 (3.86), 2.523 (2.64), 3.558 (0.81), 3.575 (2.54), 3.594 (2.48), 3.611 (0.75), 4.976 (0.42), 4.991 (1.04), 5.007 (1.43), 5.022 (1.05), 5.283 (0.62), 5.299

(0.78), 5.315 (0.59), 7.191 (1.16), 7.211 (2.34), 7.231 (1.46), 7.386 (0.72), 7.407 (0.80), 7.428 (0.51), 7.549 (1.79), 7.556 (1.58), 7.573 (2.36), 9.939 (3.20).

Example 118

4-(4-benzyl-3-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide

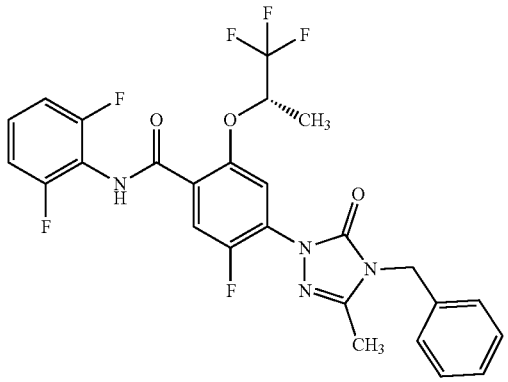 [SMILES: Cc1nn(-c2cc(O[C@@H](C)C(F)(F)F)c(C(=O)Nc3c(F)cccc3F)cc2F)c(=O)n1Cc1ccccc1]

Synthesized analogously to Example 92 from Intermediate 70 and 4-benzyl-3-methyl-1H-1,2,4-triazol-5-one.

LC-MS (Method A): $R_t$=1.36 min; MS (ESIpos): m/z=551 [M+H]$^+$.

$^1$H-NMR (400 MHz, DMSO-d6) δ [ppm]: 1.433 (5.20), 1.449 (5.14), 2.229 (16.00), 2.327 (1.01), 2.331 (0.73), 2.518 (4.26), 2.523 (2.99), 2.669 (1.05), 2.673 (0.73), 4.933 (6.79), 5.324 (0.81), 5.340 (1.05), 5.356 (0.78), 7.195 (1.62), 7.215 (3.41), 7.235 (2.18), 7.324 (3.48), 7.344 (5.91), 7.358 (1.93), 7.360 (1.76), 7.374 (0.63), 7.396 (4.43), 7.402 (1.66), 7.414 (4.14), 7.417 (2.84), 7.433 (1.88), 7.581 (2.31), 7.606 (2.55), 7.613 (2.26), 7.628 (2.03), 10.001 (4.88).

Example 119

N-(2-chloro-6-fluorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide

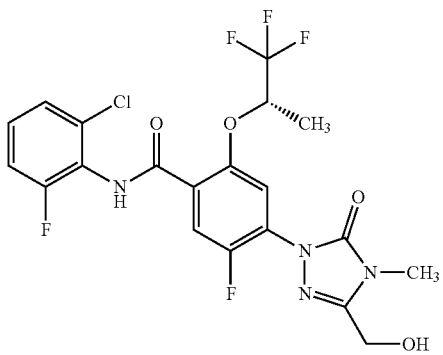 [SMILES: C[C@H](Oc1cc(-n2nc(CO)n(C)c2=O)c(F)cc1C(=O)Nc1c(F)cccc1Cl)C(F)(F)F]

Synthesized analogously to Example 92 from Intermediate 71 and Intermediate 8.

LC-MS (Method A): $R_t$=1.11 min; MS (ESIpos): m/z=507 [M+H]$^+$.

$^1$H-NMR (400 MHz, DMSO-d6) δ [ppm]: 1.435 (4.35), 1.451 (4.32), 2.084 (2.30), 2.332 (0.82), 2.518 (4.49), 2.522 (3.03), 2.539 (0.42), 2.673 (0.81), 3.311 (16.00), 4.467 (4.30), 4.482 (4.39), 5.328 (0.67), 5.344 (0.84), 5.360 (0.61), 5.739 (1.40), 5.753 (3.18), 5.758 (0.71), 5.768 (1.32), 7.332 (0.40), 7.336 (0.44), 7.355 (1.02), 7.372 (0.63), 7.380 (0.77), 7.388 (0.54), 7.402 (0.44), 7.409 (1.00), 7.422 (1.15), 7.433 (2.15), 7.439 (2.69), 7.453 (0.52), 7.553 (1.69), 7.577 (2.42), 7.588 (1.55), 10.065 (3.45).

Example 120

N-(2-chloro-6-fluorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide

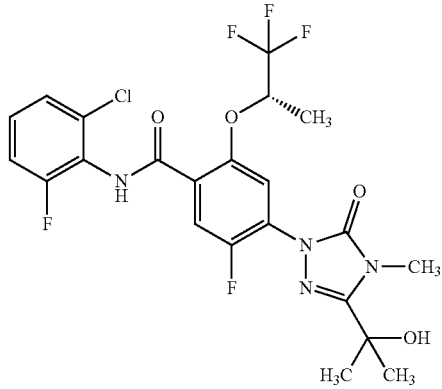 [SMILES: C[C@H](Oc1cc(-n2nc(C(C)(C)O)n(C)c2=O)c(F)cc1C(=O)Nc1c(F)cccc1Cl)C(F)(F)F]

Synthesized analogously to Example 92 from Intermediate 71 and Intermediate 7.

LC-MS (Method A): $R_t$=1.22 min; MS (ESIpos): m/z=535 [M+H]$^+$.

$^1$H-NMR (400 MHz, DMSO-d6) δ [ppm]: 1.437 (2.92), 1.453 (2.88), 1.526 (16.00), 2.084 (5.04), 2.322 (0.47), 2.326 (0.63), 2.331 (0.44), 2.518 (3.19), 2.522 (2.07), 2.664 (0.48), 2.668 (0.63), 2.673 (0.44), 3.299 (0.48), 3.453 (9.26), 5.326 (0.44), 5.342 (0.57), 5.358 (0.42), 5.750 (4.37), 7.355 (0.79), 7.374 (0.44), 7.382 (0.52), 7.410 (0.67), 7.424 (0.84), 7.435 (1.49), 7.441 (1.76), 7.549 (1.11), 7.573 (1.77), 7.586 (1.01), 10.046 (2.47).

Example 121

N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide

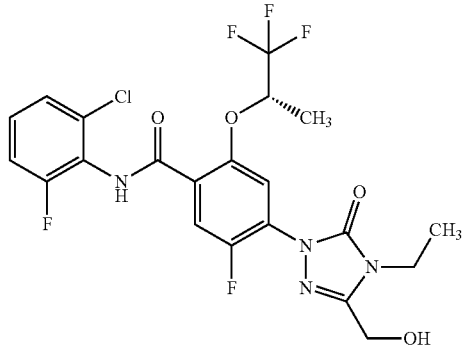 [SMILES: CCn1c(CO)nn(-c2cc(O[C@@H](C)C(F)(F)F)c(C(=O)Nc3c(F)cccc3Cl)cc2F)c1=O]

4-Bromo-N-(2-chloro-6-fluorophenyl)-5-fluoro-2-{[(2S)-1,1,1-trifluoropropan-2-yl]oxy}benzamide (Intermediate 71, 100 mg, 218 μmol), 4-ethyl-5-(hydroxymethyl)-2,4-dihydro-3H-1,2,4-triazol-3-one (Intermediate 6, 46.8 mg, 327 μmol), tris(dibenzylideneacetone)dipalladium(0) (20 mg, 22 μmol), 4,5-bis(diphenylphosphino)-9,9-dimethylxanthene (38 mg, 65 μmol), and cesium carbonate (142 mg, 436 μmol) were loaded into a microwave vial. The vial was purged with argon, dioxane (2 mL, degassed) was added, and the vial was sealed. The mixture was stirred for 17 h at 110° C. The resulting suspension was filtered over Celite, washed with ethyl acetate and concentrated. Mass triggered preparative chromatography yielded the desired product (47.0 mg, 40% yield).

LC-MS (Method A): $R_t$=1.16 min; MS (ESIpos): m/z=521 [M+H]$^+$.

$^1$H-NMR (400 MHz, DMSO-d6) δ [ppm]: 1.137 (0.43), 1.233 (0.49), 1.264 (6.16), 1.282 (13.73), 1.300 (6.05), 1.436 (9.08), 1.451 (8.92), 2.084 (8.00), 2.322 (2.38), 2.326 (3.08), 2.331 (2.22), 2.518 (16.00), 2.522 (10.27), 2.664 (2.43), 2.669 (3.14), 2.673 (2.27), 3.764 (1.73), 3.782 (5.24), 3.800 (5.08), 3.818 (1.51), 4.479 (8.00), 4.493 (8.00), 5.331 (0.59), 5.347 (1.41), 5.363 (1.78), 5.380 (1.24), 5.396 (0.49), 5.759 (1.24), 5.789 (2.65), 5.803 (5.89), 5.817 (2.38), 7.337 (0.97), 7.356 (2.16), 7.372 (1.35), 7.380 (1.62), 7.388 (1.14), 7.408 (2.00), 7.422 (2.43), 7.433 (4.54), 7.439 (5.08), 7.453 (1.14), 7.550 (3.41), 7.575 (3.57), 7.588 (3.19), 7.602 (2.92), 10.065 (7.03).

Example 122

N-(2-chloro-6-fluorophenyl)-5-fluoro-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide

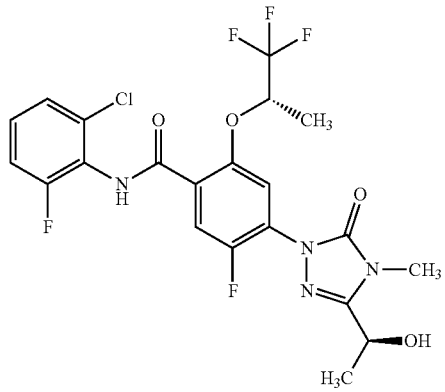 [SMILES: C[C@H](O)c1nn(-c2cc(O[C@@H](C)C(F)(F)F)c(C(=O)Nc3c(F)cccc3Cl)cc2F)c(=O)n1C]

Synthesized analogously to Example 92 from Intermediate 71 and Intermediate 9.

LC-MS (Method A): $R_t$=1.16 min; MS (ESIpos): m/z=521 [M+H]$^+$.

$^1$H-NMR (400 MHz, DMSO-d6) δ [ppm]: 1.437 (0.84), 1.457 (1.55), 1.474 (1.20), 2.084 (0.41), 2.522 (0.55), 3.331 (16.00), 3.341 (2.70), 5.821 (0.52), 5.836 (0.51), 7.440 (0.44), 7.575 (0.40), 10.056 (0.62).

Example 123

5-fluoro-4-[3-(hydroxymethyl)-4-methyl-5-oxo-4,5-dihydro-1H-1,2,4-triazol-1-yl]-N-(2-methoxy-4-methylpyridin-3-yl)-2-{[(2S)-1,1,1-trifluoropropan-2-yl]oxy}benzamide

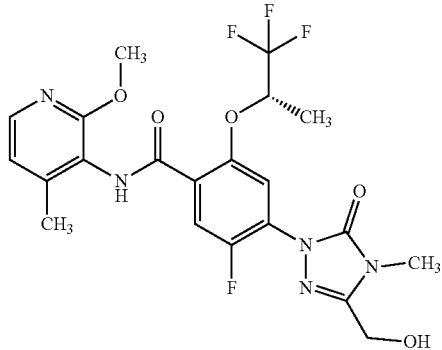 [SMILES: COc1nccc(C)c1NC(=O)c1cc(F)c(-n2nc(CO)n(C)c2=O)cc1O[C@@H](C)C(F)(F)F]

Synthesized analogously to Example 92 from Intermediate 72 and Intermediate 8.

LC-MS (Method A): $R_t$=1.01 min; MS (ESIpos): m/z=500 [M+H]$^+$.

$^1$H-NMR (400 MHz, DMSO-d6) δ [ppm]: 1.444 (4.25), 1.460 (4.23), 2.084 (2.42), 2.220 (10.56), 2.331 (0.41), 2.518 (2.63), 2.522 (1.71), 2.539 (0.80), 2.669 (0.58), 2.673 (0.41), 3.312 (14.96), 3.321 (2.01), 3.860 (16.00), 4.468 (2.85), 4.482 (2.83), 5.363 (0.67), 5.378 (0.86), 5.395 (0.63), 5.742 (0.76), 5.756 (1.84), 5.770 (0.69), 6.932 (1.90), 6.946 (1.94), 7.552 (1.84), 7.569 (3.24), 7.594 (2.25), 7.968 (2.48), 7.981 (2.33), 9.663 (2.57).

Example 124

4-[4-ethyl-3-(hydroxymethyl)-5-oxo-4,5-dihydro-1H-1,2,4-triazol-1-yl]-5-fluoro-N-(2-methoxy-4-methylpyridin-3-yl)-2-{[(2S)-1,1,1-trifluoropropan-2-yl]oxy}benzamide

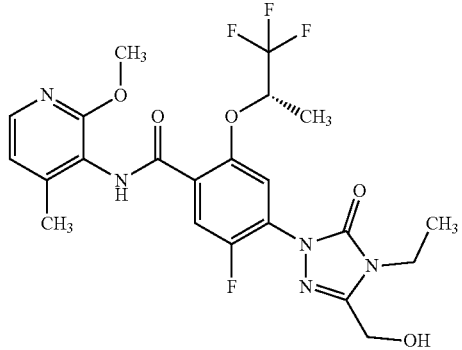 [SMILES: CCn1c(CO)nn(-c2cc(O[C@@H](C)C(F)(F)F)c(C(=O)Nc3c(C)ccnc3OC)cc2F)c1=O]

Synthesized analogously to Example 92 from Intermediate 72 and Intermediate 6.

LC-MS (Method A): $R_t$=1.04 min; MS (ESIneg): m/z=512 [M−H]$^-$.

$^1$H-NMR (400 MHz, DMSO-d6) δ [ppm]: 1.265 (2.79), 1.283 (6.36), 1.301 (2.76), 1.445 (4.67), 1.461 (4.64), 2.084

(1.75), 2.220 (11.39), 2.322 (0.54), 2.326 (0.72), 2.331 (0.50), 2.518 (3.15), 2.522 (2.07), 2.664 (0.55), 2.668 (0.73), 2.673 (0.53), 3.765 (0.77), 3.783 (2.39), 3.801 (2.36), 3.820 (0.83), 3.860 (16.00), 4.479 (3.13), 4.494 (3.09), 5.382 (0.72), 5.398 (0.94), 5.414 (0.68), 5.790 (0.86), 5.804 (2.02), 5.818 (0.80), 6.933 (2.05), 6.946 (2.10), 7.568 (4.64), 7.583 (2.02), 7.592 (2.39), 7.969 (2.59), 7.981 (2.48), 9.661 (2.82).

Example 125

5-fluoro-4-[3-(2-hydroxypropan-2-yl)-4-methyl-5-oxo-4,5-dihydro-1H-1,2,4-triazol-1-yl]-N-(2-methoxy-4-methylpyridin-3-yl)-2-{[(2S)-1,1,1-trifluoropropan-2-yl]oxy}benzamide

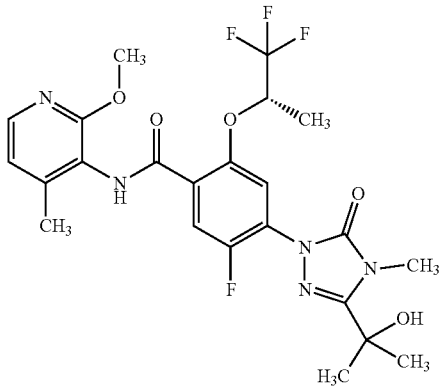 [SMILES: COc1nccc(C)c1NC(=O)c1cc(F)c(-n2nc(C(C)(C)O)n(C)c2=O)cc1O[C@@H](C)C(F)(F)F]

Synthesized analogously to Example 92 from Intermediate 72 and Intermediate 7.

LC-MS (Method A): $R_t$=1.11 min; MS (ESIpos): m/z=528 [M+H]$^+$.

$^1$H-NMR (400 MHz, DMSO-d6) δ [ppm]: 1.447 (3.41), 1.463 (3.40), 1.526 (16.00), 2.084 (2.52), 2.221 (8.01), 2.322 (0.45), 2.326 (0.59), 2.331 (0.42), 2.518 (2.97), 2.522 (1.92), 2.539 (1.85), 2.664 (0.45), 2.668 (0.60), 2.673 (0.43), 3.454 (9.56), 3.861 (10.42), 5.363 (0.52), 5.378 (0.68), 5.394 (0.49), 5.750 (3.64), 5.759 (0.75), 6.934 (1.46), 6.947 (1.49), 7.550 (1.40), 7.566 (2.80), 7.591 (1.59), 7.969 (1.78), 7.983 (1.66), 9.645 (2.04).

Example 126

5-fluoro-4-{3-[(1S)-1-hydroxyethyl]-4-methyl-5-oxo-4,5-dihydro-1H-1,2,4-triazol-1-yl}-N-(2-methoxy-4-methylpyridin-3-yl)-2-{[(2S)-1,1,1-trifluoropropan-2-yl]oxy}benzamide

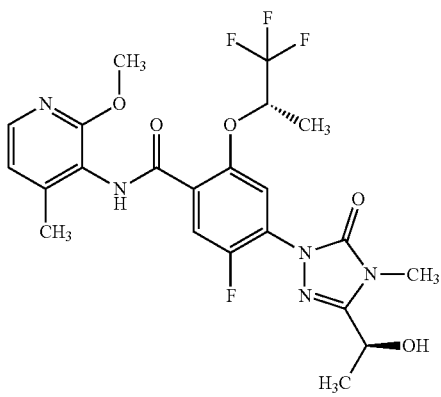 [SMILES: COc1nccc(C)c1NC(=O)c1cc(F)c(-n2nc([C@H](C)O)n(C)c2=O)cc1O[C@@H](C)C(F)(F)F]

Synthesized analogously to Example 92 from Intermediate 72 and Intermediate 9.

LC-MS (Method A): $R_t$=1.07 min; MS (ESIpos): m/z=514 [M+H]$^+$.

$^1$H-NMR (400 MHz, DMSO-d6) δ [ppm]: 1.447 (1.23), 1.458 (2.02), 1.462 (1.44), 1.475 (1.63), 2.084 (0.59), 2.221 (2.83), 2.518 (0.60), 3.331 (16.00), 3.342 (3.71), 5.822 (0.74), 5.836 (0.72), 6.934 (0.51), 6.947 (0.52), 7.547 (0.48), 7.562 (0.52), 7.568 (0.67), 7.593 (0.60), 7.969 (0.65), 7.982 (0.62), 9.653 (0.69).

Example 127

5-fluoro-N-(2-fluoro-6-methylphenyl)-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide

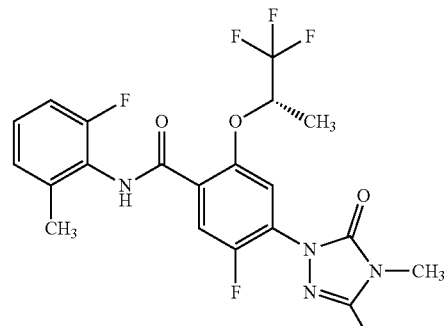

4-Bromo-5-fluoro-N-(2-fluoro-6-methylphenyl)-2-{[(2S)-1,1,1-trifluoropropan-2-yl]oxy}benzamide (Intermediate 73, 100 mg, 228 µmol), 5-(hydroxymethyl)-4-methyl-2,4-dihydro-3H-1,2,4-triazol-3-one (Intermediate 8, 44 mg, 342 µmol), tris(dibenzylideneacetone)dipalladium(0) (21 mg, 23 µmol), 4,5-bis(diphenylphosphino)-9,9-dimethylxanthene (40 mg, 68 µmol), and cesium carbonate (149 mg, 456 µmol) were loaded into a microwave vial. The vial was purged with argon, dioxane (2 mL, degassed) was added, and the vial was sealed. The mixture was stirred for 17 h at 110° C. overnight. The resulting suspension was filtered over Celite, washed with ethyl acetate and concentrated. Mass triggered preparative chromatography yielded the desired product (75 mg, 67% yield).

LC-MS (Method A): $R_t$=1.10 min; MS (ESIpos): m/z=487 [M+H]$^+$.

$^1$H-NMR (400 MHz, DMSO-d6) δ [ppm]: 1.429 (1.77), 1.444 (1.76), 2.084 (0.46), 2.272 (4.04), 2.518 (0.63), 2.522 (0.42), 3.312 (5.92), 3.331 (16.00), 4.467 (1.28), 4.482 (1.28), 5.755 (0.87), 7.117 (0.60), 7.121 (0.58), 7.134 (0.64), 7.247 (0.40), 7.557 (0.88), 7.561 (1.14), 7.572 (0.77), 7.586 (0.93), 9.825 (1.07).

Example 128

4-[4-ethyl-3-(hydroxymethyl)-5-oxo-4,5-dihydro-1H-1,2,4-triazol-1-yl]-5-fluoro-N-(2-fluoro-6-methylphenyl)-2-{[(2S)-1,1,1-trifluoropropan-2-yl]oxy}benzamide

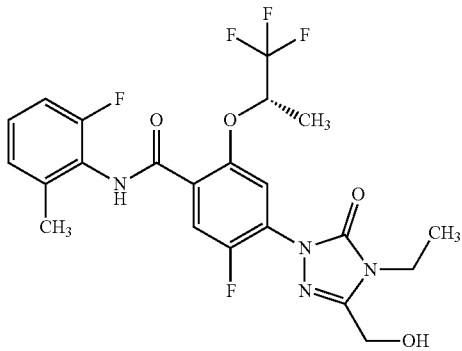 [SMILES: CCn1c(CO)nn(-c2cc(O[C@@H](C)C(F)(F)F)c(C(=O)Nc3c(C)cccc3F)cc2F)c1=O]

Synthesized analogously to Example 92 from Intermediate 73 and Intermediate 6.

LC-MS (Method A): $R_t$=1.15 min; MS (ESIpos): m/z=501 [M+H]$^+$.

$^1$H-NMR (400 MHz, DMSO-d6) δ [ppm]: 1.265 (4.21), 1.283 (9.63), 1.301 (4.15), 1.429 (7.02), 1.445 (6.97), 2.084 (3.62), 2.272 (16.00), 2.322 (0.49), 2.326 (0.63), 2.331 (0.45), 2.518 (2.93), 2.522 (1.84), 2.539 (0.57), 2.664 (0.49), 2.668 (0.64), 2.673 (0.45), 3.765 (1.15), 3.783 (3.62), 3.801 (3.50), 3.818 (1.04), 4.479 (4.44), 4.493 (4.41), 5.345 (0.45), 5.361 (1.10), 5.377 (1.41), 5.393 (1.03), 5.789 (1.19), 5.803 (2.91), 5.817 (1.10), 7.101 (0.95), 7.117 (2.38), 7.122 (2.32), 7.134 (2.57), 7.144 (1.44), 7.228 (1.11), 7.241 (1.24), 7.247 (1.61), 7.261 (1.24), 7.267 (0.79), 7.280 (0.67), 7.559 (3.84), 7.571 (3.09), 7.584 (5.27), 9.824 (4.24).

Example 129

5-fluoro-N-(2-fluoro-6-methylphenyl)-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide

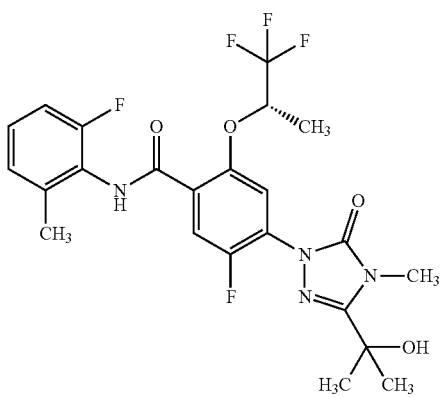 [SMILES: Cc1cccc(F)c1NC(=O)c1cc(F)c(-n2nc(C(C)(C)O)n(C)c2=O)cc1O[C@@H](C)C(F)(F)F]

Synthesized analogously to Example 92 from Intermediate 73 and Intermediate 7.

LC-MS (Method A): $R_t$=1.22 min; MS (ESIpos): m/z=515 [M+H]$^+$.

$^1$H-NMR (400 MHz, DMSO-d6) δ [ppm]: 1.431 (3.30), 1.447 (3.27), 1.526 (16.00), 2.084 (1.07), 2.272 (7.50), 2.518 (1.61), 2.522 (1.04), 3.454 (10.04), 3.566 (0.51), 5.341 (0.51), 5.357 (0.66), 5.373 (0.48), 5.750 (3.35), 7.103 (0.45), 7.119 (1.12), 7.123 (1.08), 7.136 (1.20), 7.145 (0.67), 7.228 (0.52), 7.242 (0.59), 7.248 (0.75), 7.262 (0.58), 7.555 (2.56), 7.568 (1.40), 7.580 (1.72), 9.805 (1.93).

Example 130

5-fluoro-N-(2-fluoro-6-methylphenyl)-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide

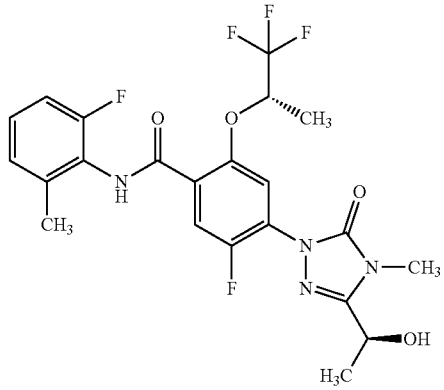 [SMILES: Cc1cccc(F)c1NC(=O)c1cc(F)c(-n2nc([C@H](C)O)n(C)c2=O)cc1O[C@@H](C)C(F)(F)F]

Synthesized analogously to Example 92 from Intermediate 73 and Intermediate 9.

LC-MS (Method A): $R_t$=1.15 min; MS (ESIpos): m/z=501 [M+H]$^+$.

$^1$H-NMR (400 MHz, DMSO-d6) δ [ppm]: 1.431 (1.09), 1.447 (1.14), 1.458 (1.53), 1.474 (1.49), 2.084 (0.64), 2.272 (2.44), 2.518 (0.53), 3.332 (16.00), 3.342 (3.43), 5.821 (0.66), 5.836 (0.63), 7.551 (0.49), 7.558 (0.64), 7.566 (0.47), 7.583 (0.56), 9.813 (0.65).

Example 131

N-(2,6-dichlorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide

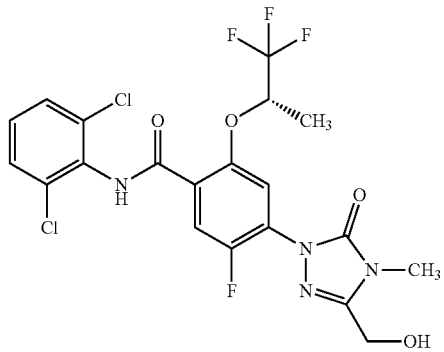 [SMILES: C[C@H](Oc1cc(-n2nc(CO)n(C)c2=O)c(F)cc1C(=O)Nc1c(Cl)cccc1Cl)C(F)(F)F]

Synthesized analogously to Example 92 from Intermediate 74 and Intermediate 8.

LC-MS (Method A): $R_t$=1.14 min; MS (ESIpos): m/z=523 [M+H]$^+$.

$^1$H-NMR (400 MHz, DMSO-d6) δ [ppm]: 1.137 (0.85), 1.433 (3.02), 1.449 (2.96), 1.526 (1.59), 2.272 (0.80), 2.322 (2.56), 2.326 (3.42), 2.331 (2.39), 2.518 (16.00), 2.522 (10.19), 2.664 (2.56), 2.668 (3.42), 2.673 (2.45), 3.311 (11.79), 3.453 (1.02), 4.468 (1.99), 4.482 (2.05), 5.354 (0.40), 5.369 (0.51), 5.756 (0.97), 5.770 (0.46), 7.405 (0.57), 7.426 (0.46), 7.528 (1.48), 7.552 (1.71), 7.581 (1.99), 7.601 (1.25), 10.227 (1.31).

Example 132

N-(2,6-dichlorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide

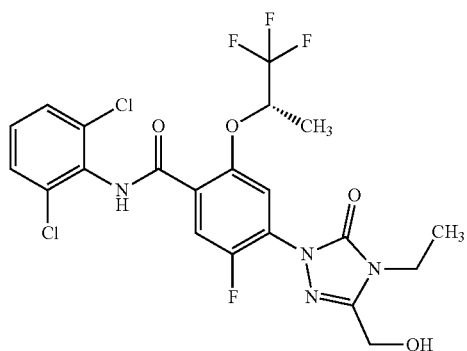 [SMILES: CCn1c(CO)nn(-c2cc(O[C@@H](C)C(F)(F)F)c(C(=O)Nc3c(Cl)cccc3Cl)cc2F)c1=O]

Synthesized analogously to Example 92 from Intermediate 74 and Intermediate 6.

LC-MS (Method A): $R_t$=1.18 min; MS (ESIpos): m/z=537 [M+H]$^+$.

$^1$H-NMR (400 MHz, DMSO-d6) δ [ppm]: 1.137 (0.53), 1.265 (7.31), 1.283 (16.00), 1.301 (7.10), 1.357 (0.46), 1.374 (0.40), 1.436 (12.55), 1.451 (12.45), 1.526 (0.53), 1.987 (0.51), 2.084 (9.22), 2.518 (6.57), 2.522 (4.25), 2.539 (0.68), 3.566 (2.01), 3.766 (2.03), 3.784 (6.24), 3.802 (6.13), 3.820 (1.88), 4.481 (8.03), 4.495 (7.97), 5.353 (0.82), 5.370 (1.92), 5.385 (2.49), 5.401 (1.80), 5.416 (0.72), 5.758 (2.13), 5.791 (2.03), 5.806 (4.14), 5.820 (1.90), 7.386 (3.02), 7.406 (4.92), 7.426 (4.21), 7.526 (5.85), 7.551 (5.81), 7.583 (15.94), 7.589 (5.81), 7.603 (15.87), 10.226 (7.55).

Example 133

N-(2,6-dichlorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide

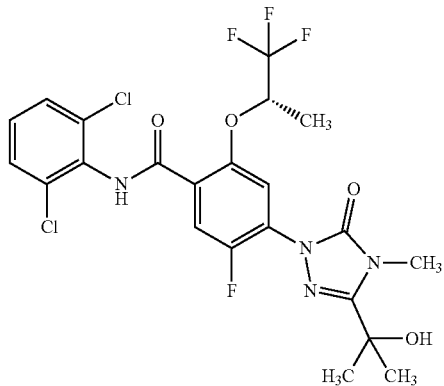 [SMILES: C[C@H](Oc1cc(-n2nc(C(C)(C)O)n(C)c2=O)c(F)cc1C(=O)Nc1c(Cl)cccc1Cl)C(F)(F)F]

4-Bromo-N-(2,6-dichlorophenyl)-5-fluoro-2-{[(2S)-1,1,1-trifluoropropan-2-yl]oxy}benzamide (Intermediate 74, 200 mg, 421 μmol), 5-(2-hydroxypropan-2-yl)-4-methyl-2,4-dihydro-3H-1,2,4-triazol-3-one (Intermediate 7, 99 mg, 631 μmol), tris(dibenzylideneacetone)dipalladium(0) (42 mg, 42 μmol), 4,5-bis(diphenylphosphino)-9,9-dimethylxanthene (73 mg, 126 μmol), and cesium carbonate (274 mg, 842 μmol) were loaded into a microwave vial. The vial was purged with argon, dioxane (4 mL, degassed) was added, and the vial was sealed. The mixture was stirred for 17 h at 110° C. overnight. The resulting suspension was filtered over Celite, washed with ethyl acetate and concentrated. Preparative chromatography (water+0.5% formic acid/acetonitrile gradient) yielded the desired product (81 mg, 31% yield).

LC-MS (Method A): $R_t$=1.25 min; MS (ESIpos): m/z=551 [M+H]$^+$.

$^1$H-NMR (400 MHz, DMSO-d6) δ [ppm]: 1.390 (0.51), 1.405 (0.54), 1.439 (3.53), 1.455 (3.51), 1.527 (16.00), 2.084 (0.57), 3.455 (9.05), 5.350 (0.55), 5.366 (0.71), 5.382 (0.51), 5.751 (2.97), 7.388 (0.80), 7.408 (1.36), 7.428 (1.11), 7.526 (1.56), 7.550 (1.59), 7.572 (1.54), 7.585 (5.04), 7.605 (3.12), 10.207 (2.30).

Example 134

N-(2,6-dichlorophenyl)-5-fluoro-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide

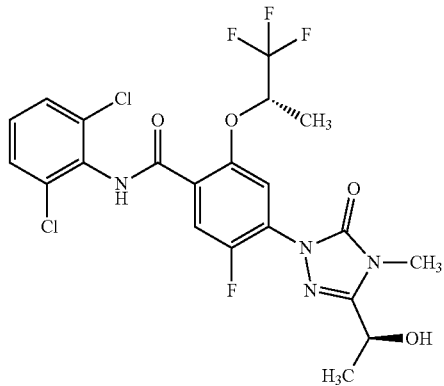 [SMILES: C[C@H](O)c1nn(-c2cc(O[C@@H](C)C(F)(F)F)c(C(=O)Nc3c(Cl)cccc3Cl)cc2F)c(=O)n1C]

Synthesized analogously to Example 92 from Intermediate 74 and Intermediate 9.

LC-MS (Method A): $R_t$=1.18 min; MS (ESIpos): m/z=537 [M+H]⁺.

¹H-NMR (400 MHz, DMSO-d6) δ [ppm]: 1.437 (1.52), 1.455 (1.87), 1.458 (2.15), 1.475 (1.80), 2.522 (0.41), 3.331 (16.00), 3.343 (3.88), 4.792 (0.45), 5.822 (0.81), 5.837 (0.76), 7.407 (0.55), 7.427 (0.44), 7.527 (0.64), 7.552 (0.66), 7.569 (0.61), 7.584 (2.15), 7.604 (1.24), 10.216 (0.92).

Example 135

N-(2-chloro-6-fluorophenyl)-5-fluoro-4-[3-(hydroxymethyl)-4-methyl-5-oxo-4,5-dihydro-1H-1,2,4-triazol-1-yl]-2-[(2S)-pentan-2-yloxy]benzamide

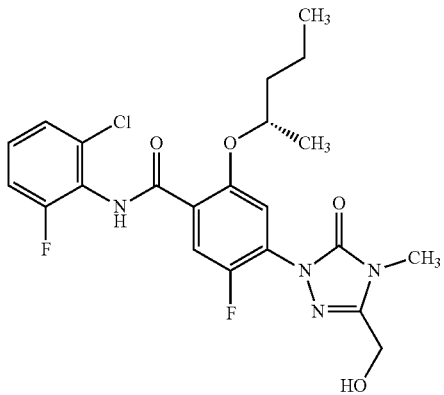 [SMILES: CCC[C@H](C)Oc1cc(-n2nc(CO)n(C)c2=O)c(F)cc1C(=O)Nc1c(F)cccc1Cl]

Synthesized analogously to Example 92 from Intermediate 76 and Intermediate 8.

LC-MS (Method A): $R_t$=1.22 min; MS (ESIneg): m/z=479 [M–H]⁻.

¹H-NMR (400 MHz, DMSO-d6) δ [ppm]: 0.860 (3.52), 0.879 (8.40), 0.897 (3.94), 1.310 (4.20), 1.324 (4.23), 1.351 (0.50), 1.366 (0.45), 1.376 (0.53), 1.394 (0.47), 1.409 (0.49), 1.427 (0.42), 1.440 (0.44), 1.446 (0.46), 1.465 (0.46), 1.594 (0.44), 1.606 (0.56), 1.618 (0.44), 1.755 (0.40), 1.769 (0.43), 1.780 (0.43), 2.518 (1.71), 2.522 (1.17), 3.305 (16.00), 4.460 (4.12), 4.474 (4.10), 4.624 (0.72), 4.638 (0.73), 5.728 (1.22), 5.742 (2.79), 5.757 (1.12), 7.336 (0.45), 7.356 (1.12), 7.375 (0.75), 7.380 (0.89), 7.409 (1.65), 7.419 (1.61), 7.425 (1.94), 7.440 (2.05), 7.445 (1.93), 7.462 (0.68), 7.661 (1.39), 7.687 (1.37), 9.838 (3.19).

Example 136

N-(2-chloro-6-fluorophenyl)-5-fluoro-4-{3-[(1S)-1-hydroxyethyl]-4-methyl-5-oxo-4,5-dihydro-1H-1,2,4-triazol-1-yl}-2-[(2S)-pentan-2-yloxy]benzamide

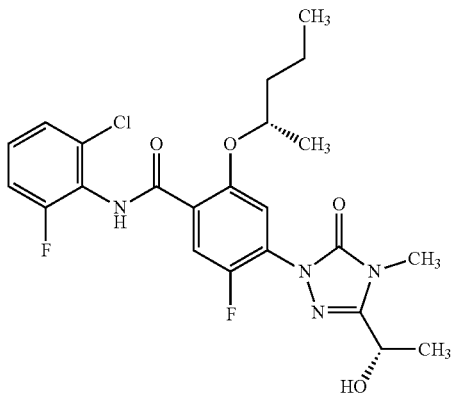 [SMILES: CCC[C@H](C)Oc1cc(-n2nc([C@H](C)O)n(C)c2=O)c(F)cc1C(=O)Nc1c(F)cccc1Cl]

Synthesized analogously to Example 92 from Intermediate 76 and Intermediate 9.

LC-MS (Method A): $R_t$=1.27 min; MS (ESIpos): m/z=495 [M+H]⁺.

¹H-NMR (400 MHz, DMSO-d6) δ [ppm]: 0.864 (1.26), 0.882 (3.04), 0.901 (1.43), 1.315 (1.50), 1.330 (1.53), 1.453 (2.64), 1.470 (2.62), 2.518 (0.45), 3.333 (16.00), 3.337 (7.21), 4.765 (0.42), 4.781 (0.60), 4.797 (0.42), 5.806 (1.01), 5.820 (1.00), 7.358 (0.44), 7.382 (0.55), 7.407 (0.75), 7.421 (0.68), 7.442 (0.70), 7.447 (0.68), 7.665 (0.50), 7.691 (0.48), 9.831 (1.25).

Example 137

N-(2-chloro-6-fluorophenyl)-5-fluoro-4-[3-(2-hydroxypropan-2-yl)-4-methyl-5-oxo-4,5-dihydro-1H-1,2,4-triazol-1-yl]-2-[(2S)-pentan-2-yloxy]benzamide

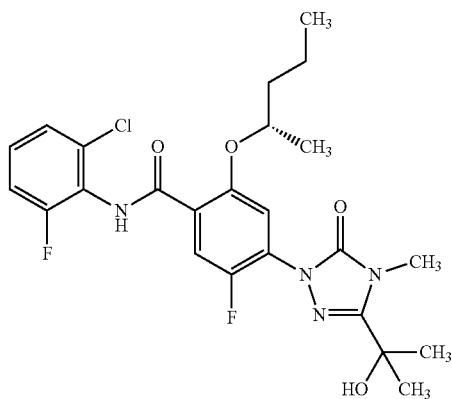 [SMILES: CCC[C@H](C)Oc1cc(-n2nc(C(C)(C)O)n(C)c2=O)c(F)cc1C(=O)Nc1c(F)cccc1Cl]

Synthesized analogously to Example 92 from Intermediate 76 and Intermediate 7.

LC-MS (Method A): $R_t$=1.35 min; MS (ESIpos): m/z=509 [M+H]⁺.

¹H-NMR (400 MHz, DMSO-d6) δ [ppm]: 0.867 (2.19), 0.885 (5.11), 0.903 (2.45), 1.318 (2.72), 1.333 (2.73), 1.521 (16.00), 2.522 (0.76), 3.448 (9.18), 4.627 (0.49), 4.642 (0.47), 5.734 (3.86), 7.357 (0.74), 7.377 (0.53), 7.382 (0.63), 7.406 (0.81), 7.419 (1.17), 7.430 (1.03), 7.442 (1.31), 7.447 (1.22), 7.463 (0.44), 7.665 (0.89), 7.691 (0.87), 9.824 (2.15).

Example 138

5-fluoro-4-[3-(hydroxymethyl)-4-methyl-5-oxo-4,5-dihydro-1H-1,2,4-triazol-1-yl]-N-(2-methoxy-4-methylpyridin-3-yl)-2-[(2S)-pentan-2-yloxy]benzamide

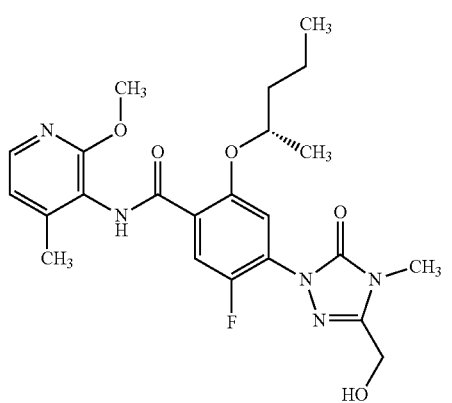 [SMILES: CCC[C@H](C)Oc1cc(-n2nc(CO)n(C)c2=O)c(F)cc1C(=O)Nc1c(C)ccnc1OC]

Synthesized analogously to Example 92 from Intermediate 77 and Intermediate 8.

LC-MS (Method A): R$_t$=1.13 min; MS (ESIpos): m/z=474 [M+H]$^+$.

$^1$H-NMR (400 MHz, DMSO-d6) δ [ppm]: 0.871 (3.46), 0.889 (7.84), 0.908 (3.93), 1.316 (6.96), 1.331 (7.02), 1.350 (0.46), 1.369 (0.56), 1.394 (0.72), 1.411 (0.79), 1.428 (0.79), 1.447 (0.67), 1.453 (0.64), 1.472 (0.63), 1.595 (0.50), 1.615 (0.58), 1.629 (0.78), 1.639 (0.56), 1.653 (0.61), 1.741 (0.58), 1.756 (0.59), 1.767 (0.62), 1.775 (0.53), 2.208 (13.26), 2.327 (0.51), 2.668 (0.50), 3.306 (15.25), 3.876 (16.00), 4.461 (4.18), 4.475 (4.27), 4.641 (0.59), 4.657 (1.16), 4.672 (1.14), 4.688 (0.58), 5.728 (1.18), 5.742 (2.53), 5.757 (1.14), 6.942 (2.40), 6.955 (2.46), 7.408 (2.20), 7.423 (2.20), 7.691 (2.61), 7.718 (2.55), 7.965 (2.82), 7.979 (2.68), 9.634 (3.42).

Example 139

5-fluoro-4-{3-[(1S)-1-hydroxyethyl]-4-methyl-5-oxo-4,5-dihydro-1H-1,2,4-triazol-1-yl}-N-(2-methoxy-4-methylpyridin-3-yl)-2-[(2S)-pentan-2-yloxy]benzamide

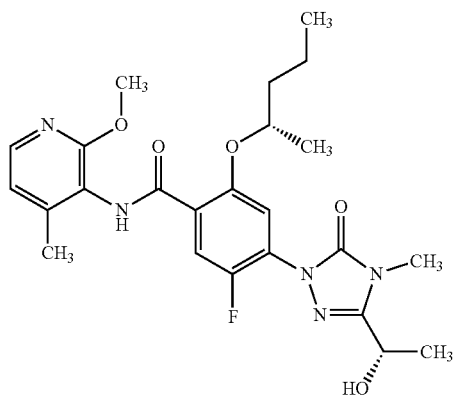 [SMILES: CCC[C@H](C)Oc1cc(-n2nc([C@H](C)O)n(C)c2=O)c(F)cc1C(=O)Nc1c(C)ccnc1OC]

Synthesized analogously to Example 92 from Intermediate 77 and Intermediate 9.

LC-MS (Method A): R$_t$=1.18 min; MS (ESIpos): m/z=488 [M+H]$^+$.

$^1$H-NMR (400 MHz, DMSO-d6) δ [ppm]: 0.875 (3.28), 0.893 (7.60), 0.912 (3.66), 1.321 (6.50), 1.336 (6.60), 1.372 (0.50), 1.397 (0.68), 1.415 (0.79), 1.430 (0.84), 1.453 (7.23), 1.470 (7.04), 1.596 (0.46), 1.616 (0.51), 1.630 (0.72), 1.640 (0.48), 1.655 (0.54), 1.744 (0.54), 1.758 (0.50), 1.770 (0.53), 1.777 (0.45), 2.207 (12.32), 2.326 (0.55), 2.522 (1.74), 2.668 (0.57), 3.877 (16.00), 4.641 (0.54), 4.657 (1.03), 4.672 (1.02), 4.687 (0.51), 4.765 (1.07), 4.780 (1.55), 4.796 (1.05), 5.806 (2.38), 5.820 (2.32), 6.943 (2.22), 6.956 (2.29), 7.405 (2.00), 7.421 (1.98), 7.693 (2.49), 7.720 (2.41), 7.966 (2.72), 7.979 (2.61), 9.632 (3.13).

Example 140

5-fluoro-4-[3-(2-hydroxypropan-2-yl)-4-methyl-5-oxo-4,5-dihydro-1H-1,2,4-triazol-1-yl]-N-(2-methoxy-4-methylpyridin-3-yl)-2-[(2S)-pentan-2-yloxy]benzamide

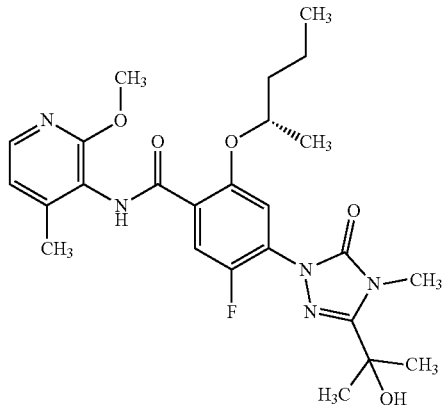 [SMILES: CCC[C@H](C)Oc1cc(-n2nc(C(C)(C)O)n(C)c2=O)c(F)cc1C(=O)Nc1c(C)ccnc1OC]

4-Bromo-5-fluoro-N-(2-methoxy-4-methylpyridin-3-yl)-2-[(2S)-pentan-2-yloxy]benzamide (Intermediate 77, 200 mg, 470 µmol), 5-(2-hydroxypropan-2-yl)-4-methyl-2,4-dihydro-3H-1,2,4-triazol-3-one (Intermediate 7, 67 mg, 427 µmol), tris(dibenzylideneacetone)dipalladium(0) (39 mg, 43 µmol), 4,5-bis(diphenylphosphino)-9,9-dimethylxanthene (74 mg, 128 µmol), and cesium carbonate (278 mg, 855 µmol) were loaded into a microwave vial. The vial was purged with argon, dioxane (2 mL, degassed) was added, and the vial was sealed. The mixture was stirred for 17 h at 110° C. overnight. The resulting suspension was filtered over Celite, washed with ethyl acetate and concentrated. Preparative chromatography (water+0.1% formic acid/acetonitrile gradient) yielded the desired product (35.0 mg, 15% yield).

LC-MS (Method A): R$_t$=1.24 min; MS (ESIpos): m/z=502 [M+H]$^+$.

$^1$H-NMR (400 MHz, DMSO-d6) δ [ppm]: 0.878 (2.20), 0.896 (4.86), 0.915 (2.44), 1.324 (4.31), 1.339 (4.36), 1.401 (0.51), 1.416 (0.62), 1.433 (0.61), 1.454 (0.54), 1.473 (0.49), 1.522 (16.00), 1.618 (0.42), 1.632 (0.54), 1.645 (0.42), 1.747 (0.43), 1.772 (0.44), 2.207 (8.28), 3.449 (8.87), 3.878 (9.62), 4.660 (0.77), 4.675 (0.75), 5.734 (3.35), 6.944 (1.52), 6.956 (1.55), 7.414 (1.37), 7.429 (1.37), 7.694 (1.55), 7.721 (1.52), 7.967 (1.70), 7.979 (1.65), 9.630 (2.22).

Example 141

5-fluoro-N-(2-fluoro-6-methylphenyl)-4-[3-(hydroxymethyl)-4-methyl-5-oxo-4,5-dihydro-1H-1,2,4-triazol-1-yl]-2-[(2S)-pentan-2-yloxy]benzamide

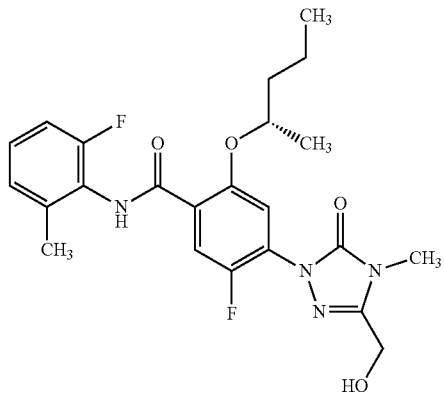 [SMILES: CCC[C@H](C)Oc1cc(-n2nc(CO)n(C)c2=O)c(F)cc1C(=O)Nc1c(C)cccc1F]

319

Synthesized analogously to Example 92 from Intermediate 78 and Intermediate 8.

LC-MS (Method A): $R_t$=1.21 min; MS (ESIpos): m/z=461 [M+H]$^+$.

$^1$H-NMR (400 MHz, DMSO-d6) δ [ppm]: 0.860 (3.66), 0.878 (8.27), 0.896 (4.12), 1.293 (7.16), 1.308 (7.30), 1.329 (0.45), 1.346 (0.60), 1.354 (0.53), 1.363 (0.62), 1.372 (0.71), 1.379 (0.59), 1.389 (0.69), 1.398 (0.55), 1.405 (0.62), 1.411 (0.61), 1.422 (0.63), 1.436 (0.66), 1.455 (0.64), 1.557 (0.56), 1.577 (0.62), 1.591 (0.82), 1.602 (0.60), 1.615 (0.59), 1.715 (0.59), 1.730 (0.63), 1.740 (0.62), 2.084 (1.38), 2.276 (13.44), 2.327 (0.41), 3.305 (16.00), 4.459 (4.21), 4.473 (4.23), 4.575 (0.62), 4.590 (1.18), 4.605 (1.16), 4.621 (0.59), 5.725 (1.16), 5.739 (2.58), 5.754 (1.09), 7.106 (0.86), 7.127 (3.02), 7.144 (2.49), 7.229 (0.90), 7.244 (1.07), 7.249 (1.34), 7.264 (1.06), 7.282 (0.50), 7.363 (2.31), 7.378 (2.28), 7.607 (2.66), 7.633 (2.62), 9.656 (3.60).

Example 142

5-fluoro-N-(2-fluoro-6-methylphenyl)-4-{3-[(1S)-1-hydroxyethyl]-4-methyl-5-oxo-4,5-dihydro-1H-1,2,4-triazol-1-yl}-2-[(2S)-pentan-2-yloxy]benzamide

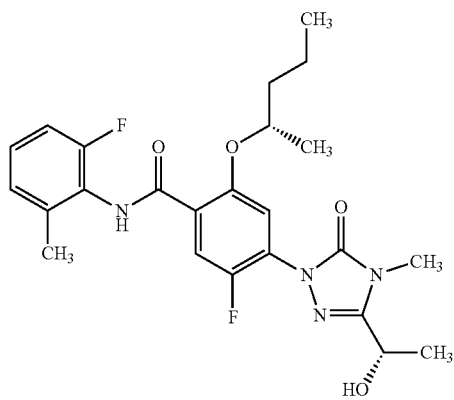 [SMILES: CCC[C@H](C)Oc1cc(-n2nc([C@H](C)O)n(C)c2=O)c(F)cc1C(=O)Nc1c(C)cccc1F]

Synthesized analogously to Example 92 from Intermediate 78 and Intermediate 9.

LC-MS (Method A): $R_t$=1.27 min; MS (ESIpos): m/z=475 [M+H]$^+$.

$^1$H-NMR (400 MHz, DMSO-d6) δ [ppm]: 0.863 (4.32), 0.881 (9.61), 0.899 (4.83), 1.297 (8.50), 1.312 (8.60), 1.332 (0.58), 1.350 (0.75), 1.375 (0.91), 1.392 (1.00), 1.411 (0.98), 1.453 (9.31), 1.469 (9.07), 1.544 (0.40), 1.558 (0.68), 1.578 (0.79), 1.591 (1.01), 1.602 (0.76), 1.616 (0.74), 1.647 (0.67), 1.703 (0.49), 1.717 (0.75), 1.733 (0.79), 1.744 (0.78), 1.777 (0.44), 2.084 (0.91), 2.276 (16.00), 2.327 (0.48), 2.670 (0.43), 4.575 (0.76), 4.590 (1.44), 4.605 (1.44), 4.620 (0.75), 4.764 (1.45), 4.779 (2.12), 4.795 (1.42), 5.803 (3.14), 5.818 (3.06), 7.108 (1.00), 7.127 (3.69), 7.145 (3.08), 7.230 (1.07), 7.245 (1.30), 7.250 (1.63), 7.264 (1.32), 7.284 (0.62), 7.360 (2.96), 7.375 (2.92), 7.393 (0.65), 7.608 (3.10), 7.634 (3.03), 9.647 (4.40).

Example 143

5-fluoro-N-(2-fluoro-6-methylphenyl)-4-[3-(2-hydroxypropan-2-yl)-4-methyl-5-oxo-4,5-dihydro-1H-1,2,4-triazol-1-yl]-2-[(2S)-pentan-2-yloxy]benzamide

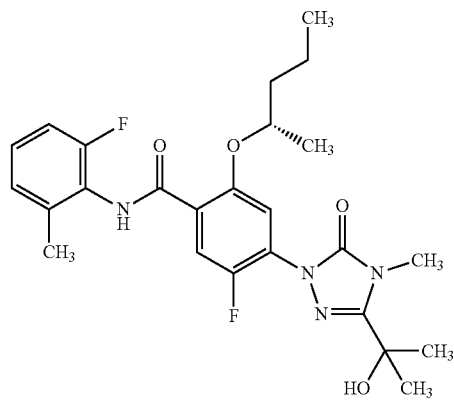 [SMILES: CCC[C@H](C)Oc1cc(-n2nc(C(C)(C)O)n(C)c2=O)c(F)cc1C(=O)Nc1c(C)cccc1F]

Synthesized analogously to Example 92 from Intermediate 78 and Intermediate 7.

LC-MS (Method A): $R_t$=1.34 min; MS (ESIneg): m/z=487 [M−H]$^-$.

$^1$H-NMR (400 MHz, DMSO-d6) δ [ppm]: 0.866 (2.19), 0.884 (4.82), 0.903 (2.44), 1.300 (4.32), 1.315 (4.34), 1.353 (0.43), 1.360 (0.42), 1.378 (0.51), 1.395 (0.56), 1.411 (0.57), 1.436 (0.48), 1.455 (0.48), 1.520 (16.00), 1.559 (0.43), 1.579 (0.45), 1.593 (0.57), 1.603 (0.42), 1.647 (0.42), 1.720 (0.42), 1.736 (0.43), 1.745 (0.43), 2.275 (8.06), 3.447 (8.88), 4.593 (0.76), 4.608 (0.75), 5.730 (3.40), 7.108 (0.55), 7.128 (1.93), 7.146 (1.62), 7.231 (0.57), 7.250 (0.85), 7.264 (0.71), 7.367 (1.65), 7.383 (1.80), 7.608 (1.55), 7.634 (1.51), 9.640 (2.25).

Example 144

5-fluoro-4-[3-(hydroxymethyl)-4-methyl-5-oxo-4,5-dihydro-1H-1,2,4-triazol-1-yl]-N-(pentan-3-yl)-2-[(2S)-pentan-2-yloxy]benzamide

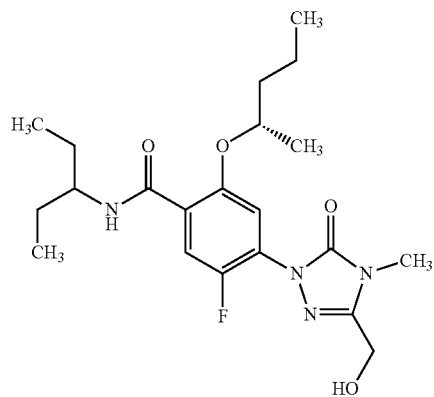 [SMILES: CCC[C@H](C)Oc1cc(-n2nc(CO)n(C)c2=O)c(F)cc1C(=O)NC(CC)CC]

Synthesized analogously to Example 92 from Intermediate 79 and Intermediate 8.

LC-MS (Method A): $R_t$=1.22 min; MS (ESIpos): m/z=423 [M+H]$^+$.

$^1$H-NMR (400 MHz, DMSO-d6) δ [ppm]: 0.867 (7.77), 0.885 (16.00), 0.903 (8.54), 1.254 (6.10), 1.269 (6.10), 1.391 (1.79), 1.405 (2.17), 1.422 (2.18), 1.439 (1.52), 1.524 (1.20), 1.540 (1.79), 1.557 (2.08), 1.574 (1.86), 1.590 (1.60), 1.612 (1.00), 1.633 (0.89), 1.648 (0.79), 1.658 (0.77), 2.084 (0.91), 2.328 (0.59), 2.669 (0.58), 3.291 (12.37), 3.779 (0.87), 3.799 (0.87), 4.445 (3.36), 4.457 (3.37), 4.569 (0.62), 4.583 (1.13), 4.597 (1.12), 4.612 (0.61), 5.731 (1.69), 7.303 (2.01), 7.318 (1.97), 7.584 (2.05), 7.611 (2.04), 7.901 (1.46), 7.923 (1.42).

Example 145

5-fluoro-4-[3-(2-hydroxypropan-2-yl)-4-methyl-5-oxo-4,5-dihydro-1H-1,2,4-triazol-1-yl]-N-(pentan-3-yl)-2-[(2S)-pentan-2-yloxy]benzamide

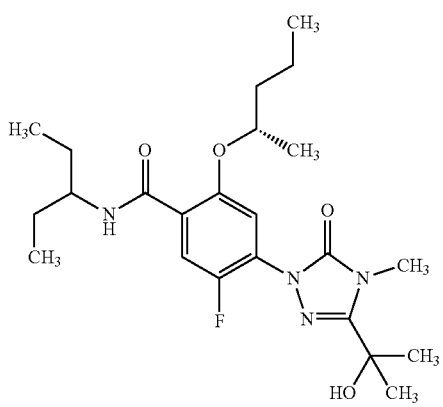 [SMILES: CCC[C@H](C)Oc1cc(-n2nc(C(C)(C)O)n(C)c2=O)c(F)cc1C(=O)NC(CC)CC]

Synthesized analogously to Example 92 from Intermediate 79 and Intermediate 7.

LC-MS (Method A): $R_t$=1.35 min; MS (ESIpos): m/z=451 [M+H]$^+$.

$^1$H-NMR (400 MHz, DMSO-d6) δ [ppm]: 0.866 (3.28), 0.875 (3.04), 0.885 (7.22), 0.893 (5.83), 0.903 (3.83), 0.911 (2.71), 1.261 (4.33), 1.276 (4.33), 1.358 (0.43), 1.368 (0.70), 1.375 (0.63), 1.386 (0.93), 1.394 (0.77), 1.403 (1.03), 1.409 (1.03), 1.423 (1.07), 1.428 (1.04), 1.442 (0.79), 1.507 (16.00), 1.527 (0.83), 1.541 (0.97), 1.546 (0.89), 1.559 (1.07), 1.576 (0.93), 1.593 (0.80), 1.600 (0.54), 1.614 (0.50), 1.640 (0.47), 1.649 (0.41), 1.655 (0.40), 1.665 (0.45), 2.084 (2.21), 3.434 (9.28), 3.783 (0.46), 3.804 (0.46), 4.588 (0.65), 4.603 (0.65), 5.718 (3.35), 7.310 (1.36), 7.325 (1.34), 7.592 (1.62), 7.619 (1.58), 7.896 (0.88), 7.918 (0.86).

Example 146

N-(2,6-difluorophenyl)-4-(3-ethyl-4-methyl-5-oxo-4,5-dihydro-1H-1,2,4-triazol-1-yl)-2-{[(2S)-1,1,1-trifluoropropan-2-yl]oxy}benzamide

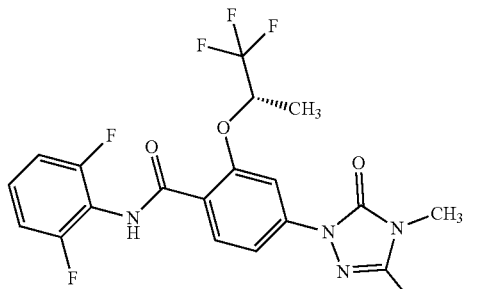

Synthesized analogously to Example 92 from Intermediate 75 and 3-ethyl-4-methyl-1H-1,2,4-triazol-5(4H)-one.

LC-MS (Method A): $R_t$=1.27 min; MS (ESIpos): m/z=471 [M+H]$^+$.

$^1$H-NMR (400 MHz, DMSO-d6) δ [ppm]: 1.237 (4.30), 1.256 (9.64), 1.275 (4.45), 1.496 (3.45), 1.512 (3.43), 2.085 (1.81), 2.518 (1.43), 2.523 (0.98), 2.652 (1.28), 2.671 (4.17), 2.689 (3.89), 2.708 (1.12), 3.231 (16.00), 5.260 (0.57), 5.276 (0.74), 5.292 (0.55), 7.183 (1.03), 7.203 (2.12), 7.223 (1.29), 7.375 (0.58), 7.395 (0.90), 7.412 (0.44), 7.733 (4.45), 7.893 (1.89), 9.684 (3.29).

Example 147

5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(tetrahydrofuran-3-yl)benzamide, Mixture of Stereoisomers

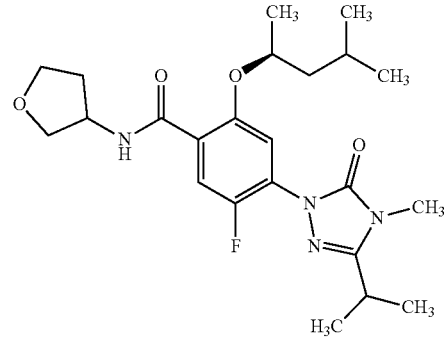 [SMILES: CC(C)C[C@H](C)Oc1cc(-n2nc(C(C)C)n(C)c2=O)c(F)cc1C(=O)NC1CCOC1]

5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzoic acid (Intermediate 82, 150 mg, 395 μmol) and tetrahydrofuran-3-amine (44.0 mg, 505 μmol) were dissolved in dichloromethane (20 mL). Triethylamine (167 μL, 1.2 mmol) was added, followed by HATU (190 mg, 499 μmol). The mixture was stirred at room temperature overnight. The solvent was removed and the mixture was purified using preparative TLC to yield 66 mg of desired product (37% yield).

Example 148

5-fluoro-N-[(2R)-1-hydroxypropan-2-yl]-4-[4-methyl-5-oxo-3-(propan-2-yl)-4,5-dihydro-1H-1,2,4-triazol-1-yl]-2-{[(2S)-4-methylpentan-2-yl]oxy}benzamide

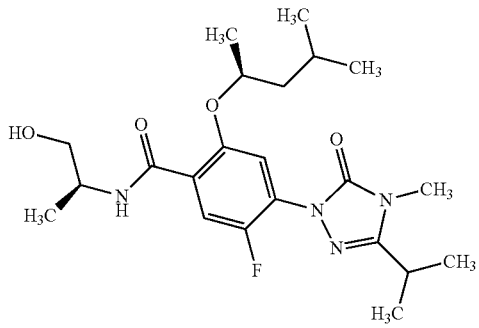 [SMILES: CC(C)C[C@H](C)Oc1cc(-n2nc(C(C)C)n(C)c2=O)c(F)cc1C(=O)N[C@@H](C)CO]

Synthesized analogously to Example 147 from Intermediate 82 and (2R)-2-aminopropan-1-ol.

Example 149

5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(1H-pyrazol-3-yl)benzamide

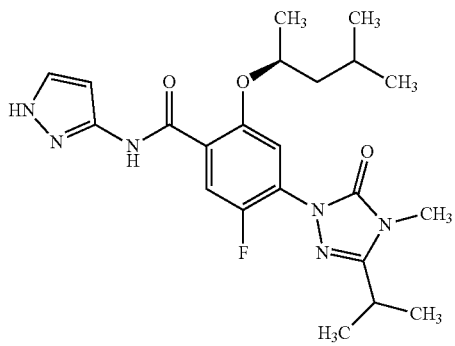 [SMILES: CC(C)C[C@H](C)Oc1cc(-n2nc(C(C)C)n(C)c2=O)c(F)cc1C(=O)Nc1cc[nH]n1]

Synthesized analogously to Example 147 from Intermediate 82 and 1H-pyrazol-3-amine.

Example 150

5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyridin-2-yl)benzamide

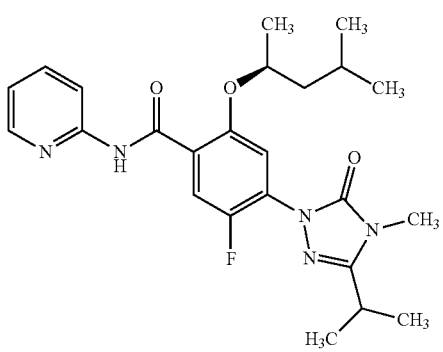 [SMILES: CC(C)C[C@H](C)Oc1cc(-n2nc(C(C)C)n(C)c2=O)c(F)cc1C(=O)Nc1ccccn1]

Synthesized analogously to Example 147 from Intermediate 82 and pyridin-2-amine.

Example 151

5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyridin-4-yl)benzamide

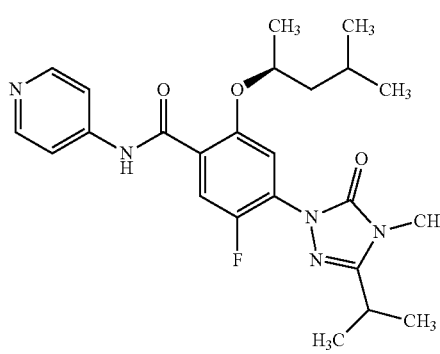

Synthesized analogously to Example 147 from Intermediate 82 and pyridin-4-amine.

Example 152

5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(1-methylpiperidin-4-yl)benzamide

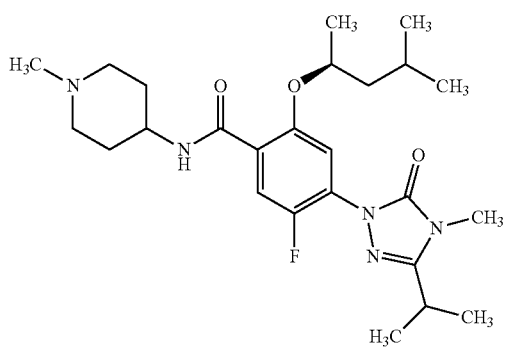

Synthesized analogously to Example 147 from Intermediate 82 and 1-methylpiperidin-4-amine.

Example 153

5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(tetrahydro-2H-pyran-4-yl)benzamide

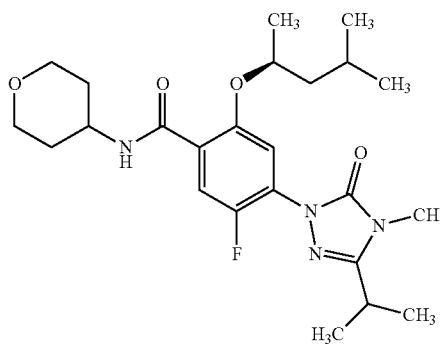

Synthesized analogously to Example 147 from Intermediate 82 and tetrahydro-2H-pyran-4-amine.

Example 154

5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyrimidin-4-yl)benzamide

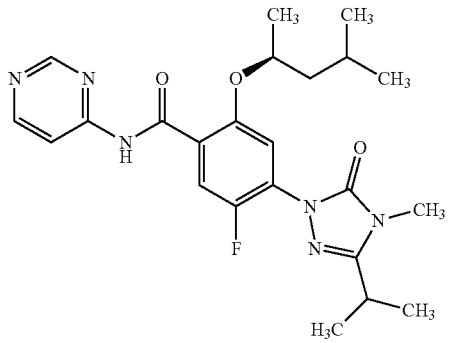 [SMILES: CC(C)C[C@H](C)Oc1cc(-n2nc(C(C)C)n(C)c2=O)c(F)cc1C(=O)Nc1ccncn1]

Synthesized analogously to Example 147 from Intermediate 82 and pyrimidin-4-amine.

Example 155

5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(1,3-oxazol-2-yl)benzamide

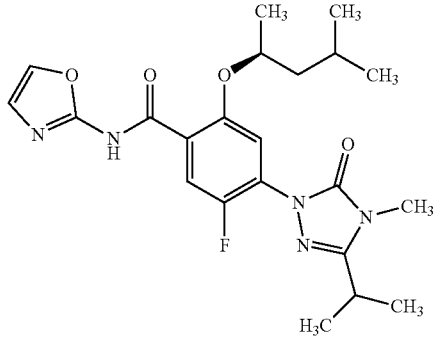 [SMILES: CC(C)C[C@H](C)Oc1cc(-n2nc(C(C)C)n(C)c2=O)c(F)cc1C(=O)Nc1ncco1]

Synthesized analogously to Example 147 from Intermediate 82 and 1,3-oxazol-2-amine.

Example 156

5-fluoro-N-[(2R)-1-hydroxybutan-2-yl]-4-[4-methyl-5-oxo-3-(propan-2-yl)-4,5-dihydro-1H-1,2,4-triazol-1-yl]-2-{[(2S)-4-methylpentan-2-yl]oxy}benzamide

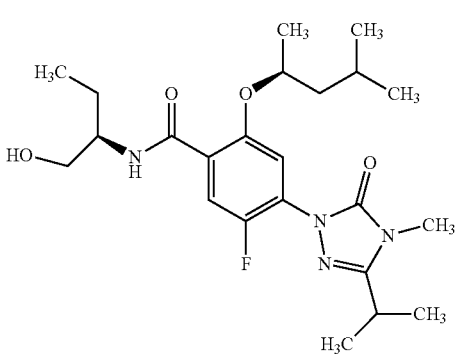 [SMILES: CC[C@H](CO)NC(=O)c1cc(F)c(-n2nc(C(C)C)n(C)c2=O)cc1O[C@@H](C)CC(C)C]

Synthesized analogously to Example 147 from Intermediate 82 and (2R)-2-aminobutan-1-ol.

Example 157

N-cyclopentyl-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide

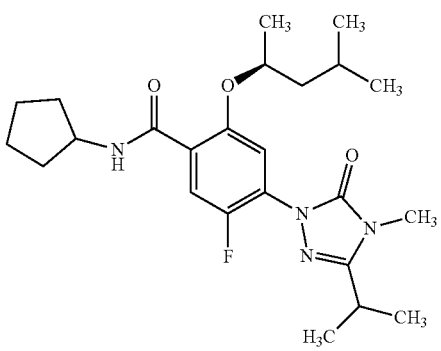 [SMILES: CC(C)C[C@H](C)Oc1cc(-n2nc(C(C)C)n(C)c2=O)c(F)cc1C(=O)NC1CCCC1]

Synthesized analogously to Example 147 from Intermediate 82 and cyclopentanamine.

MS (ESIpos): m/z=446 [M+H]$^+$.

Example 158

N-cyclohexyl-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide

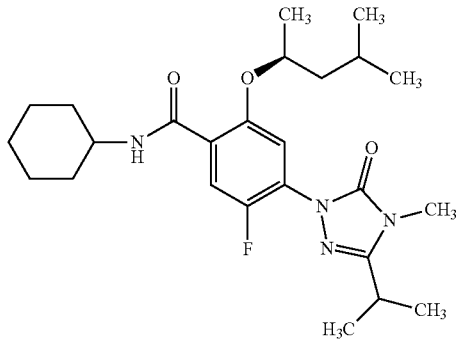 [SMILES: CC(C)C[C@H](C)Oc1cc(-n2nc(C(C)C)n(C)c2=O)c(F)cc1C(=O)NC1CCCCC1]

Synthesized analogously to Example 147 from Intermediate 82 and cyclohexanamine.
MS (ESIpos): m/z=460 [M+H]⁺.

Example 159

5-fluoro-N-(2-hydroxypropyl)-4-[4-methyl-5-oxo-3-(propan-2-yl)-4,5-dihydro-1H-1,2,4-triazol-1-yl]-2-{[(2S)-4-methylpentan-2-yl]oxy}benzamide, Mixture of Stereoisomers

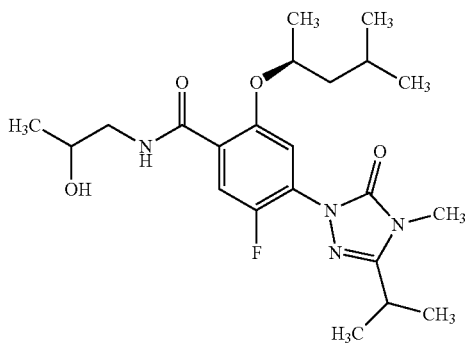 [SMILES: CC(C)C[C@H](C)Oc1cc(-n2nc(C(C)C)n(C)c2=O)c(F)cc1C(=O)NCC(C)O]

Synthesized analogously to Example 147 from Intermediate 82 and 1-aminopropan-2-ol

Example 160

5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-phenylbenzamide

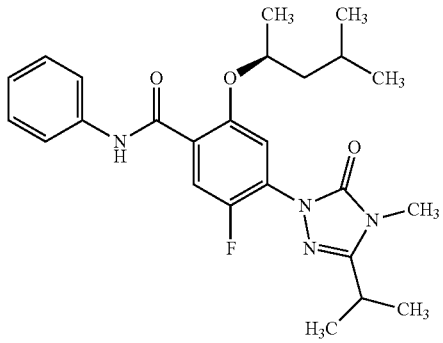 [SMILES: CC(C)C[C@H](C)Oc1cc(-n2nc(C(C)C)n(C)c2=O)c(F)cc1C(=O)Nc1ccccc1]

Synthesized analogously to Example 147 from Intermediate 82 and aniline.
MS (ESIneg): m/z=453 [M−H]⁻.

Example 161

5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyrimidin-2-yl)benzamide

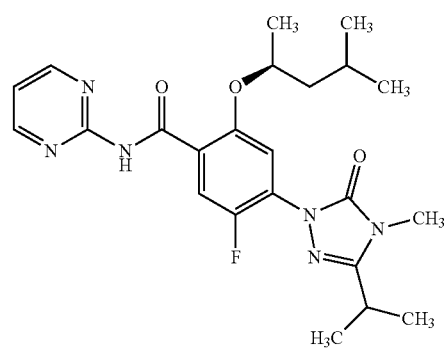 [SMILES: CC(C)C[C@H](C)Oc1cc(-n2nc(C(C)C)n(C)c2=O)c(F)cc1C(=O)Nc1ncccn1]

5-fluoro-4-[4-methyl-5-oxo-3-(propan-2-yl)-4,5-dihydro-1H-1,2,4-triazol-1-yl]-2-{[(2S)-4-methyl-pentan-2-yl]oxy}benzoic acid (Intermediate 82, 150 mg, 395 µmol) was dissolved in dichloromethane (5 mL). Oxalyl chloride (140 µl, 1.6 mmol) was added, followed by DMF (30 µl, 390 µmol). The mixture was stirred at room temperature for 3 h. The mixture was concentrated. The resulting residue was suspended in dichloromethane (5 mL), pyrimidin-2-amine (60.0 mg, 631 µmol) was added and the mixture was stirred overnight. The solvent was removed and the mixture was purified by column chromatography to yield the desired product (15 mg, 8% yield).

Example 162

N-[(2R)-1-aminopropan-2-yl]-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide

Step A 5-fluoro-4-[4-methyl-5-oxo-3-(propan-2-yl)-4,5-dihydro-1H-1,2,4-triazol-1-yl]-2-{[(2S)-4-methyl-pentan-2-yl]oxy}-N-[(2R)-1-oxopropan-2-yl]benzamide

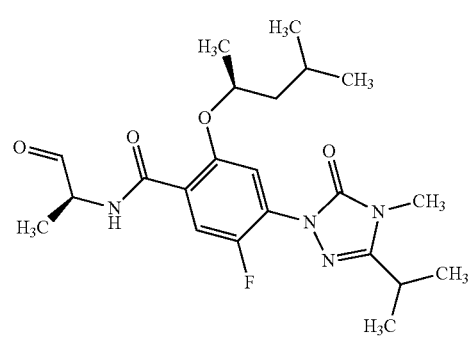 [SMILES: CC(C)C[C@H](C)Oc1cc(-n2nc(C(C)C)n(C)c2=O)c(F)cc1C(=O)N[C@@H](C)C=O]

5-fluoro-N-[(2R)-1-hydroxypropan-2-yl]-4-[4-methyl-5-oxo-3-(propan-2-yl)-4,5-dihydro-1H-1,2,4-triazol-1-yl]-2-{[(2S)-4-methylpentan-2-yl]oxy}benzamide (Example 148, 120 mg, 275 µmol) was dissolved in DCM. Dess-Martin periodinane (1,1,1-Triacetoxy-1,1-dihydro-1,2-benziodoxol-3(1H)-one, 233 mg, 550 µmol) was added and the mixture was stirred at room temperature for 4 h. The mixture was filtered and the solution was concentrated to yield the desired intermediate which was directly used in the next step.

Step B

N-[(2R)-1-aminopropan-2-yl]-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide

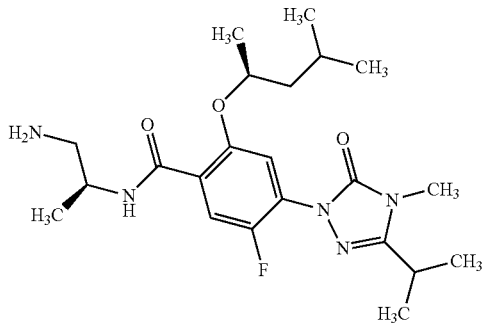 [SMILES: CC(C)C[C@H](C)Oc1cc(-n2nc(C(C)C)n(C)c2=O)c(F)cc1C(=O)N[C@@H](C)CN]

5-fluoro-4-[4-methyl-5-oxo-3-(propan-2-yl)-4,5-dihydro-1H-1,2,4-triazol-1-yl]-2-{[(2S)-4-methyl-pentan-2-yl]oxy}-N-[(2R)-1-oxopropan-2-yl]benzamide (Intermediate from above, 75.0 mg, 173 µmol) was dissolved in dry methanol (10 mL). Zinc chloride was added (1M solution in ether, 0.32 mL, 0.32 mmol) followed by ammonium formate (110 mg, 1.6 mmol). The mixture was stirred at room temperature for 1 h. Sodium cyanoborohydride (20 mg, 0.32 mmol) was added and the mixture was stirred at room temperature for 2 h. The mixture was concentrated and purified by prepH-PLC to yield the desired product (10 mg, 14% yield).

MS (ESIpos): m/z=436 [M+H]$^+$.

Example 163

N-[(2R)-1-aminobutan-2-yl]-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide

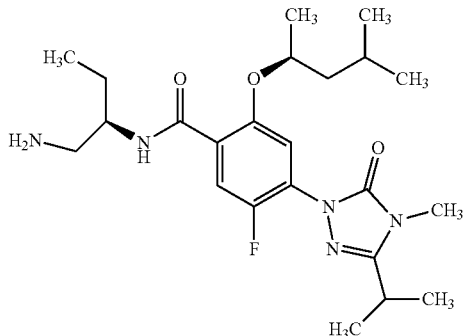

Synthesized analogously to Example 162 from Example 156 in two steps.

Example 164

5-fluoro-4-[4-methyl-5-oxo-3-(propan-2-yl)-4,5-dihydro-1H-1,2,4-triazol-1-yl]-2-{[(2S)-4-methyl-pentan-2-yl]oxy}-N-(piperidin-4-yl)benzamide, salt with hydrochloric acid Step A tert-butyl 4-[(5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzoyl)amino]piperidine-1-carboxylate

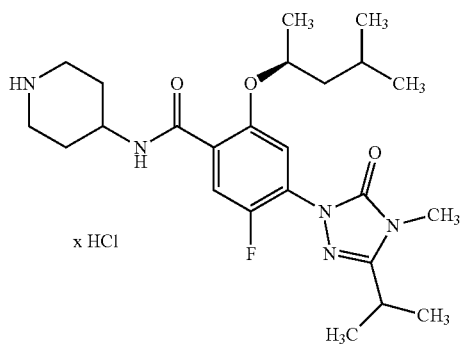 [SMILES: CC(C)C[C@H](C)Oc1cc(-n2nc(C(C)C)n(C)c2=O)c(F)cc1C(=O)NC1CCNCC1]

Synthesized analogously to Example 147 from Intermediate 82 and tert-butyl 4-aminopiperidine-1-carboxylate.

Step B 5-fluoro-4-[4-methyl-5-oxo-3-(propan-2-yl)-4,5-dihydro-1H-1,2,4-triazol-1-yl]-2-{[(2S)-4-methyl-pentan-2-yl]oxy}-N-(piperidin-4-yl)benzamide, salt with hydrochloric acid tert-butyl 4-[(5-fluoro-4-[4-methyl-5-oxo-3-(propan-2-yl)-4,5-dihydro-1H-1,2,4-triazol-1-yl]-2-{[(2S)-4-methyl-pentan-2-yl]oxy}benzoyl)amino]piperidine-1-carboxylate (136 mg, 242 µmol) was dissolved in methanol and hydrogen chloride gas was bubbled through the reaction for 20 min. The solvent was evaporated to yield the desired product (98 mg, 82% yield).

Example 165

2-(1-cyclohexylethoxy)-4-(3-ethyl-4-methyl-5-oxo-4,5-dihydro-1H-1,2,4-triazol-1-yl)-5-fluoro-N-(pentan-3-yl)benzamide, Mixture of Stereoisomers

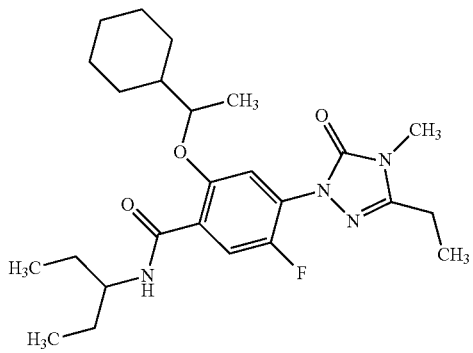 [SMILES: CCc1nn(-c2cc(OC(C)C3CCCCC3)c(C(=O)NC(CC)CC)cc2F)c(=O)n1C]

4-(3-ethyl-4-methyl-5-oxo-4,5-dihydro-1H-1,2,4-triazol-1-yl)-2,5-difluoro-N-(pentan-3-yl)benzamide (Intermediate 87, 350 mg, 993 µmol) and 1-cyclopentylethanol (227 mg, 1.99 mmol) were dissolved in DMF (20 ml). sodium hydride (95.3 mg, 50% in mineral oil, 1.99 mmol) was added carefully. The mixture was stirred at 80° C. overnight. The mixture was slowly poured into water (100 mL), extracted with ethyl acetate (3×20 ml) and the combined organic fractions were dried and concentrated. The product was purified using column chromatography (100 mg, 21% yield).

Example 166

2-[(1-cyclopropylpropan-2-yl)oxy]-4-(3-ethyl-4-methyl-5-oxo-4,5-dihydro-1H-1,2,4-triazol-1-yl)-5-fluoro-N-(pentan-3-yl)benzamide, Mixture of Stereoisomers

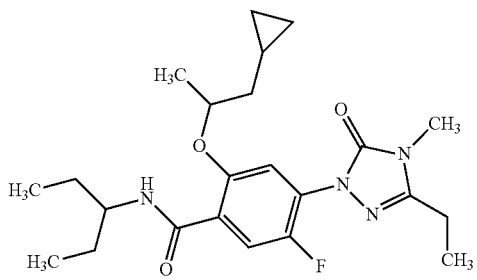 [SMILES: CCc1nn(-c2cc(OC(C)CC3CC3)c(C(=O)NC(CC)CC)cc2F)c(=O)n1C]

Synthesized analogous to Example 165 from Intermediate 87 and 1-cyclopropylpropan-2-ol.

Example 167

2-(1-cyclopentylethoxy)-4-(3-ethyl-4-methyl-5-oxo-4,5-dihydro-1H-1,2,4-triazol-1-yl)-5-fluoro-N-(pentan-3-yl)benzamide, Mixture of Stereoisomers

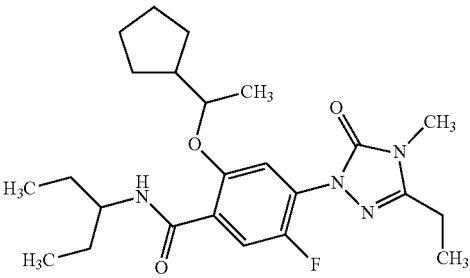 [SMILES: CCc1nn(-c2cc(OC(C)C3CCCC3)c(C(=O)NC(CC)CC)cc2F)c(=O)n1C]

Synthesized analogous to Example 165 from Intermediate 87 and 1-cyclopentylethanol.

Example 168

2-(1-cyclopropylethoxy)-4-(3-ethyl-4-methyl-5-oxo-4,5-dihydro-1H-1,2,4-triazol-1-yl)-5-fluoro-N-(pentan-3-yl)benzamide, Mixture of Stereoisomers

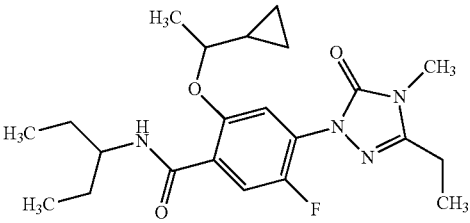 [SMILES: CCc1nn(-c2cc(OC(C)C3CC3)c(C(=O)NC(CC)CC)cc2F)c(=O)n1C]

Synthesized analogous to Example 165 from Intermediate 87 and 1-cyclopropylethanol.

Example 169

4-(3-ethyl-4-methyl-5-oxo-4,5-dihydro-1H-1,2,4-triazol-1-yl)-5-fluoro-N-(pentan-3-yl)-2-(1-phenylethoxy)benzamide, Mixture of Stereoisomers

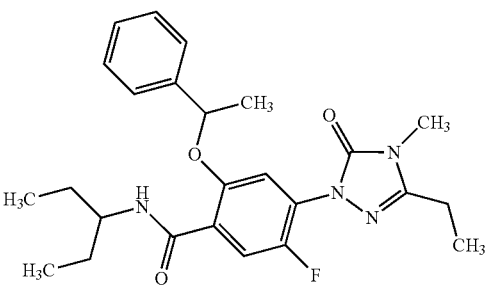 [SMILES: CCc1nn(-c2cc(OC(C)c3ccccc3)c(C(=O)NC(CC)CC)cc2F)c(=O)n1C]

Synthesized analogous to Example 165 from Intermediate 87 and 1-phenylethanol.

Example 170

4-(3-ethyl-4-methyl-5-oxo-4,5-dihydro-1H-1,2,4-triazol-1-yl)-2-[(3-ethylpentan-2-yl)oxy]-5-fluoro-N-(pentan-3-yl)benzamide, Mixture of Stereoisomers

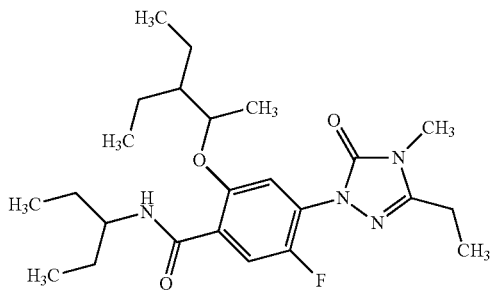 [SMILES: CCc1nn(-c2cc(OC(C)C(CC)CC)c(C(=O)NC(CC)CC)cc2F)c(=O)n1C]

Synthesized analogous to Example 165 from Intermediate 87 and 3-ethylpentan-2-ol.

Example 171

4-(3-ethyl-4-methyl-5-oxo-4,5-dihydro-1H-1,2,4-triazol-1-yl)-5-fluoro-2-[(4-methylpent-3-en-2-yl)oxy]-N-(pentan-3-yl)benzamide, Mixture of Stereoisomers

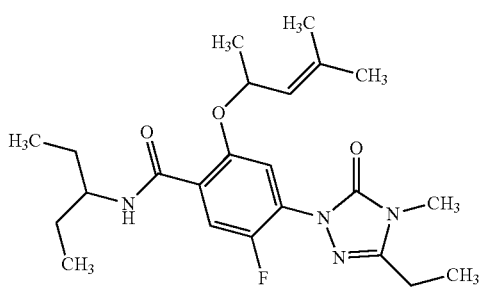 [SMILES: CCc1nn(-c2cc(OC(C)C=C(C)C)c(C(=O)NC(CC)CC)cc2F)c(=O)n1C]

Synthesized analogous to Example 165 from Intermediate 87 and 4-methylpent-3-en-2-ol.

Example 172

4-(3-ethyl-4-methyl-5-oxo-4,5-dihydro-1H-1,2,4-triazol-1-yl)-5-fluoro-N-(pentan-3-yl)-2-(pent-4-en-2-yloxy)benzamide, Mixture of Stereoisomers

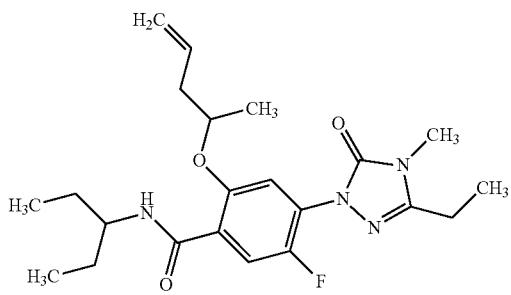 [SMILES: C=CCC(C)Oc1cc(-n2nc(CC)n(C)c2=O)c(F)cc1C(=O)NC(CC)CC]

Synthesized analogous to Example 165 from Intermediate 87 and pent-4-en-2-ol.

Example 173

2-(1-cyclobutylethoxy)-4-(3-ethyl-4-methyl-5-oxo-4,5-dihydro-1H-1,2,4-triazol-1-yl)-5-fluoro-N-(pentan-3-yl)benzamide, Mixture of Stereoisomers

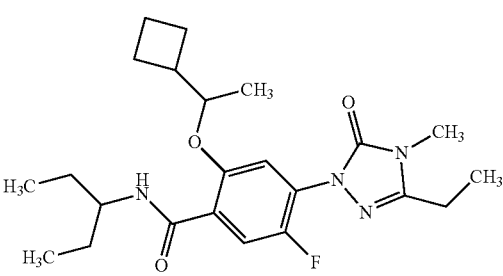 [SMILES: CCc1nn(-c2cc(OC(C)C3CCC3)c(C(=O)NC(CC)CC)cc2F)c(=O)n1C]

Synthesized analogous to Example 165 from Intermediate 87 and 1-cyclobutylethanol.

Example 174

5-fluoro-4-[3-(1-hydroxyethyl)-4-methyl-5-oxo-4,5-dihydro-1H-1,2,4-triazol-1-yl]-N-(pentan-3-yl)-2-[(2S)-pentan-2-yloxy]benzamide, Mixture of Stereoisomers Step A 4-{3-[1-(1-ethoxyethoxy)ethyl]-4-methyl-5-oxo-4,5-dihydro-1H-1,2,4-triazol-1-yl}-5-fluoro-N-(pentan-3-yl)-2-[(2S)-pentan-2-yloxy]benzamide, Mixture of Stereoisomers

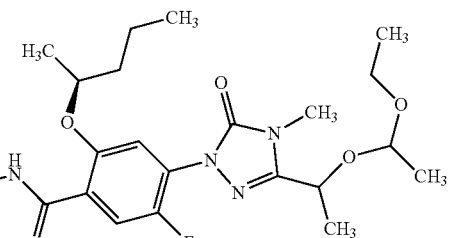

Synthesized analogously to Example 165 from Intermediate 85 and (2S)-pentan-2-ol.

Step B 5-fluoro-4-[3-(1-hydroxyethyl)-4-methyl-5-oxo-4,5-dihydro-1H-1,2,4-triazol-1-yl]-N-(pentan-3-yl)-2-[(2S)-pentan-2-yloxy]benzamide, Mixture of Stereoisomers

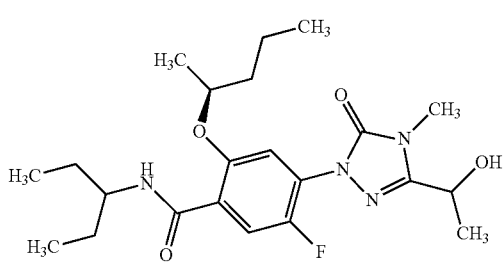 [SMILES: CCC[C@H](C)Oc1cc(-n2nc(C(C)O)n(C)c2=O)c(F)cc1C(=O)NC(CC)CC]

4-{3-[1-(1-ethoxyethoxy)ethyl]-4-methyl-5-oxo-4,5-dihydro-1H-1,2,4-triazol-1-yl}-5-fluoro-N-(pentan-3-yl)-2-[(2S)-pentan-2-yloxy]benzamide (Intermediate from STEP A above, 50.0 mg, 98.3 µmol) was dissolved in methanol (5 mL). 5 drops of hydrochloric acid (0.1N in water) were added. The mixture was stirred at room temperature until TLC showed complete conversion. Solid sodium carbonate was added and the mixture was concentrated. The product was purified using column chromatography to yield the desired product.

Example 175

5-fluoro-4-[3-(1-hydroxyethyl)-4-methyl-5-oxo-4,5-dihydro-1H-1,2,4-triazol-1-yl]-N-(2-methylphenyl)-2-(pentan-2-yloxy)benzamide, Mixture of Stereoisomers

Step A

4-{3-[1-(1-ethoxyethoxy)ethyl]-4-methyl-5-oxo-4,5-dihydro-1H-1,2,4-triazol-1-yl}-5-fluoro-N-(2-methylphenyl)-2-(pentan-2-yloxy)benzamide, Mixture of Stereoisomers

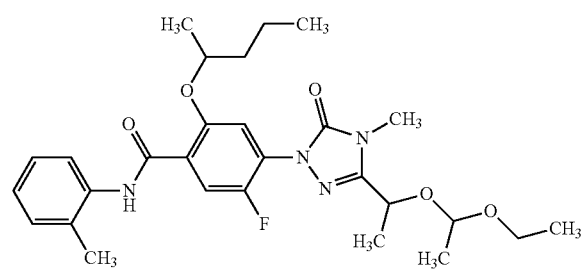 [SMILES: CCCC(C)Oc1cc(-n2nc(C(C)OC(C)OCC)n(C)c2=O)c(F)cc1C(=O)Nc1ccccc1C]

Synthesized analogously to Example 165 from Intermediate 86 and 2-pentanol.

Step B 5-fluoro-4-[3-(1-hydroxyethyl)-4-methyl-5-oxo-4,5-dihydro-1H-1,2,4-triazol-1-yl]-N-(2-methylphenyl)-2-(pentan-2-yloxy)benzamide, Mixture of Stereoisomers

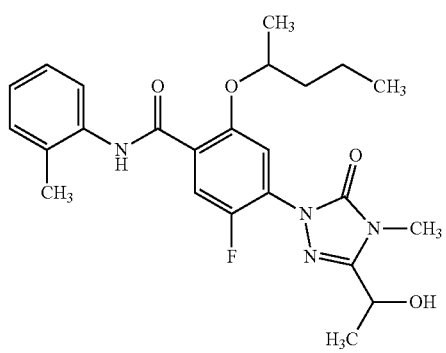 [SMILES: CCCC(C)Oc1cc(-n2nc(C(C)O)n(C)c2=O)c(F)cc1C(=O)Nc1ccccc1C]

The intermediate from STEP A was deprotected analogously to Example 174.

Example 176

N-(2-chloro-6-fluorophenyl)-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide

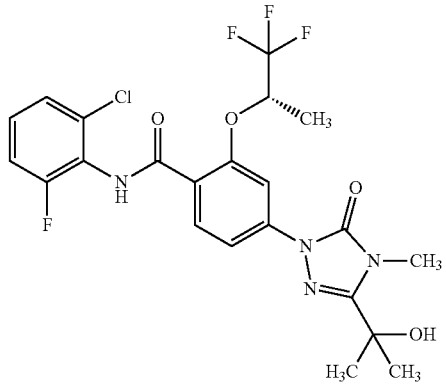 [SMILES: C[C@H](Oc1cc(-n2nc(C(C)(C)O)n(C)c2=O)ccc1C(=O)Nc1c(F)cccc1Cl)C(F)(F)F]

Synthesized analogously to Example 92 from Intermediate 100 and Intermediate 7

LC-MS (Method A): $R_t$=1.26 min; MS (ESIpos): m/z=517 [M+H]$^+$ $^1$H-NMR (400 MHz, DMSO-d6) δ [ppm]: 1.506 (2.67), 1.522 (2.71), 1.561 (16.00), 2.084 (1.89), 2.518 (1.73), 2.523 (1.13), 3.455 (9.84), 5.302 (0.49), 5.744 (4.69), 7.347 (0.62), 7.365 (0.49), 7.371 (0.47), 7.397 (0.62), 7.411 (0.60), 7.418 (0.49), 7.429 (1.33), 7.433 (1.25), 7.693 (0.45), 7.714 (0.84), 7.758 (0.94), 7.778 (0.51), 7.920 (1.14), 9.751 (2.36).

Example 177

N-(2,6-difluorophenyl)-4-[4-ethyl-3-(hydroxymethyl)-5-oxo-4,5-dihydro-1H-1,2,4-triazol-1-yl]-2-{[(2S)-1,1,1-trifluoropropan-2-yl]oxy}benzamide

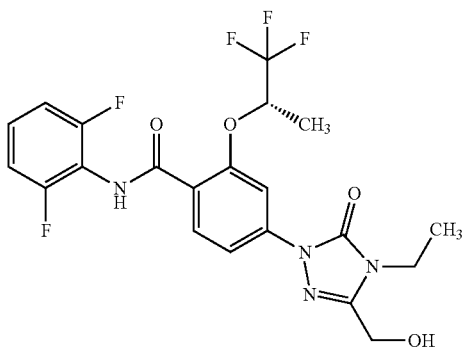 [SMILES: CCn1c(CO)nn(-c2ccc(C(=O)Nc3c(F)cccc3F)c(O[C@@H](C)C(F)(F)F)c2)c1=O]

Synthesized analogously to Example 92 from Intermediate 75 and Intermediate 6

LC-MS (Method A): $R_t$=1.13 min; MS (ESIpos): m/z=487 [M+H]$^+$ $^1$H-NMR (400 MHz, DMSO-d6) δ [ppm]: 1.108 (0.72), 1.142 (0.94), 1.154 (0.92), 1.172 (1.86), 1.190 (0.96), 1.264 (5.47), 1.282 (12.61), 1.300 (5.66), 1.467 (0.69), 1.493 (6.60), 1.509 (6.63), 1.987 (3.14), 2.518 (4.53), 2.523 (2.89), 3.771 (1.46), 3.789 (4.72), 3.807 (4.62), 3.824 (1.41), 4.017 (0.74), 4.035 (0.72), 4.507 (5.34), 4.521 (5.44), 5.273 (0.45), 5.289 (1.07), 5.305 (1.39), 5.321 (1.04), 5.336 (0.44), 5.759 (16.00), 5.803 (1.28), 5.818 (2.94), 5.832 (1.24), 7.183 (1.98), 7.203 (4.05), 7.224 (2.48), 7.360 (0.45), 7.376 (1.01), 7.396 (1.46), 7.412 (0.81), 7.740 (7.72), 7.873 (3.56), 9.713 (6.55).

Example 178

N-(2-chloro-6-fluorophenyl)-4-[4-ethyl-3-(hydroxymethyl)-5-oxo-4,5-dihydro-1H-1,2,4-triazol-1-yl]-2-{[(2S)-1,1,1-trifluoropropan-2-yl]oxy}benzamide

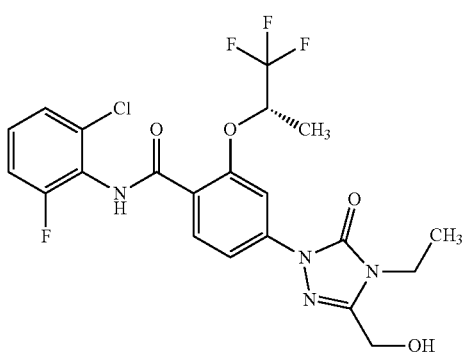 [SMILES: CCn1c(CO)nn(-c2ccc(C(=O)Nc3c(F)cccc3Cl)c(O[C@@H](C)C(F)(F)F)c2)c1=O]

Synthesized analogously to Example 92 from Intermediate 100 and Intermediate 6

LC-MS (Method A): $R_t$=1.18 min; MS (ESIpos): m/z=503 [M+H]$^+$ $^1$H-NMR (400 MHz, DMSO-d6) δ [ppm]: 1.154 (0.89), 1.172 (1.78), 1.190 (0.89), 1.265 (2.35), 1.284 (5.45), 1.301 (2.38), 1.500 (3.51), 1.516 (3.51), 1.988 (3.13), 2.518 (4.45), 2.523 (2.95), 3.772 (0.62), 3.790 (1.98), 3.808 (1.98), 3.825 (0.59), 4.017 (0.68), 4.035 (0.66), 4.509 (1.90), 4.521 (1.96), 5.321 (0.50), 5.337 (0.64), 5.354 (0.48), 5.759 (16.00), 5.821 (1.00), 7.346 (0.77), 7.369 (0.55), 7.395 (0.61), 7.409 (0.66), 7.427 (1.60), 7.431 (1.55), 7.447 (0.44), 7.752 (2.99), 7.881 (1.57), 9.772 (2.51).

Example 179

N-(2-chloro-6-fluorophenyl)-2-{[1,1-difluoropropan-2-yl]oxy}-4-[3-(2-hydroxypropan-2-yl)-4-methyl-5-oxo-4,5-dihydro-1H-1,2,4-triazol-1-yl]benzamide (Racemic)

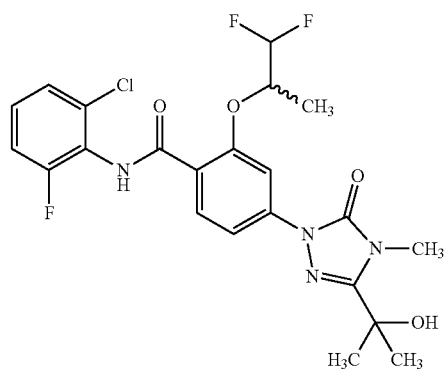 [SMILES: CC(Oc1cc(-n2nc(C(C)(C)O)n(C)c2=O)ccc1C(=O)Nc1c(F)cccc1Cl)C(F)F]

Synthesized analogously to Example 92 from Intermediate 101 and Intermediate 7

LC-MS (Method A): $R_t$=1.22 min; MS (ESIneg): m/z=497 [M−H]

$^1$H-NMR (400 MHz, DMSO-d6) δ [ppm]: 1.432 (2.27), 1.448 (2.25), 1.559 (16.00), 2.083 (1.61), 2.518 (0.65), 2.522 (0.44), 3.455 (9.56), 5.746 (4.46), 5.757 (0.55), 6.333 (0.47), 6.341 (0.47), 7.349 (0.66), 7.367 (0.45), 7.372 (0.50), 7.399 (0.63), 7.413 (0.65), 7.419 (0.46), 7.434 (1.29), 7.439 (1.20), 7.646 (0.68), 7.650 (0.68), 7.667 (0.77), 7.672 (0.78), 7.907 (0.98), 7.928 (0.85), 7.949 (1.21), 7.952 (1.17), 9.595 (2.01).

Example 180

N-(2-chloro-6-fluorophenyl)-2-{[1,1-difluoropropan-2-yl]oxy}-4-[4-ethyl-3-(hydroxymethyl)-5-oxo-4,5-dihydro-1H-1,2,4-triazol-1-yl]benzamide (Racemic)

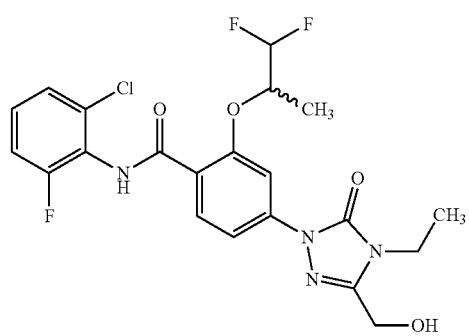 [SMILES: CCn1c(CO)nn(-c2ccc(C(=O)Nc3c(F)cccc3Cl)c(OC(C)C(F)F)c2)c1=O]

Synthesized analogously to Example 92 from Intermediate 101 and Intermediate 6

LC-MS (Method A): R$_t$=1.11 min; MS (ESIpos): m/z=485 [M+H]

$^1$H-NMR (400 MHz, DMSO-d6) δ [ppm]: 1.108 (0.56), 1.142 (0.76), 1.154 (1.29), 1.172 (2.55), 1.190 (1.31), 1.265 (5.67), 1.283 (13.21), 1.301 (5.79), 1.429 (7.52), 1.444 (7.56), 1.467 (0.58), 1.988 (4.56), 2.518 (5.65), 2.523 (3.66), 3.771 (1.49), 3.789 (4.82), 3.807 (4.76), 3.825 (1.43), 4.017 (1.01), 4.035 (1.01), 4.508 (5.05), 4.521 (5.09), 4.921 (0.82), 4.938 (0.82), 4.946 (0.80), 5.759 (16.00), 5.805 (1.17), 5.819 (2.79), 5.833 (1.15), 6.188 (0.80), 6.196 (0.78), 6.325 (1.55), 6.333 (1.57), 6.463 (0.74), 6.471 (0.76), 7.329 (0.92), 7.349 (2.21), 7.367 (1.49), 7.372 (1.65), 7.379 (1.21), 7.393 (1.15), 7.399 (2.05), 7.413 (2.09), 7.419 (1.55), 7.434 (4.36), 7.439 (4.04), 7.455 (1.31), 7.459 (1.13), 7.692 (2.15), 7.697 (2.13), 7.713 (2.43), 7.717 (2.63), 7.897 (7.06), 7.919 (2.75), 9.611 (6.13).

Example 181

N-(2-chloro-6-fluorophenyl)-4-[4-cyclopropyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide

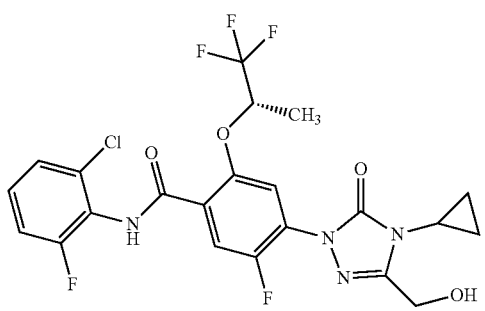 [SMILES: C[C@H](Oc1cc(-n2nc(CO)n(C3CC3)c2=O)c(F)cc1C(=O)Nc1c(F)cccc1Cl)C(F)(F)F]

Synthesized analogously to Example 92 from Intermediate 71 and 4-cyclopropyl-3-ethyl-1H-1,2,4-triazol-5(4H)-one LC-MS (Method A): R$_t$=1.13 min; MS (ESIneg): m/z=531 [M−H]

$^1$H-NMR (400 MHz, DMSO-d6) δ [ppm]: 0.835 (0.45), 0.946 (1.36), 0.965 (5.14), 0.979 (5.73), 0.983 (4.95), 0.996 (2.64), 1.014 (1.27), 1.033 (1.36), 1.041 (2.73), 1.051 (6.55), 1.059 (6.32), 1.072 (2.82), 1.081 (1.32), 1.108 (1.14), 1.143 (1.50), 1.154 (5.00), 1.172 (9.05), 1.190 (4.36), 1.232 (0.45), 1.433 (12.68), 1.449 (12.59), 1.467 (1.41), 1.484 (0.45), 1.810 (0.64), 1.987 (16.00), 2.084 (14.41), 2.322 (1.91), 2.326 (2.59), 2.331 (1.91), 2.522 (9.14), 2.664 (1.91), 2.668 (2.64), 2.673 (1.91), 2.919 (0.95), 2.928 (1.95), 2.937 (2.68), 2.946 (3.64), 2.955 (2.36), 2.963 (1.82), 2.973 (0.86), 3.469 (0.41), 4.000 (1.32), 4.017 (3.86), 4.035 (3.82), 4.053 (1.27), 4.504 (7.45), 4.515 (7.55), 4.540 (0.59), 5.299 (0.82), 5.316 (1.86), 5.331 (2.45), 5.347 (1.82), 5.363 (0.77), 5.704 (2.55), 5.758 (13.95), 7.333 (1.27), 7.352 (2.86), 7.369 (1.77), 7.376 (2.05), 7.385 (1.32), 7.405 (2.23), 7.419 (2.82), 7.430 (5.86), 7.436 (6.50), 7.450 (1.64), 7.540 (4.86), 7.552 (4.18), 7.565 (7.95), 10.065 (5.45).

Example 182

N-(2-chloro-6-fluorophenyl)-5-fluoro-4-[3-(hydroxymethyl)-5-oxo-4-propyl-4,5-dihydro-1H-1,2,4-triazol-1-yl]-2-{[(2S)-1,1,1-trifluoropropan-2-yl]oxy}benzamide

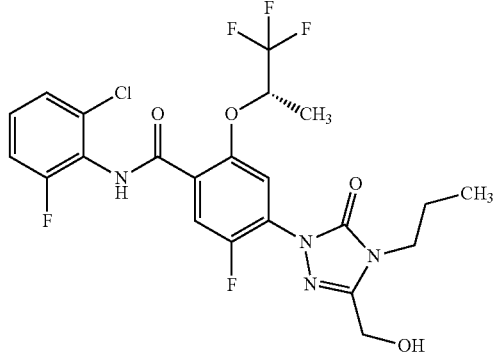 [SMILES: CCCn1c(CO)nn(-c2cc(O[C@@H](C)C(F)(F)F)c(C(=O)Nc3c(F)cccc3Cl)cc2F)c1=O]

Synthesized analogously to Example 92 from Intermediate 71 and 5-(hydroxymethyl)-4-propyl-2,4-dihydro-3H-1,2,4-triazol-3-one LC-MS (Method A): R$_t$=1.19 min; MS (ESIneg): m/z=533 [M−H]

Example 183

N-(2-chloro-6-fluorophenyl)-4-[4-cyclobutyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide

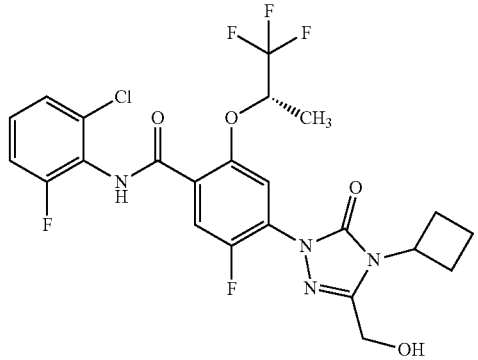 [SMILES: C[C@H](Oc1cc(-n2nc(CO)n(C3CCC3)c2=O)c(F)cc1C(=O)Nc1c(F)cccc1Cl)C(F)(F)F]

Synthesized analogously to Example 92 from Intermediate 71 and 3-cyclobutyl-4-methyl-1H-1,2,4-triazol-5(4H)-one LC-MS (Method A): R$_t$=1.22 min; MS (ESIneg): m/z=545 [M−H]

$^1$H-NMR (400 MHz, DMSO-d6) δ [ppm]: 1.154 (2.55), 1.172 (5.00), 1.190 (2.52), 1.233 (0.40), 1.437 (15.95), 1.452 (16.00), 1.488 (0.67), 1.680 (1.17), 1.700 (2.35), 1.706 (1.90), 1.726 (3.10), 1.746 (2.87), 1.770 (3.42), 1.794 (2.37), 1.820 (0.65), 1.987 (9.07), 2.084 (3.07), 2.195 (1.97), 2.215 (5.10), 2.222 (3.85), 2.236 (5.02), 2.256 (1.92), 2.326 (1.45), 2.522 (5.72), 2.669 (1.45), 2.867 (1.10), 2.891 (3.70), 2.917 (5.00), 2.945 (3.37), 2.970 (0.95), 3.566 (1.17), 4.000

(0.77), 4.017 (2.22), 4.035 (2.22), 4.053 (0.70), 4.456 (9.97), 4.468 (10.05), 4.620 (0.77), 4.642 (2.48), 4.664 (3.60), 4.686 (2.35), 4.708 (0.70), 5.325 (1.05), 5.341 (2.40), 5.357 (3.05), 5.373 (2.27), 5.389 (0.92), 5.758 (1.12), 5.770 (2.42), 5.784 (4.92), 5.797 (2.40), 7.336 (1.82), 7.355 (3.95), 7.372 (2.48), 7.379 (2.87), 7.387 (2.05), 7.408 (3.50), 7.421 (4.30), 7.433 (7.87), 7.438 (9.15), 7.453 (2.10), 7.548 (5.67), 7.573 (6.80), 7.579 (6.15), 7.594 (5.15), 10.072 (8.92).

Example 184

N-(2-chloro-6-fluorophenyl)-5-fluoro-4-[3-(hydroxymethyl)-5-oxo-4-(prop-2-en-1-yl)-4,5-dihydro-1H-1,2,4-triazol-1-yl]-2-{[(2S)-1,1,1-trifluoropropan-2-yl]oxy}benzamide

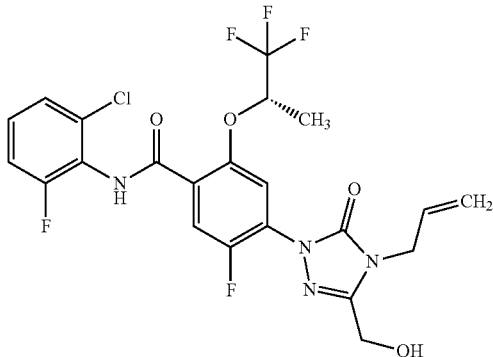 [SMILES: C=CCn1c(CO)nn(-c2cc(O[C@@H](C)C(F)(F)F)c(C(=O)Nc3c(F)cccc3Cl)cc2F)c1=O]

Synthesized analogously to Example 92 from Intermediate 71 and 5-(hydroxymethyl)-4-(prop-2-en-1-yl)-2,4-dihydro-3H-1,2,4-triazol-3-one LC-MS (Method A): $R_t$=1.16 min; MS (ESIpos): m/z=533 [M+H]$^+$ $^1$H-NMR (400 MHz, DMSO-d6) δ [ppm]: 1.437 (5.63), 1.453 (5.64), 2.074 (1.19), 2.518 (2.88), 2.523 (1.91), 4.396 (3.19), 4.409 (3.20), 4.443 (3.19), 4.450 (3.16), 5.167 (1.56), 5.170 (1.63), 5.209 (1.78), 5.213 (1.90), 5.223 (1.96), 5.227 (1.86), 5.249 (2.01), 5.253 (1.90), 5.350 (0.84), 5.366 (1.08), 5.382 (0.78), 5.759 (16.00), 5.814 (1.01), 5.922 (0.47), 5.936 (1.10), 5.948 (0.80), 5.961 (1.10), 5.978 (1.11), 5.991 (0.73), 6.004 (0.90), 7.331 (0.51), 7.351 (1.21), 7.375 (0.92), 7.400 (0.86), 7.429 (2.46), 7.433 (2.48), 7.448 (0.69), 7.555 (1.94), 7.580 (2.02), 7.597 (1.39), 7.611 (1.35), 10.077 (2.09).

Example 185

N-(2-chloro-6-fluorophenyl)-2-{[3,3-difluorobutan-2-yl]oxy}-4-[4-ethyl-3-(hydroxymethyl)-5-oxo-4,5-dihydro-1H-1,2,4-triazol-1-yl]-5-fluorobenzamide (Racemic)

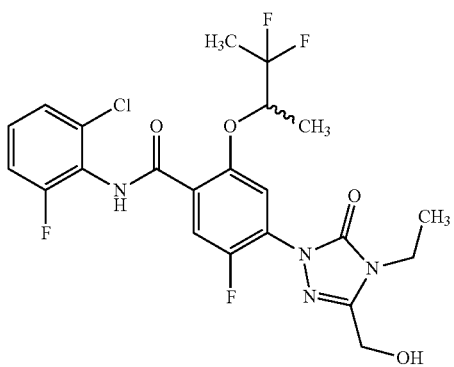 [SMILES: CCn1c(CO)nn(-c2cc(OC(C)C(C)(F)F)c(C(=O)Nc3c(F)cccc3Cl)cc2F)c1=O]

Synthesized analogously to Example 92 from Intermediate 102 and Intermediate 6

LC-MS (Method A): $R_t$=1.13 min; MS (ESIneg): m/z=515 [M−H]

$^1$H-NMR (400 MHz, DMSO-d6) δ [ppm]: 1.027 (1.52), 1.042 (2.23), 1.071 (1.10), 1.138 (0.46), 1.237 (0.66), 1.255 (0.88), 1.265 (6.98), 1.282 (16.00), 1.300 (7.08), 1.340 (10.09), 1.356 (9.96), 1.650 (6.02), 1.699 (11.55), 1.748 (5.23), 2.074 (0.50), 2.084 (13.11), 2.518 (4.37), 2.522 (2.95), 3.742 (0.44), 3.764 (1.86), 3.781 (6.02), 3.800 (5.85), 3.817 (1.68), 4.478 (9.08), 4.492 (9.12), 4.896 (0.64), 4.920 (1.26), 4.936 (1.26), 4.958 (0.60), 5.758 (1.36), 5.784 (2.79), 5.799 (6.54), 5.813 (2.63), 7.336 (0.96), 7.341 (1.06), 7.361 (2.45), 7.378 (1.50), 7.384 (1.90), 7.391 (1.30), 7.404 (1.06), 7.411 (2.33), 7.425 (2.61), 7.431 (2.17), 7.438 (4.85), 7.444 (6.40), 7.458 (1.30), 7.464 (1.00), 7.531 (3.51), 7.546 (3.49), 7.570 (3.81), 7.595 (3.65), 10.005 (8.52).

Example 186

5-fluoro-4-[3-(hydroxymethyl)-5-oxo-4-propyl-4,5-dihydro-1H-1,2,4-triazol-1-yl]-N-(2-methoxy-4-methylpyridin-3-yl)-2-{[(2S)-1,1,1-trifluoropropan-2-yl]oxy}benzamide

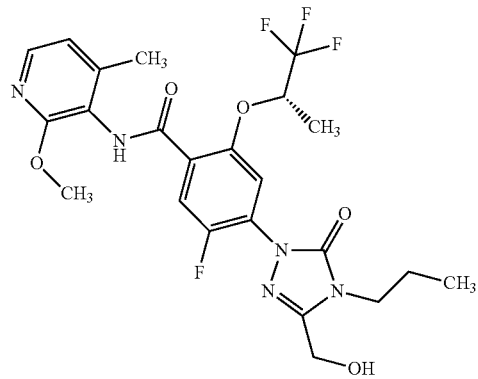 [SMILES: CCCn1c(CO)nn(-c2cc(O[C@@H](C)C(F)(F)F)c(C(=O)Nc3c(C)ccnc3OC)cc2F)c1=O]

Synthesized analogously to Example 92 from Intermediate 72 and 5-(hydroxymethyl)-4-propyl-2,4-dihydro-3H-1,2,4-triazol-3-one LC-MS (Method A): $R_t$=1.10 min; MS (ESIpos): m/z=528 [M+H]

$^1$H-NMR (400 MHz, DMSO-d6) δ [ppm]: 0.900 (3.08), 0.918 (7.06), 0.936 (3.35), 1.041 (0.70), 1.071 (0.70), 1.446 (5.15), 1.461 (5.15), 1.704 (0.97), 1.722 (1.69), 1.741 (1.65), 1.760 (0.91), 2.084 (1.19), 2.185 (0.45), 2.220 (12.10), 2.327 (0.88), 2.332 (0.65), 2.522 (3.15), 2.665 (0.65), 2.669 (0.90), 2.673 (0.65), 3.687 (1.64), 3.706 (2.16), 3.724 (1.51), 3.860 (16.00), 4.482 (2.52), 5.383 (0.79), 5.399 (1.02), 5.415 (0.74), 5.810 (0.96), 6.933 (2.24), 6.946 (2.30), 7.566 (4.59), 7.582 (2.15), 7.591 (2.60), 7.969 (2.69), 7.981 (2.55), 9.661 (3.01).

Example 187

N-(2-chloro-6-fluorophenyl)-4-[4-ethyl-3-(hydroxymethyl)-5-oxo-4,5-dihydro-1H-1,2,4-triazol-1-yl]-3-fluoro-2-{[(2S)-1,1,1-trifluoropropan-2-yl]oxy}benzamide

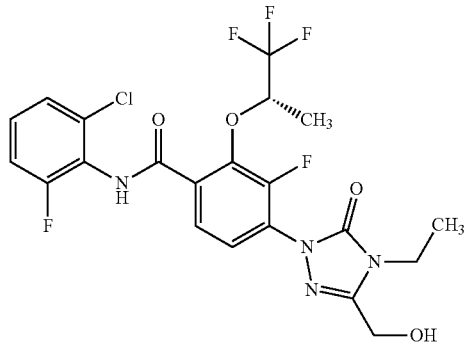 [SMILES: CCn1c(CO)nn(-c2ccc(C(=O)Nc3c(F)cccc3Cl)c(O[C@@H](C)C(F)(F)F)c2F)c1=O]

Synthesized analogously to Example 92 from Intermediate 103 and Intermediate 6

LC-MS (Method A): $R_t$=1.10 min; MS (ESIpos): m/z=521 [M+H]$^+$ $^1$H-NMR (400 MHz, DMSO-d6) δ [ppm]: 1.108 (0.47), 1.142 (0.59), 1.154 (0.98), 1.172 (1.98), 1.190 (1.02), 1.263 (2.33), 1.281 (5.28), 1.299 (2.43), 1.432 (3.66), 1.448 (3.68), 1.988 (3.42), 2.518 (4.95), 2.523 (3.16), 3.759 (0.60), 3.778 (2.11), 3.796 (1.97), 3.813 (0.66), 4.017 (0.76), 4.035 (0.72), 4.470 (2.68), 4.484 (2.71), 4.952 (0.43), 5.759 (16.00), 5.782 (0.72), 5.797 (1.61), 5.812 (0.69), 7.376 (0.60), 7.398 (0.52), 7.452 (1.29), 7.479 (0.43), 7.501 (3.12), 10.397 (1.14).

Example 188

N-(2-chloro-6-fluorophenyl)-3-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide

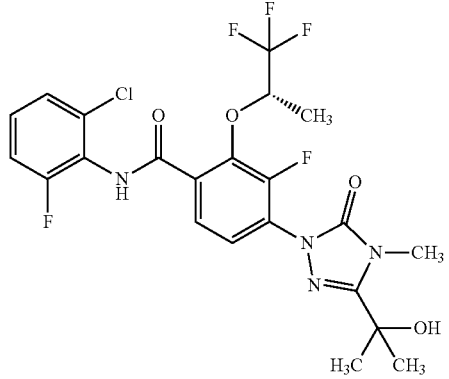 [SMILES: C[C@H](Oc1c(C(=O)Nc2c(F)cccc2Cl)ccc(-n2nc(C(C)(C)O)n(C)c2=O)c1F)C(F)(F)F]

Synthesized analogously to Example 92 from Intermediate 103 and Intermediate 7

LC-MS (Method A): $R_t$=1.19 min; MS (ESIpos): m/z=535 [M+H]$^+$ $^1$H-NMR (400 MHz, DMSO-d6) δ [ppm]: 1.431 (3.34), 1.448 (3.34), 1.520 (16.00), 2.084 (1.85), 2.518 (1.20), 2.523 (0.78), 3.451 (9.75), 4.928 (0.57), 4.944 (0.72), 4.959 (0.52), 5.745 (3.54), 7.380 (0.78), 7.396 (0.48), 7.403 (0.63), 7.427 (0.69), 7.441 (0.80), 7.453 (1.49), 7.459 (1.87), 7.473 (0.48), 7.479 (0.45), 7.487 (1.39), 7.495 (3.16), 10.371 (1.44).

Example 189

N-(6-chloro-2-fluoro-3-methoxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide

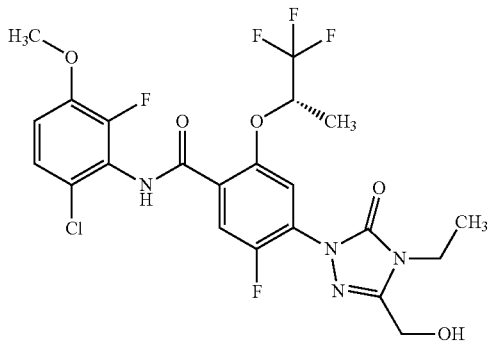 [SMILES: CCn1c(CO)nn(-c2cc(O[C@@H](C)C(F)(F)F)c(C(=O)Nc3c(Cl)ccc(OC)c3F)cc2F)c1=O]

Can be synthesized analogously to Example 92 by first reacting Intermediate 68 with 6-chloro-2-fluoro-3-methoxyaniline followed by palladium catalyzed coupling with Intermediate 6.

LC-MS (Method A): $R_t$=1.13 min; MS (ESIpos): m/z=551 [M+H]$^+$ $^1$H-NMR (400 MHz, DMSO-d6) δ [ppm]: 0.961 (12.84), 0.978 (13.80), 1.173 (0.77), 1.265 (4.22), 1.282 (9.85), 1.300 (4.30), 1.431 (5.99), 1.447 (6.02), 1.988 (1.38), 2.518 (1.20), 2.523 (0.82), 2.796 (7.38), 2.805 (0.47), 2.822 (0.85), 2.839 (1.05), 2.855 (0.78), 2.994 (7.78), 3.200 (0.42), 3.765 (1.10), 3.783 (3.60), 3.801 (3.58), 3.819 (1.11), 3.882 (16.00), 4.480 (5.32), 4.494 (5.37), 5.339 (0.91), 5.355 (1.18), 5.371 (0.87), 5.790 (1.66), 5.805 (3.88), 5.819 (1.58), 7.180 (1.04), 7.202 (2.17), 7.223 (1.37), 7.347 (1.87), 7.351 (1.85), 7.369 (1.45), 7.374 (1.44), 7.542 (2.24), 7.567 (2.26), 7.584 (2.07), 7.598 (1.99), 10.062 (4.94).

Example 190

N-(6-chloro-2-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide

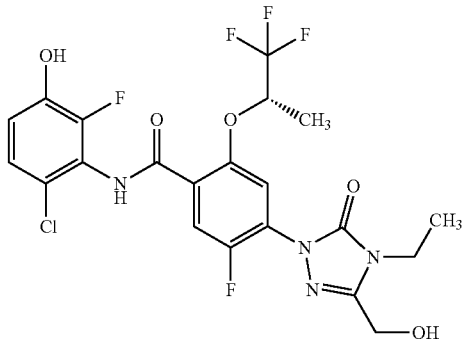 [SMILES: CCn1c(CO)nn(-c2cc(O[C@@H](C)C(F)(F)F)c(C(=O)Nc3c(Cl)ccc(O)c3F)cc2F)c1=O]

N-(6-chloro-2-fluoro-3-methoxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide (Example 189, 160 mg, 290 μmol) was dissolved in DCM and cooled to −20° C. A solution of boron tribromide in DCM (1.2 ml, 1.0 M, 1.2 mmol) was added dropwise and the solution was stirred in an ice bath for 1 h. The reaction was quenched by adding a water-methanol mixture (3:1) and the mixture was extracted with DCM (2×). The combined organic phases were washed with brine, dried over sodium sulfate, filtered, and concentrated. PrepHPLC yields the desired product (90.2 mg, 99% purity, 58% yield).

LC-MS (Method A): $R_t$=1.02 min; MS (ESIpos): m/z=537 [M+H]$^+$ $^1$H-NMR (400 MHz, DMSO-d6) δ [ppm]: 1.137 (0.46), 1.264 (4.41), 1.282 (9.64), 1.300 (4.48), 1.436 (7.00), 1.451 (7.02), 2.084 (16.00), 2.327 (0.54), 2.669 (0.55), 3.764 (1.26), 3.782 (3.87), 3.801 (3.82), 3.818 (1.27), 4.486 (5.79), 5.325 (0.46), 5.340 (1.08), 5.357 (1.39), 5.373 (1.03), 5.388 (0.42), 5.758 (5.10), 5.804 (0.83), 6.927 (1.23), 6.949 (2.57), 6.971 (1.47), 7.172 (2.08), 7.191 (1.74), 7.536 (2.58), 7.561 (2.60), 7.581 (2.48), 7.596 (2.45), 9.974 (4.33).

Example 191

3-chloro-4-(4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamido)-5-fluorophenyl 2,2-dimethylpropanoate

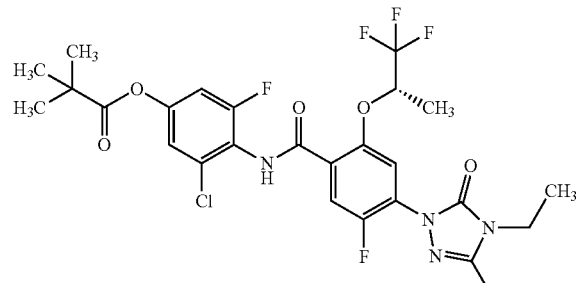

Can be synthesized analogously to Example 92 by first reacting Intermediate 68 with 4-amino-3-chloro-5-fluorophenyl pivalate followed by palladium catalyzed coupling with Intermediate 6.

LC-MS (Method A): $R_t$=1.37 min; MS (ESIpos): m/z=621 [M+H]$^+$

Example 192

N-(2-chloro-6-fluoro-4-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide

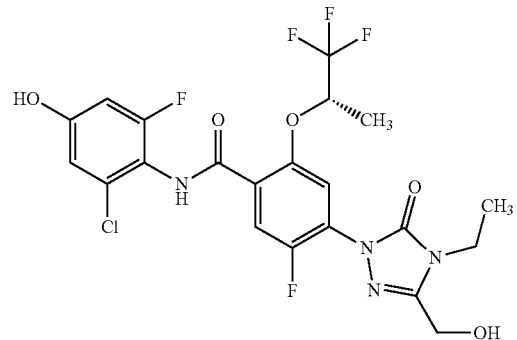 [SMILES: CCn1c(CO)nn(-c2cc(O[C@@H](C)C(F)(F)F)c(C(=O)Nc3c(F)cc(O)cc3Cl)cc2F)c1=O]

To a solution of 3-chloro-4-(4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamido)-5-fluorophenyl 2,2-dimethylpropanoate (Example 191, 200 mg, 322 μmol) in dioxane (2 mL) was added water (0.5 mL) and lithium hydroxide (23.1 mg, 966 μmol). The mixture was stirred at room temperature for 1 h. Water was added and the mixture was extracted with ethyl acetate (3×). The combined organic phases were washed with brine, dried over sodium sulfate, filtered, and concentrated. PrepHPLC followed by trituration in ethanol/water yields the desired product (67.4 mg, 98% purity, 38% yield).

LC-MS (Method A): $R_t$=1.01 min; MS (ESIpos): m/z=537 [M+H]$^+$ $^1$H-NMR (400 MHz, DMSO-d6) δ [ppm]: 1.052 (0.66), 1.201 (2.11), 1.261 (7.28), 1.279 (16.00), 1.297 (7.40), 1.311 (1.14), 1.382 (0.51), 1.425 (12.85), 1.440 (13.00), 1.514 (1.37), 2.084 (2.09), 2.322 (1.09), 2.326 (1.48), 2.668 (1.48), 2.673 (1.12), 3.762 (2.03), 3.779 (6.18), 3.797 (6.13), 3.815 (1.96), 4.482 (8.04), 5.307 (0.79), 5.323 (1.96), 5.340 (2.57), 5.356 (1.93), 5.371 (0.81), 5.801 (1.42), 6.677 (2.95), 6.683 (3.31), 6.705 (2.85), 6.710 (3.26), 6.788 (5.27), 6.794 (4.02), 7.507 (5.88), 7.531 (5.80), 7.563 (4.99), 7.578 (5.09), 9.723 (8.75).

Example 193

N-(2-chloro-6-fluoro-3-methoxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide

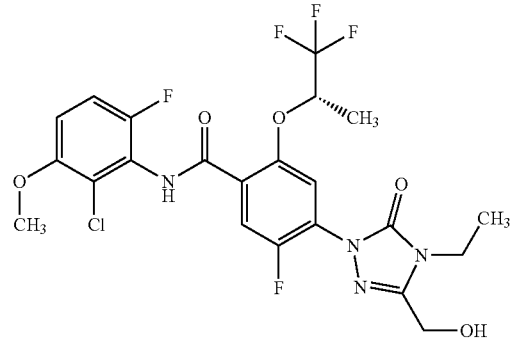 [SMILES: CCn1c(CO)nn(-c2cc(O[C@@H](C)C(F)(F)F)c(C(=O)Nc3c(F)ccc(OC)c3Cl)cc2F)c1=O]

Can be synthesized analogously to Example 92 by first reacting Intermediate 68 with 2-chloro-6-fluoro-3-methoxyaniline followed by palladium catalyzed coupling with Intermediate 6.

LC-MS (Method A): R$_t$=1.13 min; MS (ESIpos): m/z=551 [M+H]$^+$ $^1$H-NMR (400 MHz, DMSO-d6) δ [ppm]: 0.961 (1.41), 0.977 (1.27), 1.154 (1.22), 1.172 (2.40), 1.190 (1.13), 1.237 (0.47), 1.263 (3.99), 1.281 (9.54), 1.299 (4.04), 1.428 (5.25), 1.444 (5.28), 1.988 (4.34), 2.518 (2.19), 2.523 (1.46), 2.795 (0.69), 2.994 (0.71), 3.764 (1.02), 3.781 (3.35), 3.800 (3.26), 3.817 (0.98), 3.875 (16.00), 4.017 (0.98), 4.035 (0.97), 4.479 (3.16), 4.491 (3.12), 5.338 (0.76), 5.354 (1.02), 5.370 (0.74), 5.797 (0.66), 5.811 (1.29), 7.138 (0.63), 7.149 (0.69), 7.161 (0.86), 7.173 (0.80), 7.292 (0.96), 7.315 (1.57), 7.338 (0.73), 7.544 (1.68), 7.568 (1.97), 7.575 (1.46), 7.591 (1.23), 10.057 (2.24).

Example 194

N-(2-chloro-6-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide

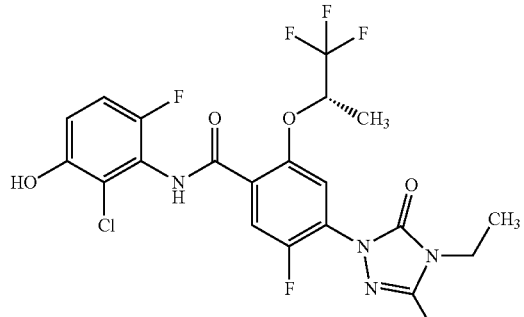

Can be synthesized analogously to Example 190 from Example 193.

LC-MS (Method A): R$_t$=0.96 min; MS (ESIpos): m/z=537 [M+H]$^+$ $^1$H-NMR (400 MHz, DMSO-d6) δ [ppm]: 1.154 (0.80), 1.172 (1.66), 1.190 (0.83), 1.263 (2.28), 1.281 (5.30), 1.299 (2.35), 1.431 (3.30), 1.447 (3.32), 1.988 (2.93), 2.084 (16.00), 2.518 (3.08), 2.523 (2.04), 3.566 (0.42), 3.764 (0.60), 3.782 (1.96), 3.799 (1.93), 3.817 (0.60), 4.017 (0.66), 4.035 (0.65), 4.485 (3.84), 5.337 (0.49), 5.353 (0.65), 5.370 (0.49), 6.918 (0.56), 6.930 (0.61), 6.941 (0.79), 6.952 (0.74), 7.102 (0.69), 7.125 (1.22), 7.148 (0.55), 7.538 (1.21), 7.563 (1.24), 7.576 (1.19), 7.591 (1.16), 9.944 (1.00).

Example 195

2-[(1S)-1-cyclohexylethoxy]-N-(1,4-dimethyl-1H-pyrazol-3-yl)-4-(3-ethyl-4-methyl-5-oxo-4,5-dihydro-1H-1,2,4-triazol-1-yl)-5-fluorobenzamide

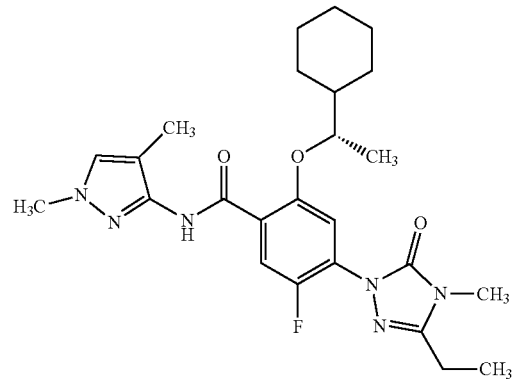 [SMILES: CCc1nn(-c2cc(O[C@@H](C)C3CCCCC3)c(C(=O)Nc3nn(C)cc3C)cc2F)c(=O)n1C]

Synthesized analogously to Example 1 from Intermediate 104 and 1,4-dimethyl-1H-pyrazol-3-amine LC-MS (Method A): R$_t$=1.30 min; MS (ESIpos): m/z=485 [M+H]$^+$ $^1$H-NMR (400 MHz, DMSO-d6) δ [ppm]: 1.042 (0.64), 1.064 (0.96), 1.096 (0.96), 1.132 (1.92), 1.146 (1.92), 1.156 (1.92), 1.173 (1.60), 1.188 (5.12), 1.207 (9.60), 1.226 (6.40), 1.229 (7.36), 1.245 (6.40), 1.600 (1.28), 1.615 (0.96), 1.688 (1.92), 1.850 (0.64), 1.881 (0.64), 1.903 (1.28), 1.913 (12.48), 2.322 (1.28), 2.326 (1.60), 2.331 (1.28), 2.517 (7.36), 2.522 (4.80), 2.539 (16.00), 2.623 (1.60), 2.642 (4.16), 2.660 (4.48), 2.668 (1.92), 2.673 (1.28), 2.678 (1.60), 3.197 (2.56), 3.216 (16.00), 3.242 (0.32), 3.252 (0.32), 3.280 (0.64), 3.327 (2.24), 3.342 (3.84), 3.422 (6.08), 3.435 (3.52), 3.450 (1.92), 3.490 (0.96), 3.500 (0.64), 3.526 (0.32), 3.718 (15.36), 4.362 (0.64), 4.376 (1.28), 4.391 (0.64), 7.308 (1.92), 7.324 (1.92), 7.440 (3.84), 7.595 (2.56), 7.622 (2.56), 9.774 (3.20).

Example 196

2-[(1S)-1-cyclohexylethoxy]-4-(3-ethyl-4-methyl-5-oxo-4,5-dihydro-1H-1,2,4-triazol-1-yl)-5-fluoro-N-[1-(4-fluorophenyl)cyclopropyl]benzamide

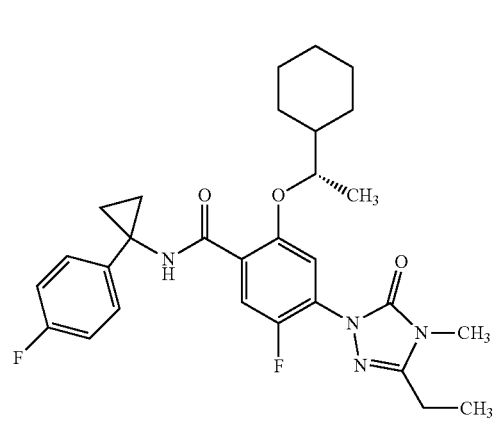 [SMILES: CCc1nn(-c2cc(O[C@@H](C)C3CCCCC3)c(C(=O)NC3(c4ccc(F)cc4)CC3)cc2F)c(=O)n1C]

Synthesized analogously to Example 1 from Intermediate 104 and 1-(4-fluorophenyl)cyclopropan-1-amine LC-MS (Method A): $R_t$=1.49 min; MS (ESIpos): m/z=525 [M+H]$^+$ $^1$H-NMR (400 MHz, DMSO-d6) δ [ppm]: 1.003 (0.45), 1.010 (0.43), 1.072 (0.57), 1.104 (0.81), 1.133 (0.85), 1.164 (0.70), 1.171 (0.61), 1.182 (4.42), 1.196 (6.57), 1.201 (11.09), 1.211 (5.89), 1.220 (4.92), 1.228 (1.07), 1.242 (5.48), 1.252 (1.93), 1.261 (0.88), 1.612 (0.54), 1.650 (0.61), 1.690 (1.30), 1.715 (0.71), 1.817 (0.44), 1.847 (0.41), 2.084 (1.44), 2.322 (0.53), 2.327 (0.72), 2.332 (0.53), 2.518 (2.90), 2.523 (1.88), 2.616 (1.12), 2.635 (3.92), 2.653 (3.62), 2.664 (0.63), 2.669 (0.95), 2.672 (1.43), 3.209 (16.00), 4.301 (0.64), 4.316 (0.94), 4.331 (0.63), 7.074 (1.86), 7.080 (0.63), 7.091 (0.72), 7.097 (3.94), 7.102 (0.72), 7.114 (0.63), 7.119 (2.25), 7.242 (1.71), 7.257 (1.71), 7.273 (2.18), 7.278 (0.85), 7.286 (2.33), 7.295 (1.95), 7.303 (0.73), 7.309 (1.67), 7.480 (2.49), 7.506 (2.49), 8.852 (2.63).

Example 197

2-[(1S)-1-cyclohexylethoxy]-4-(3-ethyl-4-methyl-5-oxo-4,5-dihydro-1H-1,2,4-triazol-1-yl)-5-fluoro-N-(oxan-4-yl)benzamide

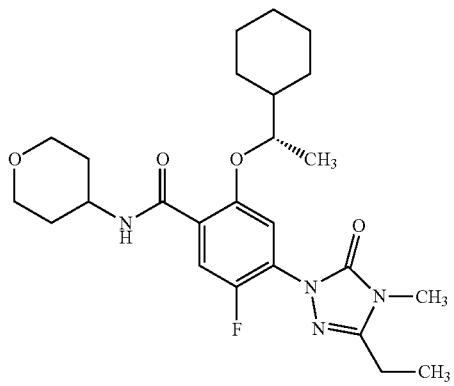 [SMILES: CCc1nn(-c2cc(O[C@@H](C)C3CCCCC3)c(C(=O)NC3CCOCC3)cc2F)c(=O)n1C]

Synthesized analogously to Example 1 from Intermediate 104 and 4-aminotetrahydropyran LC-MS (Method A): $R_t$=1.29 min; MS (ESIpos): m/z=275 [M+H]$^+$ $^1$H-NMR (400 MHz, DMSO-d6) δ [ppm]: 1.016 (0.43), 1.023 (0.43), 1.045 (0.55), 1.053 (0.54), 1.076 (0.42), 1.099 (0.62), 1.129 (0.81), 1.137 (1.11), 1.163 (0.99), 1.182 (4.70), 1.194 (1.41), 1.200 (9.75), 1.213 (6.81), 1.219 (5.97), 1.229 (6.48), 1.446 (0.76), 1.456 (0.88), 1.477 (0.97), 1.488 (0.85), 1.505 (0.49), 1.516 (0.41), 1.609 (0.51), 1.631 (0.68), 1.662 (0.56), 1.683 (0.60), 1.714 (1.70), 1.745 (0.86), 1.830 (1.10), 1.836 (1.12), 1.850 (1.16), 1.861 (1.06), 2.323 (0.49), 2.327 (0.69), 2.331 (0.49), 2.518 (3.72), 2.523 (2.46), 2.617 (1.25), 2.636 (3.98), 2.654 (3.90), 2.665 (0.65), 2.669 (0.90), 2.673 (1.57), 3.197 (0.63), 3.210 (16.00), 3.386 (0.85), 3.391 (1.05), 3.414 (1.85), 3.419 (1.80), 3.443 (1.09), 3.449 (0.86), 3.839 (1.27), 3.868 (1.11), 3.989 (0.50), 3.999 (0.41), 4.008 (0.50), 4.341 (0.72), 4.356 (1.09), 4.372 (0.72), 7.280 (1.88), 7.296 (1.88), 7.591 (2.59), 7.618 (2.56), 8.113 (1.16), 8.132 (1.16).

Example 198

2-[(1S)-1-cyclohexylethoxy]-4-(3-ethyl-4-methyl-5-oxo-4,5-dihydro-1H-1,2,4-triazol-1-yl)-5-fluoro-N-(1-phenylbutan-2-yl)benzamide

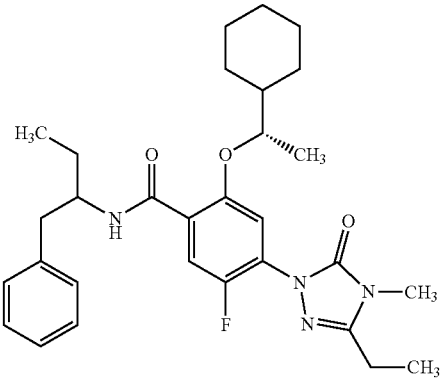 [SMILES: CCc1nn(-c2cc(O[C@@H](C)C3CCCCC3)c(C(=O)NC(CC)Cc3ccccc3)cc2F)c(=O)n1C]

Synthesized analogously to Example 1 from Intermediate 104 and 1-phenylbutane-2-amine LC-MS (Method A): $R_t$=1.61 min; MS (ESIpos): m/z=523 [M+H]$^+$ $^1$H-NMR (400 MHz, DMSO-d6) δ [ppm]: 0.889 (1.26), 0.898 (1.61), 0.908 (3.07), 0.917 (3.21), 0.926 (1.61), 0.935 (1.61), 1.015 (0.49), 1.047 (0.56), 1.076 (0.63), 1.101 (0.70), 1.137 (1.26), 1.145 (3.98), 1.147 (4.33), 1.160 (3.98), 1.163 (4.12), 1.180 (4.26), 1.188 (0.70), 1.198 (8.87), 1.217 (4.12), 1.234 (0.63), 1.356 (1.26), 1.366 (0.63), 1.385 (0.63), 1.399 (0.42), 1.570 (0.42), 1.588 (0.98), 1.599 (1.19), 1.618 (0.98), 1.634 (0.91), 1.667 (0.91), 1.754 (0.49), 2.074 (0.56), 2.084 (8.52), 2.318 (0.49), 2.322 (1.12), 2.327 (1.68), 2.332 (1.19), 2.336 (0.56), 2.518 (6.50), 2.523 (4.40), 2.539 (0.49), 2.615 (1.19), 2.634 (3.91), 2.653 (3.84), 2.660 (0.70), 2.665 (1.33), 2.669 (2.03), 2.678 (0.63), 2.774 (0.49), 2.794 (0.70), 2.817 (0.91), 2.833 (0.91), 3.209 (16.00), 3.377 (0.42), 3.382 (0.42), 4.335 (0.56), 4.342 (0.42), 4.350 (0.42), 4.357 (0.56), 5.758 (0.98), 7.179 (2.03), 7.197 (2.93), 7.199 (3.00), 7.219 (0.49), 7.222 (0.56), 7.256 (1.33), 7.273 (2.45), 7.280 (1.47), 7.288 (2.38), 7.292 (0.98), 7.305 (0.49), 7.476 (1.33), 7.503 (1.26), 7.570 (1.26), 7.597 (1.19), 7.926 (0.56), 7.948 (0.56), 7.969 (0.63), 7.990 (0.56).

Example 199

2-[(1S)-1-cyclohexylethoxy]-4-(3-ethyl-4-methyl-5-oxo-4,5-dihydro-1H-1,2,4-triazol-1-yl)-5-fluoro-N-[3-(methanesulfonyl)phenyl]benzamide

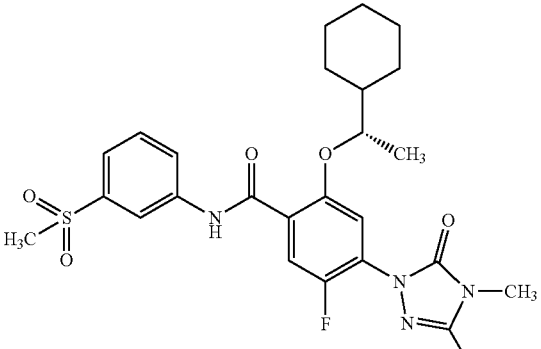

351

Synthesized analogously to Example 1 from Intermediate 104 and 3-(methanesulfonyl)aniline LC-MS (Method A): $R_t$=1.33 min; MS (ESIpos): m/z=545 [M+H]$^+$ $^1$H-NMR (400 MHz, DMSO-d6) δ [ppm]: 0.983 (0.54), 1.002 (0.60), 1.106 (0.80), 1.137 (2.21), 1.171 (1.14), 1.187 (1.27), 1.195 (3.41), 1.204 (3.41), 1.213 (7.16), 1.220 (3.55), 1.232 (3.48), 1.580 (0.60), 1.623 (1.07), 1.646 (0.94), 1.905 (1.54), 2.085 (5.76), 2.116 (0.60), 2.318 (1.14), 2.323 (2.61), 2.327 (3.82), 2.332 (2.81), 2.336 (1.21), 2.518 (16.00), 2.523 (10.85), 2.539 (0.94), 2.631 (0.94), 2.649 (2.74), 2.660 (1.34), 2.665 (3.01), 2.668 (5.89), 2.673 (2.95), 2.678 (1.27), 2.687 (0.74), 3.211 (8.70), 3.223 (11.05), 4.308 (0.40), 4.323 (0.54), 5.759 (6.36), 7.305 (1.00), 7.320 (1.07), 7.606 (1.61), 7.632 (1.74), 7.651 (1.07), 7.660 (0.94), 7.667 (2.21), 7.900 (0.54), 7.916 (0.60), 8.378 (1.21), 10.554 (1.87).

Example 200

2-[(1S)-1-cyclohexylethoxy]-4-(3-ethyl-4-methyl-5-oxo-4,5-dihydro-1H-1,2,4-triazol-1-yl)-5-fluoro-N-(1-methyl-1H-pyrazol-5-yl)benzamide

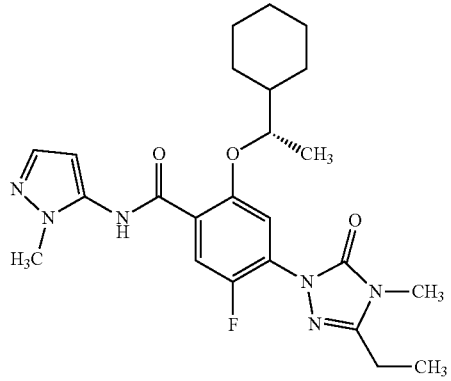 [SMILES: CCc1nn(-c2cc(O[C@@H](C)C3CCCCC3)c(C(=O)Nc3ccnn3C)cc2F)c(=O)n1C]

Synthesized analogously to Example 1 from Intermediate 104 and 1-methyl-1H-pyrazol-5-amine LC-MS (Method A): $R_t$=1.23 min; MS (ESIpos): m/z=471 [M+H]$^+$ $^1$H-NMR (400 MHz, CHLOROFORM-d) [ppm]: 0.842 (1.00), 0.849 (1.20), 0.858 (0.87), 0.865 (0.84), 1.083 (0.45), 1.090 (0.47), 1.126 (0.50), 1.132 (0.58), 1.164 (0.88), 1.194 (0.81), 1.220 (0.68), 1.226 (0.75), 1.234 (0.57), 1.250 (0.76), 1.260 (1.77), 1.280 (0.59), 1.286 (0.54), 1.354 (3.55), 1.373 (8.40), 1.389 (6.00), 1.392 (4.65), 1.404 (5.47), 1.700 (0.69), 1.708 (0.62), 1.715 (0.55), 1.737 (0.66), 1.784 (1.02), 1.815 (0.58), 2.635 (1.14), 2.654 (3.51), 2.673 (3.39), 2.692 (1.02), 3.338 (16.00), 3.830 (13.28), 4.435 (0.57), 4.450 (0.83), 4.466 (0.54), 6.418 (1.31), 6.422 (1.37), 7.377 (1.49), 7.392 (1.47), 7.481 (1.63), 7.487 (1.64), 8.116 (2.06), 8.145 (2.06), 9.850 (1.24).

352

Example 201

2-[(1S)-1-cyclohexylethoxy]-4-(3-ethyl-4-methyl-5-oxo-4,5-dihydro-1H-1,2,4-triazol-1-yl)-5-fluoro-N-[4-(methylsulfanyl)phenyl]benzamide

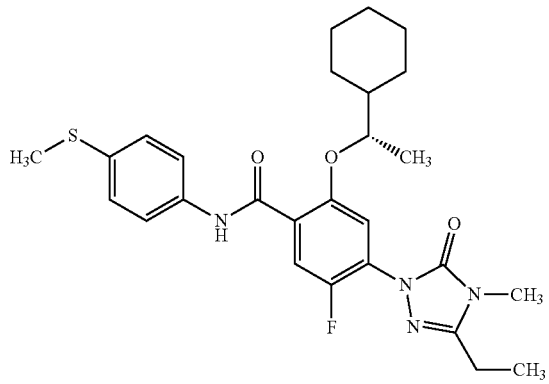 [SMILES: CCc1nn(-c2cc(O[C@@H](C)C3CCCCC3)c(C(=O)Nc3ccc(SC)cc3)cc2F)c(=O)n1C]

Synthesized analogously to Example 1 from Intermediate 104 and 4-(methylsulfanyl)aniline LC-MS (Method A): $R_t$=1.57 min; MS (ESIpos): m/z=513 [M+H]$^+$ $^1$H-NMR (400 MHz, DMSO-d6) δ [ppm]: 1.000 (0.48), 1.030 (0.64), 1.060 (0.42), 1.113 (0.71), 1.137 (1.00), 1.169 (0.58), 1.192 (3.77), 1.210 (10.78), 1.225 (4.80), 1.229 (4.31), 1.356 (0.97), 1.572 (0.55), 1.601 (0.71), 1.641 (1.29), 1.666 (1.13), 2.323 (0.68), 2.327 (0.97), 2.332 (0.71), 2.463 (16.00), 2.518 (3.80), 2.523 (2.58), 2.627 (0.97), 2.646 (3.19), 2.664 (3.61), 2.669 (1.26), 2.673 (0.80), 2.678 (0.42), 2.683 (0.90), 3.200 (0.45), 3.219 (12.17), 4.321 (0.52), 4.335 (0.71), 4.350 (0.52), 7.268 (2.80), 7.273 (0.90), 7.285 (1.00), 7.289 (3.06), 7.297 (1.67), 7.312 (1.42), 7.601 (1.96), 7.627 (2.19), 7.632 (3.25), 7.637 (1.00), 7.649 (0.93), 7.654 (2.67), 10.172 (2.22).

Example 202

4-(3-ethyl-4-methyl-5-oxo-4,5-dihydro-1H-1,2,4-triazol-1-yl)-5-fluoro-N-(4-methylpyridin-3-yl)-2-[(1S)-1-phenylethoxy]benzamide

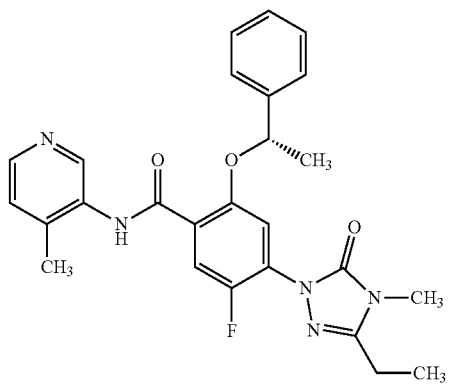 [SMILES: CCc1nn(-c2cc(O[C@@H](C)c3ccccc3)c(C(=O)Nc3cnccc3C)cc2F)c(=O)n1C]

Synthesized analogously to Example 1 from Intermediate 43 and 4-methylpyridin-3-amine LC-MS (Method B): R$_t$=1.15 min; MS (ESIneg): m/z=474 [M−H]

$^1$H-NMR (400 MHz, CHLOROFORM-d) [ppm]: 1.261 (0.50), 1.282 (2.71), 1.324 (3.60), 1.343 (8.69), 1.362 (3.78), 1.809 (5.48), 1.825 (5.33), 2.180 (9.18), 2.598 (1.22), 2.617 (3.66), 2.635 (3.56), 2.654 (1.02), 3.306 (16.00), 5.621 (1.03), 5.637 (1.02), 7.155 (0.85), 7.167 (0.88), 7.328 (0.86), 7.336 (0.49), 7.339 (0.53), 7.345 (1.22), 7.350 (0.94), 7.353 (1.18), 7.359 (0.69), 7.373 (3.89), 7.386 (2.40), 7.391 (3.55), 7.395 (2.50), 7.411 (0.88), 7.416 (0.53), 8.129 (2.06), 8.159 (2.01), 8.336 (0.79), 8.349 (0.77), 9.083 (1.21), 9.684 (1.13).

Example 203

4-(3-ethyl-4-methyl-5-oxo-4,5-dihydro-1H-1,2,4-triazol-1-yl)-5-fluoro-N-(2-methylquinolin-5-yl)-2-[(1S)-1-phenylethoxy]benzamide

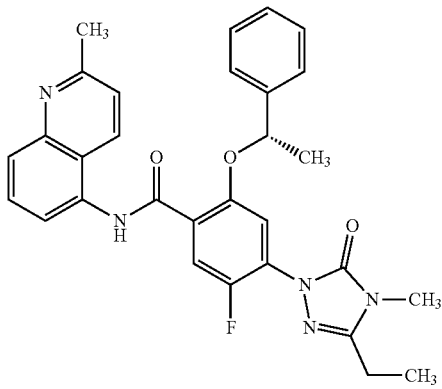 [SMILES: CCc1nn(-c2cc(O[C@@H](C)c3ccccc3)c(C(=O)Nc3cccc4nc(C)ccc34)cc2F)c(=O)n1C]

Synthesized analogously to Example 1 from Intermediate 43 and 2-methylquinolin-5-amine LC-MS (Method B): R$_t$=1.23 min; MS (ESIpos): m/z=526 [M+H]$^+$ $^1$H-NMR (400 MHz, CHLOROFORM-d) [ppm]: 1.261 (0.72), 1.282 (9.22), 1.334 (3.71), 1.353 (8.70), 1.371 (3.66), 1.616 (0.96), 1.822 (4.87), 1.838 (4.90), 2.608 (1.20), 2.626 (3.60), 2.645 (3.53), 2.664 (0.97), 2.752 (10.93), 3.281 (0.44), 3.316 (16.00), 3.927 (0.43), 5.672 (0.94), 5.688 (0.93), 7.174 (2.10), 7.196 (2.24), 7.300 (0.58), 7.303 (0.65), 7.309 (0.51), 7.312 (0.97), 7.317 (3.26), 7.322 (1.70), 7.328 (0.48), 7.332 (0.89), 7.336 (2.20), 7.343 (0.44), 7.347 (0.40), 7.351 (0.70), 7.359 (0.57), 7.403 (1.85), 7.407 (1.85), 7.419 (2.23), 7.427 (1.27), 7.434 (1.65), 7.716 (0.83), 7.736 (1.31), 7.756 (1.16), 7.899 (1.02), 7.920 (0.81), 8.053 (1.31), 8.075 (1.25), 8.105 (1.18), 8.123 (1.07), 8.175 (1.91), 8.204 (1.86), 10.346 (1.23).

Example 204

N-[3-(cyclopropylcarbamoyl)phenyl]-4-(3-ethyl-4-methyl-5-oxo-4,5-dihydro-1H-1,2,4-triazol-1-yl)-5-fluoro-2-[(1S)-1-phenylethoxy]benzamide

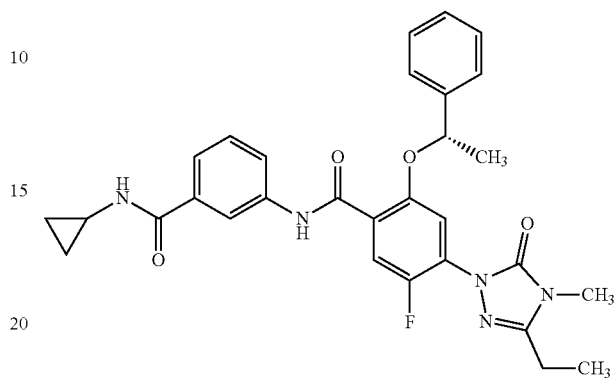

Synthesized analogously to Example 1 from Intermediate 43 and 3-amino-N-cyclopropylbenzamide LC-MS (Method B): R$_t$=1.19 min; MS (ESIneg): m/z=543 [M−H]

$^1$H-NMR (400 MHz, CHLOROFORM-d) [ppm]: 0.652 (1.16), 0.656 (1.24), 0.661 (1.25), 0.665 (1.26), 0.668 (1.11), 0.679 (0.50), 0.870 (0.52), 0.884 (1.22), 0.887 (1.58), 0.901 (1.52), 0.905 (1.17), 1.040 (1.19), 1.261 (0.98), 1.282 (16.00), 1.299 (0.75), 1.325 (3.48), 1.343 (7.54), 1.362 (3.65), 1.403 (0.53), 1.421 (1.10), 1.440 (0.55), 1.606 (5.30), 1.869 (4.89), 1.884 (5.00), 2.598 (1.11), 2.616 (3.31), 2.635 (3.30), 2.654 (0.92), 2.900 (0.47), 2.910 (0.62), 2.918 (0.61), 2.928 (0.46), 3.306 (14.37), 5.589 (1.02), 5.605 (1.02), 6.347 (0.59), 7.334 (1.66), 7.348 (1.80), 7.363 (0.83), 7.366 (0.69), 7.370 (1.15), 7.374 (0.61), 7.380 (1.19), 7.385 (0.92), 7.390 (2.02), 7.392 (1.30), 7.398 (0.69), 7.412 (2.85), 7.429 (4.30), 7.433 (2.96), 7.449 (0.79), 7.454 (0.47), 7.556 (1.69), 7.558 (1.59), 7.561 (1.20), 7.575 (1.36), 7.578 (1.18), 7.581 (0.88), 8.058 (1.02), 8.062 (1.75), 8.067 (1.00), 8.095 (1.95), 8.124 (1.93), 10.254 (1.30).

Example 205

N-[2-(difluoromethyl)phenyl]-4-(3-ethyl-4-methyl-5-oxo-4,5-dihydro-1H-1,2,4-triazol-1-yl)-5-fluoro-2-[(1S)-1-phenylethoxy]benzamide

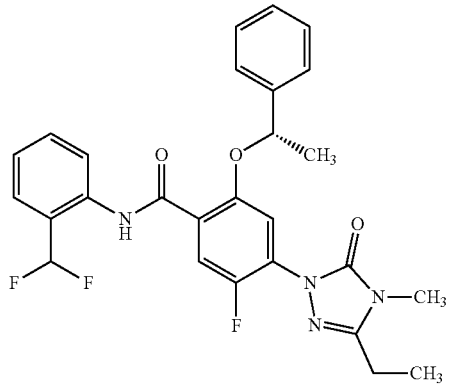 [SMILES: CCc1nn(-c2cc(O[C@@H](C)c3ccccc3)c(C(=O)Nc3ccccc3C(F)F)cc2F)c(=O)n1C]

Synthesized analogously to Example 1 from Intermediate 43 and 2-(difluoromethyl)aniline-hydrogen chloride LC-MS (Method B): $R_t$=1.35 min; MS (ESIneg): m/z=509 [M–H]

$^1$H-NMR (400 MHz, CHLOROFORM-d) [ppm]: 0.135 (0.77), 1.041 (0.45), 1.263 (1.40), 1.311 (3.60), 1.330 (7.42), 1.349 (3.76), 1.577 (0.78), 1.767 (3.52), 1.782 (3.53), 2.581 (1.13), 2.599 (3.53), 2.618 (3.26), 2.626 (0.46), 2.636 (0.92), 3.290 (16.00), 5.554 (0.84), 5.570 (0.84), 6.608 (0.76), 6.746 (1.54), 6.884 (0.72), 7.279 (0.53), 7.285 (1.67), 7.289 (0.48), 7.299 (2.17), 7.310 (0.66), 7.314 (1.71), 7.318 (1.44), 7.336 (1.56), 7.341 (0.69), 7.352 (0.91), 7.356 (2.61), 7.368 (0.42), 7.374 (1.56), 7.376 (1.16), 7.386 (2.08), 7.390 (2.32), 7.407 (1.08), 7.411 (0.73), 7.541 (0.46), 7.557 (1.54), 7.577 (1.15), 7.986 (0.81), 8.007 (0.78), 8.086 (1.83), 8.116 (1.83), 9.979 (0.92).

Example 206

4-(3-ethyl-4-methyl-5-oxo-4,5-dihydro-1H-1,2,4-triazol-1-yl)-5-fluoro-N-(6-methyl-1H-indazol-5-yl)-2-[(1S)-1-phenylethoxy]benzamide

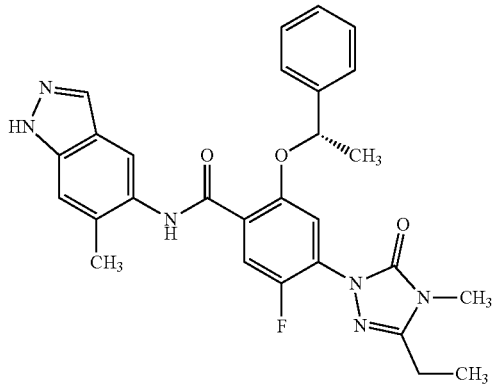 [SMILES: CCc1nn(-c2cc(O[C@@H](C)c3ccccc3)c(C(=O)Nc3cc4cn[nH]c4cc3C)cc2F)c(=O)n1C]

Synthesized analogously to Example 1 from Intermediate 43 and 6-methyl-1H-indazol-5-amine LC-MS (Method B): $R_t$=1.14 min; MS (ESIneg): m/z=513 [M–H]

$^1$H-NMR (400 MHz, CHLOROFORM-d) [ppm]: 1.041 (1.62), 1.195 (1.34), 1.262 (0.55), 1.283 (4.92), 1.300 (0.99), 1.327 (3.83), 1.345 (8.33), 1.364 (4.01), 1.418 (0.64), 1.768 (5.08), 1.784 (5.22), 2.308 (8.16), 2.599 (1.22), 2.617 (3.57), 2.636 (3.52), 2.655 (0.98), 3.316 (16.00), 5.485 (1.10), 5.502 (1.08), 7.213 (1.73), 7.228 (2.49), 7.231 (2.30), 7.312 (0.75), 7.315 (0.56), 7.321 (0.74), 7.328 (0.96), 7.333 (0.79), 7.340 (0.85), 7.343 (0.77), 7.347 (0.63), 7.355 (0.56), 7.360 (3.26), 7.370 (3.42), 7.376 (6.16), 7.391 (0.51), 7.993 (2.18), 8.128 (2.27), 8.157 (2.22), 8.361 (3.27), 9.608 (1.58).

Example 207

N-(1-cyanobutan-2-yl)-4-(3-ethyl-4-methyl-5-oxo-4,5-dihydro-1H-1,2,4-triazol-1-yl)-5-fluoro-2-[(1S)-1-phenylethoxy]benzamide

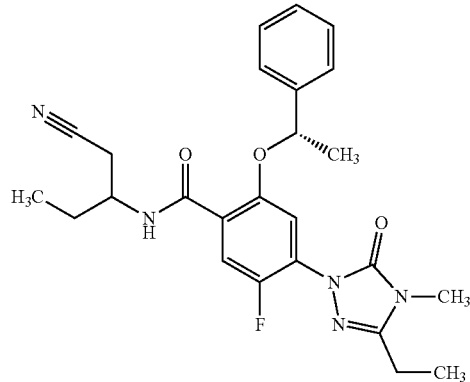 [SMILES: CCc1nn(-c2cc(O[C@@H](C)c3ccccc3)c(C(=O)NC(CC)CC#N)cc2F)c(=O)n1C]

Synthesized analogously to Example 1 from Intermediate 43 and 3-aminopentanenitrile LC-MS (Method B): $R_t$=1.19 min; MS (ESIneg): m/z=465 [M–H]

$^1$H-NMR (400 MHz, CHLOROFORM-d) [ppm]: 0.927 (2.50), 0.946 (5.97), 0.964 (2.76), 1.034 (2.24), 1.041 (0.65), 1.053 (5.33), 1.071 (2.46), 1.262 (0.99), 1.282 (12.40), 1.300 (0.45), 1.307 (3.25), 1.312 (3.77), 1.325 (7.39), 1.331 (8.31), 1.344 (3.52), 1.349 (3.81), 1.580 (3.66), 1.609 (0.50), 1.627 (0.42), 1.644 (0.61), 1.666 (0.63), 1.684 (0.54), 1.697 (0.66), 1.715 (0.84), 1.731 (1.10), 1.750 (0.91), 1.762 (0.60), 1.771 (0.61), 1.778 (0.72), 1.795 (5.35), 1.801 (6.05), 1.811 (5.25), 1.818 (6.05), 2.576 (1.08), 2.584 (1.25), 2.595 (3.24), 2.603 (4.33), 2.607 (1.36), 2.614 (3.48), 2.622 (3.64), 2.633 (0.99), 2.641 (1.30), 2.643 (1.39), 2.649 (1.32), 2.652 (1.33), 2.658 (1.10), 2.895 (1.00), 2.908 (1.06), 2.938 (1.34), 2.952 (1.49), 2.981 (0.93), 2.994 (0.89), 3.285 (13.98), 3.291 (16.00), 4.209 (0.46), 4.223 (0.42), 4.230 (0.40), 4.243 (0.43), 5.512 (0.61), 5.528 (2.02), 5.544 (1.99), 5.560 (0.60), 7.241 (1.68), 7.254 (3.00), 7.312 (1.05), 7.317 (0.49), 7.326 (0.63), 7.329 (1.27), 7.333 (0.71), 7.338 (0.78), 7.347 (0.71), 7.354 (0.99), 7.360 (1.71), 7.379 (3.02), 7.392 (0.92), 7.397 (4.39), 7.408 (3.41), 7.414 (7.32), 7.419 (2.94), 7.429 (0.73), 7.436 (1.37), 7.440 (0.86), 8.004 (2.00), 8.023 (2.30), 8.034 (2.02), 8.053 (2.26), 8.339 (0.64), 8.358 (0.64), 8.397 (0.57), 8.415 (0.56).

Example 208

2-{[(2S)-1-(dimethylamino)propan-2-yl]oxy}-4-(3-ethyl-4-methyl-5-oxo-4,5-dihydro-1H-1,2,4-triazol-1-yl)-5-fluoro-N-(2-fluoro-6-methylphenyl)benzamide

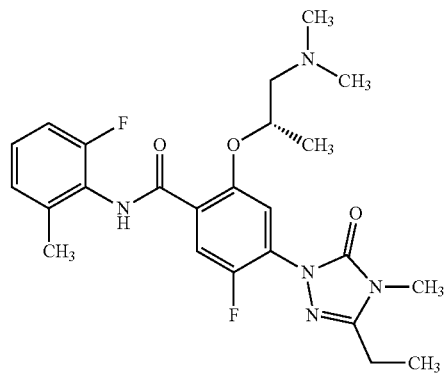 [SMILES: CCc1nn(-c2cc(O[C@@H](C)CN(C)C)c(C(=O)Nc3c(C)cccc3F)cc2F)c(=O)n1C]

Synthesized analogously to Example 73 from Intermediate 93 and 2-fluoro-6-methylaniline LC-MS (Method B): $R_t$=1.24 min; MS (ESIpos): m/z=474 [M+H]$^+$ $^1$H-NMR (400 MHz, CHLOROFORM-d) [ppm]: 0.133 (1.69), 1.262 (3.69), 1.282 (0.47), 1.351 (3.78), 1.370 (8.52), 1.389 (3.93), 1.477 (0.70), 1.486 (5.97), 1.492 (1.03), 1.501 (5.93), 1.620 (0.42), 2.123 (1.10), 2.315 (1.17), 2.325 (9.23), 2.631 (1.28), 2.649 (3.87), 2.668 (3.85), 2.687 (1.15), 3.333 (16.00), 6.958 (0.49), 6.979 (0.93), 7.002 (0.54), 7.046 (0.73), 7.065 (1.07), 7.134 (0.56), 7.148 (0.59), 7.154 (0.78), 7.167 (0.77), 7.352 (0.89), 7.366 (0.92), 7.961 (0.95), 7.989 (0.94).

Example 209

2-[(1S)-1-cyclohexylethoxy]-4-(3-ethyl-4-methyl-5-oxo-4,5-dihydro-1H-1,2,4-triazol-1-yl)-5-fluoro-N-[4-(S-methanesulfonimidoyl)phenyl]benzamide (Mixture of Stereoisomers)

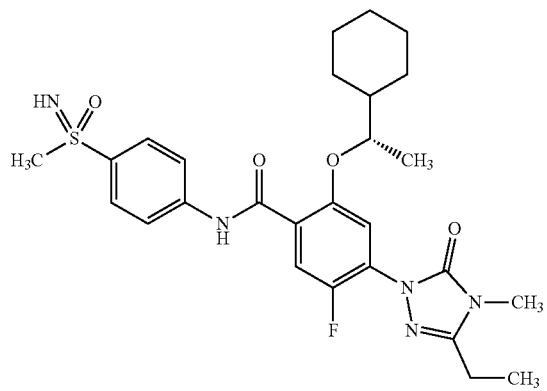

Following a procedure by Tota et al. (Chem. Commun. 2017, 53, 348-351) 2-[(1S)-1-cyclohexylethoxy]-4-(3-ethyl-4-methyl-5-oxo-4,5-dihydro-1H-1,2,4-triazol-1-yl)-5-fluoro-N-[4-(methylsulfanyl)phenyl]benzamide (Example 201, 38.0 mg, 74.1 μmol) was dissolved in methanol (500 μl). Ammonium carbamate (17.4 mg, 222 μmol) was added followed by (diacetoxyiodo)benzene (47.8 mg, 148 μmol). The mixture was stirred at room temperature for 2 h. The reaction mixture was filtered and purified by prepHPLC to yield the desired product 26.6 mg (95% purity, 63% yield).

LC-MS (Method A): $R_t$=1.15 min; MS (ESIpos): m/z=544 [M+H]$^+$ $^1$H-NMR (400 MHz, DMSO-d6) δ [ppm]: 0.982 (0.68), 1.011 (0.89), 1.042 (0.56), 1.101 (0.84), 1.125 (1.00), 1.137 (1.03), 1.165 (0.49), 1.174 (0.44), 1.194 (4.81), 1.201 (4.65), 1.213 (11.47), 1.231 (4.60), 1.448 (0.51), 1.463 (0.51), 1.522 (2.52), 1.558 (0.72), 1.586 (0.89), 1.622 (1.73), 1.650 (1.47), 1.770 (0.49), 1.800 (0.47), 2.084 (1.26), 2.323 (0.63), 2.327 (0.91), 2.331 (0.65), 2.518 (3.20), 2.523 (2.22), 2.631 (1.19), 2.649 (3.99), 2.668 (4.27), 2.673 (0.89), 2.686 (1.12), 3.043 (9.44), 3.223 (16.00), 3.452 (1.78), 4.146 (2.20), 4.316 (0.61), 4.330 (0.84), 4.344 (0.58), 5.781 (0.54), 7.310 (1.66), 7.325 (1.66), 7.608 (2.52), 7.633 (2.41), 7.855 (1.31), 7.877 (3.60), 7.899 (5.21), 7.916 (0.72), 7.922 (1.66), 10.538 (2.94).

Example 210

N-(2,6-difluorophenyl)-4-[4-ethyl-3-(S-methanesulfonimidoyl)-5-oxo-4,5-dihydro-1H-1,2,4-triazol-1-yl]-5-fluoro-2-{[(2S)-1,1,1-trifluoropropan-2-yl]oxy}benzamide (Mixture of Stereoisomers)

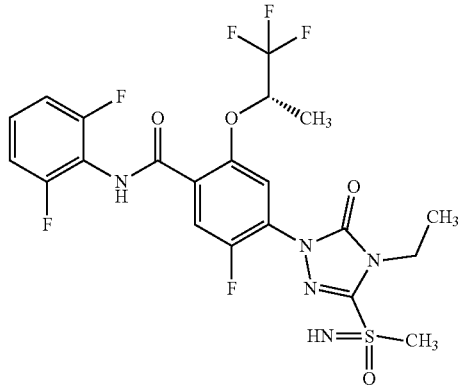 [SMILES: CCn1c(S(C)(=N)=O)nn(-c2cc(O[C@@H](C)C(F)(F)F)c(C(=O)Nc3c(F)cccc3F)cc2F)c1=O]

Synthesized analogously to Example 209 from Example 115

LC-MS (Method A): $R_t$=1.14 min; MS (ESIpos): m/z=552 [M+H]$^+$ $^1$H-NMR (400 MHz, DMSO-d6) δ [ppm]: 1.137 (0.61), 1.233 (0.57), 1.296 (4.10), 1.314 (9.02), 1.332 (4.06), 1.441 (6.01), 1.456 (6.01), 1.522 (1.83), 2.085 (4.55), 2.337 (0.77), 2.518 (8.93), 2.523 (6.09), 2.674 (1.66), 2.678 (0.77), 3.372 (16.00), 3.452 (1.30), 3.957 (0.41), 3.975 (0.89), 3.992 (2.11), 4.009 (2.92), 4.027 (2.07), 4.045 (0.89), 4.063 (0.41), 5.275 (0.41), 5.292 (0.97), 5.307 (1.30), 5.323 (0.93), 5.637 (2.96), 5.760 (3.70), 7.195 (1.66), 7.215 (3.41), 7.235 (2.11), 7.391 (0.81), 7.410 (0.97), 7.426 (0.69), 7.636 (2.80), 7.647 (1.99), 7.660 (4.22), 10.061 (4.02).

Example 211

1-(4-[(2-chloro-6-fluorophenyl)carbamoyl]-3-{[(2S)-1,1,1-trifluoropropan-2-yl]oxy}phenyl)-4-ethyl-5-oxo-4,5-dihydro-1H-1,2,4-triazole-3-carboxylic acid

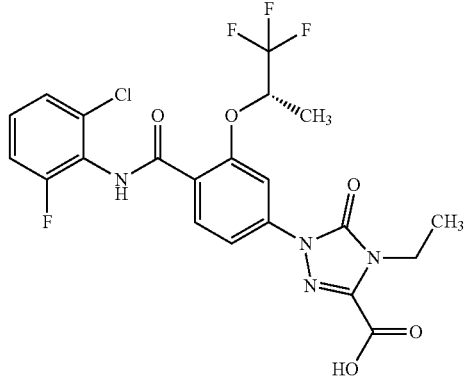 [SMILES: CCn1c(C(=O)O)nn(-c2ccc(C(=O)Nc3c(F)cccc3Cl)c(O[C@@H](C)C(F)(F)F)c2)c1=O]

Step A:

N-(2-chloro-6-fluorophenyl)-4-[4-ethyl-3-(hydroxymethyl)-5-oxo-4,5-dihydro-1H-1,2,4-triazol-1-yl]-2-{[(2S)-1, 1,1-trifluoropropan-2-yl]oxy}benzamide (Example 178, 160 mg, 318 µmol) was dissolved in dichloromethane (2 mL). Dess-Martin-periodinane (1,1,1-Tris(acetyloxy)-1,1-dihydro-1,2-benziodoxol-3-(1H)-one, 202 mg, 477 µmol) was added and the mixture was stirred overnight at room temperature. The mixture was diluted with water and extracted with DCM (3×). The combined organic phases were washed with sat. sodium bicarbonate solution and brine, dried over sodium sulfate, filtered and concentrated to yield crude N-(2-chloro-6-fluorophenyl)-4-(4-ethyl-3-formyl-5-oxo-4, 5-dihydro-1H-1,2,4-triazol-1-yl)-2-{[(2S)-1,1,1-trifluoropropan-2-yl]oxy}benzamide (157 mg, 99% yield, LC-MS (Method B): $R_t$=1.27 min; MS (ESIpos): m/z=501 [M+H]$^+$).

Step B:

The aldehyde from STEP A (157 mg, 313 µmol) was dissolved in tert-butanol (6.6 mL) and 2-methyl-2-butene (330 µl). A solution of sodium chlorite (319 mg, 80% purity, 2.82 mmol) and sodium dihydrogen phosphate dehydrate (342 mg, 2.19 mmol) in water (2.5 mL) was added dropwise at room temperature. The mixture was stirred at room temperature for 2 h. The mixture was concentrated, diluted with water and extracted with ethyl acetate (3×). The combined organic phases were dried over sodium sulfate, filtered, and concentrated. The crude product was purified using prepHPLC to yield the desired product (60.0 mg, 95% purity, 35% yield).

LC-MS (Method A): $R_t$=1.08 min; MS (ESIpos): m/z=517 [M+H]$^+$ $^1$H-NMR (400 MHz, DMSO-d6) δ [ppm]: 1.154 (1.43), 1.172 (2.86), 1.190 (1.39), 1.246 (2.61), 1.264 (6.08), 1.282 (2.63), 1.501 (4.03), 1.517 (4.04), 1.988 (4.92), 2.518 (1.93), 2.523 (1.26), 2.539 (16.00), 3.340 (1.03), 3.990 (0.64), 4.000 (0.76), 4.008 (2.08), 4.017 (1.65), 4.026 (2.06), 4.035 (1.50), 4.043 (0.64), 4.053 (0.47), 5.328 (0.58), 5.344 (0.75), 5.360 (0.55), 7.351 (0.89), 7.369 (0.56), 7.375 (0.66), 7.381 (0.51), 7.395 (0.43), 7.402 (0.83), 7.415 (0.91), 7.421 (0.75), 7.431 (1.88), 7.436 (1.99), 7.451 (0.52), 7.456 (0.41), 7.758 (2.11), 7.763 (2.37), 7.907 (1.79), 9.851 (3.81).

Example 212

1-(4-[(2-chloro-6-fluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid

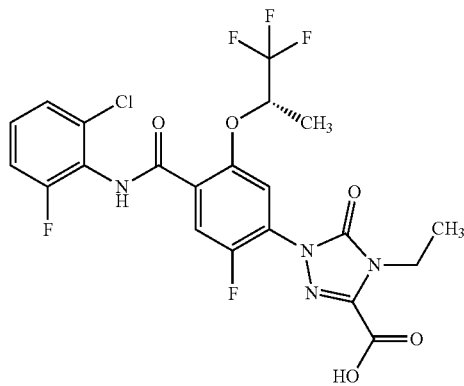 [SMILES: CCn1c(C(=O)O)nn(-c2cc(O[C@@H](C)C(F)(F)F)c(C(=O)Nc3c(F)cccc3Cl)cc2F)c1=O]

Synthesized analogously to Example 211 from Example 121

LC-MS (Method A): $R_t$=1.06 min; MS (ESIpos): m/z=535 [M+H]$^+$ $^1$H-NMR (400 MHz, DMSO-d6) δ [ppm]: 1.248 (6.93), 1.266 (15.69), 1.284 (7.36), 1.444 (11.48), 1.460 (11.69), 1.907 (1.32), 2.084 (16.00), 2.323 (0.78), 2.327 (1.13), 2.331 (0.87), 2.522 (5.96), 2.665 (0.87), 2.669 (1.22), 2.673 (0.93), 3.337 (2.33), 3.987 (1.86), 4.005 (5.69), 4.023 (5.65), 4.040 (1.86), 5.315 (0.70), 5.332 (1.73), 5.347 (2.29), 5.363 (1.69), 5.379 (0.72), 5.759 (0.45), 7.342 (1.22), 7.361 (2.76), 7.377 (1.69), 7.384 (2.12), 7.393 (1.40), 7.413 (2.58), 7.426 (3.09), 7.437 (5.77), 7.443 (7.13), 7.457 (1.55), 7.591 (4.49), 7.615 (4.47), 7.665 (3.98), 7.679 (4.00), 10.126 (9.01).

Example 213

1-(4-[(2,6-difluorophenyl)carbamoyl]-3-{[(2S)-1,1,1-trifluoropropan-2-yl]oxy}phenyl)-4-ethyl-5-oxo-4,5-dihydro-1H-1,2,4-triazole-3-carboxylic acid

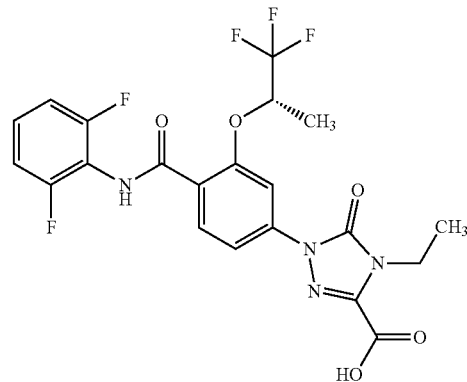 [SMILES: CCn1c(C(=O)O)nn(-c2ccc(C(=O)Nc3c(F)cccc3F)c(O[C@@H](C)C(F)(F)F)c2)c1=O]

Synthesized analogously to Example 211 from Example 177 LC-MS (Method A): $R_t$=1.04 min; MS (ESIpos): m/z=501 [M+H]$^+$ $^1$H-NMR (400 MHz, DMSO-d6) δ [ppm]: 1.107 (0.58), 1.149 (0.89), 1.154 (0.46), 1.172 (0.74), 1.180 (0.81), 1.190 (0.43), 1.228 (7.05), 1.246 (16.00), 1.264 (7.09), 1.389 (0.62), 1.406 (0.66), 1.495 (8.79), 1.511 (8.76), 1.907 (1.24), 1.987 (1.12), 2.084 (1.24), 2.332 (1.59), 2.336 (0.70), 2.518 (8.33), 2.523 (5.54), 2.539 (1.08), 2.678 (0.70), 3.992 (1.82), 4.010 (5.69), 4.027 (5.58), 4.045 (1.70), 5.278 (0.62), 5.294 (1.43), 5.310 (1.86), 5.325 (1.39), 5.341 (0.54), 5.758 (1.55), 6.971 (1.32), 7.098 (1.67), 7.186 (2.67), 7.206 (5.50), 7.226 (4.61), 7.362 (0.62), 7.378 (1.36), 7.399 (1.94), 7.415 (1.08), 7.437 (0.43), 7.727 (0.97), 7.749 (7.32), 7.776 (0.81), 7.895 (4.46), 8.136 (0.43), 9.770 (10.11).

Example 214

4-ethyl-1-(2-fluoro-4-[(2-fluoro-6-methylphenyl)carbamoyl]-5-{[(2S)-1,1,1-trifluoropropan-2-yl]oxy}phenyl)-5-oxo-4,5-dihydro-1H-1,2,4-triazole-3-carboxylic acid

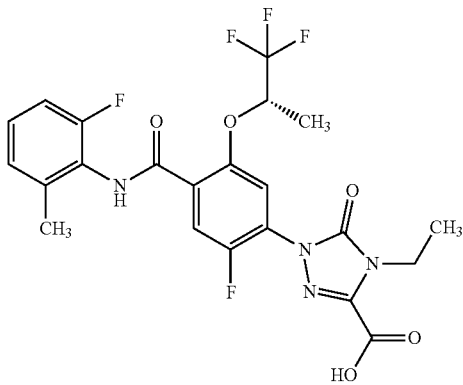 [SMILES: CCn1c(C(=O)O)nn(-c2cc(O[C@@H](C)C(F)(F)F)c(C(=O)Nc3c(C)cccc3F)cc2F)c1=O]

Synthesized analogously to Example 211 from Example 128 LC-MS (Method A): $R_t$=1.04 min; MS (ESIpos): m/z=515 [M+H]$^+$ $^1$H-NMR (400 MHz, DMSO-d6) δ [ppm]: 1.150 (0.58), 1.180 (0.56), 1.244 (0.98), 1.262 (2.20), 1.280 (0.97), 1.390 (0.41), 1.406 (0.42), 1.437 (1.78), 1.453 (1.78), 1.988 (0.44), 2.278 (4.12), 2.518 (1.26), 2.523 (0.86), 2.539 (16.00), 4.006 (0.80), 4.024 (0.79), 5.758 (2.61), 7.120 (0.55), 7.125 (0.57), 7.137 (0.65), 7.250 (0.41), 7.600 (0.92), 7.624 (0.89), 7.644 (0.65), 7.658 (0.64), 9.871 (1.14).

Example 215

1-(4-[(2,6-dichlorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid

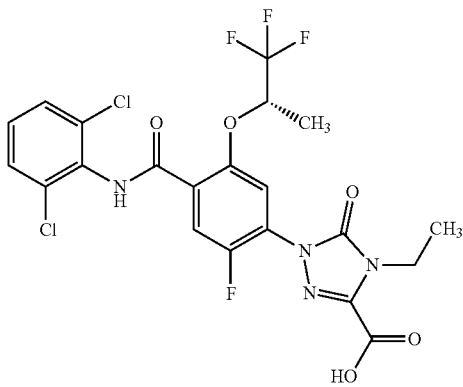 [SMILES: CCn1c(C(=O)O)nn(-c2cc(O[C@@H](C)C(F)(F)F)c(C(=O)Nc3c(Cl)cccc3Cl)cc2F)c1=O]

Synthesized analogously to Example 211 from Example 132 LC-MS (Method A): $R_t$=1.08 min; MS (ESIpos): m/z=551 [M+H]$^+$ $^1$H-NMR (400 MHz, DMSO-d6) δ [ppm]: 1.155 (1.67), 1.173 (3.63), 1.190 (1.86), 1.237 (0.84), 1.255 (1.82), 1.273 (0.82), 1.442 (1.52), 1.458 (1.52), 1.988 (6.89), 2.332 (0.41), 2.518 (2.30), 2.523 (1.54), 2.539 (16.00), 4.000 (0.65), 4.006 (0.68), 4.017 (1.69), 4.024 (0.68), 4.035 (1.58), 4.053 (0.49), 5.759 (0.80), 7.409 (0.60), 7.429 (0.55), 7.553 (0.75), 7.577 (0.78), 7.585 (2.17), 7.606 (1.58), 7.653 (0.48), 7.668 (0.47), 10.275 (1.05).

Example 216

1-(4-[(2-chloro-6-fluorophenyl)carbamoyl]-2-fluoro-3-{[(2S)-1,1,1-trifluoropropan-2-yl]oxy}phenyl)-4-ethyl-5-oxo-4,5-dihydro-1H-1,2,4-triazole-3-carboxylic acid

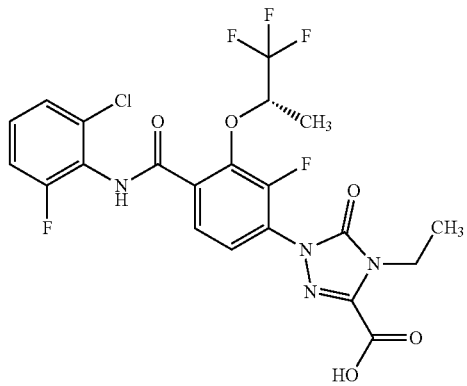 [SMILES: CCn1c(C(=O)O)nn(-c2ccc(C(=O)Nc3c(F)cccc3Cl)c(O[C@@H](C)C(F)(F)F)c2F)c1=O]

Synthesized analogously to Example 211 from Example 187 LC-MS (Method A): $R_t$=1.03 min; MS (ESIpos): m/z=535 [M+H]$^+$ $^1$H-NMR (400 MHz, DMSO-d6) δ [ppm]: 1.149 (9.59), 1.154 (5.51), 1.172 (8.74), 1.180 (9.39), 1.190 (4.47), 1.239 (7.38), 1.257 (15.42), 1.275 (7.26), 1.389 (5.70), 1.406 (5.96), 1.437 (12.96), 1.454 (12.96), 1.641 (1.04), 1.657 (1.68), 1.674 (1.10), 1.691 (0.45), 1.907 (1.75), 1.988 (16.00), 2.085 (0.65), 2.234 (1.68), 2.253 (3.04), 2.271 (1.49), 2.323 (2.79), 2.327 (3.69), 2.331 (2.79), 2.523 (12.44), 2.540 (2.59), 2.665 (2.79), 2.669 (3.76), 2.673 (2.79), 3.982 (1.94), 3.999 (7.00), 4.017 (9.26), 4.035 (5.38), 4.053 (1.30), 4.151 (0.45), 4.168 (1.43), 4.185 (1.43), 4.936 (0.91), 4.952 (2.14), 4.968 (2.79), 4.984 (2.01), 5.000 (0.78), 5.759 (1.04), 7.364 (1.23), 7.383 (2.91), 7.400 (1.81), 7.408 (2.53), 7.431 (2.85), 7.445 (3.24), 7.456 (6.02), 7.462 (7.19), 7.476 (1.62), 7.511 (2.40), 7.533 (5.31), 7.555 (3.37), 7.571 (3.17), 7.591 (1.55), 10.434 (7.90).

Example 217

1-(4-[(2-chloro-6-fluorophenyl)carbamoyl]-3-{[1,1-difluoropropan-2-yl]oxy}phenyl)-4-ethyl-5-oxo-4,5-dihydro-1H-1,2,4-triazole-3-carboxylic acid (Racemic)

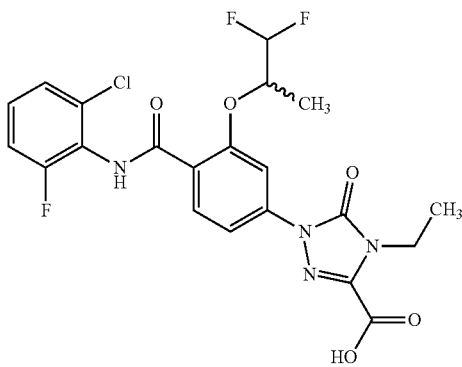 [SMILES: CCn1c(C(=O)O)nn(-c2ccc(C(=O)Nc3c(F)cccc3Cl)c(OC(C)C(F)F)c2)c1=O]

Synthesized analogously to Example 211 from Example 180 LC-MS (Method A): $R_t$=1.03 min; MS (ESIpos): m/z=499 [M+H]$^+$ $^1$H-NMR (400 MHz, DMSO-d6) δ [ppm]: 1.149 (14.12), 1.154 (4.12), 1.172 (5.56), 1.180 (14.06), 1.190 (2.88), 1.238 (7.37), 1.256 (16.00), 1.274 (7.31), 1.389 (8.75), 1.406 (9.25), 1.430 (10.06), 1.446 (10.00), 1.622 (0.50), 1.640 (1.50), 1.656 (2.50), 1.672 (1.62), 1.690 (0.63), 1.907 (1.88), 1.987 (9.63), 2.233 (2.50), 2.252 (4.63), 2.270 (2.19), 2.322 (2.63), 2.326 (3.56), 2.331 (2.56), 2.522 (11.00), 2.539 (2.12), 2.664 (2.75), 2.668 (3.69), 2.673 (2.63), 3.989 (1.88), 3.999 (2.00), 4.007 (5.94), 4.017 (3.75), 4.025 (5.81), 4.035 (3.19), 4.042 (1.81), 4.053 (0.94), 4.151 (0.69), 4.168 (2.25), 4.184 (2.19), 4.201 (0.69), 4.941 (1.12), 4.951 (1.06), 5.758 (0.44), 6.183 (1.06), 6.190 (1.00), 6.320 (2.06), 6.328 (2.06), 6.457 (0.94), 6.465 (1.00), 7.333 (1.19), 7.353 (2.88), 7.371 (1.94), 7.377 (2.12), 7.382 (1.56), 7.403 (2.63), 7.417 (2.75), 7.423 (2.00), 7.436 (6.12), 7.441 (5.06), 7.457 (1.75), 7.704 (2.75), 7.730 (3.19), 7.902 (4.63), 7.923 (8.19), 8.133 (0.44), 9.668 (8.81).

Example 218

1-(4-[(2-chloro-6-fluorophenyl)carbamoyl]-2-fluoro-5-{[(2S)-1,1,1-trifluoropropan-2-yl]oxy}phenyl)-4-methyl-5-oxo-4,5-dihydro-1H-1,2,4-triazole-3-carboxylic acid

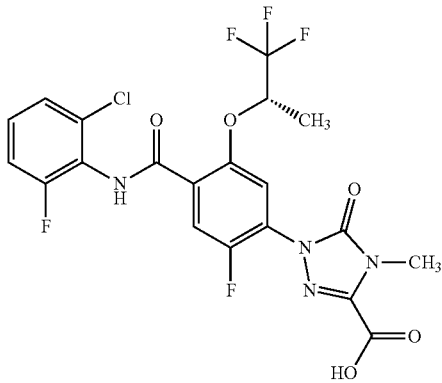 [SMILES: C[C@H](Oc1cc(-n2nc(C(=O)O)n(C)c2=O)c(F)cc1C(=O)Nc1c(F)cccc1Cl)C(F)(F)F]

Synthesized analogously to Example 211 from Example 119 LC-MS (Method A): $R_t$=0.99 min; MS (ESIpos): m/z=521 [M+H]$^+$ $^1$H-NMR (400 MHz, DMSO-d6) δ [ppm]: 1.442 (2.28), 1.458 (2.31), 1.907 (0.43), 2.084 (3.00), 2.518 (2.08), 2.523 (1.41), 2.539 (16.00), 3.334 (0.76), 5.335 (0.45), 7.360 (0.55), 7.384 (0.42), 7.412 (0.51), 7.426 (0.60), 7.436 (1.14), 7.443 (1.43), 7.590 (0.91), 7.614 (0.90), 7.638 (0.80), 7.652 (0.79), 10.126 (1.81).

Example 219

1-(2-fluoro-4-[(2-fluoro-6-methylphenyl)carbamoyl]-5-{[(2S)-1,1,1-trifluoropropan-2-yl]oxy}phenyl)-4-methyl-5-oxo-4,5-dihydro-1H-1,2,4-triazole-3-carboxylic acid

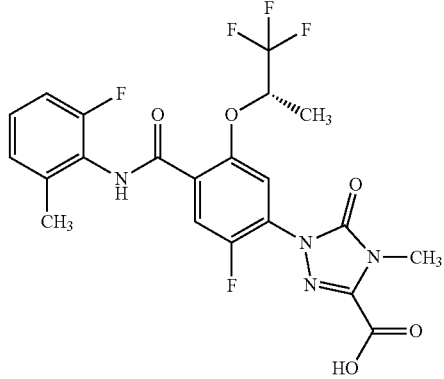 [SMILES: Cc1cccc(F)c1NC(=O)c1cc(F)c(-n2nc(C(=O)O)n(C)c2=O)cc1O[C@@H](C)C(F)(F)F]

Synthesized analogously to Example 211 from Example 127 LC-MS (Method A): $R_t$=0.99 min; MS (ESIpos): m/z=501 [M+H]$^+$ $^1$H-NMR (400 MHz, DMSO-d6) δ [ppm]: 1.436 (6.98), 1.452 (7.09), 1.907 (0.90), 2.084 (12.28), 2.278 (16.00), 2.518 (3.69), 2.523 (2.44), 3.340 (1.00), 5.320 (0.43), 5.335 (1.06), 5.351 (1.40), 5.367 (1.03), 5.383 (0.41), 7.105 (0.92), 7.120 (2.06), 7.125 (2.21), 7.137 (2.57), 7.147 (1.42), 7.230 (1.08), 7.244 (1.17), 7.250 (1.60), 7.264 (1.25), 7.269 (0.79), 7.283 (0.66), 7.602 (3.63), 7.621 (3.11), 7.626 (4.12), 7.636 (2.93), 8.136 (0.47), 9.875 (4.42).

Example 220

1-(4-[(2,6-difluorophenyl)carbamoyl]-2-fluoro-5-{[(2S)-1,1,1-trifluoropropan-2-yl]oxy}phenyl)-4-methyl-5-oxo-4,5-dihydro-1H-1,2,4-triazole-3-carboxylic acid

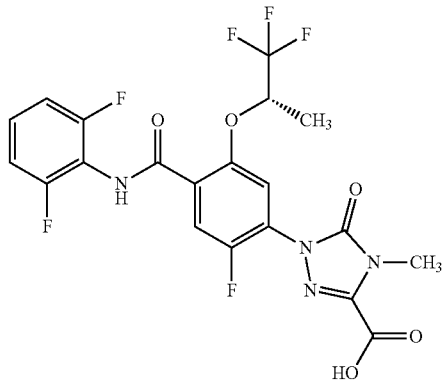 [SMILES: C[C@H](Oc1cc(-n2nc(C(=O)O)n(C)c2=O)c(F)cc1C(=O)Nc1c(F)cccc1F)C(F)(F)F]

N-(2,6-difluorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide (Example 96, 1.19 g, 2.43 mmol) was suspended in acetonitrile (10 mL) and water (10 mL). (Diacetoxyiodo)benzene (1.95 g, 6.07 mmol) was added, followed by TEMPO (2,2,6,6-tetramethylpiperidine 1-oxyl, 37.9 mg, 243 µmol). The mixture was stirred for 16 h at room temperature. Sodium hydroxide solution (1M) was added until the mixture was basic and the aqueous phase was washed with DCM. The aqueous phase was acidified with HCl (1N) and extracted with DCM twice. The combined organic phases were dried over sodium sulfate, filtered, and concentrated. Silica gel chromatography (DCM/MeOH) afforded the desired product (233 mg, 90% purity, 17% yield).

LC-MS (Method A): $R_t$=0.93 min; MS (ESIneg): m/z=503 [M−H]

$^1$H-NMR (400 MHz, DMSO-d6) δ [ppm]: 1.437 (14.48), 1.453 (14.44), 1.908 (2.02), 2.327 (0.74), 2.331 (0.56), 2.665 (0.57), 2.669 (0.76), 2.673 (0.59), 3.166 (0.64), 3.230 (0.64), 3.247 (0.69), 3.280 (1.11), 3.311 (2.86), 3.387 (1.34), 3.492 (2.12), 3.632 (0.40), 4.476 (0.86), 5.282 (1.03), 5.297 (2.32), 5.313 (2.97), 5.329 (2.23), 5.344 (0.92), 5.759 (16.00), 7.192 (4.65), 7.212 (9.56), 7.233 (5.92), 7.372 (1.07), 7.388 (2.37), 7.408 (3.37), 7.425 (1.86), 7.429 (1.86), 7.445 (0.77), 7.577 (6.72), 7.587 (6.01), 7.601 (10.94), 9.663 (0.52), 10.024 (11.69).

Example 221

1-(4-[(2-chloro-6-fluorophenyl)carbamoyl]-2-fluoro-5-{[(2S)-1,1,1-trifluoropropan-2-yl]oxy}phenyl)-5-oxo-4-propyl-4,5-dihydro-1H-1,2,4-triazole-3-carboxylic acid

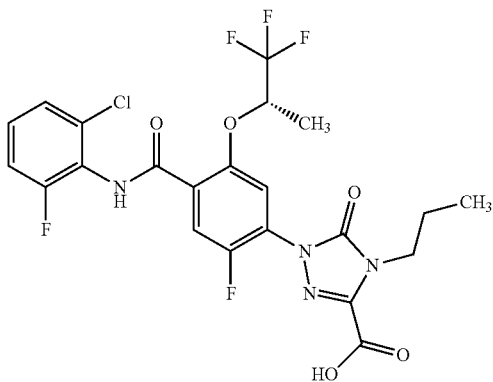 [SMILES: CCCn1c(C(=O)O)nn(-c2cc(O[C@@H](C)C(F)(F)F)c(C(=O)Nc3c(F)cccc3Cl)cc2F)c1=O]

Synthesized analogously to Example 220 from Example 182

LC-MS (Method A): $R_t$=1.08 min; MS (ESIpos): m/z=549 [M+H]$^+$ $^1$H-NMR (400 MHz, DMSO-d6) δ [ppm]: 0.877 (6.93), 0.896 (16.00), 0.914 (7.41), 1.444 (9.58), 1.460 (9.54), 1.653 (0.52), 1.670 (2.09), 1.689 (3.68), 1.707 (3.55), 1.726 (1.96), 1.745 (0.43), 2.074 (1.81), 2.084 (0.80), 2.323 (0.78), 2.327 (1.10), 2.331 (0.78), 2.518 (4.56), 2.523 (3.02), 2.665 (0.77), 2.669 (1.06), 2.673 (0.75), 3.344 (1.72), 3.925 (3.06), 3.944 (4.44), 3.961 (2.86), 5.318 (0.60), 5.334 (1.46), 5.350 (1.87), 5.366 (1.36), 5.382 (0.54), 5.759 (5.40), 7.342 (1.03), 7.361 (2.30), 7.377 (1.40), 7.385 (1.75), 7.393 (1.14), 7.413 (2.18), 7.426 (2.60), 7.437 (4.78), 7.443 (5.92), 7.458 (1.18), 7.592 (3.81), 7.616 (3.72), 7.671 (3.36), 7.686 (3.29), 10.127 (7.62).

Example 222

1-(4-[(2-chloro-6-fluorophenyl)carbamoyl]-5-{[3,3-difluorobutan-2-yl]oxy}-2-fluorophenyl)-4-ethyl-5-oxo-4,5-dihydro-1H-1,2,4-triazole-3-carboxylic acid (Racemic)

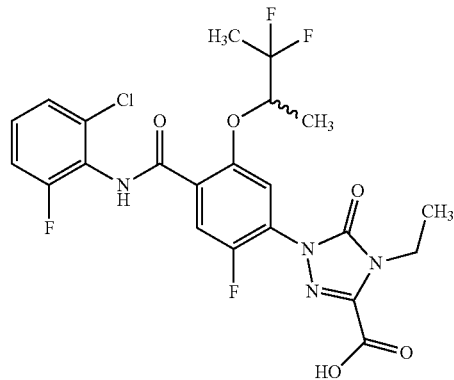 [SMILES: CCn1c(C(=O)O)nn(-c2cc(OC(C)C(C)(F)F)c(C(=O)Nc3c(F)cccc3Cl)cc2F)c1=O]

Synthesized analogously to Example 220 from Example 185

LC-MS (Method A): $R_t$=1.02 min; MS (ESIpos): m/z=531 [M+H]$^+$ $^1$H-NMR (400 MHz, DMSO-d6) δ [ppm]: 1.249 (4.49), 1.267 (9.83), 1.284 (4.47), 1.303 (0.42), 1.322 (0.53), 1.346 (7.18), 1.361 (7.08), 1.653 (4.09), 1.702 (7.88), 1.751 (3.65), 2.074 (0.59), 2.084 (16.00), 2.322 (0.95), 2.326 (1.23), 2.331 (0.89), 2.522 (4.75), 2.664 (0.93), 2.669 (1.21), 2.673 (0.89), 3.985 (1.19), 4.002 (3.58), 4.020 (3.50), 4.037 (1.10), 4.877 (0.53), 4.901 (0.95), 4.917 (0.97), 7.341 (0.72), 7.345 (0.78), 7.365 (1.80), 7.382 (1.14), 7.388 (1.42), 7.394 (1.04), 7.414 (1.72), 7.427 (1.93), 7.434 (1.78), 7.441 (3.62), 7.447 (4.39), 7.462 (0.97), 7.467 (0.70), 7.599 (3.18), 7.607 (2.90), 7.622 (5.09), 10.073 (5.79).

Example 223

1-(4-[(2-chloro-6-fluorophenyl)carbamoyl]-2-fluoro-5-{[(2S)-1,1,1-trifluoropropan-2-yl]oxy}phenyl)-4-cyclopropyl-5-oxo-4,5-dihydro-1H-1,2,4-triazole-3-carboxylic acid

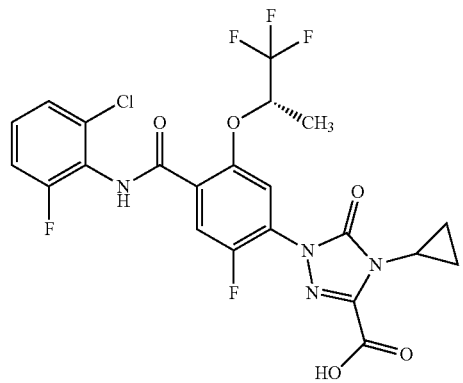 [SMILES: C[C@H](Oc1cc(-n2nc(C(=O)O)n(C3CC3)c2=O)c(F)cc1C(=O)Nc1c(F)cccc1Cl)C(F)(F)F]

Synthesized analogously to Example 220 from Example 181

LC-MS (Method A): $R_t$=1.02 min; MS (ESIpos): m/z=547 [M+H]$^+$ $^1$H-NMR (400 MHz, DMSO-d6) δ [ppm]: 0.939 (0.47), 0.984 (9.11), 0.995 (16.00), 1.309 (0.54), 1.437 (9.98), 1.453 (9.92), 2.080 (4.11), 2.323 (0.58), 2.665 (0.58), 3.096 (0.85), 3.110 (1.95), 3.123 (2.67), 3.135 (1.88), 3.150 (0.88), 3.340 (1.91), 5.275 (0.67), 5.291 (1.53), 5.307 (1.95), 5.322 (1.47), 5.337 (0.63), 5.755 (1.12), 7.336 (1.11), 7.355 (2.49), 7.372 (1.42), 7.379 (1.76), 7.387 (1.26), 7.408 (2.21), 7.421 (2.74), 7.432 (5.05), 7.438 (5.73), 7.452 (1.28), 7.573 (3.62), 7.597 (3.64), 7.616 (3.52), 7.630 (3.43), 10.117 (7.08).

Example 224

1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid

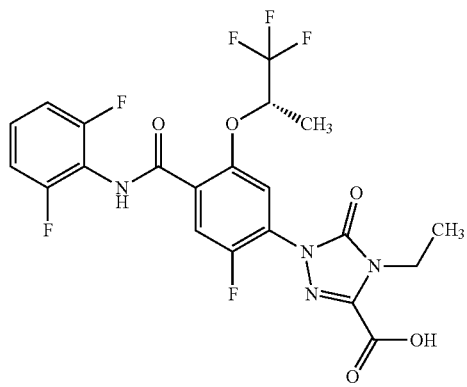 [SMILES: CCn1c(C(=O)O)nn(-c2cc(O[C@@H](C)C(F)(F)F)c(C(=O)Nc3c(F)cccc3F)cc2F)c1=O]

Synthesized analogously to Example 220 from Example 107

LC-MS (Method A): $R_t$=0.98 min; MS (ESIpos): m/z=519 [M+H]$^+$ $^1$H-NMR (400 MHz, DMSO-d6) δ [ppm]: 1.103 (0.72), 1.120 (0.43), 1.137 (0.80), 1.251 (7.48), 1.269 (15.37), 1.286 (7.61), 1.439 (12.44), 1.455 (12.09), 1.907 (5.00), 2.084 (2.93), 2.327 (1.06), 2.331 (0.80), 2.669 (1.15), 3.349 (1.72), 3.503 (0.63), 3.566 (16.00), 3.987 (2.81), 4.004 (6.30), 4.021 (5.72), 4.039 (1.87), 4.486 (0.50), 5.286 (0.91), 5.301 (1.96), 5.317 (2.57), 5.333 (1.98), 5.349 (0.89), 5.758 (4.20), 7.196 (3.85), 7.217 (7.87), 7.237 (4.93), 7.377 (0.87), 7.393 (1.98), 7.414 (2.89), 7.431 (1.63), 7.450 (0.69), 7.578 (0.72), 7.602 (0.59), 7.626 (4.63), 7.650 (5.07), 7.659 (4.89), 7.673 (4.39), 7.705 (0.69), 7.720 (0.61), 9.652 (1.43), 10.001 (0.54), 10.062 (8.74), 10.090 (1.15).

Example 225

1-(4-[(2-chloro-6-fluorophenyl)carbamoyl]-2-fluoro-5-{[(2S)-1,1,1-trifluoropropan-2-yl]oxy}phenyl)-5-oxo-4-(prop-2-en-1-yl)-4,5-dihydro-1H-1,2,4-triazole-3-carboxylic acid

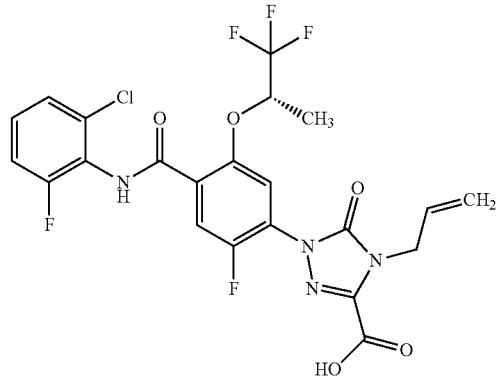 [SMILES: C=CCn1c(C(=O)O)nn(-c2cc(O[C@@H](C)C(F)(F)F)c(C(=O)Nc3c(F)cccc3Cl)cc2F)c1=O]

Synthesized analogously to Example 220 from Example 184

LC-MS (Method A): $R_t$=1.05 min; MS (ESIpos): m/z=547 [M+H]$^+$ $^1$H-NMR (400 MHz, DMSO-d6) δ [ppm]: 1.444 (14.87), 1.460 (15.35), 1.907 (0.79), 2.322 (1.44), 2.327 (2.02), 2.332 (1.50), 2.522 (16.00), 2.539 (6.80), 2.665 (1.47), 2.669 (1.95), 2.673 (1.44), 3.339 (6.19), 4.612 (7.62), 4.625 (8.00), 5.066 (4.00), 5.069 (4.03), 5.109 (4.38), 5.112 (4.44), 5.173 (4.62), 5.176 (4.48), 5.199 (4.99), 5.202 (4.85), 5.328 (0.96), 5.344 (2.22), 5.360 (2.97), 5.376 (2.29), 5.391 (0.96), 5.758 (1.74), 5.922 (1.13), 5.934 (2.56), 5.947 (2.12), 5.960 (2.70), 5.978 (2.67), 5.990 (1.98), 6.004 (2.26), 6.017 (0.96), 6.971 (1.40), 7.099 (1.81), 7.227 (1.44), 7.340 (1.61), 7.360 (3.66), 7.376 (2.26), 7.383 (2.80), 7.392 (1.98), 7.411 (3.49), 7.425 (4.10), 7.436 (7.59), 7.442 (9.33), 7.456 (2.19), 7.585 (5.78), 7.609 (5.74), 7.669 (5.09), 7.684 (5.13), 10.122 (11.62).

Example 226

1-(4-[(2-chloro-6-fluorophenyl)carbamoyl]-2-fluoro-5-{[(2S)-1,1,1-trifluoropropan-2-yl]oxy}phenyl)-4-cyclobutyl-5-oxo-4,5-dihydro-1H-1,2,4-triazole-3-carboxylic acid

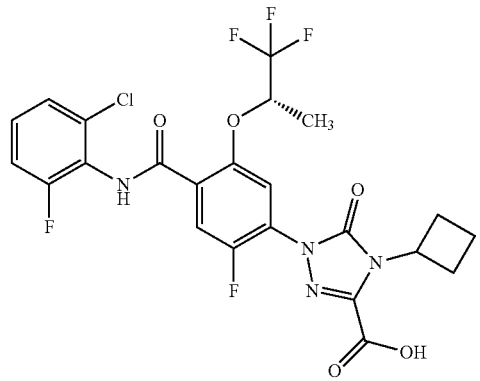 [SMILES: C[C@H](Oc1cc(-n2nc(C(=O)O)n(C3CCC3)c2=O)c(F)cc1C(=O)Nc1c(F)cccc1Cl)C(F)(F)F]

Synthesized analogously to Example 220 from Example 183

LC-MS (Method A): $R_t$=1.12 min; MS (ESIpos): m/z=561 [M+H]$^+$ $^1$H-NMR (400 MHz, DMSO-d6) δ [ppm]: 1.172 (0.43), 1.442 (8.65), 1.458 (8.79), 1.666 (0.57), 1.687 (1.15), 1.712 (1.51), 1.732 (1.33), 1.754 (1.61), 1.778 (1.26), 1.907 (0.90), 1.988 (0.75), 2.160 (0.93), 2.181 (2.55), 2.188 (1.87), 2.203 (2.51), 2.223 (0.97), 2.336 (0.86), 2.518 (16.00), 2.522 (9.47), 2.539 (3.52), 2.678 (0.75), 2.884 (0.54), 2.909 (1.87), 2.935 (2.58), 2.961 (1.79), 2.986 (0.54), 5.237 (1.29), 5.259 (1.90), 5.281 (1.29), 5.311 (0.61), 5.327 (1.33), 5.343 (1.72), 5.359 (1.29), 5.374 (0.54), 5.758 (1.51), 6.960 (1.15), 7.087 (1.40), 7.215 (1.18), 7.335 (0.86), 7.340 (0.97), 7.359 (2.15), 7.376 (1.29), 7.383 (1.61), 7.390 (1.11), 7.411 (2.01), 7.424 (2.37), 7.435 (4.45), 7.442 (5.56), 7.456 (1.18), 7.461 (0.75), 7.572 (3.48), 7.596 (3.41), 7.636 (2.83), 7.651 (2.87), 8.598 (0.72), 10.061 (0.43), 10.114 (6.71).

Example 227

1-(4-[(2,6-difluorophenyl)carbamoyl]-2-fluoro-5-{[(2S)-1,1,1-trifluoropropan-2-yl]oxy}phenyl)-4-methyl-5-oxo-4,5-dihydro-1H-1,2,4-triazole-3-carboxamide

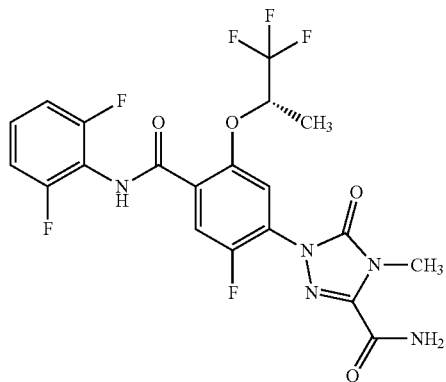 [SMILES: C[C@H](Oc1cc(-n2nc(C(N)=O)n(C)c2=O)c(F)cc1C(=O)Nc1c(F)cccc1F)C(F)(F)F]

1-(4-[(2,6-difluorophenyl)carbamoyl]-2-fluoro-5-{[(2S)-1,1,1-trifluoropropan-2-yl]oxy}phenyl)-4-methyl-5-oxo-4,5-dihydro-1H-1,2,4-triazole-3-carboxylic acid (Example 220, 100 mg, 198 μmol) was dissolved in DCM (7 mL) and DMF (0.76 μl, 9.9 μmol). Oxalyl chloride (35 μl, 400 μmol) was added dropwise and the mixture was stirred at room temperature for 20 min. The mixture was concentrated to yield the crude acid chloride.

The acid chloride was dissolved in DCM (2 mL) and added to a mixture of ammonia in dioxane (1.2 ml, 0.50 M, 590 μmol), trimethylamine (55 μl, 400 μmol) and DCM (2 mL), cooled to 0° C. The mixture was stirred at 0° C. for 1 h. The mixture was diluted with DCM and washed with water, dilute HCl, and saturated sodium bicarbonate solution. The organic phase was dried over sodium sulfate, filtered and concentrated. prepHPLC yields the desired compound (24.1 mg, 95% purity, 23% yield).

LC-MS (Method A): $R_t$=1.09 min; MS (ESIpos): m/z=504 [M+H]$^+$ $^1$H-NMR (400 MHz, DMSO-d6) δ [ppm]: 1.443 (6.24), 1.459 (6.16), 2.084 (9.13), 2.326 (0.84), 2.668 (0.85), 3.482 (16.00), 5.236 (0.43), 5.252 (0.98), 5.267 (1.29), 5.283 (0.97), 5.299 (0.41), 5.758 (1.95), 7.197 (1.85), 7.217 (3.79), 7.237 (2.33), 7.377 (0.42), 7.393 (0.95), 7.414 (1.35), 7.430 (0.77), 7.626 (2.40), 7.651 (3.11), 7.670 (2.27), 8.000 (2.10), 8.208 (2.26), 10.039 (3.60).

Example 228

1-(4-[(2-chloro-6-fluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxamide

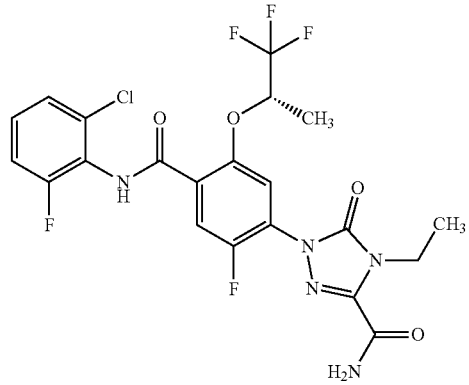 [SMILES: CCn1c(C(N)=O)nn(-c2cc(O[C@@H](C)C(F)(F)F)c(C(=O)Nc3c(F)cccc3Cl)cc2F)c1=O]

Synthesized analogously to Example 227 from Example 212 and aqueous ammonia.

LC-MS (Method A): $R_t$=1.17 min; MS (ESIpos): m/z=534 [M+H]$^+$ $^1$H-NMR (400 MHz, DMSO-d6) δ [ppm]: 1.154 (4.24), 1.172 (8.57), 1.190 (4.42), 1.241 (4.69), 1.258 (9.64), 1.276 (4.86), 1.451 (7.96), 1.467 (7.87), 1.885 (2.56), 1.988 (16.00), 2.323 (3.80), 2.327 (5.13), 2.331 (3.98), 2.665 (3.89), 2.669 (5.22), 2.673 (3.98), 3.999 (2.03), 4.017 (5.48), 4.035 (5.48), 4.053 (2.12), 5.316 (1.33), 5.333 (1.15), 5.759 (7.43), 7.361 (1.59), 7.385 (1.15), 7.413 (1.24), 7.427 (1.59), 7.438 (3.01), 7.444 (3.36), 7.593 (2.83), 7.617 (2.39), 7.650 (1.50), 7.688 (2.03), 7.702 (1.94), 8.029 (1.86), 8.237 (2.03), 10.104 (3.27).

Example 229

N-cyclopropyl-1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxamide

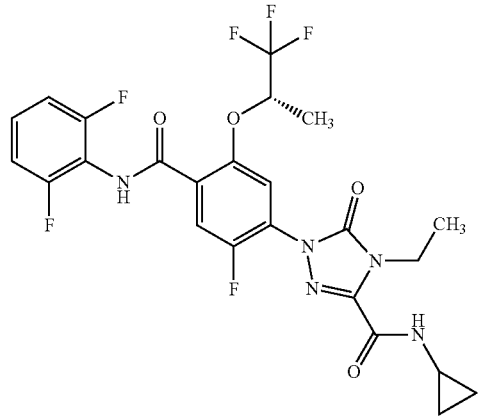 [SMILES: CCn1c(C(=O)NC2CC2)nn(-c2cc(O[C@@H](C)C(F)(F)F)c(C(=O)Nc3c(F)cccc3F)cc2F)c1=O]

Synthesized analogously to Example 227 from Example 224 and cyclopropanamine.

LC-MS (Method A): $R_t$=1.27 min; MS (ESIneg): m/z=556 [M−H]

$^1$H-NMR (400 MHz, DMSO-d6) δ [ppm]: 0.638 (1.35), 0.646 (1.84), 0.656 (0.76), 0.682 (0.73), 0.692 (1.42), 0.711 (1.46), 1.248 (1.81), 1.265 (3.94), 1.283 (1.96), 1.436 (2.98), 1.451 (3.14), 2.084 (16.00), 2.327 (0.42), 2.669 (0.42), 2.846 (0.58), 2.857 (0.64), 2.865 (0.42), 3.980 (0.52), 3.997 (1.56), 4.015 (1.55), 4.032 (0.52), 5.275 (0.47), 5.290 (0.63), 5.306 (0.49), 5.759 (15.65), 7.197 (0.95), 7.217 (2.02), 7.238 (1.28), 7.395 (0.48), 7.415 (0.72), 7.435 (0.41), 7.621 (1.25), 7.645 (1.21), 7.683 (1.11), 7.697 (1.14), 8.987 (0.87), 8.998 (0.90), 10.027 (1.11).

Example 230

1-(4-[(2,6-difluorophenyl)carbamoyl]-2-fluoro-5-{[(2S)-1,1,1-trifluoropropan-2-yl]oxy}phenyl)-N,4-dimethyl-5-oxo-4,5-dihydro-1H-1,2,4-triazole-3-carboxamide

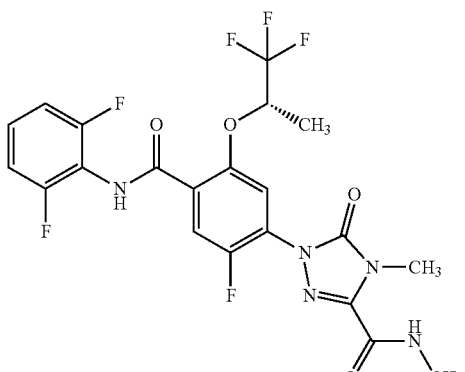

Synthesized analogously to Example 227 from Example 220 and methanamine in THF (2M).

LC-MS (Method A): $R_t$=1.13 min; MS (ESIpos): m/z=518 [M+H]$^+$ $^1$H-NMR (400 MHz, DMSO-d6) δ [ppm]: 1.439 (5.06), 1.455 (5.02), 2.331 (1.46), 2.336 (0.69), 2.518 (8.30), 2.523 (5.47), 2.761 (7.98), 2.774 (7.82), 3.485 (16.00), 5.253 (0.77), 5.269 (1.01), 5.285 (0.77), 7.193 (1.26), 7.214 (2.55), 7.234 (1.54), 7.388 (0.57), 7.408 (0.77), 7.626 (1.90), 7.650 (2.35), 7.671 (1.34), 8.801 (1.17), 8.813 (1.17), 10.043 (2.59).

Example 231

1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxamide

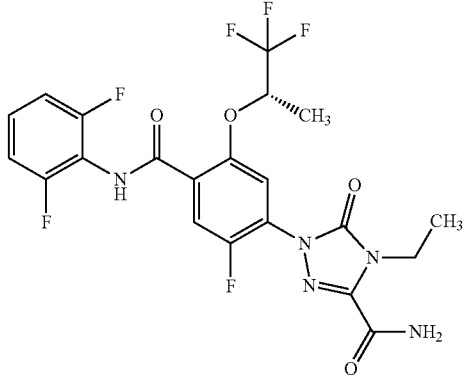 [SMILES: CCn1c(C(N)=O)nn(-c2cc(O[C@@H](C)C(F)(F)F)c(C(=O)Nc3c(F)cccc3F)cc2F)c1=O]

1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid (Example 224, 100 mg, 193 μmol) was dissolved in DCM (2 mL). 1-Chloro-1-dimethylamino-2-methyl-1-propene (38 μl, 290 μmol) was added dropwise and the mixture was stirred at room temperature for 30 min. Ammonia in methanol (7M) was added and the mixture was stirred at room temperature overnight. The mixture was diluted with water and was extracted with DCM (2×). The combined organic phases were dried over sodium sulfate, filtered and concentrated. prepHPLC yielded the desired compound (45.0 mg, 90% purity, 41% yield) as well as Example 232 and Example 233.

LC-MS (Method A): $R_t$=1.15 min; MS (ESIpos): m/z=518 [M+H]$^+$ $^1$H-NMR (400 MHz, DMSO-d6) δ [ppm]: 1.239 (4.13), 1.257 (8.41), 1.274 (4.19), 1.300 (0.60), 1.444 (6.92), 1.460 (6.60), 2.084 (2.01), 2.326 (1.02), 2.668 (1.06), 3.040 (0.76), 3.216 (0.78), 3.298 (0.60), 3.929 (0.57), 3.995 (1.22), 4.012 (3.32), 4.030 (3.23), 4.047 (1.09), 5.256 (0.46), 5.272 (1.04), 5.288 (1.38), 5.304 (1.08), 5.320 (0.55), 5.758 (16.00), 7.196 (2.10), 7.217 (4.27), 7.237 (2.63), 7.376 (0.48), 7.393 (1.11), 7.413 (1.52), 7.429 (0.92), 7.625 (2.51), 7.649 (2.56), 7.679 (2.35), 7.693 (2.26), 8.026 (2.03), 8.237 (2.28), 10.032 (1.27).

Example 232

1-(4-[(2,6-difluorophenyl)carbamoyl]-2-fluoro-5-{[(2S)-1,1,1-trifluoropropan-2-yl]oxy}phenyl)-4-ethyl-N,N-dimethyl-5-oxo-4,5-dihydro-1H-1,2,4-triazole-3-carboxamide

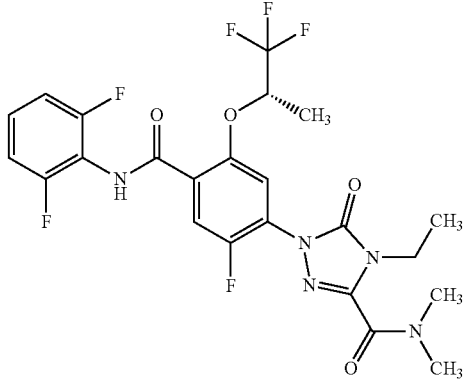 [SMILES: CCn1c(C(=O)N(C)C)nn(-c2cc(O[C@@H](C)C(F)(F)F)c(C(=O)Nc3c(F)cccc3F)cc2F)c1=O]

Isolated during the synthesis Example 231

LC-MS (Method A): $R_t$=1.22 min; MS (ESIneg): m/z=544 [M−H]

$^1$H-NMR (400 MHz, DMSO-d6) δ [ppm]: 1.242 (3.47), 1.260 (7.38), 1.277 (3.52), 1.440 (5.20), 1.456 (5.20), 2.327 (0.61), 2.669 (0.62), 3.041 (15.95), 3.217 (16.00), 3.756 (0.96), 3.773 (2.95), 3.791 (2.89), 3.809 (0.93), 5.284 (0.83), 5.299 (1.08), 5.315 (0.80), 5.760 (2.07), 7.193 (1.53), 7.214 (3.19), 7.234 (1.95), 7.389 (0.77), 7.410 (1.09), 7.426 (0.63), 7.611 (2.00), 7.635 (2.04), 7.651 (1.88), 7.666 (1.82), 10.027 (3.34).

Example 233 methyl 1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylate

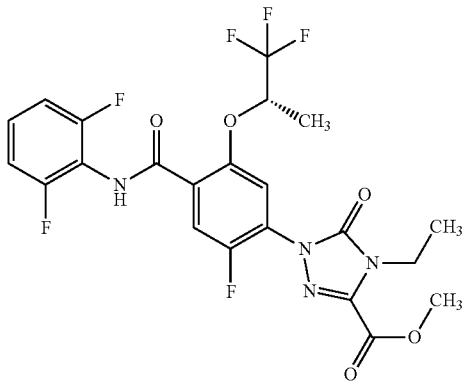 [SMILES: CCn1c(C(=O)OC)nn(-c2cc(O[C@@H](C)C(F)(F)F)c(C(=O)Nc3c(F)cccc3F)cc2F)c1=O]

Isolated during the synthesis Example 231

LC-MS (Method A): $R_t$=1.27 min; MS (ESIneg): m/z=531 [M−H]

$^1$H-NMR (400 MHz, DMSO-d6) δ [ppm]: 1.265 (3.38), 1.271 (2.25), 1.282 (6.96), 1.300 (3.50), 1.320 (1.45), 1.338 (0.71), 1.437 (5.66), 1.453 (5.56), 2.322 (1.05), 2.327 (1.40), 2.331 (0.98), 2.522 (6.20), 2.665 (1.10), 2.669 (1.45), 2.673 (1.03), 3.040 (0.44), 3.217 (0.44), 3.809 (0.56), 3.828 (0.54), 3.930 (16.00), 3.983 (1.13), 4.000 (2.89), 4.018 (2.72), 4.035 (0.86), 4.927 (1.57), 5.304 (0.93), 5.320 (1.25), 5.336 (0.98), 5.351 (0.44), 5.760 (4.61), 7.195 (1.81), 7.215 (3.72), 7.236 (2.25), 7.376 (0.42), 7.391 (0.96), 7.412 (1.27), 7.429 (0.76), 7.594 (0.42), 7.619 (0.71), 7.633 (2.23), 7.657 (3.75), 7.672 (1.81), 7.686 (0.44), 9.651 (0.91), 10.072 (2.25).

Example 234

5-fluoro-4-{3-[1-hydroxyethyl]-4-methyl-5-oxo-4,5-dihydro-1H-1,2,4-triazol-1-yl}-N-(2-methylphenyl)-2-{[(2S)-1,1,1-trifluoropropan-2-yl]oxy}benzamide (Mixture of Stereoisomers)

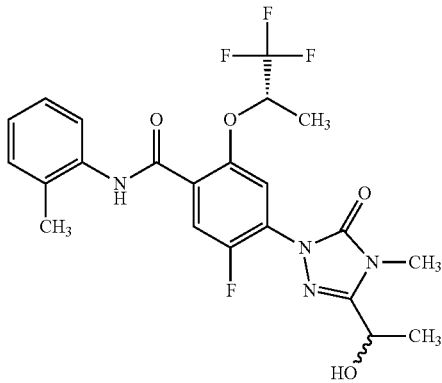 [SMILES: Cc1ccccc1NC(=O)c1cc(F)c(-n2nc(C(C)O)n(C)c2=O)cc1O[C@@H](C)C(F)(F)F]

Step A:

5-fluoro-4-{3-[(1R)-1-hydroxyethyl]-4-methyl-5-oxo-4,5-dihydro-1H-1,2,4-triazol-1-yl}-N-(2-methylphenyl)-2-[(2S)-1,1,1-trifluoropropan-2-yl]oxy}benzamide (Example 73, 150 mg, 311 μmol) was dissolved in dichloromethane (10 mL). Dess-Martin-periodinane (1,1,1-Tris(acetyloxy)-1,1-dihydro-1,2-benziodoxol-3-(1H)-one, 198 mg, 466 μmol) was added and the mixture was stirred overnight at room temperature. The mixture was diluted with water and extracted with DCM (3×). The combined organic phases were washed with sat. sodium bicarbonate solution and brine, dried over sodium sulfate, filtered and concentrated to yield crude 4-(3-acetyl-4-methyl-5-oxo-4,5-dihydro-1H-1,2,4-triazol-1-yl)-5-fluoro-N-(2-methylphenyl)-2-{[(2S)-1,1,1-trifluoropropan-2-yl]oxy}benzamide (159 mg, 106% yield, LC-MS (Method A): $R_t$=1.30 min; MS (ESIpos): m/z=481 [M+H]$^+$).

Step B:

The crude ketone from above (159 mg, 331 μmol) was dissolved in methanol (2 mL) and THF (1.5 mL) and cooled to 0° C. Sodium borohydride (22.5 mg, 596 μmol) was added and the mixture was stirred at 0° C. for an additional 30 min. The reaction was quenched with saturated ammonium chloride solution (10 mL) and extracted with DCM (3×). The combined organic phases were dried over sodium sulfate, filtered and concentrated. PrepHPLC yielded the desired product (47.0 mg, 90% purity, 26% yield).

LC-MS (Method A): $R_t$=1.17 min; MS (ESIpos): m/z=483 [M+H]$^+$ $^1$H-NMR (400 MHz, DMSO-d6) δ [ppm]: 1.438 (2.09), 1.458 (3.81), 1.474 (3.06), 2.263 (5.20), 2.518 (0.69), 2.523 (0.46), 3.334 (16.00), 3.343 (7.64), 4.792 (0.49), 5.361 (0.42), 5.828 (0.59), 5.843 (0.58), 7.145 (0.63), 7.148 (0.63), 7.163 (0.51), 7.167 (0.49), 7.223 (0.58), 7.251 (0.68), 7.269 (0.48), 7.478 (0.72), 7.495 (0.61), 7.545 (0.86), 7.560 (0.85), 7.641 (1.09), 7.666 (1.10), 9.729 (1.24).

Example 235

4-{4-ethyl-5-oxo-3-[(1S)-2,2,2-trifluoro-1-hydroxyethyl]-4,5-dihydro-1H-1,2,4-triazol-1-yl}-5-fluoro-N-(2-methoxy-4-methylpyridin-3-yl)-2-{[(2S)-1,1,1-trifluoropropan-2-yl]oxy}benzamide (Mixture of Stereoisomers)

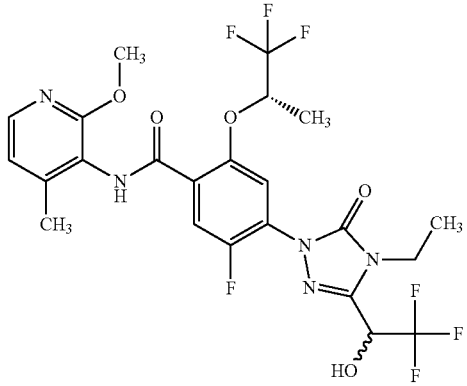 [SMILES: CCn1c(C(O)C(F)(F)F)nn(-c2cc(O[C@@H](C)C(F)(F)F)c(C(=O)Nc3c(C)ccnc3OC)cc2F)c1=O]

Step A:

4-[4-ethyl-3-(hydroxymethyl)-5-oxo-4,5-dihydro-1H-1,2,4-triazol-1-yl]-5-fluoro-N-(2-methoxy-4-methylpyridin-3-yl)-2-{[(2S)-1,1,1-trifluoropropan-2-yl]oxy}benzamide (Example 124, 620 mg, 95% purity, 1.15 mmol) was dissolved in dichloromethane (15 mL). Dess-Martin-periodinane (1,1,1-Tris(acetyloxy)-1,1-dihydro-1,2-benziodoxol-3-(1H)-one, 730 mg, 1.72 mmol) was added and the mixture was stirred for 2 h at room temperature. The mixture was diluted with water and extracted with DCM (3×). The combined organic phases were washed with sat. sodium bicarbonate solution and brine, dried over sodium sulfate, filtered and concentrated to yield crude 4-(4-ethyl-3-formyl-5-oxo-4,5-dihydro-1H-1,2,4-triazol-1-yl)-5-fluoro-N-(2-methoxy-4-methylpyridin-3-yl)-2-{[(2S)-1,1,1-trifluoropropan-2-yl]oxy}benzamide (695 mg, 90% purity, 107% yield, LC-MS (Method B): $R_t$=1.14 min; MS (ESIneg): m/z=510 [M−H]$^-$).

Step B:

The crude aldehyde from above (200 mg, 391 μmol) was dissolved in THF (2 mL) and cooled to 0° C. TBAF (tetra-n-butylammonium fluoride, 1M in THF, 20 μl, 20 μmol) was added followed by trifluoromethyltrimethylsilane (100 μl, 700 μmol). The resulting red solution was stirred at room temperature overnight. Additional TBAF (1M in THF, 20 μl, 20 μmol) was added followed by trifluoromethyltrimethylsilane (60 μl, 420 μmol) and the mixture was stirred at room temperature for 2 days. The mixture was filtered and purified using prepHPLC to yield the desired product (32.0 mg, 98% purity, 13% yield).

LC-MS (Method A): $R_t$=1.20 min; MS (ESIpos): m/z=582 [M+H]$^+$ $^1$H-NMR (400 MHz, DMSO-d6) δ [ppm]: 0.914 (1.42), 0.932 (3.62), 0.951 (1.73), 1.230 (0.30), 1.258 (2.36), 1.275 (5.39), 1.293 (2.72), 1.314 (0.76), 1.332 (0.44), 1.446 (3.95), 1.462 (3.96), 1.543 (0.34), 1.563 (0.42), 1.605 (0.21), 2.223 (10.84), 2.336 (0.17), 2.470 (0.35), 2.474 (0.37), 2.480 (0.49), 2.518 (2.32), 2.522 (1.45), 3.137 (0.49), 3.158 (0.43), 3.179 (0.47), 3.810 (0.21), 3.829 (0.53), 3.847 (1.21), 3.862 (16.00), 3.875 (1.28), 3.892 (0.49), 3.910 (0.20), 5.361 (0.25), 5.376 (0.59), 5.392 (0.77), 5.408 (0.57), 5.425 (0.23), 5.517 (0.29), 5.534 (0.77), 5.553 (0.72), 5.570 (0.24), 6.934 (1.91), 6.947 (2.04), 7.583 (2.26), 7.598 (1.68), 7.608 (2.56), 7.613 (1.78), 7.969 (2.59), 7.983 (2.57), 9.680 (1.27).

Experimental Section—Reference Compounds

Reference Compound 1

4-[3-(2,6-dichlorophenyl)-4-ethyl-5-oxo-4,5-dihydro-1H-1,2,4-triazol-1-yl]-2-methoxy-N-[3-(trifluoromethyl)phenyl]benzamide

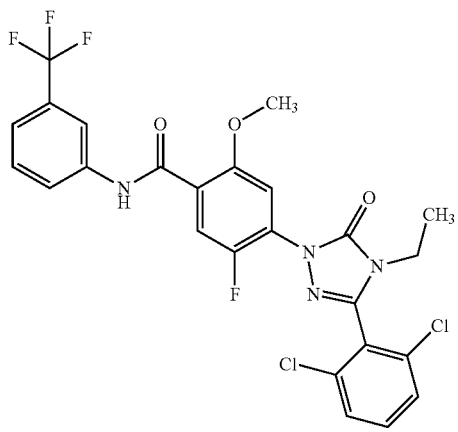 [SMILES: CCn1c(-c2c(Cl)cccc2Cl)nn(-c2cc(OC)c(C(=O)Nc3cccc(C(F)(F)F)c3)cc2F)c1=O]

Synthesis described in WO 2013/186692 A1, Example-70.

Experimental Section—Biological Assays

The following table 2 lists the abbreviations used herein, in particular in the Biological Assays part of the Experimental Section:

TABLE 2

Abbreviations

| | |
|---|---|
| ATCC | American Type Culture Collection |
| DDK | Name of a polypeptide tag |
| DCM | dichloromethane |
| DHODH | Dihydroorotate Dehydrogenase |
| DMSO | dimethylsulfoxide |
| h | hour(s) |
| IC$_{50}$ | half maximal inhibitory concentration |
| μM | micromolar |
| mM | millimolar |
| MTP | Microtiter plate |
| MYC | name of a polypeptide tag |
| μl | microliter |
| nM | nanomolar |
| PBS | Phosphate Buffered Saline |
| RPMI | Roswell Park Memorial Institute |
| rt | room temperature |
| THP | cell line name |
| Triton X | name of a detergent |
| Tris | tris(hydroxymethyl)aminomethane |

Examples were tested in selected biological assays one or more times. When tested more than once, data are reported as either average values or as median values, wherein
the average value, also referred to as the arithmetic mean value, represents the sum of the values obtained divided by the number of times tested, and
the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

The in vitro activity of the compounds of the present invention can be demonstrated in the following assays:

In Vitro Assay 1: DHODH Enzymatic Assay-1

The enzymatic assay couples DHODH activity with bleaching of the dye 2,6-dichlorophenolindophenol (DCIP) (Knecht and Loffler, 1998; Miller et al., 1968). The assay was conducted in buffer containing 50 mM Tris, 0.1% Triton X-100, 150 mM potassium chloride, 2 nM DHODH, 1 mM dihydroorotate, 0.1 mM decylubiquinone, 0.06 mM DCIP, and 2% DMSO at pH 8.0 at 32 degree Celsius. The reaction was initiated by addition of substrates. Enzyme activity was monitored kinetically by the reduction in DCIP absorbance at 600 nm. Purified recombinant human DHODH enzyme was purchased from Novus (cat. no. NBP1-98916). Other chemicals were purchased from Sigma-Aldrich. Absorbance measurements were obtained using a BMG clarion star plate-reading spectrophotometer.

In Vitro Assay 2: DHODH Enzymatic Assay-2

The enzymatic assay couples DHODH activity with bleaching of the dye 2,6-Dichlorophenolindophenol (DCIP) (Knecht and Loffler, 1998; Miller et al., 1968). The assay was conducted in aqueous buffer containing 50 mM Tris, 0.1% Triton X-100, 150 mM potassium chloride, 0.4 µg/mL DHODH, 1 mM dihydroorotate, 0.1 mM decylubiquinone, 0.06 mM DCIP, and 0.17% DMSO at pH 8.0 at room temperature. Compounds were added via pin transfer or via D300 digital dispenser, and the reaction was initiated by addition of substrates. Enzyme activity was monitored kinetically by the reduction in DCIP absorbance at 600 nm. Purified recombinant human DHODH (full-length, C-terminal MYC/DDK-tag) enzyme was purchased from Origene (cat. no. TP039034). Other chemicals, including leflunomide and teriflunomide, were purchased from Sigma-Aldrich. Absorbance measurements were obtained using a Molecular Devices Spectramax M5 plate-reading spectrophotometer.

In Vitro Assay 3: H460 (Lung Cancer)
Alamar Blue:

4000 cells/well of NCI-H460 cells were seeded in 90% RPMI 1640 (Invitrogen, #22400-089) and 10% fetal bovine serume (Invitrogen, #10099-141) and Penicillin/Streptomycin in 96 well plates. The next day, cells were incubated with different concentrations of test compounds for 72 h. Cellular viability was analysed incubating cells with 121 µl of Alamar Blue (Invitrogen) per well for 2 hours at 37° C. Finally the plate was analysed using excitation wavelength: 544 nm and emission wavelength: 590 nm.

CellTiter-Glo®:

250 cells/well of NCI-H460 cells were seeded in 90% RPMI 1640 (Invitrogen, #22400-089) and 10% fetal bovine serume (Invitrogen, #10099-141) and Penicillin/Streptomycin in 96 well plates. The next day, cells were incubated with different concentrations of test compounds for 72 h. Cellular viability was analyzed using CellTiter-Glo® Luminescent Cell Viability Assay (Promega, # G7572) according to manufacturer's instructions.

In Vitro Assay 4: THP-1 Proliferation Assay-1 (AML)

2000 cells/well of THP-1 cells were seeded in RPMI 1640 with Glutamax (Gibco, #11875-093) and 10% fetal calf serum (Biochrom, # S0615) in 384-well plates. The next day, cells were incubated with different concentrations of test compounds for 72 h. Cellular viability was analyzed using CellTiter-Glo® Luminescent Cell Viability Assay (Promega, # G7570) according to manufacturer's instructions.

TABLE 3

IC$_{50}$ values of examples and reference compound in in vitro assays 1-4

| Example No | In vitro Assay 1: DHODH enzymatic assay 1 IC$_{50}$ [mol/l] (mean values) | In vitro Assay 2: DHODH enzymatic assay 2 IC$_{50}$ [mol/l] (mean values) | In vitro Assay 3: H460 (lung cancer) IC$_{50}$ [mol/l] (mean values) | In vitro Assay 4: THP-1 proliferation assay (AML) IC$_{50}$ [mol/l] |
|---|---|---|---|---|
| 1 | 4.43E−08 | 9.00E−09 | | 3.73E−08 |
| 2 | 4.30E−08 | 1.40E−08 | | 9.43E−08 |
| 3 | 4.25E−07 | 1.49E−07 | | |
| 4 | 2.27E−06 | 1.10E−06 | | |
| 5 | 2.00E−08 | 1.90E−08 | | |
| 6 | 3.85E−06 | 7.55E−07 | | |
| 7 | 5.25E−08 | 1.70E−08 | | 3.12E−08 |
| 8 | 7.25E−08 | 5.20E−08 | | 5.01E−08 |
| 9 | 5.00E−06 | 2.10E−06 | | |
| 10 | 1.40E−07 | 2.10E−08 | | |
| 11 | 4.80E−08 | 8.00E−09 | | 7.18E−09 |
| 12 | 1.00E−07 | 1.70E−08 | | 3.70E−08 |
| 13 | 3.50E−08 | 1.10E−08 | | |
| 14 | 2.35E−06 | 7.38E−07 | | |
| 15 | 8.00E−07 | 6.65E−07 | | |
| 16 | 5.33E−09 | 1.30E−05 | 8.00E−10 | |
| 17 | 6.00E−09 | 1.00E−09 | | 2.35E−09 |
| 18 | 5.22E−09 | 3.00E−09 | | 4.78E−09 |
| 19 | 1.53E−07 | 6.43E−08 | 1.96E−08 | 6.21E−08 |
| 20 | 3.27E−07 | 5.68E−08 | 4.13E−08 | |
| 21 | 7.50E−07 | 8.57E−08 | 6.65E−08 | |
| 22 | 5.00E−07 | 7.16E−08 | 4.29E−08 | |
| 23 | 3.00E−08 | 1.70E−06 | 2.00E−09 | |
| 24 | 1.50E−08 | 5.40E−09 | 6.80E−09 | |
| 25 | | | | |
| 26 | 1.50E−07 | 1.60E−05 | 3.17E−08 | |
| 27 | | 2.13E−07 | 9.60E−09 | |
| 28 | 2.80E−08 | 5.46E−08 | 1.20E−08 | |
| 29 | 7.50E−07 | 8.49E−07 | 5.81E−08 | |
| 30 | | 2.52E−07 | 3.20E−08 | |
| 31 | 8.00E−08 | 1.90E−07 | 2.25E−08 | |
| 32 | | | 9.00E−10 | |
| 33 | 1.60E−08 | | 2.50E−09 | |
| 34 | 1.00E−07 | 4.09E−07 | 2.71E−08 | |
| 35 | 1.60E−07 | 4.18E−07 | 2.37E−08 | |
| 36 | 1.10E−08 | 2.80E−09 | 1.60E−09 | |
| 37 | 2.00E−08 | 2.24E−08 | 7.80E−09 | |
| 38 | 2.90E−08 | 3.77E−08 | 5.40E−09 | 2.16E−08 |
| 39 | 1.90E−07 | 5.50E−09 | 2.46E−08 | |
| 40 | 4.50E−07 | 2.19E−07 | 3.25E−08 | |
| 41 | 9.00E−07 | 1.10E−06 | 9.03E−08 | |
| 42 | | 2.00E−06 | 3.98E−08 | |
| 43 | 7.00E−08 | 2.89E−07 | 1.12E−08 | |

TABLE 3-continued

IC$_{50}$ values of examples and reference compound in in vitro assays 1-4

| Example No | In vitro Assay 1: DHODH enzymatic assay 1 IC$_{50}$ [mol/l] (mean values) | In vitro Assay 2: DHODH enzymatic assay 2 IC$_{50}$ [mol/l] (mean values) | In vitro Assay 3: H460 (lung cancer) IC$_{50}$ [mol/l] (mean values) | In vitro Assay 4: THP-1 proliferation assay (AML) IC$_{50}$ [mol/l] |
|---|---|---|---|---|
| 44 |  | 1.53E−08 | 3.50E−09 |  |
| 45 |  | 1.52E−07 | 1.50E−09 |  |
| 46 | 7.00E−07 | 3.50E−06 | 4.08E−08 |  |
| 47 | 1.70E−08 |  |  | 1.22E−08 |
| 48 | 7.50E−09 |  |  | 3.45E−09 |
| 49 | 1.60E−07 |  |  |  |
| 50 | 5.00E−08 |  |  | 1.61E−08 |
| 51 | 1.40E−08 |  |  |  |
| 52 | 4.00E−07 |  |  |  |
| 53 | 1.25E−08 |  |  | 6.00E−09 |
| 54 | 6.05E−09 |  |  |  |
| 55 | 1.00E−07 |  |  |  |
| 56 | 1.20E−07 |  |  |  |
| 57 | 4.40E−08 |  |  |  |
| 58 | 5.00E−07 |  |  |  |
| 59 | 9.00E−08 |  |  | 1.65E−07 |
| 60 | 1.50E−08 |  |  |  |
| 61 | 4.00E−07 |  |  |  |
| 62 | 1.50E−07 |  |  |  |
| 63 | 4.50E−07 |  |  |  |
| 64 | 2.00E−06 |  |  |  |
| 65 | 1.30E−08 |  |  | 3.55E−08 |
| 66 | 5.00E−09 |  |  | 1.23E−08 |
| 67 | 9.00E−08 |  |  |  |
| 68 | 1.30E−08 |  |  | 3.98E−09 |
| 69 | 1.50E−08 |  |  |  |
| 70 | 1.60E−07 |  |  |  |
| 71 | 7.75E−09 |  |  |  |
| 72 | 2.65E−08 |  |  | 1.92E−08 |
| 73 | 4.30E−08 |  |  | 3.60E−08 |
| 74 | 2.50E−06 | 1.10E−06 | 1.00E−12 |  |
| 75 |  | 7.20E−06 | 1.20E−12 |  |
| 76 |  | 2.00E−05 | 1.00E−12 |  |
| 77 |  |  | 3.29E−08 |  |
| 78 |  |  | 9.00E−10 |  |
| 79 |  |  | 1.90E−09 |  |
| 80 |  |  | 1.50E−09 |  |
| 81 |  |  | 7.00E−10 |  |
| 82 | 1.00E−06 |  | 1.50E−09 |  |
| 83 |  | 8.67E−07 | 2.90E−09 |  |
| 84 |  |  | 1.00E−09 |  |
| 85 |  | 2.12E−08 | 2.30E−09 |  |
| 86 |  |  |  |  |
| 87 |  |  | 6.00E−10 |  |
| 88 |  | 1.00E−06 | 1.51E−08 |  |
| 89 |  |  | 1.21E−08 |  |
| 90 |  | 1.30E−05 | 2.93E−07 |  |
| 91 |  | 5.90E−06 | 1.38E−08 |  |
| 92 | 3.00E−05 |  |  |  |
| 93 | 9.00E−07 |  |  |  |
| 94 | 1.43E−08 |  |  |  |
| 95 | 5.43E−08 |  |  | 8.33E−08 |
| 96 | 4.98E−08 |  |  | 1.06E−07 |
| 97 | 3.00E−06 |  |  |  |
| 98 | 1.13E−07 |  |  | 8.75E−08 |
| 99 | 6.00E−08 |  |  | 7.42E−08 |
| 100 | 8.50E−06 |  |  |  |
| 101 | 7.00E−07 |  |  |  |
| 102 | 9.00E−07 |  |  |  |
| 103 | 6.50E−08 |  |  | 1.73E−07 |
| 104 | 1.50E−07 |  |  |  |
| 105 | 1.50E−08 |  |  | 2.24E−08 |
| 106 | 1.31E−08 |  |  | 1.59E−08 |
| 107 | 1.43E−08 |  |  | 2.96E−08 |
| 108 | 1.10E−06 |  |  |  |
| 109 | 1.60E−08 |  |  | 3.40E−08 |
| 110 | 2.40E−07 |  |  |  |
| 111 | 3.50E−08 |  |  | 3.68E−08 |
| 112 | 6.00E−07 |  |  |  |
| 113 | 5.00E−07 |  |  |  |
| 114 | 2.50E−06 |  |  |  |

TABLE 3-continued

IC$_{50}$ values of examples and reference compound in in vitro assays 1-4

| Example No | In vitro Assay 1: DHODH enzymatic assay 1 IC$_{50}$ [mol/l] (mean values) | In vitro Assay 2: DHODH enzymatic assay 2 IC$_{50}$ [mol/l] (mean values) | In vitro Assay 3: H460 (lung cancer) IC$_{50}$ [mol/l] (mean values) | In vitro Assay 4: THP-1 proliferation assay (AML) IC$_{50}$ [mol/l] |
|---|---|---|---|---|
| 115 | 1.50E−07 | | | |
| 116 | 1.60E−07 | | | |
| 117 | 4.00E−06 | | | |
| 118 | 8.50E−06 | | | |
| 119 | 9.75E−09 | | | 8.66E−09 |
| 120 | 6.17E−09 | | | 2.40E−09 |
| 121 | 4.17E−09 | | | 4.25E−09 |
| 122 | 1.50E−08 | | | 1.05E−08 |
| 123 | 8.00E−08 | | | 9.33E−08 |
| 124 | 1.90E−08 | | | 3.33E−08 |
| 125 | 2.50E−08 | | | 3.20E−08 |
| 126 | 1.40E−07 | | | 1.13E−07 |
| 127 | 1.95E−08 | | | 2.45E−08 |
| 128 | 4.50E−09 | | | 1.12E−08 |
| 129 | 5.50E−09 | | | 6.28E−09 |
| 130 | 2.00E−08 | | | 1.77E−08 |
| 131 | 4.33E−09 | | | 6.64E−09 |
| 132 | 3.00E−09 | | | 4.02E−09 |
| 133 | 4.50E−09 | | | 3.18E−09 |
| 134 | 3.50E−09 | | | 5.95E−09 |
| 135 | 3.20E−09 | | | 2.21E−09 |
| 136 | 5.00E−09 | | | 3.51E−09 |
| 137 | 4.50E−09 | | | 7.23E−10 |
| 138 | 1.50E−08 | | | 1.74E−08 |
| 139 | 2.30E−08 | | | 1.60E−08 |
| 140 | 1.50E−08 | | | 5.83E−09 |
| 141 | 7.50E−09 | | | 4.28E−09 |
| 142 | 7.00E−09 | | | 1.73E−09 |
| 143 | 4.50E−09 | | | 1.02E−09 |
| 144 | 6.00E−08 | | | 3.98E−08 |
| 145 | 1.30E−08 | | | 1.51E−08 |
| 146 | 2.20E−08 | | | |
| 147 | 5.00E−06 | 2.00E−05 | 1.00E−12 | |
| 148 | | | | |
| 149 | | 2.00E−05 | 1.00E−13 | |
| 150 | | 1.80E−05 | 1.30E−12 | |
| 151 | 1.60E−06 | 7.10E−06 | 1.00E−12 | |
| 152 | 2.00E−05 | 1.90E−05 | 1.00E−12 | |
| 153 | 3.00E−06 | 8.70E−06 | 1.00E−13 | |
| 154 | 7.50E−06 | 1.10E−05 | 1.00E−12 | |
| 155 | | 2.00E−05 | 1.00E−12 | |
| 156 | | | | |
| 157 | | | 9.28E−08 | |
| 158 | | | 7.46E−08 | |
| 159 | 1.00E−05 | 9.40E−06 | 1.00E−12 | |
| 160 | | | 7.86E−08 | |
| 161 | 7.00E−06 | 2.00E−05 | 1.00E−12 | |
| 162 | | 2.00E−05 | 1.00E−13 | |
| 163 | | | 1.00E−12 | |
| 164 | | 2.00E−05 | 1.00E−13 | |
| 165 | | | 5.02E−07 | |
| 166 | 1.50E−07 | 2.95E−07 | 5.04E−08 | |
| 167 | | 9.29E−08 | 7.70E−09 | |
| 168 | 4.00E−07 | 4.15E−08 | 1.46E−08 | |
| 169 | 9.00E−08 | 8.05E−08 | 1.51E−08 | |
| 170 | 5.50E−07 | 2.46E−07 | 1.56E−07 | |
| 171 | | | 1.00E−12 | |
| 172 | 1.80E−08 | 1.80E−09 | 3.60E−09 | 2.89E−08 |
| 173 | 2.50E−08 | 1.04E−07 | 9.10E−09 | 2.43E−08 |
| 174 | 5.50E−08 | | 8.90E−09 | 3.80E−08 |
| 175 | | | 4.50E−09 | |
| 176 | 3.90E−9 | | | 1.63E−9 |
| 177 | 2.50E−8 | | | 2.00E−8 |
| 178 | 6.00E−9 | | | 3.29E−9 |
| 179 | 2.10E−8 | | | 2.16E−8 |
| 180 | 4.20E−8 | | | 1.95E−8 |
| 181 | 1.70E−8 | | | 4.53E−8 |
| 182 | 2.80E−9 | | | 2.63E−9 |
| 183 | 7.00E−9 | | | 1.54E−8 |
| 184 | 2.50E−9 | | | 7.89E−9 |
| 185 | 1.00E−8 | | | 2.86E−9 |

TABLE 3-continued

IC$_{50}$ values of examples and reference compound in in vitro assays 1-4

| Example No | In vitro Assay 1: DHODH enzymatic assay 1 IC$_{50}$ [mol/l] (mean values) | In vitro Assay 2: DHODH enzymatic assay 2 IC$_{50}$ [mol/l] (mean values) | In vitro Assay 3: H460 (lung cancer) IC$_{50}$ [mol/l] (mean values) | In vitro Assay 4: THP-1 proliferation assay (AML) IC$_{50}$ [mol/l] |
|---|---|---|---|---|
| 186 | 1.20E−7 | | | 1.80E−7 |
| 187 | 2.50E−7 | | | |
| 188 | 4.50E−8 | | | 5.21E−8 |
| 189 | 2.00E−8 | | | 1.19E−8 |
| 190 | 5.00E−9 | | | 5.18E−8 |
| 191 | 2.40E−8 | | | |
| 192 | 4.30E−9 | | | 3.64E−9 |
| 193 | 5.20E−9 | | | |
| 194 | 5.20E−9 | | | |
| 195 | 2.80E−8 | | | 6.34E−9 |
| 196 | 4.50E−8 | | | |
| 197 | 4.20E−7 | | | |
| 198 | 1.70E−7 | | | |
| 199 | 8.50E−7 | | | |
| 200 | 7.00E−8 | | | |
| 201 | 2.20E−7 | | | |
| 202 | 4.50E−8 | | | |
| 203 | 1.60E−7 | | | |
| 204 | 5.50E−8 | | | |
| 205 | 7.00E−8 | | | |
| 206 | 6.50E−8 | | | |
| 207 | 2.90E−6 | | | |
| 208 | 3.10E−8 | | | |
| 209 | 6.50E−7 | | | |
| 210 | 9.00E−6 | | | |
| 211 | 6.00E−9 | | | |
| 212 | 1.50E−9 | | | 5.08E−7 |
| 213 | 9.00E−9 | | | |
| 214 | 8.50E−9 | | | |
| 215 | 1.50E−9 | | | |
| 216 | 3.00E−7 | | | |
| 217 | 5.00E−8 | | | |
| 218 | 6.50E−9 | | | 2.48E−6 |
| 219 | 2.50E−8 | | | 4.52E−6 |
| 220 | 4.00E−8 | | | 5.28E−7 |
| 221 | 1.00E−9 | | | 5.33E−7 |
| 222 | 7.00E−9 | | | 8.81E−7 |
| 223 | 1.40E−8 | | | 1.20E−7 |
| 224 | 7.50E−9 | | | 2.18E−7 |
| 225 | 2.00E−9 | | | 9.83E−7 |
| 226 | 1.30E−8 | | | 8.59E−8 |
| 227 | 6.30E−8 | | | 7.54E−8 |
| 228 | 3.00E−9 | | | 1.33E−9 |
| 229 | 2.20E−7 | | | |
| 230 | 7.50E−7 | | | |
| 231 | 2.00E−8 | | | 1.93E−8 |
| 232 | 1.50E−6 | | | |
| 233 | !2.35E−8 | | | 1.49E−7 |
| 234 | 2.50E−8 | | | |
| 235 | 1.70E−7 | | | 8.87E−8 |
| Ref. Cpd. 1 | 3.00E−05 | | | |

In accordance with further embodiments, the present invention provides compounds of general formula (I), that inhibit DHODH as described in in vitro assay 1 with an IC$_{50}$≤50 nM.

In accordance with further embodiments, the present invention provides compounds of general formula (I), that inhibit DHODH as described in in vitro assay 1 with an IC$_{50}$≤15 nM.

In accordance with further embodiments, the present invention provides compounds of general formula (I), that inhibit DHODH as described in in vitro assay 1 with an IC$_{50}$≤10 nM.

In accordance with further embodiments, the present invention provides compounds of general formula (I), that have shown activity in in vitro Assay 3.

In accordance with further embodiments, the present invention provides compounds of general formula (I), that have shown activity in any lung cancer assay (in vitro or cell based assay).

In Vitro Assay 5: THP-1 Proliferation Assay-2

Tumor and normal cells were cultivated in their respective media (ATCC recommended media). On day 1 of the assay, adherent cells were detached from the culture vessels by trypsinization. Suspension cells were centrifuged at 300×g and resuspended in fresh media. Cells were seeded at densities of 300-1000 cells/30 μL/well in the inner wells of white 384-well plates (Perkin Elmer). The outer wells of each plate were filled with 60 μL PBS/well to reduce evaporation. One plate was used for treatment of cells, the second plate was the start plate. All plates were incubated at 37° C., 5% $CO_2$ for 24 hrs. On day 2, 30 μL/well of CellTiter Glow (CTG, Promega) was added to the start plate, the plate was shaken at rt for 10 min on a laboratory plate shaker and then the plate was read in a Infinite M200 Pro MTP Reader (Tecan, Luminescence, 0.1s). Compounds from a 10 mM stock (in DMSO) were added in triplicates to the treatment plate in tenfold dilutions (from $1E^{-6}M$ to $1E^{-12}M$) with a HP D300 Digital Dispenser (the dispenser adds substances to wells in nanoliter volumes, therefore any volume added with this device does not count toward the final volume in the well). For rescue/specificity experiments with uridine, 100 μM uridine/well (diluted from a 10 mM stock solution in DMSO; Sigma-Aldrich) were added with the HP D300 Digital Dispenser. Treatment plates are incubated for a further 72 hrs at 37° C., 5% carbon dioxide, On day 5 of the assay, 30 μL/well of CellTiter Glow (CTG, Promega) was added to the treatment plate, the plate was shaken at rt for 10 min on a laboratory plate shaker and then the plate was read in a Infinite M200 Pro MTP Reader (Tecan, Luminescence, 0.1s).

In Vitro Assay 6: SUDHL-10 Proliferation Assay (Lymphom)

2000 cells/well of SUDHL-10 cells were seeded in RPMI 1640 with Glutamax (Gibco, #11875-093) and 10% fetal calf serum (Biochrom, # S0615) in 384-well plates. The next day, cells were incubated with different concentrations of test compounds for 72 h. Cellular viability was analyzed using CellTiter-Glo® Luminescent Cell Viability Assay (Promega, # G7570) according to manufacturer's instructions.

In Vitro Assay 7: xCelligence Proliferation Assay (HCT116 (Colorectal Carcinoma, A498 (Kidney Carcinoma), Panc1 (Pancreas Carcinoma) Cell Lines)

Impedance measurement is a dimensionless parameter termed Cell Index (CI) which is derived as a relative change in measured electrical impedance caused by an increase of cell number on the bottom of the cell culture well.

To determine CI, 2000 cells/well were seeded into 96-well E-plates. Cells were placed in the Real-Time Cell Analyzer (RTCA) station (ACEA Biosciences) and incubated for 24 h. Subsequently, compounds were added at concentrations as indicated and cells were replaced in the Real-Time Cell Analyzer (RTCA) station and analyzed until cells reach confluency. Impedance was measured every 60 min. Cell index was determined by the xCelligence software and presented as CI over time.

In Vitro Assay 8: U-87 MG Proliferation Assay (Glioblastoma)

U-87 MG cells were plated in MEM Earle's medium+10% FCS with 4000 cells/well in a 96-well microtiter plate (d−1). Compound was added at d0. Cell number was determined by Alamar Blue staining (2 h) at d0 and d3. Fluorescence was determined in Victor3 (Excitation 530 nm; emission 590 nm). C0 was defined as the signal measured at d4 for cells without treatment (0.1% DMSO). CI was defined as the signal measured at d0.

In Vitro Assay 9: Colo 205 Proliferation Assay (Colorectal Carcinoma)

COLO 205 cells were plated in RPM11640 medium with stable glutamine+10% FCS+10 mM Hepes+1 mM Natriumpyruvat+1× Non Essential Amino Acids with 4000 cells/well in a 96-well microtiter plate (d−1). Compound was added at d0. Cell number was determined by Alamar Blue staining (2 h) at d0 and d3. Fluorescence was determined in Victor3 (Excitation 530 nm; emission 590 nm). C0 was defined as the signal measured at d4 for cells without treatment (0.1% DMSO). CI was defined as the signal measured at d0.

| Example No. | in vitro assay 9: Colo 205 $IC_{50}$ [mol/l] (mean values) |
| --- | --- |
| 1 | 3.0E−6 |

In Vitro Assay 10: MKN-45 Proliferation Assay (Gastric Cancer)

MKN-45 cells were plated in RPM11640 medium with stable glutamine+20% FCS with 4000 cells/well in a 96-well microtiter plate (d−1). Compound was added at d0. Cell number was determined by Alamar Blue staining (2 h) at d0 and d3. Fluorescence was determined in Victor3 (Excitation 530 nm; emission 590 nm). C0 was defined as the signal measured at d4 for cells without treatment (0.1% DMSO). CI was defined as the signal measured at d0.

TABLE 4

$IC_{50}$ values of examples in in vitro assay 10

| Example No. | in vitro assay 10: MKN-45 $IC_{50}$ [mol/l] (mean values) |
| --- | --- |
| 1 | 2.6E−6 |

In Vitro Assay 11: MIA PaCa2 Proliferation Assay (Pancreatic Carcinoma)

MIA PaCa 2 cells were plated in DMEM/HAMS F12 medium+10% FCS+2,5% Horse Serum with 4000 cells/well in a 96-well microtiter plate (d−1). Compound was added at d0. Cell number was determined by Alamar Blue staining (2 h) at d0 and d3. Fluorescence was determined in Victor3 (Excitation 530 nm; emission 590 nm). C0 was defined as the signal measured at d4 for cells without treatment (0.1% DMSO). CI was defined as the signal measured at d0.

In Vitro Assay 12: DU 145 Proliferation Assay (Prostate Cancer)

DU 145 cells were plated in DMEM/HAMS F12 medium+10% FCS with 4000 cells/well in a 96-well microtiter plate (d−1). Compound was added at d0. Cell number was determined by Alamar Blue staining (2 h) at d0 and d3. Fluorescence was determined in Victor3 (Excitation 530 nm; emission 590 nm). C0 was defined as the signal measured at d4 for cells without treatment (0.1% DMSO). CI was defined as the signal measured at d0.

TABLE 5

$IC_{50}$ values of examples in in vitro assay 12

| Example No. | in vitro assay 12: DU 145 $IC_{50}$ [mol/l] (mean values) |
| --- | --- |
| 1 | 2.9E−7 |

Assay 13: MOLM 13 Differentiation Assay (AML)

20000 cells per well of MOLM 13 cells were seeded in RPMI 1640 with Glutamax (Gibco, #11875-093) and 10% fetal calf serum (Biochrom, # S0615) and incubated with different concentrations of test compounds for 96 h. After treatment for 10 min with Human TruStain FcX, (Biolegend, #422302) or BD Human Fc Block (#564220) at RT, cells were incubated with 2 μg/ml APC anti-mouse/human CD11b Antibody (Biolegend, Cat #101212) for 30 min at 4° C. Cells were analyzed by Fluorescence-activating cell sorting (FACS) (BD FACS Canto, BD Biosciences).

Assay 14: Cancer Cell Proliferation Panel

The CellTiter-Blue® Cell Viability Assay (# G8081, Promega) was used according to manufacturer's instructions. Briefly, cells were harvested from exponential phase cultures, counted and plated in 96-well flat-bottom microtiter plates at a cell density of 4,000-60,000 cells/well depending on the cell line's growth rate. After a 24 h recovery period to allow the cells to resume exponential growth, 10 μl of culture medium (four control wells/plate) or of culture medium with test compound were added. The compound was applied at 10 concentrations in duplicate in half-log increments up to 30 μM and treatment continued for three days. After three days treatment of cells, 20 μl/well CellTiter-Blue® reagent was added. Following an incubation period of up to four hours, fluorescence (FU) was measured by using the Enspire Multimode Plate Reader (excitation λ=531 nm, emission λ=615 nm).

For calculations, the mean values of duplicate/quadruplicate (untreated control) data were used.

TABLE 6

$IC_{50}$ values of Example 1 in assay 14 (Cancer Cell Proliferation Panel)

| Cell line | Origin* | abs $IC_{50}$ [μM] |
|---|---|---|
| SF-539 | gliosarcoma | 0.221 |
| HCT-116 | colorectal carcinoma | 0.028 |
| HT-29 | colorectal carcinoma | 0.041 |
| SNU-899 | head & neck cancer | 0.235 |
| CAL-27 | head & neck cancer | 0.087 |
| Jurkat | Leukemia | 0.014 |
| MOLT-3 | leukemia | 0.029 |
| MOLT-4 | leukemia | 0.019 |
| HL-60 | leukemia | 0.026 |
| MOLM-13 | leukemia | 0.014 |
| MV4-11 | leukemia | 0.033 |
| EM-2 | leukemia | 0.037 |
| JURL-MK1 | leukemia | 0.047 |
| SNU-398 | hepatocellular carcinoma | 0.1 |
| SNU-449 | hepatocellular carcinoma | 0.08 |
| NCI-H460 | lung cancer | 0.147 |
| NCI-H69 | lung cancer | 0.175 |
| OCI-LY7 | lymphoma | 0.073 |
| SUDHL-1 | lymphoma | 0.008 |
| HUT-78 | lymphoma | 0.029 |
| MINO | lymphoma | 0.01 |
| RAJI | lymphoma | 0.01 |
| MDA-MB-453 | breast cancer | 0.112 |
| SK-BR-3 | breast cancer | 0.289 |
| MM.1S | multiple myeloma | 0.094 |
| OPM-2 | multiple myeloma | 0.032 |
| IMR-32 | neuroblastoma | 0.005 |
| SH-SY5Y | neuroblastoma | 0.032 |
| A2780 | ovarian cancer | 0.033 |
| PANC-1 | pancreatic cancer | 0.041 |
| PA-TU-8902 | pancreatic cancer | 0.281 |
| PC-3M | prostate cancer | 0.306 |
| ACHN | renal cell carcinoma | 0.024 |
| Caki-1 | renal cell carcinoma | 0.186 |
| HT-1080 | sarcoma | 0.025 |
| SK-LMS-1 | sarcoma | 0.259 |

Cell Proliferation Panel 2 Assay

Cells were grown in RPMI 1640, 10% FBS, 2 mM L-alanyl-L-glutamine, 1 mM Na pyruvate or a special medium. Cells were seeded into 384-well plates and incubated in a humidified atmosphere of 5% $CO_2$ at 37° C. Compounds were added the day following cell seeding. At the same time, a time zero untreated cell plate was generated. After a 3-day incubation period, cells were fixed and stained to allow fluorescence imaging of nuclei.

Compounds were serially diluted in half-log steps from the highest test concentration 10 1M, and assayed over 10 concentrations with a maximum assay concentration of 0.1% DMSO. Automated fluorescence microscopy was carried out using a Molecular Devices ImageXpress Micro XL high-content imager, and images were collected with a 4× objective. 16-bit TIFF images were acquired and analyzed with MetaXpress 5.1.0.41 software.

Data Analysis

Cell proliferation was measured by the fluorescence intensity of an incorporated nuclear dye. The output is referred to as the relative cell count, where the measured nuclear intensity is transformed to percent of control (POC) using the following formula:

$$POC = \frac{I_x}{I_0} \times 100$$

Where $I_x$ is the nuclear intensity at concentration x, and $I_0$ is the average nuclear intensity of the untreated vehicle wells.

Cellular response parameters were calculated using non-linear regression to a sigmoidal single-site dose response model:

$$y = A + \frac{B - A}{1 + (C/x)^D}$$

Where y is a response measured at concentration x, A and B are the lower and upper limits of the response, C is the concentration at the response midpoint ($EC_{50}$), and D is the Hill Slope (Fallahi-Sichani, M., S. Honardejad, L. M. Heiser, J. W. Gray, and P. K. Sorger (2013). Metrics other than potency reveal systematic variation in responses to cancer drugs. Nat. Chem. Biol. 9: 708-714.).

Time zero non-treated plates were used to determine the number of doublings during the assay period, using the formula:

$$\text{Doublings} = \log_2\left(\frac{N}{N_{T0}}\right)$$

Where N is the cell number in untreated wells at the assay end point and $N_{T0}$ is the cell number at the time of compound addition.

Cell count $IC_{50}$ is the test compound concentration at 50% of maximal possible response. $EC_{50}$ is the test compound concentration at the curve inflection point or half the effective response (parameter C of the fitted curve solution).

Curve-fitting, calculations, and report generation was performed using a custom data reduction engine and MathIQ based software (AIM).

| Compound | Cell Line | Origin | Cell Count EC50 (microM) | Cell Count IC50 (microM) |
|---|---|---|---|---|
| Example 106 | Colo 320DM | Colorectal carcinoma | 3.40E−03 | 2.08E−02 |
| Example 106 | 786-O | Renal cell carcinoma | 3.67E−03 | 1.71E−02 |
| Example 106 | A498 | Renal cell carcinoma | >1.00E+01 | >1.00E+01 |
| Example 106 | ACHN | Renal cell carcinoma | 1.34E−02 | 8.69E−02 |
| Example 106 | ARH-77 | Leukemia | 3.21E−03 | 5.07E−03 |
| Example 106 | BC-1 | Lymphoma | 5.41E−03 | 9.14E−03 |
| Example 106 | BV-173 | Leukemia | 1.13E−02 | >1.00E+01 |
| Example 106 | Colo 205 | Colorectal carcinoma | 2.83E−03 | 3.99E−03 |
| Example 106 | CA46 | Lymphoma | 2.16E−02 | 1.45E−01 |
| Example 106 | CCRFCEM | Leukemia | 3.39E−03 | 5.52E−03 |
| Example 106 | CEM-C1 | Leukemia | 3.48E−03 | 4.95E−03 |
| Example 106 | CFPAC-1 | Pancreatic cancer | 1.74E−02 | 6.43E−02 |
| Example 106 | CML-T1 | Leukemia | 1.24E−03 | 1.69E−03 |
| Example 106 | CaOV3 | Ovarian carcinoma | 3.21E−01 | >1.00E+01 |
| Example 106 | DMS114 | Lung cancer | 3.40E−02 | >1.00E+01 |
| Example 106 | Daudi | Lymphoma | 3.64E−03 | 5.90E−03 |
| Example 106 | DLD-1 | Colorectal carcinoma | 3.27E−03 | 1.97E−02 |
| Example 106 | EM-2 | Leukemia | 2.85E−03 | 5.46E−03 |
| Example 106 | G-401 | Renal cell carcinoma | 5.53E−03 | 4.18E−02 |
| Example 106 | HCT-15 | Colorectal carcinoma | 1.80E−03 | 4.59E−03 |
| Example 106 | HCT-8 | Colorectal carcinoma | 2.26E−03 | 4.23E−03 |
| Example 106 | HCT-116 | Colorectal carcinoma | 4.07E−03 | 7.95E−03 |
| Example 106 | HT-29 | Colorectal carcinoma | 1.25E−02 | 7.54E−02 |
| Example 106 | JeKo-1 | Lymphoma | 6.22E−03 | 1.07E−02 |
| Example 106 | Jurkat | Leukemia | 2.47E−03 | 3.46E−03 |
| Example 106 | K562 | Leukemia | 3.76E−03 | 4.74E−03 |
| Example 106 | MOLT-3 | Leukemia | 4.32E−03 | 5.59E−03 |
| Example 106 | MOLT-16 | Leukemia | 2.97E−03 | 3.84E−03 |
| Example 106 | MEG01 | Leukemia | 2.53E−03 | 3.36E−02 |
| Example 106 | MHH-PREB-1 | Lymphoma | 2.31E−03 | 2.54E−03 |
| Example 106 | Mia PaCa-2 | Pancreatic cancer | 7.49E−03 | >1.00E+01 |
| Example 106 | MV-4-11 | Leukemia | 2.74E−03 | 4.14E−03 |
| Example 106 | NAMALWA | Lymphoma | 1.78E−03 | 4.13E−03 |
| Example 106 | NALM-6 | Leukemia | 3.25E−03 | 4.29E−03 |
| Example 106 | PA-1 | Ovarian carcinoma | 7.49E−03 | 1.07E−02 |
| Example 106 | PANC-1 | Pancreatic cancer | 2.29E−02 | >1.00E+01 |
| Example 106 | PSN-1 | Pancreatic cancer | 2.17E−03 | 1.24E−02 |
| Example 106 | Raji | Lymphoma | 3.81E−03 | 6.04E−03 |
| Example 106 | Ramos (RA 1) | Lymphoma | 2.52E−03 | 3.11E−03 |
| Example 106 | RPMI 8226 | Multiple Myeloma | 1.02E−02 | 1.82E−02 |
| Example 106 | SU-DHL-10 | Lymphoma | 1.99E−04 | >1.00E+01 |
| Example 106 | SHP-77 | Lung cancer | 7.46E−03 | 1.28E−01 |
| Example 106 | SU.86.86 | Pancreatic cancer | 2.64E−02 | >1.00E+01 |
| Example 106 | U266B1 | Multiple Myeloma | 3.45E−02 | >1.00E+01 |
| Example 121 | Colo 320DM | Colorectal carcinoma | 1.23E−03 | 5.10E−03 |
| Example 121 | 786-O | Renal cell carcinoma | 8.59E−04 | 2.36E−03 |
| Example 121 | A498 | Renal cell carcinoma | >1.00E+01 | >1.00E+01 |
| Example 121 | ACHN | Renal cell carcinoma | 3.12E−03 | 1.83E−02 |
| Example 121 | ARH-77 | Leukemia | 9.20E−04 | 1.39E−03 |
| Example 121 | BC-1 | Lymphoma | 1.02E−03 | 1.59E−03 |
| Example 121 | BV-173 | Leukemia | 9.06E−04 | 7.79E−02 |

-continued

| Compound | Cell Line | Origin | Cell Count EC50 (microM) | Cell Count IC50 (microM) |
|---|---|---|---|---|
| Example 121 | Colo 205 | Colorectal carcinoma | 8.36E−04 | 1.22E−03 |
| Example 121 | CA46 | Lymphoma | 3.11E−03 | 1.35E−02 |
| Example 121 | CCRFCEM | Leukemia | 9.93E−04 | 1.56E−03 |
| Example 121 | CEM-C1 | Leukemia | 9.10E−04 | 1.28E−03 |
| Example 121 | CFPAC-1 | Pancreatic cancer | 4.55E−03 | 1.64E−02 |
| Example 121 | CML-T1 | Leukemia | 3.52E−04 | 4.95E−04 |
| Example 121 | CaOV3 | Ovarian carcinoma | 1.29E−02 | >1.00E+01 |
| Example 121 | DMS114 | Lung cancer | 7.62E−03 | >1.00E+01 |
| Example 121 | Daudi | Lymphoma | 6.13E−04 | 1.02E−03 |
| Example 121 | DLD-1 | Colorectal carcinoma | 1.06E−03 | 4.01E−03 |
| Example 121 | EM-2 | Leukemia | 1.06E−03 | 1.97E−03 |
| Example 121 | G-401 | Kidney cancer | 2.19E−03 | >1.00E+01 |
| Example 121 | HCT-15 | Colorectal carcinoma | 9.21E−04 | 2.83E−03 |
| Example 121 | HCT-8 | Colorectal carcinoma | 1.27E−03 | 2.34E−03 |
| Example 121 | HCT-116 | Colorectal carcinoma | 8.64E−04 | 1.67E−03 |
| Example 121 | HT-29 | Colorectal carcinoma | 2.72E−03 | 1.10E−02 |
| Example 121 | JeKo-1 | Lymphoma | 1.79E−03 | 3.01E−03 |
| Example 121 | Jurkat | Leukemia | 6.38E−04 | 9.25E−04 |
| Example 121 | K562 | Leukemia | 1.03E−03 | 1.31E−03 |
| Example 121 | MOLT-3 | Leukemia | 1.14E−03 | 1.49E−03 |
| Example 121 | MOLT-16 | Leukemia | 8.42E−04 | 1.08E−03 |
| Example 121 | MEG01 | Leukemia | 6.60E−04 | 3.05E−03 |
| Example 121 | MHH-PREB-1 | Lymphoma | 7.42E−04 | 8.30E−04 |
| Example 121 | Mia PaCa-2 | Pancreatic cancer | 2.23E−03 | >1.00E+01 |
| Example 121 | MV-4-11 | Leukemia | 8.14E−04 | 1.20E−03 |
| Example 121 | NAMALWA | Lymphoma | 2.53E−04 | 1.56E−03 |
| Example 121 | NALM-6 | Leukemia | 9.23E−04 | 1.27E−03 |
| Example 121 | PA-1 | Ovarian carcinoma | 2.07E−03 | 2.88E−03 |
| Example 121 | PANC-1 | Pancreatic cancer | 3.50E−03 | >1.00E+01 |
| Example 121 | PSN-1 | Pancreatic cancer | 8.57E−04 | 6.46E−03 |
| Example 121 | Raji | Lymphoma | 8.56E−04 | 1.35E−03 |
| Example 121 | Ramos (RA 1) | Lymphoma | 7.18E−04 | 8.78E−04 |
| Example 121 | RPMI 8226 | Multiple Myeloma | 2.32E−03 | 4.21E−03 |
| Example 121 | SU-DHL-10 | Lymphoma | 1.26E−03 | 4.09E−03 |
| Example 121 | SHP-77 | Lung cancer | 1.53E−03 | 1.63E−02 |
| Example 121 | SU.86.86 | Pancreatic cancer | 5.08E−03 | >1.00E+01 |
| Example 121 | U266B1 | Multiple Myeloma | 4.88E−03 | >1.00E+01 |

The invention claimed is:

1. A compound of formula (I)

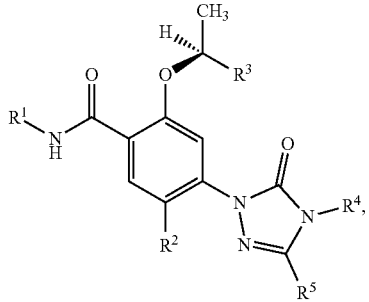

(I)

in which $R^1$ represents a group selected from
- a $C_5$-$C_8$-alkyl group,
- a $C_2$-$C_8$-haloalkyl group,
- a $C_4$-$C_8$-cycloalkyl group,
  which is optionally partially unsaturated and which is optionally substituted, one or two times, each substituent independently selected from a halogen atom or a group selected from
  hydroxy, phenyl and —N($R^7$)($R^8$),
  and wherein said phenyl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
- a $C_1$-$C_6$-alkyl group which is substituted with a $C_3$-$C_8$-cycloalkyl group, a $C_2$-$C_6$-alkyl group which is substituted with a cyano group, a hydroxy group, a phenyl group or a $C_3$-$C_8$-heterocycloalkyl group, a $C_3$-$C_6$-alkyl group which is substituted with a monocyclic—or bicyclic heteroaryl group, a ($C_2$-$C_6$-hydroxyalkyl)-O—($C_2$-$C_6$-alky)- group, a —($C_3$-$C_6$-alkyl)-N($R^7$)($R^8$) group, a —($C_3$-$C_8$-cycloalkyl)-N($R^7$)($R^8$) group, a —($C_3$-$C_6$-alkyl)-C(=O)N($R^7$)($R^8$) group, a 4-7-membered heterocycloalkyl group, a 5- to 7-membered heterocycloalkenyl group, wherein said 4-7-membered heterocycloalkyl group and said 5- to 7-membered heterocycloalkenyl group are connected to the rest of the molecule via a carbon atom, and which is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_6$-alkyl), —C(=O)($C_3$-$C_6$-cycloalkyl), —S(=O)$_2$($C_1$-$C_6$-alkyl) and oxo (=O), wherein said 5- to 6-membered heteroaryl substituent is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy, a phenyl group, which is optionally substituted, one, two, three, four or five times, each substituent independently selected from a halogen atom or a group selected from $C_1$-$C_6$-alkyl, $C_3$-$C_8$-cycloalkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), hydroxy, cyano, $C_1$-$C_6$-hydroxyalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)O$R^6$, —C(=O)N($R^7$)($R^8$), —N($R^7$)($R^8$), —($C_1$-$C_6$-alkyl))-N($R^7$)($R^8$), —($C_1$-$C_6$-alkyl)-C(=O)O$R^6$, —($C_1$-$C_6$-alkyl)-C(=O)N($R^7$)($R^8$), —O—C(=O)—($C_1$-$C_6$-alkyl)-, —SH, —S—($C_1$-$C_6$-alkyl), —S—($C_2$-$C_6$-alkenyl), —S(=O)$_2$N($R^7$)($R^8$), —S(=O)$_2$($C_1$-$C_6$-alkyl), —S(=O)$_2$—($C_2$-$C_6$-alkenyl), —S(=O)(=N$R^{11}$)($C_1$-$C_3$-alkyl), —N(O)$_2$, —P(=O)($C_1$-$C_3$-alkyl)$_2$ and SF$_5$, or wherein two vicinal substituents may form together a 5- or 6-membered, optionally heterocyclic, aromatic or non-aromatic ring, having optionally 1-3 heteroatoms independently selected from —N=, —NH—, —N($R^7$)—, —O—, —S—, and optionally containing a C(=O) group, and wherein the so formed ring is optionally substituted one or two times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —N(O)$_2$, and —N($R^7$)($R^8$) and a bicyclic aryl group, a partially saturated mono- or bicyclic aryl- or heteroaryl group, a monocyclic—or bicyclic heteroaryl group, which is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, —($C_1$-$C_6$-alkyl)-aryl, -aryl-($C_1$-$C_6$-alkyl), $C_3$-$C_8$-cycloalkyl, $C_1$-$C_6$-alkoxy, $C_1$-$C_6$-haloalkoxy, —O($C_2$-$C_6$-alkenyl), $C_3$-$C_8$-cycloalkoxy, aryl, —O-aryl, cyano, C(=O)O$R^6$, hydroxy, —SH, —S—($C_1$-$C_6$-alkyl), —S—($C_2$-$C_6$-alkenyl), —S(=O)$_2$($C_1$-$C_6$-alkyl), —S(=O)$_2$—($C_2$-$C_6$-alkenyl), —N(O)$_2$, and —N($R^7$)($R^8$), $R^2$ represents a hydrogen atom or a halogen atom, $R^3$ represents a group selected from, a $C_1$-$C_6$-alkyl group, which is optionally substituted with a $C_3$-$C_8$-cycloalkyl group, a $C_3$-$C_8$-cycloalkyl group, a $C_1$-$C_6$-haloalkyl group, a $C_1$-$C_6$-hydroxyalkyl group, a $C_2$-$C_6$-alkenyl group, a $C_2$-$C_6$-alkynyl group, a $C_4$-$C_8$-cycloalkenyl group, a ($C_1$-$C_6$-alkyl)-N($R^7$)$R^8$ group, a —($C_1$-$C_6$-alkyl)-(4- to 7-membered nitrogen containing heterocycloalkyl) group, wherein said 4- to 7-membered nitrogen containing heterocycloalkyl group is connected to the alkyl group via a carbon atom of the heterocycloalkyl group and which is optionally substituted with a $C_1$-$C_3$-alkyl group, and a phenyl group, which is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(O)OH, hydroxy, —SH, —S—($C_1$-$C_6$-alkyl), —S—($C_2$-$C_6$-alkenyl), —S(=O)$_2$($C_1$-$C_6$-alkyl), —S(=O)$_2$—($C_2$-$C_6$-alkenyl), —N(O)$_2$, and —N($R^7$)($R^8$)

$R^4$ represents a group selected from, a $C_1$-$C_6$-alkyl group, which is optionally substituted with a group selected from $C_3$-$C_8$-cycloalkyl and phenyl, wherein said phenyl group is optionally substituted, one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_8$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(=O)O$R^6$, hydroxy, —SH, —S—($C_1$-$C_6$-alkyl), —S—($C_2$-$C_6$-alkenyl), S(=O)$_2$($C_1$-$C_6$-alkyl), —S(=O)$_2$—($C_2$-$C_6$-alkenyl),—N(O)$_2$, and —N($R^7$)($R^8$)

a $C_2$-$C_6$-alkenyl group, a $C_3$-$C_8$-cycloalkyl group, a $C_2$-$C_6$-haloalkyl group, a $C_2$-$C_6$-hydroxyalkyl group, a —($C_2$-$C_6$-alkyl)-N($R^7$)($R^8$) group,

395

$R^5$ represents a halogen atom or a group selected from
- a $C_1$-$C_6$-alkyl group,
- a $C_3$-$C_8$-cycloalkyl group,
- a $C_1$-$C_6$-haloalkyl group, which is optionally substituted with a hydroxy group,
- a $C_1$-$C_6$-hydroxyalkyl group,
- a —($C_1$-$C_6$-alkyl)-N($R^7$)($R^8$) group,
- a —($C_1$-$C_6$-alkyl)-O—($C_1$-$C_6$-alkyl) group,
- a $C_2$-$C_6$-alkenyl group,
- a $C_2$-$C_6$-alkynyl group,
- a $C_1$-$C_6$-alkoxy group,
- a $C_1$-$C_6$-alkylsulfanyl group, and
- a —N($R^7$)($R^8$) group,
- a —C(═O)O$R^6$ group,
- a —C(═O)N($R^7$)($R^8$) group,
- a —S(═O)(═N$R^{11}$)($C_1$-$C_3$-alkyl) group, and
- a phenyl group
  which is optionally substituted one, two or three times, each substituent independently selected from a halogen atom or a group selected from $C_1$-$C_6$-alkyl, $C_1$-$C_6$-haloalkyl, $C_2$-$C_6$-alkenyl, $C_2$-$C_6$-alkynyl, aryl, —($C_1$-$C_6$-alkyl)-aryl, -aryl-($C_1$-$C_6$-alkyl), $C_3$-$C_5$-cycloalkyl, $C_1$-$C_6$-alkoxy, —O($C_2$-$C_6$-alkenyl), $C_1$-$C_6$-haloalkoxy, $C_3$-$C_8$-cycloalkoxy, aryl, —O-aryl, cyano, —C(═O)O$R^6$, hydroxy, —SH, —S—($C_1$-$C_6$-alkyl), —S—($C_2$-$C_6$-alkenyl), S(═O)$_2$($C_1$-$C_6$-alkyl), —S(═O)$_2$—($C_2$-$C_6$-alkenyl),—N(O)$_2$, and —N($R^7$)($R^8$)

$R^6$ represents a hydrogen atom or a group selected from
- a $C_1$-$C_6$-alkyl group and a benzyl group, $R^7$ and $R^8$ represent, independently for each occurrence, a hydrogen atom or a group selected from a $C_1$-$C_6$-alkyl group, a $C_2$-$C_6$-hydroxyalkyl group, a $C_3$-$C_6$-cycloalkyl group, and a —($C_2$-$C_6$-alkyl)-N($R^9$)($R^{10}$) group,
or
$R^7$ and $R^8$ together with the nitrogen to which they are attached represent a nitrogen containing 4- to 7-membered heterocycloalkyl group,
  which is optionally substituted with a group selected from $C_1$-$C_3$-alkyl, —S(═O)$_2$($C_1$-$C_3$-alkyl) and —C(═O)O($C_1$-$C_4$-alkyl), $R^9$ and $R^{10}$ represent, independently for each occurrence, a hydrogen atom or a $C_1$-$C_3$-alkyl group,
or
$R^9$ and $R^{10}$ together with the nitrogen to which they are attached represent a nitrogen containing 4- to 7-membered heterocycloalkyl group, $R^{11}$ represents a hydrogen atom or a group selected from
- a cyano group and a —C(═O)($C_1$-$C_3$-haloalkyl) group, or a tautomer, an N-oxide, a salt, a salt of a tautomer or a salt of an N-oxide thereof.

2. The compound according to claim 1 in which
$R^1$ represents a group selected from
- a $C_5$-$C_8$-alkyl group,
- a $C_2$-$C_8$-haloalkyl group,
- a $C_4$-$C_8$-cycloalkyl group,
  wherein said cycloalkyl groups are optionally substituted, one or two times, each substituent independently selected from a halogen atom or a group selected from hydroxy, phenyl and —N($R^7$)($R^8$),
  wherein said phenyl substituent is optionally substituted, one, two or three times, each substituent independently selected from a halogen atom or a group selected from

396

$C_1$-$C_3$-alkyl, $C_1$-$C_4$-haloalkyl, $C_1$-$C_3$-alkoxy and hydroxy,
- a $C_1$-$C_6$-alkyl group which is substituted with a $C_3$-$C_8$-cycloalkyl group,
- a $C_2$-$C_6$-alkyl group which is substituted with a cyano group, a hydroxy group or a phenyl group,
- a $C_3$-$C_6$-alkyl group which is substituted with a monocyclic—or bicyclic heteroaryl group,
- a ($C_2$-$C_6$-hydroxyalkyl)-O—($C_2$-$C_6$-alky)- group,
- a —($C_3$-$C_6$-alkyl)-N($R^7$)($R^8$) group,
- a —($C_3$-$C_8$-cycloalkyl)-N($R^7$)($R^8$) group,
- a —($C_3$-$C_6$-alkyl)-C(═O)N($R^7$)($R^8$) group,
- a 4- to 7-membered heterocycloalkyl group,
  which is optionally substituted one or two times, each substituent independently selected from a group selected from
  $C_1$-$C_3$-alkyl, 5- to 6-membered heteroaryl, —C(═O)O($C_1$-$C_4$-alkyl), —C(═O)($C_1$-$C_6$-alkyl), —C(═O)($C_3$-$C_6$-cycloalkyl), —S(═O)$_2$($C_1$-$C_6$-alkyl) and oxo (═O),
    wherein said 5- to 6-membered heteroaryl substituent is optionally substituted, one, two or three times, each substituent independently selected from a halogen atom or a group selected from
    $C_1$-$C_3$-alkyl, $C_1$-$C_4$-haloalkyl, $C_1$-$C_3$-alkoxy and hydroxy,
  and wherein said- to 7-membered heterocycloalkyl group is connected to the rest of the molecule via a carbon atom of the said heterocycloalkyl- or heterocycloalkenyl group,
- a 5- to 7-membered heterocycloalkenyl group,
  which is optionally substituted one or two times, each substituent independently selected from a group selected from
  $C_1$-$C_3$-alkyl, 5- to 6-membered heteroaryl, —C(═O)O($C_1$-$C_4$-alkyl), —C(═O)($C_1$-$C_6$-alkyl), —C(═O)($C_3$-$C_6$-cycloalkyl), —S(═O)$_2$($C_1$-$C_6$-alkyl) and oxo (═O),
    wherein said 5- to 6-membered heteroaryl substituent is optionally substituted, one, two or three times, each substituent independently selected from a halogen atom or a group selected from
    $C_1$-$C_3$-alkyl, $C_1$-$C_4$-haloalkyl, $C_1$-$C_3$-alkoxy and hydroxy,
  and wherein said 5- to 7-membered heterocycloalkenyl group is connected to the rest of the molecule via a carbon atom of the said heterocycloalkyl- or heterocycloalkenyl group,
- a phenyl group,
  wherein said phenyl group is optionally substituted, one, two, three, four or five times, each substituent independently selected from a halogen atom or a group selected from
  $C_1$-$C_6$-alkyl, $C_3$-$C_8$-cycloalkyl, $C_1$-$C_6$-haloalkyl, $C_1$-$C_6$-hydroxyalkyl, $C_1$-$C_6$-alkoxy, $C_1$-$C_6$-haloalkoxy, $C_3$-$C_5$-cycloalkoxy, hydroxy, cyano, —C(═O)O$R^6$, —C(═O)N($R^7$)($R^8$), —N($R^7$)($R^8$), —($C_1$-$C_6$-alkyl)-N($R^7$)($R^8$), —($C_1$-$C_6$-alkyl)-C(═O)O$R^6$, —($C_1$-$C_6$-alkyl)-C(═O)N($R^7$)($R^8$), —S(═O)$_2$N($R^7$)($R^8$), —S(═O)$_2$($C_1$-$C_3$-alkyl), —S(═O)(═N$R^{11}$)($C_1$-$C_3$-alkyl), —P(═O)($C_1$-$C_3$-alkyl)$_2$ and SF$_5$,
  or in which two substituents of said phenyl groups, when they are attached to adjacent ring atoms, are optionally linked to one another in such a way that they jointly form a group selected from —$CH_2$—$N(R^7)$—$CH_2$—, —$CH_2$—O—$CH_2$—, —O—$CH_2$—C(=O)—NH— and —NH—C(=O)—NH—, an indanyl group, a tetralinyl group
  wherein said indanyl or tetralinyl group is optionally substituted one or two times, each substituent independently selected from a halogen atom or a group selected from
    $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —$N(R^7)(R^8)$,
and
a monocyclic—or bicyclic heteroaryl group,
  which is optionally substituted one, two or three times, each substituent independently selected from a halogen atom or a group selected from
    $C_1$-$C_6$-alkyl, $C_1$-$C_6$-haloalkyl, $C_3$-$C_8$-cycloalkyl, $C_1$-$C_6$-alkoxy, $C_1$-$C_6$-haloalkoxy, $C_3$-$C_8$-cycloalkoxy, cyano, hydroxy and —$N(R^7)(R^8)$,
$R^2$ represents a hydrogen atom or a halogen atom,
$R^3$ represents a group selected from
  a $C_1$-$C_6$-alkyl group,
    which is optionally substituted with a $C_3$-$C_8$-cycloalkyl group,
  a $C_3$-$C_8$-cycloalkyl group,
  a $C_1$-$C_6$-haloalkyl group,
  a $C_1$-$C_6$-hydroxyalkyl group,
  a $C_2$-$C_6$-alkenyl group,
  a $C_2$-$C_6$-alkynyl group,
  a $C_4$-$C_8$-cycloalkenyl group,
  a ($C_1$-$C_6$-alkyl)-$N(R^7)R^8$ group,
  a —($C_1$-$C_6$-alkyl)-(4- to 7-membered nitrogen containing heterocycloalkyl) group and wherein said 4- to 7-membered nitrogen containing heterocycloalkyl group is optionally substituted with a $C_1$-$C_3$-alkyl group,
    and
    wherein said 4- to 7-membered nitrogen containing heterocycloalkyl group is connected to the alkyl group via a carbon atom of the heterocycloalkyl group,
  a phenyl group,
    wherein said phenyl group is optionally substituted, one, two or three times, each substituent independently selected from a halogen atom or a group selected from $C_1$-$C_3$-alkyl, $C_1$-$C_4$-haloalkyl, $C_1$-$C_3$-alkoxy and hydroxy,
$R^4$ represents a group selected from
  a $C_2$-$C_6$-alkylenyl group, a $C_3$-$C_8$-cycloalkyl group, a $C_2$-$C_6$-haloalkyl group,
  a $C_2$-$C_6$-hydroxyalkyl group and a-($C_2$-$C_6$-alkyl)-$N(R^7)(R^8)$ group, and
  a $C_1$-$C_6$-alkyl group,
    which is optionally substituted with a group selected from $C_3$-$C_8$-cycloalkyl and phenyl,
      wherein said phenyl group is optionally substituted, one, two or three times, each substituent independently selected from a halogen atom or a group selected from
        $C_1$-$C_3$-alkyl, $C_1$-$C_4$-haloalkyl, $C_1$-$C_3$-alkoxy and hydroxy,
$R^5$ represents a halogen atom or a group selected from
  a $C_1$-$C_6$-alkyl group,
  a $C_3$-$C_8$-cycloalkyl group,
  a $C_1$-$C_6$-haloalkyl group,
  a $C_1$-$C_6$-hydroxyalkyl group, which is optionally substituted with a hydroxy group,
  a ($C_1$-$C_3$-alkoxy)-($C_1$-$C_6$-alkyl)- group,
  a $C_2$-$C_6$-alkenyl group, a $C_2$-$C_6$-alkynyl group,
  a $C_1$-$C_6$-alkoxy group,
  a $C_1$-$C_6$-alkylsulfanyl group,
  a —($C_1$-$C_6$-alkyl)-$N(R^7)(R^8)$ group,
  a —$N(R^7)(R^8)$ group,
  a —C(=O)$OR^6$ group,
  a —C(=O)$N(R^7)(R^8)$ group, and a —S(=O)(=$NR^{11}$)($C_1$-$C_3$-alkyl) group,
$R^6$ represents a hydrogen atom or a group selected from a $C_1$-$C_6$-alkyl group and a benzyl group,
$R^7$ and $R^8$ represent, independently for each occurrence, a hydrogen atom or a group selected from a $C_1$-$C_6$-alkyl group, a $C_2$-$C_6$-hydroxyalkyl group, a —($C_2$-$C_6$-alkyl)-$N(R^9)(R^{10})$ group, and $C_3$-$C_6$-cycloalkyl group
or
$R^7$ and $R^8$ together with the nitrogen to which they are attached represent a nitrogen containing 4- to 7-membered heterocycloalkyl group,
  wherein said 4- to 7-membered nitrogen containing heterocycloalkyl group is optionally substituted with a group selected from
    $C_1$-$C_3$-alkyl, —S(=O)$_2$($C_1$-$C_3$-alkyl) and —C(=O)O($C_1$-$C_4$-alkyl),
$R^9$ and $R^{10}$ represent, independently for each occurrence, a hydrogen atom or a $C_1$-$C_3$-alkyl group,
or
$R^9$ and $R^{10}$ together with the nitrogen to which they are attached represent a nitrogen containing 4- to 7-membered heterocycloalkyl group,
$R^{11}$ represents a hydrogen atom or a group selected from a cyano group and a —C(=O)($C_1$-$C_3$-haloalkyl) group,
or a tautomer, an N-oxide, a salt, a salt of a tautomer or a salt of an N-oxide thereof.

3. The compound according to claim 1, wherein
$R^1$ represents a group selected from
  a $C_5$-$C_8$-alkyl group,
  a $C_2$-$C_8$-haloalkyl group,
  a $C_4$-$C_8$-cycloalkyl group,
    which is optionally substituted, one or two times, each substituent independently selected from a halogen atom or a group selected from
    hydroxy, phenyl and —$N(R^7)(R^8)$,
      wherein said phenyl substituent is optionally substituted, one, two or three times, each substituent independently selected from a halogen atom or a group selected from
        $C_1$-$C_3$-alkyl, $C_1$-$C_3$-haloalkyl, $C_1$-$C_3$-alkoxy and hydroxy,
  a $C_1$-$C_3$-alkyl group which is substituted with a $C_3$-$C_6$-cycloalkyl group,
  a $C_2$-$C_6$-alkyl group which is substituted with a cyano group, a hydroxy group or a phenyl group,
  a $C_3$-$C_6$-alkyl group which is substituted with a monocyclic or bicyclic heteroaryl group, a ($C_2$-$C_3$-hydroxyalkyl)-O—($C_2$-$C_6$-alky)- group,
  a —($C_3$-$C_6$-alkyl)-$N(R^7)(R^8)$ group,
  a —($C_3$-$C_6$-cycloalkyl)-$N(R^7)(R^8)$ group,
  a —($C_3$-$C_6$-alkyl)-C(=O)$N(R^7)(R^8)$ group,
  a 4- to 6-membered heterocycloalkyl group,
    which is optionally substituted one or two times, each substituent independently selected from a group selected from $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
   wherein said 5- to 6-membered heteroaryl group is optionally substituted, one, two or three times, each substituent independently selected from a halogen atom or a group selected from
   $C_1$-$C_3$-alkyl, $C_1$-$C_3$-haloalkyl, $C_1$-$C_3$-alkoxy and hydroxy,
   wherein said 4- to 6-membered heterocycloalkyl group is connected to the rest of the molecule via a carbon atom or nitrogen atom of the said heterocycloalkyl- or heterocycloalkenyl group,
a 5- to 6-membered heterocycloalkenyl group,
   which is optionally substituted one or two times, each substituent independently selected from a group selected from
   $C_1$-$C_3$-alkyl, 5- to 6-membered heteroaryl, —C(=O)O($C_1$-$C_4$-alkyl), —C(=O)($C_1$-$C_3$-alkyl), —C(=O)($C_3$-$C_6$-cycloalkyl), —S(=O)$_2$($C_1$-$C_3$-alkyl) and oxo (=O),
      wherein said 5- to 6-membered heteroaryl group is optionally substituted, one, two or three times, each substituent independently selected from a halogen atom or a group selected from
      $C_1$-$C_3$-alkyl, $C_1$-$C_3$-haloalkyl, $C_1$-$C_3$-alkoxy and hydroxy,
   wherein said 5- to 6-membered heterocycloalkenyl group is connected to the rest of the molecule via a carbon atom or nitrogen atom of the said heterocycloalkyl- or heterocycloalkenyl group,
a phenyl group,
   which is optionally substituted, one, two, three, four or five times, each substituent independently selected from a halogen atom or a group selected from $C_1$-$C_4$-alkyl, $C_3$-$C_6$-cycloalkyl, $C_1$-$C_3$-haloalkyl, $C_1$-$C_3$-hydroxyalkyl, $C_1$-$C_3$-alkoxy, $C_1$-$C_3$-haloalkoxy, $C_3$-$C_6$-cycloalkoxy, hydroxy, cyano, —C(=O)OR$^6$, —C(=O)N(R$^7$)(R$^8$), —N(R$^7$)(R$^8$), —($C_1$-$C_3$-alkyl)-N(R$^7$)(R$^8$), —($C_1$-$C_3$-alkyl)-C(=O)OR$^6$, —($C_1$-$C_3$-alkyl)-C(=O)N(R$^7$)(R$^8$), —S(=O)$_2$N(R$^7$)(R$^8$), —S(=O)$_2$($C_1$-$C_3$-alkyl), —S(=O)(=NR$^{11}$)($C_1$-$C_3$-alkyl), —P(=O)($C_1$-$C_3$-alkyl)$_2$ and SF$_5$, or in which two substituents of said phenyl groups, when they are attached to adjacent ring atoms, are optionally linked to one another in such a way that they jointly form a group selected from —CH$_2$—N(R$^7$)—CH$_2$—, —CH$_2$—O—CH$_2$—, —O—CH$_2$—C(=O)—NH— and —NH—C(=O)—NH—,
an indanyl group,
   which is optionally substituted one or two times, each substituent independently selected from a halogen atom or a group selected from
   $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N(R$^7$)(R$^8$),
a tetralinyl group and
   which is optionally substituted one or two times, each substituent independently selected from a halogen atom or a group selected from
   $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N(R$^7$)(R$^8$),
a monocyclic—or bicyclic heteroaryl group,
   which is optionally substituted one, two or three times, each substituent independently selected from a halogen atom or a group selected from
   $C_1$-$C_3$-alkyl, $C_1$-$C_3$-haloalkyl, $C_3$-$C_6$-cycloalkyl, $C_1$-$C_3$-alkoxy, $C_1$-$C_3$-haloalkoxy, $C_3$-$C_6$-cycloalkoxy, cyano, hydroxy and —N(R$^7$)(R$^8$),
R$^2$ represents a hydrogen atom or a halogen atom,
R$^3$ represents a group selected from
   a $C_1$-$C_6$-alkyl group,
   a $C_3$-$C_8$-cycloalkyl group,
   a $C_1$-$C_6$-haloalkyl group,
   a $C_1$-$C_6$-hydroxyalkyl group,
   a $C_2$-$C_6$-alkenyl group,
   a $C_2$-$C_6$-alkynyl group,
   a $C_4$-$C_6$-cycloalkenyl group,
   a ($C_1$-$C_6$-alkyl)-N(R$^7$)R$^8$ group,
   a —($C_1$-$C_6$-alkyl)-(4- to 6-membered nitrogen containing heterocycloalkyl) group and
   a phenyl group,
      wherein said $C_1$-$C_6$-alkyl group is optionally substituted with a $C_3$-$C_6$-cycloalkyl group or a NR$^7$R$^8$ group,
      and
      wherein said 4- to 6-membered nitrogen containing heterocycloalkyl group is optionally substituted with a $C_1$-$C_3$-alkyl group,
      and
      wherein said 4- to 6-membered nitrogen containing heterocycloalkyl group is connected to the alkyl group via a carbon atom of the heterocycloalkyl group, and
      wherein said phenyl group is optionally substituted, one, two or three times, each substituent independently selected from a halogen atom or a group selected from $C_1$-$C_3$-alkyl, $C_1$-$C_3$-haloalkyl, $C_1$-$C_3$-alkoxy and hydroxy,
R$^4$ represents a group selected from
   a $C_2$-$C_6$-alkylenyl group,
   a $C_3$-$C_6$-cycloalkyl group,
   a $C_2$-$C_6$-haloalkyl group,
   a $C_2$-$C_6$-hydroxyalkyl group,
   a —($C_2$-$C_6$-alkyl)-N(R$^7$)(R$^8$) group, and
   a $C_1$-$C_6$-alkyl group,
      which is optionally substituted with a group selected from
      $C_3$-$C_6$-cycloalkyl and phenyl,
         wherein said phenyl substituent is optionally substituted, one, two or three times, each substituent independently selected from a halogen atom or a group selected from
         $C_1$-$C_3$-alkyl, $C_1$-$C_3$-haloalkyl, $C_1$-$C_3$-alkoxy and hydroxy,
R$^5$ represents a halogen atom or a group selected from
   a $C_1$-$C_6$-alkyl group,
   a $C_3$-$C_6$-cycloalkyl group,
   a $C_1$-$C_6$-haloalkyl group, which is optionally substituted with a hydroxy group,
   a $C_1$-$C_6$-hydroxyalkyl group,
   a ($C_1$-$C_3$-alkoxy)-($C_1$-$C_6$-alkyl)- group,
   a $C_2$-$C_6$-alkenyl group,
   a $C_2$-$C_6$-alkynyl group,
   a $C_1$-$C_6$-alkoxy group,
   a $C_1$-$C_6$-alkylsulfanyl group,
   a —($C_1$-$C_6$-alkyl)-N(R$^7$)(R$^8$) group,
   a —N(R$^7$)(R$^8$) group,
   a —C(=O)OR$^6$ group, a —C(=O)N($R^7$)($R^8$) group, and a —S(=O)(=$NR^{11}$)($C_1$-$C_3$-alkyl) group $R^6$ represents a hydrogen atom or a group selected from a $C_1$-$C_4$-alkyl group and a benzyl group, $R^7$ and $R^8$ represent, independently for each occurrence, a hydrogen atom or a group selected from a $C_1$-$C_3$-alkyl group, a $C_2$-$C_3$-hydroxyalkyl group, a —($C_2$-$C_3$-alkyl)-N($R^9$)($R^{10}$) group and $C_3$-$C_6$-cycloalkyl group, or $R^7$ and $R^8$ together with the nitrogen to which they are attached represent a nitrogen containing 4- to 6-membered heterocycloalkyl group,
  wherein said 4- to 6-membered nitrogen containing heterocycloalkyl group is optionally substituted with a group selected from
  $C_1$-$C_3$-alkyl, —S(=O)$_2$($C_1$-$C_3$-alkyl) and —C(=O)O($C_1$-$C_4$-alkyl), $R^9$ and $R^{10}$ represent, identically or differently, a hydrogen atom or a $C_1$-$C_3$-alkyl group, or $R^9$ and $R^{10}$ together with the nitrogen to which they are attached represent a nitrogen containing 4- to 6-membered heterocycloalkyl group, $R^{11}$ represents a hydrogen atom or a group selected from a cyano group and a —C(=O)($C_1$-$C_3$-haloalkyl) group, or a tautomer, an N-oxide, a salt, a salt of a tautomer or a salt of an N-oxide thereof.

4. The compound according to claim 1, wherein $R^1$ represents a group selected from
  a $C_5$-$C_8$-alkyl group,
  a $C_4$-$C_8$-cycloalkyl group,
    which is optionally substituted, one or two times, with a phenyl group, wherein said phenyl substituent is optionally substituted, one, two or three times, each substituent independently selected from a halogen atom,
  a $C_1$-$C_3$-alkyl group which is substituted with a $C_3$-$C_6$-cycloalkyl group,
  a $C_2$-$C_6$-alkyl group which is substituted with a hydroxy group or a phenyl group,
  a $C_3$-$C_6$-alkyl group which is substituted with a monocyclic or bicyclic heteroaryl group, a —($C_3$-$C_6$-alkyl)-N($R^7$)($R^8$) group,
  a —($C_3$-$C_6$-alkyl)-C(=O)N($R^7$)($R^8$) group,
  a 4- to 6-membered heterocycloalkyl group,
    which is optionally substituted one or two times, each substituent independently selected from a $C_1$-$C_3$-alkyl group,
    and
    which is connected to the rest of the molecule via a carbon atom of the said heterocycloalkyl group,
  a phenyl group,
    which is optionally substituted, one, two, three or four times, each substituent independently selected from a halogen atom or a group selected from $C_1$-$C_4$-alkyl, $C_1$-$C_3$-haloalkyl, $C_1$-$C_3$-hydroxyalkyl, $C_1$-$C_3$-alkoxy, hydroxy, —C(=O)$OR^6$, —C(=O)N($R^7$)($R^8$), N($R^7$)($R^8$), —($C_1$-$C_3$-alkyl)-N($R^7$)($R^8$), —O—C(=O)—($C_1$-$C_4$-alkyl), —S—$C_1$-$C_3$-alkyl, —S(=O)$_2$($C_1$-$C_3$-alkyl), —S(=O)(=$NR^{11}$)($C_1$-$C_3$-alkyl) and —P(=O)($C_1$-$C_3$-alkyl)$_2$,
  an indanyl group and
  a monocyclic- or bicyclic heteroaryl group,
    which are optionally substituted one, two or three times, each substituent independently selected from a halogen atom or a group selected from $C_1$-$C_3$-alkyl and $C_1$-$C_3$-alkoxy, $R^2$ represents a hydrogen atom or a halogen atom, $R^3$ represents a group selected from
  a $C_1$-$C_6$-alkyl group,
  a $C_3$-$C_8$-cycloalkyl group,
  a $C_1$-$C_6$-haloalkyl group,
  a $C_2$-$C_6$-alkenyl group, and
  a phenyl group,
    wherein said $C_1$-$C_6$-alkyl group is optionally substituted with a $C_3$-$C_6$-cycloalkyl group or a $NR^7R^8$ group $R^4$ represents a group selected from
  a $C_2$-$C_6$-alkenyl group,
  a $C_3$-$C_6$-cycloalkyl group,
  a $C_2$-$C_6$-hydroxyalkyl group, and
  a $C_1$-$C_6$-alkyl group,
    which is optionally substituted with a group selected from $C_3$-$C_6$-cycloalkyl and phenyl, $R^5$ represents a halogen atom or a group selected from
  a $C_1$-$C_6$-alkyl group,
  a $C_3$-$C_6$-cycloalkyl group,
  a $C_1$-$C_6$-haloalkyl group, which is optionally substituted with a hydroxy group,
  a $C_1$-$C_6$-hydroxyalkyl group,
  a ($C_1$-$C_3$-alkoxy)-($C_1$-$C_6$-alkyl)- group,
  a $C_1$-$C_6$-alkoxy group,
  $C_1$-$C_6$-alkylsulfanyl group,
  ($C_1$-$C_6$-alkyl)-N($R^7$)($R^8$) group,
  a —N($R^7$)($R^8$) group,
  a —C(=O)$OR^6$ group,
  a —C(=O)N($R^7$)($R^8$) group,
  a —S(=O)(=$NR^{11}$)($C_1$-$C_3$-alkyl) group $R^6$ represents a hydrogen atom or a $C_1$-$C_4$-alkyl group, $R^7$ and $R^8$ represent, independently for each occurrence, a hydrogen atom or a $C_1$-$C_3$-alkyl group or a cyclopropyl group, and $R^{11}$ represents a hydrogen atom, or a tautomer, an N-oxide, a salt, a salt of a tautomer or a salt of an N-oxide thereof.

5. The compound according to claim 1, wherein $R^1$ represents a group selected from
  a $C_5$-$C_7$-alkyl group,
  a $C_5$-$C_7$-cycloalkyl group,
  a $C_1$-$C_2$-alkyl group which is substituted with a $C_5$-$C_7$-cycloalkyl group,
  a $C_2$-$C_6$-alkyl group which is substituted with a phenyl group,
  a $C_2$-$C_5$-hydroxyalkyl group,
  a —($C_3$-$C_8$-alkyl)-N($R^7$)($R^8$) group,
  a —($C_3$-$C_8$-alkyl)-C(=O)N($R^7$)($R^8$) group,
  a 5- to 6-membered heterocycloalkyl group,
    which is optionally substituted one or two times, with a $C_1$-$C_3$-alkyl group, and
    which is connected to the rest of the molecule via a carbon atom,
  a phenyl group,
    which is optionally substituted, one, two or three times, each substituent independently selected from a halogen atom or a group selected from $C_1$-$C_3$-alkyl, $C_1$-$C_3$-haloalkyl, $C_1$-$C_3$-alkoxy, hydroxy, —C(=O)$OR^6$, —C(=O)N($R^7$)($R^8$), —N($R^7$)($R^8$), —($C_1$-$C_3$-alkyl)-N($R^7$)($R^8$), —O—C(=O)—($C_1$-$C_4$-alkyl), —S—$C_1$-$C_3$-alkyl, —S(=O)$_2$—$C_1$-$C_3$-alkyl, —S(=O)(=NH)($C_1$-$C_3$-alkyl) and
  an indanyl group, and
  a monocyclic heteroaryl group, which is optionally substituted one or two times, each substituent independently selected from a group selected from $C_1$-$C_3$-alkyl and $C_1$-$C_3$-alkoxy,
$R^2$ represents a hydrogen atom or a halogen atom,
$R^3$ represents a group selected from
  a $C_1$-$C_6$-alkyl group,
  a $C_3$-$C_6$-cycloalkyl group,
  a $C_1$-$C_6$-haloalkyl group,
  a $C_2$-$C_6$-alkenyl group and
  a phenyl group,
    wherein said $C_1$-$C_6$-alkyl group is optionally substituted with a cyclopropyl group or a $NR^7R^8$ group,
$R^4$ represents a group selected from
  a $C_2$-$C_4$-alkenyl group,
  a $C_3$-$C_6$-cycloalkyl group,
  a $C_1$-$C_3$-hydroxyalkyl group, and
  a $C_1$-$C_8$-alkyl group,
    which is optionally substituted with a group selected from cyclopropyl and phenyl,
$R^5$ represents a halogen atom or a group selected from
  a $C_1$-$C_4$-alkyl group,
  a $C_3$-$C_6$-cycloalkyl group,
  a $C_1$-$C_3$-haloalkyl group, which is optionally substituted with a hydroxy group,
  a $C_1$-$C_3$-hydroxyalkyl group,
  ($C_1$-$C_3$-alkyl)-O—($C_1$-$C_3$-alkyl)- group,
  a $C_1$-$C_4$-alkoxy group,
  a $C_1$-$C_3$-alkylsulfanyl group,
  a —($C_1$-$C_3$-alkyl)-$N(R^7)(R^8)$ group,
  a —$N(R^7)(R^8)$ group,
  a —$C(=O)OR^6$ group,
  a —$C(=O)N(R^7)(R^8)$ group, and
  a —$S(=O)(=NR^{11})(C_1$-$C_3$-alkyl) group
$R^6$ represents a hydrogen atom or a $C_1$-$C_3$-alkyl group,
$R^7$ and $R^8$ represent, independently for each occurrence, a hydrogen atom or a $C_1$-$C_3$-alkyl group or a cyclopropyl group,
$R^{11}$ represents a hydrogen atom,
or a tautomer, an N-oxide, a salt, a salt of a tautomer or a salt of an N-oxide thereof.

6. The compound according to claim 1, wherein
$R^1$ represents a group selected from
  a $C_5$-$C_7$-alkyl group,
  a $C_5$-$C_7$-cycloalkyl group,
  a $C_1$-$C_2$-alkyl group which is substituted with a $C_5$-$C_6$-cycloalkyl group,
  a $C_2$-$C_6$-alkyl group which is substituted with a phenyl group,
  a $C_3$-$C_4$-hydroxyalkyl group,
  a —($C_3$-$C_4$-alkyl)-$N(R^7)(R^8)$ group,
  a $CH_3CH_2CH=C(=O)NH_2$ group,
  a 5- to 6-membered heterocycloalkyl group,
    which is optionally substituted one or two times, with a $C_1$-$C_3$-alkyl group, and
    which is connected to the rest of the molecule via a carbon atom,
  a phenyl group,
    which is optionally substituted, one, two or three times, each substituent independently selected from a halogen atom or a group selected from $C_1$-$C_3$-alkyl, $C_1$-$C_3$-haloalkyl, $C_1$-$C_3$-alkoxy, hydroxy, —$C(=O)OR^6$, —$C(=O)N(R^7)(R^8)$, —$N(R^7)(R^8)$, —O—$C(=O)$—($C_1$-$C_4$-alkyl), —S—$C_1$-$C_3$-alkyl, —$S(=O)_2$—$C_1$-$C_3$-alkyl, —$S(=O)(=NH)(C_1$-$C_3$-alkyl) and —($C_1$-$C_3$-alkyl)-$N(R^7)(R^8)$,
  an indanyl group, and
  a monocyclic heteroaryl group,
    which is optionally substituted one or two times, each substituent independently selected from a group selected from $C_1$-$C_3$-alkyl and $C_1$-$C_3$-alkoxy,
$R^2$ represents a hydrogen atom or a halogen atom,
$R^3$ represents a group selected from
  a $C_1$-$C_6$-alkyl group,
  a $C_3$-$C_6$-cycloalkyl group,
  a $C_1$-$C_3$-haloalkyl group,
  a $C_2$-$C_6$-alkenyl group and
  a phenyl group,
    wherein said $C_1$-$C_6$-alkyl group is optionally substituted with a cyclopropyl group or a $N(R^7)(R^8)$ group,
$R^4$ represents a group selected from
  a $C_2$-$C_4$-alkenyl group,
  a $C_3$-$C_8$-cycloalkyl group,
  a $C_1$-$C_3$-hydroxyalkyl group,
  a $C_1$-$C_4$-alkyl group,
    which is optionally substituted with a group selected from cyclopropyl and phenyl,
$R^5$ represents a halogen atom or a group selected from
  a $C_1$-$C_4$-alkyl group,
  a $C_3$-$C_5$-cycloalkyl group,
  a $C_1$-$C_3$-haloalkyl group, which is optionally substituted with a hydroxy group,
  a $C_1$-$C_3$-hydroxyalkyl group,
  a $CH_3O$—($C_1$-$C_2$-alkyl)- group,
  a $C_1$-$C_3$-alkoxy group,
  a methylsulfanyl group,
  a —($C_1$-$C_2$-alkyl)-$N(R^7)(R^8)$ group,
  a —$N(R^7)(R^8)$ group,
  a —$C(=O)OR^6$ group,
  a —$C(=O)N(R^7)(R^8)$ group, and
  a —$S(=O)(=NR^{11})(C_1$-$C_3$-alkyl) group
$R^6$ represents a hydrogen atom or a methyl group,
$R^7$ and $R^8$ represent, independently for each occurrence, a hydrogen atom or a $C_1$-$C_3$-alkyl group or a cyclopropyl group,
$R^{11}$ represents a hydrogen atom,
or a tautomer, an N-oxide, a salt, a salt of a tautomer or a salt of an N-oxide thereof.

7. The compound according to claim 1, wherein
$R^1$ represents a group selected from
  3-pentyl, 2,2-dimethylpropyl, 4-heptyl, 4-fluorophenylcyclopropyl, cyclopentyl, cyclohexyl, cycloheptyl, cyclopentylmethyl, cyclohexylmethyl, 1-cyclohexylethyl, 1-hydroxypropan-2-yl,
  2-hydroxypropyl, 1-hydroxybutan-2-yl, 1-cyanobutan-2-yl, 1-phenylbutan-2-yl, 1-amino-2-propyl, 1-amino-2-butyl, 1-amino-1-oxobutan-2-yl, indan-2-yl,
  a 5- to 6-membered heterocycloalkyl group, which is selected from tetrahydrofuran-3-yl, tetrahydro-2H-pyran-4-yl and piperidin-4-yl, and which is optionally substituted one or two times with a methyl group,
  a phenyl group, which is optionally substituted, one, two or three times, each substituent independently selected from a fluorine atom or a chlorine atom or a group selected from methyl, ethyl, propyl, isopropyl, difluoromethyl, trifluoromethyl, methoxy, —O—C(=O)—1,1-dimethylethyl, hydroxy, —C(=O)OCH$_3$, —C(=O)NH-cyclopropyl, amino, methylamino, aminomethyl, —S—CH$_3$, —S(=O)$_2$CH$_3$, and —S(=O)(NH)CH$_3$, and a monocyclic heteroaryl group, which is selected from oxazol-2-yl, pyrazol-3-yl, pyrazol-5-yl, pyridin-2-yl, pyridin-3-yl, pyridin-4-yl, pyrimidin-2-yl, pyrimidin-4-yl, chinolin-5-yl, indazol-5-yl, and which is optionally substituted one or two times, each substituent independently selected from methyl and methoxy, R$^2$ represents a hydrogen atom or a fluorine or chlorine atom, R$^3$ represents a group selected from propyl, 2-methylpropyl, 3-pentyl, cyclopropylmethyl, cyclopropyl, cyclopropylmethyl, cyclobutyl, cyclopentyl, cyclohexyl, difluoromethyl, trifluoromethyl, 1,1-difluoroethyl, prop-2-en-1-yl, 2-methyl-prop-1-en-1-yl, N,N-dimethylaminoethyl, and phenyl, R$^4$ represents a group selected from methyl, ethyl, propyl, isopropyl, 2-butyl, prop-2-en-1-yl, cyclopropylmethyl, benzyl, cyclopropyl, cyclobutyl, cyclopentyl, 2-hydroxyethyl, R$^5$ represents a chlorine atom or a group selected from methyl, ethyl, propyl, isopropyl, 2-butyl, isobutyl, tert-butyl, cyclopropyl, cyclobutyl, cyclopentyl, trifluoromethyl, hydroxymethyl, 1-hydroxyethyl, 2-hydroxypropan-2-yl, 1-chloroethyl, 1-hydroxy-2,2,2-trifluoroethyl, 1-methoxyethyl, methoxy, isopropoxy, methylsulfanyl, aminomethyl, (methylamino)methyl, (dimethylamino)methyl, 1-aminoethyl, 2-aminoethyl, methylamino and ethyl(methyl)amino, —C(=O)OH, —C(=O)OCH$_3$, —C(=O)NH$_2$, —C(=O)NHCH$_3$, —C(=O)NHcyclopropyl, —C(=O)N(CH$_3$)$_2$, and —S(=O)(=NH)CH$_3$, or a tautomer, an N-oxide, a salt, a salt of a tautomer or a salt of an N-oxide thereof.

8. The compound according to claim 1 which is selected from the group consisting of:

5-fluoro-4-[3-methyl-5-oxo-4-(propan-2-yl)-4,5-dihydro-1H-1,2,4-triazol-1-yl]-N-(2-methylphenyl)-2-{[(2S)-1,1,1-trifluoropropan-2-yl]oxy}benzamide, N-(2,6-difluorophenyl)-5-fluoro-4-[3-methyl-5-oxo-4-(propan-2-yl)-4,5-dihydro-1H-1,2,4-triazol-1-yl]-2-{[(2S)-1,1,1-trifluoropropan-2-yl]oxy}benzamide, 5-fluoro-N-(2-fluorophenyl)-4-[3-methyl-5-oxo-4-(propan-2-yl)-4,5-dihydro-1H-1,2,4-triazol-1-yl]-2-{[(2S)-1,1,1-trifluoropropan-2-yl]oxy})benzamide, 5-fluoro-4-[3-methyl-5-oxo-4-(propan-2-yl)-4,5-dihydro-1H-1,2,4-triazol-1-yl]-N-[3-(trifluoromethyl)phenyl]-2-{[(2S)-1,1,1-trifluoropropan-2-yl]oxy}benzamide, 5-fluoro-N-(2-fluoro-6-methylphenyl)-4-[3-methyl-5-oxo-4-(propan-2-yl)-4,5-dihydro-1H-1,2,4-triazol-1-yl]-2-{[(2S)-1,1,1-trifluoropropan-2-yl]oxy})benzamide, 5-fluoro-N-(2-fluorophenyl)-4-[3-methyl-5-oxo-4-(propan-2-yl)-4,5-dihydro-1H-1,2,4-triazol-1-yl]-2-[(1S)-1-phenylethoxy]benzamide, 5-fluoro-N-(2-fluoro-6-methylphenyl)-4-[3-methyl-5-oxo-4-(propan-2-yl)-4,5-dihydro-1H-1,2,4-triazol-1-yl]-2-[(1S)-1-phenylethoxy]benzamide, N-(2,6-difluorophenyl)-5-fluoro-4-[3-methyl-5-oxo-4-(propan-2-yl)-4,5-dihydro-1H-1,2,4-triazol-1-yl]-2-[(1S)-1-phenylethoxy]benzamide, 5-fluoro-4-[3-methyl-5-oxo-4-(propan-2-yl)-4,5-dihydro-1H-1,2,4-triazol-1-yl]-2-[(1S)-1-phenylethoxy]-N-[3-(trifluoromethyl)phenyl]benzamide, 5-fluoro-4-[3-methyl-5-oxo-4-(propan-2-yl)-4,5-dihydro-1H-1,2,4-triazol-1-yl]-N-(2-methylphenyl)-2-[(1S)-1-phenylethoxy]benzamide, 5-fluoro-N-(2-fluoro-6-methylphenyl)-4-[3-methyl-5-oxo-4-(propan-2-yl)-4,5-dihydro-1H-1,2,4-triazol-1-yl]-2-[(2S)-pentan-2-yloxy]benzamide, N-(2,6-difluorophenyl)-5-fluoro-4-[3-methyl-5-oxo-4-(propan-2-yl)-4,5-dihydro-1H-1,2,4-triazol-1-yl]-2-[(2S)-pentan-2-yloxy]benzamide, 5-fluoro-4-[3-methyl-5-oxo-4-(propan-2-yl)-4,5-dihydro-1H-1,2,4-triazol-1-yl]-N-(2-methylphenyl)-2-[(2S)-pentan-2-yloxy]benzamide, 5-fluoro-4-[3-methyl-5-oxo-4-(propan-2-yl)-4,5-dihydro-1H-1,2,4-triazol-1-yl]-2-[(2S)-pentan-2-yloxy]-N-[3-(trifluoromethyl)phenyl]benzamide, 5-fluoro-N-(2-fluorophenyl)-4-[3-methyl-5-oxo-4-(propan-2-yl)-4,5-dihydro-1H-1,2,4-triazol-1-yl]-2-[(2S)-pentan-2-yloxy]benzamide, 4-(3-ethyl-4-methyl-5-oxo-4,5-dihydro-1H-1,2,4-triazol-1-yl)-5-fluoro-N-(2-methylphenyl)-2-[(2S)-pentan-2-yloxy]benzamide, 4-(3-ethyl-4-methyl-5-oxo-4,5-dihydro-1H-1,2,4-triazol-1-yl)-5-fluoro-N-(2-fluoro-6-methylphenyl)-2-[(2S)-pentan-2-yloxy]benzamide, N-(2,6-difluorophenyl)-4-(3-ethyl-4-methyl-5-oxo-4,5-dihydro-1H-1,2,4-triazol-1-yl)-5-fluoro-2-[(2S)-pentan-2-yloxy]benzamide, 4-(3-ethyl-4-methyl-5-oxo-4,5-dihydro-1H-1,2,4-triazol-1-yl)-5-fluoro-N-(2-fluorophenyl)-2-[(2S)-pentan-2-yloxy]benzamide, 4-(3-ethyl-4-methyl-5-oxo-4,5-dihydro-1H-1,2,4-triazol-1-yl)-5-fluoro-2-[(2S)-pentan-2-yloxy]-N-[3-(trifluoromethyl)phenyl]benzamide, 4-(3-ethyl-4-methyl-5-oxo-4,5-dihydro-1H-1,2,4-triazol-1-yl)-5-fluoro-N-(4-methoxyphenyl)-2-[(2S)-pentan-2-yloxy]benzamide, 4-(3-ethyl-4-methyl-5-oxo-4,5-dihydro-1H-1,2,4-triazol-1-yl)-5-fluoro-2-[(2S)-pentan-2-yloxy]-N-[4-(trifluoromethyl)phenyl]benzamide, 4-(3-ethyl-4-methyl-5-oxo-4,5-dihydro-1H-1,2,4-triazol-1-yl)-5-fluoro-2-[(2S)-pentan-2-yloxy]-N-[2-(trifluoromethyl)phenyl]benzamide, N-(3-amino-2-methylphenyl)-4-(3-ethyl-4-methyl-5-oxo-4,5-dihydro-1H-1,2,4-triazol-1-yl)-5-fluoro-2-[(2S)-pentan-2-yloxy]benzamide, N-(2-cyano-6-methylphenyl)-4-(3-ethyl-4-methyl-5-oxo-4,5-dihydro-1H-1,2,4-triazol-1-yl)-5-fluoro-2-[(2S)-pentan-2-yloxy]benzamide, 4-(3-ethyl-4-methyl-5-oxo-4,5-dihydro-1H-1,2,4-triazol-1-yl)-5-fluoro-N-(3-methylphenyl)-2-[(2S)-pentan-2-yloxy]benzamide, N-(2,2-dimethylpropyl)-4-(3-ethyl-4-methyl-5-oxo-4,5-dihydro-1H-1,2,4-triazol-1-yl)-5-fluoro-2-[(2S)-pentan-2-yloxy]benzamide, N-cycloheptyl-4-(3-ethyl-4-methyl-5-oxo-4,5-dihydro-1H-1,2,4-triazol-1-yl)-5-fluoro-2-[(2S)-pentan-2-yloxy]benzamide, 4-(3-ethyl-4-methyl-5-oxo-4,5-dihydro-1H-1,2,4-triazol-1-yl)-5-fluoro-N-(2-hydroxyphenyl)-2-[(2S)-pentan-2-yloxy]benzamide, N-(cyclohexylmethyl)-4-(3-ethyl-4-methyl-5-oxo-4,5-dihydro-1H-1,2,4-triazol-1-yl)-5-fluoro-2-[(2S)-pentan-2-yloxy]benzamide, N-(1-cyclohexyl ethyl)-4-(3-ethyl-4-methyl-5-oxo-4,5-dihydro-1H-1,2,4-triazol-1-yl)-5-fluoro-2-[(2S)-pentan-2-yloxy]benzamide, mixture of stereoisomers, N-(2,4-dimethylphenyl)-4-(3-ethyl-4-methyl-5-oxo-4,5-dihydro-1H-1,2,4-triazol-1-yl)-5-fluoro-2-[(2S)-pentan-2-yloxy]benzamide, 4-(3-ethyl-4-methyl-5-oxo-4,5-dihydro-1H-1,2,4-triazol-1-yl)-5-fluoro-N-[2-(methylamino)phenyl]-2-[(2S)-pentan-2-yloxy]benzamide, 4-(3-ethyl-4-methyl-5-oxo-4,5-dihydro-1H-1,2,4-triazol-1-yl)-5-fluoro-N-(2-methoxyphenyl)-2-[(2S)-pentan-2-yloxy]benzamide, 4-(3-ethyl-4-methyl-5-oxo-4,5-dihydro-1H-1,2,4-triazol-1-yl)-5-fluoro-N-(3-methoxyphenyl)-2-[(2S)-pentan-2-yloxy]benzamide, 4-(3-ethyl-4-methyl-5-oxo-4,5-dihydro-1H-1,2,4-triazol-1-yl)-N-(2-ethylphenyl)-5-fluoro-2-[(2S)-pentan-2-yloxy]benzamide, 4-(3-ethyl-4-methyl-5-oxo-4,5-dihydro-1H-1,2,4-triazol-1-yl)-5-fluoro-2-[(2S)-pentan-2-yloxy]-N-[2-(propan-2-yl)phenyl]benzamide, 4-(3-ethyl-4-methyl-5-oxo-4,5-dihydro-1H-1,2,4-triazol-1-yl)-5-fluoro-2-[(2S)-pentan-2-yloxy]-N-(2-propylphenyl)benzamide, 4-(3-ethyl-4-methyl-5-oxo-4,5-dihydro-1H-1,2,4-triazol-1-yl)-N-(4-ethylphenyl)-5-fluoro-2-[(2S)-pentan-2-yloxy]benzamide, 4-(3-ethyl-4-methyl-5-oxo-4,5-dihydro-1H-1,2,4-triazol-1-yl)-5-fluoro-2-[(2S)-pentan-2-yloxy]-N-[4-(propan-2-yl)phenyl]benzamide, N-(2,3-dihydro-1H-inden-2-yl)-4-(3-ethyl-4-methyl-5-oxo-4,5-dihydro-1H-1,2,4-triazol-1-yl)-5-fluoro-2-[(2S)-pentan-2-yloxy]benzamide, N-(cyclopentylmethyl)-4-(3-ethyl-4-methyl-5-oxo-4,5-dihydro-1H-1,2,4-triazol-1-yl)-5-fluoro-2-[(2S)-pentan-2-yloxy]benzamide, 4-(3-ethyl-4-methyl-5-oxo-4,5-dihydro-1H-1,2,4-triazol-1-yl)-5-fluoro-N-(4-methylphenyl)-2-[(2S)-pentan-2-yloxy]benzamide, N-(4-amino-2,6-dimethylphenyl)-4-(3-ethyl-4-methyl-5-oxo-4,5-dihydro-1H-1,2,4-triazol-1-yl)-5-fluoro-2-[(2S)-pentan-2-yloxy]benzamide, N-(2-amino-4,6-dimethylphenyl)-4-(3-ethyl-4-methyl-5-oxo-4,5-dihydro-1H-1,2,4-triazol-1-yl)-5-fluoro-2-[(2S)-pentan-2-yloxy]benzamide, N-[4-(aminomethyl)-3-methylphenyl]-4-(3-ethyl-4-methyl-5-oxo-4,5-dihydro-1H-1,2,4-triazol-1-yl)-5-fluoro-2-(pentan-2-yloxy)benzamide, 4-(3-cyclopropyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-cyclopropyl-4-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(3-cyclopropyl-4-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy})benzamide, 4-(3-cyclobutyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-cyclobutyl-4-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(3-cyclobutyl-4-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy})benzamide, 4-(3-cyclopropyl-4-ethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-cyclopropyl-4-ethyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(3-cyclopropyl-4-ethyl-5-oxo-4,5-dihydro-1H-1,2,4-triazol-1-yl)-5-fluoro-N-(2-fluorophenyl)-2-{[(2S)-1,1,1-trifluoropropan-2-yl]oxy})benzamide, 4-(4-cyclopropyl-3-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(4-cyclopropyl-3-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(4-cyclopropyl-3-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy})benzamide, N-(2,6-difluorophenyl)-5-fluoro-4-[4-methyl-5-oxo-3-(trifluoromethyl)-4,5-dihydro-1H-1,2,4-triazol-1-yl]-2-{[(2S)-1,1,1-trifluoropropan-2-yl]oxy}benzamide, 5-fluoro-N-(2-fluoro-6-methylphenyl)-4-[4-methyl-5-oxo-3-(trifluoromethyl)-4,5-dihydro-1H-1,2,4-triazol-1-yl]-2-{[(2S)-1,1,1-trifluoropropan-2-yl]oxy}benzamide, 5-fluoro-N-(2-fluorophenyl)-4-[4-methyl-5-oxo-3-(trifluoromethyl)-4,5-dihydro-1H-1,2,4-triazol-1-yl]-2-{[(2S)-1,1,1-trifluoropropan-2-yl]oxy}benzamide, 4-(4-cyclopropyl-3-ethyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(4-cyclopropyl-3-ethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(4-cyclopropyl-3-ethyl-5-oxo-4,5-dihydro-1H-1,2,4-triazol-1-yl)-5-fluoro-N-(2-fluorophenyl)-2-{[(2S)-1,1,1-trifluoropropan-2-yl]oxy})benzamide, N-(2,6-difluorophenyl)-5-fluoro-4-[4-methyl-1-oxo-3-(propan-2-yl)-4,5-dihydro-1H-1,2,4-triazol-1-yl]-2-{[(2S)-1,1,1-trifluoropropan-2-yl]oxy}benzamide, 5-fluoro-N-(2-fluoro-6-methylphenyl)-4-[4-methyl-5-oxo-3-(propan-2-yl)-4,5-dihydro-1H-1,2,4-triazol-1-yl]-2-{[(2S)-1,1,1-trifluoropropan-2-yl]oxy}benzamide, 5-fluoro-N-(2-fluorophenyl)-4-[4-methyl-5-oxo-3-(propan-2-yl)-4,5-dihydro-1H-1,2,4-triazol-1-yl]-2-{[(2S)-1,1,1-trifluoropropan-2-yl]oxy}benzamide, 4-(3-ethyl-4-methyl-5-oxo-4,5-dihydro-1H-1,2,4-triazol-1-yl)-5-fluoro-N-(2-fluoro-6-methylphenyl)-2-[(1S)-1-phenylethoxy]benzamide, N-(2,6-difluorophenyl)-4-(3-ethyl-4-methyl-5-oxo-4,5-dihydro-1H-1,2,4-triazol-1-yl)-5-fluoro-2-[(1S)-1-phenylethoxy]benzamide, 4-(3-ethyl-4-methyl-5-oxo-4,5-dihydro-1H-1,2,4-triazol-1-yl)-5-fluoro-N-(2-fluorophenyl)-2-{[(2S)-1,1,1-trifluoropropan-2-yl]oxy})benzamide, 4-(3-ethyl-4-methyl-5-oxo-4,5-dihydro-1H-1,2,4-triazol-1-yl)-5-fluoro-N-(2-fluoro-6-methylphenyl)-2-{[(2S)-1,1,1-trifluoropropan-2-yl]oxy}benzamide, 4-(3-ethyl-4-methyl-5-oxo-4,5-dihydro-1H-1,2,4-triazol-1-yl)-5-fluoro-N-(4-fluoro-2-methylphenyl)-2-{[(2S)-1,1,1-trifluoropropan-2-yl]oxy}benzamide, 5-fluoro-4-{3-[(1S)-1-hydroxyethyl]-4-methyl-5-oxo-4,5-dihydro-1H-1,2,4-triazol-1-yl}-N-(2-methylphenyl)-2-{[(2S)-1,1,1-trifluoropropan-2-yl]oxy}benzamide, 5-fluoro-N-[(2R)-1-hydroxypropan-2-yl]-4-[4-methyl-5-oxo-3-(propan-2-yl)-4,5-dihydro-1H-1,2,4-triazol-1-yl]-2-[(2S)-pentan-2-yloxy]benzamide, 5-fluoro-N-[(2R)-1-hydroxybutan-2-yl]-4-[4-methyl-5-oxo-3-(propan-2-yl)-4,5-dihydro-1H-1,2,4-triazol-1-yl]-2-[(2S)-pentan-2-yloxy]benzamide, N-[(2R)-1-amino-1-oxobutan-2-yl]-5-fluoro-4-[4-methyl-5-oxo-3-(propan-2-yl)-4,5-dihydro-1H-1,2,4-triazol-1-yl]-2-[(2S)-pentan-2-yloxy]benzamide, 5-fluoro-N-(heptan-4-yl)-4-[4-methyl-5-oxo-3-(propan-2-yl)-4,5-dihydro-1H-1,2,4-triazol-1-yl]-2-[(2S)-pentan-2-yloxy]benzamide, 2-(1-cyclohexylethoxy)-N-(2,4-dimethylphenyl)-5-fluoro-4-[3-(1-hydroxyethyl)-4-methyl-5-oxo-4,5-dihydro-1H-1,2,4-triazol-1-yl]benzamide, mixture of stereoisomers, N-(2-amino-6-methylphenyl)-2-(1-cyclohexylethoxy)-5-fluoro-4-[3-(1-hydroxyethyl)-4-methyl-5-oxo-4,5-dihydro-1H-1,2,4-triazol-1-yl]benzamide, mixture of stereoisomers, N-(4-amino-2-methylphenyl)-2-(1-cyclohexylethoxy)-5-fluoro-4-[3-(1-hydroxyethyl)-4-methyl-5-oxo-4,5-dihydro-1H-1,2,4-triazol-1-yl]benzamide, mixture of stereoisomers, 2-(1-cyclohexylethoxy)-N-(2,6-dimethylphenyl)-5-fluoro-4-[3-(1-hydroxyethyl)-4-methyl-5-oxo-4,5-dihydro-1H-1,2,4-triazol-1-yl]benzamide, mixture of stereoisomers, 5-fluoro-4-{3-[(1S)-1-hydroxyethyl]-4-methyl-5-oxo-4,5-dihydro-1H-1,2,4-triazol-1-yl}-N-(2-methylphenyl)-2-(pentan-2-yloxy)benzamide, mixture of stereoisomers, N-(2-amino-6-methylphenyl)-4-(3-ethyl-4-methyl-5-oxo-4,5-dihydro-1H-1,2,4-triazol-1-yl)-5-fluoro-2-(pent-4-en-2-yloxy)benzamide, mixture of stereoisomers, N-(2,6-dimethylphenyl)-5-fluoro-4-{3-[(1-hydroxyethyl]-4-methyl-5-oxo-4,5-dihydro-1H-1,2,4-triazol-1-yl}-2-[(2R)-pentan-2-yloxy]benzamide, mixture of stereoisomers, N-(4-amino-2-methylphenyl)-4-(3-ethyl-4-methyl-5-oxo-4,5-dihydro-1H-1,2,4-triazol-1-yl)-5-fluoro-2-[pent-4-en-2-yloxy]benzamide, mixture of stereoisomers, 5-fluoro-4-{4-methyl-3-[(methylamino)methyl]-5-oxo-4,5-dihydro-1H-1,2,4-triazol-1-yl}-N-(pentan-3-yl)-2-[(2S)-pentan-2-yloxy]benzamide, 2-(1-cyclohexylethoxy)-N-(2,6-dimethylphenyl)-5-fluoro-4-[3-(hydroxymethyl)-4-methyl-5-oxo-4,5-dihydro-1H-1,2,4-triazol-1-yl]benzamide, mixture of stereoisomers, 4-[3-(aminomethyl)-4-methyl-5-oxo-4,5-dihydro-1H-1,2,4-triazol-1-yl]-5-fluoro-N-(2-methylphenyl)-2-[(2S)-pentan-2-yloxy]benzamide, N-[4-amino-2-(trifluoromethyl)phenyl]-4-(3-ethyl-4-methyl-5-oxo-4,5-dihydro-1H-1,2,4-triazol-1-yl)-5-fluoro-2-[(2S)-pentan-2-yloxy]benzamide, N-[2-(aminomethyl)-6-methylphenyl]-4-(3-ethyl-4-methyl-5-oxo-4,5-dihydro-1H-1,2,4-triazol-1-yl)-5-fluoro-2-[(2S)-pentan-2-yloxy]benzamide, 4-{3-[(1R)-1-aminoethyl]-4-methyl-5-oxo-4,5-dihydro-1H-1,2,4-triazol-1-yl}-N-(4-amino-2-methylphenyl)-2-(1-cyclohexylethoxy)-5-fluorobenzamide, mixture of stereoisomers, 4-(4-cyclopentyl-3-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, N-(2,6-difluorophenyl)-4-{3-[ethyl(methyl)amino]-4-methyl-5-oxo-4,5-dihydro-1H-1,2,4-triazol-1-yl}-5-fluoro-2-{[(2S)-1,1,1-trifluoropropan-2-yl]oxy})benzamide, N-(2,6-difluorophenyl)-4-(3-ethyl-4-methyl-1-oxo-4,5-dihydro-1H-1,2,4-triazol-1-yl)-5-fluoro-2-{[(2S)-1,1,1-trifluoropropan-2-yl]oxy}benzamide, N-(2,6-difluorophenyl)-5-fluoro-4-[3-(1-hydroxyethyl)-4-methyl-5-oxo-4,5-dihydro-1H-1,2,4-triazol-1-yl]-2-{[(2S)-1,1,1-trifluoropropan-2-yl]oxy}benzamide, single stereomer, N-(2,6-difluorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide, N-(2,6-difluorophenyl)-4-{3-[(dimethylamino)methyl]-4-methyl-5-oxo-4,5-dihydro-1H-1,2,4-triazol-1-yl}-5-fluoro-2-{[(2S)-1,1,1-trifluoropropan-2-yl]oxy}benzamide, N-(2,6-difluorophenyl)-5-fluoro-4-(4-methyl-5-oxo-3-propyl-4,5-dihydro-1H-1,2,4-triazol-1-yl)-2-{[(2S)-1,1,1-trifluoropropan-2-yl]oxy}benzamide, N-(2,6-difluorophenyl)-5-fluoro-4-[4-methyl-3-(methylsulfanyl)-5-oxo-4,5-dihydro-1H-1,2,4-triazol-1-yl]-2-{[(2S)-1,1,1-trifluoropropan-2-yl]oxy}benzamide, 4-[3-(2-aminoethyl)-4-methyl-5-oxo-4,5-dihydro-1H-1,2,4-triazol-1-yl]-N-(2,6-difluorophenyl)-5-fluoro-2-{[(2S)-1,1,1-trifluoropropan-2-yl]oxy}benzamide, N-(2,6-difluorophenyl)-5-fluoro-4-[4-methyl-3-(methylamino)-5-oxo-4,5-dihydro-1H-1,2,4-triazol-1-yl]-2-{[(2S)-1,1,1-trifluoropropan-2-yl]oxy}benzamide, 4-(3-tert-butyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-chloro-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-[4-(cyclopropylmethyl)-3-methyl-5-oxo-4,5-dihydro-1H-1,2,4-triazol-1-yl]-N-(2,6-difluorophenyl)-5-fluoro-2-{[(2S)-1,1,1-trifluoropropan-2-yl]oxy)}benzamide, N-(2,6-difluorophenyl)-5-fluoro-4-(3-methyl-5-oxo-4-propyl-4,5-dihydro-1H-1,2,4-triazol-1-yl)-2-{[(2S)-1,1,1-trifluoropropan-2-yl]oxy}benzamide, N-(2,6-difluorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, N-(2,6-difluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2,6-difluorophenyl)-4-[3-ethyl-4-(2-hydroxyethyl)-5-oxo-4,5-dihydro-1H-1,2,4-triazol-1-yl]-5-fluoro-2-{[(2S)-1,1,1-trifluoropropan-2-yl]oxy}benzamide, 4-(3,4-diethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(4-cyclopropyl-3-methoxy-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-chloro-4-ethyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-(3-cyclopentyl-4-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, 4-[4-(butan-2-yl)-3-methyl-5-oxo-4,5-dihydro-1H-1,2,4-triazol-1-yl]-N-(2,6-difluorophenyl)-5-fluoro-2-{[(2S)-1,1,1-trifluoropropan-2-yl]oxy}benzamide, mixture of stereoisomers, 4-[3-(butan-2-yl)-4-methyl-5-oxo-4,5-dihydro-1H-1,2,4-triazol-1-yl]-N-(2,6-difluorophenyl)-5-fluoro-2-{[(2S)-1,1,1-trifluoropropan-2-yl]oxy}benzamide, mixture of stereoisomers, N-(2,6-difluorophenyl)-4-[4-ethyl-3-(methylsulfanyl)-5-oxo-4,5-dihydro-1H-1,2,4-triazol-1-yl]-5-fluoro-2-{[(2S)-1,1,1-trifluoropropan-2-yl]oxy}benzamide, N-(2,6-difluorophenyl)-5-fluoro-4-[3-(1-methoxyethyl)-4-methyl-5-oxo-4,5-dihydro-1H-1,2,4-triazol-1-yl]-2-{[(2S)-1,1,1-trifluoropropan-2-yl]oxy}benzamide, mixture of stereoisomers, N-(2,6-difluorophenyl)-4-[4-ethyl-5-oxo-3-(propan-2-yloxy)-4,5-dihydro-1H-1,2,4-triazol-1-yl]-5-fluoro-2-{[(2S)-1,1,1-trifluoropropan-2-yl]oxy}benzamide, 4-(4-benzyl-3-methyl-5-oxo-4,5-dihydro-1H-1,2,4-triazol-1-yl)-N-(2,6-difluorophenyl)-5-fluoro-2-{[(2S)-1,1,1-trifluoropropan-2-yl]oxy}benzamide, N-(2-chloro-6-fluorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy})benzamide, N-(2-chloro-6-fluorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, N-(2-chloro-6-fluorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2-chloro-6-fluorophenyl)-5-fluoro-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide, 5-fluoro-4-[3-(hydroxymethyl)-4-methyl-5-oxo-4,5-dihydro-1H-1,2,4-triazol-1-yl]-N-(2-methoxy-4-methylpyridin-3-yl)-2-{[(2S)-1,1,1-trifluoropropan-2-yl]oxy}benzamide, 4-[4-ethyl-3-(hydroxymethyl)-5-oxo-4,5-dihydro-1H-1,2,4-triazol-1-yl]-5-fluoro-N-(2-methoxy-4-methylpyridin-3-yl)-2-{[(2S)-1,1,1-trifluoropropan-2-yl]oxy}benzamide, 5-fluoro-4-[3-(2-hydroxypropan-2-yl)-4-methyl-5-oxo-4,5-dihydro-1H-1,2,4-triazol-1-yl]-N-(2-methoxy-4-methylpyridin-3-yl)-2-{[(2S)-1,1,1-trifluoropropan-2-yl]oxy}benzamide, 5-fluoro-4-{3-[(1S)-1-hydroxyethyl]-4-methyl-5-oxo-4,5-dihydro-1H-1,2,4-triazol-1-yl}-N-(2-methoxy-4-methylpyridin-3-yl)-2-{[(2S)-1,1,1-trifluoropropan-2-yl]oxy}benzamide, 5-fluoro-N-(2-fluoro-6-methylphenyl)-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide, 4-[4-ethyl-3-(hydroxymethyl)-5-oxo-4,5-dihydro-1H-1,2,4-triazol-1-yl]-5-fluoro-N-(2-fluoro-6-methylphenyl)-2-{[(2S)-1,1,1-trifluoropropan-2-yl]oxy})benzamide, 5-fluoro-N-(2-fluoro-6-methylphenyl)-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, 5-fluoro-N-(2-fluoro-6-methylphenyl)-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide, N-(2,6-dichlorophenyl)-5-fluoro-4-[3-(hydroxymethyl)-4-methyl-5-oxo-4,5-dihydro-1H-1,2,4-triazol-1-yl]-2-{[(2S)-1,1,1-trifluoropropan-2-yl]oxy}benzamide, N-(2,6-dichlorophenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamide, N-(2,6-dichlorophenyl)-5-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, N-(2,6-dichlorophenyl)-5-fluoro-4-{3-[(1S)-1-hydroxyethyl]-4-methyl-5-oxo-4,5-dihydro-1H-1,2,4-triazol-1-yl}-2-{[(2S)-1,1,1-trifluoropropan-2-yl]oxy}benzamide, N-(2-chloro-6-fluorophenyl)-5-fluoro-4-[3-(hydroxymethyl)-4-methyl-5-oxo-4,5-dihydro-1H-1,2,4-triazol-1-yl]-2-[(2S)-pentan-2-yloxy]benzamide, N-(2-chloro-6-fluorophenyl)-5-fluoro-4-{3-[(1S)-1-hydroxyethyl]-4-methyl-5-oxo-4,5-dihydro-1H-1,2,4-triazol-1-yl}-2-[(2S)-pentan-2-yloxy]benzamide, N-(2-chloro-6-fluorophenyl)-5-fluoro-4-[3-(2-hydroxypropan-2-yl)-4-methyl-5-oxo-4,5-dihydro-1H-1,2,4-triazol-1-yl]-2-[(2S)-pentan-2-yloxy]benzamide, 5-fluoro-4-[3-(hydroxymethyl)-4-methyl-5-oxo-4,5-dihydro-1H-1,2,4-triazol-1-yl]-N-(2-methoxy-4-methylpyridin-3-yl)-2-[(2S)-pentan-2-yloxy]benzamide, 5-fluoro-4-{3-[(1S)-1-hydroxyethyl]-4-methyl-5-oxo-4,5-dihydro-1H-1,2,4-triazol-1-yl}-N-(2-methoxy-4-methylpyridin-3-yl)-2-[(2S)-pentan-2-yloxy]benzamide, 5-fluoro-4-[3-(2-hydroxypropan-2-yl)-4-methyl-5-oxo-4,5-dihydro-1H-1,2,4-triazol-1-yl]-N-(2-methoxy-4-methylpyridin-3-yl)-2-[(2S)-pentan-2-yloxy]benzamide, 5-fluoro-N-(2-fluoro-6-methylphenyl)-4-[3-(hydroxymethyl)-4-methyl-5-oxo-4,5-dihydro-1H-1,2,4-triazol-1-yl]-2-[(2S)-pentan-2-yloxy]benzamide, 5-fluoro-N-(2-fluoro-6-methylphenyl)-4-{3-[(1S)-1-hydroxyethyl]-4-methyl-5-oxo-4,5-dihydro-1H-1,2,4-triazol-1-yl}-2-[(2S)-pentan-2-yloxy]benzamide, 5-fluoro-N-(2-fluoro-6-methylphenyl)-4-[3-(2-hydroxypropan-2-yl)-4-methyl-5-oxo-4,5-dihydro-1H-1,2,4-triazol-1-yl]-2-[(2S)-pentan-2-yloxy]benzamide, 5-fluoro-4-[3-(hydroxymethyl)-4-methyl-5-oxo-4,5-dihydro-1H-1,2,4-triazol-1-yl]-N-(pentan-3-yl)-2-[(2S)-pentan-2-yloxy]benzamide, 5-fluoro-4-[3-(2-hydroxypropan-2-yl)-4-methyl-5-oxo-4,5-dihydro-1H-1,2,4-triazol-1-yl]-N-(pentan-3-yl)-2-[(2S)-pentan-2-yloxy]benzamide, N-(2,6-difluorophenyl)-4-(3-ethyl-4-methyl-5-oxo-4,5-dihydro-1H-1,2,4-triazol-1-yl)-2-{[(2S)-1,1,1-trifluoropropan-2-yl]oxy}benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(tetrahydrofuran-3-yl)benzamide, mixture of stereoisomers, 5-fluoro-N-[(2R)-1-hydroxypropan-2-yl]-4-[4-methyl-5-oxo-3-(propan-2-yl)-4,5-dihydro-1H-1,2,4-triazol-1-yl]-2-{[(2S)-4-methylpentan-2-yl]oxy}benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(1H-pyrazol-3-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyridin-2-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyridin-4-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(1-methylpiperidin-4-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(tetrahydro-2H-pyran-4-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyrimidin-4-yl)benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(1,3-oxazol-2-yl)benzamide, 5-fluoro-N-[(2R)-1-hydroxybutan-2-yl]-4-[4-methyl-5-oxo-3-(propan-2-yl)-4,5-dihydro-1H-1,2,4-triazol-1-yl]-2-{[(2S)-4-methylpentan-2-yl]oxy}benzamide, N-cyclopentyl-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide, N-cyclohexyl-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide, 5-fluoro-N-(2-hydroxypropyl)-4-[4-methyl-5-oxo-3-(propan-2-yl)-4,5-dihydro-1H-1,2,4-triazol-1-yl]-2-{[(2S)-4-methylpentan-2-yl]oxy}benzamide, mixture of stereoisomers, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-phenylbenzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(pyrimidin-2-yl)benzamide, N-[(2R)-1-aminopropan-2-yl]-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide, N-[(2R)-1-aminobutan-2-yl]-5-fluoro-4-[4-methyl-5-oxo-3-(propan-2-yl)-4,5-dihydro-1H-1,2,4-triazol-1-yl]-2-{[(2S)-4-methylpentan-2-yl]oxy}benzamide, 5-fluoro-4-[4-methyl-5-oxo-3-(propan-2-yl)-4,5-dihydro-1H-1,2,4-triazol-1-yl]-2-{[(2S)-4-methylpentan-2-yl]oxy}-N-(piperidin-4-yl)benzamide, 2-(1-cyclohexylethoxy)-4-(3-ethyl-4-methyl-5-oxo-4,5-dihydro-1H-1,2,4-triazol-1-yl)-5-fluoro-N-(pentan-3-yl)benzamide, mixture of stereoisomers, 2-[(1-cyclopropylpropan-2-yl)oxy]-4-(3-ethyl-4-methyl-5-oxo-4,5-dihydro-1H-1,2,4-triazol-1-yl)-5-fluoro-N-(pentan-3-yl)benzamide, mixture of stereoisomers, 2-(1-cyclopentyl ethoxy)-4-(3-ethyl-4-methyl-5-oxo-4,5-dihydro-1H-1,2,4-triazol-1-yl)-5-fluoro-N-(pentan-3-yl)benzamide, mixture of stereoisomers, 2-(1-cyclopropylethoxy)-4-(3-ethyl-4-methyl-5-oxo-4,5-dihydro-1H-1,2,4-triazol-1-yl)-5-fluoro-N-(pentan-3-yl)benzamide, mixture of stereoisomers, 4-(3-ethyl-4-methyl-5-oxo-4,5-dihydro-1H-1,2,4-triazol-1-yl)-5-fluoro-N-(pentan-3-yl)-2-(1-phenylethoxy)benzamide, mixture of stereoisomers, 4-(3-ethyl-4-methyl-5-oxo-4,5-dihydro-1H-1,2,4-triazol-1-yl)-2-[(3-ethylpentan-2-yl)oxy]-5-fluoro-N-(pentan-3-yl)benzamide, mixture of stereoisomers, 4-(3-ethyl-4-methyl-5-oxo-4,5-dihydro-1H-1,2,4-triazol-1-yl)-5-fluoro-2-[(4-methylpent-3-en-2-yl)oxy]-N-(pentan-3-yl)benzamide, mixture of stereoisomers, 4-(3-ethyl-4-methyl-5-oxo-4,5-dihydro-1H-1,2,4-triazol-1-yl)-5-fluoro-N-(pentan-3-yl)-2-(pent-4-en-2-yloxy)benzamide, mixture of stereoisomers, 2-(1-cyclobutylethoxy)-4-(3-ethyl-4-methyl-5-oxo-4,5-dihydro-1H-1,2,4-triazol-1-yl)-5-fluoro-N-(pentan-3-yl)benzamide, mixture of stereoisomers, 5-fluoro-4-[3-(1-hydroxyethyl)-4-methyl-5-oxo-4,5-dihydro-1H-1,2,4-triazol-1-yl]-N-(pentan-3-yl)-2-[(2S)-pentan-2-yloxy]benzamide, mixture of stereoisomers, and 5-fluoro-4-[3-(1-hydroxyethyl)-4-methyl-5-oxo-4,5-dihydro-1H-1,2,4-triazol-1-yl]-N-(2-methylphenyl)-2-(pentan-2-yloxy)benzamide, mixture of stereoisomers, N-(2-chloro-6-fluorophenyl)-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide, N-(2,6-difluorophenyl)-4-[4-ethyl-3-(hydroxymethyl)-5-oxo-4,5-dihydro-1H-1,2,4-triazol-1-yl]-2-{[(2S)-1,1,1-trifluoropropan-2-yl]oxy}benzamide, N-(2-chloro-6-fluorophenyl)-4-[4-ethyl-3-(hydroxymethyl)-5-oxo-4,5-dihydro-1H-1,2,4-triazol-1-yl]-2-{[(2S)-1,1,1-trifluoropropan-2-yl]oxy}benzamide, N-(2-chloro-6-fluorophenyl)-2-{[1,1-difluoropropan-2-yl]oxy}-4-[3-(2-hydroxypropan-2-yl)-4-methyl-5-oxo-4,5-dihydro-1H-1,2,4-triazol-1-yl]benzamide (Racemic)

N-(2-chloro-6-fluorophenyl)-2-{[1,1-difluoropropan-2-yl]oxy}-4-[4-ethyl-3-(hydroxymethyl)-5-oxo-4,5-dihydro-1H-1,2,4-triazol-1-yl]benzamide (Racemic)

N-(2-chloro-6-fluorophenyl)-4-[4-cyclopropyl-3-(hydroxymethyl)-5-oxo-4,5-dihydro-1H-1,2,4-triazol-1-yl]-5-fluoro-2-{[(2S)-1,1,1-trifluoropropan-2-yl]oxy})benzamide N-(2-chloro-6-fluorophenyl)-5-fluoro-4-[3-(hydroxymethyl)-5-oxo-4-propyl-4,5-dihydro-1H-1,2,4-triazol-1-yl]-2-{[(2S)-1,1,1-trifluoropropan-2-yl]oxy}benzamide, N-(2-chloro-6-fluorophenyl)-4-[4-cyclobutyl-3-(hydroxymethyl)-5-oxo-4,5-dihydro-1H-1,2,4-triazol-1-yl]-5-fluoro-2-{[(2S)-1,1,1-trifluoropropan-2-yl]oxy})benzamide, N-(2-chloro-6-fluorophenyl)-5-fluoro-4-[3-(hydroxymethyl)-5-oxo-4-(prop-2-en-1-yl)-4,5-dihydro-1H-1,2,4-triazol-1-yl]-2-{[(2S)-1,1,1-trifluoropropan-2-yl]oxy})benzamide, N-(2-chloro-6-fluorophenyl)-2-{[3,3-difluorobutan-2-yl]oxy}-4-[4-ethyl-3-(hydroxymethyl)-5-oxo-4,5-dihydro-1H-1,2,4-triazol-1-yl]-5-fluorobenzamide (Racemic), 5-fluoro-4-[3-(hydroxymethyl)-5-oxo-4-propyl-4,5-dihydro-1H-1,2,4-triazol-1-yl]-N-(2-methoxy-4-methylpyridin-3-yl)-2-{[(2S)-1,1,1-trifluoropropan-2-yl]oxy}benzamide, N-(2-chloro-6-fluorophenyl)-4-[4-ethyl-3-(hydroxymethyl)-5-oxo-4,5-dihydro-1H-1,2,4-triazol-1-yl]-3-fluoro-2-{[(2S)-1,1,1-trifluoropropan-2-yl]oxy}benzamide N-(2-chloro-6-fluorophenyl)-3-fluoro-4-[3-(2-hydroxypropan-2-yl)-4-methyl-5-oxo-4,5-dihydro-1H-1,2,4-triazol-1-yl]-2-{[(2S)-1,1,1-trifluoropropan-2-yl]oxy}benzamide N-(6-chloro-2-fluoro-3-methoxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy})benzamide, N-(6-chloro-2-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy})benzamide N-(6-chloro-2-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy})benzamide, 3-chloro-4-(4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy}benzamido)-5-fluorophenyl 2,2-dimethylpropanoate, N-(2-chloro-6-fluoro-4-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy})benzamide, N-(2-chloro-6-fluoro-3-methoxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy})benzamide, N-(2-chloro-6-fluoro-3-hydroxyphenyl)-4-[4-ethyl-3-(hydroxymethyl)-5-oxo-4,5-dihydro-1H-1,2,4-triazol-1-yl]-5-fluoro-2-{[(2S)-1,1,1-trifluoropropan-2-yl]oxy})benzamide, 2-[(1S)-1-cyclohexylethoxy]-N-(1,4-dimethyl-1H-pyrazol-3-yl)-4-(3-ethyl-4-methyl-5-oxo-4,5-dihydro-1H-1,2,4-triazol-1-yl)-5-fluorobenzamide, 2-[(1S)-1-cyclohexylethoxy]-4-(3-ethyl-4-methyl-5-oxo-4,5-dihydro-1H-1,2,4-triazol-1-yl)-5-fluoro-N-[1-(4-fluorophenyl)cyclopropyl]benzamide 2-[(1S)-1-cyclohexylethoxy]-4-(3-ethyl-4-methyl-5-oxo-4,5-dihydro-1H-1,2,4-triazol-1-yl)-5-fluoro-N-(oxan-4-yl)benzamide 2-[(1S)-1-cyclohexylethoxy]-4-(3-ethyl-4-methyl-5-oxo-4,5-dihydro-1H-1,2,4-triazol-1-yl)-5-fluoro-N-(1-phenylbutan-2-yl)benzamide 2-[(1S)-1-cyclohexylethoxy]-4-(3-ethyl-4-methyl-5-oxo-4,5-dihydro-1H-1,2,4-triazol-1-yl)-5-fluoro-N-[3-(methanesulfonyl)phenyl]benzamide, 2-[(1S)-1-cyclohexylethoxy]-4-(3-ethyl-4-methyl-5-oxo-4,5-dihydro-1H-1,2,4-triazol-1-yl)-5-fluoro-N-(1-methyl-1H-pyrazol-5-yl)benzamide, 2-[(1S)-1-cyclohexylethoxy]-4-(3-ethyl-4-methyl-5-oxo-4,5-dihydro-1H-1,2,4-triazol-1-yl)-5-fluoro-N-[4-(methylsulfanyl)phenyl]benzamide, 4-(3-ethyl-4-methyl-5-oxo-4,5-dihydro-1H-1,2,4-triazol-1-yl)-5-fluoro-N-(4-methylpyridin-3-yl)-2-[(1S)-1-phenylethoxy]benzamide, 4-(3-ethyl-4-methyl-5-oxo-4,5-dihydro-1H-1,2,4-triazol-1-yl)-5-fluoro-N-(2-methylquinolin-5-yl)-2-[(1S)-1-phenylethoxy]benzamide, N-[3-(cyclopropylcarbamoyl)phenyl]-4-(3-ethyl-4-methyl-5-oxo-4,5-dihydro-1H-1,2,4-triazol-1-yl)-5-fluoro-2-[(1S)-1-phenylethoxy]benzamide, N-[2-(difluoromethyl)phenyl]-4-(3-ethyl-4-methyl-5-oxo-4,5-dihydro-1H-1,2,4-triazol-1-yl)-5-fluoro-2-[(1S)-1-phenylethoxy]benzamide, 4-(3-ethyl-4-methyl-5-oxo-4,5-dihydro-1H-1,2,4-triazol-1-yl)-5-fluoro-N-(6-methyl-1H-indazol-5-yl)-2-[(1S)-1-phenylethoxy]benzamide, N-(1-cyanobutan-2-yl)-4-(3-ethyl-4-methyl-5-oxo-4,5-dihydro-1H-1,2,4-triazol-1-yl)-5-fluoro-2-[(1S)-1-phenylethoxy]benzamide, 2-{[(2S)-1-(dimethylamino)propan-2-yl]oxy}-4-(3-ethyl-4-methyl-5-oxo-4,5-dihydro-1H-1,2,4-triazol-1-yl)-5-fluoro-N-(2-fluoro-6-methylphenyl)benzamide, 2-[(1S)-1-cyclohexylethoxy]-4-(3-ethyl-4-methyl-5-oxo-4,5-dihydro-1H-1,2,4-triazol-1-yl)-5-fluoro-N-[4-(S-methanesulfonimidoyl)phenyl]benzamide (mixture of stereoisomers), N-(2,6-difluorophenyl)-4-[4-ethyl-3-(S-methanesulfonimidoyl)-5-oxo-4,5-dihydro-1H-1,2,4-triazol-1-yl]-5-fluoro-2-{[(2S)-1,1,1-trifluoropropan-2-yl]oxy}benzamide (Mixture of stereoisomers), 1-(4-[(2-chloro-6-fluorophenyl)carbamoyl]-3-{[(2S)-1,1,1-trifluoropropan-2-yl]oxy}phenyl)-4-ethyl-5-oxo-4,5-dihydro-1H-1,2,4-triazole-3-carboxylic acid, 1-(4-[(2-chloro-6-fluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid, 1-(4-[(2,6-difluorophenyl)carbamoyl]-3-{[(2S)-1,1,1-trifluoropropan-2-yl]oxy}phenyl)-4-ethyl-5-oxo-4,5-dihydro-1H-1,2,4-triazole-3-carboxylic acid, 4-ethyl-1-(2-fluoro-4-[(2-fluoro-6-methylphenyl)carbamoyl]-5-{[(2S)-1,1,1-trifluoropropan-2-yl]oxy}phenyl)-5-oxo-4,5-dihydro-1H-1,2,4-triazole-3-carboxylic acid, 1-(4-[(2,6-dichlorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid, 1-(4-[(2-chloro-6-fluorophenyl)carbamoyl]-2-fluoro-3-{[(2S)-1,1,1-trifluoropropan-2-yl]oxy}phenyl)-4-ethyl-5-oxo-4,5-dihydro-1H-1,2,4-triazole-3-carboxylic acid, 1-(4-[(2-chloro-6-fluorophenyl)carbamoyl]-3-{[1,1-difluoropropan-2-yl]oxy}phenyl)-4-ethyl-5-oxo-4,5-dihydro-1H-1,2,4-triazole-3-carboxylic acid (Racemic), 1-(4-[(2-chloro-6-fluorophenyl)carbamoyl]-2-fluoro-5-{[(2S)-1,1,1-trifluoropropan-2-yl]oxy}phenyl)-4-methyl-5-oxo-4,5-dihydro-1H-1,2,4-triazole-3-carboxylic acid, 1-(2-fluoro-4-[(2-fluoro-6-methylphenyl)carbamoyl]-5-{[(2S)-1,1,1-trifluoropropan-2-yl]oxy}phenyl)-4-methyl-5-oxo-4,5-dihydro-1H-1,2,4-triazole-3-carboxylic acid, 1-(4-[(2,6-difluorophenyl)carbamoyl]-2-fluoro-5-{[(2S)-1,1,1-trifluoropropan-2-yl]oxy}phenyl)-4-methyl-5-oxo-4,5-dihydro-1H-1,2,4-triazole-3-carboxylic acid, 1-(4-[(2-chloro-6-fluorophenyl)carbamoyl]-2-fluoro-5-{[(2S)-1,1,1-trifluoropropan-2-yl]oxy}phenyl)-5-oxo-4-propyl-4,5-dihydro-1H-1,2,4-triazole-3-carboxylic acid, 1-(4-[(2-chloro-6-fluorophenyl)carbamoyl]-5-{[3,3-difluorobutan-2-yl]oxy}-2-fluorophenyl)-4-ethyl-5-oxo-4,5-dihydro-1H-1,2,4-triazole-3-carboxylic acid (racemic), 1-(4-[(2-chloro-6-fluorophenyl)carbamoyl]-2-fluoro-5-{[(2S)-1,1,1-trifluoropropan-2-yl]oxy}phenyl)-4-cyclopropyl-5-oxo-4,5-dihydro-1H-1,2,4-triazole-3-carboxylic acid, 1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylic acid 1-(4-[(2-chloro-6-fluorophenyl)carbamoyl]-2-fluoro-5-{[(2S)-1,1,1-trifluoropropan-2-yl]oxy}phenyl)-5-oxo-4-(prop-2-en-1-yl)-4,5-dihydro-1H-1,2,4-triazole-3-carboxylic acid, 1-(4-[(2-chloro-6-fluorophenyl)carbamoyl]-2-fluoro-5-{[(2S)-1,1,1-trifluoropropan-2-yl]oxy}phenyl)-4-cyclobutyl-5-oxo-4,5-dihydro-1H-1,2,4-triazole-3-carboxylic acid, 1-(4-[(2,6-difluorophenyl)carbamoyl]-2-fluoro-5-{[(2S)-1,1,1-trifluoropropan-2-yl]oxy}phenyl)-4-methyl-5-oxo-4,5-dihydro-1H-1,2,4-triazole-3-carboxamide, 1-(4-[(2-chloro-6-fluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxamide, N-cyclopropyl-1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxamide, 1-(4-[(2,6-difluorophenyl)carbamoyl]-2-fluoro-5-{[(2S)-1,1,1-trifluoropropan-2-yl]oxy}phenyl)-N,4-dimethyl-5-oxo-4,5-dihydro-1H-1,2,4-triazole-3-carboxamide 1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxamide 1-(4-[(2,6-difluorophenyl)carbamoyl]-2-fluoro-5-{[(2S)-1,1,1-trifluoropropan-2-yl]oxy}phenyl)-4-ethyl-N,N-dimethyl-5-oxo-4,5-dihydro-1H-1,2,4-triazole-3-carboxamide Methyl-1-(4-[(2,6-difluorophenyl)carbamoyl]-2-fluoro-5-{[(2S)-1,1,1-trifluoropropan-2-yl]oxy}phenyl)-4-ethyl-5-oxo-4,5-dihydro-1H-1,2,4-triazole-3-carboxylate, 5-fluoro-4-{3-[1-hydroxyethyl]-4-methyl-5-oxo-4,5-dihydro-1H-1,2,4-triazol-1-yl}-N-(2-methylphenyl)-2-{[(2S)-1,1,1-trifluoropropan-2-yl]oxy}benzamide (Mixture of stereoisomers) and 4-{4-ethyl-5-oxo-3-[(1S)-2,2,2-trifluoro-1-hydroxyethyl]-4,5-dihydro-1H-1,2,4-triazol-1-yl}-5-fluoro-N-(2-methoxy-4-methylpyridin-3-yl)-2-{[(2S)-1,1,1-trifluoropropan-2-yl]oxy}benzamide (mixture of stereoisomers)

or a tautomer, an N-oxide, a salt, a salt of a tautomer or a salt of an N-oxide thereof.

9. A method of preparing a compound of general formula (I) according to claim 1, comprising the step of allowing an intermediate compound of general formula (VIII):

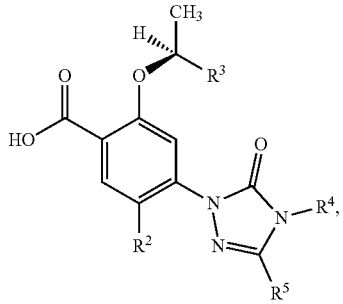

(VIII)

in which $R^2$, $R^3$, $R^4$ and $R^5$ are as defined for the compound of general formula (I) as defined in claim 1, to react with a compound of general formula (X):

$R^1$—$NH_2$ (X), in which $R^1$ is as defined for the compound of general formula (I) in claim 1, thereby giving a compound of general formula (I):

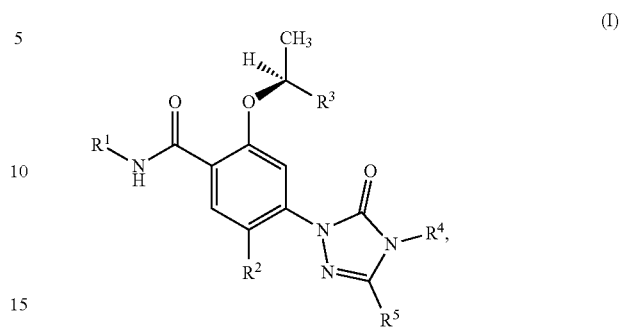

(I)

in which $R^1$, $R^2$, $R^3$, $R^4$ and $R^5$ are as defined in claim 1, then optionally converting said compound into solvates, salts and/or solvates of such salts using the corresponding (i) solvents and/or (ii) bases or acids.

10. An intermediate compound of formula (VIII)

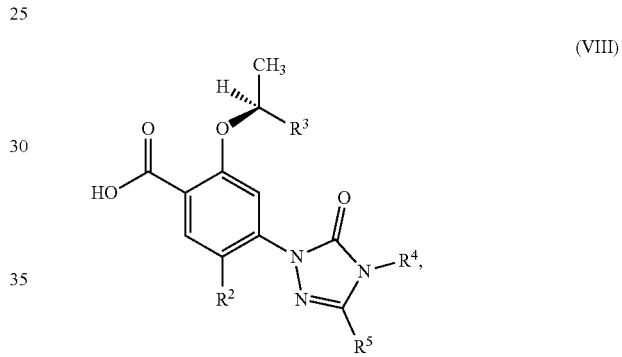

(VIII)

in which $R^2$, $R^3$, $R^4$ and $R^5$ are as defined for the compound of general formula (I) in claim 1.

11. A method of preparing a compound of general formula (I) according to claim 1, said method comprising the step of allowing an intermediate compound of general formula (XV):

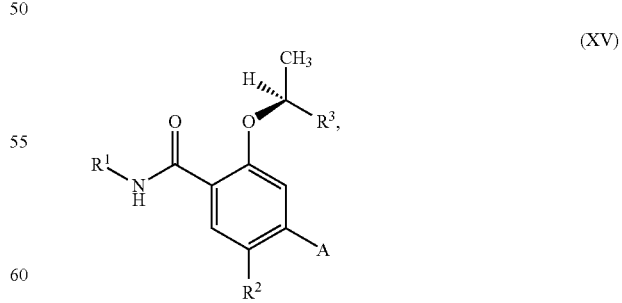

(XV)

in which A represents a chlorine, bromine or iodine atom, to react with a compound of general formula (IV):

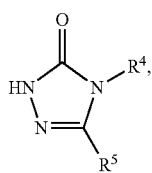

(IV)

thereby giving a compound of general formula (I):

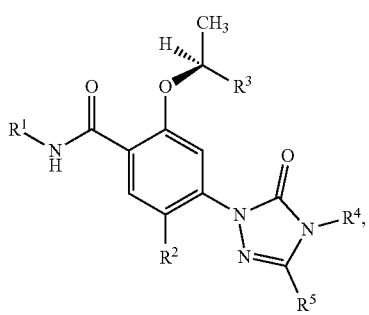

(I)

in which $R^1$, $R^2$, $R^3$, $R^4$ and $R^5$ are as defined for the compound of general formula (I) according to claim 1,
then optionally converting said compound into solvates, salts and/or solvates of such salts using the corresponding (i) solvents and/or (ii) bases or acids.

12. A pharmaceutical composition comprising a compound of general formula (I) according to claim 1 and one or more pharmaceutically acceptable excipients.

13. A pharmaceutical combination comprising:
one or more active ingredients comprising a compound of general formula (I) according to claim 1, and
one or more further active ingredients comprising an anti-cancer agent.

14. An intermediate compound of formula (XV)

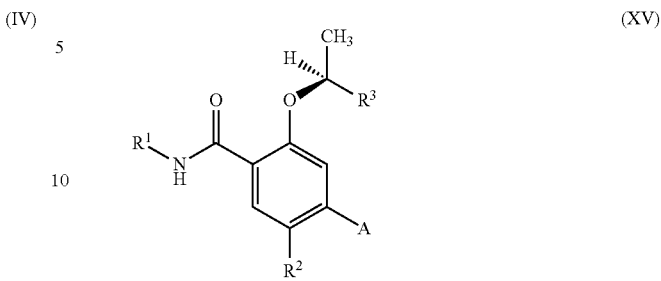

(XV)

in which $R^1$, $R^2$ and $R^3$ are as defined for the compound of general formula (I) according to claim 1, and A represents a chlorine, bromine or iodine atom.

15. A method for inhibiting cell proliferation or viability in a cancer cell, the method comprising contacting the cell with a compound of claim 1, thereby inhibiting cell proliferation or viability.

16. A method for inhibiting Dihydroorotate Dehydrogenase (DHODH) enzymatic activity, the method comprising contacting DHODH with a compound of claim 1, thereby inhibiting DHODH enzymatic activity.

17. A method for treating lymphoma or leukemia in a subject, the method comprising administering to the subject an effective amount of a compound of claim 1, thereby treating the lymphoma or leukemia.

18. The compound according to claim 8, wherein said compound is N-(2-chloro-6-fluorophenyl)-4-[4-ethyl-3-(hydroxymethyl)-5-oxo-4, 5-dihydro-1H-1,2,4-triazol-1-yl]-5-fluoro-2{[(2S)-1, 1,1-trifluoropropan-2-yl]oxy}benzamide;
or a tautomer, an N-oxide, a salt, a salt of a tautomer or a salt of an N-oxide thereof.

19. The pharmaceutical composition according to claim 12, wherein said compound is N-(2-chloro-6-fluorophenyl)-4-[4-ethyl-3-(hydroxymethyl)-5-oxo-4, 5-dihydro-1H-1,2,4-triazol-1-yl]-5-fluoro-2{[(2S)-1, 1,1-trifluoropropan-2-yl]oxy}benzamide;
or a tautomer, an N-oxide, a salt, a salt of a tautomer or a salt of an N-oxide thereof.

20. The method according to claim 17, wherein said compound is N-(2-chloro-6-fluorophenyl)-4-[4-ethyl-3-(hydroxymethyl)-5-oxo-4, 5-dihydro-1H-1,2,4-triazol-1-yl]-5-fluoro-2{[(2S)-1, 1,1-trifluoropropan-2-yl]oxy}benzamide;
or a tautomer, an N-oxide, a salt, a salt of a tautomer or a salt of an N-oxide thereof.

\* \* \* \* \*